(12) United States Patent
Macielag et al.

(10) Patent No.: US 10,118,900 B2
(45) Date of Patent: Nov. 6, 2018

(54) BENZIMIDAZOLE DERIVATIVES USEFUL AS CB-1 INVERSE AGONISTS

(71) Applicant: Janssen Pharmaceutica NV, Beerse (BE)

(72) Inventors: Mark J. Macielag, Gwynedd Valley, PA (US); Rui Zhang, Belle Mead, NJ (US); Yue-Mei Zhang, Wellesley, MA (US); Bin Zhu, Newtown, PA (US); Michael H. Parker, Chalfont, PA (US); Donald W. Ludovici, Quakertown, PA (US); Daniel J. Parks, Pepperell, MA (US); Bart L. DeCorte, Southampton, PA (US); Michael N. Greco, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/244,372

(22) Filed: Aug. 23, 2016

(65) Prior Publication Data

US 2017/0057929 A1   Mar. 2, 2017

Related U.S. Application Data

(60) Provisional application No. 62/209,381, filed on Aug. 25, 2015, provisional application No. 62/233,655, filed on Sep. 28, 2015.

(51) Int. Cl.

| | |
|---|---|
| *C07D 235/08* | (2006.01) |
| *C07D 235/18* | (2006.01) |
| *C07D 471/08* | (2006.01) |
| *C07D 403/04* | (2006.01) |
| *C07D 403/06* | (2006.01) |
| *C07D 403/12* | (2006.01) |
| *C07D 401/04* | (2006.01) |
| *C07C 53/18* | (2006.01) |
| *C07D 401/14* | (2006.01) |
| *C07D 405/14* | (2006.01) |
| *C07D 409/14* | (2006.01) |
| *C07D 417/14* | (2006.01) |
| *C07D 409/10* | (2006.01) |
| *C07D 401/06* | (2006.01) |
| *C07D 417/06* | (2006.01) |
| *C07D 405/06* | (2006.01) |
| *C07D 405/04* | (2006.01) |

(52) U.S. Cl.
CPC ............ *C07D 235/18* (2013.01); *C07C 53/18* (2013.01); *C07D 401/04* (2013.01); *C07D 401/06* (2013.01); *C07D 401/14* (2013.01); *C07D 403/04* (2013.01); *C07D 405/04* (2013.01); *C07D 405/06* (2013.01); *C07D 405/14* (2013.01); *C07D 409/10* (2013.01); *C07D 409/14* (2013.01); *C07D 417/06* (2013.01); *C07D 417/14* (2013.01); *C07D 471/08* (2013.01)

(58) Field of Classification Search
CPC .. C07D 235/18; C07D 403/04; C07D 417/06; C07D 401/06; C07D 409/10; C07D 471/08; C07D 405/04; C07D 405/06; C07D 409/14; C07D 405/14; C07D 401/14; C07D 401/04; C07D 417/14; C07C 53/18

See application file for complete search history.

(56) References Cited

U.S. PATENT DOCUMENTS

| | | |
|---|---|---|
| RE33,833 E | 2/1992 | Janssens et al. |
| 5,216,003 A | 6/1993 | Vazquez |
| 7,786,128 B2 | 8/2010 | Bleicher et al. |
| 8,217,060 B2 | 7/2012 | Calvo et al. |
| 2008/0227811 A1 | 9/2008 | Chen |

FOREIGN PATENT DOCUMENTS

| | | |
|---|---|---|
| WO | WO 2002 / 083143 A1 | 10/2002 |
| WO | WO 03/088967 | 10/2003 |

OTHER PUBLICATIONS

Felder, C. C., et al., "Cannabinoid agonists stimulate both receptor- and non-receptor-mediated signal transdiction pathways in cells transfected with and expressing cannabinoid receptor clones", *Molecular Pharmacology*, 1992, pp. 838-845, vol. 42.

Reggio, P.H., "Toward the Design of Cannabinoid CB1 Receptor Inverse Agonists and Neutral Antagonists", *Drug Dev. Res.*, 2009, pp. 585-600, vol. 70.

Database PubChem [O] Aug. 8, 2005 (Aug. 8, 2005). XP055385694, Database accession No. 163148, (PubChem CID 163148, create date; Aug. 8, 2005 (Aug. 8, 2005), p. 3 compound).

International Search Report re: PCT/US2016/48130 dated Jan. 9, 2017.

*Primary Examiner* — Timothy Thomas
(74) *Attorney, Agent, or Firm* — Thomas J. Dodd

(57) ABSTRACT

The present invention is directed to benzimidazole derivatives, pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

14 Claims, No Drawings

BENZIMIDAZOLE DERIVATIVES USEFUL AS CB-1 INVERSE AGONISTS

CROSS REFERENCE TO RELATED APPLICATIONS

This application claims the benefit of U.S. Provisional Application 62/209,381, filed on Aug. 25, 2015, and U.S. Provisional Application 62/233,655, filed on Sep. 28, 2015 which is incorporated by reference herein in its entirety.

FIELD OF THE INVENTION

The present invention is directed to benzimidazole derivatives, pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated with serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/or skeletal muscle, to avoid these adverse effects.

Thus, there is a need for peripherally restricted cannabanoid-1 receptor (CB1R) inverse agonists for the treatment of, for example metabolic disorders, such as obesity, Type II diabetes mellitus, metabolic syndrome, Syndrome X, and the like.

SUMMARY OF THE INVENTION

The present invention is directed to compounds of formula (I)

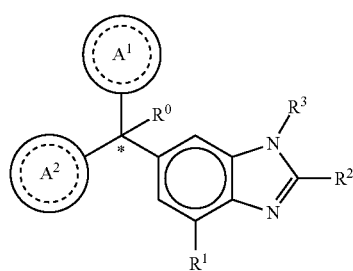
(I)

wherein $R^0$ is selected from the group consisting of hydrogen, —OH, —C(O)OH, —C(O)O—($C_{1-4}$alkyl), —$CH_2$—OH, —$CH_2$—O—($C_{1-2}$alkyl) and —$CH_2$—O—($C_{1-2}$alkyl)-$CO_2H$;

is selected from the group consisting of cyclopropyl, cyclobutyl, cyclopentyl, cyclohexyl, phenyl, furyl, thienyl, thiazolyl, benzothiazolyl and benzo[d][1,3]dioxolyl;

wherein the phenyl, furyl, thienyl, thiazolyl or benzothiazolyl is optionally substituted with one or more substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, —C(O)O—($C_{1-4}$alkyl), —C(O)$NR^AR^B$ and $NR^AR^B$; wherein $R^A$ and $R^B$ are each independently selected from the group consisting of hydrogen, alkyl and hydroxy substituted $C_{1-2}$alkyl; provided that each substituent is bound to a carbon atom;

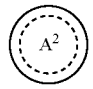

is selected from the group consisting of cyclopropyl, cyclobutyl, cyclopentyl, cyclohexyl, phenyl, furyl, thienyl, thiazolyl, benzothiazolyl and benzo[d][1,3]dioxolyl;

wherein the phenyl, furyl, thienyl, thiazolyl or benzothiazolyl is optionally substituted with one or more substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, —C(O)O—($C_{1-4}$alkyl), —C(O)$NR^CR^D$ and $NR^CR^D$; wherein $R^C$ and $R^D$ are each independently selected from the group consisting of hydrogen, alkyl and hydroxy substituted $C_{1-2}$alkyl; provided that each substituent is bound to a carbon atom;

$R^1$ is selected from the group consisting of hydrogen, hydroxy and $C_{1-4}$alkoxy;

$R^2$ is selected from the group consisting of hydrogen, halogen, $C_{1-4}$alkyl, fluorinated $C_{1-2}$alkyl, —($C_{1-2}$alkyl)-OH, —($C_{1-2}$alkyl)-C(O)OH, —($C_{1-2}$alkyl)-$NR^ER^F$, —($C_{2-4}$alkenyl)-OH, —C(O)OH, —C(O)O—($C_{1-2}$alkyl), —$NR^ER^F$, $C_{3-6}$cycloalkyl, phenyl, furyl, thienyl, pyridyl, azetidin-3-yl, oxetan-3-yl, tetrahydrofuran-2-yl and tetrahydropyran-4-yl; wherein the phenyl is optionally substituted with one to two halogen; wherein the azetidin-3-yl is optionally substituted with —C(O)O—($C_{1-4}$alkyl); and wherein $R^E$ and $R^F$ are each independently selected from the group consisting of hydrogen and $C_{1-4}$alkyl;

provided that when $R^2$ is selected from the group consisting of pyridyl, furyl and thienyl, then the $R^2$ is bound to the benzimidazole core through a carbon atom;

$R^3$ is selected from the group consisting of (a) through (k); wherein (a) is

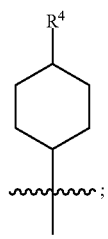

wherein $R^4$ is selected from the group consisting of hydrogen, —C(O)OH, —C(O)O—($C_{1-2}$alkyl), —C(O)NR$^G$R$^H$, —NH-(phenyl), and —NH—SO$_2$-(phenyl); wherein the phenyl is optionally substituted with one or more substituents independently selected from the group consisting of halogen, hydroxy and carboxy; and wherein R$^G$ and R$^H$ are each independently selected from the group consisting of hydrogen and $C_{1-4}$alkyl;

(b) is

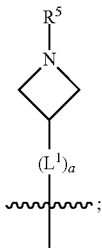

(c) is

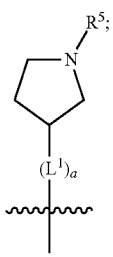

(d) is

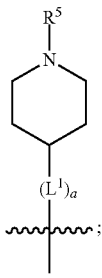

(e) is

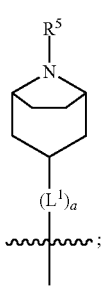

(f) is

wherein a is an integer from 0 to 1;

wherein $L^1$ is selected from the group consisting of —CH$_2$—, —CH$_2$—CH$_2$—, —CH$_2$CH$_2$CH$_2$—, —CH(CH$_3$)CH$_2$— and —CH$_2$—CH(CH$_3$)—;

wherein $R^5$ is selected from the group consisting of hydrogen, $C_{1-2}$alkyl, fluorinated $C_{1-2}$alkyl, $C_{2-4}$alkenyl, —($C_{1-2}$alkyl)-C(O)OH, —($C_{1-2}$alkyl)-C(O)O—($C_{1-2}$alkyl), —($C_{2-3}$alkyl)-O-(phenyl), —C(O)—($C_{1-2}$alkyl)-OH, —C(O)—($C_{1-2}$alkyl)-C(O)OH, —C(O)—($C_{1-2}$alkyl)-C(O)O—($C_{1-2}$alkyl), —C(O)—($C_{1-2}$alkyl)-C(O)—NH$_2$, —C(O)OH, —C(O)O—($C_{1-4}$alkyl), —C(O)O—($C_{3-5}$ cycloalkyl), —C(O)—NR$^J$R$^K$, —C(O)NH—($C_{3-5}$cycloalkyl), —C(O)NH-(phenyl), —C(O)NH—($C_{1-2}$alkyl)-(phenyl), —SO$_2$—($C_{1-2}$alkyl), —SO$_2$-(fluorinated $C_{1-2}$alkyl), —SO$_2$—($C_{1-2}$alkyl)-C(O)OH, —SO$_2$—($C_{1-2}$alkyl)-C(O)O—($C_{1-2}$alkyl), —SO$_2$—NR$^J$R$^K$, —SO$_2$—($C_{1-2}$alkyl)-C(O)NR$^J$R$^K$, phenyl, —($C_{1-3}$alkyl)-phenyl, —C(O)-(phenyl), —C(O)O-(phenyl), —C(O)O—($C_{1-2}$alkyl)-(phenyl), —SO$_2$-(phenyl), pyrimidin-2-yl, pyridyl, —($C_{1-2}$alkyl)-pyridyl, —C(O)-(pyridyl), —SO$_2$-(pyridyl), furyl, —($C_{1-2}$alkyl)-furyl, —C(O)-furyl, —SO$_2$-(furyl), thienyl, —($C_{1-2}$alkyl)-thienyl, —C(O)-thienyl, —SO$_2$-(thienyl), —C(O)-(1,2,3-triazol-4-yl), —C(O)-(1,2,4-triazol-3-yl) and —SO$_2$—($C_{1-2}$alkyl)-(piperazin-1-yl);

wherein the phenyl, pyrimidin-2-yl, pyridyl, furyl, thienyl or pyridyl, is optionally substituted with one or more substituents independently selected from the group consisting of halogen, hydroxy, $C_{1-4}$alkyl, fluorinated $C_{1-2}$alkyl, —($C_{1-2}$alkyl)-OH, —($C_{1-2}$alkyl)-C(O)OH, —($C_{1-2}$alkyl)-C(O)O—($C_{1-2}$alkyl), —C($_{1-2}$alkyl)-C(O)OH, —($C_{1-2}$alkyl)-C(O)O—($C_{1-2}$alkyl), —($C_{1-2}$alkyl)-C(O)—NR$^L$R$^M$, —O—($C_{1-4}$alkyl), —O-(fluorinated $C_{1-2}$alkyl), —O—($C_{2-6}$alkenyl), —O—($C_{1-2}$alkyl)-C(O)OH, —O—($C_{1-2}$alkyl)-C(O)O—($C_{1-2}$alkyl), —O—($C_{1-2}$alkyl)-C(O)NR$^L$R$^M$, —O—($C_{1-2}$alkyl)-C(O)—NR$^L$R$^M$, —C(O)OH, —C(O)O—($C_{1-4}$alkyl), —C(O)—NR$^L$R$^M$, —C(O)—NH—($C_{1-3}$alkyl)-OH, —C(O)—NH—($C_{1-2}$alkyl)-C(O)OH, —C(O)—NH—($C_{1-2}$alkyl)-C(O)O—($C_{1-2}$alkyl), —NR$^L$R$^M$ and —SO$_2$—NR$^L$R$^M$;

wherein R$^J$ and R$^K$ are each independently selected from the group consisting of hydrogen and $C_{1-4}$alkyl; and wherein R$^L$ and R$^M$ are each independently selected from the group consisting of hydrogen and $C_{1-4}$alkyl;

(g) is

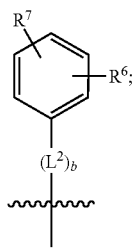

wherein b is an integer from 0 to 1;
wherein $L^2$ is selected from the group consisting of —$CH_2$—, —$CH_2CH_2$—, —$CH(CH_3)$—, —$CH(CH_3)$—$CH_2$—, —$CH_2$—$CH(CH_3)$—, —$CH_2CH_2$—O—, —$CH_2$—CH(OH)—, —$CH(CH_3)$—CH(OH) and —$CH_2CH_2CH_2$—NH—$SO_2$—;
wherein $R^6$ is selected from the group consisting of hydrogen, halogen, hydroxy, $C_{1-2}$alkyl, fluorinated $C_{1-2}$alkyl, $C_{1-2}$alkoxy, fluorinated $C_{1-2}$alkoxy, —C(O)OH, —C(O)O—($C_{1-2}$alkyl), —O—($C_{1-2}$alkyl)-O—($C_{1-2}$alkyl), —O—($C_{1-2}$alkyl)-C(O)OH, —O—($C_{1-2}$alkyl)-C(O)O—($C_{1-2}$alkyl), —C(O)—$NR^N R^P$, —O—($C_{1-2}$alkyl)-C(O)—$NR^N R^P$, phenyl, furyl and thienyl; wherein the phenyl, furyl or thienyl is optionally substituted with a substituent selected from the group consisting of halogen, $C_{1-4}$alkyl and carboxy; and wherein $R^N$ and $R^P$ are each independently selected from the group consisting of hydrogen and $C_{1-4}$alkyl;
wherein $R^7$ is selected from the group consisting of hydrogen, halogen, hydroxy, $C_{1-4}$alkyl, fluorinated $C_{1-2}$alkyl, $C_{1-4}$alkoxy, fluorinated $C_{1-2}$alkoxy, —C(O)OH and —C(O)O—($C_{1-4}$alkyl);
(h) is

wherein $L^3$ is selected from the group consisting of —$CH_2$—, —$CH_2CH_2$—, —$CH_2CH_2CH_2$—, —$CH(CH_3)CH_2$—, —$CH_2CH(CH_3)$— and —$CH_2CH_2$—O—;
wherein $R^8$ is selected from the group consisting of hydrogen, halogen, $C_{1-4}$alkyl, $C_{1-4}$alkoxy, —C(O)OH and —C(O)O—($C_{1-4}$alkyl);
(i) is

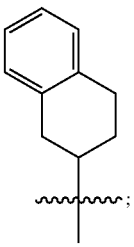

wherein c is an integer from 0 to 1;
and wherein $L^4$ is selected from the group consisting of —$CH_2$— and —$CH_2$—$CH_2$—;
(j) is

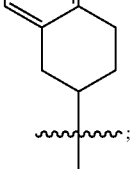

and (k) is

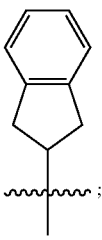

and stereoisomers, tautomers and pharmaceutically acceptable salts thereof.
The present invention is further directed to a compound of formula (II)

(II)

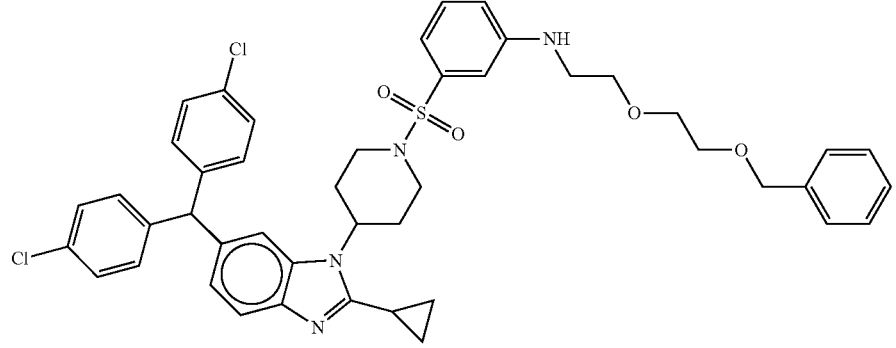

and stereoisomers, tautomers and pharmaceutically acceptable salts thereof.

The present invention is further directed to processes for the preparation of the compounds of formula (I) and the compound of formula (II). The present invention is further directed to a product prepared according to any of the process(es) described herein.

The present invention is further directed to intermediate compounds useful in the synthesis of the compounds of formula (I) and the compound of formula (II), as described and defined in the synthesis schemes and examples which follow herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) or compound of formula (II) for use in the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain). In another embodiment, the present invention is directed to a composition comprising a compound of formula (I) or compound of formula (II) for the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain).

Another example of the invention is the use of any of the compounds described herein in the preparation of a medicament for treating: (a) obesity, (b) Type I diabetes, (c) Type II diabetes, (d) gestational diabetes, (e) latent autoimmune diabetes of adults (LADA), (f) pre-diabetes, (g) insulin resistance, (h) inadequate glucose tolerance, (i) dyslipidemia (including, but not limited to elevated triglycerides and LDL, and low HDL), (j) nonalcoholic steatohepatitis (NASH), (k) cirrhosis, (l) fatty liver disease, (m) atherosclerosis, (n) hypertension, (o) inflammatory bowel disease, (p) Alzheimer's disease, (q) osteoporosis, (r) multiple sclerosis, (s) traumatic brain injury, (t) arthritis, or (u) neuropathic pain, in a subject in need thereof. In another example, the present invention is directed to a compound as described herein for use in method for treating a disorder selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain, in a subject in need thereof.

In additional embodiments the present invention is as described herein.

DETAILED DESCRIPTION OF THE INVENTION

The present invention is directed to compounds of formula (I)

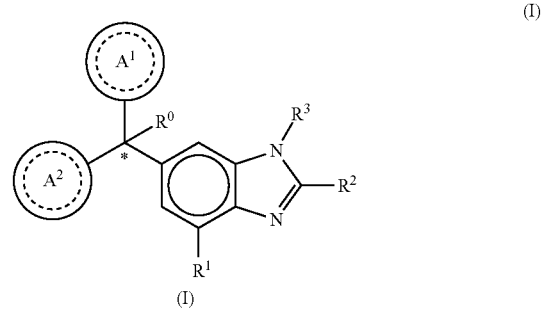

wherein

$R^0$, $R^1$, $R^2$ and $R^3$ are as herein defined; and stereoisomers, tautomers and pharmaceutically acceptable salts thereof. The present invention is further directed to a compound of formula (II)

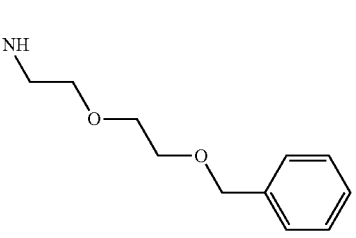
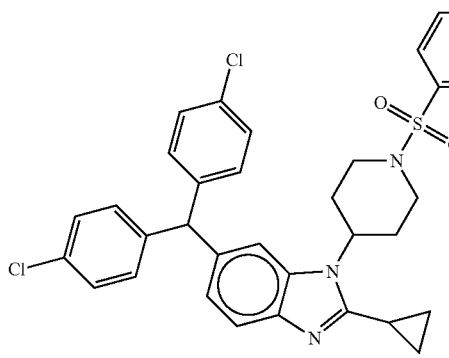

(also known as N-(2-(2-(benzyloxy)ethoxy)ethyl)-3-((4-(6-(bis(4-chlorophenyl)methyl)-2-cyclopropyl-1H-benzo[d]imidazol-1-yl)piperidin-1-yl)sulfonyl)aniline) and stereoisomers, tautomers and pharmaceutically acceptable salts thereof.

The compounds of formula (I) and the compound of formula (II) of the present invention are CB-1 receptor inverse agonists, useful in the treatment of metabolic disorders, including but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

In an embodiment, the present invention is directed to compounds of formula (I) wherein $R^0$ is selected from the group consisting of hydrogen, —OH, —C(O)OH, —C(O)O—($C_{1-2}$alkyl), —CH$_2$—OH, —CH$_2$—O—($C_{1-2}$alkyl) and —CH$_2$—O—($C_{1-2}$alkyl)-CO$_2$H. In another embodiment, the present invention is directed to compounds of formula (I) wherein $R^0$ is selected from the group consisting of hydrogen, —OH, —C(O)OH, —C(O)O—($C_{1-2}$alkyl), —CH$_2$—OH, —CH$_2$—O—($C_{1-2}$alkyl) and —CH$_2$—O—($C_{1-2}$alkyl)-CO$_2$H. In another embodiment, the present invention is directed to compounds of formula (I) wherein $R^0$ is selected from the group consisting of hydrogen, —OH, —C(O)OH, —C(O)OCH$_3$, —CH$_2$—OH, —CH$_2$—OCH$_3$ and —CH$_2$—OCH$_2$—CO$_2$H. In another embodiment, the present invention is directed to compound of formula (I) wherein $R^0$ is selected from the group consisting of hydrogen and —OH. In another embodiment, the present invention is directed to compound of formula (I) wherein $R^0$ is selected from the group consisting of hydrogen, —C(O)OH and —C(O)OCH$_3$. In another embodiment, the present invention is directed to compound of formula (I) wherein $R^0$ is selected from the group consisting of hydrogen, —OH, —CH$_2$OH and —CH$_2$—OCH$_3$. In another embodiment, the present invention is directed to compound of formula (I) wherein $R^0$ is hydrogen.

In an embodiment, the present invention is directed to compounds of formula (I) wherein $R^0$ is selected from the group consisting of hydrogen, —OH, —CO$_2$H, —C(O)OCH$_3$ and —CH$_2$OCH$_3$. In another embodiment, the present invention is directed to compounds of formula (I) wherein $R^0$ is selected from the group consisting of hydrogen, —OH, —CO$_2$H and —C(O)OCH$_3$. In another embodiment, the present invention is directed to compounds of formula (I) wherein $R^0$ is selected from the group consisting of hydrogen, —OH and —CO$_2$H. In another embodiment, the present invention is directed to compounds of formula (I) wherein $R^0$ is selected from the group consisting of hydrogen and —OH.

In an embodiment, the present invention is directed to compounds of formula (I) wherein

is selected from the group consisting of phenyl, thiazolyl and benzo[d][1,3]dioxolyl; wherein the phenyl or thiazolyl is optionally substituted with one to two substituents independently selected from the group consisting of halogen $C_{1-4}$alkyl, fluorinated $C_{1-2}$alkyl, $C_{1-2}$alkoxy, fluorinated $C_{1-2}$alkoxy, —C(O)OH and —C(O)O—($C_{1-4}$alkyl). In another embodiment, the present invention is directed to compounds of formula (I) wherein

is phenyl; wherein the phenyl is optionally substituted a substituent independently selected from the group consisting of halogen and $C_{1-2}$alkoxy.

In another embodiment, the present invention is directed to compounds of formula (I) wherein

is selected from the group consisting of phenyl, 2-chlorophenyl, 4-chlorophenyl and 4-methoxyphenyl. In another embodiment, the present invention is directed to compounds of formula (I) wherein

is selected from the group consisting of 4-chlorophenyl and 4-methoxyphenyl.

In an embodiment, the present invention is directed to compounds of formula (I) wherein

is selected from the group consisting of 4-chlorophenyl, 4-fluorophenyl, 4-methylphenyl and 4-methoxyphenyl. In another embodiment, the present invention is directed to compounds of formula (I) wherein

is selected from the group consisting of 4-chlorophenyl, 4-fluorophenyl and 4-methylphenyl. In another embodiment, the present invention is directed to compounds of formula (I) wherein

is 4-chlorophenyl.

In an embodiment, the present invention is directed to compounds of formula (I) wherein

is selected from the group consisting of phenyl, thiazolyl and benzo[d][1,3]dioxolyl; wherein the phenyl or thiazolyl is optionally substituted with one to two substituents independently selected from the group consisting of halogen $C_{1-4}$alkyl, fluorinated $C_{1-2}$alkyl, $C_{1-2}$alkoxy, fluorinated $C_{1-2}$alkoxy, —C(O)OH and —C(O)O—($C_{1-4}$alkyl). In another embodiment, the present invention is directed to compounds of formula (I) wherein

is selected from the group consisting of phenyl, thiazol-2-yl and benzo[d][1,3]dioxol-5-yl; wherein the phenyl or thiazol-2-yl is optionally substituted with a substituent selected from the group consisting of halogen, $C_{1-4}$alkyl, fluorinated $C_{1-2}$alkyl, $C_{1-2}$alkoxy and —C(O)OH.

In another embodiment, the present invention is directed to compounds of formula (I) wherein

is selected from the group consisting of phenyl, 4-chlorophenyl, 4-fluorophenyl, 4-methylphenyl, 4-trifluoromethylphenyl, 4-carboxyphenyl, 4-methoxyphenyl, thiazol-2-yl, 4-ethyl-thiazol-2-yl, 5-ethyl-thiazol-2-yl, 4-t-butyl-thiazol-2-yl, 4-trifluoromethyl-thiazol-2-yl and benzo[d][1,3]dioxol-5-yl. In another embodiment, the present invention is directed to compounds of formula (I) wherein

is selected from the group consisting of 4-chlorophenyl, 4-methoxyphenyl and thiazol-2-yl.

In an embodiment, the present invention is directed to compounds of formula (I) wherein

is selected from the group consisting of phenyl, 4-chlorophenyl, 4-fluorphenyl, 4-methylphenyl, 4-trifluoromethylphenyl, 4-methoxyphenyl, 4-carboxyphenyl, thiazol-2-yl and benzo[d][1.3]dioxol-5-yl. In another embodiment, the present invention is directed to compounds of formula (I) wherein

is selected from the group consisting of phenyl, 4-chlorophenyl, 4-fluorphenyl, 4-methylphenyl, 4-trifluoromethylphenyl, thiazol-2-yl and benzo[d][1.3]dioxol-5-yl. In another embodiment, the present invention is directed to compounds of formula (I) wherein

is selected from the group consisting of 4-chlorophenyl, thiazol-2-yl and benzo[d][1.3]dioxol-5-yl. In another embodiment, the present invention is directed to compounds of formula (I) wherein

is 4-chlorophenyl.

In an embodiment, the present invention is directed to compounds of formula (I) wherein $R^1$ is selected from the group consisting of hydrogen, hydroxy and $C_{1-2}$alkoxy. In another embodiment, the present invention is directed to compounds of formula (I) wherein $R^1$ is selected from the group consisting of hydrogen, hydroxy and methoxy. In another embodiment, the present invention is directed to compounds of formula (I) wherein $R^1$ is selected from the group consisting of hydroxy and methoxy. In another embodiment, the present invention is directed to compounds of formula (I) wherein $R^1$ is selected from the group consisting of hydrogen and methoxy. In another embodiment, the present invention is directed to compounds of formula (I) wherein $R^1$ is hydrogen.

In an embodiment, the present invention is directed to compounds of formula (I) wherein $R^2$ is selected from the group consisting of hydrogen, halogen, $C_{1-4}$alkyl, fluorinated $C_{1-2}$alkyl, —$(C_{1-2}$alkyl)-OH, —$(C_{1-2}$alkyl)-C(O)OH, —$(C_{1-2}$alkyl)-NH$_2$, —$(C_{2-4}$alkenyl)-OH, —C(O)O—$(C_{1-2}$ alkyl), —NR$^E$R$^F$, $C_{3-6}$cycloalkyl, phenyl, furyl, thienyl, pyridyl, oxetan-3-yl, azetidin-3-yl, tetrahydrofuran-2-yl and tetrahydropyran-4-yl; wherein the phenyl is optionally substituted with one to two halogen; wherein the azetidin-3-yl is optionally substituted with —C(O)O—$(C_{1-4}$alkyl); and wherein R$^E$ and R$^F$ are each independently selected from the group consisting of hydrogen and $C_{1-4}$alkyl; provided that when $R^2$ is selected from the group consisting of pyridyl, furyl and thienyl, then the $R^2$ is bound to the benzimidazole core through a carbon atom. In another embodiment, the present invention is directed to compounds of formula (I) wherein $R^2$ is selected from the group consisting of hydrogen, halogen, $C_{1-4}$alkyl, fluorinated $C_{1-2}$alkyl, —$(C_{1-2}$alkyl)-OH, —$(C_{1-2}$alkyl)-C(O)OH, —$(C_{1-2}$alkyl)-NH$_2$, —$(C_{2-4}$alkenyl)-OH, —C(O)O—$(C_{1-2}$alkyl), —NR$^E$R$^F$, $C_{3-6}$cycloalkyl, phenyl, fur-2-yl, fur-3-yl, thien-3-yl, pyrid-2-yl, pyrid-3-yl, pyrid-4-yl, oxetan-3-yl, azetidin-3-yl, tetrahydrofuran-2-yl and tetrahydro-pyran-4-yl; wherein the phenyl is optionally substituted with one to two halogen; wherein the azetidin-3-yl is optionally substituted with —C(O)O—$(C_{1-4}$alkyl); and wherein R$^E$ and R$^F$ are each independently selected from the group consisting of hydrogen, methyl and ethyl.

In another embodiment, the present invention is directed to compounds of formula (I) wherein $R^2$ is selected from the group consisting of hydrogen, chloro, methyl, ethyl, n-propyl, isopropyl, isobutyl, t-butyl, —CHF$_2$, —CF$_3$, —CH$_2$—CF$_3$, —CH$_2$OH, —CH$_2$CH$_2$—C(O)OH, —CH$_2$CH$_2$—NH$_2$, —C(=CH$_2$)—CH$_2$OH, —C(O)OCH$_3$, —C(O)OCH$_2$CH$_3$, —NH$_2$, —N(CH$_3$)$_2$, cyclopropyl, cyclobutyl, cyclopentyl, oxetan-3-yl, azetidin-3-yl, 1-(t-butoxycarbonyl)-azetidin-3-yl, tetrahydrofuran-2-yl, tetrahydro-pyran-4-yl, 4-chlorophenyl, 2,4-dichlorophenyl, pyrid-2-yl, pyrid-3-yl, pyrid-4-yl, fur-2-yl, fur-3-yl and thien-3-yl. In another embodiment, the present invention is directed to compounds of formula (I) wherein $R^2$ is selected from the group consisting of ethyl, cyclopropyl and cyclobutyl. In another embodiment, the present invention is directed to compounds of formula (I) wherein $R^2$ is selected from the group consisting of ethyl and cyclopropyl. In another embodiment, the present invention is directed to compounds of formula (I) wherein $R^2$ is cyclopropyl.

In an embodiment, the present invention is directed to compounds of formula (I) wherein $R^2$ is selected from the group consisting of hydrogen, methyl, ethyl, cyclopropyl, cyclobutyl, amino-ethyl-, —C=(CH$_2$)—CH$_2$OH, oxetan-3-yl, tetrahydrofur-2-yl and pyrid-3-yl. In another embodiment, the present invention is directed to compounds of formula (I) wherein $R^2$ is selected from the group consisting of hydrogen, methyl, ethyl, cyclopropyl, cyclobutyl, oxetan-3-yl and tetrahydrofur-2-yl. In another embodiment, the present invention is directed to compounds of formula (I) wherein $R^2$ is selected from the group consisting of ethyl, cyclopropyl, cyclobutyl, oxetan-3-yl and tetrahydrofur-2-yl. In another embodiment, the present invention is directed to compounds of formula (I) wherein $R^2$ is selected from the group consisting of cyclopropyl, cyclobutyl and tetrahydrofur-2-yl.

In an embodiment, the present invention is directed to compounds of formula (I) wherein $R^3$ is selected from the group consisting of (a) through (k); wherein (a) is

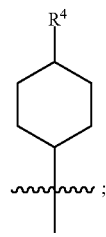

wherein $R^4$ is selected from the group consisting of hydrogen, —C(O)OH, —C(O)O—$(C_{1-2}$alkyl), —C(O)NR$^G$R$^H$, —NH-(phenyl), and —NH—SO$_2$-(phenyl); wherein the phenyl is optionally substituted with hydroxy or carboxy; and wherein R$^G$ and R$^H$ are each independently selected from the group consisting of hydrogen and methyl;

(b) is

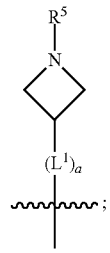

(c) is

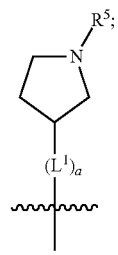

(d) is

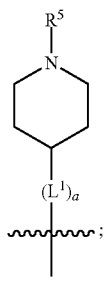

(e) is

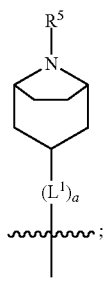

(f) is

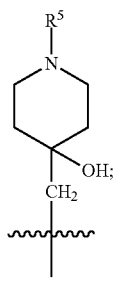

wherein a is an integer from 0 to 1; wherein $L^1$ is selected from the group consisting of —CH$_2$—, —CH$_2$—CH$_2$, —CH(CH$_3$)CH$_2$— and —CH$_2$—CH(CH$_3$)—; wherein $R^5$ is selected from the group consisting of hydrogen, C$_{1-2}$alkyl, fluorinated C$_{1-2}$alkyl, C$_{2-4}$alkenyl, —(C$_{1-2}$alkyl)-C(O)OH, —(C$_{1-2}$alkyl)-C(O)O—(C$_{1-2}$alkyl), —(C$_2$alkyl)-O-(phenyl), —C(O)—(C$_{1-2}$alkyl)-OH, —C(O)—(C$_{1-2}$alkyl)-C(O)OH, —C(O)—(C$_{1-2}$alkyl)-C(O)O—(C$_{1-2}$alkyl), —C(O)—(C$_{1-2}$alkyl)-C(O)—NH$_2$, —C(O)O—(C$_{1-4}$alkyl), —C(O)O—(C$_{3-5}$cycloalkyl), —C(O)O-(phenyl), —C(O)O—CH$_2$-(phenyl), —C(O)—NH$_2$, —C(O)NH—(C$_{1-2}$alkyl), —C(O)NH—(C$_{3-5}$cycloalkyl), —C(O)NH-(phenyl), —C(O)NH—(C$_{1-2}$alkyl)-(phenyl), —SO$_2$—(C$_{1-2}$alkyl), —SO$_2$-(fluorinated C$_{1-2}$alkyl), —SO$_2$—(C$_{1-2}$alkyl)-C(O)OH, —SO$_2$—(C$_{1-2}$alkyl)-C(O)O—(C$_{1-2}$alkyl), —SO$_2$—NH$_2$, —SO$_2$—NH—(C$_{1-2}$alkyl), —SO$_2$—(C$_{1-2}$alkyl)-C(O)NH$_2$, phenyl, —(C$_{1-3}$alkyl)-phenyl, —C(O)-(phenyl), —C(O)O-(phenyl), —C(O)O—(C$_{1-2}$alkyl)-(phenyl), —SO$_2$-(phenyl), pyrimidin-2-yl, pyrid-2-yl, pyrid-3-yl, —(C$_{1-2}$alkyl)-pyrid-2-yl, —(C$_{1-2}$alkyl)-pyrid-3-yl, —(C$_{1-2}$alkyl)-fur-2-yl, —(C$_{1-2}$alkyl)-thien-2-yl, —C(O)-fur-2-yl, —C(O)-thien-2-yl, —C(O)-(pyrid-3-yl), —C(O)-(1,2,3-triazol-4-yl), —C(O)-(1,2,4-triazol-3-yl), —SO$_2$—(C$_{1-2}$alkyl)-(piper-azin-1-yl), —SO$_2$-(fury-2-yl), —SO$_2$-(thien-2-yl) and —SO$_2$-(pyrid-3-yl); wherein the phenyl, pyrimidin-2-yl, pyridyl, furyl, thienyl or pyridyl, is optionally substituted with one to three substituents independently selected from the group consisting of halogen, hydroxy, C$_{1-2}$alkyl, fluorinated C$_{1-2}$alkyl, —(C$_{1-2}$alkyl)-OH, —C$_{(1-2}$alkyl)-C(O)OH, —(C$_{1-2}$alkyl)-C(O)O—(C$_{1-2}$alkyl), —O—(C$_{1-2}$alkyl), —O-(fluorinated C$_{1-2}$alkyl), —O—(C$_{2-6}$alkenyl), —O—(C$_{1-2}$alkyl)-C(O)OH, —O—(C$_{1-2}$alkyl)-C(O)NH$_2$, —C(O)OH, —C(O)O—(C$_{1-4}$alkyl), —C(O)—NH$_2$, —C(O)—NH—(C$_{1-2}$alkyl), —C(O)—NH—(C$_{1-3}$alkyl)-OH, —C(O)—NH—(C$_{1-2}$alkyl)-C(O)OH, —C(O)—NH—(C$_{1-2}$alkyl)-C(O)O—(C$_{1-2}$alkyl), —(C$_{1-2}$alkyl)-C(O)—NH$_2$, —O—(C$_{1-2}$alkyl)-C(O)—NH$_2$, —O—(C$_{1-2}$alkyl)-C(O)OH, —NH$_2$, —NH(C$_{1-2}$alkyl), —SO$_2$—NH$_2$ and —SO$_2$—NH(C$_{1-2}$alkyl);

(g) is

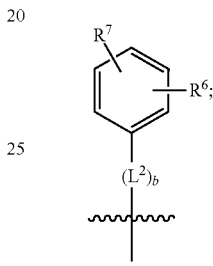

wherein b is an integer from 0 to 1; wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and —CH$_2$CH$_2$CH$_2$—NH—SO$_2$—; wherein $R^6$ is selected from the group consisting of hydrogen, halogen, hydroxy, C$_{1-2}$alkyl, fluorinated C$_{1-2}$alkyl, C$_{1-2}$alkoxy, fluorinated C$_{1-2}$alkoxy, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl, furyl and thienyl; wherein the phenyl, furyl or thienyl is optionally substituted with carboxy; and wherein $R^7$ is selected from the group consisting of hydrogen, hydroxy, C$_{1-2}$alkyl, fluorinated C$_{1-2}$alkyl, C$_{1-2}$alkoxy, fluorinated C$_{1-2}$alkoxy, —C(O)OH and —C(O)O—(C$_{1-4}$alkyl);

(h) is

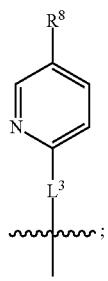

wherein $L^3$ is selected from the group consisting of —CH$_2$—, —CH$_2$CH$_2$— and —CH$_2$CH$_2$—O—; and wherein $R^8$ is selected from the group consisting of hydrogen, -halogen, C$_{1-2}$alkyl, C$_{1-2}$alkoxy, —C(O)OH and —C(O)O—(C$_{1-4}$alkyl);

(i) is

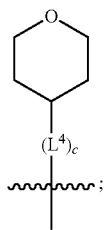

wherein c is an integer from 0 to 1; and wherein $L^4$ is selected from the group consisting of —CH$_2$— and —CH$_2$—CH$_2$—;

(j) is

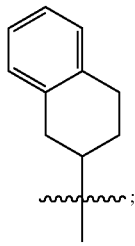

and (k) is

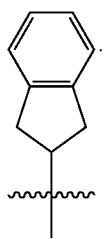

In another embodiment, the present invention is directed to compounds of formula (I) wherein $R^3$ is selected from the group consisting of (a) through (k); wherein (a) is

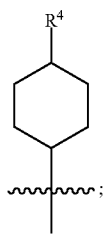

wherein $R^4$ is selected from the group consisting of hydrogen, —C(O)OH, —C(O)NR$^G$R$^H$, —NH-(phenyl) and —NH—SO$_2$-(phenyl); wherein the phenyl is optionally substituted with hydroxy or carboxy; wherein $R^G$ and $R^H$ are each independently selected from the group consisting of hydrogen and methyl;

(b) is

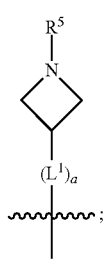

(c) is

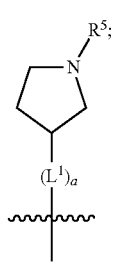

(d) is

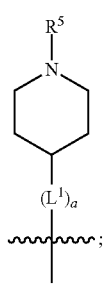

(e) is

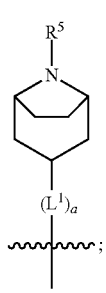

(f) is

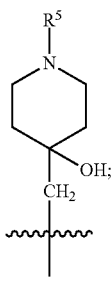

wherein a is an integer from 0 to 1; and wherein $L^1$ is selected from the group consisting of —CH$_2$— and —CH$_2$—CH(CH$_3$)—; wherein $R^5$ is selected from the group consisting of hydrogen, C$_{2-4}$alkenyl, —(C$_{1-2}$alkyl)-C(O)OH, —(C$_{1-2}$alkyl)-C(O)O—(C$_{1-2}$alkyl), —(C$_2$alkyl)-O-(phenyl), —C(O)—(C$_{1-2}$alkyl)-OH, —C(O)—(C$_{1-2}$alkyl)-C(O)OH, —C(O)—(C$_{1-2}$alkyl)-C(O)—NH$_2$, —C(O)O—(C$_{1-4}$ alkyl), —C(O)O-(hydroxy substituted C$_{1-4}$alkyl), —C(O)O—(C$_{3-5}$cycloalkyl), —C(O)NH—(C$_{1-2}$alkyl), —C(O)NH—(C$_{3-5}$cycloalkyl), —C(O)NH-(phenyl), —C(O)NH—(C$_{1-2}$alkyl)-(phenyl), —SO$_2$—(C$_{1-2}$alkyl), —SO$_2$-(fluorinated C$_{1-2}$alkyl), —SO$_2$—(C$_{1-2}$alkyl)-C(O)OH, —SO$_2$—NH$_2$, —SO$_2$—NH—(C$_{1-2}$alkyl), —SO$_2$—(C$_{1-2}$ alkyl)-C(O)NH$_2$, phenyl, —(C$_{1-3}$alkyl)-phenyl, —C(O)-(phenyl), —C(O)O-(phenyl), —C(O)O—(C$_{1-2}$ alkyl)-(phenyl), —SO$_2$-(phenyl), pyrimidin-2-yl, —(C$_{1-2}$ alkyl)-pyrid-2-yl, —(C$_{1-2}$alkyl)-pyrid-3-yl, —(C$_{1-2}$alkyl)-fur-2-yl, —(C$_{1-2}$alkyl)-thien-2-yl, —C(O)-(pyrid-3-yl), —C(O)-(1,2,3-triazol-4-yl), —C(O)-(1,2,4-triazol-3-yl), —SO$_2$—(C$_{1-2}$ alkyl)-(piperazin-1-yl), —SO$_2$-(fury-2-yl), —SO$_2$-(thien-2-yl) and —SO$_2$-(pyrid-3-yl); wherein the phenyl is optionally substituted with one to three substituents independently selected from the group consisting of halogen, hydroxy, C$_{1-2}$alkyl, fluorinated C$_{1-2}$alkyl, —O—(C$_{1-2}$alkyl), —O-(fluorinated C$_{1-2}$alkyl), —O—(C$_{2-6}$alkenyl), —O—(C$_{1-2}$alkyl)-C(O)OH, —O—(C$_{1-2}$alkyl)-C(O)NH$_2$, —C(O)OH, —C(O)O—(C$_{1-2}$alkyl), —C$_{(1-2}$ alkyl)-C(O)OH, —C(O)—NH$_2$, —C(O)—NH—(C$_{1-2}$alkyl), —C(O)—NH—(C$_{1-3}$alkyl)-OH, —C(O)—NH—(C$_{1-2}$alkyl)-C(O)OH, —C(O)—NH—(C$_{1-2}$alkyl)-C(O)O—(C$_{1-2}$ alkyl), —(C$_{1-2}$ alkyl)-C(O)—NH$_2$, —O—(C$_{1-2}$alkyl)-C(O)—NH$_2$, —O—(C$_{1-2}$alkyl)-C(O)OH, —NH$_2$ and —SO$_2$—NH$_2$; and wherein the pyrimidin-2-yl, pyrid-2-yl, pyrid-3-yl, fur-2-yl or thien-2-yl is optionally substituted with one to two substituents independently selected from the group consisting of C$_{1-2}$alkyl, —(C$_{1-2}$alkyl)-OH, —C(O)OH, —C(O)O—(C$_{1-2}$alkyl), —C(O)—NH$_2$, —C(O)NH—(C$_{1-2}$alkyl)-OH, —C(O)NH—(C$_{1-2}$alkyl)-C(O)OH and —C(O)NH—(C$_{1-2}$ alkyl)-C(O)O—(C$_{1-2}$alkyl);

(g) is

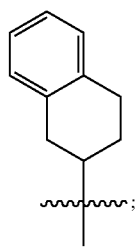

wherein b is an integer from 0 to 1; and wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and —CH$_2$CH$_2$CH$_2$—NH—SO$_2$—; wherein $R^6$ is selected from the group consisting of hydrogen, halogen, hydroxy, C$_{1-2}$alkoxy, fluorinated C$_{1-2}$alkyl, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl and thienyl; wherein the phenyl or thienyl is optionally substituted with carboxy; and wherein $R^7$ is selected from the group consisting of hydrogen and fluorinated C$_{1-2}$alkyl;

(h) is

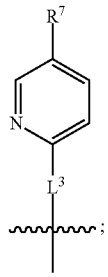

wherein $L^3$ is selected from the group consisting of —CH$_2$— and —CH$_2$CH$_2$—O—; and wherein $R^8$ is selected from the group consisting of hydrogen, —C(O)OH and —C(O)O—(C$_{1-2}$alkyl);

(i) is

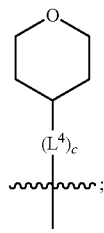

wherein c is an integer from 0 to 1; wherein $L^4$ is —CH$_2$—;

(j) is

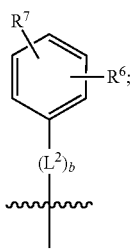

and (k) is

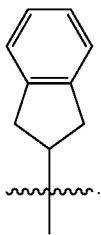 [SMILES: *C1Cc2ccccc2C1]

In another embodiment, the present invention is directed to compounds of formula (I) wherein $R^3$ is selected from the group consisting of (a) through (k); wherein (a) is

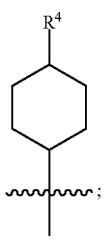

wherein $R^4$ is selected from the group consisting of hydrogen, —C(O)OH, —C(O)NH$_2$, —NH—SO$_2$-(3-carboxyphenyl), —NH-(3-hydroxyphenyl), —NH-(3-carboxyphenyl), —NH-(4-carboxyphenyl) and —NH—SO$_2$-(4-carboxyphenyl); and wherein the cyclohexyl is bound to the benzimidazole core in a cis-, trans- or racemic stereo-orientation;

(b) is

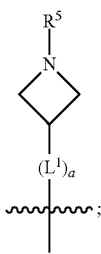

wherein a 0; and wherein $R^5$ is selected from the group consisting of 3-carboxybenzyl-, 4-carboxyphenyl-sulfonyl- and 5-carboxyfur-2-yl-sulfonyl-;

(c) is

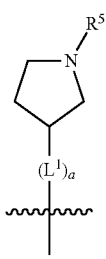

wherein a is 0; and wherein $R^5$ is selected from the group consisting of 3-carboxybenzyl-, 4-carboxyphenyl-sulfonyl- and 5-carboxy-fur-2-yl-sulfonyl-;

(d) is

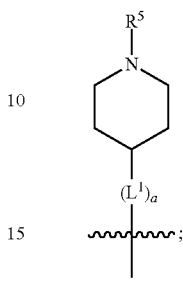

wherein a is an integer from 0 to 1; $L^1$ is selected from the group consisting of —CH$_2$— and —CH$_2$—CH(R*—CH$_3$)—; and wherein $R^5$ is selected from the group consisting of hydrogen, propyn-3-yl, carboxy-methyl-, methoxycarbonyl-methyl-, 3-carboxyphenyl-oxy-ethyl-, 2-hydroxyethyl-carbonyl-, hydroxymethyl-carbonyl-, 2-carboxy-ethyl-carbonyl-, aminocarbonyl-methyl-carbonyl-, 2-(aminocarbonyl)-ethyl-carbonyl-, ethoxycarbonyl-, t-butoxycarbonyl-, cyclopentyloxy-carbonyl-, 2,3,4-trihydroxy-n-butyloxy-carbonyl-, 3-carboxyphenyl, 4-carboxyphenyl, 3-(carboxy-methyl)-phenyl, 4-(carboxy-methyl)-phenyl, 3-(methoxycarbonyl)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-(carboxy-methoxy)-phenyl, 4-(carboxy-methoxy)-phenyl, 3-hydroxy-benzyl, 3-(hex-2-en-1-yloxy)-benzyl, 2-trifluoromethyl-benzyl, 3-carboxy-benzyl, 4-carboxy-benzyl, 3-(methoxycarbonyl)-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-hydroxy-5-carboxy-benzyl, 2-fluoro-3-carboxy-benzyl, 2-fluoro-5-carboxy-benzyl, 2-chloro-3-carboxy-benzyl, 2-chloro-5-carboxy-benzyl, 2-trifluoromethyl-5-carboxy-benzyl, 3-fluoro-5-carboxy-benzyl, 3-carboxy-4-fluoro-benzyl, 3-carboxy-4-hydroxy-benzyl, 3-trifluoromethyl-5-carboxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 4-carboxy-pyrimidin-2-yl, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-amino-carbonyl-, 4-carboxy-phenyl-carbonyl-, 4-aminocarbonyl-phenyl-carbonyl-, 3-aminosulfonyl-phenyl-carbonyl-, 4-aminosulfonyl-phenyl-carbonyl-, 6-carboxy-pyrid-3-yl-carbonyl-, 6-aminocarbonyl-pyrid-3-yl-carbonyl-, 1,2,3-triazol-4-yl-carbonyl-, 1,2,4-triazol-3-yl-carbonyl-, methylsulfonyl-, trifluoromethyl-sulfonyl-, carboxymethylsulfonyl-, carboxyethyl-sulfonyl-, amino-sulfonyl-, aminoethyl-sulfonyl-, aminocarbonyl-methyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 2-carboxyphenyl-sulfonyl-, 3-carboxyphenyl-sulfonyl-, 4-carboxyphenyl-sulfonyl-, 4-carboxy-methoxy-phenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(carboxy-ethyl-amino-carbonyl)-phenyl-sulfonyl-, 3-(3-hydroxy-n-propyl-amino-carbonyl)-phenyl-sulfonyl-, 3-(2-(methoxy-carbonyl)-ethyl-amino-carbonyl)-phenyl-sulfonyl-, 3-(2-hydroxyethyl-amino-carbonyl)-phenyl-sulfonyl-, 3-fluoro-4-hydroxy-phenyl-sulfonyl-, 3-fluoro-4-methoxy-phenyl-sulfonyl-, 3-fluoro-4-aminocarbonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl-, 3-methyl-4-aminocarbonyl-phenyl-sulfonyl-, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl, 3-methoxy-4-carboxy-phenyl-sulfonyl, 3-methoxy-4-aminocarbonyl-phenyl-sulfonyl-, 3-carboxy-4-chloro-phenyl-sulfonyl-, 3-carboxy-4-fluoro-phenyl-sulfonyl-, 3-carboxy-4-methyl-phenyl-sulfonyl-, 3-carboxy-4-methoxy-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, piperazin-1-yl-ethyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-;

(e) is

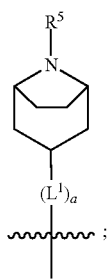

wherein a is 0; and wherein $R^5$ is selected from the group consisting of ethoxycarbonyl- and trifluoromethyl-sulfonyl-;

(f) is

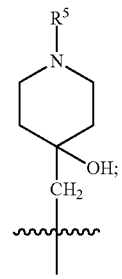

wherein $R^5$ is trifluoromethyl-sulfonyl-;

(g) is

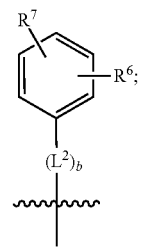

wherein b is an integer from 0 to 1; wherein $L^2$ is selected from the group consisting of —$CH_2$—, —$CH_2CH_2$—, —$CH(CH_3)$—, —$CH(CH_3)$—$CH_2$—, —$CH_2$—CH($CH_3$)—, —$CH_2$—CH($R^*$—$CH_3$)—, —$CH_2$—CH($S^*$—$CH_3$)—, —$CH_2CH_2$—O—, —$CH_2$—CH(OH)—, —$CH_2$—CH($R^*$—OH), —CH($CH_3$)—CH(OH) and —$CH_2CH_2$—NH—$SO_2$—; wherein $R^6$ is selected from the group consisting of hydrogen, 3-bromo, 3-chloro, 4-chloro, 3-hydroxy, 4-hydroxy, 3-methoxy, 4-methoxy, 4-trifluoromethyl, 3-carboxy, 4-carboxy, 3-carboxy-methoxy-, 4-carboxy-methoxy-3-methoxycarbonyl-, 4-methoxycarbonyl-, 3-ethoxy-carbonyl-methoxy-, 4-ethoxycarbonyl-methoxy-, 4-aminocarbonyl-, 3-aminocarbonyl-methoxy-, 4-amino-carbonyl-methoxy-, 3-(3-carboxyphenyl), 3-(4-carboxy-phenyl), 4-(3-carboxyphenyl), 4-(4-carboxyphenyl) and 3-(5-carboxy-thien-2-yl); and wherein $R^7$ is selected from the group consisting of hydrogen and 5-trifluoromethyl;

(h) is

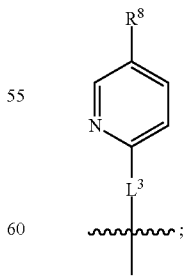

wherein $L^3$ is selected from the group consisting of —$CH_2$— and —$CH_2CH_2$—O—; and wherein $R^8$ is selected from the group consisting of hydrogen, carboxy and methoxycarbonyl-;

(i) is

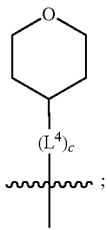

wherein c is an integer from 0 to 1; wherein $L^4$ is —CH$_2$—;

(j) is

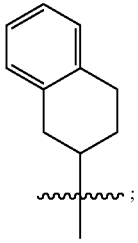

and (k) is

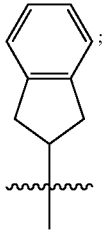

In an embodiment, the present invention is directed to compounds of formula (I) wherein $R^3$ is selected from the group consisting of (a), (b), (d), (f), (g), (h) and (i); wherein (a) is

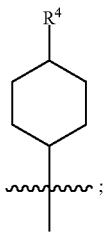

wherein the cyclohexyl group is bound in a cis-, trans- or racemic orientation; and wherein $R^4$ is selected from the group consisting of hydrogen, aminocarbonyl-, 3-hydroxyphenyl-amino-, 3-carboxyphenyl-amino-, 4-carboxyphenyl-amino-, 3-carboxyphenyl-sulfonyl-amino- and 4-carboxyphenyl-sulfonyl-amino-;

(b) is

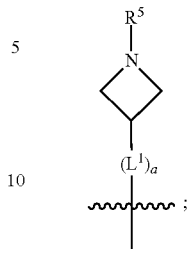

wherein a 0; and wherein $R^5$ is selected from the group consisting of 3-carboxybenzyl- and 4-carboxyphenyl-sulfonyl-;

(d) is

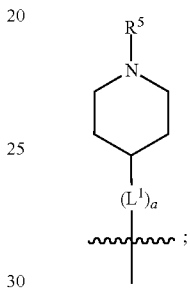

wherein a is an integer from 0 to 1; wherein $L^1$ is —CH$_2$—; and wherein $R^5$ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, aminocarbonyl-methyl-carbonyl-, aminocarbonyl-ethyl-carbonyl-, ethoxycarbonyl-, t-butoxycarbonyl-, cyclopentyloxy-carbonyl-, 2,3,4-trihydroxy-n-butyloxy-carbonyl-, 3-carboxyphenyl, 4-carboxyphenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-hydroxy-benzyl, 2-trifluoromethyl-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-fluoro-5-carboxy-benzyl, 3-fluoro-5-carboxy-benzyl, 2-chloro-3-carboxy-benzyl, 2-chloro-5-carboxy-benzyl, 2-trifluoromethyl-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 1-(5-carboxy-fur-2-yl)-ethyl-, 5-aminocarbonyl-fur-2-yl-methyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-amino-carbonyl-, 4-aminocarbonyl-phenyl-carbonyl-, 3-aminosulfonyl-phenyl-carbonyl-, 4-aminosulfonyl-phenyl-carbonyl-, 6-aminocarbonyl-pyrid-3-yl-carbonyl-, 1,2,4-triazol-3-yl-carbonyl-, methylsulfonyl-, trifluoromethyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 3-carboxyphenyl-sulfonyl-, 4-carboxyphenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-(2-(methoxycarbonyl)-ethyl-amino-carbonyl)-phenyl-sulfonyl-, 3-(2-hydroxyethyl-amino-carbonyl)-phenyl-sulfonyl-, 3-fluoro-4-methoxy-phenyl-sulfonyl-, 3-fluoro-4-aminocarbonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl, 3-methoxy-4-aminocarbonyl-phenyl-sulfonyl-, 3-methoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-;

(f) is

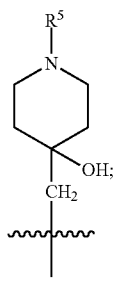

wherein $R^5$ is trifluoromethyl-sulfonyl-;

(g) is

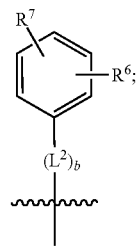

wherein b is an integer from 0 to 1; $L^2$ is selected from the group consisting of —CH$_2$—, —CH$_2$CH$_2$—, —CH(CH$_3$)—CH$_2$—, —CH$_2$—CH(R*—CH$_3$)—, —CH$_2$—CH(S*—CH$_3$)—, —CH$_2$CH$_2$—O—, —CH$_2$—CH(OH)— and —CH$_2$CH$_2$CH$_2$—NH—SO$_2$—; and wherein $R^6$ is selected from the group consisting of hydrogen, 3-chloro-, 4-chloro-, 3-bromo-, 4-bromo-, 3-hydroxy, 4-hydroxy-, 4-trifluoromethyl, 3-methoxy-, 4-methoxy-, 4-methoxycarbonyl-, 3-(ethoxy-carbonyl-methoxy)-, 4-(ethoxy-carbonyl-methoxy)-, 3-(aminocarbonyl-methoxy)-, 4-(aminocarbonyl-methoxy)-, 3-(3-carboxyphenyl), 3-(4-carboxyphenyl) and 3-(5-carboxy-therein-2-yl); and $R^7$ is selected from the group consisting of hydrogen and 5-trifluoromethyl;

(h) is

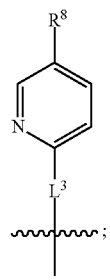

wherein $L^3$ is —CH$_2$CH$_2$— and wherein $R^8$ is 5-methoxycarbonyl-;

and (i) is

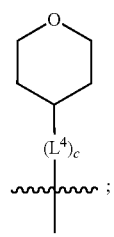

wherein c is an integer from 0 to 1; and wherein $L^4$ is —CH$_2$—.

In another embodiment, the present invention is directed to compounds of formula (I) wherein $R^3$ is selected from the group consisting of (a), (b), (d), (f), (g) and (i); wherein (a) is

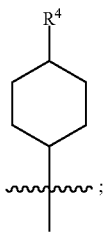

wherein the cyclohexyl group is bound in trans-orientation; and wherein $R^4$ is 3-hydroxyphenyl-amino-;

(b) is

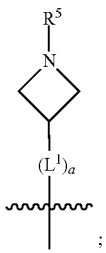

wherein a 0; and wherein $R^5$ is 3-carboxybenzyl-;

(d) is

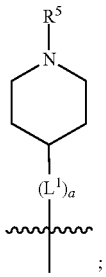

wherein a is an integer from 0 to 1; wherein $L^1$ is —CH$_2$—; and wherein $R^5$ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, ethoxycarbonyl-cyclopentyloxy-carbonyl-, 4-carboxyphenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-hydroxy-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-fluoro-5-carboxy-benzyl, 3-fluoro-5-carboxy-benzyl, 2-chloro-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, 3-aminosulfonyl-phenyl-carbonyl-, 6-aminocarbonyl-pyrid-3-yl-carbonyl-, methylsulfonyl-, trifluoromethyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 3-carboxyphenyl-sulfonyl-, 4-carboxyphenyl-sulfonyl-, 3-aminophenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-fluoro-4-aminocarbonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-aminocarbonyl-phenyl-sulfonyl-, 3-methoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl- and 6-(methoxycarbonyl-ethyl-amino-carbonyl)-pyrid-3-yl-sulfonyl-;

(f) is

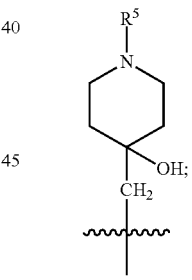

wherein $R^5$ is trifluoromethyl-sulfonyl-;

(g) is

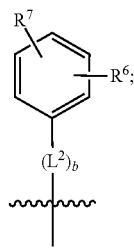

wherein b is an integer from 0 to 1; $L^2$ is selected from the group consisting of —CH$_2$—, —CH$_2$CH$_2$—, —CH$_2$—CH (R*—CH₃)—, —CH₂CH₂—O—, —CH₂—CH(OH)— and —CH₂CH₂CH₂—NH—SO₂—; and wherein $R^6$ is selected from the group consisting of hydrogen, 3-chloro-, 3-bromo-, 4-bromo-, 3-hydroxy, 4-trifluoromethyl, 3-methoxy-, 4-methoxy-, 3-(ethoxy-carbonyl-methoxy)-, 4-(ethoxy-carbonyl-methoxy)-, and 3-(5-carboxy-thein-2-yl); and $R^7$ is hydrogen;

and (i) is

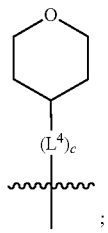

wherein c is 1; and wherein $L^4$ is —CH₂—.

In another embodiment, the present invention is directed to compounds of formula (I) wherein $R^3$ is selected from the group consisting of (d), (f) and (g); wherein (d) is

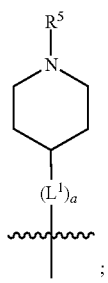

wherein a is an integer from 0 to 1; wherein $L^1$ is —CH₂—; and wherein $R^5$ is selected from the group consisting of propyn-3-yl, methoxy-carbonyl-methyl-, 3-(aminocarbonyl)-phenyl, 4-(aminocarbonyl)-phenyl, 3-(aminocarbonyl-methyl)-phenyl, 3-(aminocarbonyl-methoxy)-phenyl, 3-carboxy-benzyl, 3-(aminocarbonyl)-benzyl, 3-(2-hydroxyethyl-aminocarbonyl)-benzyl, 3-fluoro-5-carboxy-benzyl, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-aminocarbonyl-fur-2-yl-methyl-, 5-carboxy-thien-2-yl-methyl-, 5-aminocarbonyl-thien-2-yl-methyl-, 4-aminocarbonyl-thien-2-yl-methyl-, benzyloxy-carbonyl-, methylsulfonyl-, trifluoromethyl-sulfonyl-, phenyl-sulfonyl-, 4-fluorophenyl-sulfonyl-, 4-chlorophenyl-sulfonyl-, 3-hydroxyphenyl-sulfonyl-, 4-hydroxyphenyl-sulfonyl-, 2-methoxy-phenyl-sulfonyl-, 3-trifluoromethyl-phenyl-sulfonyl-, 4-carboxyphenyl-sulfonyl-, 3-aminophenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-aminocarbonyl-phenyl-sulfonyl-, 3-methoxy-4-carboxy-phenyl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl- and 6-aminocarbonyl-pyrid-3-yl-sulfonyl-;

(f) is

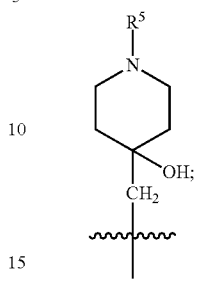

wherein $R^5$ is trifluoromethyl-sulfonyl-;

and (g) is

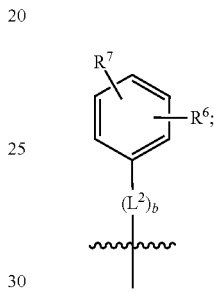

wherein b is an integer from 0 to 1; $L^2$ is —CH₂CH₂—; and wherein $R^6$ is selected from the group consisting of 3-chloro-, 4-trifluoromethyl, 4-methoxy- and 4-(ethoxy-carbonyl-methoxy)-; and $R^7$ is hydrogen.

In another embodiment, the present invention is directed to compounds of formula (I) wherein $R^3$ is selected from the group consisting of (d), (f) and (g); wherein (d) is

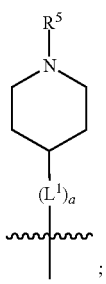

wherein a is an integer from 0 to 1; wherein $L^1$ is —CH₂—; and wherein $R^5$ is selected from the group consisting of methoxy-carbonyl-methyl-, 3-(aminocarbonyl)-benzyl, 1R*-(3-carboxyphenyl)-ethyl-, 5-aminocarbonyl-pyrid-2-yl-methyl-, 1-(4-carboxy-pyrid-2-yl)-ethyl 5-aminocarbonyl-thien-2-yl-methyl-, 4-aminocarbonyl-thien-2-yl-methyl-, trifluoromethyl-sulfonyl-, phenyl-sulfonyl-, 4-chlorophenyl-sulfonyl, 3-hydroxyphenyl-sulfonyl-, 2-methoxy-phenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-trifluoromethyl-4-carboxy-phenyl-sulfonyl3-methyl-5-(aminocarbonyl)-thien-2-yl-sulfonyl- and 6-aminocarbonyl-pyrid-3-yl-sulfonyl-;

(f) is

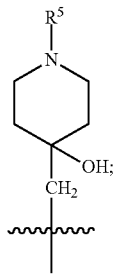

wherein $R^5$ is trifluoromethyl-sulfonyl-;
and (g) is

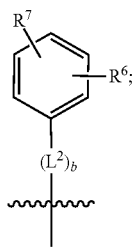

wherein b is an integer from 0 to 1; $L^2$ is —CH$_2$CH$_2$—; and wherein $R^6$ is selected from the group consisting of 4-trifluoromethyl, 4-methoxy- and 4-(ethoxy-carbonyl-methoxy)-; and $R^7$ is hydrogen.

In another embodiment, the present invention is directed to compounds of formula (I) wherein $R^3$ is (a)

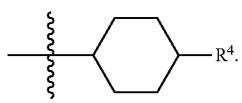

In another embodiment, the present invention is directed to compounds of formula (I) wherein $R^3$ is (b)

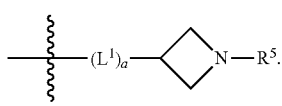

In another embodiment, the present invention is directed to compounds of formula (I) wherein $R^3$ is (c)

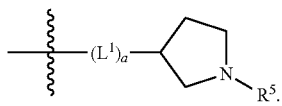

In another embodiment, the present invention is directed to compounds of formula (I) wherein $R^3$ is (d)

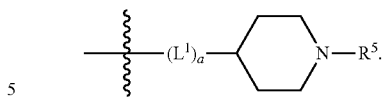

In another embodiment, the present invention is directed to compounds of formula (I) wherein $R^3$ is (e)

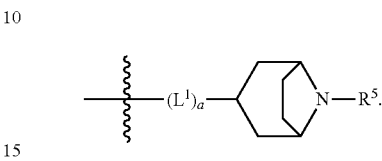

In another embodiment, the present invention is directed to compounds of formula (I) wherein $R^3$ is (f)

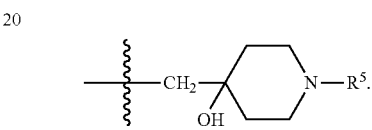

In another embodiment, the present invention is directed to compounds of formula (I) wherein $R^3$ is (g)

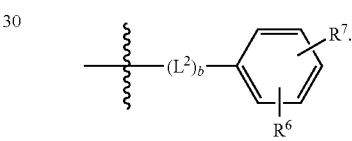

In another embodiment, the present invention is directed to compounds of formula (I) wherein $R^3$ is (h)

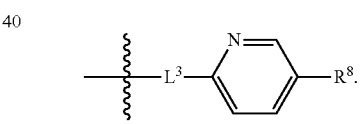

In another embodiment, the present invention is directed to compounds of formula (I) wherein $R^3$ is (i)

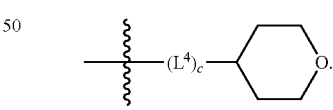

In another embodiment, the present invention is directed to compounds of formula (I) wherein $R^3$ is (j)

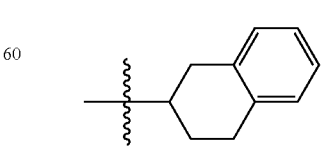

In another embodiment, the present invention is directed to compounds of formula (I) wherein $R^3$ is (k)

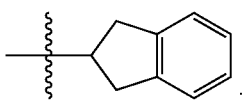 [SMILES: *C1Cc2ccccc2C1]

In another embodiment, the present invention is directed to compounds of formula (I) wherein $R^3$ is (a); wherein (a) is

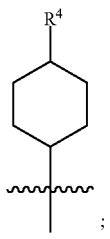

wherein $R^4$ is selected from the group consisting of hydrogen, —C(O)OH, —C(O)O—($C_{1-12}$alkyl), —C(O)NR$^G$R$^H$, —NH-(phenyl), and —NH—SO$_2$-(phenyl); wherein the phenyl is optionally substituted with hydroxy or carboxy; and wherein R$^G$ and R$^H$ are each independently selected from the group consisting of hydrogen and methyl.

In another embodiment, the present invention is directed to compounds of formula (I) wherein $R^3$ is (a); wherein (a) is

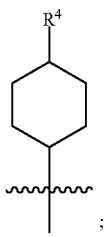

wherein $R^4$ is selected from the group consisting of hydrogen, —C(O)OH, —C(O)NR$^G$R$^H$, —NH-(phenyl) and —NH—SO$_2$-(phenyl); wherein the phenyl is optionally substituted with hydroxy or carboxy; wherein R$^G$ and R$^H$ are each independently selected from the group consisting of hydrogen and methyl.

In another embodiment, the present invention is directed to compounds of formula (I) wherein $R^3$ is (a); wherein (a) is

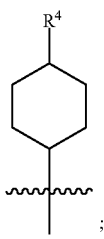

wherein $R^4$ is selected from the group consisting of hydrogen, —C(O)OH, —C(O)NH$_2$, —NH—SO$_2$-(3-carboxyphenyl), —NH-(3-hydroxyphenyl), —NH-(3-carboxyphenyl), —NH-(4-carboxyphenyl) and —NH—SO$_2$-(4-carboxyphenyl); and wherein the cyclohexyl is bound to the benzimidazole core in a cis-, trans- or racemic stereo-orientation.

In an embodiment, the present invention is directed to compounds of formula (I) wherein $R^3$ is (a) is

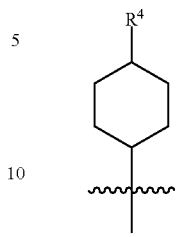

wherein the cyclohexyl group is bound in a cis-, trans- or racemic orientation; and wherein $R^4$ is selected from the group consisting of hydrogen, aminocarbonyl-, 3-hydroxyphenyl-amino-, 3-carboxyphenyl-amino-, 4-carboxyphenyl-amino-, 3-carboxyphenyl-sulfonyl-amino- and 4-carboxyphenyl-sulfonyl-amino-. In another embodiment, the present invention is directed to compounds of formula (I) wherein $R^3$ is (a) is

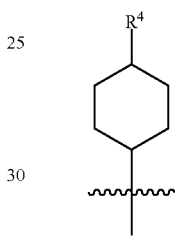

wherein the cyclohexyl group is bound in trans-orientation; and wherein $R^4$ is 3-hydroxyphenyl-amino-.

In another embodiment, the present invention is directed to compounds of formula (I) wherein $R^3$ is selected from the group consisting of (b) through (f); wherein (b) is

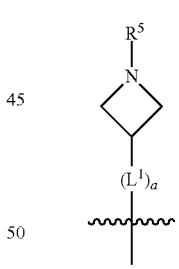

(c) is

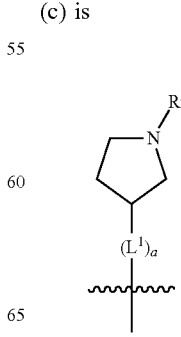

(d) is

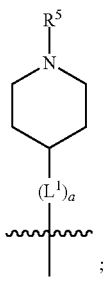

(e) is

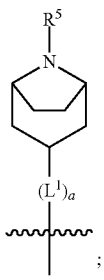

(f) is

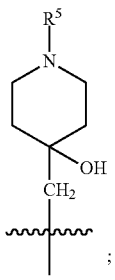

wherein a is an integer from 0 to 1; wherein $L^1$ is selected from the group consisting of —CH$_2$—, —CH$_2$—CH$_2$, —CH(CH$_3$)CH$_2$— and —CH$_2$—CH(CH$_3$)—; wherein $R^5$ is selected from the group consisting of hydrogen, C$_{1-2}$alkyl, fluorinated C$_{1-2}$alkyl, C$_{2-4}$alkenyl, —(C$_{1-2}$alkyl)-C(O)OH, —(C$_{1-2}$alkyl)-C(O)O—(C$_{1-2}$alkyl), —(C$_2$alkyl)-O-(phenyl), —C(O)—(C$_{1-2}$alkyl)-OH, —C(O)—(C$_{1-2}$alkyl)-C(O)OH, —C(O)—(C$_{1-2}$alkyl)-C(O)O—(C$_{1-2}$alkyl), —C(O)—(C$_{1-2}$alkyl)-C(O)—NH$_2$, —C(O)O—(C$_{1-4}$alkyl), —C(O)O—(C$_{3-5}$cycloalkyl), —C(O)O-(phenyl), —C(O)O—CH$_2$-(phenyl), —C(O)—NH$_2$, —C(O)NH—(C$_{1-2}$alkyl), —C(O)NH—(C$_{3-5}$cycloalkyl), —C(O)NH-(phenyl), —C(O)NH—(C$_{1-2}$alkyl)-(phenyl), —SO$_2$—(C$_{1-2}$alkyl), —SO$_2$-(fluorinated C$_{1-2}$alkyl), —SO$_2$—(C$_{1-2}$alkyl)-C(O)OH, —SO$_2$—(C$_{1-2}$alkyl)-C(O)O—(C$_{1-2}$alkyl), —SO$_2$—NH$_2$, —SO$_2$—NH—(C$_{1-2}$alkyl), —SO$_2$—(C$_{1-2}$alkyl)-C(O)NH$_2$, phenyl, —(C$_{1-3}$alkyl)-phenyl, —C(O)-(phenyl), —C(O)O-(phenyl), —C(O)O—(C$_{1-2}$alkyl)-(phenyl), —SO$_2$-(phenyl), pyrimidin-2-yl, pyrid-2-yl, pyrid-3-yl, —(C$_{1-2}$alkyl)-pyrid-2-yl, —(C$_{1-2}$alkyl)-pyrid-3-yl, —(C$_{1-2}$alkyl)-fur-2-yl, —(C$_{1-2}$alkyl)-thien-2-yl, —C(O)-fur-2-yl, —C(O)-thien-2-yl, —C(O)-(pyrid-3-yl), —C(O)-(1,2,3-triazol-4-yl), —C(O)-(1,2,4,-triazol-3-yl), —SO$_2$—(C$_{1-2}$alkyl)-(piperazin-1-yl), —SO$_2$-(fury-2-yl), —SO$_2$-(thien-2-yl) and —SO$_2$-(pyrid-3-yl); wherein the phenyl, pyrimidin-2-yl, pyridyl, furyl, thienyl or pyridyl, is optionally substituted with one to three substituents independently selected from the group consisting of halogen, hydroxy, C$_{1-2}$alkyl, fluorinated C$_{1-2}$alkyl, —(C$_{1-2}$alkyl)-OH, —C$_{(1-2}$alkyl)-C(O)OH, —(C$_{1-2}$alkyl)-C(O)O—(C$_{1-2}$alkyl), —O—(C$_{1-2}$alkyl), —O-(fluorinated C$_{1-2}$alkyl), —O—(C$_{2-6}$alkenyl), —O—(C$_{1-2}$alkyl)-C(O)OH, —O—(C$_{1-2}$alkyl)-C(O)NH$_2$, —C(O)OH, —C(O)O—(C$_{1-4}$alkyl), —C(O)—NH$_2$, —C(O)—NH—(C$_{1-2}$alkyl), —C(O)—NH—(C$_{1-3}$alkyl)-OH, —C(O)—NH—(C$_{1-2}$alkyl)-C(O)OH, —C(O)—NH—(C$_{1-2}$alkyl)-C(O)O—(C$_{1-2}$alkyl), —(C$_{1-2}$alkyl)-C(O)—NH$_2$, —O—(C$_{1-2}$alkyl)-C(O)—NH$_2$, —O—(C$_{1-2}$alkyl)-C(O)OH, —NH$_2$, —NH(C$_{1-2}$alkyl), —SO$_2$—NH$_2$ and —SO$_2$—NH(C$_{1-2}$alkyl).

In another embodiment, the present invention is directed to compounds of formula (I) wherein $R^3$ is selected from the group consisting of (b) through (f); wherein (b) is

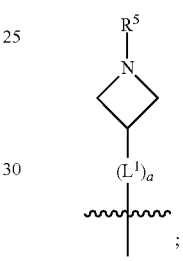

(c) is

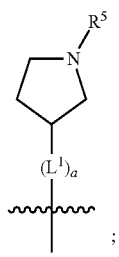

(d) is

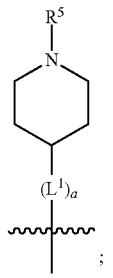

(e) is

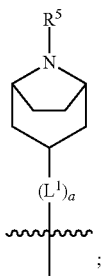

;

(f) is

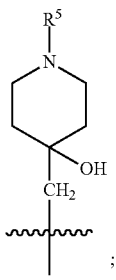

;

wherein a is an integer from 0 to 1; and wherein L¹ is selected from the group consisting of —CH₂— and —CH₂—CH(CH₃)—; wherein R⁵ is selected from the group consisting of hydrogen, C$_{2-4}$alkenyl, —(C$_{1-2}$alkyl)-C(O)OH, —(C$_{1-2}$alkyl)-C(O)O—(C$_{1-2}$alkyl), —(C$_2$alkyl)-O-(phenyl), —C(O)—(C$_{1-2}$alkyl)-OH, —C(O)—(C$_{1-2}$alkyl)-C(O)OH, —C(O)—(C$_{1-2}$alkyl)-C(O)—NH₂, —C(O)O—(C$_{1-4}$ alkyl), —C(O)O-(hydroxy substituted C$_{1-4}$alkyl), —C(O)O—(C$_{3-5}$cycloalkyl), —C(O)NH—(C$_{1-2}$alkyl), —C(O)NH—(C$_{3-5}$cycloalkyl), —C(O)NH-(phenyl), —C(O)NH—(C$_{1-2}$alkyl)-(phenyl), —SO₂—(C$_{1-2}$alkyl), —SO₂-(fluorinated C$_{1-2}$alkyl), —SO₂—(C$_{1-2}$alkyl)-C(O)OH, —SO₂—NH₂, —SO₂—NH—(C$_{1-2}$alkyl), —SO₂—(C$_{1-2}$ alkyl)-C(O)NH₂, phenyl, —(C$_{1-3}$alkyl)-phenyl, —C(O)-(phenyl), —C(O)O-(phenyl), —C(O)O—(C$_{1-2}$alkyl)-(phenyl), —SO₂-(phenyl), pyrimidin-2-yl, —(C$_{1-2}$alkyl)-pyrid-2-yl, —(C$_{1-2}$alkyl)-pyrid-3-yl, —(C$_{1-2}$alkyl)-fur-2-yl, —(C$_{1-2}$alkyl)-thien-2-yl, —C(O)-(pyrid-3-yl), —C(O)-(1,2,3-triazol-4-yl), —C(O)-(1,2,4,-triazol-3-yl), —SO₂—(C$_{1-2}$alkyl)-(piperazin-1-yl), —SO₂-(fury-2-yl), —SO₂-(thien-2-yl) and —SO₂-(pyrid-3-yl); wherein the phenyl is optionally substituted with one to three substituents independently selected from the group consisting of halogen, hydroxy, C$_{1-2}$alkyl, fluorinated C$_{1-2}$alkyl, —O—(C$_{1-2}$alkyl), —O-(fluorinated C$_{1-2}$alkyl), —O—(C$_{2-6}$alkenyl), —O—(C$_{1-2}$alkyl)-C(O)OH, —O—(C$_{1-2}$alkyl)-C(O)NH₂, —C(O)OH, —C(O)O—(C$_{1-2}$alkyl), —C(${1-2}$alkyl)-C(O)OH, —C(O)—NH₂, —C(O)—NH—(C$_{1-2}$alkyl), —C(O)—NH—(C$_{1-3}$alkyl)-OH, —C(O)—NH—(C$_{1-2}$ alkyl)-C(O)OH, —C(O)—NH—(C$_{1-2}$alkyl)-C(O)O—(C$_{1-2}$ alkyl), —(C$_{1-2}$alkyl)-C(O)—NH₂, —O—(C$_{1-2}$alkyl)-C(O)—NH₂, —O—(C$_{1-2}$alkyl)-C(O)OH, —NH₂ and —SO₂—NH₂; and wherein the pyrimidin-2-yl, pyrid-2-yl, pyrid-3-yl, fur-2-yl or thien-2-yl is optionally substituted with one to two substituents independently selected from the group consisting of C$_{1-2}$alkyl, —(C$_{1-2}$alkyl)-OH, —C(O)OH, —C(O)O—(C$_{1-2}$alkyl), —C(O)—NH₂, —C(O)NH—(C$_{1-2}$alkyl)-OH, —C(O)NH—(C$_{1-2}$alkyl)-C(O)OH and —C(O)NH—(C$_{1-2}$alkyl)-C(O)O—(C$_{1-2}$alkyl).

In another embodiment, the present invention is directed to compounds of formula (I) wherein R³ is (b); wherein (b) is

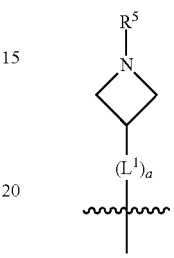

wherein a 0; and wherein R⁵ is selected from the group consisting of 3-carboxybenzyl-, 4-carboxyphenyl-sulfonyl- and 5-carboxyfur-2-yl-sulfonyl-.

In an embodiment, the present invention is directed to compounds of formula (I) wherein R³ is (b) is

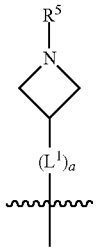

;

wherein a 0; and wherein R⁵ is selected from the group consisting of 3-carboxybenzyl- and 4-carboxyphenyl-sulfonyl-. In another embodiment, the present invention is directed to compounds of formula (I) wherein R³ is (b) is


;

wherein a 0; and wherein R⁵ is 3-carboxybenzyl-.

In another embodiment, the present invention is directed to compounds of formula (I) wherein R³ is (c); wherein (c) is

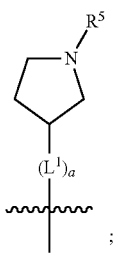

wherein a is 0; and wherein $R^5$ is selected from the group consisting of 3-carboxybenzyl-, 4-carboxyphenyl-sulfonyl- and 5-carboxy-fur-2-yl-sulfonyl-.

In another embodiment, the present invention is directed to compounds of formula (I) wherein $R^3$ is (d); wherein (d) is

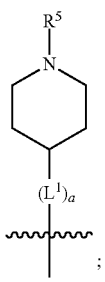

wherein a is an integer from 0 to 1; $L^1$ is selected from the group consisting of —CH$_2$— and —CH$_2$—CH(R*—CH$_3$)—; and wherein $R^5$ is selected from the group consisting of hydrogen, propyn-3-yl, carboxy-methyl-, methoxycarbonyl-methyl-, 3-carboxyphenyl-oxy-ethyl-, 2-hydroxyethyl-carbonyl-, hydroxymethyl-carbonyl-, 2-carboxy-ethyl-carbonyl-, aminocarbonyl-methyl-carbonyl-, 2-(aminocarbonyl)-ethyl-carbonyl-, ethoxycarbonyl-, t-butoxycarbonyl-, cyclopentyloxy-carbonyl-, 2,3,4-trihydroxy-n-butyloxy-carbonyl-, 3-carboxyphenyl, 4-carboxyphenyl, 3-(carboxy-methyl)-phenyl, 4-(carboxy-methyl)-phenyl, 3-(methoxycarbonyl)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-(carboxy-methoxy)-phenyl, 4-(carboxy-methoxy)-phenyl, 3-hydroxy-benzyl, 3-(hex-2-en-1-yloxy)-benzyl, 2-trifluoromethyl-benzyl, 3-carboxy-benzyl, 4-carboxy-benzyl, 3-(methoxycarbonyl)-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-hydroxy-5-carboxy-benzyl, 2-fluoro-3-carboxy-benzyl, 2-fluoro-5-carboxy-benzyl, 2-chloro-3-carboxy-benzyl, 2-chloro-5-carboxy-benzyl, 2-trifluoromethyl-5-carboxy-benzyl, 3-fluoro-5-carboxy-benzyl, 3-carboxy-4-fluoro-benzyl, 3-carboxy-4-hydroxy-benzyl, 3-trifluoromethyl-5-carboxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 4-carboxy-pyrimidin-2-yl, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-aminocarbonyl-, 4-carboxy-phenyl-carbonyl-, 4-aminocarbonyl-phenyl-carbonyl-, 3-aminosulfonyl-phenyl-carbonyl-, 4-aminosulfonyl-phenyl-carbonyl-, 6-carboxy-pyrid-3-yl-carbonyl-, 6-aminocarbonyl-pyrid-3-yl-carbonyl-, 1,2,3-triazol-4-yl-carbonyl-, 1,2,4-triazol-3-yl-carbonyl-, methyl-sulfonyl-, trifluoromethyl-sulfonyl-, carboxymethyl-sulfonyl-, carboxyethyl-sulfonyl-, amino-sulfonyl-, amino-ethyl-sulfonyl-, aminocarbonyl-methyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 2-carboxyphenyl-sulfonyl-, 3-carboxyphenyl-sulfonyl-, 4-carboxyphenyl-sulfonyl-, 4-carboxy-methoxy-phenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(carboxy-ethyl-amino-carbonyl)-phenyl-sulfonyl-, 3-(3-hydroxy-n-propyl-amino-carbonyl)-phenyl-sulfonyl-, 3-(2-(methoxy-carbonyl)-ethyl-amino-carbonyl)-phenyl-sulfonyl-, 3-(2-hydroxyethyl-amino-carbonyl)-phenyl-sulfonyl-, 3-fluoro-4-hydroxy-phenyl-sulfonyl-, 3-fluoro-4-methoxy-phenyl-sulfonyl-, 3-fluoro-4-aminophenyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl-, 3-methyl-4-aminophenyl-phenyl-sulfonyl-, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl-, 3-methoxy-4-carboxy-phenyl-sulfonyl, 3-methoxy-4-aminocarbonyl-phenyl-sulfonyl-, 3-carboxy-4-chloro-phenyl-sulfonyl-, 3-carboxy-4-fluoro-phenyl-sulfonyl-, 3-carboxy-4-methyl-phenyl-sulfonyl-, 3-carboxy-4-methoxy-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, piperazin-1-yl-ethyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-.

In an embodiment, the present invention is directed to compounds of formula (I) wherein $R^3$ is (d) is

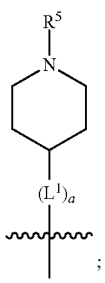

wherein a is an integer from 0 to 1; wherein L¹ is —CH$_2$—; and wherein R⁵ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, aminocarbonyl-methyl-carbonyl-, aminocarbonyl-ethyl-carbonyl-, ethoxycarbonyl-, t-butoxycarbonyl-, cyclopentyloxy-carbonyl-, 2,3,4-trihydroxy-n-butyloxy-carbonyl-, 3-carboxyphenyl, 4-carboxyphenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-hydroxy-benzyl, 2-trifluoromethyl-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-fluoro-5-carboxy-benzyl, 3-fluoro-5-carboxy-benzyl, 2-chloro-3-carboxy-benzyl, 2-chloro-5-carboxy-benzyl, 2-trifluoromethyl-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 1-(5-carboxy-fur-2-yl)-ethyl-, 5-aminocarbonyl-fur-2-yl-methyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-amino-carbonyl-, 4-aminocarbonyl-phenyl-carbonyl-, 3-aminosulfonyl-phenyl-carbonyl-, 4-aminosulfonyl-phenyl-carbonyl-, 6-aminocarbonyl-pyrid-3-yl-carbonyl-, 1,2,4-triazol-3-yl-carbonyl-, methylsulfonyl-, trifluoromethyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 3-carboxyphenyl-sulfonyl-, 4-carboxyphenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-(2-(methoxycarbonyl)-ethyl-amino-carbonyl)-phenyl-sulfonyl-, 3-(2-hydroxyethyl-amino-carbonyl)-phenyl-sulfonyl-, 3-fluoro-4-methoxy-phenyl-sulfonyl-, 3-fluoro-4-aminocarbonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl, 3-methoxy-4-aminocarbonyl-phenyl-sulfonyl-, 3-methoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-.

In another embodiment, the present invention is directed to compounds of formula (I) wherein R³ is (d) is

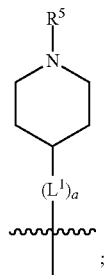

wherein a is an integer from 0 to 1; wherein L¹ is —CH$_2$—; and wherein R⁵ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, ethoxycarbonyl-cyclopentyloxy-carbonyl-, 4-carboxyphenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-hydroxy-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-fluoro-5-carboxy-benzyl, 3-fluoro-5-carboxy-benzyl, 2-chloro-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, 3-aminosulfonyl-phenyl-carbonyl-, 6-aminocarbonyl-pyrid-3-yl-carbonyl-, methylsulfonyl-, trifluoromethylsulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 3-carboxyphenyl-sulfonyl-, 4-carboxyphenyl-sulfonyl-, 3-aminophenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-fluoro-4-aminocarbonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-aminocarbonyl-phenyl-sulfonyl-, 3-methoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl- and 6-(methoxycarbonyl-ethyl-amino-carbonyl)-pyrid-3-yl-sulfonyl-.

In another embodiment, the present invention is directed to compounds of formula (I) wherein R³ is (d) is

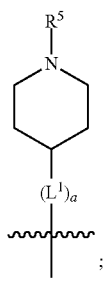

wherein a is an integer from 0 to 1; wherein L¹ is —CH₂—; and wherein R⁵ is selected from the group consisting of propyn-3-yl, methoxy-carbonyl-methyl-, 3-(aminocarbonyl)-phenyl, 4-(aminocarbonyl)-phenyl, 3-(aminocarbonyl-methyl)-phenyl, 3-(aminocarbonyl-methoxy)-phenyl, 3-carboxy-benzyl, 3-(aminocarbonyl)-benzyl, 3-(2-hydroxyethyl-aminocarbonyl)-benzyl, 3-fluoro-5-carboxy-benzyl, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-aminocarbonyl-fur-2-yl-methyl-, 5-carboxy-thien-2-yl-methyl-, 5-aminocarbonyl-thien-2-yl-methyl-, 4-aminocarbonyl-thien-2-yl-methyl-, benzyloxy-carbonyl-, methylsulfonyl-, trifluoromethyl-sulfonyl-, phenyl-sulfonyl-, 4-fluorophenyl-sulfonyl-, 4-chlorophenyl-sulfonyl-, 3-hydroxyphenyl-sulfonyl-, 4-hydroxyphenyl-sulfonyl-, 2-methoxy-phenyl-sulfonyl-, 3-trifluoromethyl-phenyl-sulfonyl-, 4-carboxyphenyl-sulfonyl-, 3-aminophenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-aminocarbonyl-phenyl-sulfonyl-, 3-methoxy-4-carboxy-phenyl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl- and 6-aminocarbonyl-pyrid-3-yl-sulfonyl-.

In another embodiment, the present invention is directed to compounds of formula (I) wherein R³ is (d) is

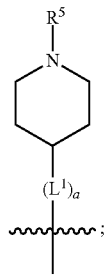

wherein a is an integer from 0 to 1; wherein L¹ is —CH₂—; and wherein R⁵ is selected from the group consisting of methoxy-carbonyl-methyl-, 3-(aminocarbonyl)-benzyl, 1R*-(3-carboxyphenyl)-ethyl-, 5-aminocarbonyl-pyrid-2-yl-methyl-, 1-(4-carboxy-pyrid-2-yl)-ethyl 5-aminocarbonyl-thien-2-yl-methyl-, 4-aminocarbonyl-thien-2-yl-methyl-, trifluoromethyl-sulfonyl-, phenyl-sulfonyl-, 4-chlorophenyl-sulfonyl, 3-hydroxyphenyl-sulfonyl-, 2-methoxy-phenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-trifluoromethyl-4-carboxy-phenyl-sulfonyl3-methyl-5-(aminocarbonyl)-thien-2-yl-sulfonyl- and 6-aminocarbonyl-pyrid-3-yl-sulfonyl-.

In another embodiment, the present invention is directed to compounds of formula (I) wherein R³ is (e); wherein (e) is

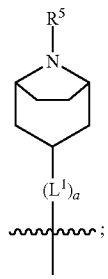

wherein a is 0; and wherein R⁵ is selected from the group consisting of ethoxycarbonyl- and trifluoromethyl-sulfonyl-.

In another embodiment, the present invention is directed to compounds of formula (I) wherein R³ is (f); wherein (f) is

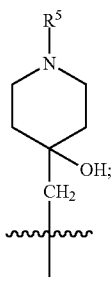

wherein $R^5$ is trifluoromethyl-sulfonyl-.

In another embodiment, the present invention is directed to compounds of formula (I) wherein $R^3$ is (g); wherein (g) is

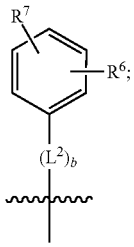

wherein b is an integer from 0 to 1; wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and CH$_2$CH$_2$CH$_2$—NH—SO$_2$—; wherein $R^6$ is selected from the group consisting of hydrogen, halogen, hydroxy, C$_{1-2}$alkyl, fluorinated C$_{1-2}$alkyl, C$_{1-2}$alkoxy, fluorinated C$_{1-2}$alkoxy, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl, furyl and thienyl; wherein the phenyl, furyl or thienyl is optionally substituted with carboxy; and wherein $R^7$ is selected from the group consisting of hydrogen, hydroxy, C$_{1-2}$alkyl, fluorinated C$_{1-2}$alkyl, C$_{1-2}$alkoxy, fluorinated C$_{1-2}$alkoxy, —C(O)OH and —C(O)O—(C$_{1-4}$alkyl).

In another embodiment, the present invention is directed to compounds of formula (I) wherein $R^3$ is (g); wherein (g) is

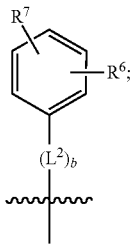

wherein b is an integer from 0 to 1; and wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and CH$_2$CH$_2$CH$_2$—NH—SO$_2$—; wherein $R^6$ is selected from the group consisting of hydrogen, halogen, hydroxy, C$_{1-2}$alkoxy, fluorinated C$_{1-2}$alkyl, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl and thienyl; wherein the phenyl or thienyl is optionally substituted with carboxy; and wherein $R^7$ is selected from the group consisting of hydrogen and fluorinated C$_{1-2}$alkyl.

In another embodiment, the present invention is directed to compounds of formula (I) wherein $R^3$ is (g); wherein (g) is

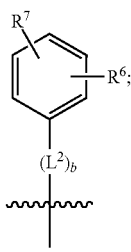

wherein b is an integer from 0 to 1; wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$—CH(R*—CH$_3$)—, —CH$_2$—CH(S*—CH$_3$)—, —CH$_2$CH$_2$—O—, —CH$_2$—CH(OH)—, —CH$_2$—CH(R*—OH), —CH(CH$_3$)—CH(OH) and CH$_2$CH$_2$CH$_2$—NH—SO$_2$—; wherein $R^6$ is selected from the group consisting of hydrogen, 3-bromo, 3-chloro, 4-chloro, 3-hydroxy, 4-hydroxy, 3-methoxy, 4-methoxy, 4-trifluoromethyl, 3-carboxy, 4-carboxy, 3-carboxy-methoxy-, 4-carboxy-methoxy-, 3-methoxycarbonyl-, 4-methoxycarbonyl-, 3-ethoxy-carbonyl-methoxy-, 4-ethoxy-carbonyl-methoxy-, 4-aminocarbonyl-, 3-amino-carbonyl-methoxy-, 4-amino-carbonyl-methoxy-, 3-(3-carboxyphenyl), 3-(4-carboxyphenyl), 4-(3-carboxyphenyl), 4-(4-carboxyphenyl) and 3-(5-carboxy-thien-2-yl); and wherein $R^7$ is selected from the group consisting of hydrogen and 5-trifluoromethyl.

In an embodiment, the present invention is directed to compounds of formula (I) wherein $R^3$ is (g) is

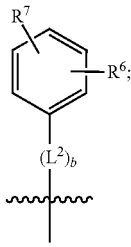

wherein b is an integer from 0 to 1; $L^2$ is selected from the group consisting of —CH$_2$—, —CH$_2$CH$_2$—, —CH(CH$_3$)—CH$_2$—, —CH$_2$—CH(R*—CH$_3$)—, —CH$_2$—CH(S*—CH$_3$)—, —CH$_2$CH$_2$—O—, —CH$_2$—CH(OH)— and —CH$_2$CH$_2$CH$_2$—NH—SO$_2$—; and wherein $R^6$ is selected from the group consisting of hydrogen, 3-chloro-, 4-chloro-, 3-bromo-, 4-bromo-, 3-hydroxy, 4-hydroxy-, 4-trifluoromethyl, 3-methoxy-, 4-methoxy-, 4-methoxycarbonyl-, 3-(ethoxy-carbonyl-methoxy)-, 4-(ethoxy-carbonyl-methoxy)-, 3-(aminocarbonyl-methoxy)-, 4-(aminocarbonyl-methoxy)-, 3-(3-carboxyphenyl), 3-(4-carboxyphenyl)

and 3-(5-carboxy-thein-2-yl); and $R^7$ is selected from the group consisting of hydrogen and 5-trifluoromethyl.

In another embodiment, the present invention is directed to compounds of formula (I) wherein $R^3$ is (g) is

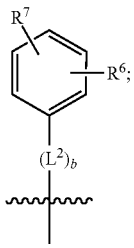

wherein b is an integer from 0 to 1; $L^2$ is selected from the group consisting of —$CH_2$—, —$CH_2CH_2$—, —$CH_2$—CH($R^*$—$CH_3$)—, —$CH_2CH_2$—O—, —$CH_2$—CH(OH)— and —$CH_2CH_2CH_2$—NH—$SO_2$—; and wherein $R^6$ is selected from the group consisting of hydrogen, 3-chloro-, 3-bromo-, 4-bromo-, 3-hydroxy, 4-trifluoromethyl, 3-methoxy-, 4-methoxy-, 3-(ethoxy-carbonyl-methoxy)-, 4-(ethoxy-carbonyl-methoxy)-, and 3-(5-carboxy-thein-2-yl); and $R^7$ is hydrogen.

In another embodiment, the present invention is directed to compounds of formula (I) wherein $R^3$ is (g) is

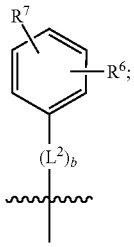

wherein b is an integer from 0 to 1; $L^2$ is —$CH_2CH_2$—; and wherein $R^6$ is selected from the group consisting of 3-chloro-, 4-trifluoromethyl, 4-methoxy- and 4-(ethoxy-carbonyl-methoxy)-; and $R^7$ is hydrogen.

In another embodiment, the present invention is directed to compounds of formula (I) wherein $R^3$ is (g) is

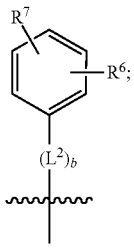

wherein b is an integer from 0 to 1; $L^2$ is —$CH_2CH_2$—; and wherein $R^6$ is selected from the group consisting of 4-trifluoromethyl, 4-methoxy- and 4-(ethoxy-carbonyl-methoxy)-; and $R^7$ is hydrogen.

In another embodiment, the present invention is directed to compounds of formula (I) wherein $R^3$ is (h); wherein (h) is

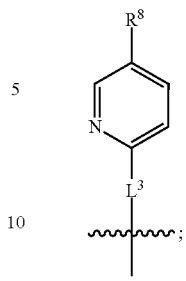

wherein $L^3$ is selected from the group consisting of —$CH_2$—, —$CH_2CH_2$— and —$CH_2CH_2$—O—; and wherein $R^8$ is selected from the group consisting of hydrogen, -halogen, $C_{1-2}$alkyl, $C_{1-2}$alkoxy, —C(O)OH and —C(O)O—($C_{1-4}$alkyl).

In another embodiment, the present invention is directed to compounds of formula (I) wherein $R^3$ is (h); wherein (h) is


wherein $L^3$ is selected from the group consisting of —$CH_2$— and —$CH_2CH_2$—O—; and wherein $R^8$ is selected from the group consisting of hydrogen, —C(O)OH and —C(O)O—($C_{1-2}$alkyl).

In another embodiment, the present invention is directed to compounds of formula (I) wherein $R^3$ is (h); wherein (h) is

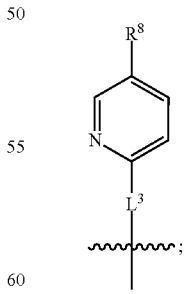

wherein $L^3$ is selected from the group consisting of —$CH_2$— and —$CH_2CH_2$—O—; and wherein $R^8$ is selected from the group consisting of hydrogen, carboxy and methoxycarbonyl-. In an embodiment, the present invention is directed to compounds of formula (I) wherein $R^3$ is (h) is

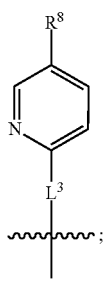

wherein L³ is —CH₂CH₂— and wherein R⁸ is 5-methoxy-carbonyl-.

In another embodiment, the present invention is directed to compounds of formula (I) wherein R³ is (i); wherein (i) is

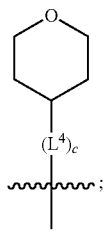

wherein c is an integer from 0 to 1; and wherein L⁴ is selected from the group consisting of —CH₂— and —CH₂—CH₂—. In another embodiment, the present invention is directed to compounds of formula (I) wherein R³ is (i); wherein (i) is

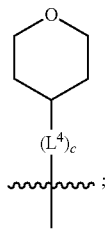

wherein c is an integer from 0 to 1; wherein L⁴ is —CH₂—. In another embodiment, the present invention is directed to compounds of formula (I) wherein R³ is (i) is

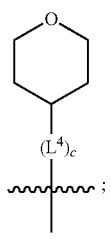

wherein c is 1; and wherein L⁴ is —CH₂—.

In another embodiment, the present invention is directed to compounds of formula (I) wherein R³ is selected from the group consisting of 1-(3-fluoro-5-carboxy-benzyl)-piperidin-4-yl, 1-(2-fluoro-5-carboxy-benzyl)-piperidin-4-yl, 1-(5-carboxy-pyrid-2-yl-methyl)-piperidin-4-yl, 1-(6-carboxy-pyrid-2-yl-methyl)-piperidin-4-yl, 1-(5-carboxy-thien-2-yl-methyl)-piperidin-4-yl, 1-(4-carboxy-thien-2-yl-sulfonyl)-piperidin-4-yl, 1-(5-carboxy-fur-2-yl-sulfonyl)-piperidin-4-yl, 1-(3-carboxy-benzyl)-piperidin-4-yl, 1-(3-carboxy-phenyl-sulfonyl)-piperidin-4-yl, 1-(3-hydroxy-phenyl-sulfonyl)-piperidin-4-yl, 1-(4-carboxy-phenyl-sulfonyl)-piperidin-4-yl, 1-trifluoromethyl-sulfonyl-piperidin-4-yl-methyl- and 1-trifluoromethyl-sulfonyl-piperidin-4-yl.

In another embodiment, the present invention is directed to compounds of formula (I) wherein R³ is selected from the group consisting of 1-(3-fluoro-5-carboxy-benzyl)-piperidin-4-yl, 1-(2-fluoro-5-carboxy-benzyl)-piperidin-4-yl, 1-(5-carboxy-pyrid-2-yl-methyl)-piperidin-4-yl, 1-(6-carboxy-pyrid-2-yl-methyl)-piperidin-4-yl, 1-(5-carboxy-thien-2-yl-methyl)-piperidin-4-yl, 1-(3-carboxy-benzyl)-piperidin-4-yl, 1-(3-carboxy-phenyl-sulfonyl)-piperidin-4-yl, 1-(3-hydroxy-phenyl-sulfonyl)-piperidin-4-yl, 1-trifluoromethyl-sulfonyl-piperidin-4-yl-methyl-, 1-trifluoromethyl-sulfonyl-piperidin-4-yl.

In additional embodiments, the present invention is directed to compounds of formula (I) wherein the substituents selected for the variables defined herein (e.g.


R⁰, R¹, R² and R³, etc.) are independently selected to be any individual substituent or any subset of substituents selected from the substituents found on compounds listed in Table BIO-1 as exhibiting CB-1 binding EC₅₀ (as measured according to the procedure described in Biological Example 1) of less than about 0.1 μM, preferably exhibiting CB-1 binding EC₅₀ of less than about 0.01 μM, more preferably, exhibiting CB-1 binding EC₅₀ less than about 0.05 μM, more preferably, exhibiting CB-1 binding EC₅₀ less than about 0.025 μM.

Additional embodiments, the present invention is directed to compound of formula (I), wherein the substituents selected for one or more of the variables defined herein (e.g.

R⁰, R¹, R² and R³, etc.) are independently selected to be any individual substituent or any subset of substituents selected from the complete list as defined herein.

Additional embodiments of the present invention, include those wherein the substituents selected for one or more of the variables defined herein (e.g.

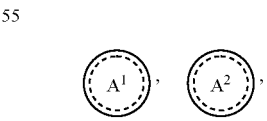

R⁰, R¹, R² and R³, etc.) are independently selected to be any individual substituent or subset of substituents selected from those exemplified in the Tables which follow herein.

In additional embodiments, the present invention is directed to any single compound or subset of compounds selected from the representative compounds listed in Tables 1-5 below.

Representative compounds of the present invention are as listed in Tables 1-5, below. Unless otherwise noted, wherein a stereogenic center is present in the listed compound, the compound was prepared as a mixture of stereo-configurations. Where a stereogenic center is present, the S*— and R* designations are intended to indicate that the exact stereo-configuration of the center has not been determined.

TABLE 1

Representative Compounds of Formula (I)

| ID No. | A¹ | A² | R² | Stereo* | R⁴ |
|---|---|---|---|---|---|
| 21 | 4-chlorophenyl | 4-chlorophenyl | cyclopropyl | trans-cyclohexyl | 4-carboxy-phenyl-sulfonyl-amino- |
| 22 | 4-chlorophenyl | 4-chlorophenyl | cyclopropyl | trans-cyclohexyl | 3-carboxy-phenyl-sulfonyl-amino- |
| 28 | 4-chlorophenyl | 4-chlorophenyl | cyclopropyl | trans-cyclohexyl | 3-hydroxy-phenyl-amino- |
| 29 | 4-chlorophenyl | 4-chlorophenyl | cyclopropyl | cis-cyclohexyl | 3-hydroxy-phenyl-amino- |
| 30 | 4-chlorophenyl | 4-chlorophenyl | cyclopropyl | trans-cyclohexyl | 4-carboxy-phenyl-amino- |
| 31 | 4-chlorophenyl | 4-chlorophenyl | cyclopropyl | trans-cyclohexyl | 3-carboxy-phenyl-amino- |
| 32 | 4-chlorophenyl | 4-chlorophenyl | cyclopropyl | cis-cyclohexyl | 4-carboxy-phenyl-amino- |
| 40 | 4-chlorophenyl | 4-chlorophenyl | cyclopropyl | cis-cyclohexyl | 3-carboxy-phenyl-amino- |
| 42 | 4-chlorophenyl | 4-chlorophenyl | cyclopropyl | cis-cyclohexyl | 4-carboxy-phenyl-sulfonyl-amino- |
| 43 | 4-chlorophenyl | 4-chlorophenyl | cyclopropyl | cis-cyclohexyl | 3-carboxy-phenyl-sulfonyl-amino- |
| 134 | 4-chlorophenyl | 4-chlorophenyl | cyclopropyl | trans-cyclohexyl | carboxy |
| 135 | 4-chlorophenyl | 4-chlorophenyl | cyclopropyl | trans-cyclohexyl | amino-carbonyl- |
| 136 | 4-chlorophenyl | 4-chlorophenyl | cyclopropyl | cis-cyclohexyl | amino-carbonyl- |
| 137 | 4-chlorophenyl | 4-chlorophenyl | cyclopropyl | cis-cyclohexyl | carboxy |
| 442 | 4-chlorophenyl | thiazol-2-yl | 4-chlorophenyl | cyclohexyl | H |
| 444 | 4-chlorophenyl | thiazol-2-yl | 2,4-dichlorophenyl | cyclohexyl | H |
| 446 | 4-chlorophenyl | thiazol-2-yl | methyl | cyclohexyl | H |
| 465 | 4-chlorophenyl | thiazol-2-yl | H | cyclohexyl | H |

*The column headed "Stereo" indicates the stereo-orientation of the bonds at the 1- and 4-positions of the cyclohexyl ring. Where neither "cis-" nor "trans-" is indicated, the compound was prepared as a racemate.

TABLE 2

Representative Compounds of Formula (I)

| ID No. | R⁰ | A¹ | A² | R² | (L²)ᵦ | R⁶ and R⁷* |
|---|---|---|---|---|---|---|
| 6 | H | 4-chlorophenyl | 4-chlorophenyl | cyclopropyl | —CH₂CH₂— | 3-(5-carboxy-thien-2-yl) |
| 7 | H | 4-chlorophenyl | 4-chlorophenyl | cyclopropyl | —CH₂CH₂O— | 3-bromo |
| 8 | H | 4-chlorophenyl | 4-chlorophenyl | cyclopropyl | —CH₂CH₂—CH₂—NH—SO₂— | 3-(4-carboxy-phenyl) |
| 9 | H | 4-chlorophenyl | 4-chlorophenyl | cyclopropyl | —CH₂CH₂—CH₂—NH—SO₂— | 3-bromo |
| 11 | H | 4-chlorophenyl | 4-chlorophenyl | cyclopropyl | —CH₂CH₂— | 3-(3-carboxy-phenyl) |

TABLE 2-continued

Representative Compounds of Formula (I)

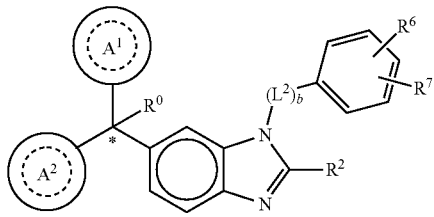

| ID No. | R⁰ | A¹ | A² | R² | (L²)_b | R⁶ and R⁷* |
|---|---|---|---|---|---|---|
| 16 | H | 4-chlorophenyl | 4-chlorophenyl | cyclopropyl | —CH₂CH₂O— | 3-carboxy-5-trifluoromethyl |
| 17 | H | 4-chlorophenyl | 4-chlorophenyl | cyclopropyl | —CH₂CH₂— | 3-(4-carboxyphenyl) |
| 18 | H | 4-chlorophenyl | 4-chlorophenyl | cyclopropyl | —CH₂CH₂O— | 3-methoxycarbonyl-5-trifluoromethyl |
| 19 | CO₂H | 4-chlorophenyl | 4-chlorophenyl | cyclopropyl | —CH₂CH₂— | 3-bromo |
| 20 | H | 4-chlorophenyl | 4-chlorophenyl | cyclopropyl | —CH₂CH₂— | 3-bromo |
| 23 | H | 4-chlorophenyl | 4-chlorophenyl | cyclopropyl | —CH₂CH₂O— | 3-carboxy |
| 24 | H | 4-chlorophenyl | 4-chlorophenyl | cyclopropyl | —CH₂CH₂— | 4-(3-carboxyphenyl) |
| 25 | H | 4-chlorophenyl | 4-chlorophenyl | cyclopropyl | —CH₂CH₂— | 4-(4-carboxyphenyl) |
| 26 | H | 4-chlorophenyl | 4-chlorophenyl | cyclopropyl | —CH₂CH₂O— | 3-methoxycarbonyl- |
| 27 | H | 4-chlorophenyl | 4-chlorophenyl | cyclopropyl | —CH₂CH₂— | 4-bromo- |
| 35 | H | 4-chlorophenyl | 4-chlorophenyl | cyclopropyl | —CH₂CH₂O— | 4-carboxy |
| 36 | H | 4-chlorophenyl | 4-chlorophenyl | cyclopropyl | —CH₂CH₂O— | 4-methoxycarbonyl- |
| 37 | H | 4-chlorophenyl | 4-chlorophenyl | cyclopropyl | —CH₂CH₂— | 4-hydroxy |
| 38 | H | 4-chlorophenyl | 4-chlorophenyl | cyclopropyl | —CH₂CH₂— | 4-carboxy |
| 132 | H | 4-chlorophenyl | 4-chlorophenyl | cyclopropyl | —CH₂— | 4-carboxy |
| 133 | H | 4-chlorophenyl | 4-chlorophenyl | cyclopropyl | —CH₂— | 4-aminocarbonyl |
| 144 | H | 4-chlorophenyl | 4-chlorophenyl | cyclopropyl | —CH₂— | 3-(ethoxycarbonylmethoxy-) |
| 145 | H | 4-chlorophenyl | 4-chlorophenyl | cyclopropyl | —CH₂— | 3-hydroxy |
| 146 | H | 4-chlorophenyl | 4-chlorophenyl | cyclopropyl | —CH₂— | 3-methoxy |
| 165 | H | 4-chlorophenyl | 4-chlorophenyl | cyclopropyl | b = 0 | 4-carboxymethoxy- |
| 169 | H | 4-chlorophenyl | 4-chlorophenyl | cyclopropyl | b = 0 | 4-aminocarbonylmethoxy- |
| 170 | H | 4-chlorophenyl | 4-chlorophenyl | cyclopropyl | b = 0 | 4-ethoxycarbonylmethoxy- |
| 171 | H | 4-chlorophenyl | 4-chlorophenyl | cyclopropyl | b = 0 | 4-hydroxy |
| 172 | H | 4-chlorophenyl | 4-chlorophenyl | cyclopropyl | b = 0 | 3-aminocarbonylmethoxy- |
| 173 | H | 4-chlorophenyl | 4-chlorophenyl | cyclopropyl | b = 0 | 3-ethoxycarbonylmethoxy- |
| 174 | H | 4-chlorophenyl | 4-chlorophenyl | cyclopropyl | b = 0 | 3-carboxymethoxy- |

TABLE 2-continued

Representative Compounds of Formula (I)

| ID No. | R⁰ | A¹ | A² | R² | (L²)_b | R⁶ and R⁷* |
|---|---|---|---|---|---|---|
| 175 | H | 4-chlorophenyl | 4-chlorophenyl | cyclopropyl | —CH₂— | 4-ethoxycarbonylmethoxy- |
| 176 | H | 4-chlorophenyl | 4-chlorophenyl | cyclopropyl | —CH₂— | 4-carboxymethoxy- |
| 177 | H | 4-chlorophenyl | 4-chlorophenyl | cyclopropyl | —CH₂— | 4-methoxy |
| 179 | H | 4-chlorophenyl | 4-chlorophenyl | cyclopropyl | b = 0 | 4-methoxy |
| 180 | H | 4-chlorophenyl | 4-chlorophenyl | cyclopropyl | b = 0 | 3-hydroxy |
| 181 | H | 4-chlorophenyl | 4-chlorophenyl | cyclopropyl | b = 0 | 3-methoxy |
| 182 | H | 4-chlorophenyl | 4-chlorophenyl | cyclopropyl | —CH₂— | 4-aminocarbonylmethoxy- |
| 183 | H | 4-chlorophenyl | 4-chlorophenyl | cyclopropyl | —CH₂— | 4-hydroxy |
| 268 | H | 4-chlorophenyl | 4-chlorophenyl | cyclopropyl | —CH₂—CH(OH)— | — |
| 286 | H | 4-chlorophenyl | 4-chlorophenyl | ethyl | —CH(CH₃)—CH₂— | 4-chloro |
| 289 | H | 4-chlorophenyl | 4-chlorophenyl | cyclopropyl | —CH₂—CH(R*—OH)— | — |
| 299 | H | 4-chlorophenyl | 4-chlorophenyl | cyclopropyl | —CH(CH₃)—CH(OH)— | — |
| 301 | H | 4-chlorophenyl | 4-chlorophenyl | cyclopropyl | —CH₂—CH(OH)— | — |
| 305 | H | phenyl | phenyl | cyclopropyl | —CH₂—CH(S*—CH₃)— | — |
| 306 | H | phenyl | 4-chlorophenyl | cyclopropyl | —CH₂—CH(S*—CH₃)— | — |
| 309 | H | 4-chlorophenyl | 4-chlorophenyl | cyclopropyl | —CH₂CH₂— | 4-trifluoromethyl- |
| 311 | H | 4-chlorophenyl | 4-chlorophenyl | ethyl | —CH₂CH₂— | 3-chloro |
| 312 | H | 4-chlorophenyl | 4-chlorophenyl | ethyl | —CH₂—CH(S*—CH₃)— | — |
| 313 | H | 4-chlorophenyl | 4-chlorophenyl | methyl | —CH₂—CH(S*—CH₃)— | — |
| 314 | H | 4-chlorophenyl | 4-chlorophenyl | ethyl | —CH₂CH₂ | 4-trifluoromethyl- |
| 317 | H | 4-chlorophenyl | 4-chlorophenyl | ethyl | —CH₂—CH(R*—CH₃)— | — |
| 329 | H | 4-chlorophenyl | thiazol-2-yl | —CHF₂ | —CH(CH₃)—CH₂— | 4-chloro |
| 330 | H | 4-chlorophenyl | thiazol-2-yl | ethyl | —CH(CH₃)—CH₂— | 4-chloro |
| 331 | H | 4-chlorophenyl | thiazol-2-yl | cyclopropyl | —CH(CH₃)—CH₂— | 4-chloro |
| 333 | H | 4-chlorophenyl | thiazol-2-yl | cyclopropyl | —CH₂—CH(OH)— | 4-chloro |
| 334 | H | 4-chlorophenyl | thiazol-2-yl | ethyl | —CH₂—CH(OH)— | 4-chloro |
| 336 | H | 4-chlorophenyl | thiazol-2-yl | cyclopropyl | —CH₂—CH(CH₃)— | 4-chloro |
| 337 | H | 4-chlorophenyl | thiazol-2-yl | 2,2,2-trifluoroethyl | —CH₂—CH(CH₃)— | 4-chloro |
| 338 | H | 4-chlorophenyl | thiazol-2-yl | cyclopropyl | —CH₂CH₂— | 4-chloro |

TABLE 2-continued

Representative Compounds of Formula (I)

| ID No. | R⁰ | A¹ | A² | R² | (L²)_b | R⁶ and R⁷* |
|---|---|---|---|---|---|---|
| 339 | OH | 4-chloro-phenyl | thiazol-2-yl | 2,2,2-trifluoro-ethyl | —CH₂CH₂— | 3-chloro |
| 340 | H | 4-chloro-phenyl | thiazol-2-yl | 2,2,2-trifluoro ethyl | —CH₂CH₂— | 3-chloro |
| 374 | H | 4-chloro-phenyl | thiazol-2-yl | —CH₂—OH | b = 0 | 3-chloro |
| 375 | H | 4-chloro-phenyl | thiazol-2-yl | thien-3-yl | b = 0 | 3-chloro |
| 376 | H | 4-chloro-phenyl | thiazol-2-yl | fur-3-yl | b = 0 | 3-chloro |
| 377 | H | 4-chloro-phenyl | thiazol-2-yl | fur-2-yl | b = 0 | 3-chloro |
| 401 | H | 4-chloro-phenyl | thiazol-2-yl | cyclo-propyl | —CH(CH₃)— | 4-chloro |
| 402 | H | 4-chloro-phenyl | thiazol-2-yl | iso-propyl | b = 0 | 3-chloro |
| 404 | H | 4-chloro-phenyl | thiazol-2-yl | azetidin-3-yl | —CH₂CH₂— | 3-chloro |
| 405 | OH | 4-chloro-phenyl | thiazol-2-yl | H | —CH₂CH₂— | 3-chloro |
| 406 | H | 4-chloro-phenyl | thiazol-2-yl | 1-t-butoxy-carbonyl-azetidin-3-yl | —CH₂CH₂— | 3-chloro |
| 409 | H | 4-chloro-phenyl | thiazol-2-yl | ethyl | —CH₂CH₂— | 3-chloro |
| 410 | H | 4-chloro-phenyl | thiazol-2-yl | n-propyl | —CH₂CH₂— | 3-chloro |
| 423 | H | 4-chloro-phenyl | thiazol-2-yl | cyclo-propyl | —CH₂CH₂— | 3-chloro |
| 424 | H | 4-chloro-phenyl | thiazol-2-yl | —CF₃ | —CH₂CH₂— | 3-chloro |
| 429 | H | 4-chloro-phenyl | thiazol-2-yl | —C(O)O—CH₂CH₃ | b = 0 | 3-chloro |
| 431 | H | 4-chloro-phenyl | thiazol-2-yl | n-propyl | b = 0 | 3-chloro |
| 432 | H | 4-chloro-phenyl | thiazol-2-yl | cyclo-propyl | b = 0 | 3-chloro |
| 433 | H | 4-chloro-phenyl | thiazol-2-yl | isobutyl | b = 0 | 3-chloro |
| 434 | H | 4-chloro-phenyl | thiazol-2-yl | ethyl | b = 0 | 3-chloro |
| 435 | H | 4-chloro-phenyl | thiazol-2-yl | H | b = o | 3-chloro |
| 436 | H | 4-chloro-phenyl | thiazol-2-yl | methyl | b = 0 | 3-chloro |
| 437 | H | 4-chloro-phenyl | thiazol-2-yl | methyl | —CH₂CH₂— | 3-chloro |
| 438 | H | 4-chloro-phenyl | thiazol-2-yl | H | —CH₂CH₂— | 3-chloro |
| 449 | H | 4-chloro-phenyl | 4-t-butyl-thiazol-2-yl | H | —CH₂— | 4-chloro |
| 451 | H | 4-chloro-phenyl | 5-ethyl-thiazol-2-yl | methyl | —CH₂— | 4-chloro |
| 452 | H | 4-chloro-phenyl | 4-ethyl-thiazol-2-yl | methyl | —CH₂— | 4-chloro |

TABLE 2-continued

Representative Compounds of Formula (I)

| ID No. | R⁰ | A¹ | A² | R² | (L²)_b | R⁶ and R⁷* |
|---|---|---|---|---|---|---|
| 455 | H | 4-chloro-phenyl | 4-trifluoro-methyl-thiazol-2-yl | methyl | —CH₂— | 4-chloro |
| 456 | H | 4-chloro-phenyl | 4-ethyl-thiazol-2-yl | 4-chloro-phenyl | —CH₂— | 4-chloro |
| 460 | H | 4-chloro-phenyl | 4-ethyl-thiazol-2-yl | H | —CH₂— | 4-chloro |
| 462 | H | 4-chloro-phenyl | 4-trifluoro-methyl-thiazol-2-yl | H | —CH₂— | 4-chloro |
| 463 | H | 4-chloro-phenyl | thiazol-2-yl | methyl | —CH₂— | 4-chloro |
| 464 | H | 4-chloro-phenyl | thiazol-2-yl | 4-chloro-phenyl | —CH₂— | 4-chloro |
| 466 | H | 4-chloro-phenyl | thiazol-2-yl | H | —CH₂— | 4-chloro |
| 474 | H | 2-chloro-phenyl | thiazol-2-yl | H | —CH₂— | — |

*In the column titled "R⁶ and R⁷", if no substituent group(s) are listed, then both R⁶ and R⁷ are hydrogen; if only one substituent group is listed, then one of R⁶ or R⁷ is hydrogen.

TABLE 3

Representative Compounds of Formula (I)

| ID No. | R⁰ | A¹ | A² | R² | R³ |
|---|---|---|---|---|---|
| 33 | H | 4-chloro-phenyl | 4-chloro-phenyl | cyclo-propyl | 5-carboxy-pyrid-2-yl-O—CH₂CH₂— |
| 34 | H | 4-chloro-phenyl | 4-chloro-phenyl | cyclo-propyl | 5-(methoxy-carbonyl)-pyrid-2-yl-O—CH₂CH₂— |
| 119 | H | 4-chloro-phenyl | 4-chloro-phenyl | cyclo-propyl | tetrahydro-pyran-4-yl |
| 120 | H | 4-chloro-phenyl | 4-chloro-phenyl | cyclo-propyl | tetrahydro-pyran-4-yl-CH₂— |
| 297 | H | 4-chloro-phenyl | 4-chloro-phenyl | ethyl | 2,3-dihydro-1H-inden-2-yl |
| 298 | H | 4-chloro-phenyl | 4-chloro-phenyl | H | 2,3-dihydro-1H-inden-2-yl |
| 300 | H | 4-chloro-phenyl | 4-chloro-phenyl | cyclo-propyl | 2,3-dihydro-1H-inden-2-yl |
| 341 | OH | 4-chloro-phenyl | thiazol-2-yl | cyclo-propyl | 1,2,3,4-tetrahydro-naphth-2-yl |
| 342 | H | 4-chloro-phenyl | thiazol-2-yl | cyclo-propyl | 1,2,3,4-tetrahydro-naphth-2-yl |
| 361 | H | 4-chloro-phenyl | thiazol-2-yl | methyl | 2,3-dihydro-1H-inden-2-yl |
| 362 | H | 4-chloro-phenyl | thiazol-2-yl | cyclo-propyl | 2,3-dihydro-1H-inden-2-yl |
| 403 | H | 4-chloro-phenyl | thiazol-2-yl | cyclo-propyl | pyrid-2-yl-CH₂— |

TABLE 4

Representative Compounds of Formula (I)

| ID No. | R⁰ | A¹ | A² | R¹ | R² | (L¹)ₐ | R⁵ |
|---|---|---|---|---|---|---|---|
| 1 | H | 4-chlorophenyl | 4-chlorophenyl | H | cyclopropyl | —CH₂— | 4-carboxyphenyl |
| 2 | H | 4-chlorophenyl | 4-chlorophenyl | H | cyclopropyl | —CH₂— | 4-carboxypyrimidin-2-yl |
| 3 | H | 4-chlorophenyl | 4-chlorophenyl | H | cyclopropyl | a = 0 | 3-(hex-2-en-1-yloxy)-benzyl |
| 4 | H | 4-chlorophenyl | 4-chlorophenyl | H | cyclopropyl | —CH₂— | 5-carboxypyrimidin-2-yl |
| 5 | H | 4-chlorophenyl | 4-chlorophenyl | H | cyclopropyl | —CH₂— | 5-methoxycarbonylpyrimidin-2-yl |
| 10 | H | 4-chlorophenyl | 4-chlorophenyl | H | cyclopropyl | —CH₂— | 3-carboxybenzyl |
| 12 | —CO₂H | 4-chlorophenyl | 4-chlorophenyl | H | cyclopropyl | —CH₂— | trifluoromethylsulfonyl |
| 13 | H | 4-chlorophenyl | 4-chlorophenyl | H | cyclopropyl | —CH₂— | 3-methoxycarbonylphenyl |
| 14 | —C(O)OCH₃ | 4-chlorophenyl | 4-chlorophenyl | H | cyclopropyl | —CH₂— | trifluoromethylsulfonyl |
| 15 | H | 4-chlorophenyl | 4-chlorophenyl | H | cyclopropyl | —CH₂— | 4-carboxyphenylsulfonyl |
| 41 | —OH | 4-chlorophenyl | 4-chlorophenyl | H | cyclopropyl | a = 0 | t-butoxycarbonyl |
| 44 | H | 4-chlorophenyl | 4-chlorophenyl | H | cyclopropyl | a = 0 | 3-carboxyphenyl-oxy-ethyl- |
| 45 | H | 4-chlorophenyl | 4-chlorophenyl | H | cyclopropyl | a = 0 | piperazin-1yl-ethyl-sulfonyl- |
| 46 | H | 4-chlorophenyl | 4-chlorophenyl | H | cyclopropyl | a = 0 | amino-ethyl-sulfonyl- |
| 47 | H | 4-chlorophenyl | 4-chlorophenyl | H | cyclopropyl | a = 0 | 1R*-(3-carboxyphenyl)-ethyl- |
| 48 | H | 4-chlorophenyl | 4-chlorophenyl | H | cyclopropyl | a = 0 | 1R*-(3-carboxyphenyl)-ethyl- |
| 49 | H | 4-chlorophenyl | 4-chlorophenyl | H | cyclopropyl | a = 0 | 1-(3-carboxyphenyl)-n-propyl |
| 50 | H | 4-chlorophenyl | 4-chlorophenyl | H | cyclopropyl | a = 0 | phenyl-aminocarbonyl- |
| 52 | H | 4-chlorophenyl | 4-chlorophenyl | H | cyclopropyl | a = 0 | 3-aminophenylsulfonyl- |
| 55 | H | 4-chlorophenyl | 4-chlorophenyl | H | cyclopropyl | a = 0 | 5-(hydroxymethyl)-fur-2-yl-sulfonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 56 | H | 4-chloro-phenyl | 4-chloro-phenyl | H | cyclo-propyl | a = 0 | 1-(3-hydroxy-phenyl)-ethyl- |
| 59 | H | 4-chloro-phenyl | 4-chloro-phenyl | H | cyclo-propyl | a = 0 | 1-(4-carboxy-pyrid-2-yl)-ethyl- |
| 61 | H | 4-chloro-phenyl | 4-chloro-phenyl | H | cyclo-propyl | a = 0 | phenoxy-carbonyl- |
| 63 | H | 4-chloro-phenyl | 4-chloro-phenyl | H | cyclo-propyl | a = 0 | carboxy-methyl- |
| 64 | H | 4-chloro-phenyl | 4-chloro-phenyl | H | cyclo-propyl | a = 0 | methoxy-carbonyl-methyl- |
| 69 | H | 4-chloro-phenyl | 4-chloro-phenyl | H | cyclo-propyl | a = 0 | benzyloxy-carbonyl- |
| 70 | H | 4-chloro-phenyl | 4-chloro-phenyl | H | cyclo-propyl | a = 0 | 3-(2-hydroxy-ethyl-amino-carbonyl)-benzyl |
| 71 | H | 4-chloro-phenyl | 4-chloro-phenyl | H | cyclo-propyl | a = 0 | cyclopentyl-oxy-carbonyl- |
| 72 | H | 4-chloro-phenyl | 4-chloro-phenyl | H | 2-carboxy-ethyl- | a = 0 | 3-methoxy-carbonyl-benzyl |
| 73 | H | 4-chloro-phenyl | 4-chloro-phenyl | H | cyclo-propyl | a = 0 | ethyl-amino-carbonyl- |
| 74 | H | 4-chloro-phenyl | 4-chloro-phenyl | H | cyclo-propyl | a = 0 | cyclopentyl-amino-carbonyl- |
| 75 | H | 4-chloro-phenyl | 4-chloro-phenyl | H | cyclo-propyl | a = 0 | benzyl-amino-carbonyl- |
| 76 | H | 4-chloro-phenyl | 4-chloro-phenyl | H | cyclo-propyl | a = 0 | propyn-3-yl |
| 77 | H | 4-chloro-phenyl | 4-chloro-phenyl | H | amino-ethyl- | a = 0 | 3-carboxy-benzyl |
| 78 | H | 4-chloro-phenyl | 4-chloro-phenyl | H | 2-carboxy-ethyl- | a = 0 | trifluoro-methyl-sulfonyl |
| 79 | H | 4-chloro-phenyl | 4-chloro-phenyl | H | cyclo-propyl | a = 0 | 2-hydroxy-3-carboxy-benzyl |
| 80 | H | 4-chloro-phenyl | 4-chloro-phenyl | H | cyclo-propyl | a = 0 | 2-trifluoro-methyl-5-carboxy-benzyl |
| 81 | H | 4-chloro-phenyl | 4-chloro-phenyl | H | cyclo-propyl | a = 0 | 3-carboxy-4-hydroxy-benzyl |
| 82 | H | 4-chloro-phenyl | 4-chloro-phenyl | H | cyclo-propyl | a = 0 | 2-hydroxy-5-carboxy-benzyl |
| 83 | H | 4-chloro-phenyl | 4-chloro-phenyl | H | cyclo-propyl | a = 0 | 2-carboxy-pyrid-4-yl-methyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 84 | H | 4-chloro-phenyl | 4-chloro-phenyl | H | cyclo-propyl | a = 0 | 2-trifluoro-methyl-benzyl |
| 85 | H | 4-chloro-phenyl | 4-chloro-phenyl | H | cyclo-propyl | a = 0 | 2-fluoro-3-carboxy-benzyl |
| 86 | H | 4-chloro-phenyl | 4-chloro-phenyl | H | cyclo-propyl | a = 0 | 1-(5-carboxy-fur-2-yl)-ethyl |
| 87 | H | 4-chloro-phenyl | 4-chloro-phenyl | H | cyclo-propyl | a = 0 | 1-(3-carboxy-phenyl)-ethyl |
| 88 | H | 4-chloro-phenyl | 4-chloro-phenyl | H | cyclo-propyl | a = 0 | 4-carboxy-pyrid-2-yl-methyl |
| 89 | H | 4-chloro-phenyl | 4-chloro-phenyl | H | cyclo-propyl | a = 0 | 3-fluoro-5-carboxy-benzyl |
| 90 | H | 4-chloro-phenyl | 4-chloro-phenyl | H | cyclo-propyl | a = 0 | 3-hydroxy-benzyl |
| 91 | H | 4-chloro-phenyl | 4-chloro-phenyl | H | cyclo-propyl | a = 0 | 2-chloro-3-carboxy-benzyl |
| 92 | H | 4-chloro-phenyl | 4-chloro-phenyl | H | cyclo-propyl | a = 0 | 2-fluoro-5-carboxy-benzyl |
| 93 | H | 4-chloro-phenyl | 4-chloro-phenyl | H | cyclo-propyl | a = 0 | 3-trifluoro-methyl-5-carboxy-benzyl |
| 94 | H | 4-chloro-phenyl | 4-chloro-phenyl | H | cyclo-propyl | a = 0 | 2-chloro-5-carboxy-benzyl |
| 95 | H | 4-chloro-phenyl | 4-chloro-phenyl | H | cyclo-propyl | a = 0 | 3-carboxy-4-fluoro-benzyl |
| 96 | H | 4-methyl-phenyl | 4-methyl-phenyl | H | cyclo-propyl | a = 0 | 3-carboxy-benzyl |
| 97 | H | 4-fluoro-phenyl | 4-fluoro-phenyl | H | cyclo-propyl | a = 0 | 3-carboxy-benzyl |
| 98 | H | 4-chloro-phenyl | 4-fluoro-phenyl | H | cyclo-propyl | a = 0 | 3-carboxy-benzyl |
| 99 | H | 4-chloro-phenyl | 4-trifluoro-methyl-phenyl | H | cyclo-propyl | a = 0 | 3-carboxy-benzyl |
| 100 | H | 4-chloro-phenyl | 4-methyl-phenyl | H | cyclo-propyl | a = 0 | 3-carboxy-benzyl |
| 101 | H | 4-chloro-phenyl | 4-chloro-phenyl | H | cyclo-propyl | a = 0 | 3-carboxy-benzyl |
| 102 | H | 4-chloro-phenyl | 4-chloro-phenyl | H | cyclo-propyl | a = 0 | 2,3,4-trihydroxy-n-butyl-oxy-carbonyl |
| 104 | H | 4-chloro-phenyl | 4-chloro-phenyl | H | cyclo-propyl | a = 0 | 6-amino-carbonyl-pyrid-2-yl-methyl |
| 105 | H | 4-chloro-phenyl | 4-chloro-phenyl | H | cyclo-propyl | a = 0 | 6-amino-carbonyl-pyrid-3-yl-methyl |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 106 | H | 4-chloro-phenyl | 4-chloro-phenyl | H | cyclo-propyl | a = 0 | 6-carboxy-pyrid-3-yl-methyl- |
| 118 | H | 4-chloro- | 4-chloro- | H | —C(=CH₂)—CH₂OH | a = 0 | trifluoro-methyl-sulfonyl |
| 121 | H | 4-chloro-phenyl | 4-chloro-phenyl | H | cyclo-propyl | a = 0 | 5-amino-carbonyl-pyrid-3-yl-methyl- |
| 122 | H | 4-chloro-phenyl | 4-chloro-phenyl | H | cyclo-propyl | a = 0 | 5-amino-carbonyl-pyrid-2-yl-methyl- |
| 123 | H | 4-chloro-phenyl | 4-chloro-phenyl | H | cyclo-propyl | a = 0 | 5-carboxy-pyrid-3-yl-methyl- |
| 124 | H | 4-chloro-phenyl | 4-chloro-phenyl | H | cyclo-propyl | a = 0 | 5-carboxy-pyrid-2-yl-methyl- |
| 125 | H | 4-chloro-phenyl | 4-chloro-phenyl | H | cyclo-propyl | a = 0 | 6-carboxy-pyrid-2-yl-methyl- |
| 126 | H | 4-chloro-phenyl | 4-chloro-phenyl | H | cyclo-propyl | a = 0 | 5-amino-carbonyl-thien-2-yl-methyl- |
| 127 | H | 4-chloro-phenyl | 4-chloro-phenyl | H | cyclo-propyl | a = 0 | 4-amino-carbonyl-thien-2-yl-methyl- |
| 128 | H | 4-chloro-phenyl | 4-chloro-phenyl | H | cyclo-propyl | a = 0 | 5-carboxy-thien-2-yl-methyl- |
| 129 | H | 4-chloro-phenyl | 4-chloro-phenyl | H | cyclo-propyl | a = 0 | 5-carboxy-fur-2-yl-methyl- |
| 130 | H | 4-chloro-phenyl | 4-chloro-phenyl | H | cyclo-propyl | a = 0 | 4-carboxy-thien-2-yl-methyl- |
| 131 | H | 4-chloro-phenyl | 4-chloro-phenyl | H | cyclo-propyl | a = 0 | 5-amino-carbonyl-fur-2-yl-methyl- |
| 138 | H | 4-chloro-phenyl | 4-chloro-phenyl | H | cyclo-propyl | a = 0 | 4-amino-carbonyl-benzyl |
| 140 | H | 4-chloro-phenyl | 4-carboxy-phenyl | H | cyclo-propyl | a = 0 | trifluoro-methyl-sulfonyl |
| 141 | H | 4-chloro-phenyl | 4-chloro-phenyl | H | cyclo-propyl | a = 0 | 3-amino-carbonyl-benzyl |
| 142 | H | 4-chloro-phenyl | 4-chloro-phenyl | H | cyclo-propyl | a = 0 | 4-(amino-carbonyl-methoxy)-phenyl |
| 143 | —CH₂—O—CH₂—CO₂H | 4-chloro-phenyl | 4-chloro-phenyl | H | cyclo-propyl | a = 0 | trifluoro-methyl-sulfonyl |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 147 | H | 4-chlorophenyl | 4-chlorophenyl | H | cyclopropyl | a = 0 | 4-carboxybenzyl |
| 148 | H | 4-chlorophenyl | 4-chlorophenyl | H | cyclopropyl | a = 0 | 3-carboxybenzyl |
| 150 | —OH | 4-chlorophenyl | 4-carboxyphenyl | H | cyclopropyl | a = 0 | trifluoromethylsulfonyl |
| 151 | H | 4-chlorophenyl | 4-chlorophenyl | H | cyclopropyl | a = 0 | 4-aminophenylsulfonyl- |
| 152 | H | 4-chlorophenyl | 4-chlorophenyl | H | cyclopropyl | a = 0 | 4-(carboxymethoxy)phenyl |
| 153 | H | 4-chlorophenyl | 4-chlorophenyl | H | cyclopropyl | a = 0 | 3-(aminocarbonylmethoxy)phenyl |
| 154 | H | 4-chlorophenyl | 4-chlorophenyl | H | cyclopropyl | a = 0 | 3-(carboxymethoxy)phenyl |
| 155 | H | 4-chlorophenyl | 4-chlorophenyl | H | cyclopropyl | a = 0 | 3-aminocarbonylmethylphenyl |
| 157 | H | 4-chlorophenyl | 4-chlorophenyl | H | cyclopropyl | a = 0 | 4-carboxymethylphenyl |
| 158 | H | 4-chlorophenyl | 4-chlorophenyl | H | cyclopropyl | a = 0 | 3-carboxymethylphenyl |
| 159 | H | 4-chlorophenyl | 4-chlorophenyl | H | cyclopropyl | a = 0 | 4-carboxyphenyl- |
| 160 | H | 4-chlorophenyl | 4-chlorophenyl | H | cyclopropyl | a = 0 | 4-aminocarbonylmethylphenyl |
| 161 | H | 4-chlorophenyl | 4-chlorophenyl | H | cyclopropyl | a = 0 | 4-aminocarbonylphenyl- |
| 162 | H | 4-chlorophenyl | 4-chlorophenyl | H | cyclopropyl | a = 0 | 3-aminocarbonylphenyl- |
| 163 | H | 4-chlorophenyl | 4-chlorophenyl | H | cyclopropyl | a = 0 | 3-carboxyphenyl |
| 164 | H | 4-chlorophenyl | 4-chlorophenyl | H | cyclopropyl | a = 0 | 6-(methoxycarbonylethyl-aminocarbonyl)-pyrid-3-ylsulfonyl- |
| 166 | H | 4-chlorophenyl | 4-chlorophenyl | H | cyclopropyl | a = 0 | 3-trifluoromethyl-4-carboxyphenylsulfonyl- |
| 167 | H | 4-chlorophenyl | 4-chlorophenyl | H | cyclopropyl | a = 0 | 6-(carboxyethyl-aminocarbonyl)-pyrid-3-ylsulfonyl |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 168 | H | 4-chloro-phenyl | 4-chloro-phenyl | H | cyclo-propyl | a = 0 | 3-amino-carbonyl-4-methyl-phenyl-sulfonyl- |
| 178 | —CH₂—OCH₃ | 4-chloro-phenyl | 4-chloro-phenyl | H | cyclo-propyl | a = 0 | 3-chloro-4-carboxy-phenyl-sulfonyl- |
| 184 | H | 4-chloro-phenyl | 4-chloro-phenyl | H | cyclo-propyl | a = 0 | 3-trifluoro-methyl-4-amino-carbonyl-phenyl-sulfonyl |
| 185 | H | 4-chloro-phenyl | 4-chloro-phenyl | H | cyclo-propyl | a = 0 | 3-(carboxy-ethyl-amino-carbonyl)-phenyl-sulfonyl |
| 186 | H | 4-chloro-phenyl | 4-chloro-phenyl | H | cyclo-propyl | a = 0 | 3-methylamino-carbonyl-phenyl-sulfonyl- |
| 187 | H | 4-chloro-phenyl | 4-chloro-phenyl | H | cyclo-propyl | a = 0 | 3-amino-carbonyl-4-methoxy-phenyl-sulfonyl- |
| 188 | H | 4-chloro-phenyl | 4-chloro-phenyl | H | cyclo-propyl | a = 0 | 3-carboxy-4-methyl-phenyl-sulfonyl- |
| 189 | H | 4-chloro-phenyl | 4-chloro-phenyl | H | cyclo-propyl | a = 0 | 3-fluoro-4-amino-carbonyl-phenyl-sulfonyl- |
| 190 | H | 4-chloro-phenyl | 4-chloro-phenyl | H | cyclo-propyl | a = 0 | 3-fluoro-4-carboxy-phenyl-sulfonyl- |
| 191 | H | 4-chloro-phenyl | 4-chloro-phenyl | H | cyclo-propyl | a = 0 | 3-(3-hydroxy-n-propyl-amino-carbonyl)-phenyl-sulfonyl- |
| 192 | —CH₂—OH | 4-chloro-phenyl | 4-chloro-phenyl | H | cyclo-propyl | a = 0 | 3-methoxy-4-amino-carbonyl-phenyl-sulfonyl- |
| 193 | —CH₂—OH | 4-chloro-phenyl | 4-chloro-phenyl | H | cyclo-propyl | a = 0 | 3-methoxy-4-carboxy-phenyl-sulfonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 198 | H | phenyl | phenyl | H | cyclopropyl | a = 0 | 1,2,3-triazol-4-yl-carbonyl- |
| 199 | H | 4-chlorophenyl | 4-chlorophenyl | H | cyclopropyl | a = 0 | 1,2,3-triazol-4-yl-carbonyl- |
| 200 | H | phenyl | phenyl | H | cyclopropyl | a = 0 | 1,2,4-triazol-3-yl-carbonyl- |
| 201 | H | 4-chlorophenyl | 4-chlorophenyl | H | cyclopropyl | a = 0 | 1,2,4-triazol-3-yl-carbonyl- |
| 202 | H | 4-chlorophenyl | 4-chlorophenyl | —OH | cyclopropyl | a = 0 | trifluoromethylsulfonyl |
| 203 | H | 4-chlorophenyl | 4-chlorophenyl | H | cyclopropyl | a = 0 | 3-(2-(methoxycarbonyl)-ethyl-aminocarbonyl)-phenylsulfonyl- |
| 204 | H | 4-chlorophenyl | 4-chlorophenyl | H | cyclopropyl | a = 0 | 6-(2-hydroxyethyl-aminocarbonyl)-pyrid-3-yl-sulfonyl- |
| 205 | H | 4-chlorophenyl | 4-chlorophenyl | H | cyclopropyl | a = 0 | 3-(2-hydroxyethyl-aminocarbonyl)-phenylsulfonyl- |
| 206 | H | 4-chlorophenyl | 4-chlorophenyl | H | cyclopropyl | a = 0 | 3-methyl-4-aminocarbonyl-phenylsulfonyl- |
| 207 | H | 4-chlorophenyl | 4-chlorophenyl | H | cyclopropyl | a = 0 | 3-methyl-4-carboxyphenylsulfonyl- |
| 211 | H | 4-chlorophenyl | 4-chlorophenyl | H | cyclopropyl | a = 0 | 3-carboxy-4-methoxyphenylsulfonyl- |
| 212 | —CH₂—OH | 4-chlorophenyl | 4-chlorophenyl | H | cyclopropyl | a = 0 | 3-chloro-4-aminocarbonyl-phenylsulfonyl- |
| 213 | —CH₂—OH | 4-chlorophenyl | 4-chlorophenyl | H | cyclopropyl | a = 0 | 3-chloro-4-carboxyphenylsulfonyl- |
| 214 | H | 4-chlorophenyl | 4-chlorophenyl | H | cyclopropyl | a = 0 | 3-carboxy-4-chlorophenylsulfonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 215 | H | 4-chloro-phenyl | 4-chloro-phenyl | H | cyclo-propyl | a = 0 | 3-methyl-5-amino-carbonyl-thien-2-yl-sulfonyl- |
| 216 | H | 4-chloro-phenyl | 4-chloro-phenyl | H | cyclo-propyl | a = 0 | 4-amino-carbonyl-thien-2-yl-sulfonyl- |
| 217 | H | 4-chloro-phenyl | 4-chloro-phenyl | H | cyclo-propyl | a = 0 | 3-amino-carbonyl-4-fluoro-phenyl-sulfonyl- |
| 218 | H | 4-chloro-phenyl | 4-chloro-phenyl | H | cyclo-propyl | a = 0 | 3-methyl-5-carboxy-thien-2-yl-sulfonyl- |
| 220 | H | 4-chloro-phenyl | 4-chloro-phenyl | H | cyclo-propyl | a = 0 | 3-fluoro-4-hydroxy-phenyl-sulfonyl- |
| 221 | H | 4-chloro-phenyl | 4-chloro-phenyl | H | cyclo-propyl | a = 0 | 4-carboxy-thien-2-yl-sulfonyl- |
| 222 | H | 4-chloro-phenyl | 4-chloro-phenyl | H | cyclo-propyl | a = 0 | 3,5-dichloro-4-hydroxy-phenyl-sulfonyl- |
| 223 | H | 4-chloro-phenyl | 4-chloro-phenyl | H | cyclo-propyl | a = 0 | 6-amino-carbonyl-pyrid-3-yl-carbonyl- |
| 224 | H | 4-chloro-phenyl | 4-chloro-phenyl | H | cyclo-propyl | a = 0 | 5-amino-carbonyl-fur-2-yl-sulfonyl- |
| 225 | H | 4-chloro-phenyl | 4-chloro-phenyl | H | cyclo-propyl | a = 0 | 3-fluoro-4-methoxy-phenyl-sulfonyl- |
| 226 | H | 4-chloro-phenyl | 4-chloro-phenyl | H | cyclo-propyl | a = 0 | 3-carboxy-4-fluoro-phenyl-sulfonyl- |
| 227 | —CH₂—OH | 4-chloro-phenyl | 4-chloro-phenyl | H | cyclo-propyl | a = 0 | 4-amino-carbonyl-phenyl-sulfonyl- |
| 228 | —CH₂—OH | 4-chloro-phenyl | 4-chloro-phenyl | H | cyclo-propyl | a = 0 | 4-carboxy-phenyl-sulfonyl- |
| 229 | H | 4-chloro-phenyl | 4-chloro-phenyl | H | cyclo-propyl | a = 0 | 3-amino-sulfonyl-phenyl-carbonyl- |
| 230 | H | 4-chloro-phenyl | 4-chloro-phenyl | H | cyclo-propyl | a = 0 | 4-amino-sulfonyl-phenyl-carbonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 231 | H | 4-chlorophenyl | 4-chlorophenyl | H | cyclopropyl | a = 0 | 6-carboxy-pyrid-3-yl-carbonyl- |
| 232 | H | 4-chlorophenyl | 4-chlorophenyl | H | cyclopropyl | a = 0 | 5-carboxy-fur-2-yl-sulfonyl- |
| 234 | H | 4-chlorophenyl | 4-chlorophenyl | H | cyclopropyl | a = 0 | 2-hydroxy-ethyl-carbonyl- |
| 235 | H | 4-chlorophenyl | 4-chlorophenyl | H | cyclopropyl | a = 0 | carboxy-ethyl-sulfonyl- |
| 238 | H | 4-chlorophenyl | 4-chlorophenyl | H | cyclopropyl | a = 0 | 6-amino-carbonyl-pyrid-3-yl-sulfonyl- |
| 239 | H | 4-chlorophenyl | 4-chlorophenyl | H | cyclopropyl | a = 0 | 6-carboxy-pyrid-3-yl-sulfonyl- |
| 240 | H | 4-chlorophenyl | 4-chlorophenyl | H | cyclopropyl | a = 0 | hydroxy-methyl-carbonyl- |
| 241 | H | 4-chlorophenyl | 4-chlorophenyl | H | cyclopropyl | a = 0 | 2-carboxy-phenyl-sulfonyl- |
| 242 | H | 4-chlorophenyl | 4-chlorophenyl | H | cyclopropyl | a = 0 | 3-carboxy-phenyl-sulfonyl- |
| 243 | H | 4-chlorophenyl | 4-chlorophenyl | H | cyclopropyl | a = 0 | 2-amino-carbonyl-phenyl-sulfonyl- |
| 244 | —CH₂—OH | 4-chlorophenyl | 4-chlorophenyl | H | ethyl | a = 0 | trifluoro-methyl-sulfonyl |
| 245 | —CH₂—OH | 4-chlorophenyl | 4-chlorophenyl | H | cyclopropyl | a = 0 | trifluoro-methyl-sulfonyl |
| 246 | H | 4-chlorophenyl | 4-chlorophenyl | H | cyclopropyl | a = 0 | 4-carboxy-phenyl-carbonyl- |
| 247 | H | 4-chlorophenyl | 4-chlorophenyl | H | cyclopropyl | a = 0 | amino-carbonyl-methyl-sulfonyl- |
| 248 | H | 4-chlorophenyl | 4-chlorophenyl | H | cyclopropyl | a = 0 | carboxy-methyl-sulfonyl- |
| 249 | H | 4-chlorophenyl | 4-chlorophenyl | H | cyclopropyl | a = 0 | 4-amino-carbonyl-methoxy-phenyl-sulfonyl- |
| 250 | H | 4-chlorophenyl | 4-chlorophenyl | H | cyclopropyl | a = 0 | carbonyl-phenyl-sulfonyl- |
| 251 | H | 4-chlorophenyl | 4-chlorophenyl | H | cyclopropyl | a = 0 | 3-methoxy-4-carboxy-phenyl-sulfonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 252 | H | 4-chloro-phenyl | 4-chloro-phenyl | H | cyclo-propyl | a = 0 | 3-chloro-4-amino-carbonyl-phenyl-sulfonyl- |
| 253 | H | 4-chloro-phenyl | 4-chloro-phenyl | H | cyclo-propyl | a = 0 | 3-chloro-4-carboxy-phenyl-sulfonyl- |
| 254 | H | 4-chloro-phenyl | 4-chloro-phenyl | H | cyclo-propyl | a = 0 | 4-amino-carbonyl-phenyl-carbonyl- |
| 255 | OH | 4-chloro-phenyl | 4-chloro-phenyl | H | oxetan-3-yl | a = 0 | trifluoro-methyl-sulfonyl |
| 256 | H | 4-chloro-phenyl | 4-chloro-phenyl | H | cyclo-propyl | a = 0 | 4-carboxy-methoxy-phenyl-sulfonyl- |
| 257 | H | 4-chloro-phenyl | 4-chloro-phenyl | H | cyclo-propyl | a = 0 | 4-hydroxy-phenyl-sulfonyl- |
| 258 | H | 4-chloro-phenyl | 4-chloro-phenyl | H | cyclo-propyl | a = 0 | 2-hydroxy-phenyl-sulfonyl- |
| 259 | H | 4-chloro-phenyl | 4-chloro-phenyl | H | cyclo-propyl | a = 0 | 3-hydroxy-phenyl-sulfonyl- |
| 260 | H | 4-chloro-phenyl | 4-chloro-phenyl | H | cyclo-propyl | a = 0 | 3-amino-carbonyl-phenyl-sulfonyl- |
| 261 | H | 4-chloro-phenyl | 4-chloro-phenyl | H | cyclo-propyl | a = 0 | 3-methoxy-phenyl-sulfonyl- |
| 262 | H | 4-chloro-phenyl | 4-chloro-phenyl | H | cyclo-propyl | a = 0 | 4-amino-carbonyl-phenyl-sulfonyl- |
| 266 | —CO₂H | 4-chloro-phenyl | 4-chloro-phenyl | H | ethyl | a = 0 | trifluoro-methyl-sulfonyl |
| 267 | —CO₂H | 4-chloro-phenyl | 4-chloro-phenyl | H | cyclo-propyl | a = 0 | trifluoro-methyl-sulfonyl |
| 269 | H | 4-chloro-phenyl | 4-chloro-phenyl | H | cyclo-propyl | a = 0 | 2-carboxy-ethyl-carbonyl- |
| 270 | H | 4-chloro-phenyl | 4-chloro-phenyl | H | cyclo-propyl | a = 0 | methyl-sulfonyl- |
| 271 | H | 4-chloro-phenyl | 4-chloro-phenyl | H | tetra-hydro-fur-2-yl | a = 0 | trifluoro-methyl-sulfonyl |
| 272 | H | 4-chloro-phenyl | 4-chloro-phenyl | H | cyclo-propyl | a = 0 | 2-trifluoro-methyl-phenyl-sulfonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 273 | H | 4-chlorophenyl | 4-chlorophenyl | H | cyclopropyl | a = 0 | 2-aminocarbonyl-ethyl-carbonyl- |
| 274 | H | 4-chlorophenyl | 4-chlorophenyl | H | cyclopropyl | a = 0 | aminosulfonyl- |
| 275 | H | 4-chlorophenyl | 4-chlorophenyl | H | cyclopropyl | a = 0 | 2-methoxyphenyl-sulfonyl- |
| 276 | H | 4-chlorophenyl | 4-chlorophenyl | H | cyclopropyl | a = 0 | 4-carboxyphenyl-sulfonyl- |
| 277 | H | 4-chlorophenyl | 4-chlorophenyl | H | cyclopropyl | a = 0 | 4-chlorophenyl-sulfonyl- |
| 278 | H | 4-chlorophenyl | 4-chlorophenyl | H | cyclopropyl | a = 0 | aminocarbonyl-methyl-carbonyl- |
| 279 | H | 4-chlorophenyl | 4-chlorophenyl | H | cyclopropyl | a = 0 | 4-trifluoromethoxy-phenyl-sulfonyl- |
| 280 | H | 4-chlorophenyl | 4-chlorophenyl | H | cyclopropyl | a = 0 | 4-trifluoromethyl-phenyl-sulfonyl- |
| 281 | H | 4-chlorophenyl | 4-chlorophenyl | H | cyclopropyl | a = 0 | 4-methoxyphenyl-sulfonyl- |
| 282 | H | 4-chlorophenyl | 4-chlorophenyl | H | cyclopropyl | a = 0 | 4-fluorophenyl-sulfonyl- |
| 283 | H | 4-chlorophenyl | 4-chlorophenyl | H | cyclopropyl | a = 0 | phenyl-sulfonyl- |
| 284 | H | 4-chlorophenyl | 4-chlorophenyl | H | cyclopropyl | a = 0 | 3-trifluoromethyl-phenyl-sulfonyl- |
| 285 | OH | 4-chlorophenyl | 4-chlorophenyl | H | tetrahydro-o-fur-2-yl | a = 0 | trifluoromethyl-sulfonyl |
| 287 | H | 4-chlorophenyl | 4-chlorophenyl | —O—CH₃ | cyclopropyl | a = 0 | trifluoromethyl-sulfonyl |
| 288 | H | 4-chlorophenyl | 4-chlorophenyl | H | cyclobutyl | —CH₂— | trifluoromethyl-sulfonyl |
| 291 | H | 4-chlorophenyl | 4-chlorophenyl | H | t-butyl | a = 0 | trifluoromethyl-sulfonyl |
| 292 | OH | 4-chlorophenyl | 4-chlorophenyl | H | t-butyl | a = 0 | trifluoromethyl-sulfonyl |
| 293 | OH | 4-chlorophenyl | 4-chlorophenyl | H | —CH₂OH | a = 0 | trifluoromethyl-sulfonyl |
| 294 | OH | 4-chlorophenyl | 4-chlorophenyl | H | cyclopropyl | —CH₂— | trifluoromethyl-sulfonyl |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 303 | OH | 4-chloro-phenyl | 4-chloro-phenyl | H | cyclo-propyl | a = 0 | trifluoro-methyl-sulfonyl |
| 308 | OH | 4-chloro-phenyl | 4-chloro-phenyl | H | ethyl | a = 0 | trifluoro-methyl-sulfonyl |
| 315 | H | 4-chloro-phenyl | 4-chloro-phenyl | H | ethyl | —CH₂— | trifluoro-methyl-sulfonyl |
| 316 | H | 4-chloro-phenyl | 4-chloro-phenyl | H | cyclo-propyl | —CH₂— | trifluoro-methyl-sulfonyl |
| 318 | H | 4-chloro-phenyl | 4-chloro-phenyl | H | cyclo-butyl | a = 0 | trifluoro-methyl-sulfonyl |
| 319 | OH | 4-chloro-phenyl | 4-chloro-phenyl | H | cyclo-butyl | a = 0 | trifluoro-methyl-sulfonyl |
| 320 | H | 4-methoxy-phenyl | 4-methoxy-phenyl | H | cyclo-butyl | a = 0 | trifluoro-methyl-sulfonyl |
| 321 | H | 4-chloro-phenyl | benzo[d][1,3]-dioxol-5-yl | H | cyclo-propyl | a = 0 | trifluoro-methyl-sulfonyl |
| 322 | H | 4-chloro-phenyl | thiazol-2-yl | H | H | —CH₂— | trifluoro-methyl-sulfonyl |
| 323 | H | 4-chloro-phenyl | thizol-2-yl | H | ethyl | —CH₂— | trifluoro-methyl-sulfonyl |
| 324 | H | 4-chloro-phenyl | thiazol-2-yl | H | cyclo-propyl | —CH₂— | trifluoro-methyl-sulfonyl |
| 328 | H | 4-chloro-phenyl | 4-chloro-phenyl | H | ethyl | a = 0 | trifluoro-methyl-sulfonyl |
| 332 | H | 4-chloro-phenyl | 4-chloro-phenyl | H | ethyl | a = 0 | ethoxy-carbonyl- |
| 335 | H | 4-chloro-phenyl | 4-chloro-phenyl | H | cyclo- | a = 0 | trifluoro-methyl-sulfonyl |
| 384 | H | 4-chloro-phenyl | thiazol-2-yl | H | cyclo- | a = 0 | trifluoro-methyl-sulfonyl |
| 385 | H | 4-chloro-phenyl | thiazol-2-yl | H | pyrid-2-yl | a = 0 | trifluoro-methyl-sulfonyl |
| 386 | H | 4-chloro-phenyl | thiazol-2-yl | H | methyl | a = 0 | trifluoro-methyl-sulfonyl |
| 387 | H | 4-chloro-phenyl | thiazol-2-yl | H | —C(O)O—CH₂—CH₃ | a = 0 | trifluoro-methyl-sulfonyl |
| 390 | H | 4-chloro-phenyl | thiazol-2-yl | H | pyrid-4-yl | a = 0 | trifluoro-methyl-sulfonyl |
| 391 | H | 4-chloro-phenyl | thiazol-2-yl | H | cylco-butyl | a = 0 | trifluoro-methyl-sulfonyl |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 393 | H | 4-chloro-phenyl | thiazol-2-yl | H | pyrid-3-yl | a = 0 | trifluoro-methyl-sulfonyl |
| 394 | H | 4-chloro-phenyl | thiazol-2-yl | H | 4-chloro-phenyl | a = 0 | trifluoro-methyl-sulfonyl |
| 395 | H | 4-chloro-phenyl | thiazol-2-yl | H | cyclo-pentyl | a = 0 | trifluoro-methyl-sulfonyl |
| 396 | H | 4-chloro-phenyl | thiazol-2-yl | H | isobutyl | a = 0 | trifluoro-methyl-sulfonyl |
| 397 | H | 4-chloro-phenyl | thiazol-2-yl | H | isopropyl | a = 0 | trifluoro-methyl-sulfonyl |
| 398 | H | 4-chloro-phenyl | thiazol-2-yl | H | H | a = 0 | trifluoro-methyl-sulfonyl |
| 399 | H | 4-chloro-phenyl | thiazol-2-yl | H | n-propyl | a = 0 | trifluoro-methyl-sulfonyl |
| 400 | H | 4-chloro-phenyl | thiazol-2-yl | H | ethyl | a = 0 | trifluoro-methyl-sulfonyl |
| 408 | H | 4-chloro-phenyl | thiazol-2-yl | H | t-butyl | a = 0 | trifluoro-methyl-sulfonyl |
| 411 | H | 4-chloro-phenyl | thiazol-2-yl | H | tetra-hydro-fur-2-yl | a = 0 | ethoxy-carbonyl- |
| 412 | H | 4-chloro-phenyl | thiazol-2-yl | H | tetra-hydro-pyran-4-yl | a = 0 | ethoxy-carbonyl- |
| 413 | H | 4-chloro-phenyl | thiazol-2-yl | H | —C(O)O—CH₂CH₃ | a = 0 | ethoxy-carbonyl- |
| 414 | H | 4-chloro-phenyl | thiazol-2-yl | H | azetidin-3-yl | a = 0 | ethoxy-carbonyl- |
| 415 | H | 4-chloro-phenyl | thiazol-2-yl | H | —CF₃ | a = 0 | ethoxy-carbonyl- |
| 416 | H | 4-chloro-phenyl | thiazol-2-yl | H | n-propyl | a = 0 | ethoxy-carbonyl- |
| 417 | H | 4-chloro-phenyl | thiazol-2-yl | H | 1-t-butoxy-carbonyl-azetidin-3-yl | a = 0 | ethoxy-carbonyl- |
| 418 | H | 4-chloro-phenyl | thiazol-2-yl | H | 4-chloro-phenyl | a = 0 | ethoxy-carbonyl- |
| 419 | H | 4-chloro-phenyl | thiazol-2-yl | H | thiazol-2-yl | a = 0 | ethoxy-carbonyl- |
| 420 | H | 4-chloro-phenyl | thiazol-2-yl | H | isobutyl | a = 0 | ethoxy-carbonyl- |
| 421 | H | 4-chloro-phenyl | thiazol-2-yl | H | cyclo-propyl | a = 0 | ethoxy-carbonyl- |
| 422 | H | 4-chloro-phenyl | thiazol-2-yl | H | chloro | a = 0 | ethoxy-carbonyl- |
| 439 | H | 4-chloro-phenyl | thiazol-2-yl | H | dimethyl-amino | a = 0 | ethoxy-carbonyl- |
| 440 | H | 4-chloro-phenyl | thiazol-2-yl | H | amino | a = 0 | ethoxy-carbonyl- |

TABLE 4-continued

Representative Compounds of Formula (I)

| ID No. | R⁰ | A¹ | A² | R¹ | R² | (L¹)ₐ | R⁵ |
|---|---|---|---|---|---|---|---|
| 441 | H | 4-chloro-phenyl | thiazol-2-yl | H | 4-chloro-phenyl | a = 0 | ethoxy-carbonyl- |
| 443 | H | 4-chloro-phenyl | thiazol-2-yl | H | 2,4-dichloro-phenyl | a = 0 | ethoxy-carbonyl- |
| 445 | H | 4-chloro-phenyl | thiazol-2-yl | H | methyl | a = 0 | ethoxy-carbonyl- |
| 448 | H | 4-chloro-phenyl | thiazol-2-yl | H | H | a = 0 | ethoxy-carbonyl- |

TABLE 5

Representative Compounds of Formula (I)

| ID No. | A¹ | A² | R² | R³ |
|---|---|---|---|---|
| 53 | 4-chloro-phenyl | 4-chloro-phenyl | cyclo-propyl | 3-(carboxy-benzyl)-azetidin-3-yl |
| 54 | 4-chloro-phenyl | 4-chloro-phenyl | cyclo-propyl | 5-(carboxy-fur-2-yl-sulfonyl)-azetidin-3-yl |
| 57 | 4-chloro-phenyl | 4-chloro-phenyl | cyclo-propyl | 4-(carboxy-phenyl-sulfonyl)-azetidin-3-yl |
| 65 | 4-chloro-phenyl | 4-chloro-phenyl | cyclo-propyl | 4-(carboxy-phenyl-sulfonyl)-pyrrolidin-3-yl |
| 67 | 4-chloro-phenyl | 4-chloro-phenyl | cyclo-propyl | 3-(carboxy-benzyl)-pyrrolidin-3-yl |
| 68 | 4-chloro-phenyl | 4-chloro-phenyl | cyclo-propyl | 5-(carboxy-fur-2-yl-sulfonyl)-pyrrolidin-3-yl |
| 295 | 4-chloro-phenyl | 4-chloro-phenyl | cyclo-propyl | 1-(trifluoro-methyl-sulfonyl)-4-hydroxy-piperidin-4-yl-CH₂— |
| 343 | 4-chloro-phenyl | thiazol-2-yl | —C(O)O—CH₃ | 1-(trifluoro-methyl-sulfonyl)-8-azabicylco[3.2.1]octan-3-yl |
| 344 | 4-chloro-phenyl | thiazol-2-yl | cyclo-butyl | 1-(trifluoro-methyl-sulfonyl)-8-azabicylco[3.2.1]octan-3-yl |
| 345 | 4-chloro-phenyl | thiazol-2-yl | —C(O)O—CH₂CH₃ | 1-(ethoxy-carbonyl)-8-azabicyclo[3.2.1]octan-3-yl |
| 347 | 4-chloro-phenyl | thiazol-2-yl | pyrid-3-yl | 1-(trifluoro-methyl-sulfonyl)-8-azabicyclo[3.2.1]octan-3-yl |
| 348 | 4-chloro-phenyl | thiazol-2-yl | ethyl | 1-(trifluoro-methyl-sulfonyl)-8-azabicyclo[3.2.1]octan-3-yl |
| 349 | 4-chloro-phenyl | thiazol-2-yl | pyrid-4-yl | 1-(trifluoro-methyl-sulfonyl)-8-azabicyclo[3.2.1]octan-3-yl |
| 350 | 4-chloro-phenyl | thiazol-2-yl | H | 1-(trifluoro-methyl-sulfonyl)-8-azabicyclo[3.2.1]octan-3-yl |
| 351 | 4-chloro-phenyl | thiazol-2-yl | 4-chloro-phenyl | 1-(trifluoro-methyl-sulfonyl)-8-azabicyclo[3.2.1]octan-3-yl |

TABLE 5-continued

Representative Compounds of Formula (I)

| ID No. | A¹ | A² | R² | R³ |
|---|---|---|---|---|
| 352 | 4-chloro-phenyl | thiazol-2-yl | cyclo-pentyl | 1-(trifluoro-methyl-sulfonyl)-8-azabicyclo[3.2.1]octan-3-yl |
| 353 | 4-chloro-phenyl | thiazol-2-yl | n-propyl | 1-(trifluoro-methyl-sulfonyl)-8-azabicyclo[3.2.1]octan-3-yl |
| 356 | 4-chloro-phenyl | thiazol-2-yl | isopropyl | 1-(trifluoro-methyl-sulfonyl)-8-azabicyclo[3.2.1]octan-3-yl |
| 357 | 4-chloro-phenyl | thiazol-2-yl | methyl | 1-(trifluoro-methyl-sulfonyl)-8-azabicyclo[3.2.1]octan-3-yl |
| 358 | 4-chloro-phenyl | thiazol-2-yl | pyrid-2-yl | 1-(trifluoro-methyl-sulfonyl)-8-azabicyclo[3.2.1]octan-3-yl |
| 359 | 4-chloro-phenyl | thiazol-2-yl | isobutyl | 1-(trifluoro-methyl-sulfonyl)-8-azabicyclo[3.2.1]octan-3-yl |
| 360 | 4-chloro-phenyl | thiazol-2-yl | cyclo-propyl | 1-(trifluoro-methyl-sulfonyl)-8-azabicyclo[3.2.1]octan-3-yl |
| 363 | 4-chloro-phenyl | thiazol-2-yl | cyclo-propyl | 1-(ethoxy-carbonyl)-8-azabicyclo[3.2.1]octan-3-yl |
| 366 | 4-chloro-phenyl | thiazol-2-yl | pyrid-4-yl | 1-(ethoxy-carbonyl)-8-azabicyclo[3.2.1]octan-3-yl |
| 367 | 4-chloro-phenyl | thiazol-2-yl | pyrid-4-yl | 1-(ethoxy-carbonyl)-8-azabicyclo[3.2.1]octan-3-yl |
| 368 | 4-chloro-phenyl | thiazol-2-yl | cyclo-propyl | 1-(ethoxy-carbonyl)-8-azabicyclo[3.2.1]octan-3-yl |
| 369 | 4-chloro-phenyl | thiazol-2-yl | isobutyl | 1-(ethoxy-carbonyl)-8-azabicyclo[3.2.1]octan-3-yl |
| 378 | 4-chloro-phenyl | thiazol-2-yl | pyrid-2-yl | 1-(ethoxy-carbonyl)-8-azabicyclo[3.2.1]octan-3-yl |
| 379 | 4-chloro-phenyl | thiazol-2-yl | methyl | 1-(ethoxy-carbonyl)-8-azabicyclo[3.2.1]octan-3-yl |
| 380 | 4-chloro-phenyl | thiazol-2-yl | H | 1-(ethoxy-carbonyl)-8-azabicyclo[3.2.1]octan-3-yl |
| 381 | 4-chloro-phenyl | thiazol-2-yl | isopropyl | 1-(ethoxy-carbonyl)-8-azabicyclo[3.2.1]octan-3-yl |
| 382 | 4-chloro-phenyl | thiazol-2-yl | n-propyl | 1-(ethoxy-carbonyl)-8-azabicyclo[3.2.1]octan-3-yl |
| 383 | 4-chloro-phenyl | thiazol-2-yl | ethyl | 1-(ethoxy-carbonyl)-8-azabicyclo[3.2.1]octan-3-yl |
| 388 | 4-chloro-phenyl | thiazol-2-yl | 4-chloro-phenyl | 1-(ethoxy-carbonyl)-8-azabicyclo[3.2.1]octan-3-yl |
| 389 | 4-chloro-phenyl | thiazol-2-yl | cyclo-pentyl | 1-(ethoxy-carbonyl)-8-azabicyclo[3.2.1]octan-3-yl |

Definitions

As used herein, unless otherwise noted, "halogen" shall mean chlorine, bromine, fluorine and iodine.

As used herein, unless otherwise noted, the term "carboxy" shall mean —C(O)OH.

As used herein, unless otherwise noted, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$alkyl" shall mean any straight or branched chain composition of between 1 and 4 carbon atoms (including methyl, ethyl, n-propyl, isopropyl, n-butyl, isobutyl and t-butyl).

One skilled in the art will recognize that the term "—($C_{X-Y}$ alkyl)-" shall denote any $C_{X-Y}$alkyl straight or branched chain composition as defined above, wherein said $C_{X-Y}$alkyl straight or branched chain composition is divalent and is therefore bound through two points of attachment, preferably through two terminal carbon atoms.

As used herein, unless otherwise noted, the term "halogenated $C_{1-4}$alkyl" shall mean any $C_{X-Y}$alkyl group as defined above substituted with at least one halogen atom, preferably substituted with a least one fluoro atom. Suitable examples include but are not limited to —$CH_2F$, —$CH_2I$, —$CH_2Br$, —$CH_2Cl$, —$CF_3$, —$CCl_3$, —$CH_2$—$CF_3$, $CH_2$—$CCl_3$, —$CF_2$—$CF_2$—$CF_2$—$CF_3$, and the like. Similarly, the term "fluorinated $C_{1-4}$alkyl" shall mean any $C_{X-Y}$alkyl group as defined above substituted with at least one fluoro atom, preferably one to three fluoro atoms. Suitable examples include, but are not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{X-Y}$alkyl" shall mean any $C_{X-Y}$alkyl group as defined above, substituted with at least one hydroxy group, preferably one to two hydroxy groups, more preferably one hydroxy group; provided that when the "hydroxy substituted $C_{X-Y}$alkyl" is bound to a N or O atom of a substituent group as defined herein, then the hydroxy group(s) on the "hydroxy substituted $C_{X-Y}$alkyl" are not bound to C-1 carbon atom of the $C_{X-Y}$alkyl portion of the "hydroxy substituted $C_{X-Y}$alkyl" (i.e. the hydroxy group(s) are not bound to the carbon atom which is directly bound to the N or O atom of said substituent group). Suitable examples include but are not limited to —$CH_2OH$, —$CH_2CH_2OH$, —$CH(OH)CH_3$, —$CH_2CH_2CH_2OH$, —$CH_2CH(OH)CH_3$, —$CH_2CH_2CH_2CH_2OH$, —$C(CH_2CH_2OH)_2$—$CH_2CH_2OH$, and the like. In an embodiment, the $C_{X-Y}$alkyl is substituted with the hydroxy group(s) at terminal carbon atom(s).

As used herein, unless otherwise noted, the term "$C_{X-Y}$alkenyl" wherein X and Y are integers, shall mean a carbon chain composition of between X and Y carbon atoms wherein the carbon chain contains at least one, preferably one, double bond. For example, "$C_{3-4}$alkenyl" shall mean a 3 to 4 carbon chain composition containing at least one, preferably one, double bond. Suitable example include, but are not limited to —$CH_2$—$CH$=$CH_2$, —$CH$=$CH$—$CH_2$ and the like.

One skilled in the art will recognize that the term "—($C_{X-Y}$alkenyl)-" shall denote any $C_{X-Y}$alkenyl carbon chain composition as defined above, wherein said $C_{X-Y}$alkenyl is divalent and is therefore bound through two points of attachment, preferably through two terminal carbon atoms. For example, the term "—($C_{2-4}$alkenyl)-" shall mean any 2 to 4 carbon atom chain containing at least one, preferably one double bond. Suitable examples include, but are not limited to —$CH$=$CH$—, —$CH_2$—$CH$=$CH$—, —$CH$=$CH$—$CH_2$—, —$CH$=$CH$—$CH(CH_3)$— and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched chain carbon chain composition of between X and Y carbon atoms. For example, "$C_{1-4}$alkoxy" shall mean any oxygen ether radical of the above described straight or branched chain composition of between 1 and 4 carbon atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCH_2F$, —$OCH_2I$, —$OCH_2Br$, —$OCH_2Cl$, —$OCF_3$, —$OCCl_3$, —$OCH_2$—$CF_3$, —$OCH_2$—$CCl_3$, —$OCF_2$—$CF_2$—$CF_2$—$CF_3$, and the like. Similarly, the term "fluorinated $C_{1-4}$alkoxy" shall mean any $C_{1-4}$alkoxy group as defined above substituted with at least one fluoro atom, preferably one to three fluoro atoms. Suitable examples include but are not limited to —$OCF_3$, —$OCH_2$—$CF_3$, —$OCF_2$—$CF_2$—$CF_3$, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl. Unless otherwise noted, "$C_{X-Y}$cycloalkyl" wherein X and Y are integers, shall mean a cycloalkyl ring structure as herein defined wherein the ring structure contains between X and Y carbon atoms. For example, $C_{3-6}$cycloalkyl shall include cyclopropyl, cyclobutyl, cyclopentyl and cyclohexyl.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

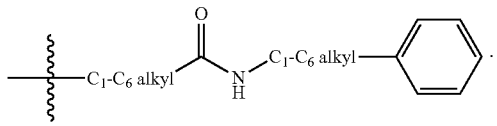

Abbreviations used in the specification, particularly the Schemes and Examples, are as follows:
AcOH or HOAc=Acetic acid
Alloc=Allyloxycarbonyl
aq. or aq=Aqueous
Boc or BOC=tert-butoxycarbonyl
Boc$_2$O=Boc anhydride (i.e. di-tert-butyl dicarbonate)
BSA=Bovine Serum Albumin
cAMP=Cyclic Adenosine Monophosphate
CB1 or CB1R or CB$_1$R=Cannabinoid 1 Receptor
CB2 or CB2R or CB$_2$R=Cannabinoid 2 Receptor
CDI=Carbonyldiimidazole
conc.=Concentrated
DBU=1,8-Diazabicyclo[5.4.0]undec-7-ene
DCE=1,1-Dichloroethane
DCM=Dichloromethane
DIAD=Diisopropylazodicarboxylate
DIC=N,N'-diisopropylcarbodiimide
DIO=Diet-Induced Obesity (Mouse Model)
DIPEA or DIEA or Hunig's Base=Diisopropylethylamine
DME=Dimethoxyethane
DMEM=Dulbecco's Modified Eagle Medium
DMF=N,N-Dimethylformamide
DMP=Dess-Martin Periodinane (1,1,1-Triacetoxy-1,1-dihydro-1,2-benziodoxol-3(1H)-one)
DMSO=Dimethylsulfoxide
DPPA=Diphenylphosphoryl azide
dppf=1,1'-Bis(diphenylphosphino)ferrocene
EDCI=1-Ethyl-3-(3-dimethylaminopropyl)carbodiimide
EtOAc or EA=Ethyl acetate
EtOH=Ethanol
Et$_2$O=Diethyl ether
Et$_3$SiH=Triethylsilane
FBS=Fetal Bovine Serum
GCMS or GC-MS=Gas Chromatography-Mass Spectroscopy
GPCR=G-coupled Receptor
HATU=O-(7-Azabenzotriazol-1-yl)-N,N,N'',N'''-Tetramethyl Uronium Hexafluorophosphate
HBSS=Hank's Balanced Salt Solution
HBTU=N N,N,N',N'-Tetramethyl-O-(1H-benzotriazol-1-yl) uronium hexafluorophosphate
HDL=High Density Lipoprotein
HEPES=4-(2-Hydroxyethyl)-1-Piperazine Ethane Sulfonic Acid
HPLC=High Performance Liquid Chromatography
IPA or i-PrOH=Isopropyl alcohol
KOt-Bu or t-BuOK=Potassium t-butoxide
LADA=Latent Autoimmune Diabetes of Adults
LAH=Lithium Aluminum Hydride
LCMS or LC-MS=Liquid Chromatography-Mass Spectrometry
LDL=Low Density Lipoprotein
LiHMDS or LiN(SiMe$_3$)$_2$=Lithium bis(trimethylsilyl)amide
MeOH=Methanol
Mesyl=Methylsulfonyl
MOMBr=Bromomethyl methyl ether
MTBE=Methyl t-butyl ether
n-BuLi=n-Butyl Lithium
NaBH(OAc)$_3$=Sodium triacetoxyborohydride
NaHMDS or NaN(SiMe$_3$)$_2$=Sodium bis(trimethylsilyl)amide
NaOt-Bu or t-BuONa=Sodium tert-butoxide
NASH=NonAlcoholic Steatohepatitis
NMR=Nuclear magnetic Resonance
NSB=Non-Specific Binding
PBS=Phosphate Buffered Saline
Pd/C=Palladium on Carbon (catalyst)
Pd$_2$(Oac)$_2$=Palladium(II)acetate
Pd$_2$(dba)$_3$=Tris(dibenzylidene acetone)dipalladium(0)
Pd(dppf)Cl$_2$=[1,1'-Bis(diphenylphosphino) ferrocene]dichloro palladium(II)
PE=Petroleum Ether
PPh$_3$=Triphenyl Phosphine
Raney nickel or Raney Ni or RaNi W.R. Grace and Co. Trademarked Nickel Catalyst
sat.=Saturated
t-BuLi=tert-Butyl lithium
t-BuOH=tert-Butanol
TEA or Et$_3$N=Triethylamine
TFA=Trifluoroacetic Acid
THF=Tetrahydrofuran
Ti(OiPr)$_4$=Titanium isopropoxide
TLC=Thin Layer Chromatography
Tosyl=p-Toluenesulfonyl
Tris HCl or Tris-Cl=Tris[hydroxymethyl]aminomethyl hydrochloride
XantPhos=4,5-Bis(diphenylphosphino)-9,9-dimethylxanthene
XPhos=2-Dicyclohexylphosphino-2',4',6'-triisopropylbiphenyl The compounds of the present invention are CB-1 inverse agonists useful for the treatment and/or prevention of metabolic disorders, including obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain. Preferably, the metabolic disorder is selected from the group consisting of obesity, Type II diabetes, and dyslipidemias. More preferably, the metabolic disorder is obesity or Type II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of one or more additional symptoms; and/or (d) delay or avoidance of the development or progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named. One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

One skilled in the art will recognize that during any of the processes for preparation of the compounds of the present invention, as herein described in more detail, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($R$moles−$S$moles)/($R$moles+$S$moles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee=([\alpha\text{-obs}]/[\alpha\text{-max}])\times 100$.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Synthesis Schemes

Compounds of formula (I) (preferably compounds of formula (I) wherein

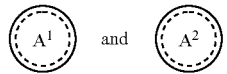

are both aromatic, and more preferably,

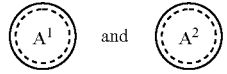

are each optionally substituted phenyl), may be prepared according to the process outlined in Schemes 1-2, below.

Scheme 1

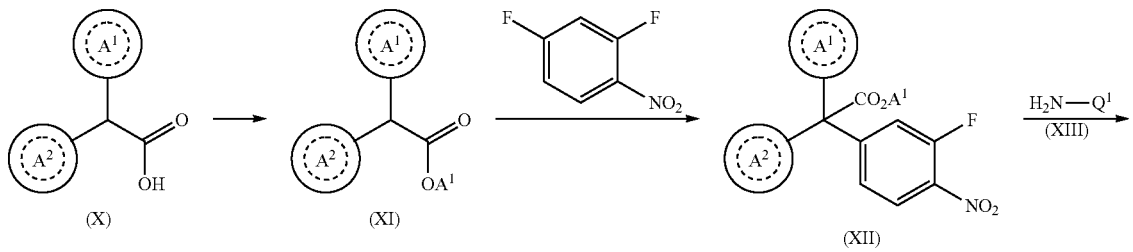

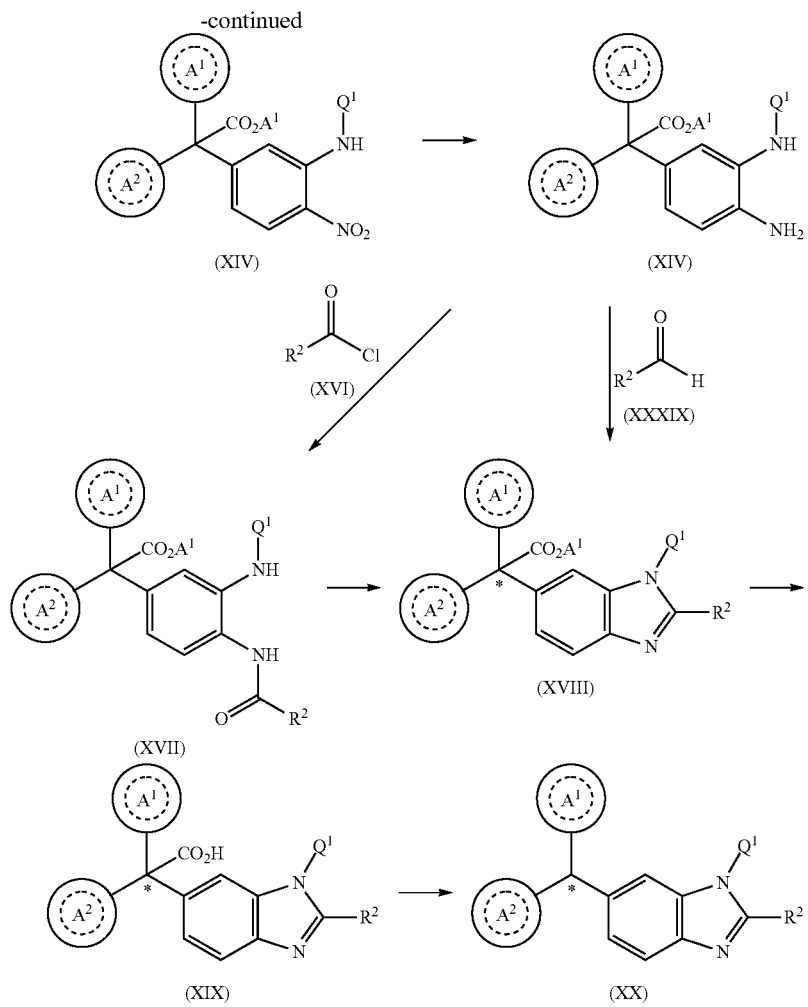

Accordingly, a suitably substituted compound of formula (X), a known compound or compound prepared by known methods, is reacted with a suitably selected alcohol of the formula $A^1OH$, wherein $A^1$ is $C_{1-4}$alkyl, in the presence of a suitably selected acid such as $H_2SO_4$, p-toluenesulfonic acid, HCl, and the like; in a suitably selected solvent such as methanol, ethanol, and the like; to yield the corresponding compound of formula (XI).

The compound of formula (XI) is reacted with 2,4-difluoro-1-nitrobenzene, a known compound, in the presence of a suitably selected base such as KOt-Bu, LiHMDS, NaHMDS, NaOt-Bu, and the like; in a suitably selected solvent such as THF, DME, and the like; to yield the corresponding compound of formula (XII).

The compound of formula (XII) is reacted with a suitably substituted compound of formula (XIII), wherein $Q^1$ is selected from the group consisting of —$R^3$,

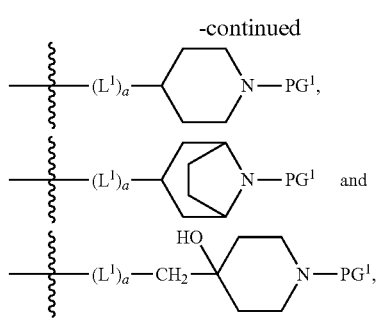

wherein $PG^1$ is a suitably selected nitrogen protecting group such as Boc, alloc, and the like; a known compound or compound prepared by known methods, in the presence of a suitably selected base such as DIPEA, TEA, pyridine, and the like; in a suitably selected solvent such as acetonitrile, DMSO, DMF, and the like; at a temperature in the range of from about 60° C. to about 100° C., for example at about 85° C.; to yield the corresponding compound of formula (XIV).

The compound of formula (XIV) is hydrogenated according to known methods, for example, by reacting with $H_2$ gas, in the presence of Raney nickel catalyst or Pd/C catalyst, in a suitably selected solvent or mixture of solvents such as methanol/THF or ethanol/THF; to yield the corresponding compound of formula (XV).

The compound of formula (XV) is reacted with a suitably substituted compound of formula (XVI), a known compound or compound prepared by known methods; in the presence of a suitably selected base such as TEA, DIPEA, pyridine, and the like; in a suitably selected solvent such as DCM, DCE, and the like; to yield the corresponding compound of formula (XVII).

The compound of formula (XVII) is reacted with a suitably selected acid such as acetic acid, and the like; neat or in a suitably selected solvent; at a temperature in the range of from about 80° C. to about reflux temperature, for example at about 120° C., to yield the corresponding compound of formula (XVIII).

Alternatively, the compound of formula (XV) is reacted with a suitably substituted compound of formula (XXXIX), a known compound or compound prepared by known methods; in the presence of air; in a suitably selected solvent such as DMSO, and the like; at a temperature in the range of from about room temperature to about 75° C., for example at about 50° C., to yield the corresponding compound of formula (XVIII).

The compound of formula (XVIII) is reacted with a suitably selected base such as NaOH, LiOH, and the like; in a suitably selected solvent or mixture of solvents such as methanol/THF, ethanol/THF, and the like; to yield the corresponding compound of formula (XIX).

The compound of formula (XIX) is reacted with DBU; in a suitably selected solvent such as toluene, and the like; at a temperature in the range of from about 75° C. to about reflux temperature, for example, at about 90° C.; to yield the corresponding compound of formula (XX).

One skilled in the art will recognize that wherein the compound of formula (XVIII), formula (XIX) and/or formula (XX), $Q^1$ is $R^3$, then said compounds of formula (XVIII), formula (XIX) and/or formula (XX) correspond to compounds of formula (I) wherein $R^0$ is —C(O)O—($C_{1-4}$ alkyl), —C(O)OH and hydrogen, respectively.

Wherein the compounds of formula (XVIII), formula (XIX) and/or formula (XX) $Q^1$ is selected from the group consisting of

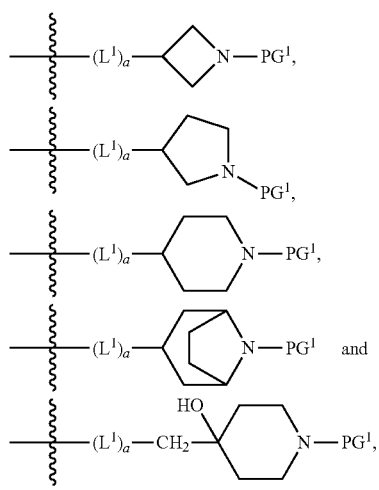

then the desired compound of formula (I) may be prepared by further reacting the corresponding compound of formula (XVIII), as described in Scheme 2 below.

Scheme 2

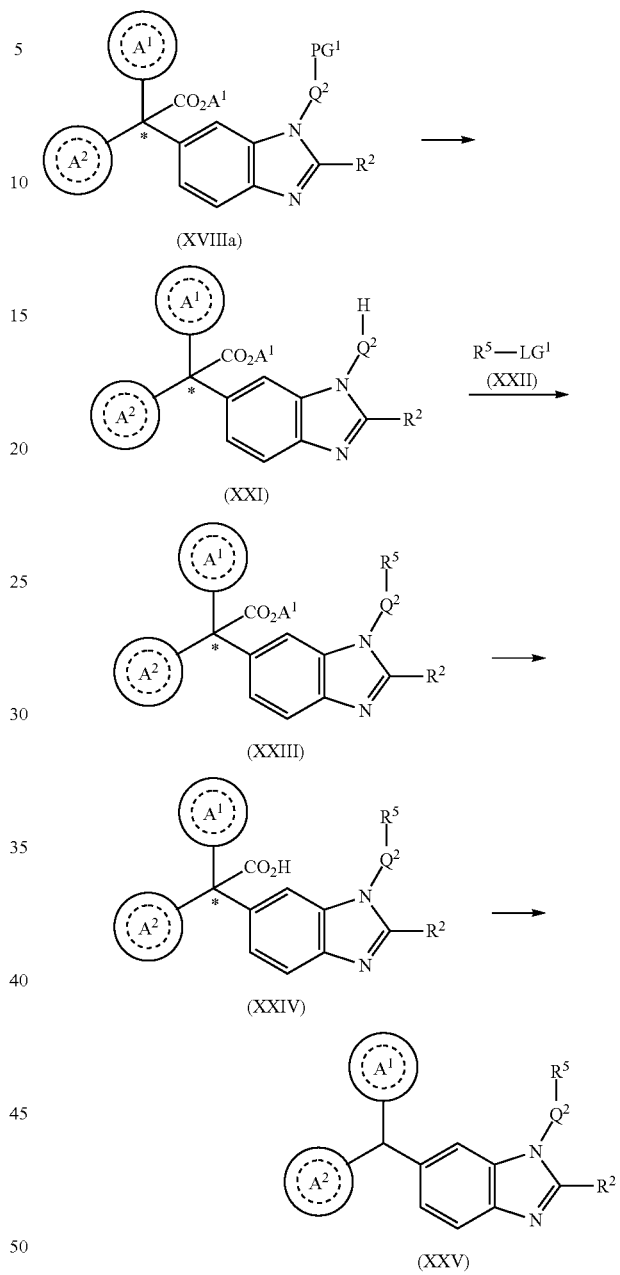

Accordingly, a suitably substituted compound of formula (XVIIIa), a compound of formula (XVIII) wherein $Q^2$ is selected from the group consisting of

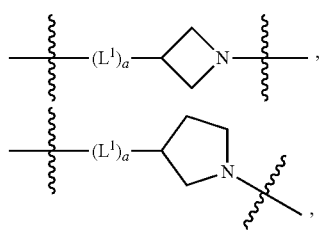

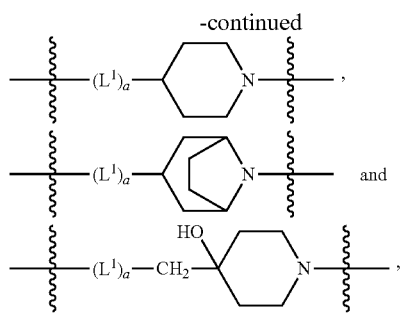

and wherein PG¹ is a suitably selected nitrogen protecting group such as Boc, alloc and the like; is de-protected according to known methods, (for example, wherein PG¹ is Boc, the compound of formula (XVIII) is reacted with a suitably selected acid such as TFA, HCl, and the like, in a suitably selected solvent such as 1,4-dioxane, DCM, DCE, and the like; to yield the corresponding compound of formula (XXI).

The compound of formula (XXI) is reacted with a suitably substituted compound of formula (XXII), wherein LG¹ is a suitably selected leaving group such as, Cl (for example, wherein the compound of formula (XXII) is an acyl chloride or a sulfonyl chloride), Br, and the like, a known compound or compound prepared by known methods; according to known methods; to yield the corresponding compound of formula (XXIII). For example, when the compound of formula (XXII) is an acyl chloride or a sulfonyl chloride, the compound of formula (XXI) is reacted with the compound of formula (XXII) in the presence of a base such as TEA, DIPEA, pyridine, and the like; in a suitably selected solvent such as DCM, DCE, THF, and the like. Alternatively, wherein the compound of formula (XXII) is for example an optionally substituted phenyl bromide, and the like; the compound of formula (XXI) is reacted with the compound of formula (XXII); in the presence of a suitably selected catalyst such as Pd₂(dba)₃, Pd(OAc)₂, and the like; in the presence of a suitably selected ligand such as dppf, XantPhos, XPhos, and the like; in the presence of a suitably selected base such as Cs₂CO₃, K₂CO₃, K₃PO₄, and the like; in a suitably selected organic solvent such as 1,4-dioxane, toluene, THF, DME, and the like; at an elevated temperature in the range of from about 75° C. to about 150° C.

The compound of formula (XXIII) is reacted with a suitably selected base such as NaOH, LiOH, and the like; in a suitably selected solvent or mixture of solvents such as methanol/THF, ethanol/THF, and the like; to yield the corresponding compound of formula (XXIV).

The compound of formula (XXIV) is reacted with DBU, and the like; in a suitably selected solvent such as toluene, and the like; at a temperature in the range of from about 75° C. to about reflux temperature; to yield the corresponding compound of formula (XXV).

One skilled in the art will recognize that the compound of formula (XXII), formula (XXIII) and/or formula (XXIV), correspond to compounds of formula (I) wherein R⁰ is —C(O)O—(C₁₋₄alkyl), —C(O)OH and hydrogen, respectively.

Alternatively, the compound of formula (XVIIIa) is reacted with a suitably substituted base such as NaOH, LiOH, and the like; in a suitably selected solvent such as a mixture of methanol/THF, ethanol/THF, and the like; to yield the corresponding compound wherein the R⁰—C(O)OA¹ ester group is converted to acid (—C(O)OH). This intermediate is then reacted with DBU; in a suitably selected solvent such as toluene, and the like; at a temperature in the range of from about 75° C. to about reflux temperature, for example, at about 90° C.; to yield the corresponding compound wherein the R⁰ acid group (—C(O)OH) is removed, such that R⁰ is hydrogen, a compound of formula (XVIII-ALT).

(XVIII-ALT)

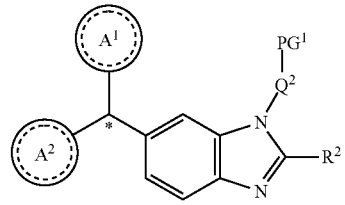

The compound of formula (XVIII-ALT) is then substituted for the compound of formula (XVIIIa) in the Scheme 2 and reacted as described therein, (to remove the PG¹ protecting group, and further to attach the desired R⁵ group), to yield the desired compound of formula (I).

Compounds of formula (I) wherein R⁰ is —CH₂OH may be prepared from the corresponding compound of formula (XVIII), wherein R⁰ is CO₂A¹ by reduction. In an example, a suitably substituted compound of formula (XVIIIa) is reacted with a suitably selected reducing agent such as LAH, and the like; in a suitably selected solvent such as THF, DME, and the like; to yield the corresponding compound wherein the —CO₂A¹ ester at the R⁰ position is converted to —CH₂OH. The resulting compound is then substituted for the compound of formula (XVIIIa) in Scheme 2 and reacted as described therein, to yield the desired compound of formula (I).

Compounds of formula (I) wherein R⁰ is —CH₂—O—(C₁₋₂alkyl) may be prepared by reacting a suitably substituted compound of formula (I) wherein R⁰ is —CH₂OH with a suitably selected alkylating agent such as CH₃I (for the corresponding methyl ether) or CH₃CH₂I (for the corresponding ethyl ether), in the presence of a suitably selected base such as NaH, KOt-Bu, NaOt-Bu, and the like; in a suitably selected solvent such as DMF, THF, and the like.

Compound of formula (I) wherein R⁰ is —CH₂—O—(C₁₋₂ alkyl)-CO₂H may be prepared by reacting a suitably substituted compound of formula (I) wherein R⁰ is —CH₂OH with a suitably selected C₃-4alken-1-yl bromide, a known compound or compound prepared by known methods; in the presence of a suitably selected base such as KOt-Bu, NaOt-Bu, and the like; in a suitably selected solvent such as DMSO, THF, DMF, and the like; to yield the corresponding intermediate compound, wherein the —CH₂—OH at the R⁰ position is converted to the corresponding —CH₂—O—(CH₂)₁₋₂—CH═CH₂ group. This intermediate is then reacted with a suitably selected oxidizing agent such as a mixture of NaIO₄ and RuCl₃, and the like; in a suitably selected solvent or mixture of solvent such as a mixture of acetonitrile, DCM and water to yield the corresponding compound of formula (I) wherein R⁰ is —CH₂—O—(C₁₋₂alkyl)-CO₂H.

Compounds of formula (I) wherein R³ is

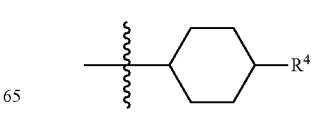

may be similarly prepared according to the procedure as described in Scheme 1. More particularly, a suitably substituted compound of formula (CXXV)

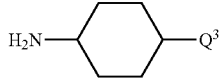
(CXXV)

wherein $Q^3$ is selected from the group consisting of $R^4$, —C(O)OA$^2$ and —NH—PG$^2$, wherein A$^2$ is selected from the group consisting of $C_{1-4}$alkyl, and wherein PG$^2$ is a suitably selected nitrogen protecting group, is substituted for the compound of formula (XIII) and reacted as described in Scheme 1 to yield the corresponding compound of formula (XVIII), formula (XIX) and formula (XX), wherein the $Q^1$ group is replaced with corresponding

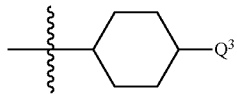

group.

One skilled in the art will recognize that the compound of formula (XVIII), formula (XIX) or formula (XX) wherein the $Q^1$ group is replaced with

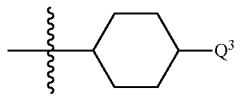

and wherein $Q^3$ is —NH—PG$^2$ may be de-protected according to known methods (to remove the PG$^2$ protecting group) to yield the corresponding compound of formula (I) wherein $R^3$ 4-amino-cyclohex-1-yl. This intermediate is then further reacted with a compound of formula LG$^2$-Q$^4$, wherein LG$^2$ is a suitably selected leaving group such as Cl, Br, and the like; and wherein Q$^4$ is selected from the group consisting of -phenyl and —SO$_2$— phenyl, and wherein the phenyl is optionally substituted as defined above for the R$^4$ substituent group; to yield the corresponding compound of formula (I) wherein R$^3$ is

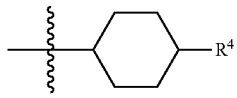

and wherein R$^4$ is selected from the group consisting of —NH-(optionally substituted phenyl) and —NH—SO$_2$-(optionally substituted phenyl).

One skilled in the art will recognize that the compounds of formula (XVIII), formula (XIX) and formula (XX) wherein Q$^1$ is replaced with

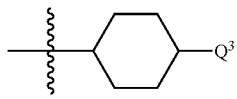

and Q$^3$ is —C(O)OA$^2$, represent the corresponding compounds of formula (I) wherein R$^3$ is

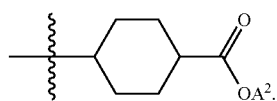

One skilled in the art will recognize that the compound of formula (XVIII), formula (XIX) or formula (XX) wherein the Q$^1$ group is replaced with

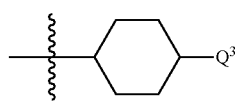

and wherein Q$^3$ is —C(O)OA$^2$ may be reacted to convert the alkyl ester (i.e. —C(O)OA$^2$) to the corresponding acid group (i.e. —C(O)OH), by for example reacting with a suitably selected base such as NaOH, LiOH, and the like; in a suitably selected solvent or mixture of solvents such as methanol/THF, ethanol/THF, and the like. The acid group (i.e. —C(O)OH) may be further, optionally reacted with NH$_4$Cl or a suitably substituted amine (e.g. a compound of the formula NHR$^G$R$^H$, a known compound or compound prepared by known methods), in the presence of a suitably selected coupling agent such as HATU, DIC, EDCI, and the like; in the presence of a suitably selected base such as DIPEA, TEA, pyridine, and the like; in a suitably selected solvent such as DMF, DCM, THF and the like; to yield the corresponding compound, wherein the R$^4$ substituent group is the corresponding amide (i.e. —C(O)—NH$_2$ or —C(O)—NR$^G$R$^H$).

One skilled in the art will recognize that the above described transformations and variations thereof will result in the preparation of the corresponding compounds of formula (I) wherein R$^3$ is

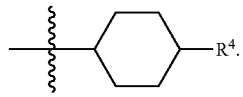

Compounds of formula (I) wherein R$^3$ is selected from the group consisting

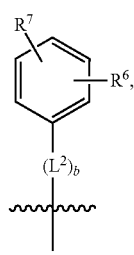

wherein b is 1 and L$^2$ is —CH$_2$CH$_2$—O— and

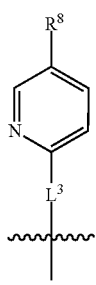

wherein L³ is —CH₂CH₂—O— may be similarly prepared as described in Scheme 1 above, by reacting a suitably substituted compound of formula (XII) with 2-hydroxyethylamine, a known compound, to yield the corresponding compound of formula (XIV), wherein the —NH-Q¹ group is replaced with —NH—CH₂CH₂—OH. This intermediate is then reacted as described in Scheme 1 to yield the corresponding compound of formula (XX), wherein the Q¹ group is replaced with —CH₂CH₂—OH, a compound of formula (CXX)

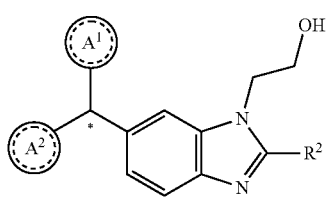
(CXX)

The compound of formula (CXX) is then reacted with a suitably substituted phenol or hydroxy-pyridyl; under Mitsunobu conditions (for example, in the presence of DIAD, PPH₃ and in a solvent such as THF); to yield the corresponding compound of formula (I) wherein R³ is selected from the group consisting

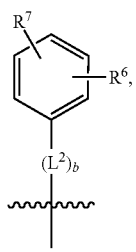

wherein b is 1 and L² is —CH₂CH₂—O— and

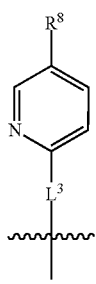

wherein L³ is —CH₂CH₂—O—, respectively.

Compounds of formula (I) wherein R³ is selected from the group consisting

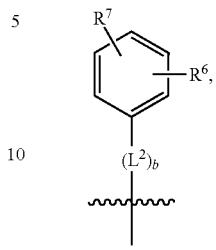

wherein b is 1 and L² is —CH₂CH₂CH₂—NH—SO₂— may be similarly prepared as described in Scheme 1 and 2, by preparing the corresponding compounds wherein the -Q²-PG¹ substituent group is replaced with —CH₂CH₂CH₂—NH—PG⁵ (by reacting with a suitably substituted and suitably protected amine of the formula NH₂—CH₂CH₂CH₂—NH—PG⁵ wherein PG⁵ is a suitably selected nitrogen protecting group such as Boc, alloc, and the like); and then reacting as described above to remove the PG⁵ protecting group and further functionalizing to the desired product by reacting with a suitably substituted sulfonyl chloride, according to known methods.

Compounds of formula (I) wherein R³ is selected from the group consisting of

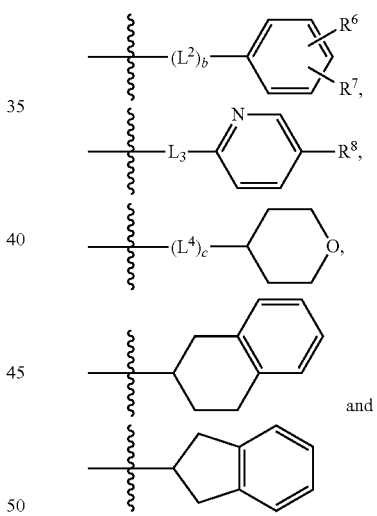

and may be prepared as described in Scheme 1 above.

Compounds of formula (I) wherein

is an optionally substituted phenyl and wherein

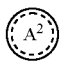

is thiazol-2-yl may alternatively be prepared as described in Scheme 3, below.

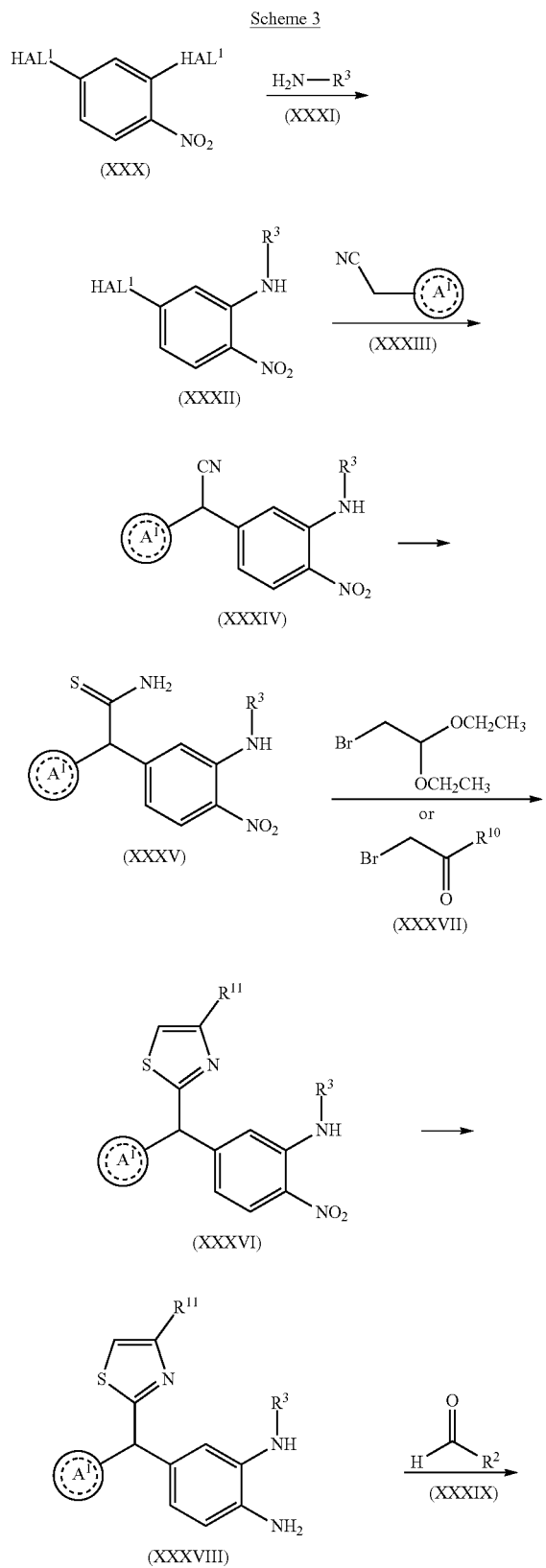

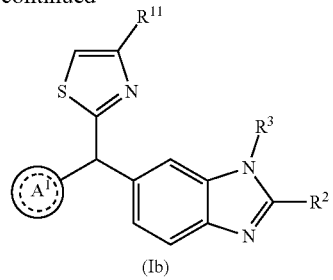

Accordingly, a suitably substituted compound of formula (XXX), wherein each HAL$^1$ is independently selected from F or Cl, a known compound or compound prepared by known methods, is reacted with a suitably substituted compound of formula (XXXI), a known compound or compound prepared by known methods; in the presence of a suitably selected base such as DIPEA, TEA, pyridine, and the like; in a suitably selected solvent such as DMSO, acetonitrile, and the like; to yield the corresponding compound of formula (XXXII).

The compound of formula (XXXII) is reacted with a suitably substituted compound of formula (XXXIII), a known compound or compound prepared by known methods; in the presence of a suitably selected base such as KOt-Bu, NaOt-Bu, and the like; in a suitably selected solvent such as THF, i-PrOH, and the like; to yield the corresponding compound of formula (XXXIV).

The compound of formula (XXXIV) is reacted with P$_2$S$_5$, a known compound; in a suitably selected solvent such as ethanol, methanol, and the like; to yield the corresponding compound of formula (XXXV). Alternatively, the compound of formula (XXIV) is reacted with H$_2$S; in the presence of a base such as TEA; in a suitably selected solvent such as pyridine, and the like; to yield the corresponding compound of formula (XXXV).

The compound of formula (XXXV) is reacted with 2-bromo-1,1-diethoxyethane, a known compound; in the presence of a suitably selected acid such as acetic acid, and the like; in water; to yield the corresponding compound of formula (XXXVI) wherein

is thiazol-2-yl and R$^{11}$ is hydrogen.

Alternatively, the compound of formula (XXXV) is reacted with a suitably substituted compound of formula (XXXVII), wherein R$^{10}$ is a substituent on the

thiazolyl ring, as defined herein, a known compound or compound prepared by known methods; in the presence of a suitably selected acid such as acetic acid, and the like; at a temperature in the range of from about 50° C. to about 120° C., for example at about 100° C.; to yield the corresponding compound of formula (XXXVI) wherein

is the corresponding 4-($R^{11}$ substituted)-thiazol-2-yl.

The compound of formula (XXXVI) is reacted with hydrogen (preferably hydrogen gas); in the presence of a suitably selected catalyst, such as Raney nickel or Pd/C; in a suitably selected solvent or mixture of solvents such as ethanol, THF, and the like; to yield the corresponding compound of formula (XXXVIII).

The compound of formula (XXXVIII) is reacted with a suitably substituted compound of formula (XXXIX), a known compound or compound prepared by known methods; in a suitably selected solvent such as DMSO, and the like; in air; at a temperature in the range of from about 20° C. to about 50° C.; to yield the corresponding compound of formula (Ib).

Wherein the desired compound of formula (Ib) $R^2$ is hydrogen, the compound of formula (XXXVII) is reacted with triethylorthoformate, a known compound; in the presence of an acid such as conc HCl, and the like; neat; at a temperature in the range of from about 75° C. to about 150° C., for example, at about 125° C.

Wherein the desired compound of formula (Ib) $R^2$ is methyl, the compound of formula (XXXVIII) is reacted with trimethylorthoacetate, a known compound; in the presence of an acid such as conc HCl, and the like; neat; at a temperature in the range of from about 75° C. to about reflux temperature.

Compounds of formula (I) wherein $R^1$ is hydrogen may alternatively be prepared as described in Scheme 4, below.

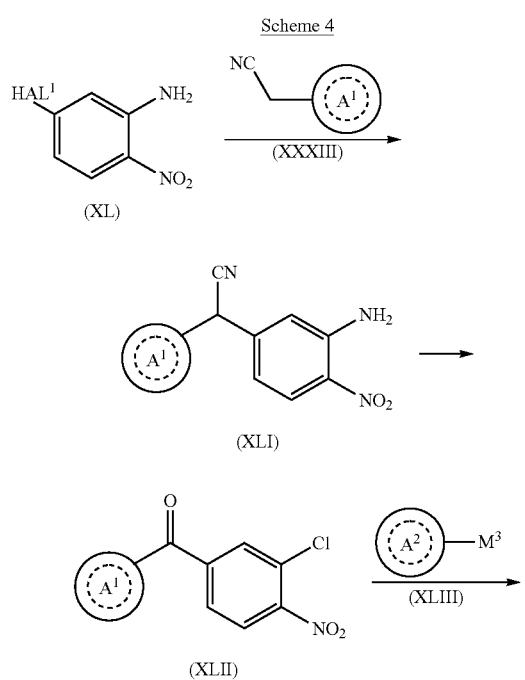

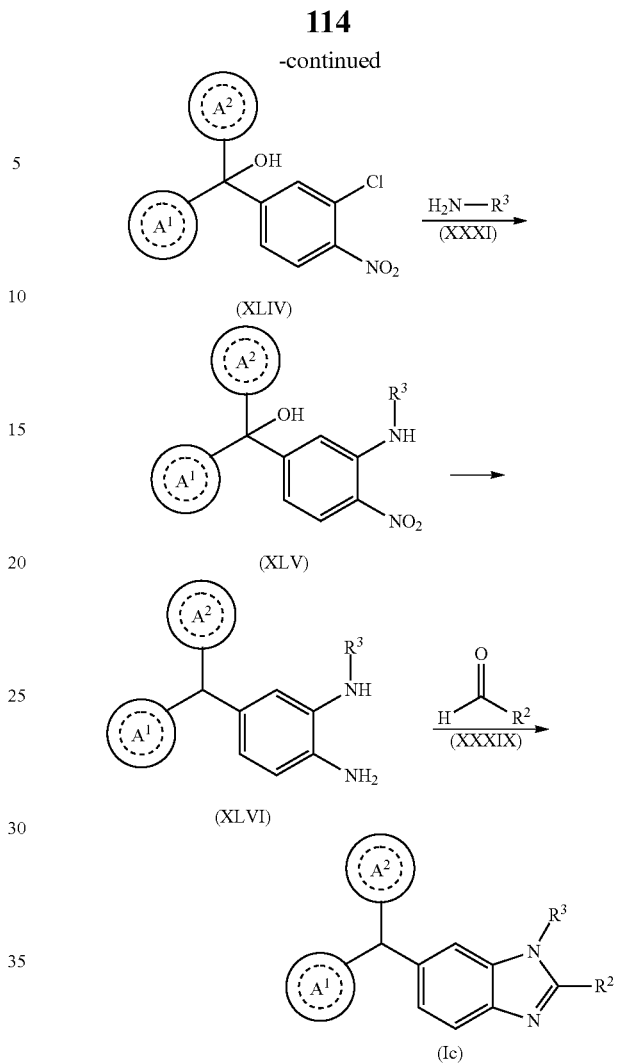

Accordingly, a suitably substituted compound of formula (XL), wherein $HAL^1$ is selected from F or Cl, a known compound or compound prepared by known methods, is reacted with a suitably substituted compound of formula (XXXIII), a known compound or compound prepared by known methods; in the presence of a suitably selected base such as KOt-Bu, NaOt-Bu, and the like; in a suitably selected solvent such as THF, i-PrOH, and the like; to yield the corresponding compound of formula (XLI).

The compound of formula (XLI) is reacted with t-BuONO, $NaNO_2$, and the like, a known compound; in the presence of a suitably selected source of chlorine such as $CuCl_2$, CuCl, and the like; in a suitably selected solvent such as acetonitrile, water, and the like; to yield the corresponding compound of formula (XLII). One skilled in the art will recognize that the reaction of the compound of formula (XLI) may alternative be carried out in the presence of a source of bromide such as $CuBr_2$, and the like; to yield the corresponding compound of formula (XLII) wherein the Cl is replaced with a Br.

The compound of formula (XLII) is reacted with a suitably substituted compound of formula (XLIII), wherein $M^3$ is H or Br, a known compound or compound prepared by known methods; in the presence of a suitably selected lithiating agent such as n-BuLi, t-BuLi, and the like; in a suitably selected solvent or mixture of solvents such as hexanes, THF, DME, and the like; to yield the corresponding compound of formula (XLIV).

Alternatively, the compound of formula (XLII) is reacted with a suitably substituted compound of formula (XLIII), wherein M³ is MgBr or MgCl, a known compound or compound prepared by known methods; under Grignard conditions, to yield the corresponding compound of formula (XLIV).

The compound of formula (XLIV) is reacted with a suitably substituted compound of formula (XXXI), a known compound or compound prepared by known methods; in the presence of a suitably selected base such as KF, $K_2CO_3$, DIPEA, and the like; in a suitably selected solvent such as DMSO, DMF, and the like; to yield the corresponding compound of formula (XLV).

The compound of formula (XLV) is reacted with a suitably selected reducing agent such as $SnCl_2$, and the like; in the presence of a suitably selected acid such as acetic acid, conc. HCl, and the like; in water; at a temperature in the range of from about 20° C. to about 60° C., for example, at about 50° C.; to yield the corresponding compound of formula (XLVI).

The compound of formula (XLVI) is reacted with a suitably substituted compound of formula (XXXIX), a known compound or compound prepared by known methods; in air; in a suitably selected solvent such as DMSO, and the like; to yield the corresponding compound of formula (Ic).

Compounds of formula (I) (for example, compounds of formula (I) wherein

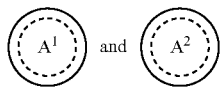

and are each an optionally substituted phenyl) may alternatively be prepared as described in Scheme 5, below.

Scheme 5

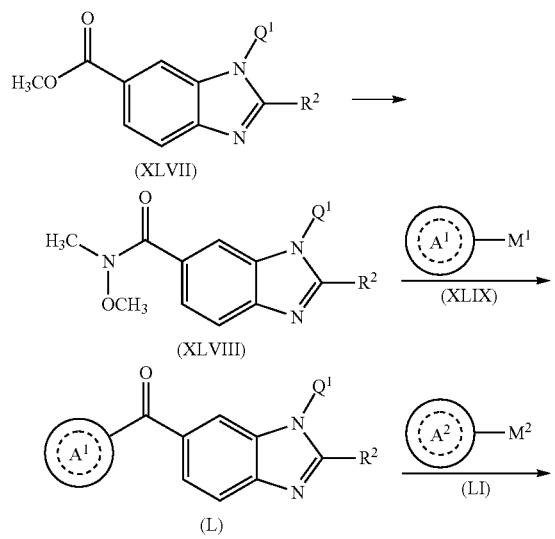

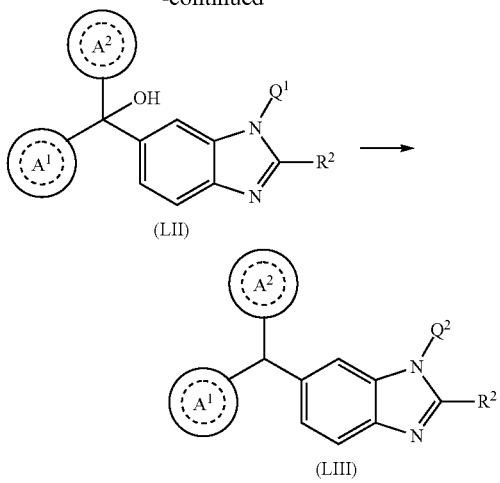

Accordingly, a suitably substituted compound of formula (XLVII), wherein $Q^1$ is selected from the group consisting of —$R^3$,

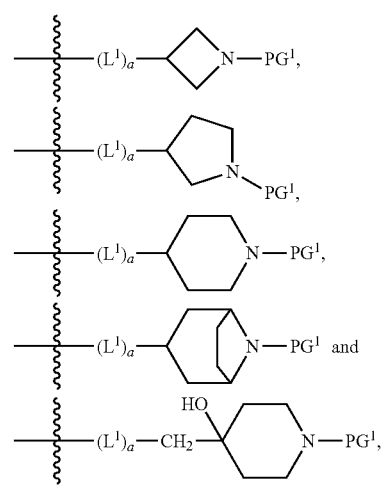

a known compound or compound prepared as described herein, is reacted with N,O-dimethylhydroxylamine, a known compound; in the presence of a suitably selected base such as LiHMDS, NaHMDS, and the like; in a suitably selected solvent such as THF, DME, and the like; to yield the corresponding compound of formula (XLVIII).

The compound of formula (XLVIII) is reacted with a suitably substituted compound of formula (XLIX), wherein $M^1$ is MgBr or MgCl, a known compound or compound prepared by known methods; under Grignard conditions; to yield the corresponding compound of formula (L).

The compound of formula (L) is reacted with a suitably substituted compound of formula (LI), where $M^2$ is I, a known compound or compound prepared by known methods; in the presence of magnesium; in the presence of $I_2$, in a suitably selected solvent such as THF; to yield the corresponding compound of formula (LII). Alternatively, the compound of formula (L) is reacted with a suitably substituted compound of formula (LI) wherein $M^2$ is MgBr or MgCl; under Grignard conditions; to yield the corresponding compound of formula (LII). Alternatively, the compound of formula (L) is reacted with a suitably substituted compound of formula (LI) wherein M² is Li; according to known methods; to yield the corresponding compound of formula (LII).

The compound of formula (LII) is reacted with Et₃SiH in combination with TFA or SnCl₂ in combination with HCl or TiCl₄; in a suitably selected organic solvent such as DCM, DCE, and the like; to yield the corresponding compound of formula (LIII), wherein Q² is selected from the group consisting of —R³,

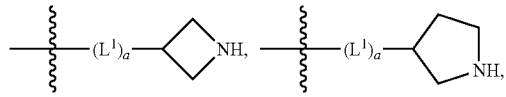

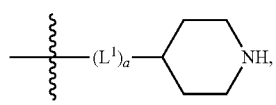

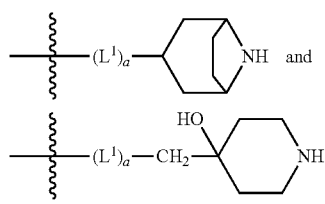

One skilled in the art will recognize that in the reaction of the compound of formula (LII) to yield the corresponding compound of formula (LIII), wherein Q¹ is R³, the R³ group does not participate in the reaction, whereas when Q¹ is selected from the group consisting of

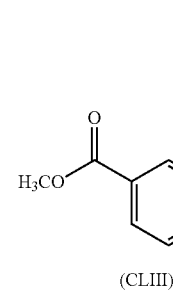

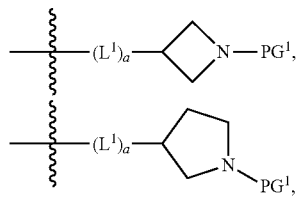

the PG¹ group is simultaneously removed.

One skilled in the art will further recognize that for the compound of formula (LIII) when Q² is R³, then the compound of formula (LIII) corresponds to the compound of formula (I). Wherein the compound of formula (LIII), Q² is selected from the group consisting of

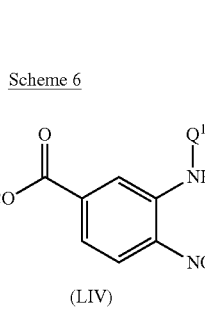

the desired compounds of formula (I) may be prepared by further reacting the compound of formula (LIII), as described in more detail hereinafter (for example by reacting with a suitably substituted alkylating reagent, with a suitably selected acid chloride, a suitably selected sulfonyl chloride, and the like).

Compounds of formula (LVII) may be prepared as described in Scheme 6, below.

Scheme 6

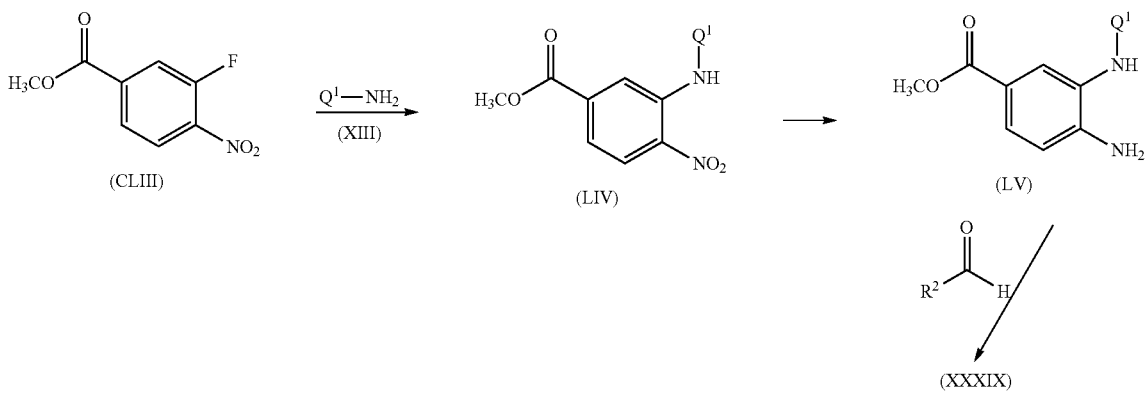

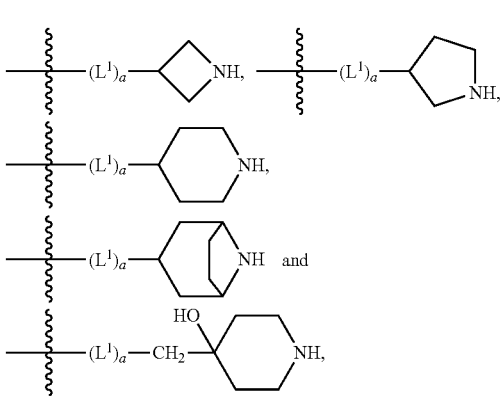

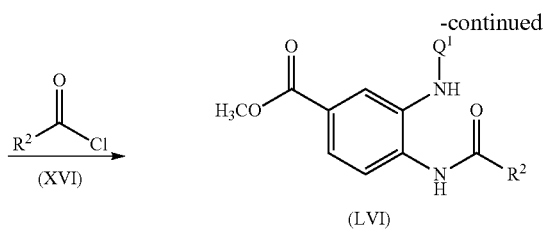

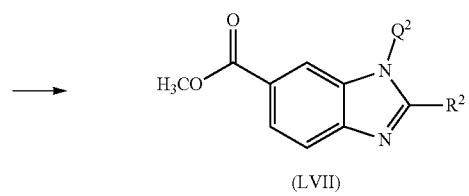

Accordingly, a suitably substituted compound of formula (CLIII), a known compound or compound prepared by known methods, is reacted with a suitably substituted compound of formula (XIII), wherein $Q^1$ is selected from the group consisting of —$R^3$,

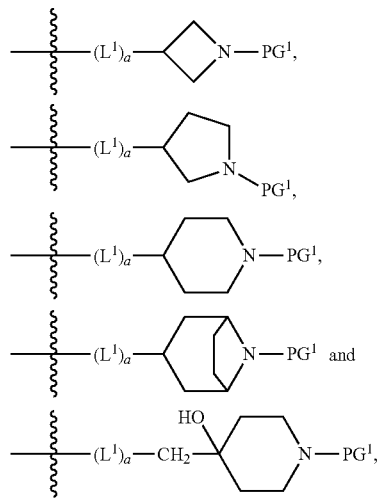

a known compound or compound prepared by known methods; in the presence of s suitably selected base such as DIPEA, TEA, pyridine, and the like; in a suitably selected solvent such as acetonitrile, DMF, and the like; at a temperature in the range of from about 20° C. to about reflux, for example at about 85° C.; to yield the corresponding compound of formula (LIV).

The compound of formula (LIV) is hydrogenated by reacting with, for example hydrogen gas, in the presence of a suitably selected catalyst such as Raney nickel, Pd/C, and the like; in a suitably selected solvent or mixture of solvents such as methanol/THF, ethanol/THF, and the like; to yield the corresponding compound of formula (LV).

The compound of formula (LV) is reacted with a suitably substituted compound of formula (XVI), a known compound or compound prepared by known methods; in the presence of a suitably selected base such as TEA, DIPEA, pyridine, and the like; in a suitably selected solvent such as DCM, THF, and the like; to yield the corresponding compound of formula (LVI).

The compound of formula (LVI) is reacted with a suitably selected acid such as acetic acid; neat; at a temperature in the range of from about 60° C. to about 150° C., for example at about 120° C.; to yield the corresponding compound of formula (LVII), wherein $Q^2$ is selected from the group consisting of —$R^3$,

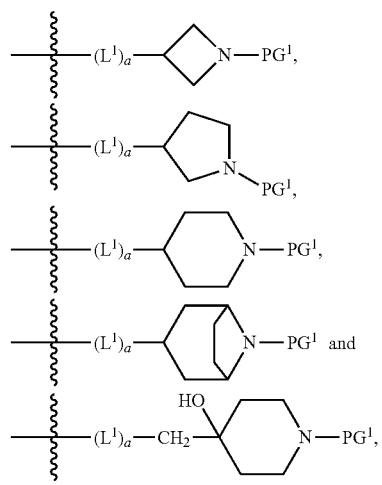

Alternatively, the compound of formula (LV) is reacted with a suitably substituted compound of formula (XXXIX), a known compound or compound prepared by known methods; in air; in a suitably selected solvent such as DMSO, and the like; to yield the corresponding compound of formula (LVII).

One skilled in the art will recognize that wherein the compound of formula (LVII) $Q^2$ is $R^3$, then the compound of formula (LVII) corresponds to the compound of formula (XLVII).

One skilled in the art will further recognize that wherein the compound of formula (LVI) $Q^1$ is selected from the group consisting of the reaction of the compound of formula (LVI) with acetic acid will result in not only the cyclization of the benzimidazole ring structure, but also the removal of the $PG^1$ group, to yield the corresponding compound of formula (LVII) wherein $Q^2$ is selected from the group consisting of

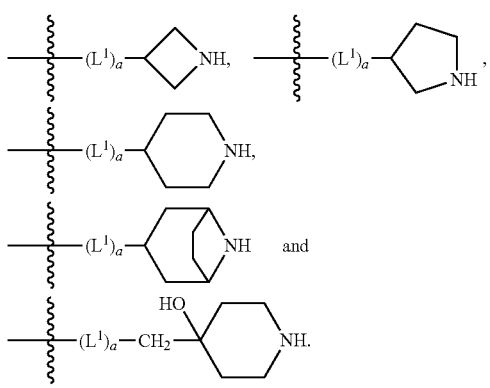

The compound of formula (LVII) is then further reacted, according to known methods, to protect the nitrogen atom of the $Q^1$ group, as needed or desired. For example, the compound of formula (LVII) may be reacted with BOC anhydride, in the presence of a base such as $NaHCO_3$, and the like, in a solvent such as DCM, and the like; to yield the corresponding compound of formula (XLVII), wherein $PG^1$ is BOC.

Compounds of formula (I) wherein $R^1$ is $C_{1-4}$alkoxy may be prepared from a suitably substituted intermediate compound of formula (LIX), which may prepared as described in Scheme 7 below.

Scheme 7

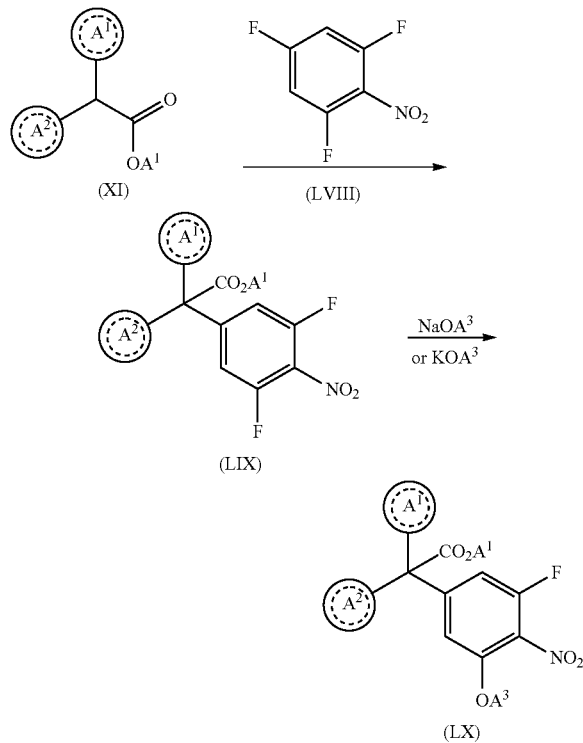

Accordingly, a suitably substituted compound of formula (XI) is reacted with a suitably substituted compound of formula (LVIII), a known compound or compound prepared by known methods; in the presence of a base such as LiHMDS, NaHMDS, and the like; in a suitably selected solvent such as 1,4-dioxane, THF, and the like; to yield the corresponding compound of formula (LIX).

The compound of formula (LIX) is reacted with a suitably selected sodium alkoxide ($NaOA^3$) or potassium alkoxide ($KOA^3$), wherein $A^3$ is a $C_{1-4}$alkyl and wherein $—OA^3$ corresponds to the desired $R^1$ alkoxy group; in a suitably selected solvent such as DMF, THF, and the like; to yield the corresponding compound of formula (LX). One skilled in the art will recognize that wherein the sodium alkoxide is sodium methoxide, said reagent is preferably added as a mixture with methanol.

The compound of formula (LX) is then substituted for the compound of formula (XII) in Scheme 1, and reacted as described in the Schemes herein; to yield the desired compound of formula (I) wherein $R^1$ is $C_{1-4}$alkoxy.

One skilled in the art will recognize that the $R^2$ group may be incorporated into the compound of formula (I) as a single substituent group (as described in the Schemes above and the examples which follow hereinafter) or may alternatively, be incorporated into the compound of formula (I) via two or more reaction steps. More particularly, the $R^2$ group may be incorporated into the desired compound of formula (I) as described in Scheme 8, below.

Scheme 8

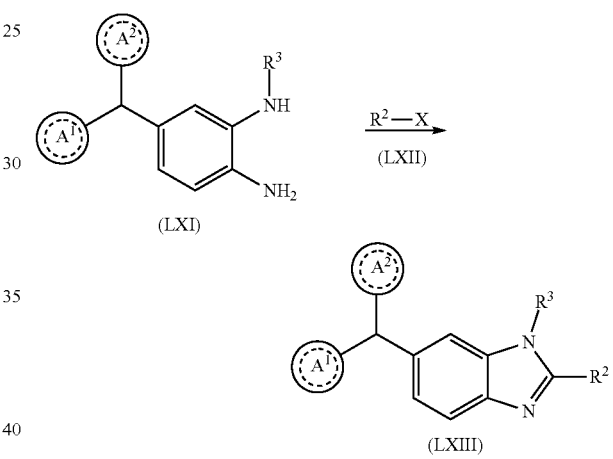

Accordingly, a suitably substituted compound of formula (LXI), prepared according to the processes as herein described is reacted with a suitably substituted $R^2$ containing reagent, a compound of formula (LXII); to yield the corresponding compound of formula (LXIII) (a compound of formula (I) wherein $R^1$ and $R^0$ are each hydrogen).

In an example, the compound of formula (LXII) corresponds to a suitably substituted aldehyde (wherein X is —CHO); and the compound of formula (LXI) is reacted with the compound of formula (LXII) in air; in a suitably selected solvent such as DMSO, and the like; to yield the corresponding compound of formula (LXIII).

In another example, the compound of formula (LXII) corresponds to a suitably substituted acid (wherein X is —C(O)OH); and the compound of formula (LXI) is reacted with the compound of formula (LXII), in the presence of a suitably selected acid such as TFA, and the like; neat in a suitably selected solvent; to yield the corresponding compound of formula (LXIII).

In another example, the compound of formula (LXII) corresponds to $R^2$—$C(OCH_3)_3$, wherein $R^2$ is $C_{1-4}$alkyl, and the compound of formula (LXI) is reacted with the compound of formula (LXII) in the presence of a suitably selected acid such as HCl; neat or in a suitably selected solvent; to yield the corresponding compound of formula (LXIII). One skilled in the art will recognize that compounds of formula (I) wherein R² is hydrogen, may be similarly prepared from the compound of formula (LXI) with a compound of the formula H—C(OCH₃)₃, as described above.

Compounds of formula (I) wherein R² is NH₂ may be similarly prepared by reacting a suitably substituted compound of formula (LXI) with cyanogen bromide, a known compound; in a suitably selected solvent such as ethanol, methanol, and the like; to yield the corresponding compound of formula (LXIII) wherein R₂ is NH₂.

Compounds of formula (I) wherein R² is NR^E R^F (and wherein one or both of R^E and R^F are selected C₁₋₄alkyl) may be similarly prepared by reacting a suitably substituted compound of formula (LXI) with 1,1-carbonyldiimidazole, a known compound; in a suitably selected solvent such as THF, DCM, and the like; to yield the corresponding compound of formula (LXIII) wherein R² group is replaced with a =O group; which compound is then reacted with a suitably selected source of chlorine such as POCl₃, and the like; neat or in a suitably selected solvent; at a temperature in the range of from about 50° C. to about 120° C., for example at about 90° C.; to yield the corresponding compound of formula (LXIII) wherein R² is chloro; and which compound is further reacted with a suitably substituted amine of the formula NHR^E R^F, a known compound or compound prepared by known methods; in a suitably selected solvent such as THF, DCM, 1,4-dioxane, and the like; to yield the corresponding compound of formula (LXIII) wherein R² is NR^E R^F.

One skilled in the art will further recognize that the R² group may be incorporated into the desired compound of formula (I) as a complete substituent group, or may alternatively be incorporated via two or more reaction steps. For example, wherein R² is —CH₂CH₂—NH₂, a compound of formula (LXIII) wherein R² is —CH₂CH₂—C(O)O—CH₂CH₃ may be prepared as described herein and then reacted with a suitably selected base such as NaOH, and the like, according to known methods; to yield the corresponding compound wherein the ester is converted to the corresponding acid (i.e. R² is —CH₂CH₂—C(O)OH). This compound may then be further reacted in a mixture of DPPA, TEA, benzene, according to known methods, to yield the corresponding compound wherein R² is —CH₂CH₂—NH₂. Additional transformations would be readily known to those skilled in the art, and are further described in specific examples which follow hereinafter.

Compounds of formula (I) wherein R³ is selected from the group consisting of

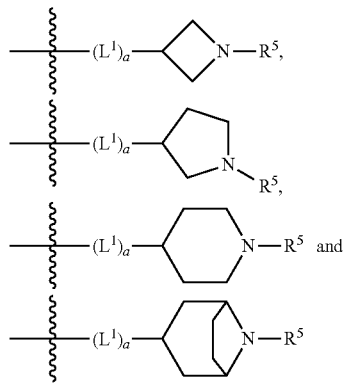

may alternatively be prepared according to the process as outlined in Scheme 9, below.

Scheme 9

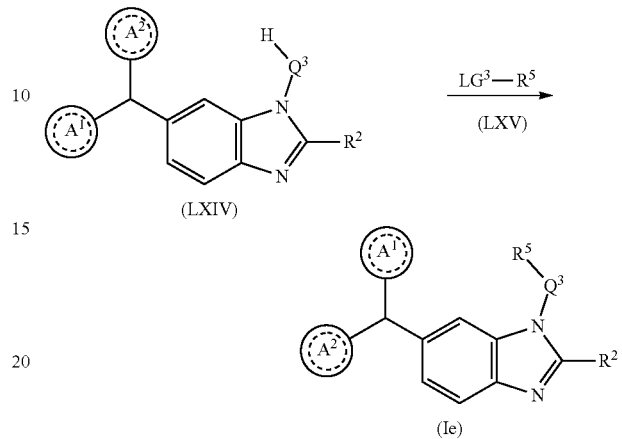

Accordingly, a suitably substituted compound of formula (LXIV), wherein Q³ is

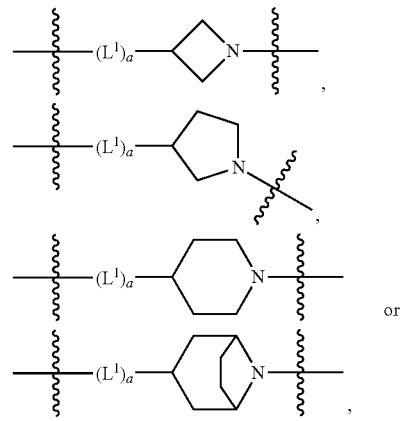

a compound prepared for example as described in the Schemes 1-2 above, is reacted with a suitably substituted compound of formula (LXV), wherein LG³ is a suitably selected leaving group, a known compound or compound prepared by known methods; to yield the corresponding compound of formula (Ie).

In an example, the compound of formula (LXIV) is reacted with a compound of formula (LXV), a suitably substituted sulfonyl chloride, wherein LG³ is chloro; in the presence of a suitably selected base such as K₂CO₃, Na₂CO₃, TEA, DIPEA, pyridine, and the like; to yield the corresponding compound of formula (Ie) wherein R⁵ is a substituent group bound through a sulfonyl (i.e. —SO₂—) group.

In another example, the compound of formula (LXIV) is reacted with a compound of formula (LXV), a suitably substituted phenyl bromide, and the like, wherein LG³ is bromo; in the presence of a suitably selected catalyst such as Pd₂(dba)₃, Pd(OAc)₂, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; at an elevated temperature in the range of from about 75° C. to about 150° C.; to yield the corresponding compound of formula (Ie) wherein $R^5$ is the corresponding optionally substituted phenyl, and the like.

In another example, the compound of formula (LXIV) is reacted with a compound of formula (LXV), a suitably substituted $C_{1-4}$alkyl bromide, and the like, wherein $LG^3$ is bromo; in the presence of a suitably selected base such as Hunig's base, $K_2CO_3$, and the like; in a suitably selected solvent such as acetonitrile, and the like; to yield the corresponding compound of formula (Ia) wherein $R^5$ is the corresponding optionally substituted $C_{1-4}$alkyl, and the like.

In another example, the compound of formula (LXIV) is reacted with a compound of formula (LXV), a suitably substituted aldehyde, wherein $LG^3$ is =O; in the presence of a suitably selected reducing agent such as $NaBH(OAc)_3$, and the like; in a suitably selected solvent such as DCE, methanol, ethanol, and the like; to yield the corresponding compound of formula (Ia). One skilled in the art will recognize that the carbon atom of the aldehyde of formula (LXV) is incorporated into the $R^5$ substituent group as a —$CH_2$— (for example wherein the compound of formula (LXV) is an optionally substituted phenyl aldehyde, then the resulting $R^5$ substituent group is the corresponding, optionally substituted benzyl group.)

Alternatively, the compound of formula (LXIV) is reacted with a suitably substituted isocyanate, in the presence of a suitably selected base such as TEA, DIPEA, pyridine, and the like; in a suitably selected solvent such as DCM, THF, DMF, and the like; to yield the corresponding compound wherein the $R^5$ group is bound through a —C(O)—NH— group.

Alternatively, the compound of formula (LXIV) is reacted with a suitably substituted chloroformate, in the presence of a suitably selected base such as TEA, DIPEA, pyridine, and the like; in a suitably selected solvent such as THF, and the like; to yield the corresponding compound wherein the $R^5$ group is bound through a —C(O)—O— group.

Alternatively, the compound of formula (LXIV) is reacted with CDI, a known compound; in the presence of a suitably selected base such as TEA, DIPEA, pyridine, and the like; in a suitably selected solvent such as DCM, THF, and the like; to yield the corresponding compound wherein the $R^5$ group replaced with —C(O)-imidazol-1-yl; which compound is further reacted with a suitably substituted alcohol or amine; in the presence of a suitably selected base such as $Cs_2CO_3$, $K_2CO_3$, TEA, DIPEA, and the like; in a suitably selected solvent such as DMF, acetonitrile, and the like; to yield the corresponding compound wherein the $R^5$ group is bound through —C(O)—O— or a —C(O)—NH— group, respectively.

Compounds of formula (I), wherein $R^0$ is hydroxy may alternatively be prepared as described in Scheme 10, below.

Scheme 10

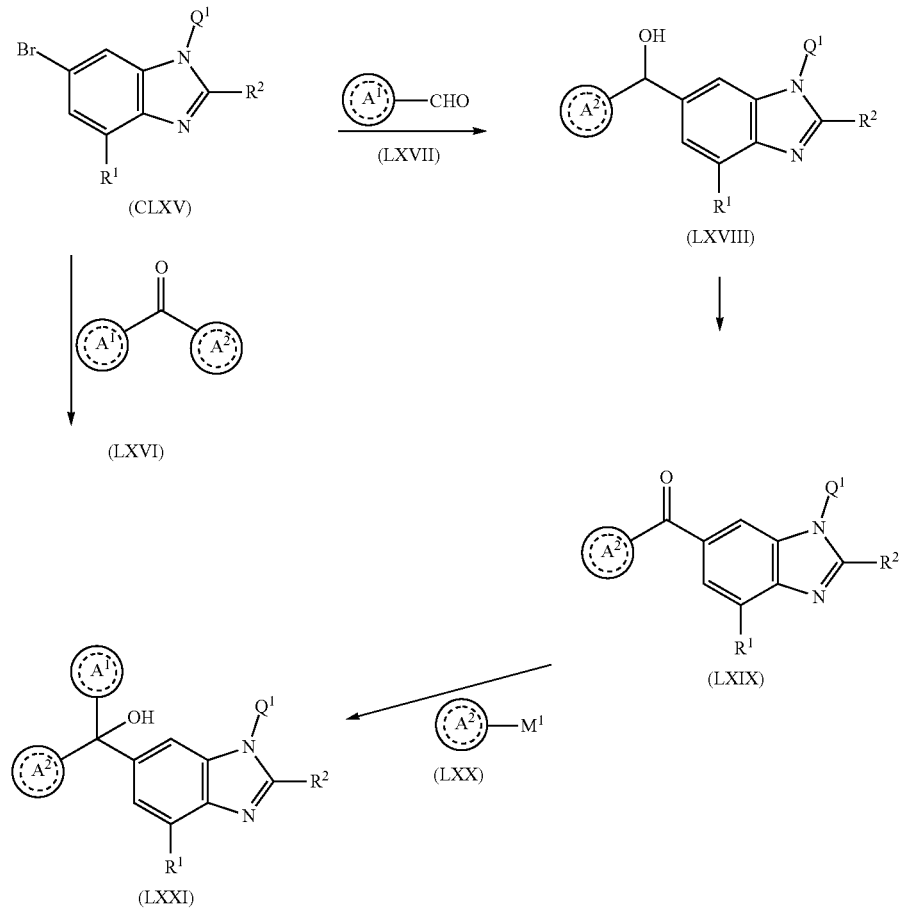

Accordingly, a suitably substituted compound of formula (CLXV), wherein $Q^1$ is as defined above, a known compound or compound prepared as described herein, is reacted with a suitably substituted compound of formula (LXVI), a known compound or compound prepared by known methods; in the presence of a suitably selected lithiating reagent such as n-BuLi, t-BuLi, and the like; in a suitably selected solvent such as THF, DME, and the like; to yield the corresponding compound of formula (LXXI).

Alternatively, a suitably substituted compound of formula (CLXV), a known compound or compound prepared by known methods, is reacted with a suitably substituted compound of formula (LXVII), a known compound or compound prepared by known methods; in the presence of a suitably selected lithiating reagent such as n-BuLi, t-BuLi, and the like; in a suitably selected solvent such as THF, DME, and the like; to yield the corresponding compound of formula (LXVIII).

The compound or formula (LXVIII) is reacted with a suitably selected oxidizing agent such as DMP, and the like; in a suitably selected solvent such as DCM, and the like; to yield the corresponding compound of formula (LXIX).

The compound of formula (LXIX) is reacted with a suitably substituted compound of formula (LXX), wherein $M^1$ is MgBr or MgCl, a known compound or compound prepared by known methods; under Grignard conditions; to yield the corresponding compound of formula (LXXI). One skilled in the art will recognize that the compound of formula (LXIX) may alternatively be reacted with a compound of formula (LXX) wherein $M^1$ is replaced with lithium, according to known methods, to yield the corresponding compound of formula (LXXI).

One skilled in the art will recognize that wherein $Q^1$ is $R^3$, then the compound of formula (LXXI) is the corresponding compound of formula (I). One skilled in the art will further recognize that when in the compound of formula (LXXI), $Q^1$ is other than $R^3$, then the compound of formula (LXXI) may be further reacted, as described herein, to yield the desired compound of formula (I). For example, the compound of formula (LXXI) may be substituted for the compound of formula (XVIIIa) in Scheme 2 and reacted as described therein to yield the desired $R^3$ substituent group.

One skilled in the art will further recognize that the compound of formula (LXXI) may be further optionally reacted, as described herein to convert the hydroxy group at the $R^0$ position to hydrogen.

One skilled in the art will further recognize that the compounds of formula (LXV) may be prepared according to known methods, and/or by adapting the procedures as described in the Example which follow hereinafter.

Compounds of formula (LXV) wherein $R^1$ is hydrogen may alternative be prepared as described in Scheme 11 below.

Scheme 11

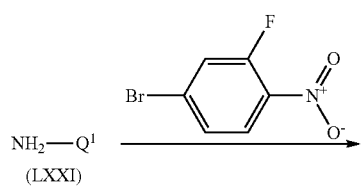
(LXXI)

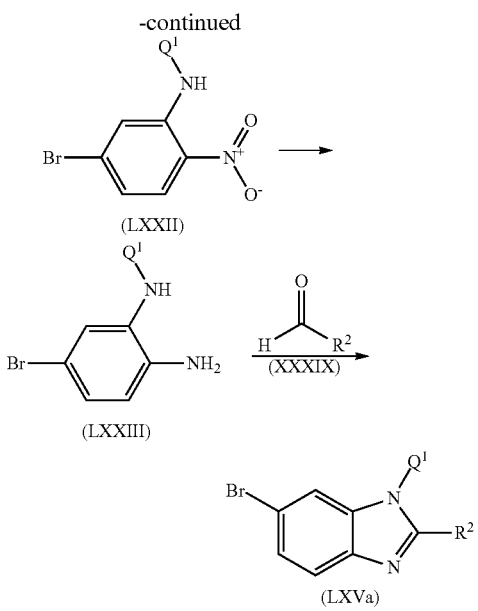

Accordingly, a suitably substituted compound of formula (LXXI), wherein $Q^1$ is as defined above, a known compound or compound prepared by known methods, is reacted with 4-bromo-2-fluoro-1-nitrobenzene, a known compound; in the presence of a suitably selected base such as DIPEA, TEA, pyridine and the like; in a suitably selected solvent such as acetonitrile, DCM, and the like; to yield the corresponding compound of formula (LXXII).

The compound of formula (LXXII) is reacted Fe in the presence of $NH_4Cl$; in a suitably selected solvent such as methanol, ethanol, and the like; in the presence of water; at a temperature in the range of from about 50° C. to about 100° C., for example at about 80° C.; to yield the corresponding compound of formula (LXXIII). One skilled in the art will recognize that alternate reduction conditions, for example reacting the compound of formula (LXXII) with $H_2$ gas in the presence of Raney nickel in a mixture of methanol/THF may also be used to yield the corresponding compound of formula (LXXIII).

The compound of formula (LXXIII) is reacted with a suitably substituted compound of formula (XXXIX), a known compound or compound prepared by known methods; in the presence of air; in a suitably selected solvent such as DMSO, and the like; at a temperature in the range of from about room temperature to about 75° C., for example at about 50° C., to yield the corresponding compound of formula (LXVa).

Compounds of formula (LXV) wherein $R^1$ is $-OC_{1-4}$ alkyl may alternatively be prepared as described in Scheme 12 below.

Scheme 12

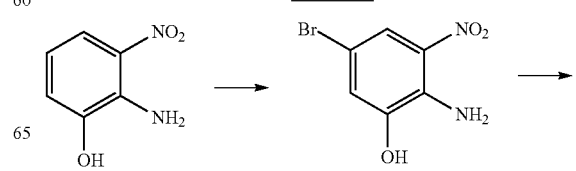

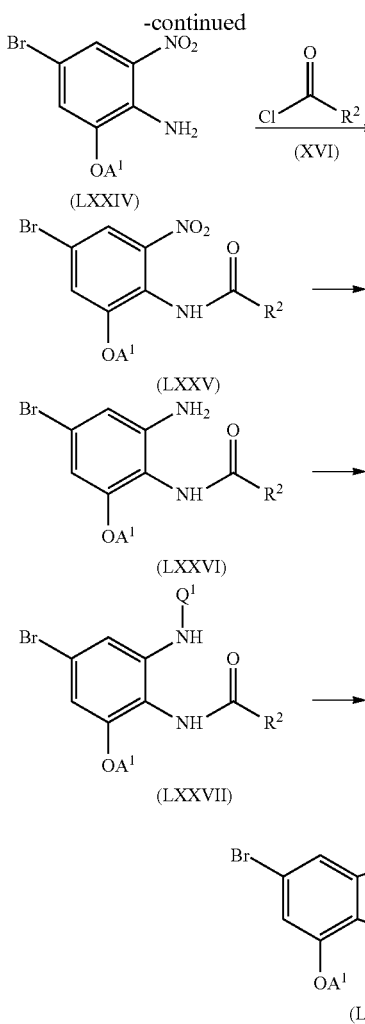

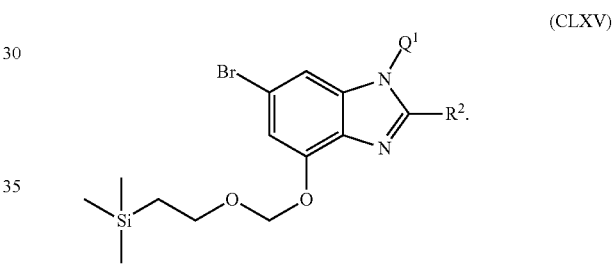

The compound of formula (LXXVI) is reacted with a suitably substituted aldehyde or carbonyl compound, according to known methods or methods as described in the Schemes and Examples herein; to yield the corresponding compound of formula (LXXVII), wherein $Q^1$ is as defined herein. For example, the compound of formula (LXXVI) may be reacted with 1-((trifluoromethyl)sulfonyl)piperidin-4-one, in the presence of $NaBH(OAc)_3$, in the presence of acetic acid, in DCE, to yield the corresponding compound of formula (LXXVII) wherein $Q^1$ is 1-trifluoromethyl-sulfonyl-piperidin-4-yl.

The compound of formula (LXXVII) is reacted with a suitably selected acid such as acetic acid, and the like; neat or in a suitably selected solvent; to yield the corresponding compound of formula (LXVb).

One skilled in the art will recognize that the 2-amino-5-bromo-3-nitrophenol may alternatively be reacted with $(CH_3)_3Si$—$CH_2CH_2$—O—$CH_2Cl$, a known compound, in the presence of a suitably selected base such as $K_2CO_3$, $Na_2CO_3$, and the like; in a suitably selected solvent such as DMF, acetonitrile, and the like; to yield the corresponding compound of formula (LXXIV) wherein the —$OA^1$ group is replaced with —O—$CH_2$—O—$CH_2CH_2$—$Si(CH_3)_3$. Said intermediate is then reacted as described in Scheme 12 above to yield the corresponding compound of formula (CLXV)

Accordingly, 2-amino-3-nitrophenol, a known compound, is reacted with a suitably selected source of bromine such as $Br_2$, and the like; in the presence of a suitably selected acid such as acetic acid, and the like; neat or in a suitably selected solvent and the like; to yield 2-amino-5-bromo-3-nitrophenol.

The 2-amino-5-bromo-3-nitrophenol is reacted with a suitably selected alkylating agent, according to known methods, to yield the corresponding compound of formula (LXXIV), wherein $A^1$ is the corresponding $C_{1-4}$alkyl. For example, wherein the compound of formula (LXXIV) $A^1$ is —$CH_3$, the 2-amino-5-bromo-3-nitrophenol may be reacted with $CH_3I$, in the presence of a base such as $K_2CO_3$, and the like; in a solvent such as DMF, and the like.

The compound of formula (LXXIV) is reacted with a suitably substituted compound of formula (XVI), a known compound or compound prepared by known methods; in the presence of a suitably selected base such as TEA, DIPEA, pyridine, and the like; in a suitably selected solvent such as DCM, DCE, and the like; to yield the corresponding compound of formula (LXXV).

The compound of formula (LXXV) is reacted Fe in the presence of $NH_4Cl$; in a suitably selected solvent such as methanol, ethanol, and the like; in the presence of water; at a temperature in the range of from about 50° C. to about 100° C., for example at about 80° C.; to yield the corresponding compound of formula (LXXVI).

The compound of formula (CLXV) may then be reacted according to the procedures as described in the Schemes and Examples herein to yield the corresponding compound of formula (I) wherein the $R^1$ group is replaced with —O—$CH_2$—O—$CH_2CH_2$—$Si(CH_3)_3$, which compound is then de-protected according to known methods, to yield the desired compound of formula (I) wherein $R^1$ is hydroxy.

One skilled in the art will further recognize that the $R^5$ substituent group may alternatively be incorporated into the desired compound of formula (I) via multiple reaction steps, according to known methods, and as exemplified for representative compounds in the Synthesis Examples which follow hereinafter.

One skilled in the art will further recognize that additional substituent groups as defined herein may be similarly incorporated into the desired compound of formula (I) via one or more coupling reactions and/or substituent transformations (e.g. removal of an alkyl group, conversion of a —$CO_2H$ group to corresponding —$C(O)NH_2$ group, hydrogenation, reductive amination, nucleophilic substitution, Suzuki coupling, Mitsunobu coupling, etc.), according to the methods known in the art, and/or according to procedures as described in the general synthesis schemes and examples herein. One skilled in the art will further recognize that the reaction steps and processes described herein (in the synthesis schemes and examples) may be adapted and/or applied to the synthesis of any of the compounds of the present invention.

One skilled in the art will further recognize that in any of the processes described herein, the

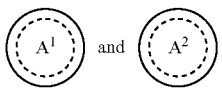

and rings (as substituent groups or in reagents containing said substituent groups) may be interchanged, and the synthesis completed as described, to yield the corresponding desired compound.

One skilled in the art will further recognize that in the synthesis of the compounds of formula (I) of the present invention, the various substituent groups may be incorporated in the order specifically described in the Scheme and Examples herein, or may alternatively be incorporated in a different order, adapting and/or adjusting the individual reaction step conditions to yield the desired intermediate or product compound.

Pharmaceutical Compositions and Methods of Treatment

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.5 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may contain suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of metabolic disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.01 to about 50.0 mg/kg of body weight per day, or any amount or range therein. More preferably, from about 0.05 to about 15.0 mg/kg of body weight per day, or any amount or range therein. More preferably, from about 0.07 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Synthesis Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example PH-1

4-(4-[6-[bis(4-chlorophenyl)methyl]-2-cycopropyl-1H-1,3-benzodiazol-1-yl]piperidine-1-sulfonyl)benzoic acid

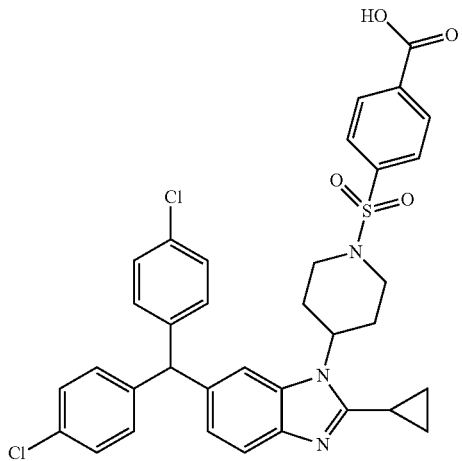 [SMILES: O=C(O)c1ccc(S(=O)(=O)N2CCC(n3c(C4CC4)nc4ccc(C(c5ccc(Cl)cc5)c5ccc(Cl)cc5)cc43)CC2)cc1]

Step 1: Synthesis of methyl 2,2-bis(4-chlorophenyl)acetate

Into a 1000-mL round-bottom flask, was placed a solution of 2,2-bis(4-chlorophenyl)acetic acid (150 g, 533.55 mmol, 1.00 equiv) in methanol (600 mL) and sulfuric acid (50 mL). The resulting solution was stirred overnight at 80° C. The mixture was concentrated under vacuum. The reaction was then quenched by the addition of water (500 mL). The pH value of the solution was adjusted to pH 7 with sodium hydroxide. The resulting solution was extracted with ethyl acetate (3×500 mL) and the organic layers combined and dried over anhydrous sodium sulfate to yield methyl 2,2-bis(4-chlorophenyl)acetate as yellow oil. LC/MS (ES, m/z): 295 [M+H]+.

Step 2: Synthesis of methyl 2,2-bis(4-chlorophenyl)-2-(3-fluoro-4-nitrophenyl)acetate Into a 1000-mL 3-necked round-bottom flask purged and maintained with an inert atmosphere of nitrogen, was placed a solution of methyl 2,2-bis(4-chlorophenyl)acetate (54 g, 182.95 mmol, 1.00 equiv) in tetrahydrofuran (250 mL). To the mixture was then added t-BuOK (201 mL, 1.10 equiv) dropwise with stirring at 0° C. in 20 min. To the resulting mixture was added a solution of 2,4-difluoro-1-nitrobenzene (37.5 g, 235.72 mmol, 1.05 equiv) in tetrahydrofuran (250 mL) dropwise with stirring. The resulting solution was stirred overnight at room temperature. The residue was applied onto a silica gel column with ethyl acetate/petroleum ether (1:20) to yield methyl 2,2-bis(4-chlorophenyl)-2-(3-fluoro-4-nitrophenyl)acetate as yellow oil. LC/MS (ES, m/z): 434 [M+H]$^+$.

Step 3: Synthesis of tert-butyl 4-([5-[1,1-bis(4-chlorophenyl)-2-methoxy-2-oxoethyl]-2-nitrophenyl]amino)piperidine-1-carboxylate Into a 1000-mL round-bottom flask, was placed a solution of methyl 2,2-bis(4-chlorophenyl)-2-(3-fluoro-4-nitrophenyl)acetate (35 g, 80.60 mmol, 1.00 equiv) in CH$_3$CN (200 mL), tert-butyl 4-aminopiperidine-1-carboxylate (19 g, 94.87 mmol, 1.20 equiv) and DIEA (26 g, 201.18 mmol, 2.50 equiv). The resulting solution was stirred overnight at 85° C. The resulting mixture was concentrated under vacuum. The solids were collected by filtration to yield tert-butyl 4-([5-[1,1-bis(4-chlorophenyl)-2-methoxy-2-oxoethyl]-2-nitrophenyl]amino)piperidine-1-carboxylate as a yellow solid. LC/MS (ES, m/z): 614 [M+H]+.

Step 4: Synthesis of tert-butyl 4-([2-amino-5-[1,1-bis(4-chlorophenyl)-2-methoxy-2-oxoethyl]phenyl]amino)piperidine-1-carboxylate Into a 500-mL round-bottom flask, was placed a solution of tert-butyl 4-([5-[1,1-bis(4-chlorophenyl)-2-methoxy-2-oxoethyl]-2-nitrophenyl]amino)piperidine-1-carboxylate (31 g, 25.22 mmol, 1.00 equiv, 50%) in methanol/THF (200/100 mL) and Raney Ni (20 g). The resulting solution was stirred overnight at room temperature. The resulting mixture was concentrated under vacuum to yield tert-butyl 4-([2-amino-5-[1,1-bis(4-chlorophenyl)-2-methoxy-2-oxoethyl]phenyl]amino)piperidine-1-carboxylate as a red solid. LC/MS (ES, m/z): 584 [M+H]+.

Step 5: Synthesis of tert-butyl 4-([5-[1,1-bis(4-chlorophenyl)-2-methoxy-2-oxoethyl]-2-cyclopropaneamidophenyl]amino)piperidine-1-carboxylate Into a 25-mL round-bottom flask, was placed a solution of tert-butyl 4-([2-amino-5-[1,1-bis(4-chlorophenyl)-2-methoxy-2-oxoethyl]phenyl]amino)piperidine-1-carboxylate (24 g, 41.06 mmol, 1.00 equiv) in dichloromethane (400 ml), cyclopropanecarbonyl chloride (4.2 g, 40.18 mmol, 1.00 equiv) and triethylamine (15 g, 148.24 mmol, 3.00 equiv). The resulting solution was stirred overnight at room temperature. The resulting mixture was concentrated under vacuum to yield tert-butyl 4-([5-[1,1-bis(4-chlorophenyl)-2-methoxy-2-oxoethyl]-2-cyclopropaneamidophenyl]amino) piperidine-1-carboxylate as red oil. LC/MS (ES, m/z): 652 [M+H]+.

Step 6: Synthesis of tert-butyl 4-[6-[1,1-bis(4-chlorophenyl)-2-methoxy-2-oxoethyl]-2-cyclopropyl-1H-1,3-benzodiazol-1-yl]piperidine-1-carboxylate Into a 500-mL round-bottom flask, was placed a solution of tert-butyl 4-([5-[1,1-bis(4-chlorophenyl)-2-methoxy-2-oxoethyl]-2-cyclopropaneamidophenyl]amino)piperidine-1-carboxylate (25 g, 38.31 mmol, 1.00 equiv) in acetic acid (300 mL). The resulting solution was stirred for 3 h at 120° C. The resulting mixture was concentrated under vacuum to yield tert-butyl 4-[6-[1,1-bis(4-chlorophenyl)-2-methoxy-2-oxoethyl]-2-cyclopropyl-1H-1,3-benzodiazol-1-yl]piperidine-1-carboxylate as red oil. LC/MS (ES, m/z): 634 [M+H]+.

Step 7: Synthesis of 2-(1-[1-[(tert-butoxy)carbonyl]piperidin-4-yl]-2-cyclopropyl-1H-1,3-benzodiazol-6-yl)-2,2-bis(4-chlorophenyl)acetic acid Into a 1000-mL round-bottom flask, was placed a solution of tert-butyl 4-[6-[1,1-bis(4-chlorophenyl)-2-methoxy-2-oxoethyl]-2-cyclopropyl-1H-1,3-benzodiazol-1-yl]piperidine-1-carboxylate (26 g, 40.97 mmol, 1.00 equiv) in tetrahydrofuran/MeOH (150/150 mL) and sodium hydroxide (3N) (300 mL). The resulting solution was stirred for 4 h at 50° C. The pH value of the solution was adjusted to pH 6 with hydrogen chloride (12 mol/L). The resulting solution was extracted with ethyl acetate (3×500 mL) and the organic layers combined to yield 2-(1-[1-[(tert-butoxy)carbonyl]piperidin-4-yl]-2-cyclopropyl-1H-1,3-benzodiazol-6-yl)-2,2-bis(4-chlorophenyl)acetic acid as red oil. LC/MS (ES, m/z): 620 [M+H]+.

Step 8: Synthesis of tert-butyl 4-[6-[bis(4-chlorophenyl)methyl]-2-cyclopropyl-1H-1,3-benzodiazol-1-yl]piperidine-1-carboxylate Into a 500-mL round-bottom flask, was placed a solution of 2-(1-[1-[(tert-butoxy)carbonyl]piperidin-4-yl]-2-cyclopropyl-1H-1,3-benzodiazol-6-yl)-2,2-bis(4-chlorophenyl) acetic acid (23 g, 37.06 mmol, 1.00 equiv) in toluene (200 mL) and DBU (36 g, 236.47 mmol, 6.00 equiv). The resulting solution was stirred for 3 h at 90° C. The resulting mixture was concentrated under vacuum. The residue was applied onto a silica gel column with DCM:MeOH (1:10) to yield tert-butyl 4-[6-[bis(4-chlorophenyl)methyl]-2-cyclopropyl-1H-1,3-benzodiazol-1-yl]piperidine-1-carboxylate as a light-yellow solid. LC/MS (ES, m/z): 576 [M+H]+.

Step 9: Synthesis of 6-[bis(4-chlorophenyl)methyl]-2-cyclopropyl-1-(piperidin-4-yl)-1H-1,3-benzodiazole Into a 500-mL round-bottom flask, was placed a solution of tert-butyl 4-[6-[bis(4-chlorophenyl)methyl]-2-cyclopropyl-1H-1,3-benzodiazol-1-yl]piperidine-1-carboxylate (24 g, 41.63 mmol, 1.00 equiv) in dichloromethane (100 mL) and $CF_3COOH$ (20 g, 175.41 mmol, 4.21 equiv). The resulting solution was stirred overnight at room temperature. The resulting mixture was concentrated under vacuum. The reaction was then quenched by the addition of water (100 mL). The pH value of the solution was adjusted to pH 8 with sodium carbonate (100%). The resulting solution was extracted with DCM (3×100 mL) and the organic layers combined and dried over anhydrous sodium sulfate, then concentrated under vacuum to yield 6-[bis(4-chlorophenyl) methyl]-2-cyclopropyl-1-(piperidin-4-yl)-1H-1,3-benzodiazole as a red solid. LC/MS (ES, m/z): 476 [M+H]+.

Step 10: Synthesis of 4-(4-[6-[bis(4-chlorophenyl) methyl]-2-cyclopropyl-1H-1,3-benzodiazol-1-yl] piperidine-1-sulfonyl)benzoic acid Into a 8-mL vial, was placed a solution of 6-[bis(4-chlorophenyl)methyl]-2-cyclopropyl-1-(piperidin-4-yl)-1H-1,3-benzodiazole (200 mg, 0.42 mmol, 1.00 equiv) in tetrahydrofuran (4 mL), triethylamine (85 mg, 0.84 mmol, 2.00 equiv) and 4-(chlorosulfonyl)benzoic acid (93 mg, 0.42 mmol, 1.00 equiv). The resulting solution was stirred overnight at room temperature. The resulting mixture was concentrated under vacuum. The product residue was purified by Prep-HPLC with the following conditions (Waters-2767-1): Column, Column, Column, Sunfire prep C18, 5 um, 19*100 mm; mobile phase, water in 0.05% TFA and $CH_3CN$ (45% $CH_3CN$ up to 65% in 8 min, up to 100% in 9 min, down to 45% in 10 min; Detector, UV 254 nm to yield 4-(4-[6-[bis(4-chlorophenyl)methyl]-2-cyclopropyl-1H-1,3-benzodiazol-1-yl]piperidine-1-sulfonyl)benzoic acid as a white solid.

$^1$H NMR (300 MHz, $CD_3OD$) δ: 8.29 (d, J=8.1 Hz, 2H), 7.98 (d, J=8.1 Hz, 2H), 7.78 (s, 1H), 7.65 (d, J=8.4 Hz, 1H), 7.34-7.37 (m, 5H), 7.13-7.15 (m, 4H), 5.88 (s, 1H), 4.07 (d, J=10.8 Hz, 2H), 2.47-2.74 (m, 5H), 2.13-2.16 (m, 2H), 1.26-1.42 (m, 4H). LC/MS (ES, m/z): 660 [M+H]+.

Example PH-2

6-(bis(4-chlorophenyl)methyl)-2-cyclopropyl-1-(1-(methylsulfonyl)piperidin-4-yl)-1H-benzo[d]imidazole

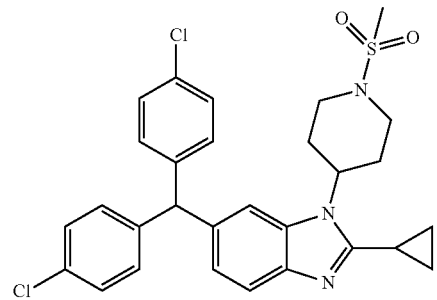 [SMILES: CS(=O)(=O)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting methanesulfonyl chloride for 4-(chlorosulfonyl)benzoic acid in Step 10.

$^1$H NMR (300 MHz, CDCl3) δ: 7.61 (d, J=8.4 Hz, 1H), 7.25-7.28 (m, 4H), 7.18 (s, 1H), 7.02-7.04 (m, 4H), 6.92 (d, J=8.4 Hz, 1H), 5.62 (s, 1H), 4.52-4.60 (m, 1H), 4.05 (d, J=12.6 Hz, 2H), 2.86-2.93 (m, 5H), 2.49-2.62 (m, 2H), 1.89-2.03 (m, 3H), 1.20-1.24 (m, 2H), 1.12-1.17 (m, 2H). LC/MS (ES, m/z): 554 [M+H]+.

Example PH-3

4-(4-(6-(bis(4-chlorophenyl)methyl)-2-cyclopropyl-1H-benzo[d]imidazol-1-yl)piperidin-1-yl)-4-oxobutanamide

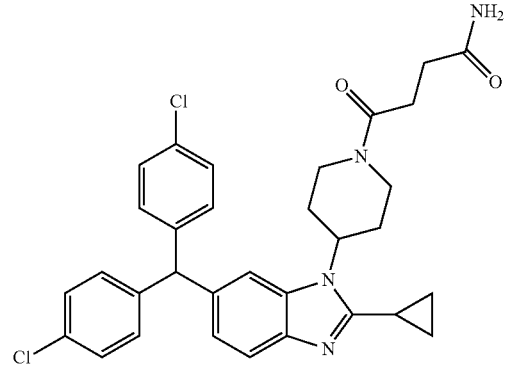 [SMILES: NC(=O)CCC(=O)N1CCC(n2c(C3CC3)nc3ccc(C(c4ccc(Cl)cc4)c4ccc(Cl)cc4)cc32)CC1]

Step 1: Synthesis of ethyl 4-(4-[6-[bis(4-chlorophenyl)methyl]-2-cyclopropyl-1H-1,3-benzodiazol-1-yl] piperidin-1-yl)-4-oxobutanoate Into a 100-mL round-bottom flask, was placed a solution of 6-[bis(4-chlorophenyl)methyl]-2-cyclopropyl-1-(piperidin-4-yl)-1H-1,3-benzodiazole (100 mg, 0.21 mmol, 1.00 equiv) in $CH_3CN$ (10 mL), potassium carbonate (87 mg, 0.63 mmol, 3.00 equiv) and ethyl 4-chloro-4-oxobutanoate (41.25 mg, 0.25 mmol, 1.20 equiv). The resulting solution was stirred overnight at room temperature. The reaction was then quenched by the addition of water (10 mL). The resulting solution was extracted with DCM (3×10 mL) and the organic layers combined, then dried over anhydrous sodium sulfate and concentrated under vacuum to yield ethyl 4-(4-[6-[bis(4-chlorophenyl)methyl]-2-cyclopropyl-1H-1,3-benzodiazol-1-yl]piperidin-1-yl)-4-oxobutanoate as a white solid.

Step 2: Synthesis of 4-(4-[6-[bis(4-chlorophenyl)methyl]-2-cyclopropyl-1H-1,3-benzodiazol-1-yl]piperidin-1-yl)-4-oxobutanamide Into a 30-mL sealed tube, was placed a solution of ethyl 4-(4-[6-[bis(4-chlorophenyl)methyl]-2-cyclopropyl-1H-1,3-benzodiazol-1-yl]piperidin-1-yl)-4-oxobutanoate (100 mg, 0.17 mmol, 1.00 equiv) in methanol/NH$_3$ (10 mL). The resulting solution was stirred for 1 min at 70° C. The resulting mixture was concentrated under vacuum. The product residue was purified by Prep-HPLC with the following conditions (Waters-2767-1): Column, Sunfire prep C18, 5 um, 19*100 mm; mobile phase, water in 0.05% NH$_4$HCO$_3$ and CH$_3$CN (30% CH$_3$CN up to 80% in 7 min, up to 100% in 9 min, down to 65% in 11 min); Detector, UV 254 nm to yield 4-(4-[6-[bis(4-chlorophenyl)methyl]-2-cyclopropyl-1H-1,3-benzodiazol-1-yl]piperidin-1-yl)-4-oxobutanamide as a white solid.

$^1$H NMR (300 MHz, CD3OD) δ: 7.48 (d, J=9.3 Hz, 1H), 7.30-7.33 (m, 5H), 7.09-7.12 (m, 4H), 6.97 (d, J=8.4 Hz, 1H), 5.77 (s, 1H), 4.87-4.95 (m, 1H), 4.73 (d, J=12.0 Hz, 1H), 4.21 (d, J=15.3 Hz, 1H), 3.30-3.35 (m, 1H), 2.59-2.83 (m, 5H), 2.22-2.40 (m, 3H), 1.90-2.10 (m, 2H), 1.12-1.17 (m, 4H). LC/MS (ES, m/z): 575 [M+H]+.

Example PH-4

1-[1-(benzenesulfonyl)piperidin-4-yl]-6-[bis(4-chlorophenyl)methyl]-2-cyclopropyl-1H-1,3-benzodiazole

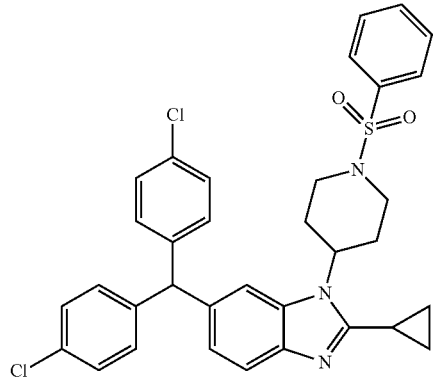 [SMILES: O=S(=O)(c1ccccc1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting benzenesulfonyl chloride for 4-(chlorosulfonyl)benzoic acid in Step 10.

$^1$H NMR (300 MHz, CDCl3) δ: 7.82 (d, J=6.9 Hz, 1H), 7.56-7.68 (m, 4H), 7.22-7.32 (m, 5H), 7.01-7.04 (m, 4H), 6.90 (d, J=8.1 Hz, 1H), 5.61 (s, 1H), 4.34-4.42 (m, 1H), 4.08 (d, J=11.1 Hz, 2H), 2.43-2.64 (m, 4H), 1.80-1.99 (m, 3H), 1.20-1.30 (m, 2H), 1.02-1.12 (m, 2H). LC/MS (ES, m/z): 616 [M+H]+.

Example PH-5

6-(bis(4-chlorophenyl)methyl)-2-cyclopropyl-1-(1-(4-fluorophenylsulfonyl)piperidin-4-yl)-1H-benzo[d]imidazole

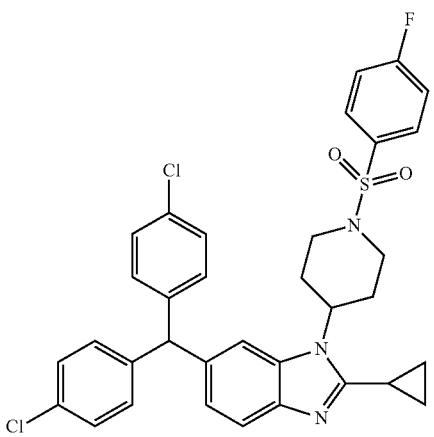 [SMILES: O=S(=O)(c1ccc(F)cc1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 4-fluorobenzene-1-sulfonyl chloride for 4-(chlorosulfonyl)benzoic acid in Step 10.

$^1$H NMR (300 MHz, CDCl3) δ: 7.84-7.89 (m, 2H), 7.64 (d, J=8.4 Hz, 1H), 7.24-7.32 (m, 7H), 7.04-7.07 (m, 4H), 6.94 (d, J=8.1 Hz, 1H), 5.64 (s, 1H), 4.39-4.46 (m, 1H), 4.09 (d, J=11.4 Hz, 2H), 2.46-2.68 (m, 4H), 1.90-2.03 (m, 3H), 1.23-1.33 (m, 2H), 1.06-1.12 (m, 2H). LC/MS (ES, m/z): 634 [M+H]+.

Example PH-6

6-(bis(4-chlorophenyl)methyl)-1-(1-(4-chlorophenylsulfonyl)piperidin-4-yl)-2-cyclopropyl-1H-benzo[d]imidazole

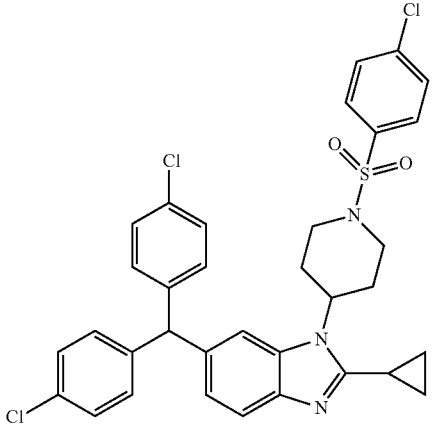 [SMILES: O=S(=O)(c1ccc(Cl)cc1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 4-chlorobenzene-1-sulfonyl chloride for 4-(chlorosulfonyl)benzoic acid in Step 10.

$^1$H NMR (300 MHz, DMSO-d6) δ: 7.84 (dd, J1=2.1 Hz, J2=6.6 Hz, 2H), 7.77 (dd, J1=2.1 Hz, J2=6.6 Hz, 2H), 7.52 (s, 1H), 7.35-7.43 (m, 5H), 7.12-7.14 (m, 4H), 6.81 (d, J=8.7 Hz, 1H), 5.82 (s, 1H), 4.64-4.74 (m, 1H), 3.84 (d, J=11.1 Hz,

2H), 2.51-2.61 (m, 2H), 2.35-2.42 (m, 2H), 2.14-2.20 (m, 1H), 1.85-1.95 (m, 2H), 0.96-0.98 (m, 4H). LC/MS (ES, m/z): 651 [M+H]+.

Example PH-7

6-(bis(4-chlorophenyl)methyl)-2-cyclopropyl-1-(1-(4-methoxyphenylsulfonyl)piperidin-4-yl)-1H-benzo[d]imidazole

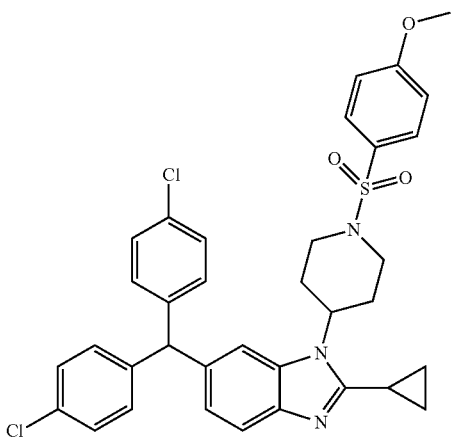 [SMILES: COc1ccc(S(=O)(=O)N2CCC(n3c(C4CC4)nc4ccc(C(c5ccc(Cl)cc5)c5ccc(Cl)cc5)cc43)CC2)cc1]

The title compound was prepared according to the procedure as described in Example PH-1 substituting 4-methoxybenzene-1-sulfonyl chloride for 4-(chlorosulfonyl)benzoic acid in Step 10.

$^1$H NMR (300 MHz, CDCl3) δ: 7.78 (d, J=9.0 Hz, 2H), 7.66 (d, J=8.4 Hz, 1H), 7.28-7.31 (m, 5H), 7.04-7.08 (m, 6H), 6.94 (d, J=8.4 Hz, 1H), 5.64 (s, 1H), 4.36-4.46 (m, 1H), 4.07 (d, J=11.1 Hz, 2H), 3.93 (s, 3H), 2.44-2.64 (m, 4H), 1.90-2.01 (m, 3H), 1.15-1.35 (m, 3H), 1.11-1.18 (m, 2H). LC/MS (ES, m/z): 646 [M+H]+.

Example PH-8

6-(bis(4-chlorophenyl)methyl)-2-cyclopropyl-1-(1-(4-(trifluoromethyl)phenylsulfonyl)piperidin-4-yl)-1H-benzo[d]imidazole

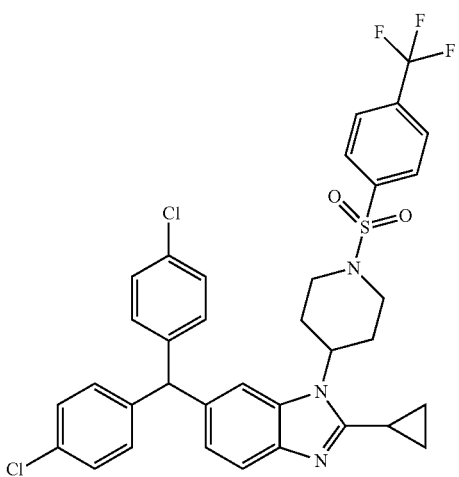 [SMILES: O=S(=O)(c1ccc(C(F)(F)F)cc1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 4-(trifluoromethyl)benzene-1-sulfonyl chloride 4-(chlorosulfonyl)benzoic acid in Step 10.

$^1$H NMR (300 MHz, CDCl3) δ: 7.90-8.01 (m, 2H), 7.84-7.87 (m, 2H), 7.62 (d, J=8.4 Hz, 1H), 7.22-7.26 (m, 5H), 7.01-7.08 (m, 4H), 6.92 (d, J=9.0 Hz, 1H), 5.62 (s, 1H), 4.40-4.50 (m, 1H), 4.09 (d, J=10.8 Hz, 2H), 2.45-2.66 (m, 4H), 1.98-2.02 (m, 2H), 1.85-1.95 (m, 1H), 1.20-1.35 (m, 2H), 1.07-1.15 (m, 2H). LC/MS (ES, m/z): 684 [M+H]+.

Example PH-9

6-(bis(4-chlorophenyl)methyl)-2-cyclopropyl-1-(1-(4-(trifluoromethoxy)phenylsulfonyl)piperidin-4-yl)-1H-benzo[d]imidazole

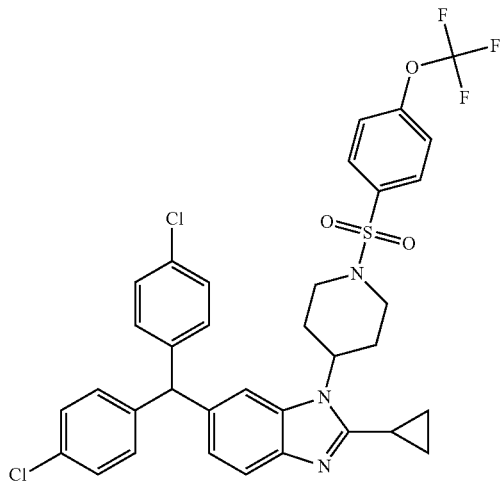 [SMILES: O=S(=O)(c1ccc(OC(F)(F)F)cc1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 4-(trifluoromethoxy)benzene-1-sulfonyl chloride for 4-(chlorosulfonyl)benzoic acid in Step 10.

$^1$H NMR (300 MHz, CDCl3) δ: 7.87 (d, J=8.7 Hz, 2H), 7.61-7.66 (m, 1H), 7.41 (d, J=8.4 Hz, 2H), 7.24-7.28 (m, 5H), 7.01-7.04 (m, 4H), 6.93 (d, J=7.8 Hz, 2H), 5.62 (s, 1H), 4.39-4.47 (m, 1H), 4.08 (d, J=11.4 Hz, 2H), 2.45-2.67 (m, 4H), 1.92-2.02 (m, 3H), 1.25-1.35 (m, 2H), 1.10-1.15 (m, 2H). LC/MS (ES, m/z): 700 [M+H]+.

Example PH-10

4-(4-(6-(bis(4-chlorophenyl)methyl)-2-cyclopropyl-1H-benzo[d]imidazol-1-yl)piperidin-1-ylsulfonyl)benzamide 2,2,2-trifluoroacetate

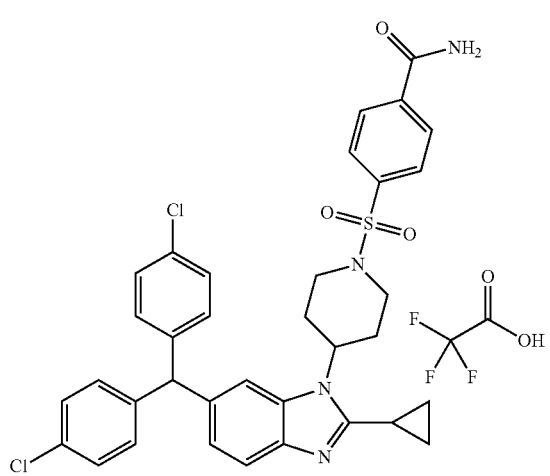

Into a 8-mL vial, was placed solution of 4-(4-[6-[bis(4-chlorophenyl)methyl]-2-cyclopropyl-1H-1,3-benzodiazol-1-yl]piperidine-1-sulfonyl)benzoic acid (45 mg, 0.07 mmol, 1.00 equiv) in N,N-dimethylformamide (4 mL), HATU (31 mg, 0.08 mmol, 5.00 equiv), NH₄Cl (18 mg, 0.34 mmol, 1.20 equiv) and DIEA (26 mg, 0.20 mmol, 3.00 equiv). The resulting solution was stirred overnight at room temperature. The resulting mixture was concentrated under vacuum. The product residue was purified by Prep-HPLC with the following conditions (Waters-2767-1): Column, Sunfire prep C18, 5 um, 19*100 mm; mobile phase, water in 0.05% TFA and CH₃CN (50% CH₃CN up to 70% in 5 min, up to 100% in 7 min, down to 50% in 9 min); Detector, UV 254 nm to yield 4-(4-[6-[bis(4-chlorophenyl)methyl]-2-cyclopropyl-1H-1,3-benzodiazol-1-yl]piperidine-1-sulfonyl)benzamide trifluoroacetic acid as a white solid.

$^1$H NMR (400 MHz, CD3OD) δ: 8.13 (d, J=8.4 Hz, 2H), 7.96 (d, J=8.4 Hz, 2H), 7.78 (s, 1H), 7.64 (d, J=8.8 Hz, 1H), 7.34-7.37 (m, 5H), 7.14-7.16 (m, 4H), 5.88 (s, 1H), 4.88-4.93 (m, 1H), 4.07 (d, J=10.8 Hz, 2H), 2.66-2.72 (m, 2H), 2.44-2.60 (m, 3H), 2.13-2.16 (m, 2H), 1.40-1.42 (m, 2H), 1.26-1.29 (m, 2H). LC/MS (ES, m/z): 659 [M+H]+.

Example PH-11

6-(bis(4-chlorophenyl)methyl)-2-cyclopropyl-1-(1-(3-(trifluoromethyl)phenylsulfonyl)piperidin-4-yl)-1H-benzo[d]imidazole

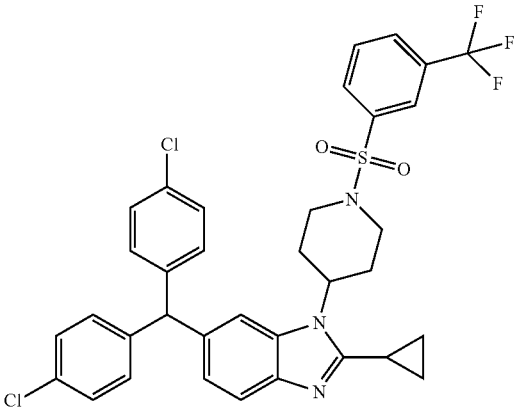 [SMILES: O=S(=O)(c1cccc(C(F)(F)F)c1)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 3-(trifluoromethyl)benzene-1-sulfonyl chloride for 4-(chlorosulfonyl)benzoic acid in Step 10.

$^1$H NMR (300 MHz, CDCl3) δ: 8.07 (s, 1H), 8.02 (d, J=7.8 Hz, 1H), 7.92 (d, J=7.8 Hz, 1H), 7.75 (t, J=8.1 Hz, 1H), 7.60-7.64 (m, 1H), 7.23-7.29 (m, 5H), 7.01-7.08 (m, 4H), 6.94 (d, J=8.7 Hz, 1H), 5.62 (s, 1H), 4.38-4.48 (m, 1H), 4.10 (d, J=11.7 Hz, 2H), 2.46-2.67 (m, 4H), 1.96-2.04 (m, 2H), 1.89-1.93 (m, 1H), 1.25-1.36 (m, 2H), 1.12-1.18 (m, 2H). LC/MS (ES, m/z): 684 [M+H]+.

Example PH-12

6-(bis(4-chlorophenyl)methyl)-2-cyclopropyl-1-(1-(3-methoxyphenylsulfonyl)piperidin-4-yl)-1H-benzo[d]imidazole 2,2,2-trifluoroacetate

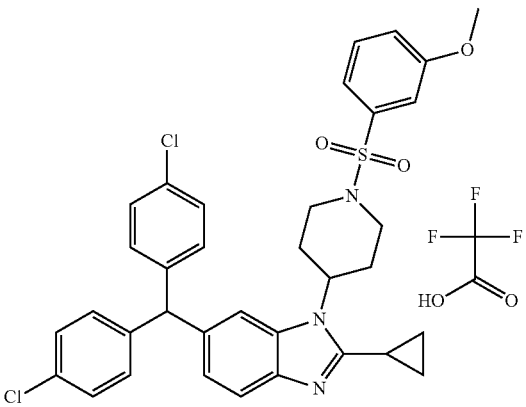

The title compound was prepared according to the procedure as described in Example PH-1 substituting 3-methoxybenzene-1-sulfonyl chloride for 4-(chlorosulfonyl)benzoic acid in Step 10.

$^1$H NMR (400 MHz, CD3OD) δ: 7.76 (s, 1H), 7.64 (d, J=8.8 Hz, 1H), 7.58 (t, J=8.0 Hz, 1H), 7.43 (d, J=8.0 Hz, 1H), 7.27-7.36 (m, 7H), 7.13-7.15 (m, 4H), 5.87 (s, 1H), 4.87-4.94 (m, 1H), 4.04 (d, J=12.4 Hz, 2H), 3.90 (s, 3H), 2.52-2.68 (m, 2H), 2.43-2.47 (m, 3H), 2.11-2.14 (m, 2H), 1.30-1.41 (m, 2H), 1.27-1.29 (m, 2H). LC/MS (ES, m/z): 646 [M+H]+.

Example PH-13

3-((4-(6-(bis(4-chlorophenyl)methyl)-2-cyclopropyl-1H-benzo[d]imidazol-1-yl)piperidin-1-yl)sulfonyl)benzamide 2,2,2-trifluoroacetate

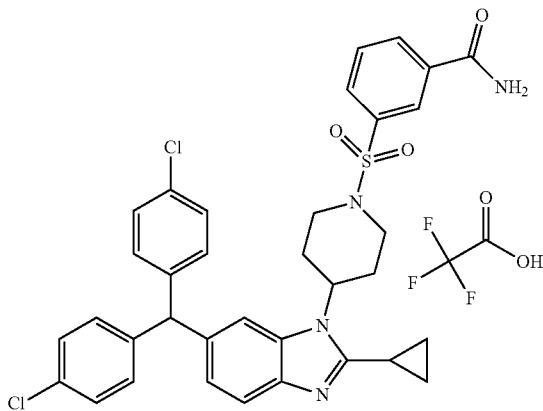

Step 1: Synthesis of 3-(4-[6-[bis (4-chlorophenyl) methyl]-2-cyclopropyl-1H-1, 3-benzodiazol-1-yl] piperidine-1-sulfonyl) benzoic acid Into a 8-mL vial, was placed a solution of 6-[bis(4-chlorophenyl)methyl]-2-cyclopropyl-1-(piperidin-4-yl)-1H-1,3-benzodiazole (150 mg, 0.31 mmol, 1.00 equiv) in tetrahydrofuran (4 mL), triethylamine (65 mg, 0.64 mmol, 2.00 equiv) and 3-(chlorosulfonyl)benzoic acid (70 mg, 0.32 mmol, 1.00 equiv). The resulting solution was stirred overnight at room temperature. The resulting mixture was concentrated under vacuum to yield 3-(4-[6-[bis (4-chlorophenyl) methyl]-2-cyclopropyl-1H-1, 3-benzodiazol-1-yl] piperidine-1-sulfonyl) benzoic acid as a white solid. LC/MS (ES, m/z): 661 [M+H]+.

Step 2: Synthesis of 3-(4-[6-[bis (4-chlorophenyl) methyl]-2-cyclopropyl-1H-1, 3-benzodiazol-1-yl] piperidine-1-sulfonyl) benzamide trifluoroacetic acid Into a 8-mL vial, was placed a solution of 3-(4-[6-[bis(4-chlorophenyl)methyl]-2-cyclopropyl-1H-1,3-benzodiazol-1-yl]piperidine-1-sulfonyl)benzoic acid (200 mg, 0.30 mmol, 1.00 equiv) in N,N-dimethylformamide (4 mL), NH$_4$Cl (80 mg, 1.50 mmol, 5.00 equiv), HATU (138 mg, 0.36 mmol, 1.20 equiv) and DIEA (117 mg, 0.91 mmol, 3.00 equiv). The resulting solution was stirred overnight at room temperature. The resulting mixture was concentrated under vacuum. The product residue was purified by Prep-HPLC with the following conditions (Waters-2767-1): Column, Sunfire prep C18, 5 um, 19*100 mm; mobile phase, water in 0.05% TFA and CH$_3$CN (40% CH$_3$CN up to 60% in 6 min, up to 100% in 8 min, down to 55% in 10 min); Detector, UV 254 nm to yield 3-(4-[6-[bis (4-chlorophenyl) methyl]-2-cyclopropyl-1H-1, 3-benzodiazol-1-yl] piperidine-1-sulfonyl) benzamide trifluoroacetic acid as a white solid.

$^1$H NMR (300 MHz, CD3OD) δ: 8.36 (s, 1H), 8.21 (d, J=7.8 Hz, 1H), 8.04 (d, J=8.4 Hz, 1H), 7.74-7.79 (m, 2H), 7.63 (d, J=8.4 Hz, 1H), 7.29-7.36 (m, 5H), 7.12-7.15 (m, 4H), 5.87 (s, 1H), 4.87-4.94 (m, 1H), 4.07 (d, J=11.4 Hz, 2H), 2.39-2.73 (m, 5H), 2.11-2.14 (m, 2H), 1.30-1.42 (m, 2H), 1.25-1.29 (m, 2H). LC/MS (ES, m/z): 649 [M+H]+.

Example PH-14

3-(4-(6-(bis (4-chlorophenyl) methyl)-2-cyclopropyl-1H-benzo[d]imidazol-1-yl) piperidin-1-ylsulfonyl) phenol 2, 2, 2-trifluoroacetate

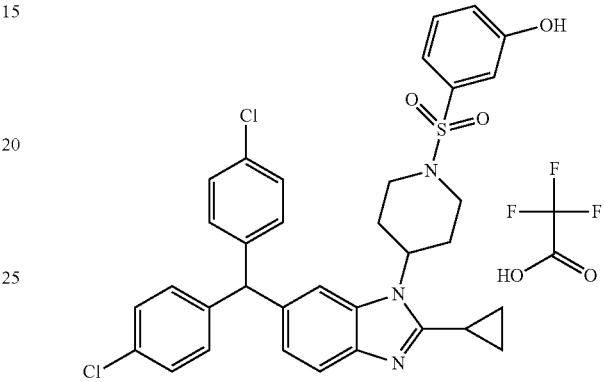

Step 1: Synthesis of 6-[bis (4-chlorophenyl) methyl]-2-cyclopropyl-1-[1-[(3-methoxybenzene) sulfonyl] piperidin-4-yl]-1H-1, 3-benzodiazole Into a 25-mL round-bottom flask, was placed 6-[bis(4-chlorophenyl)methyl]-2-cyclopropyl-1-(piperidin-4-yl)-1H-1,3-benzodiazole (400 mg, 0.84 mmol, 1.00 equiv), 3-methoxybenzene-1-sulfonyl chloride (190 mg, 0.92 mmol, 1.10 equiv) and a solution of triethylamine (254 mg, 2.51 mmol, 2.99 equiv) in dichloromethane (10 mL). The resulting solution was stirred for 2 h at room temperature. The resulting mixture was concentrated under vacuum to yield 6-[bis (4-chlorophenyl) methyl]-2-cyclopropyl-1-[1-[(3-methoxybenzene) sulfonyl] piperidin-4-yl]-1H-1, 3-benzodiazole as yellow oil. LC/MS (ES, m/z): 647 [M+H]+.

Step 2: Synthesis of 3-(4-[6-[bis(4-chlorophenyl)methyl]-2-cyclopropyl-1H-1,3-benzodiazol-1-yl]piperidine-1-sulfonyl)phenol trifluoroacetic acid Into a 50-mL round-bottom flask, was placed a solution of 6-[bis (4-chlorophenyl) methyl]-2-cyclopropyl-1-[1-[(3-methoxybenzene) sulfonyl]piperidin-4-yl]-1H-1, 3-benzodiazole (200 mg, 0.31 mmol, 1.00 equiv) in dichloromethane (5 ml) and BBr$_3$ (0.29 mL, 10.00 equiv). The resulting solution was stirred for 4 h at room temperature. The pH value of the solution was adjusted to pH 7 with sodium bicarbonate (100%). The resulting solution was extracted with DCM (3×5 mL) and the organic layers combined and concentrated under vacuum. The product residue was purified by Prep-HPLC with the following conditions (Waters-2767-1): Column, Sunfire prep C18, 5 um, 19*100 mm; mobile phase, water in 0.05% TFA and CH$_3$CN (50% CH$_3$CN up to 65% in 6 min, up to 100% in 2 min, down to 50% in 2 min); Detector, UV 254 nm to yield 3-(4-[6-[bis (4-chlorophenyl)methyl]-2-cyclopropyl-1H-1,3-benzodiazol-1-yl]piperidine-1-sulfonyl)phenol trifluoroacetic acid as a white solid.

¹H NMR (300 MHz, CD3OD) δ: 7.79 (s, 1H), 7.65 (d, J=8.4 Hz, 1H), 7.46 (t, J=8.1 Hz, 1H), 7.29-7.37 (m, 6H), 7.24 (t, J=2.1 Hz, 1H), 7.09-7.16 (m, 5H), 5.89 (s, 1H), 4.87-4.93 (m, 1H), 4.02 (d, J=12.3 Hz, 2H), 2.66-2.74 (m, 2H), 2.45-2.60 (m, 3H), 2.12-2.16 (m, 2H), 1.40-1.47 (m, 2H), 1.33-1.36 (m, 2H). LC/MS (ES, m/z): 632 [M+H]+.

Example PH-15

6-(bis(4-chlorophenyl)methyl)-2-cyclopropyl-1-(1-(2-(trifluoromethyl)phenylsulfonyl)piperidin-4-yl)-1H-benzo[d]imidazole

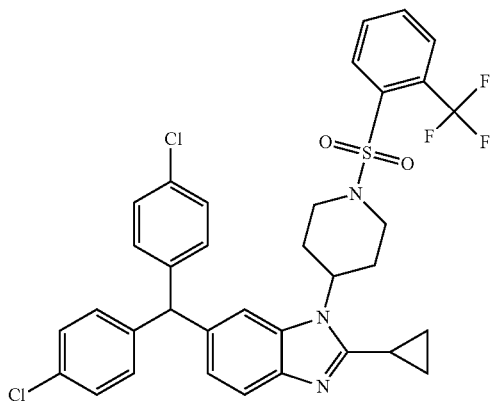 [SMILES: O=S(=O)(c1ccccc1C(F)(F)F)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 2-(trifluoromethyl) benzene-1-sulfonyl chloride for 4-(chlorosulfonyl) benzoic acid in Step 10.

¹H NMR (300 MHz, CDCl3) δ: 8.22-8.26 (m, 1H), 7.91-7.94 (m, 1H), 7.73-7.76 (m, 2H), 7.62 (d, J=7.5 Hz, 1H), 7.23-7.28 (m, 5H), 7.03-7.06 (m, 4H), 6.94 (d, J=8.7 Hz, 1H), 5.59 (s, 1H), 4.51-4.61 (m, 1H), 4.02 (d, J=13.2 Hz, 2H), 2.89-2.97 (m, 2H), 2.53-2.58 (m, 2H), 1.93-1.97 (m, 3H), 1.20-1.30 (m, 2H), 1.11-1.18 (m, 2H). LC/MS (ES, m/z): 684 [M+H]+.

Example PH-16

6-(bis(4-chlorophenyl)methyl)-2-cyclopropyl-1-(1-(2-methoxyphenylsulfonyl)piperidin-4-yl)-1H-benzo[d]imidazole

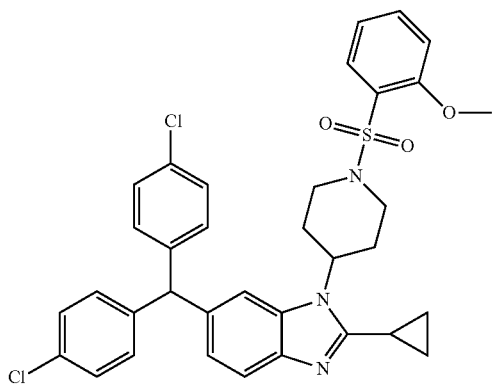 [SMILES: COc1ccccc1S(=O)(=O)N1CCC(n2c(C3CC3)nc3ccc(C(c4ccc(Cl)cc4)c4ccc(Cl)cc4)cc32)CC1]

The title compound was prepared according to the procedure as described in Example PH-1 substituting 2-methoxybenzene-1-sulfonyl chloride for 4-(chlorosulfonyl)benzoic acid in Step 10.

¹H NMR (300 MHz, CDCl3) δ: 7.94 (d, J=7.8 Hz, 1H), 7.54-7.66 (m, 2H), 7.23-7.28 (m, 5H), 7.01-7.11 (m, 6H), 6.92 (d, J=8.1 Hz, 1H), 5.60 (s, 1H), 4.45-4.55 (m, 1H), 4.15 (d, J=11.1 Hz, 2H), 3.92 (s, 3H), 2.79-2.86 (m, 2H), 2.47-2.58 (m, 2H), 1.93-1.97 (m, 3H), 1.25-1.35 (m, 2H), 1.14-1.19 (m, 2H). LC/MS (ES, m/z): 646 [M+H]+.

Example PH-17

2-(4-(6-(bis(4-chlorophenyl)methyl)-2-cyclopropyl-1H-benzo[d]imidazol-1-yl)piperidin-1-ylsulfonyl)phenol 2,2,2-trifluoroacetate

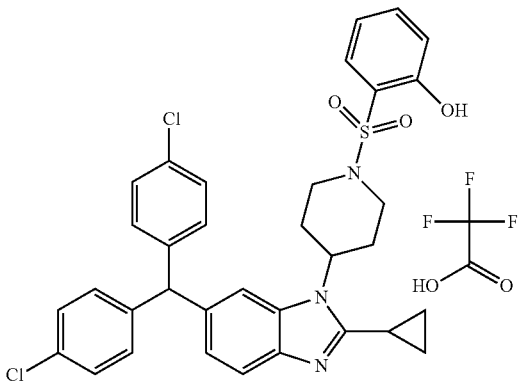

The title compound was prepared according to the procedure as described in Example PH-14 substituting 2-methoxybenzene-1-sulfonyl chloride for 3-methoxybenzene-1-sulfonyl chloride in Step 1.

¹H NMR (400 MHz, CD3OD) δ: 7.76-7.80 (m, 2H), 7.64 (d, J=8.4 Hz, 1H), 7.49-7.52 (m, 1H), 7.32-7.37 (m, 5H), 7.13-7.15 (m, 4H), 7.01-7.04 (m, 2H), 5.86 (s, 1H), 4.90-4.99 (m, 1H), 4.11 (d, J=11.2 Hz, 2H), 2.94-3.01 (m, 2H), 2.50-2.56 (m, 3H), 2.10-2.12 (m, 2H), 1.41-1.43 (m, 2H), 1.29-1.30 (m, 2H). LC/MS (ES, m/z): 632 [M+H]+.

Example PH-18

2-(4-(6-(bis(4-chlorophenyl)methyl)-2-cyclopropyl-1H-benzo[d]imidazol-1-yl)piperidin-1-ylsulfonyl)benzamide 2,2,2-trifluoroacetate

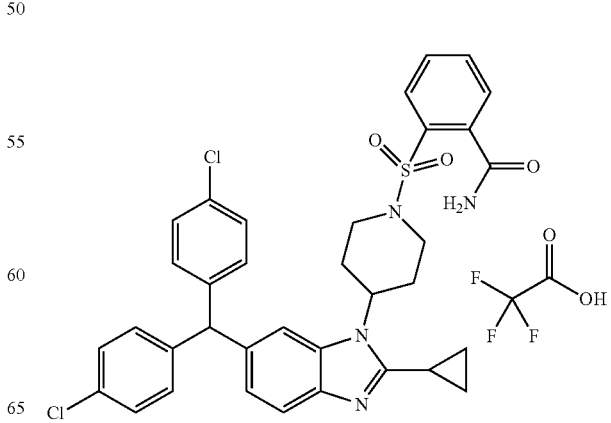

Step 1: Synthesis of methyl 2-(4-[6-[bis(4-chlorophenyl)methyl]-2-cyclopropyl-1H-1,3-benzodiazol-1-yl]piperidine-1-sulfonyl)benzoate Into a 8-mL vial, was placed a solution of 6-[bis(4-chlorophenyl)methyl]-2-cyclopropyl-1-(piperidin-4-yl)-1H-1,3-benzodiazole (150 mg, 0.31 mmol, 1.00 equiv) in CH3CN (5 ml), potassium carbonate (131 mg, 0.95 mmol, 3.00 equiv) and methyl 2-(chlorosulfonyl)benzoate (89 mg, 0.38 mmol, 1.20 equiv). The resulting solution was stirred overnight at room temperature. The reaction was then quenched by the addition of water (5 mL). The resulting solution was extracted with DCM (3×5 mL) and the organic layers combined and dried over anhydrous sodium sulfate, then concentrated under vacuum to yield methyl 2-(4-[6-[bis(4-chlorophenyl)methyl]-2-cyclopropyl-1H-1,3-benzodiazol-1-yl]piperidine-1-sulfonyl)benzoate as a white solid. LC/MS (ES, m/z): 674 [M+H]+.

Step 2: Synthesis of 2-(4-[6-[bis(4-chlorophenyl)methyl]-2-cyclopropyl-1H-1,3-benzodiazol-1-yl]piperidine-1-sulfonyl)benzoic acid Into a 50-mL round-bottom flask, was placed a solution of methyl 2-(4-[6-[bis(4-chlorophenyl)methyl]-2-cyclopropyl-1H-1,3-benzodiazol-1-yl]piperidine-1-sulfonyl)benzoate (150 mg, 0.22 mmol, 1.00 equiv) in methanol/THF (5/1 mL), sodiumol (5 mL, 3N). The resulting solution was stirred overnight at room temperature. The pH value of the solution was adjusted to pH 6 with hydrogen chloride (3 mol/L). The resulting solution was extracted with DCM (3×10 mL) and the organic layers combined, then dried over anhydrous sodium sulfate to yield 2-(4-[6-[bis(4-chlorophenyl)methyl]-2-cyclopropyl-1H-1,3-benzodiazol-1-yl]piperidine-1-sulfonyl)benzoic acid as colorless oil.

Step 3: Synthesis of 2-(4-[6-[bis(4-chlorophenyl)methyl]-2-cyclopropyl-1H-1,3-benzodiazol-1-yl]piperidine-1-sulfonyl)benzamide trifluoroacetic acid Into a 8-mL vial, was placed a solution of 2-(4-[6-[bis(4-chlorophenyl)methyl]-2-cyclopropyl-1H-1,3-benzodiazol-1-yl]piperidine-1-sulfonyl)benzoic acid (150 mg, 0.23 mmol, 1.00 equiv) in N,N-dimethylformamide (4 ml), NH$_4$Cl (60 mg, 1.12 mmol, 5.00 equiv), HATU (104 mg, 0.27 mmol, 1.20 equiv) and DIEA (88 mg, 0.68 mmol, 3.00 equiv). The resulting solution was stirred overnight at room temperature. The product residue was purified by Prep-HPLC with the following conditions (Waters-2767-1): Column, Sunfire prep C18, 5 um, 19*100 mm; mobile phase, water in 0.05% TFA and CH$_3$CN (40% CH$_3$CN up to 50% in 6 min, up to 100% in 7 min, down to 40% in 8 min); Detector, UV254 nm to yield 2-(4-[6-[bis(4-chlorophenyl)methyl]-2-cyclopropyl-1H-1,3-benzodiazol-1-yl]piperidine-1-sulfonyl)benzamide trifluoroacetic acid as a white solid.

$^1$H NMR (300 MHz, CD3OD) δ: 8.04 (d, J=7.8 Hz, 1H), 7.95 (s, 1H), 7.60-7.76 (m, 4H), 7.33-7.37 (m, 5H), 7.14-7.17 (m, 4H), 5.87 (s, 1H), 5.00-5.08 (m, 1H), 4.04 (d, J=13.5 Hz, 2H), 2.99-3.07 (m, 2H), 2.51-2.63 (m, 3H), 2.06-2.11 (m, 2H), 1.42-1.49 (m, 2H), 1.28-1.33 (m, 2H). LC/MS (ES, m/z): 659 [M+H]+.

Example PH-19

4-(4-(6-(bis(4-chlorophenyl)methyl)-2-cyclopropyl-1H-benzo[d]imidazol-1-yl)piperidin-1-ylsulfonyl)phenol hydrochloride

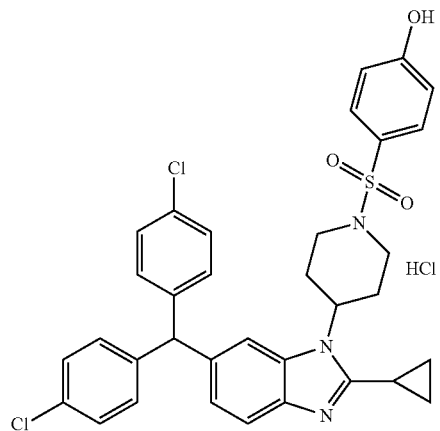 [SMILES: O=S(=O)(c1ccc(O)cc1)N1CCC(n2c(C3CC3)nc3ccc(C(c4ccc(Cl)cc4)c4ccc(Cl)cc4)cc32)CC1 ; Cl]

The title compound was prepared according to the procedure as described in Example PH-1 substituting 4-hydroxybenzene-1-sulfonyl chloride for 4-(chlorosulfonyl)benzoic acid in Step 10.

$^1$H NMR (400 MHz, CD3OD) δ: 7.81 (s, 1H), 7.65-7.72 (m, 3H), 7.34-7.36 (m, 5H), 7.14-7.16 (m, 4H), 7.00 (d, J=8.8 Hz, 2H), 5.87 (s, 1H), 4.87-4.95 (m, 1H), 4.00 (d, J=12.0 Hz, 2H), 2.47-2.68 (m, 5H), 2.11-2.14 (m, 2H), 1.42-1.47 (m, 2H), 1.30-1.34 (m, 2H). LC/MS (ES, m/z): 632 [M+H]+.

Example PH-20

2-(4-(4-(6-(bis(4-chlorophenyl)methyl)-2-cyclopropyl-3aH-benzo[d]imidazol-1 (7aH)-yl)piperidin-1-ylsulfonyl)phenoxy)acetamide 2,2,2-trifluoroacetate

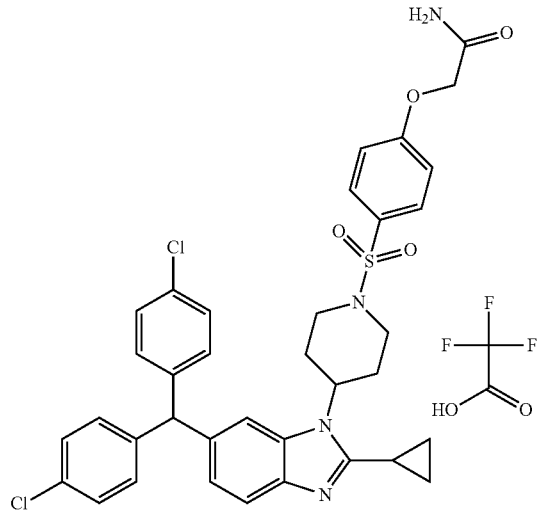

Step 1: Synthesis of ethyl 2-[4-(4-[6-[bis(4-chlorophenyl)methyl]-2-cyclopropyl-1H-1,3-benzodiazol-1-yl]piperidin-1-yl)phenoxy]acetate Into a 50-mL round-bottom flask, was placed a solution of 4-(4-[6-[bis(4-chlorophenyl)methyl]-2-cyclopropyl-1H-1,3-benzodiazol-1-yl]piperidine-1-sulfonyl)phenol (266 mg, 0.42 mmol, 1.00 equiv) in N,N-dimethylformamide (10 mL), ethyl 2-bromoacetate (105 mg, 0.63 mmol, 1.50 equiv) and potassium carbonate (174 mg, 1.26 mmol, 3.00 equiv). The resulting solution was stirred overnight at room temperature. The reaction was then quenched by the addition of water (10 mL). The resulting solution was extracted with DCM (3×10 mL) and the organic layers combined, then dried over anhydrous sodium sulfate and concentrated under vacuum to yield ethyl 2-[4-(4-[6-[bis(4-chlorophenyl)methyl]-2-cyclopropyl-1H-1,3-benzodiazol-1-yl]piperidin-1-yl)phenoxy]acetate as a white solid.

Step 2: Synthesis of 2-[4-(4-[6-[bis(4-chlorophenyl)methyl]-2-cyclopropyl-1H-1,3-benzodiazol-1-yl]piperidine-1-sulfonyl)phenoxy]acetamide; trifluoroacetic acid Into a 30-mL sealed tube, was placed a solution of ethyl 2-[4-(4-[6-[bis(4-chlorophenyl)methyl]-2-cyclopropyl-1H-1,3-benzodiazol-1-yl]piperidine-1-sulfonyl)phenoxy]acetate (100 mg, 0.14 mmol, 1.00 equiv) in methanol/NH$_3$ (20 mL). The resulting solution was stirred for 1 overnight at room temperature. The resulting mixture was concentrated under vacuum. The product residue was purified by Prep-HPLC with the following conditions (Waters-2767-1): Column, Column, Sunfire prep C18, 5 um, 19*100 mm; mobile phase, water in 0.05% TFA and CH$_3$CN (30% CH$_3$CN up to 55% in 10 min, up to 100% in 12 min, down to 50% in 14 min; Detector, UV 254 nm to yield 2-[4-(4-[6-[bis(4-chlorophenyl)methyl]-2-cyclopropyl-1H-1,3-benzodiazol-1-yl]piperidine-1-sulfonyl)phenoxy]acetamide; trifluoroacetic acid as an off-white solid.
$^1$H NMR (300 MHz, CD3OD) δ: 7.81-7.84 (m, 3H), 7.65 (d, J=8.7 Hz, 1H), 7.34-7.37 (m, 5H), 7.23-7.26 (m, 2H), 7.13-7.16 (m, 4H), 5.88 (s, 1H), 4.81-4.91 (m, 1H), 3.99-4.12 (m, 2H), 2.50-2.68 (m, 5H), 2.11-2.16 (m, 2H), 1.41-1.47 (m, 2H), 1.30-1.38 (m, 2H). LC/MS (ES, m/z): 689 [M+H]+.

Example PH-21

2,2-bis(4-chlorophenyl)-2-(2-cyclopropyl-3-(1-(trifluoromethylsulfonyl)piperidin-4-yl)-3H-benzo[d]imidazol-5-yl)acetic acid hydrochloride

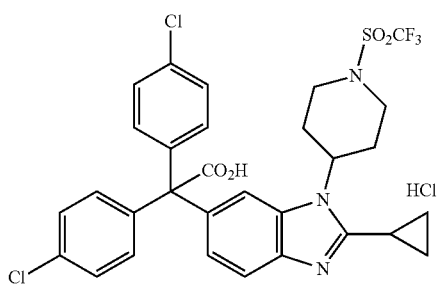

The title compound was prepared according to the procedure as described in Example PH-23 substituting cyclopropanecarbonyl chloride for propanoyl chloride in Step 4.
$^1$H NMR (400 MHz, DMSO-d6) δ: 7.46 (d, J=8.4 Hz, 1H), 7.38-7.40 (m, 4H), 7.30 (s, 1H), 7.16-7.19 (m, 4H), 6.88 (d, J=8.4 Hz, 1H), 4.93-5.03 (m, 1H), 3.93 (d, J=12.8 Hz, 2H), 3.45-3.52 (m, 2H), 2.31-2.34 (m, 1H), 2.01-2.12 (m, 4H), 1.01-1.07 (m, 4H). LC/MS (ES, m/z): 652 [M+H]+.

Example PH-22

6-(bis(4-chlorophenyl)methyl)-2-cyclopropyl-1-(1-(trifluoromethylsulfonyl)piperidin-4-yl)-1H-benzo[d]imidazole hydrochloride

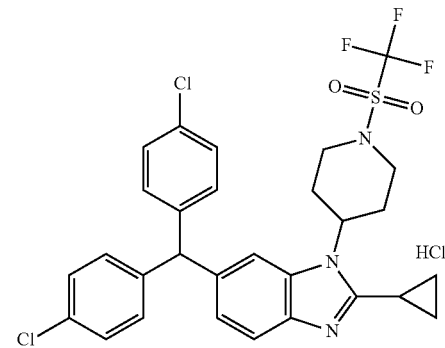 [SMILES: O=S(=O)(N1CCC(n2c(C3CC3)nc3ccc(C(c4ccc(Cl)cc4)c4ccc(Cl)cc4)cc32)CC1)C(F)(F)F ; Cl]

The title compound was prepared according to the procedure as described in Example PH-1 substituting trifluoromethanesulfonic anhydride for 4-(chlorosulfonyl)benzoic acid in Step 10.
$^1$H NMR (300 MHz, DMSO-d6) δ: 7.69-7.80 (m, 2H), 7.39-7.42 (m, 4H), 7.24 (d, J=8.7 Hz, 1H), 7.12-7.15 (m, 4H), 5.96 (s, 1H), 5.14-5.22 (m, 1H), 4.01 (d, J=12.6 Hz, 2H), 3.70-3.77 (m, 2H), 2.57-2.66 (m, 1H), 2.18-2.40 (m, 4H), 1.34-1.42 (m, 4H). LC/MS (ES, m/z): 608 [M+H]+.

Example PH-23

6-(bis(4-chlorophenyl)methyl)-2-ethyl-1-(1-(trifluoromethylsulfonyl)piperidin-4-yl)-1H-benzo[d]imidazole hydrochloride

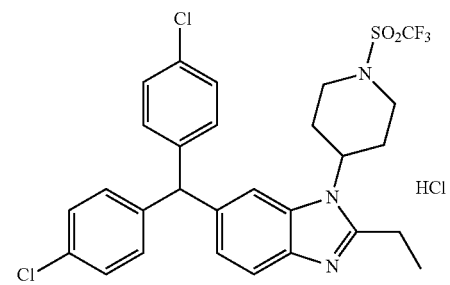

Step 1: Synthesis of methyl 2,2-bis(4-chlorophenyl)-2-(3-fluoro-4-nitrophenyl)acetate Into a 1000-mL 3-necked round-bottom flask purged and maintained with an inert atmosphere of nitrogen, was placed a solution of methyl 2,2-bis(4-chlorophenyl)acetate (50 g, 169.40 mmol, 1.00 equiv) in tetrahydrofuran (150 mL). To the mixture was then added t-BuOK (190 mL, 1M, 1.10 equiv) dropwise with stirring at 0° C. in 20 min. The resulting solution was stirred for 30 min at 0° C. To the resulting mixture was added a solution of 2,4-difluoro-1-nitrobenzene (28 g, 176.00 mmol, 1.05 equiv) in tetrahydrofuran (150 mL) dropwise with stirring. The resulting solution was stirred overnight at room temperature. The mixture was concentrated under vacuum. The residue was applied onto a silica gel column with ethyl acetate/petroleum ether (1:10) to yield methyl 2,2-bis(4-chlorophenyl)-2-(3-fluoro-4-nitrophenyl)acetate as yellow oil.

Step 2: Synthesis of methyl 2,2-bis(4-chlorophenyl)-2-(4-nitro-3-[[1-(trifluoromethane)sulfonylpiperidin-4-yl]amino]phenyl)acetate Into a 1000-mL round-bottom flask, was placed a solution of methyl 2,2-bis(4-chlorophenyl)-2-(3-fluoro-4-nitrophenyl)acetate (70 g, 161.20 mmol, 1.00 equiv) in CH$_3$CN (300 mL), DIEA (104 g, 804.70 mmol, 3.00 equiv) and 1-(trifluoromethane)sulfonylpiperidin-4-amine hydrochloride (52 g, 193.54 mmol, 1.20 equiv). The resulting solution was stirred overnight at 85° C. The reaction was then quenched by the addition of water (200 mL). The resulting solution was extracted with ethyl acetate (3×200 mL) and the organic layers combined, then dried over anhydrous sodium sulfate to yield methyl 2,2-bis(4-chlorophenyl)-2-(4-nitro-3-[[1-(trifluoromethane)sulfonylpiperidin-4-yl]amino]phenyl)acetate as yellow oil.

Step 3: Synthesis of methyl 2-(4-amino-3-[[1-(trifluoromethane)sulfonylpiperidin-4-yl]amino]phenyl)-2,2-bis(4-chlorophenyl)acetate Into a 500-mL round-bottom flask, was placed a solution of methyl 2,2-bis(4-chlorophenyl)-2-(4-nitro-3-[[1-(trifluoromethane)sulfonylpiperidin-4-yl]amino]phenyl)acetate (50 g, 77.34 mmol, 1.00 equiv) in methanol/THF (100/100 ml) and Raney Ni (2 g). To the mixture was then introduced hydrogen. The resulting solution was stirred overnight at room temperature to yield methyl 2-(4-amino-3-[[1-(trifluoromethane)sulfonylpiperidin-4-yl]amino]phenyl)-2,2-bis(4-chlorophenyl)acetate as a red solid.

Step 4: Synthesis of methyl 2,2-bis(4-chlorophenyl)-2-(4-propanamido-3-[[1-(trifluoromethane)sulfonylpiperidin-4-yl]amino]phenyl)acetate Into a 500-mL round-bottom flask, was placed a solution of methyl 2-(4-amino-3-[[1-(trifluoromethane)sulfonylpiperidin-4-yl]amino]phenyl)-2,2-bis(4-chlorophenyl)acetate (50 g, 81.11 mmol, 1.00 equiv) in dichloromethane (250 mL), triethylamine (24.6 g, 243.11 mmol, 3.00 equiv) and propanoyl chloride (7.5 g, 81.06 mmol, 1.00 equiv). The resulting solution was stirred overnight at room temperature. The resulting mixture was concentrated under vacuum to yield methyl 2,2-bis(4-chlorophenyl)-2-(4-propanamido-3-[[1-(trifluoromethane)sulfonylpiperidin-4-yl]amino]phenyl)acetate as brown oil. LC/MS (ES, m/z): 672 [M+H]+.

Step 5: Synthesis of methyl 2,2-bis(4-chlorophenyl)-2-[2-ethyl-1-[1-(trifluoromethane)sulfonylpiperidin-4-yl]-1H-1,3-benzodiazol-6-yl]acetate Into a 500-mL round-bottom flask, was placed a solution of methyl 2,2-bis(4-chlorophenyl)-2-(4-propanamido-3-[[1-(trifluoromethane)sulfonylpiperidin-4-yl]amino]phenyl)acetate (54 g, 40.15 mmol, 1.00 equiv, 50%) in acetic acid (200 mL). The resulting solution was stirred for 24 hrs at reflux. The resulting mixture was concentrated under vacuum to yield methyl 2,2-bis(4-chlorophenyl)-2-[2-ethyl-1-[1-(trifluoromethane)sulfonylpiperidin-4-yl]-1H-1,3-benzodiazol-6-yl]acetate as brown oil. LC/MS (ES, m/z): 654 [M+H]+.

Step 6: Synthesis of 2,2-bis(4-chlorophenyl)-2-[2-ethyl-1-[1-(trifluoromethane)sulfonylpiperidin-4-yl]-1H-1,3-benzodiazol-6-yl]acetic acid Into a 1000-mL round-bottom flask, was placed a solution of methyl 2,2-bis(4-chlorophenyl)-2-[2-ethyl-1-[1-(trifluoromethane)sulfonylpiperidin-4-yl]-1H-1,3-benzodiazol-6-yl]acetate (32 g, 24.45 mmol, 1.00 equiv, 50%) in tetrahydrofuran/MeOH (150/100 mL) and sodium hydroxide (250 mL). The resulting solution was stirred overnight at 50° C. The resulting solution was extracted with ethyl acetate (3×250 mL) and the organic layers combined. The pH value of the aqueous layers was adjusted to pH 2 with hydrogen chloride (3 mol/L). The resulting solution was extracted with ethyl acetate (100 mL) acetate and the organic layers combined to yield 2,2-bis(4-chlorophenyl)-2-[2-ethyl-1-[1-(trifluoromethane)sulfonylpiperidin-4-yl]-1H-1,3-benzodiazol-6-yl]acetic acid as a white solid. LC/MS (ES, m/z): 640 [M+H]+.

Step 7: Synthesis of 6-[bis(4-chlorophenyl)methyl]-2-ethyl-1-[1-(trifluoromethane)sulfonylpiperidin-4-yl]-1H-1,3-benzodiazole hydrochloride Into a 500-mL round-bottom flask, was placed 2,2-bis(4-chlorophenyl)-2-[2-ethyl-1-[1-(trifluoromethane)sulfonylpiperidin-4-yl]-1H-1,3-benzodiazol-6-yl]acetic acid (30 g, 46.84 mmol, 1.00 equiv), toluene (300 mL) and DBU (42.8 g, 281.14 mmol, 6.00 equiv). The resulting solution was stirred for 3 h at 90° C. The resulting mixture was concentrated under vacuum. The resulting solution was extracted with ethyl acetate (3×300 mL) and the organic layers combined, then dried over anhydrous sodium sulfate and concentrated under vacuum. The residue was applied onto a silica gel column with EA:PE (1:1). The residue was dissolved in diethyl ether/MeOH (100 mL) and reacted with hydrochloric acid to yield the corresponding hydrochloride salt, which precipitated from the mixture. The solids were collected by filtration. The product was re-crystallized from ethyl ether/ethanol in the ratio of 1:10 to yield 6-[bis(4-chlorophenyl)methyl]-2-ethyl-1-[1-(trifluoromethane)sulfonylpiperidin-4-yl]-1H-1,3-benzodiazole hydrochloride as an off-white solid.

$^1$H NMR (300 MHz, CD3OD) δ: 7.76 (d, J=8.7 Hz, 1H), 7.64 (s, 1H), 7.42 (d, J=8.4 Hz, 1H), 7.34-7.37 (m, 4H), 7.13-7.16 (m, 4H), 5.91 (s, 1H), 4.94-4.99 (m, 1H), 4.12 (d, J=13.2 Hz, 2H), 3.36-3.52 (m, 3H), 2.33-2.45 (m, 2H), 2.18-2.22 (m, 2H), 1.54 (t, J=7.5 Hz, 3H). LC/MS (ES, m/z): 596 [M+H]+.

Example PH-24

2,2-bis(4-chlorophenyl)-2-(2-ethyl-3-(1-(trifluoromethylsulfonyl)piperidin-4-yl)-3H-benzo[d]imidazol-5-yl)acetic acid

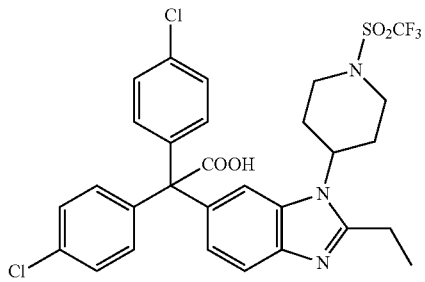

The title compound was prepared according to the procedure as describe din Example PH-23, Step 6.

$^1$H NMR (300 MHz, DMSO-d6) δ: 7.52 (d, J=8.7 Hz, 1H), 7.37-7.48 (m, 4H), 7.31 (d, J=9.0 Hz, 1H), 7.11-7.18 (m, 4H), 6.91 (d, J=8.4 Hz, 1H), 4.61-4.71 (m, 1H), 3.90 (d, J=12.3 Hz, 2H), 3.43-3.47 (m, 2H), 2.91-2.98 (m, 2H), 1.95-2.10 (m, 4H), 1.31 (t, J=7.5 Hz, 3H). LC/MS (ES, m/z): 640 [M+H]+.

Example PH-25

4-(4-(6-(bis(4-chlorophenyl)methyl)-2-cyclopropyl-1H-benzo[d]imidazol-1-yl)piperidine-1-carbonyl)benzamide

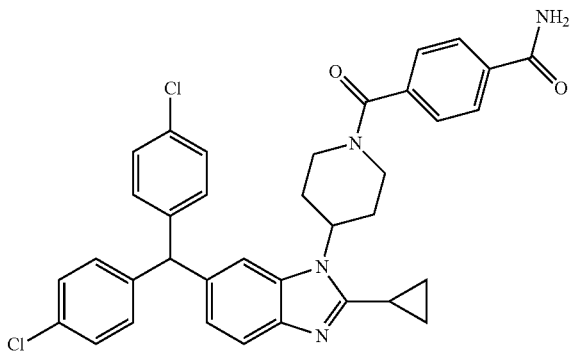 [SMILES: NC(=O)c1ccc(C(=O)N2CCC(n3c(C4CC4)nc4ccc(C(c5ccc(Cl)cc5)c5ccc(Cl)cc5)cc43)CC2)cc1]

The title compound was prepared according to the procedure as described in Example PH-18 substituting methyl 4-(chlorocarbonyl)benzoate for methyl 2-(chlorosulfonyl)benzoate in Step 1.

$^1$H NMR (300 MHz, DMSO-d6) δ: 8.04-8.07 (m, 1H), 7.95 (d, J=8.1 Hz, 2H), 7.72-7.80 (m, 1H), 7.61-7.64 (m, 1H), 7.40-7.49 (m, 7H), 7.14-7.24 (m, 5H), 5.95 (s, 1H), 4.73-4.76 (m, 1H), 4.62-4.70 (m, 1H), 3.40-3.60 (m, 8H), 1.20-1.30 (m, 4H). LC/MS (ES, m/z): 623 [M+H]+.

Example PH-26

1-(4-(6-(bis(4-chlorophenyl)methyl)-2-cyclopropyl-1H-benzo[d]imidazol-1-yl)piperidin-1-yl)-2-hydroxyethanone 2,2,2-trifluoroacetate

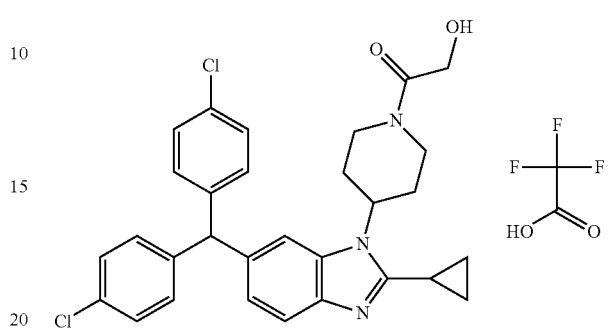

Step 1: Synthesis of 2-(4-(6-(bis(4-chlorophenyl)methyl)-2-cyclopropyl-1H-benzo[d]imidazol-1-yl)piperidin-1-yl)-2-oxoethyl acetate Into a 25-mL round-bottom flask, was placed 6-(bis(4-chlorophenyl)methyl)-2-cyclopropyl-1-(piperidin-4-yl)-1H-benzo[d]imidazole (100 mg, 0.21 mmol, 1.00 equiv), 2-chloro-2-oxoethyl acetate (34.5 mg, 0.23 mmol, 1.09 equiv) and a solution of triethylamine (63 mg, 0.62 mmol, 2.97 equiv) in dichloromethane (5 mL). The resulting solution was stirred for 3 h at room temperature. The resulting mixture was concentrated under vacuum to yield 2-(4-(6-(bis(4-chlorophenyl)methyl)-2-cyclopropyl-1H-benzo[d]imidazol-1-yl)piperidin-1-yl)-2-oxoethyl acetate as yellow oil. LC/MS (ES, m/z): 576.5 [M+H]+.

Step 2: Synthesis of 1-(4-(6-(bis(4-chlorophenyl)methyl)-2-cyclopropyl-1H-benzo[d]imidazol-1-yl)piperidin-1-yl)-2-hydroxyethanone Into a 25-mL round-bottom flask, was placed 2-(4-[6-[bis(4-chlorophenyl)methyl]-2-cyclopropyl-1H-1,3-benzodiazol-1-yl]piperidin-1-yl)-2-oxoethyl acetate (110 mg, 0.19 mmol, 1.00 equiv), a solution of LiOH.H$_2$O (48 mg, 1.14 mmol, 6.00 equiv) in tetrahydrofuran/H$_2$O (5/3 mL). The resulting solution was stirred for 3 h at room temperature. The resulting solution was extracted with ethyl acetate (3×10 mL) and the organic layers combined, then dried over anhydrous sodium sulfate and concentrated under vacuum. The product residue was purified by Prep-HPLC with the following conditions (Waters-2767-1): Column, Sunfire prep C18, 5 um, 19*100 mm; mobile phase, 0.05% TFA in water and CH$_3$CN (20% CH$_3$CN up to 65% in 8 min); Detector, 254 nm to yield 1-(4-(6-(bis(4-chlorophenyl)methyl)-2-cyclopropyl-1H-benzo[d]imidazol-1-yl)piperidin-1-yl)-2-hydroxyethanone as trifluoroacetic acid salt as an off-white solid.

1H NMR (300 MHz, DMSO-d6) δ: 7.78 (s, 1H), 7.62 (d, J=8.4 Hz, 1H), 7.37-7.40 (m, 4H), 7.09-7.15 (m, 5H), 5.90 (m, 1H), 5.01-5.06 (m, 1H), 4.57-4.61 (m, 1H), 4.16 (d, J=6.3 Hz, 2H), 3.87-3.99 (m, 2H), 3.16-3.20 (m, 1H), 2.79-2.87 (m, 1H), 1.95-2.30 (m, 5H), 1.20-1.35 (m, 4H). LC/MS (ES, m/z): 534 [M+H]+.

Example PH-27

1-(4-(6-(bis(4-chlorophenyl)methyl)-2-cyclopropyl-1H-benzo[d]imidazol-1-yl)piperidin-1-yl)-3-hydroxypropan-1-one 2,2,2-trifluoroacetate

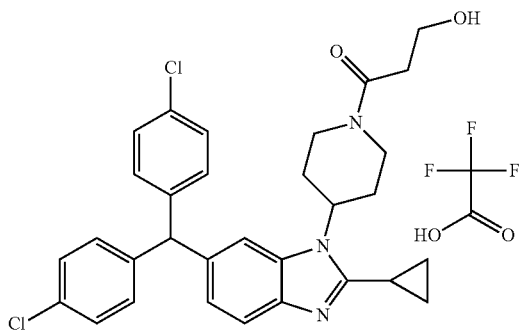

Step 1: Synthesis of methyl 3-(4-[6-[bis(4-chlorophenyl)methyl]-2-cyclopropyl-1H-1,3-benzodiazol-1-yl]piperidin-1-yl)-3-oxopropanoate Into a 8-mL vial, was placed a solution of 6-[bis(4-chlorophenyl)methyl]-2-cyclopropyl-1-(piperidin-4-yl)-1H-1,3-benzodiazole (150 mg, 0.31 mmol, 1.00 equiv) in dichloromethane (4 mL), triethylamine (96 mg, 0.95 mmol, 3.00 equiv) and methyl 3-chloro-3-oxopropanoate (52 mg, 0.38 mmol, 1.20 equiv). The resulting solution was stirred overnight at room temperature. The reaction was then quenched by the addition of water (4 mL). The resulting solution was extracted with DCM (3×4 mL) and the organic layers combined, then dried over anhydrous sodium sulfate and concentrated under vacuum to yield methyl 3-(4-[6-[bis(4-chlorophenyl)methyl]-2-cyclopropyl-1H-1,3-benzodiazol-1-yl]piperidin-1-yl)-3-oxopropanoate as colorless oil. LC/MS (ES, m/z): 576.5 [M+H]+.

Step 2: Synthesis of 1-(4-[6-[bis(4-chlorophenyl)methyl]-2-cyclopropyl-1H-1,3-benzodiazol-1-yl]piperidin-1-yl)-3-hydroxypropan-1-one trifluoroacetic acid Into a 25-mL round-bottom flask, was placed a solution of methyl 3-(4-[6-[bis(4-chlorophenyl)methyl]-2-cyclopropyl-1H-1,3-benzodiazol-1-yl]piperidin-1-yl)-3-oxopropanoate (200 mg, 0.35 mmol, 1.00 equiv) in tetrahydrofuran (4 ml), LiBH$_4$ (38 mg, 5.00 equiv) and water (0.04 mL). The resulting solution was stirred for 2 h at room temperature. The resulting mixture was concentrated under vacuum. The reaction was then quenched by the addition of water (10 mL). The resulting solution was extracted with DCM (3×10 mL) and the organic layers combined, then concentrated under vacuum to yield 1-(4-[6-[bis(4-chlorophenyl)methyl]-2-cyclopropyl-1H-1,3-benzodiazol-1-yl]piperidin-1-yl)-3-hydroxypropan-1-one trifluoroacetic acid as a light yellow semi-solid.
$^1$H NMR (400 MHz, CD3OD) δ: 7.71 (s, 1H), 7.66 (d, J=6.3 Hz, 1H), 7.33-7.36 (m, 5H), 7.12-7.14 (m, 4H), 5.87 (s, 1H), 5.15-5.25 (m, 1H), 4.82-4.87 (m, 1H), 4.27-4.30 (m, 1H), 3.92 (t, J=6.0 Hz, 2H), 3.33-3.41 (m, 1H), 2.83-2.93 (m, 1H), 2.59-2.73 (m, 3H), 2.12-2.44 (m, 4H), 1.47-1.52 (m, 2H), 1.32-1.36 (m, 2H). LC/MS (ES, m/z): 548 [M+H]+.

Example PH-28

4-(4-[6-[bis(4-chlorophenyl)methyl]-2-cyclopropyl-1H-1,3-benzodiazol-1-yl]piperidine-1-sulfonyl)-2-chlorobenzoic acid; trifluoroacetic acid

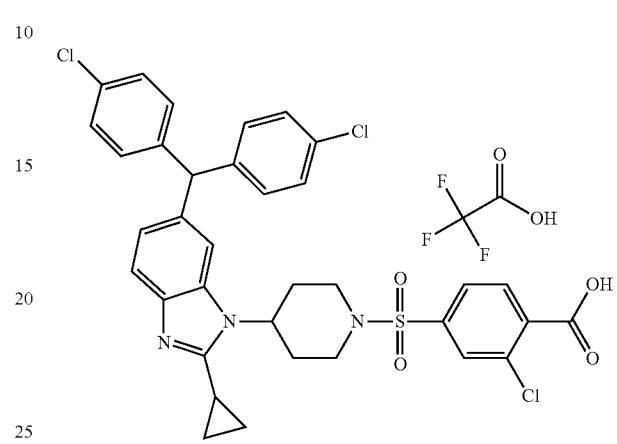

Step 1: Synthesis of methyl 2-chloro-4-(chlorosulfonyl)benzoate

Into a 100-mL round-bottom flask, was placed a solution of methyl 4-amino-2-chlorobenzoate (1.86 g, 10.02 mmol, 1.00 equiv) in hydrogen chloride(aq) (20 mL). To the mixture was then added a solution of NaNO$_2$ (759 mg, 11.00 mmol, 1.10 equiv) in water (3 mL) dropwise with stirring at 0° C. To the resulting mixture was added a solution of CuCl$_2$ (1.47 g, 10.97 mmol, 1.09 equiv) in SO$_2$/HOAc (8.3 mL) dropwise with stirring at 0° C. The resulting solution was stirred for 30 min at 0° C. The resulting solution was allowed to react, with stirring, for an additional 3 h at room temperature. The resulting solution was diluted with ethyl acetate (100 mL). The resulting mixture was washed with sodium chloride (aq) (3×10 mL). The mixture was dried over anhydrous sodium sulfate and concentrated under vacuum to yield methyl 2-chloro-4-(chlorosulfonyl)benzoate as yellow oil. LC/MS (ES, m/z): 269 [M+H]+.

Step 2: Synthesis of methyl 4-(4-[6-[bis(4-chlorophenyl)methyl]-2-cyclopropyl-1H-1,3-benzodiazol-1-yl]piperidine-1-sulfonyl)-2-chlorobenzoate Into a 50-mL round-bottom flask, was placed methyl 2-chloro-4-(chlorosulfonyl)benzoate (248 mg, 0.92 mmol, 1.10 equiv), 6-[bis(4-chlorophenyl)methyl]-2-cyclopropyl-1-(piperidin-4-yl)-1H-1,3-benzodiazole (400 mg, 0.84 mmol, 1.00 equiv) and a solution of triethylamine (254 mg, 2.51 mmol, 2.99 equiv) in dichloromethane (10 mL). The resulting solution was stirred for 2 h at room temperature. The resulting mixture was concentrated under vacuum to yield methyl 4-(4-[6-[bis(4-chlorophenyl)methyl]-2-cyclopropyl-1H-1,3-benzodiazol-1-yl]piperidine-1-sulfonyl)-2-chlorobenzoate as yellow oil. LC/MS (ES, m/z): 709 [M+H]+.

Step 3: Synthesis of 4-(4-[6-[bis(4-chlorophenyl)methyl]-2-cyclopropyl-1H-1,3-benzodiazol-1-yl]piperidine-1-sulfonyl)-2-chlorobenzoic acid in a mixture with the corresponding trifluoroacetic acid Into a 25-mL round-bottom flask, was placed methyl 4-(4-[6-[bis(4-chlorophenyl)methyl]-2-cyclopropyl-1H-1,3-benzodiazol-1-yl]piperidine-1-sulfonyl)-2-chlorobenzoate (230 mg, 0.32 mmol, 1.00 equiv) and a solution of LiOH.H$_2$O (82 mg, 1.95 mmol, 6.02 equiv) in tetrahydrofuran/H$_2$O (5/3 mL). The resulting solution was stirred for 6 h at room temperature. The pH value of the solution was adjusted to pH 3 with hydrogen chloride (1 mol/L). The resulting solution was extracted with ethyl acetate (3×10 mL) and the organic layers combined, then dried over anhydrous sodium sulfate and concentrated under vacuum. The product residue was purified by Prep-HPLC with the following conditions: Column, Sunfire prep C18, 5 um, 19*100 mm; mobile phase, 0.05% TFA in water and CH$_3$CN (20% CH$_3$CN up to 65% in 10 min); Detector, 254 nm to yield 4-(4-[6-[bis(4-chlorophenyl)methyl]-2-cyclopropyl-1H-1,3-benzodiazol-1-yl]piperidine-1-sulfonyl)-2-chlorobenzoic acid trifluoroacetic acid as a white solid. LC/MS (ES, m/z): 695 [M+H]+.

Alternate Step 2: Synthesis of 4-(4-[6-[bis(4-chlorophenyl)methyl]-2-cyclopropyl-1H-1,3-benzodiazol-1-yl]piperidine-1-sulfonyl)-2-chlorobenzoic acid hydrochloride Into a 50-mL round-bottom flask, was placed methyl 4-(4-[6-[bis(4-chlorophenyl)methyl]-2-cyclopropyl-1H-1,3-benzodiazol-1-yl]piperidine-1-sulfonyl)-2-chlorobenzoate (400 mg, 0.56 mmol, 1.00 equiv) and a solution of LiOH.H$_2$O (118 mg, 2.81 mmol, 4.99 equiv) in tetrahydrofuran/H$_2$O (5/5 mL). The resulting solution was stirred for 5 h at room temperature. The resulting mixture was concentrated under vacuum. The pH value of the solution was adjusted to pH 3 with hydrogen chloride (1 mol/L). The resulting solution was extracted with ethyl acetate (3×50 mL) and the organic layers combined, then dried over anhydrous sodium sulfate and concentrated under vacuum. The product residue was purified by Prep-HPLC with the following conditions (Waters-2767-1): Column, Sunfire prep C18, 5 um, 19*100 mm; mobile phase, 0.05% TFA in water and CH$_3$CN (22% CH$_3$CN up to 55% in 8 min); Detector, UV 254 nm. 50 mL product was obtained. The CH$_3$CN was evaporated and HCl (conc., 1 mL) was added. The resulting mixture was lyophilized to yield 4-(4-[6-[bis(4-chlorophenyl)methyl]-2-cyclopropyl-1H-1,3-benzodiazol-1-yl]piperidine-1-sulfonyl)-2-chlorobenzoic acid hydrochloride as an off-white solid.

$^1$H NMR (300 MHz, DMSO-d6) δ: 8.03 (d, J=8.1 Hz, 1H), 7.92 (d, J=1.5 Hz, 1H), 7.85 (dd, J1=1.5 Hz, J2=8.1 Hz, 1H), 7.72 (s, 1H), 7.51 (d, J=8.1 Hz, 1H), 7.36-7.39 (m, 4H), 7.11-7.14 (m, 4H), 6.97 (d, J=8.1 Hz, 1H), 5.88 (m, 1H), 4.74-4.84 (m, 1H), 3.89 (d, J=10.5 Hz, 2H), 2.50-2.65 (m, 2H), 2.26-2.43 (m, 3H), 1.98-2.07 (m, 2H), 1.05-1.15 (m, 4H). LC/MS (ES, m/z): 694 [M+H]+.

Example PH-29

4-(4-[6-[bis(4-chlorophenyl)methyl]-2-cyclopropyl-1H-1,3-benzodiazol-1-yl]piperidine-1-sulfonyl)-2-methoxybenzamide; trifluoroacetic acid

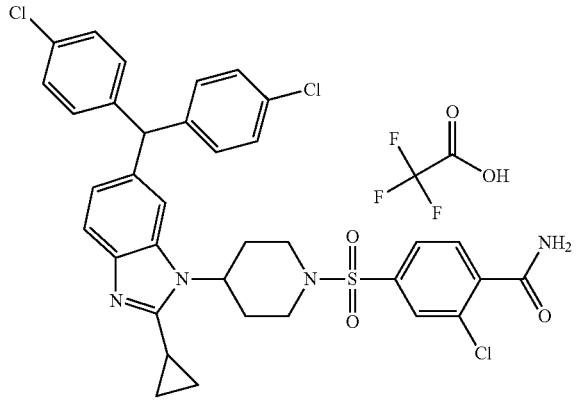

The title compound was prepared according to the procedure as described in Example PH-10 substituting 4-((4-(6-(bis(4-chlorophenyl)methyl)-2-cyclopropyl-1H-benzo[d]imidazol-1-yl)piperidin-1-yl)sulfonyl)-2-chlorobenzoic acid for 4-((4-(6-(bis(4-chlorophenyl)methyl)-2-cyclopropyl-1H-benzo[d]imidazol-1-yl)piperidin-1-yl)sulfonyl)benzoic acid.

$^1$H NMR (300 MHz, DMSO-d6) δ: 8.07 (s, 1H), 7.72-7.87 (m, 5H), 7.57 (d, J=8.4 Hz, 1H), 7.37-7.40 (m, 4H), 7.12-7.14 (m, 4H), 7.05-7.08 (m, 1H), 5.93 (s, 1H), 4.80-4.84 (m, 1H), 3.89-4.04 (m, 2H), 2.55-2.72 (m, 2H), 2.38-2.49 (m, 3H), 2.03-2.07 (m, 2H), 1.15-1.23 (m, 4H). LC/MS (ES, m/z): 693 [M+H]+.

Example PH-30

4-(4-[6-[bis(4-chlorophenyl)methyl]-2-cyclopropyl-1H-1,3-benzodiazol-1-yl]piperidine-1-sulfonyl)-2-methoxybenzoic acid; trifluoroacetic acid

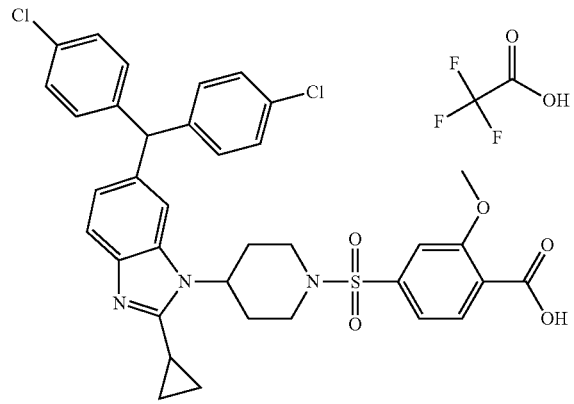

The title compound was prepared according to the procedure as described in Example PH-28 substituting 4-amino-2-methoxybenzoate for methyl 4-amino-2-chlorobenzoate in Step 1.

$^1$H NMR (300 MHz, DMSO-d6) δ: 7.80-7.86 (m, 2H), 7.55 (d, J=8.4 Hz, 1H), 7.37-7.44 (m, 6H), 7.11-7.14 (m, 4H), 7.01-7.04 (m, 1H), 5.92 (s, 1H), 4.77-4.81 (m, 1H), 3.93 (s, 3H), 3.78-3.88 (m, 2H), 2.55-2.72 (m, 2H), 2.36-2.49 (m, 3H), 2.00-2.07 (m, 2H), 1.12-1.20 (m, 4H). LC/MS (ES, m/z): 690 [M+H]+.

Example PH-31

4-(4-[6-[bis(4-chlorophenyl)methyl]-2-cyclopropyl-1H-1,3-benzodiazol-1-yl]piperidine-1-sulfonyl)-2-methoxybenzamide; trifluoroacetic acid

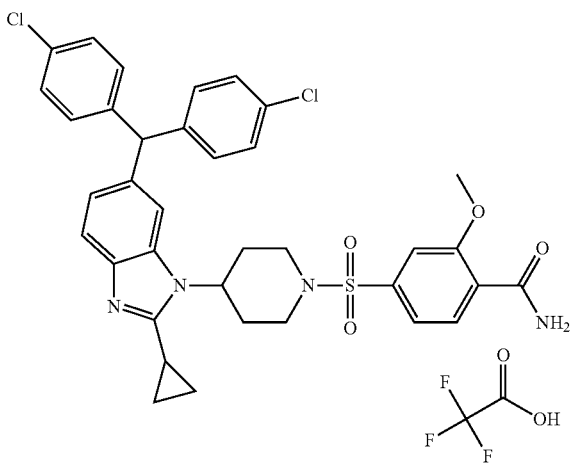

The title compound was prepared according to the procedure as described in Example PH-10 substituting 4-((4-(6-(bis(4-chlorophenyl)methyl)-2-cyclopropyl-1H-benzo[d]imidazol-1-yl)piperidin-1-yl)sulfonyl)-2-methoxybenzoic acid for 4-((4-(6-(bis(4-chlorophenyl)methyl)-2-cyclopropyl-1H-benzo[d]imidazol-1-yl)piperidin-1-yl)sulfonyl)benzoic acid.

$^1$H NMR (300 MHz, DMSO-d6) δ: 7.90-7.95 (m, 2H), 7.75 (d, J=5.7 Hz, 1H), 7.59 (d, J=8.4 Hz, 1H), 7.37-7.46 (m, 6H), 7.11-7.14 (m, 4H), 5.95 (s, 1H), 4.79-4.89 (m, 1H), 3.98 (s, 3H), 3.89-3.93 (m, 2H), 2.54-2.72 (m, 2H), 2.42-2.49 (m, 3H), 2.03-2.07 (m, 2H), 1.18-1.25 (m, 4H). LC/MS (ES, m/z): 689 [M+H]+.

Example PH-32

5-(4-[6-[bis(4-chlorophenyl)methyl]-2-cyclopropyl-1H-1,3-benzodiazol-1-yl]piperidine-1-sulfonyl)pyridine-2-carboxylic acid; trifluoroacetic acid

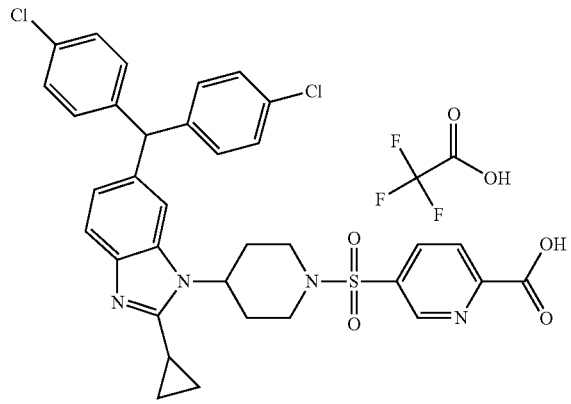

The title compound was prepared according to the procedure as described in Example PH-28 substituting methyl 5-(chlorosulfonyl)pyridine-2-carboxylate for methyl 4-amino-2-chlorobenzoate in Step 2.

$^1$H NMR (300 MHz, DMSO-d6) δ: 9.09 (s, 1H), 8.41 (d, J=9.3 Hz, 1H), 8.30 (d, J=8.4 Hz, 1H), 7.86 (s, 1H), 7.59 (d, J=8.4 Hz, 1H), 7.38-7.41 (m, 4H), 7.08-7.15 (m, 5H), 5.94 (s, 1H), 4.80-4.84 (m, 1H), 3.91-4.05 (m, 3H), 2.61-2.73 (m, 2H), 2.39-2.50 (m, 2H), 2.04-2.08 (m, 2H), 1.13-1.23 (m, 4H). LC/MS (ES, m/z): 661 [M+H]+.

Example PH-33

5-(4-[6-[bis(4-chlorophenyl)methyl]-2-cyclopropyl-1H-1,3-benzodiazol-1-yl]piperidine-1-sulfonyl)pyridine-2-carboxamide; trifluoroacetic acid

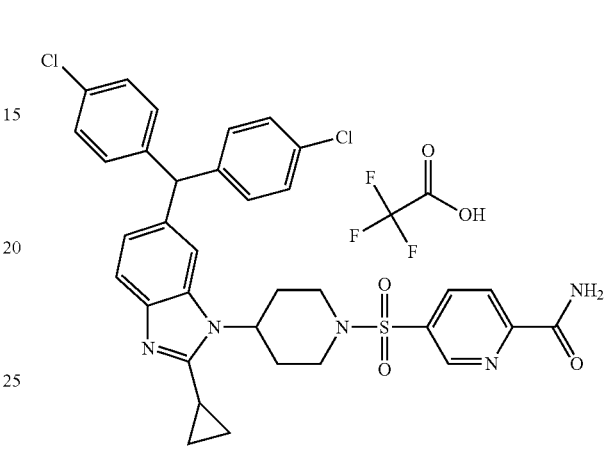

The title compound was prepared according to the procedure as described in Example PH-10 substituting 5-((4-(6-(bis(4-chlorophenyl)methyl)-2-cyclopropyl-1H-benzo[d]imidazol-1-yl)piperidin-1-yl)sulfonyl)picolinic acid for 4-((4-(6-(bis(4-chlorophenyl)methyl)-2-cyclopropyl-1H-benzo[d]imidazol-1-yl)piperidin-1-yl)sulfonyl)benzoic acid.

$^1$H NMR (300 MHz, DMSO-d6) δ: 8.99 (s, 1H), 8.30-8.43 (m, 3H), 7.89-7.95 (m, 2H), 7.60 (d, J=9.0 Hz, 1H), 7.38-7.41 (m, 4H), 7.12-7.15 (m, 5H), 5.95 (s, 1H), 4.80-4.90 (m, 1H), 3.91-3.95 (m, 3H), 2.59-2.73 (m, 2H), 2.40-2.44 (m, 2H), 2.05-2.08 (m, 2H), 1.15-1.25 (m, 4H). LC/MS (ES, m/z): 660 [M+H]+

Example PH-34

3-(4-[6-[bis(4-chlorophenyl)methyl]-2-cyclopropyl-1H-1,3-benzodiazol-1-yl]piperidine-1-sulfonyl)benzoic acid; trifluoroacetic acid

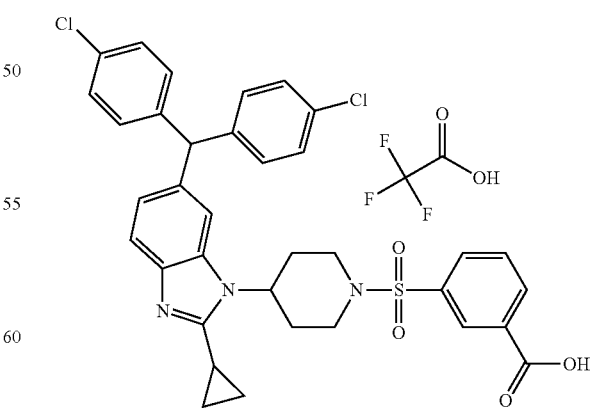

The title compound was prepared according to the procedure as described in Example PH-1 substituting 3-(chlorosulfonyl)benzoic acid for 4-(chlorosulfonyl)benzoic acid in Step 10.

¹H NMR (300 MHz, CD3OD) δ: 8.32 (d, J=1.5 Hz, 1H), 8.23 (d, J=7.8 Hz, 1H), 7.97 (d, J=8.1 Hz, 1H), 7.65-7.70 (m, 2H), 7.53 (d, J=8.4 Hz, 1H), 7.21-7.25 (m, 5H), 6.98-7.04 (m, 4H), 5.76 (s, 1H), 4.76-4.84 (m, 1H), 3.95 (d, J=11.4 Hz, 2H), 2.31-2.61 (m, 5H), 2.00-2.04 (m, 2H), 1.14-1.33 (m, 4H). LC/MS (ES, m/z): 660 [M+H]+.

Example PH-35

4-(4-[6-[bis(4-chlorophenyl)methyl]-2-cyclopropyl-1H-1,3-benzodiazol-1-yl]piperidine-1-sulfonyl)-2-fluorobenzoic acid hydrochloride

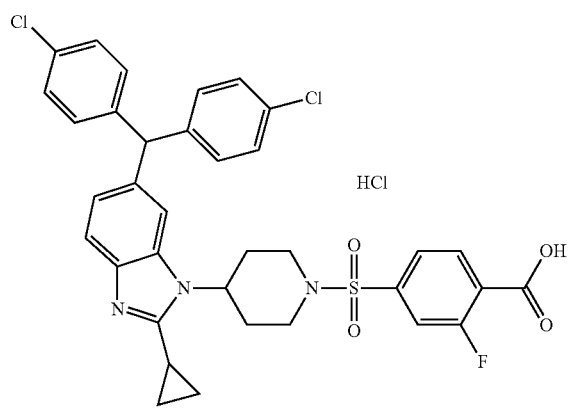 [SMILES: O=C(O)c1ccc(S(=O)(=O)N2CCC(n3c(C4CC4)nc4ccc(C(c5ccc(Cl)cc5)c5ccc(Cl)cc5)cc43)CC2)cc1F ; Cl]

The title compound was prepared according to the procedure as described in Example PH-28 substituting methyl 4-(chlorosulfonyl)-2-fluorobenzoate for methyl 4-amino-2-chlorobenzoate in Step 2.

¹H NMR (300 MHz, CD3OD) δ: 8.12-8.18 (m, 1H), 7.60-7.74 (m, 4H), 7.29-7.33 (m, 5H), 7.08-7.11 (m, 4H), 5.84 (s, 1H), 4.82-4.91 (m, 1H), 4.22 (d, J=12.0 Hz, 2H), 2.65-2.73 (m, 2H), 2.46-2.56 (m, 3H), 2.10-2.14 (m, 2H), 1.26-1.43 (m, 4H). LC/MS (ES, m/z): 678 [M+H]+.

Example PH-36

4-(4-[6-[bis(4-chlorophenyl)methyl]-2-cyclopropyl-1H-1,3-benzodiazol-1-yl]piperidine-1-sulfonyl)-2-fluorobenzamide hydrochloride

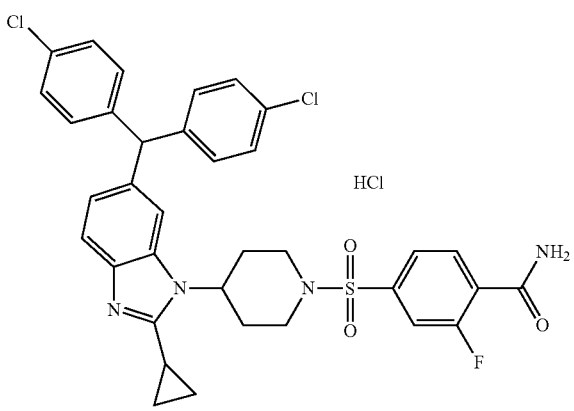 [SMILES: NC(=O)c1ccc(S(=O)(=O)N2CCC(n3c(C4CC4)nc4ccc(C(c5ccc(Cl)cc5)c5ccc(Cl)cc5)cc43)CC2)cc1F ; Cl]

The title compound was prepared according to the procedure as described in Example PH-10 substituting 4-((4-(6-(bis(4-chlorophenyl)methyl)-2-cyclopropyl-1H-benzo[d]imidazol-1-yl)piperidin-1-yl)sulfonyl)-2-fluorobenzoic acid for 4-((4-(6-(bis(4-chlorophenyl)methyl)-2-cyclopropyl-1H-benzo[d]imidazol-1-yl)piperidin-1-yl)sulfonyl)benzoic acid.

¹H NMR (300 MHz, CD3OD) δ: 7.96-8.01 (m, 1H), 7.67-7.73 (m, 3H), 7.58 (d, J=8.4 Hz, 1H), 7.24-7.32 (m, 5H), 7.08-7.11 (m, 4H), 5.82 (s, 1H), 4.82-4.90 (m, 1H), 4.01 (d, J=12.3 Hz, 2H), 2.36-2.71 (m, 5H), 2.00-2.11 (m, 2H), 1.31-1.36 (m, 2H), 1.21-1.25 (m, 2H). LC/MS (ES, m/z): 677 [M+H]+.

Example PH-37

4-(4-[6-[bis(4-chlorophenyl)methyl]-2-cyclopropyl-1H-1,3-benzodiazol-1-yl]piperidine-1-sulfonyl)-2-methylbenzoic acid; trifluoroacetic acid

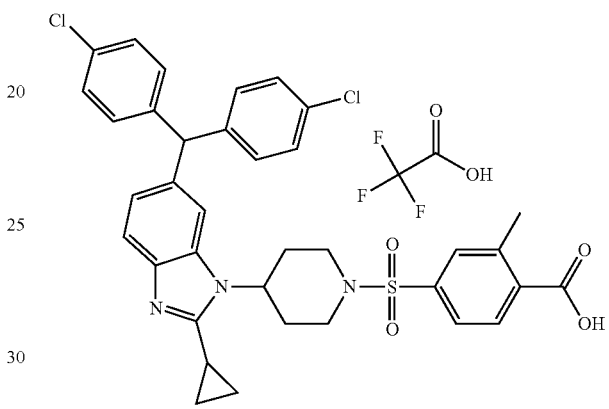

The title compound was prepared according to the procedure as described in Example PH-1 substituting 4-(chlorosulfonyl)-2-methylbenzoic acid for 4-(chlorosulfonyl)benzoic acid in Step 10.

1H NMR (300 MHz, CD3OD) δ: 8.11 (d, J=7.5 Hz, 1H), 7.73-7.76 (m, 3H), 7.63 (d, J=8.4 Hz, 1H), 7.33-7.36 (m, 5H), 7.12-7.15 (m, 4H), 5.87 (s, 1H), 4.05 (d, J=10.8 Hz, 2H), 2.43-2.71 (m, 9H), 2.11-2.14 (m, 2H), 1.32-1.41 (m, 2H), 1.26-1.28 (m, 2H). LC/MS (ES, m/z): 674 [M+H]+.

Example PH-38

3-(4-[6-[bis(4-chlorophenyl)methyl]-2-cyclopropyl-1H-1,3-benzodiazol-1-yl]piperidine-1-sulfonyl)-N-methylbenzamide hydrochloride

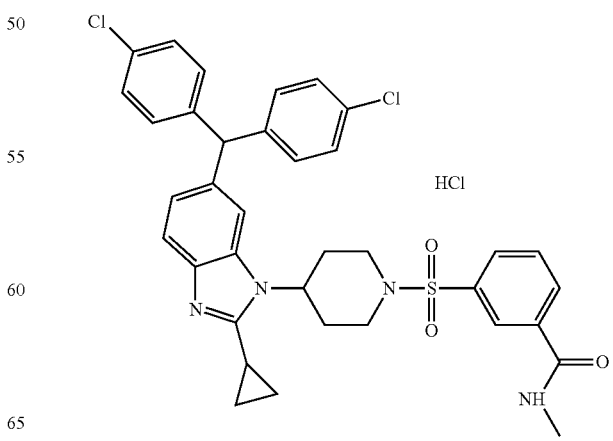

The title compound was prepared according to the procedure as described in Example PH-10 substituting CH$_3$NH$_2$.HCl for ammonium chloride in Step 1.

1H NMR (300 MHz, CD3OD) δ: 8.25 (t, J=1.8 Hz, 1H), 8.10 (t, J=1.5 Hz, 1H), 7.96-8.08 (m, 1H), 7.72-7.74 (m, 2H), 7.58-7.69 (m, 1H), 7.29-7.32 (m, 5H), 7.08-7.11 (m, 4H), 5.83 (s, 1H), 4.82-4.87 (m, 1H), 4.02 (d, J=12.6 Hz, 2H), 2.92 (s, 3H), 2.42-2.69 (m, 5H), 2.08-2.11 (m, 2H), 1.34-1.39 (m, 2H), 1.23-1.27 (m, 2H). LC/MS (ES, m/z): 673 [M+H]+.

Example PH-39

3-(4-(6-(bis(4-chlorophenyl)methyl)-2-cyclopropyl-1H-benzo[d]imidazol-1-yl)piperidin-1-ylsulfonyl)-N-(2-hydroxyethyl)benzamide; trifluoroacetic acid

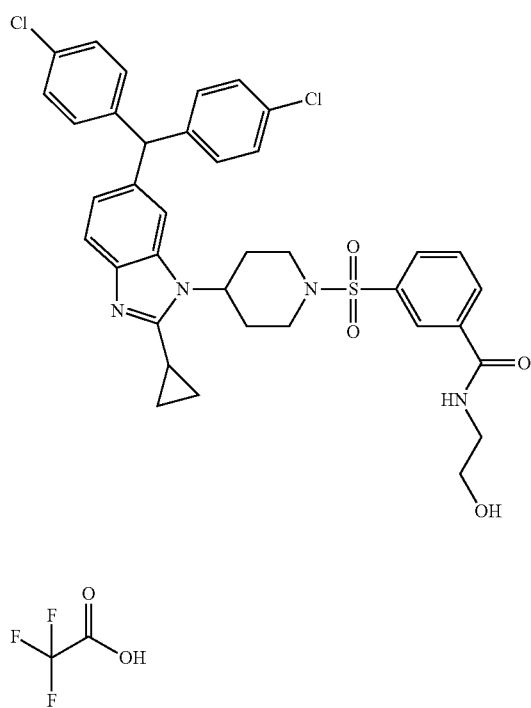

The title compound was prepared according to the procedure as described in Example PH-10 substituting 2-aminoethan-1-ol for ammonium chloride in Step 1.

¹H NMR (300 MHz, CD3OD) δ: 8.33 (s, 1H), 8.18 (d, J=6.0 Hz, 1H), 8.03 (d, J=5.7 Hz, 1H), 7.75-7.79 (m, 2H), 7.64 (d, J=6.0 Hz, 1H), 7.34-7.37 (m, 5H), 7.13-7.16 (m, 4H), 5.88 (s, 1H), 4.86-4.91 (m, 1H), 4.08 (d, J=9.0 Hz, 2H), 3.75 (t, J=4.2 Hz, 2H), 3.56 (t, J=4.2 Hz, 2H), 2.67-2.73 (m, 2H), 2.45-2.65 (m, 3H), 2.13-2.16 (m, 2H), 1.28-1.42 (m, 5H). LC/MS (ES, m/z): 703 [M+H]+.

Example PH-40

3-(4-[6-[bis(4-chlorophenyl)methyl]-2-cyclopropyl-1H-1,3-benzodiazol-1-yl]piperidine-1-sulfonyl)-N-(3-hydroxypropyl)benzamide hydrochloride

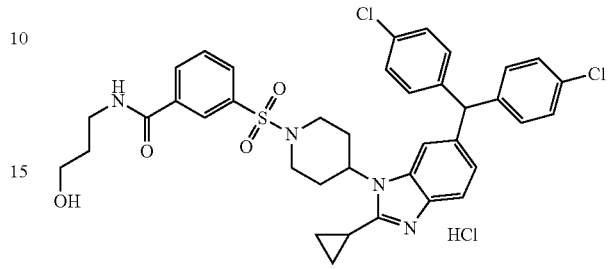

The title compound was prepared according to the procedure as described in Example PH-10 substituting 3-aminoethan-1-ol for ammonium chloride in Step 1.

¹H NMR (400 MHz, CD3OD) δ: 8.30 (s, 1H), 8.15 (d, J=7.2 Hz, 1H), 8.03 (d, J=7.6 Hz, 1H), 7.75-7.80 (m, 2H), 7.66 (d, J=8.4 Hz, 1H), 7.34-7.36 (m, 5H), 7.13-7.16 (m, 4H), 5.89 (s, 1H), 4.82-4.92 (m, 1H), 4.07 (d, J=11.6 Hz, 2H), 3.68 (t, J=6.0 Hz, 2H), 3.53 (t, J=6.0 Hz, 2H), 2.68-2.74 (m, 2H), 2.52-2.57 (m, 3H), 2.14-2.17 (m, 2H), 1.87 (t, J=6.4 Hz, 2H), 1.42-1.44 (m, 2H), 1.31-1.40 (m, 2H). LC/MS (ES, m/z): 717 [M+H]+.

Example PH-41

4-(4-[6-[bis(4-chlorophenyl)methyl]-2-cyclopropyl-1H-1,3-benzodiazol-1-yl]piperidine-1-sulfonyl)-2-(trifluoromethyl)benzoic acid hydrochloride

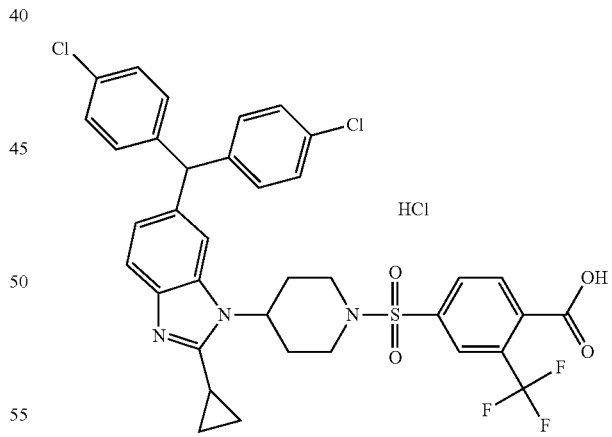

The title compound was prepared according to the procedure as described in Example PH-28 substituting 4-amino-2-(trifluoromethyl)benzoic acid for 4-amino-2-chlorobenzoate in Step 1.

¹H NMR (300 MHz, DMSO-d6) δ: 8.48-8.49 (br.m, 1H), 8.17 (d, J=8.7 Hz, 1H), 8.04-8.09 (m, 2H), 7.77 (br.s, 1H), 7.52 (d, J=8.7 Hz, 1H), 7.33-7.36 (m, 4H), 6.99-7.18 (m, 5H), 5.89 (s, 1H), 4.76-4.80 (m, 1H), 3.89 (d, J=10.5 Hz, 2H), 2.56-2.69 (m, 2H), 2.34-2.45 (m, 3H), 1.99-2.03 (m, 2H), 1.09-1.23 (m, 4H). LC/MS (ES, m/z): 728 [M+H]+.

Example PH-42

4-(4-[6-[bis(4-chlorophenyl)methyl]-2-cyclopropyl-1H-1,3-benzodiazol-1-yl]piperidine-1-sulfonyl)-2-(trifluoromethyl)benzamide hydrochloride

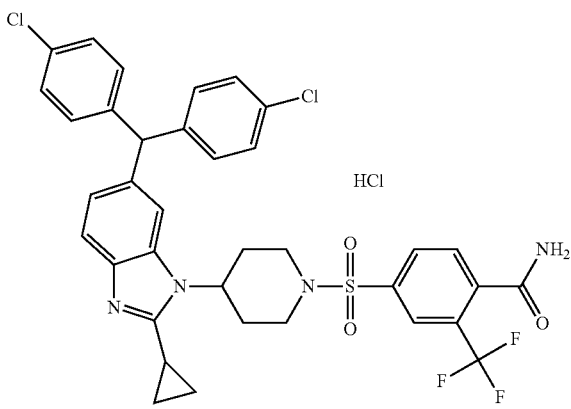 [SMILES: NC(=O)c1ccc(S(=O)(=O)N2CCC(n3c(C4CC4)nc4ccc(C(c5ccc(Cl)cc5)c5ccc(Cl)cc5)cc43)CC2)cc1C(F)(F)F ; Cl]

The title compound was prepared according to the procedure as described in Example PH-10 substituting 4-((4-(6-(bis(4-chlorophenyl)methyl)-2-cyclopropyl-1H-benzo[d]imidazol-1-yl)piperidin-1-yl)sulfonyl)-2-(trifluoromethyl)benzoic acid for 4-((4-(6-(bis(4-chlorophenyl)methyl)-2-cyclopropyl-1H-benzo[d]imidazol-1-yl)piperidin-1-yl)sulfonyl)benzoic acid.

$^1$H NMR (300 MHz, CD3OD) δ: 8.10-8.13 (m, 2H), 7.82 (d, J=8.1 Hz, 1H), 7.74 (s, 1H), 7.60 (d, J=8.4 Hz, 1H), 7.28-7.33 (m, 5H), 7.08-7.11 (m, 4H), 5.84 (s, 1H), 4.82-4.89 (m, 1H), 4.03 (d, J=11.4 Hz, 2H), 2.41-2.70 (m, 5H), 2.09-2.14 (m, 2H), 1.26-1.40 (m, 4H). LC/MS (ES, m/z): 727 [M+H]+.

Example PH-43 methyl 3-[[3-(4-[6-[bis(4-chlorophenyl)methyl]-2-cyclopropyl-1H-1,3-benzodiazol-1-yl]piperidine-1-sulfonyl)phenyl]formamido]propanoate; trifluoroacetic acid

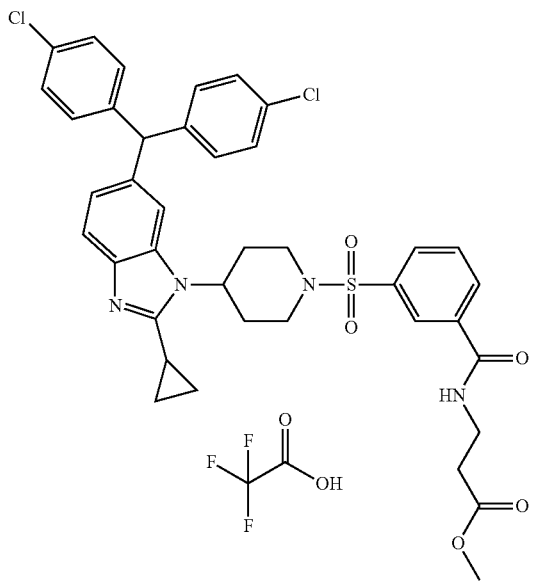 [SMILES: COC(=O)CCNC(=O)c1cccc(S(=O)(=O)N2CCC(n3c(C4CC4)nc4ccc(C(c5ccc(Cl)cc5)c5ccc(Cl)cc5)cc43)CC2)c1 ; O=C(O)C(F)(F)F]

The title compound was prepared according to the procedure as described in Example PH-13 substituting methyl 3-aminopropanoate hydrochloride for ammonium chloride in Step 2.

$^1$H NMR (300 MHz, CD3OD) δ: 8.29 (s, 1H), 8.11-8.15 (m, 1H), 8.01-8.04 (m, 1H), 7.73-7.79 (m, 2H), 7.64 (d, J=8.7 Hz, 1H), 7.31-7.37 (m, 5H), 7.12-7.16 (m, 4H), 5.87 (s, 1H), 4.85-4.91 (m, 1H), 4.07 (d, J=11.7 Hz, 2H), 3.66-3.71 (m, 5H), 2.66-2.72 (m, 4H), 2.46-2.56 (m, 3H), 2.12-2.15 (m, 2H), 1.38-1.42 (m, 2H), 1.26-1.30 (m, 2H). LC/MS (ES, m/z): 745 [M+H]+.

Example PH-44

Methyl 3-[[5-(4-[6-[bis(4-chlorophenyl)methyl]-2-cyclopropyl-1H-1,3-benzodiazol-1-yl]piperidine-1-sulfonyl)pyridin-2-yl]formamido]propanoate; trifluoroacetic acid

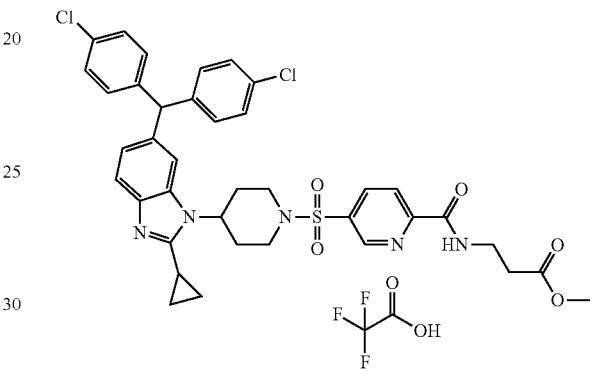

The title compound was prepared according to the procedure as described in Example PH-18 substituting methyl 5-(chlorosulfonyl)pyridine-2-carboxylate for methyl 2-(chlorosulfonyl)benzoate in Step 1, and substituting methyl 3-aminopropanoate hydrochloride for ammonium chloride in Step 3.

$^1$H NMR (300 MHz, CD3OD) δ: 9.01 (d, J=1.5 Hz, 1H), 8.28-8.39 (m, 2H), 7.68 (s, 1H), 7.58 (d, J=8.7 Hz, 1H), 7.26-7.32 (m, 5H), 7.08-7.11 (m, 4H), 5.82 (s, 1H), 4.83-4.90 (m, 1H), 4.04 (d, J=11.4 Hz, 2H), 3.66-3.72 (m, 5H), 2.63-2.73 (m, 4H), 2.36-2.56 (m, 3H), 2.08-2.12 (m, 2H), 1.31-1.35 (m, 2H), 1.23-1.35 (m, 2H). LC/MS: (m/z) 746 [M+H]+.

Example PH-45

5-(4-[6-[bis(4-chlorophenyl)methyl]-2-cyclopropyl-1H-1,3-benzodiazol-1-yl]piperidine-1-sulfonyl)furan-2-carboxylic acid trifluoroacetic acid

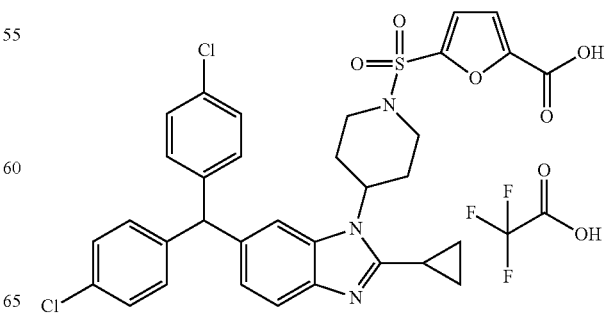

The title compound was prepared according to the procedure as described in Example PH-13 substituting 5-(chlorosulfonyl)furan-2-carboxylic acid for 3-(chlorosulfonyl)benzoic acid in Step 1.

$^1$H NMR (300 MHz, CD3OD) δ: 7.76 (s, 1H), 7.65 (d, J=8.7 Hz, 1H), 7.33-7.36 (m, 6H), 7.25 (d, J=3.6 Hz, 1H), 7.12-7.15 (m, 4H), 5.88 (s, 1H), 4.97-5.07 (m, 1H), 4.11 (d, J=12.6 Hz, 2H), 2.98-3.06 (m, 2H), 2.49-2.56 (m, 3H), 2.17-2.21 (m, 2H), 1.41-1.45 (m, 2H), 1.30-1.34 (m, 2H). LC/MS (ES, m/z): 650 [M+H]+.

Example PH-46

5-(4-[6-[bis(4-chlorophenyl)methyl]-2-cyclopropyl-1H-1,3-benzodiazol-1-yl]piperidine-1-sulfonyl)furan-2-carboxamide; trifluoroacetic acid

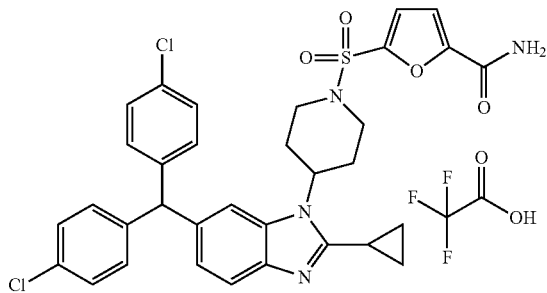

The title compound was prepared according to the procedure as described in Example PH-10 substituting 5-((4-(6-(bis(4-chlorophenyl)methyl)-2-cyclopropyl-1H-benzo[d]imidazol-1-yl)piperidin-1-yl)sulfonyl)furan-2-carboxylic acid for 4-((4-(6-(bis(4-chlorophenyl)methyl)-2-cyclopropyl-1H-benzo[d]imidazol-1-yl)piperidin-1-yl)sulfonyl)benzoic acid.

1H NMR (300 MHz, CD3OD) δ: 7.76 (s, 1H), 7.65 (d, J=8.4 Hz, 1H), 7.21-7.40 (m, 7H), 7.12-7.20 (m, 4H), 5.88 (s, 1H), 4.95-5.05 (m, 1H), 4.12 (d, J=11.4 Hz, 2H), 2.94-3.04 (m, 2H), 2.42-2.58 (m, 3H), 2.16-2.19 (m, 2H), 1.21-1.49 (m, 4H). LC/MS (ES, m/z): 649 [M+H]+.

Example PH-47

3-(4-(6-(bis(4-chlorophenyl)methyl)-2-cyclopropyl-1H-benzo[d]imidazol-1-yl)piperidin-1-yl)benzamide 2,2,2-trifluoroacetate

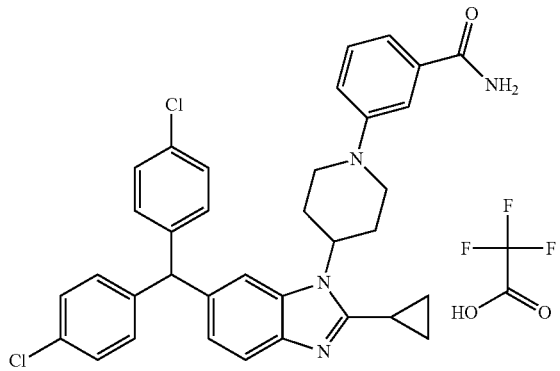

Step 1: Synthesis of methyl 3-(4-[6-[bis(4-chlorophenyl)methyl]-2-cyclopropyl-1H-1,3-benzodiazol-1-yl]piperidin-1-yl)benzoate Into a 100-mL 3-necked round-bottom flask purged and maintained with an inert atmosphere of nitrogen, was placed a solution of 6-[bis(4-chlorophenyl)methyl]-2-cyclopropyl-1-(piperidin-4-yl)-1H-1,3-benzodiazole (300 mg, 0.63 mmol, 1.00 equiv) in toluene (10 mL), methyl 3-bromobenzoate (162 mg, 0.75 mmol, 1.20 equiv), Pd$_2$(dba)$_3$ (90 mg, 0.10 mmol, 0.30 equiv), XPhos (58 mg, 0.10 equiv) and Cs$_2$CO$_3$ (411 mg, 1.26 mmol, 2.00 equiv). The resulting solution was stirred overnight at 95° C. The residue was applied onto a silica gel column with ethyl acetate/petroleum ether (1:1) to yield methyl 3-(4-[6-[bis(4-chlorophenyl)methyl]-2-cyclopropyl-1H-1,3-benzodiazol-1-yl]piperidin-1-yl)benzoate as yellow oil. LC/MS (ES, m/z): 610 [M+H]+.

Step 2: Synthesis of 3-(4-[6-[bis(4-chlorophenyl)methyl]-2-cyclopropyl-1H-1,3-benzodiazol-1-yl]piperidin-1-yl)benzoic acid; trifluoroacetic acid Into a 50-mL round-bottom flask, was placed a solution of methyl 3-(4-[6-[bis(4-chlorophenyl)methyl]-2-cyclopropyl-1H-1,3-benzodiazol-1-yl]piperidin-1-yl)benzoate (240 mg, 0.39 mmol, 1.00 equiv) in tetrahydrofuran/MeOH (10/2 mL) and LiOH (10 mL). The resulting solution was stirred overnight at room temperature. The reaction was then quenched by the addition of water (10 mL). The pH value of the solution was adjusted to pH 6 with hydrogen chloride (1 mol/L). The solids were collected by filtration. The product residue was purified by Prep-HPLC with the following conditions (Waters 2767-1): Column, SunFire Prep C18, 5 um, 19*100 mm; mobile phase, 0.05% TFA in water and CH$_3$CN (25% CH$_3$CN up to 55% in 9 min); Detector, UV 254 nm to yield 3-(4-[6-[bis(4-chlorophenyl)methyl]-2-cyclopropyl-1H-1,3-benzodiazol-1-yl]piperidin-1-yl)benzoic acid; trifluoroacetic acid as a white solid. LC/MS (ES, m/z): 596 [M+H]+.

Step 3: Synthesis of 3-(4-[6-[bis(4-chlorophenyl)methyl]-2-cyclopropyl-1H-1,3-benzodiazol-1-yl]piperidin-1-yl)benzamide; trifluoroacetic acid Into a 50-mL round-bottom flask, was placed a solution of 3-(4-[6-[bis(4-chlorophenyl)methyl]-2-cyclopropyl-1H-1,3-benzodiazol-1-yl]piperidin-1-yl)benzoic acid (100 mg, 0.17 mmol, 1.00 equiv) in N,N-dimethylformamide (5 mL), NH$_4$Cl (45 mg, 0.84 mmol, 5.00 equiv), HATU (77 mg, 0.20 mmol, 1.20 equiv) and DIEA (43 mg, 0.33 mmol, 2.00 equiv). The resulting solution was stirred overnight at room temperature. The reaction was then quenched by the addition of water. The solids were collected by filtration. The product residue (100 mg) was purified by Prep-HPLC with the following conditions (Waters 2767-1): Column, SunFire Prep C18, 5 um, 19*100 mm; mobile phase, 0.05% TFA in water and CH$_3$CN (25% CH$_3$CN up to 45% in 9 min); Detector, UV 254 nm to yield 3-(4-[6-[bis(4-chlorophenyl)methyl]-2-cyclopropyl-1H-1,3-benzodiazol-1-yl]piperidin-1-yl)benzamide; trifluoroacetic acid as a white solid.

$^1$H NMR (300 MHz, CD3OD) δ: 7.56-7.63 (m, 3H), 7.19-7.38 (m, 8H), 7.01-7.06 (m, 4H), 5.68 (s, 1H), 5.08-5.16 (m, 1H), 4.00 (d, J=12.9 Hz, 2H), 3.06-3.14 (m, 2H), 2.49-2.62 (m, 3H), 2.08-2.12 (m, 2H), 1.42-1.49 (m, 2H), 1.28-1.33 (m, 2H). LC/MS (ES, m/z): 595 [M+H]+.

Example PH-48

4-(4-(6-(bis(4-chlorophenyl)methyl)-2-cyclopropyl-1H-benzo[d]imidazol-1-yl)piperidin-1-yl)benzamide 2,2,2-trifluoroacetate

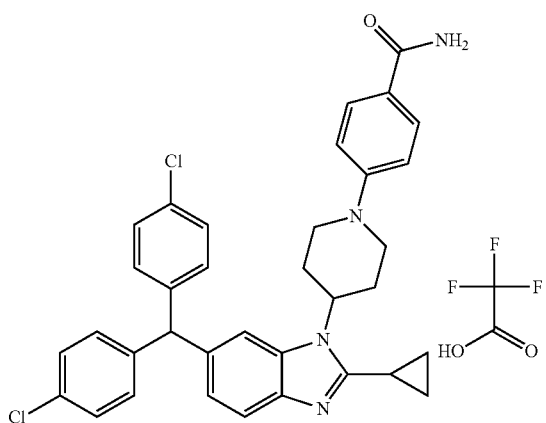

The title compound was prepared according to the procedure as described in Example PH-47 substituting methyl 4-bromobenzoate for methyl 3-bromobenzoate in Step 1.

$^1$H NMR (300 MHz, CD3OD) δ: 7.81 (d, J=8.7 Hz, 2H), 7.60 (d, J=8.4 Hz, 1H), 7.39 (s, 2H), 7.23-7.30 (m, 4H), 6.96-7.04 (m, 6H), 5.59 (s, 1H), 5.13-5.21 (m, 1H), 4.13 (d, J=14.1 Hz, 2H), 3.12-3.29 (m, 2H), 2.41-2.61 (m, 3H), 2.05-2.09 (m, 2H), 1.41-1.47 (m, 2H), 1.26-1.36 (m, 2H). LC/MS (ES, m/z): 595 [M+H]+.

Example PH-49

2-(3-(4-(6-(bis(4-chlorophenyl)methyl)-2-cyclopropyl-1H-benzo[d]imidazol-1-yl)piperidin-1-yl)phenyl)acetamide 2,2,2-trifluoroacetate

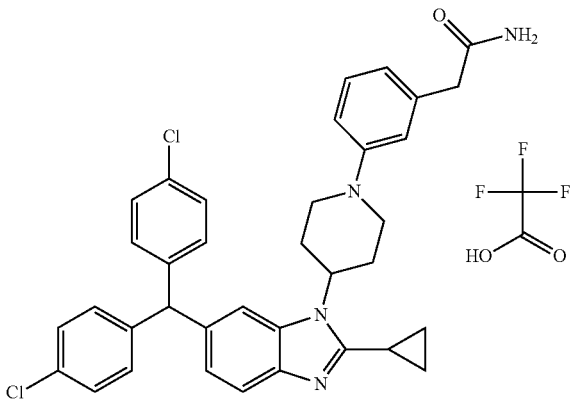 [SMILES: NC(=O)Cc1cccc(N2CCC(n3c(C4CC4)nc4ccc(C(c5ccc(Cl)cc5)c5ccc(Cl)cc5)cc43)CC2)c1 ; O=C(O)C(F)(F)F]

The title compound was prepared according to the procedure as described in Example PH-47 substituting methyl 2-(3-bromophenyl)acetate for methyl 3-bromobenzoate in Step 1.

$^1$H NMR (400 MHz, CD3OD) δ: 7.75-7.76 (m, 1H), 7.67 (d, J=8.8 Hz, 1H), 7.27-7.39 (m, 6H), 6.92-7.17 (m, 7H), 5.79 (s, 1H), 5.11-5.15 (m, 1H), 3.96 (d, J=12.0 Hz, 2H), 3.51 (s, 2H), 3.15-3.24 (m, 2H), 2.62-2.75 (m, 3H), 2.15-2.17 (m, 2H), 1.48-1.53 (m, 2H), 1.20-1.37 (m, 2H). LC/MS (ES, m/z): 609 [M+H]+.

Example PH-50

2-(4-(4-(6-(bis(4-chlorophenyl)methyl)-2-cyclopropyl-1H-benzo[d]imidazol-1-yl)piperidin-1-yl)phenyl)acetamide 2,2,2-trifluoroacetate

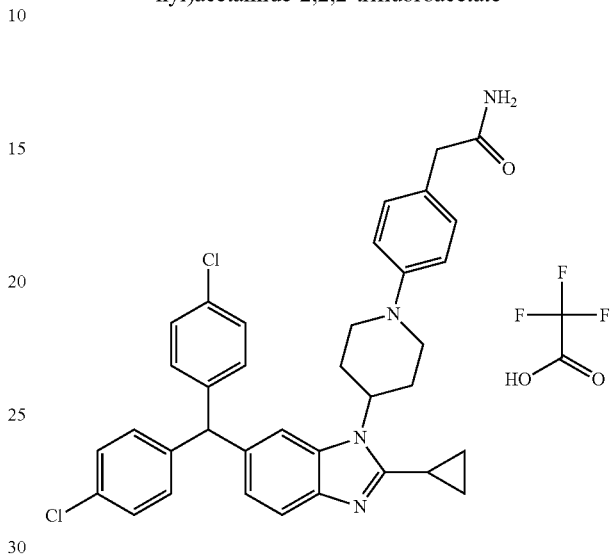

The title compound was prepared according to the procedure as described in Example PH-47 substituting methyl 2-(4-bromophenyl)acetate for methyl 3-bromobenzoate in Step 1.

$^1$H NMR (300 MHz, CD3OD) δ: 7.70-7.72 (m, 1H), 7.62 (d, J=8.4 Hz, 1H), 7.20-7.33 (m, 7H), 7.03-7.15 (m, 6H), 5.74 (s, 1H), 5.04-5.14 (m, 1H), 3.87 (d, J=11.1 Hz, 2H), 3.42-3.44 (m, 2H), 3.06-3.15 (m, 2H), 2.54-2.61 (m, 3H), 2.08-2.18 (m, 2H), 1.42-1.49 (m, 2H), 1.25-1.31 (m, 2H). LC/MS (ES, m/z): 609 [M+H]+.

Example PH-51

2-(3-(4-(6-(bis(4-chlorophenyl)methyl)-2-cyclopropyl-1H-benzo[d]imidazol-1-yl)piperidin-1-yl)phenoxy)acetamide 2,2,2-trifluoroacetate

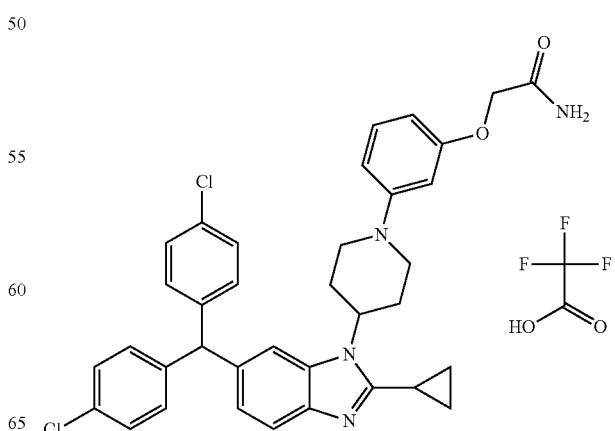

The title compound was prepared according to the procedure as described in Example PH-47 substituting ethyl 2-(3-bromophenoxy)acetate for methyl 3-bromobenzoate in Step 1.

$^1$H NMR (400 MHz, CD3OD) δ: 7.63-7.68 (m, 2H), 7.31-7.38 (m, 5H), 7.22 (t, J=8.4 Hz, 1H), 7.06-7.09 (m, 4H), 6.73-6.74 (m, 2H), 6.56 (d, J=8.4 Hz, 1H), 5.72 (s, 1H), 5.13-5.19 (m, 1H), 4.50 (s, 2H), 4.00 (d, J=13.6 Hz, 2H), 3.12-3.20 (m, 2H), 2.55-2.67 (m, 3H), 2.05-2.13 (m, 2H), 1.48-1.53 (m, 2H), 1.33-1.37 (m, 2H). LC/MS (ES, m/z): 625 [M+H]+.

Example PH-52

2-(4-(4-(6-(bis(4-chlorophenyl)methyl)-2-cyclopropyl-1H-benzo[d]imidazol-1-yl)piperidin-1-yl)phenoxy)acetamide 2,2,2-trifluoroacetate

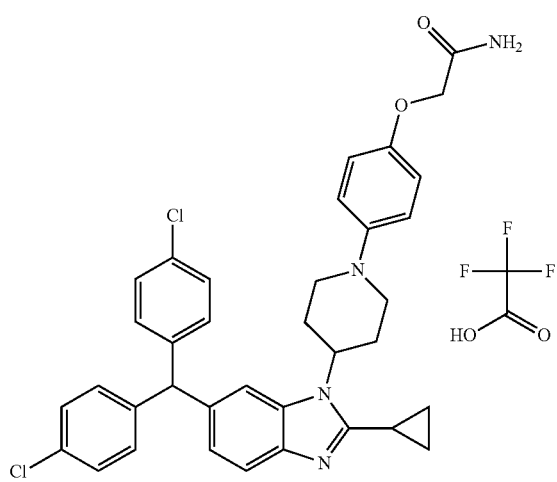 [SMILES: NC(=O)COc1ccc(N2CCC(n3c(C4CC4)nc4ccc(C(c5ccc(Cl)cc5)c5ccc(Cl)cc5)cc43)CC2)cc1 ; O=C(O)C(F)(F)F]

The title compound was prepared according to the procedure as described in Example PH-47 substituting ethyl 2-(4-bromophenoxy)acetate for methyl 3-bromobenzoate in Step 1.

$^1$H NMR (400 MHz, CD3OD) δ: 7.83 (s, 1H), 7.68 (d, J=8.8 Hz, 1H), 7.33-7.38 (m, 5H), 7.02-7.20 (m, 8H), 5.82 (s, 1H), 5.10-5.20 (m, 1H), 4.49 (s, 2H), 3.80 (d, J=12.0 Hz, 2H), 3.12-3.22 (m, 2H), 2.62-2.72 (m, 3H), 2.16-2.26 (m, 2H), 1.48-1.51 (m, 2H), 1.35-1.38 (m, 2H). LC/MS (ES, m/z): 625 [M+H]+.

Example PH-53

2,2,2-trifluoroacetic acid compound with 3-((4-(6-(bis(4-chlorophenyl)methyl)-2-cyclopropyl-1H-benzo[d]imidazol-1-yl)piperidin-1-yl)methyl)benzoic acid (1:1)

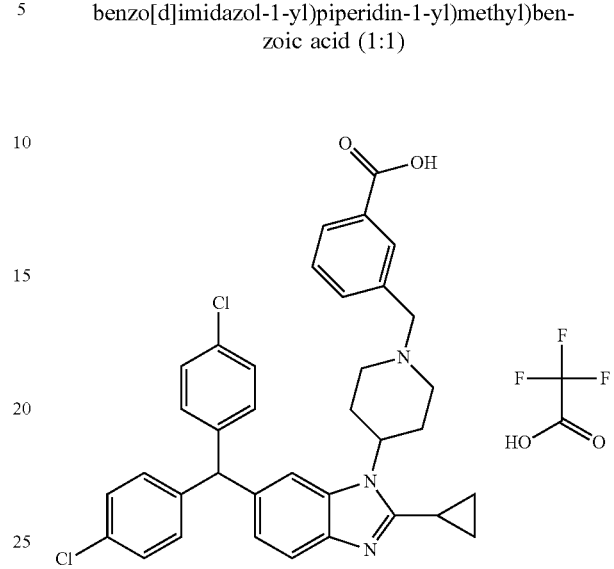

Step 1: Synthesis of yield methyl 3-[(4-[6-[bis(4-chlorophenyl)methyl]-2-cyclopropyl-1H-1,3-benzodiazol-1-yl]piperidin-1-yl)methyl]benzoate Into a 100-mL round-bottom flask, was placed a solution of 6-[bis(4-chlorophenyl)methyl]-2-cyclopropyl-1-(piperidin-4-yl)-1H-1,3-benzodiazole (2 g, 4.20 mmol, 1.00 equiv) in dichloromethane (30 mL), methyl 3-formylbenzoate (690 mg, 4.20 mmol, 1.00 equiv) and triethylamine (a catalytic amount). The resulting solution was stirred for overnight at room temperature. To the mixture was added NaBH(OAc)$_3$ (1.96 g, 9.25 mmol, 2.20 equiv). The resulting solution was stirred for 4 h at room temperature. The resulting mixture was concentrated under vacuum. The residue was applied onto a silica gel column with ethyl acetate/petroleum ether (1:1) to yield methyl 3-[(4-[6-[bis(4-chlorophenyl)methyl]-2-cyclopropyl-1H-1,3-benzodiazol-1-yl]piperidin-1-yl)methyl]benzoate as a red solid. LC/MS (ES, m/z): 624 [M+H]+.

Step 2: Synthesis of 3-[(4-[6-[bis(4-chlorophenyl)methyl]-2-cyclopropyl-1H-1,3-benzodiazol-1-yl]piperidin-1-yl)methyl]benzoic acid trifluoroacetic acid Into a 100-mL round-bottom flask, was placed a solution of methyl 3-[(4-[6-[bis(4-chlorophenyl)methyl]-2-cyclopropyl-1H-1,3-benzodiazol-1-yl]piperidin-1-yl)methyl]benzoate (780 mg, 1.25 mmol, 1.00 equiv) in tetrahydrofuran/MeOH (30/5 mL) and LiOH (30 mL, 3M). The resulting solution was stirred overnight at room temperature. The resulting mixture was concentrated under vacuum. The pH value of the solution was adjusted to pH 7 with hydrogen chloride (12 mol/L). The solids were collected by filtration. The product residue (600 mg) was purified by Flash-Prep-HPLC with the following conditions (CombiFlash-1): Column, C18 silica gel; mobile phase, 0.05% TFA in water and CH$_3$CN (CH$_3$CN 10% up to 80% in 10 min); Detector, UV 254 nm to yield 3-[(4-[6-[bis(4-chlorophenyl)methyl]-2-cyclopropyl-1H-1,3-benzodiazol-1-yl]piperidin-1-yl)methyl] benzoic acid trifluoroacetic acid as a white solid.

$^1$H NMR (300 MHz, CD3OD) δ: 8.25 (s, 1H), 8.19 (d, J=7.8 Hz, 1H), 7.79-7.82 (m, 2H), 7.64-7.69 (m, 2H), 7.31-7.34 (m, 5H), 7.09-7.12 (m, 4H), 5.81 (s, 1H), 5.26 (brs, 1H), 4.50 (s, 2H), 3.75-3.79 (m, 2H), 3.34-3.42 (m, 2H), 2.87-2.91 (m, 2H), 2.51-2.58 (m, 1H), 2.34-2.39 (m, 2H), 1.31-1.50 (m, 2H). LC/MS (ES, m/z): 610 [M+H]+.

Example PH-54

3-((4-(6-(bis(4-chlorophenyl)methyl)-2-cyclopropyl-1H-benzo[d]imidazol-1-yl)piperidin-1-yl)methyl) benzamide 2,2,2-trifluoroacetate

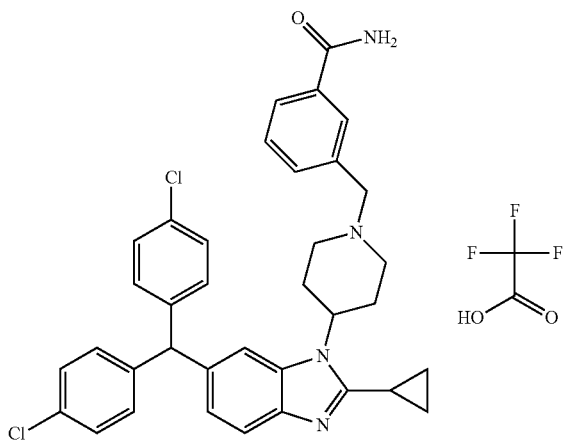 [SMILES: O=C(O)c1cccc(CN2CCC(n3c(C4CC4)nc4ccc(C(c5ccc(Cl)cc5)c5ccc(Cl)cc5)cc43)CC2)c1 ; O=C(O)C(F)(F)F]

Into a 50-mL round-bottom flask, was placed a solution of 3-[(4-[6-[bis(4-chlorophenyl)methyl]-2-cyclopropyl-1H-1,3-benzodiazol-1-yl]piperidin-1-yl)methyl]benzoic acid (70 mg, 0.11 mmol, 1.00 equiv) in N,N-dimethylformamide (5 mL), NH$_4$Cl (30.5 mg, 0.57 mmol, 5.00 equiv), HATU (52.4 mg, 0.14 mmol, 1.20 equiv) and DIEA (29.7 mg, 0.23 mmol, 2.00 equiv). The resulting solution was stirred overnight at room temperature. The reaction was then quenched by the addition of water (10 mL). The resulting solution was extracted with ethyl acetate (3×10 mL) and the organic layers combined, then dried over anhydrous sodium sulfate and concentrated under vacuum. The product residue was purified by Prep-HPLC with the following conditions (Waters 2767-1): Column, SunFire Prep C18, 5 um, 19*100 mm; mobile phase, 0.05% TFA in water and CH$_3$CN (25% CH$_3$CN up to 55% in 10 min); Detector, UV 254 nm to yield 3-[(4-[6-[bis(4-chlorophenyl)methyl]-2-cyclopropyl-1H-1,3-benzodiazol-1-yl]piperidin-1-yl)methyl]benzamide trifluoroacetic acid as a white solid.

$^1$H NMR (300 MHz, CD3OD) δ: 8.00-8.07 (m, 2H), 7.91 (s, 1H), 7.75 (d, J=7.5 Hz, 1H), 7.61-7.66 (m, 2H), 7.24-7.33 (m, 5H), 7.09 (d, J=8.4 Hz, 4H), 5.81 (s, 1H), 5.22-5.30 (m, 1H), 4.48 (s, 2H), 3.75-3.79 (m, 2H), 3.38-3.42 (m, 2H), 2.82-2.94 (m, 2H), 2.50-2.59 (m, 1H), 2.34-2.38 (m, 2H), 1.32-1.49 (m, 4H). LC/MS (ES, m/z): 609 [M+H]+.

Example PH-55

2,2,2-trifluoroacetic acid compound with 4-((4-(6-(bis(4-chlorophenyl)methyl)-2-cyclopropyl-1H-benzo[d]imidazol-1-yl)piperidin-1-yl)methyl)benzoic acid (1:1)

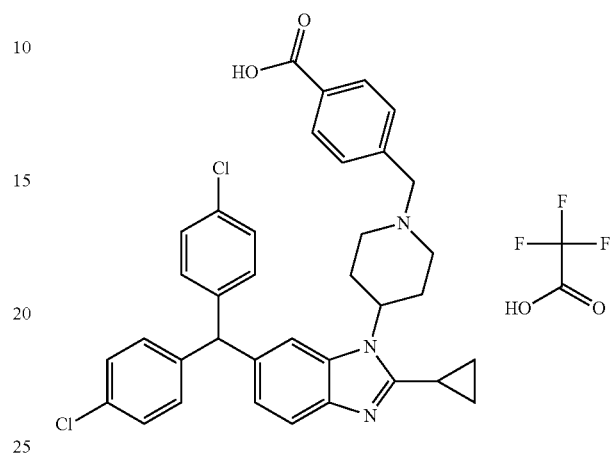

The title compound was prepared according to the procedure as described in Example PH-53 substituting methyl 4-formylbenzoate for methyl 3-formylbenzoate in Step 1.

$^1$H NMR (300 MHz, CD3OD) δ: 8.17 (d, J=8.1 Hz, 2H), 7.89-7.95 (m, 1H), 7.70-7.64 (m, 3H), 7.34-7.26 (m, 5H), 7.10 (d, J=8.4 Hz, 4H), 5.81 (s, 1H), 5.26 (m, 1H), 4.48 (s, 1H), 3.78-3.74 (m, 2H), 3.33-3.32 (m, 2H), 2.82-2.91 (m, 2H), 2.54 (brs, 1H), 2.30-2.40 (m, 2H), 1.32-1.54 (m, 4H). LC/MS (ES, m/z): 610 [M+H]+.

Example PH-56

4-((4-(6-(bis(4-chlorophenyl)methyl)-2-cyclopropyl-1H-benzo[d]imidazol-1-yl)piperidin-1-yl)methyl) benzamide 2,2,2-trifluoroacetate

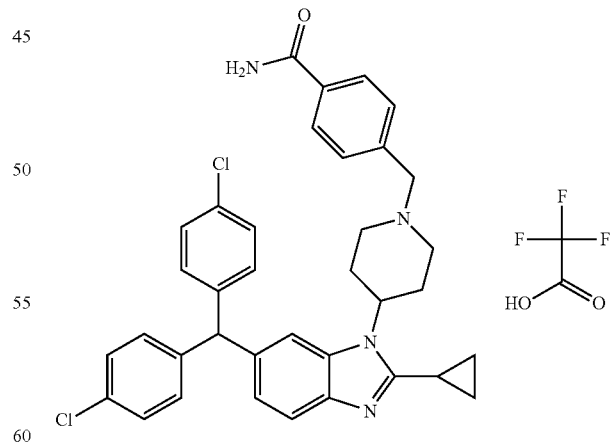

The title compound was prepared according to the procedure as described in Example PH-554 substituting 4-((4-(6-(bis(4-chlorophenyl)methyl)-2-cyclopropyl-1H-benzo[d]imidazol-1-yl)piperidin-1-yl)methyl)benzoic acid for 3-((4-(6-(bis(4-chlorophenyl)methyl)-2-cyclopropyl-1H-benzo[d]imidazol-1-yl)piperidin-1-yl)methyl)benzoic acid.

¹H NMR (300 MHz, CD3OD) δ: 8.01-8.08 (m, 2H), 7.96 (s, 1H), 7.65-7.69 (m, 3H), 7.18-7.34 (m, 5H), 7.09-7.12 (m, 4H), 5.83 (s, 1H), 5.23-5.27 (m, 1H), 4.49 (s, 2H), 3.56-3.82 (m, 2H), 3.34-3.42 (m, 2H), 2.86-2.98 (m, 2H), 2.53-2.62 (m, 1H), 2.35-2.39 (m, 2H), 1.43-1.52 (m, 2H), 1.29-1.43 (m, 2H). LC/MS: (m/z) 609 [M+H]+.

Example PH-57

5-((4-(6-(bis(4-chlorophenyl)methyl)-2-cyclopropyl-1H-benzo[d]imidazol-1-yl)piperidin-1-yl)methyl)furan-2-carboxylic acid hydrochloride

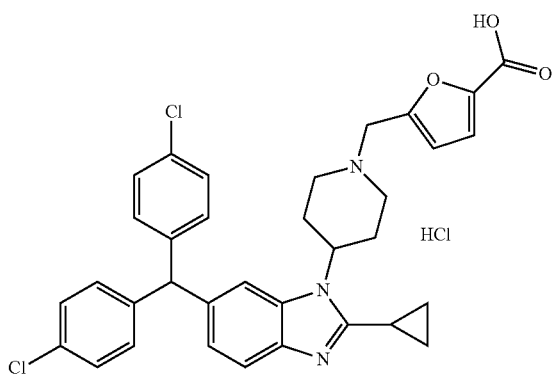

The title compound was prepared according to the procedure as described in Example PH-53 substituting 5-formylfuran-2-carboxylic acid for methyl 3-formylbenzoate in Step 1.

¹H NMR (300 MHz, CD3OD) δ: 8.28 (s, 1H), 7.66 (d, J=8.7 Hz, 1H), 7.29-7.33 (m, 6H), 7.13-7.16 (m, 4H), 6.98 (d, J=3.3 Hz, 1H), 5.91 (s, 1H), 5.28-5.36 (m, 1H), 4.57 (s, 2H), 3.76-3.80 (m, 2H), 3.39-3.55 (m, 2H), 2.97-3.09 (m, 2H), 2.58-2.67 (m, 1H), 2.35-2.39 (m, 2H), 1.35-1.53 (m, 4H). LC/MS (ES, m/z): 600 [M+H]+.

Example PH-58

5-((4-(6-(bis(4-chlorophenyl)methyl)-2-cyclopropyl-1H-benzo[d]imidazol-1-yl)piperidin-1-yl)methyl)furan-2-carboxamide hydrochloride

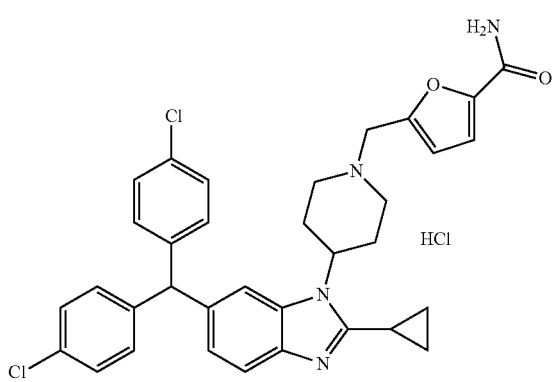 [SMILES: O=C(O)c1ccc(CN2CCC(n3c(C4CC4)nc4ccc(C(c5ccc(Cl)cc5)c5ccc(Cl)cc5)cc43)CC2)o1 ; Cl]

The title compound was prepared according to the procedure as described in Example PH-54 substituting 5-((4-(6-(bis(4-chlorophenyl)methyl)-2-cyclopropyl-1H-benzo[d]imidazol-1-yl)piperidin-1-yl)methyl)furan-2-carboxylic acid for 3-((4-(6-(bis(4-chlorophenyl)methyl)-2-cyclopropyl-1H-benzo[d]imidazol-1-yl)piperidin-1-yl)methyl)benzoic acid.

¹H NMR (300 MHz, CD3OD) δ: 8.49 (s, 1H), 7.68 (d, J=8.7 Hz, 1H), 7.30-7.42 (m, 5H), 7.15-7.21 (m, 5H), 6.95 (d, J=3.6 Hz, 1H), 5.95 (s, 1H), 5.32-5.40 (m, 1H), 4.59 (s, 1H), 3.41-3.82 (m, 2H), 3.10-3.22 (m, 2H), 2.62-2.70 (m, 1H), 2.35-2.39 (m, 2H), 1.32-1.55 (m, 4H). LC/MS (ES, m/z): 599 [M+H]+.

Example PH-59

5-((4-(6-(bis(4-chlorophenyl)methyl)-2-cyclopropyl-1H-benzo[d]imidazol-1-yl)piperidin-1-yl)methyl)thiophene-2-carboxylic acid hydrochloride

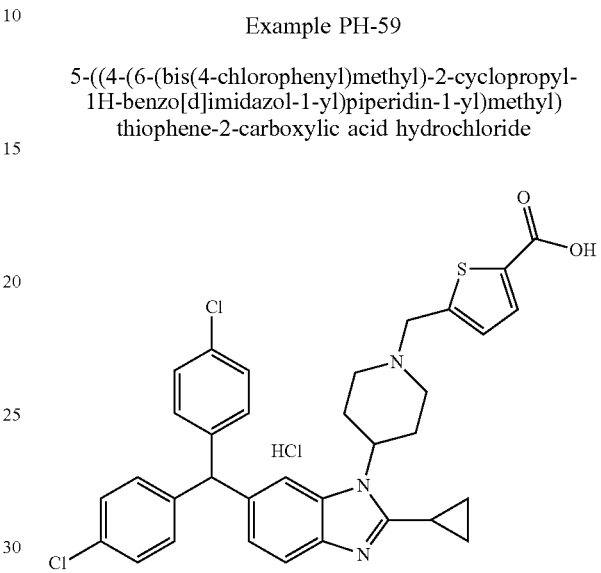

The title compound was prepared according to the procedure as described in Example PH-53 substituting 5-formylthiophene-2-carboxylic acid for methyl 3-formylbenzoate in Step 1.

¹H NMR (400 MHz, CD3OD) δ: 8.41 (s, 1H), 7.81 (s, 1H), 7.67 (d, J=8.8 Hz, 1H), 7.53 (d, J=3.6 Hz, 1H), 7.32-7.35 (m, 4H), 7.17 (d, J=8.4 Hz, 3H), 5.94 (s, 1H), 5.30-5.37 (m, 1H), 4.71 (s, 2H), 3.80 (d, J=12.0 Hz, 2H), 3.33-3.50 (m, 2H), 3.07-3.15 (m, 2H), 2.62-2.69 (m, 1H), 2.37 (d, J=12.0 Hz, 2H), 1.49-1.54 (m, 2H), 1.31-1.41 (m, 2H). LC/MS (ES, m/z): 616 [M+H]+.

Example PH-60

5-((4-(6-(bis(4-chlorophenyl)methyl)-2-cyclopropyl-1H-benzo[d]imidazol-1-yl)piperidin-1-yl)methyl)thiophene-2-carboxamide hydrochloride

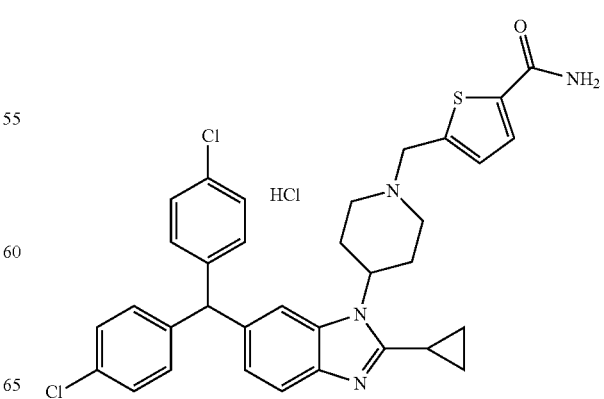

The title compound was prepared according to the procedure as described in Example PH-54 substituting 5-((4-(6-(bis(4-chlorophenyl)methyl)-2-cyclopropyl-1H-benzo[d]imidazol-1-yl)piperidin-1-yl)methyl)thiophene-2-carboxylic acid for 3-((4-(6-(bis(4-chlorophenyl)methyl)-2-cyclopropyl-1H-benzo[d]imidazol-1-yl)piperidin-1-yl)methyl)benzoic acid.

¹H NMR (400 MHz, CD3OD) δ: 8.43 (s, 1H), 7.75 (d, J=4.0 Hz, 1H), 7.67 (d, J=8.8 Hz, 1H), 7.53 (d, J=3.6 Hz, 1H), 7.32-7.37 (m, 5H), 7.17 (d, J=8.4 Hz, 4H), 5.94 (s, 1H), 5.30-5.40 (t, 1H), 4.70 (s, 2H), 3.80 (d, J=12.4 Hz, 2H), 3.33-3.50 (m, 2H), 3.10-3.15 (m, 2H), 2.64-2.68 (m, 1H), 2.38 (d, J=12.4 Hz, 2H), 1.49-1.54 (m, 2H), 1.31-1.38 (m, 2H). LC/MS (ES, m/z): 615 [M+H]+.

Example PH-61

5-((4-(6-(bis(4-chlorophenyl)methyl)-2-cyclopropyl-1H-benzo[d]imidazol-1-yl)piperidin-1-yl)methyl)thiophene-3-carboxylic acid hydrochloride

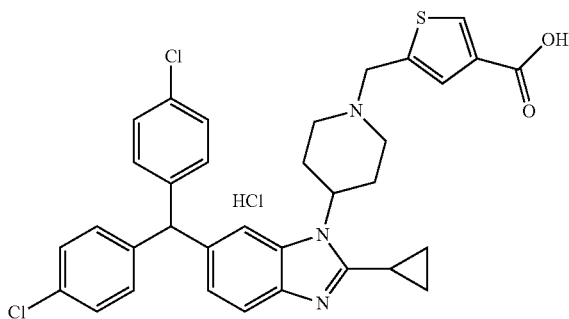 [SMILES: O=C(O)c1csc(CN2CCC(n3c(C4CC4)nc4ccc(C(c5ccc(Cl)cc5)c5ccc(Cl)cc5)cc43)CC2)c1 ; Cl]

The title compound was prepared according to the procedure as described in Example PH-53 substituting methyl 5-formylthiophene-3-carboxylate for methyl 3-formylbenzoate in Step 1.

¹H NMR (400 MHz, CD3OD) δ: 8.46 (s, 1H), 8.40 (s, 1H), 7.86 (s, 1H), 7.67 (d, J=8.4 Hz, 1H), 7.36 (s, 1H), 7.32 (d, J=8.4 Hz, 4H), 7.17 (d, J=8.4 Hz, 4H), 5.95 (s, 1H), 5.37 (t, J=12.4 Hz, 1H), 4.71 (s, 2H), 3.81 (d, J=12.0 Hz, 2H), 3.41-3.50 (m, 2H), 3.12-3.18 (m, 2H), 2.64-2.71 (m, 1H), 2.38 (d, J=13.2 Hz, 2H), 1.50-1.55 (m, 2H), 1.35-1.38 (m, 2H). LC/MS (ES, m/z): 616 [M+H]+.

Example PH-62

5-((4-(6-(bis(4-chlorophenyl)methyl)-2-cyclopropyl-1H-benzo[d]imidazol-1-yl)piperidin-1-yl)methyl)thiophene-3-carboxamide hydrochloride

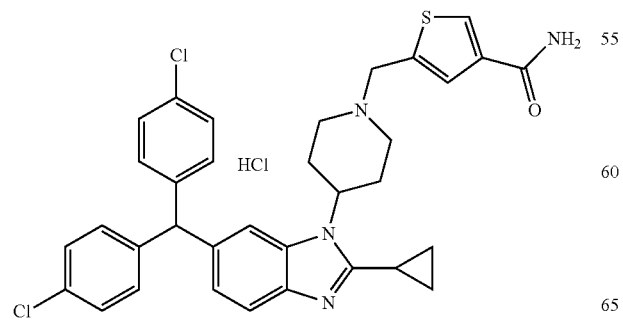

The title compound was prepared according to the procedure as described in Example PH-54 substituting 5-((4-(6-(bis(4-chlorophenyl)methyl)-2-cyclopropyl-1H-benzo[d]imidazol-1-yl)piperidin-1-yl)methyl)thiophene-3-carboxylic acid for 3-((4-(6-(bis(4-chlorophenyl)methyl)-2-cyclopropyl-1H-benzo[d]imidazol-1-yl)piperidin-1-yl)methyl)benzoic acid.

¹H NMR (400 MHz, CD3OD) δ: 8.50 (s, 1H), 8.29 (s, 1H), 7.83 (s, 1H), 7.68 (d, J=8.8 Hz, 1H), 7.31-7.36 (m, 4H), 7.17 (d, J=8.4 Hz, 4H), 5.95 (s, 1H), 5.38 (t, J=11.6 Hz, 1H), 4.71 (s, 2H), 3.82 (d, J=11.6 Hz, 2H), 3.45 (t, J=12.4 Hz, 2H), 3.17 (t, J=11.6 Hz, 3H), 2.65-2.72 (m, 1H), 2.39 (d, J=12.4 Hz, 2H), 1.51-1.56 (m, 2H), 1.35-1.41 (m, 2H). LC/MS (ES, m/z): 615 [M+H]+.

Example PH-63

6-((4-(6-(bis(4-chlorophenyl)methyl)-2-cyclopropyl-1H-benzo[d]imidazol-1-yl)piperidin-1-yl)methyl)picolinic acid

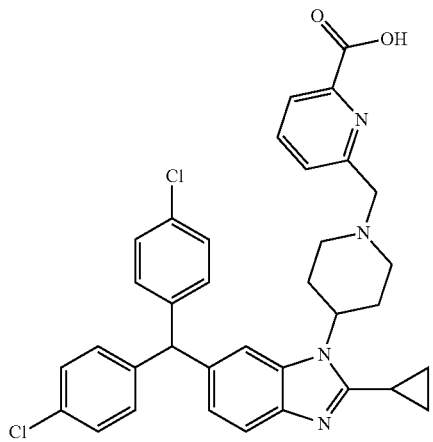 [SMILES: O=C(O)c1cccc(CN2CCC(n3c(C4CC4)nc4ccc(C(c5ccc(Cl)cc5)c5ccc(Cl)cc5)cc43)CC2)n1]

The title compound was prepared according to the procedure as described in Example PH-53 substituting methyl 6-formylpyridine-2-carboxylate in Step 1 was used instead of methyl 3-formylbenzoate in Step 1.

¹H NMR (300 MHz, DMSO) δ: 7.88-7.97 (m, 2H), 7.48-7.50 (d, J=6.0 Hz, 1H), 7.22-7.43 (m, 6H), 7.13-7.16 (m, 4H), 6.80 (d, J=12.0 Hz, 1H), 5.83 (s, 1H), 4.56 (brs, 1H), 3.62 (s, 2H), 2.90-3.06 (m, 2H), 2.19-2.33 (m, 4H), 1.90 (s, 1H), 1.75-1.79 (m, 2H), 1.00-1.25 (m, 4H). LC/MS (ES, m/z): 611 [M+H]+.

Example PH-64

6-((4-(6-(bis(4-chlorophenyl)methyl)-2-cyclopropyl-1H-benzo[d]imidazol-1-yl)piperidin-1-yl)methyl)picolinamide 2,2,2-trifluoroacetate

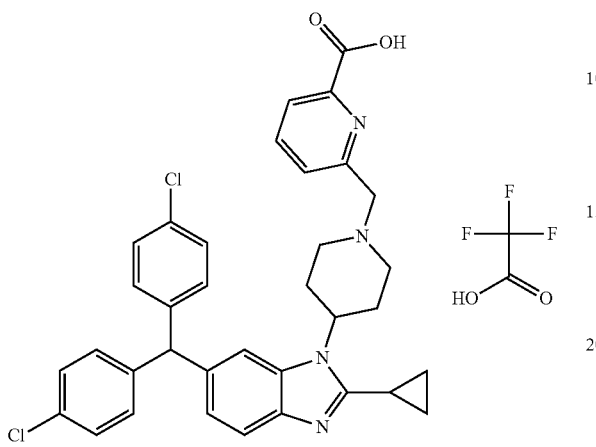

The title compound was prepared according to the procedure as described in Example PH-54 substituting 6-((4-(6-(bis(4-chlorophenyl)methyl)-2-cyclopropyl-1H-benzo[d]imidazol-1-yl)piperidin-1-yl)methyl)picolinic acid for 3-((4-(6-(bis(4-chlorophenyl)methyl)-2-cyclopropyl-1H-benzo[d]imidazol-1-yl)piperidin-1-yl)methyl)benzoic acid.

$^1$H NMR (300 MHz, DMSO) δ: 8.20 (d, J=7.8 Hz, 1H), 8.13 (d, J=7.8 Hz, 1H), 8.06-8.10 (m, J=11.7 Hz, 1H), 7.74 (d, J=7.2 Hz, 1H), 7.66 (d, J=7.8 Hz, 1H), 7.29-7.35 (m, 5H), 7.07-7.14 (m, 4H), 5.86 (s, 1H), 5.30 (m, 1H), 4.64 (s, 2H), 3.85-3.89 (m, 2H), 3.45-3.46 (m, 2H), 2.97-3.08 (m, 2H), 2.60-2.75 (m, 1H), 2.30-2.39 (m, 2H), 1.35-1.50 (m, 2H), 1.21-1.35 (m, 2H). LC/MS (ES, m/z): 610 [M+H]+.

Example PH-65

6-((4-(6-(bis(4-chlorophenyl)methyl)-2-cyclopropyl-1H-benzo[d]imidazol-1-yl)piperidin-1-yl)methyl)nicotinic acid

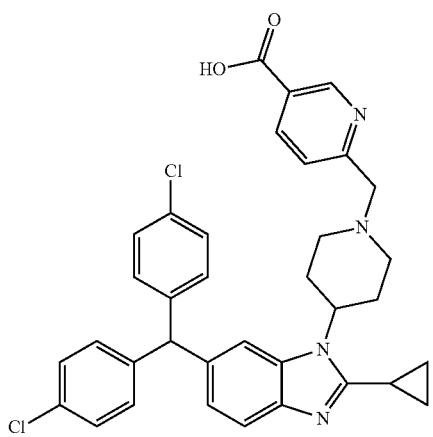 [SMILES: O=C(O)c1ccc(CN2CCC(n3c(C4CC4)nc4ccc(C(c5ccc(Cl)cc5)c5ccc(Cl)cc5)cc43)CC2)nc1]

The title compound was prepared according to the procedure as described in Example PH-53 substituting methyl 6-formylpyridine-3-carboxylate for methyl 3-formylbenzoate in Step 1.

$^1$H NMR (300 MHz, DMSO) δ: 8.92 (s, 1H), 8.22 (d, J=8.4 Hz, 1H), 7.38-7.43 (m, 7H), 7.15 (d, J=8.1 Hz, 1H), 6.82 (d, J=8.1 Hz, 1H), 5.84 (s, 1H), 4.50-4.60 (m, 1H), 3.75 (s, 2H), 2.96-3.03 (m, 2H), 2.26-2.50 (m, 4H), 1.90 (s, 1H), 1.79-1.81 (m, 2H), 0.91-1.03 (m, 4H). LC/MS (ES, m/z): 611 [M+H]+.

Example PH-66

6-((4-(6-(bis(4-chlorophenyl)methyl)-2-cyclopropyl-1H-benzo[d]imidazol-1-yl)piperidin-1-yl)methyl)nicotinamide 2,2,2-trifluoroacetate

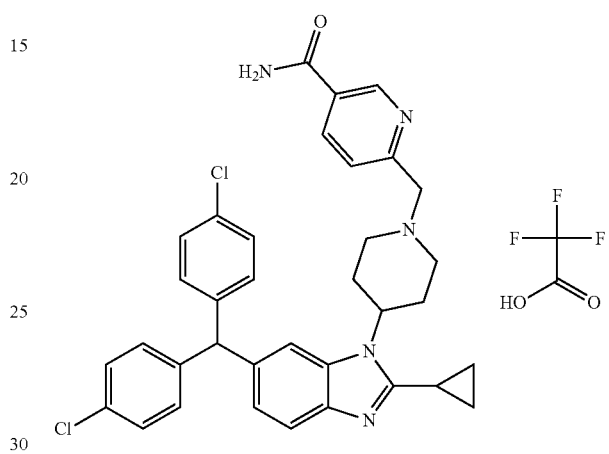

The title compound was prepared according to the procedure as described in Example PH-54 substituting 6-((4-(6-(bis(4-chlorophenyl)methyl)-2-cyclopropyl-1H-benzo[d]imidazol-1-yl)piperidin-1-yl)methyl)nicotinic acid for 3-((4-(6-(bis(4-chlorophenyl)methyl)-2-cyclopropyl-1H-benzo[d]imidazol-1-yl)piperidin-1-yl)methyl)benzoic acid.

$^1$H NMR (300 MHz, CD3COCD3) δ: 9.11 (s, 1H), 8.31-8.35 (m, 2H), 7.69-7.84 (m, 3H), 7.29-7.33 (m, 4H), 7.15-7.24 (m, 5H), 5.89 (s, 1H), 5.40-5.50 (m, 1H), 4.59 (s, 2H), 3.88-3.92 (m, 2H), 3.53-3.56 (m, 2H), 3.19-3.23 (m, 2H), 2.55-2.57 (m, 1H), 2.41-2.44 (m, 2H), 1.44-1.49 (m, 2H), 1.24-1.29 (m, 2H). LC/MS (ES, m/z): 610 [M+H]+.

Example PH-67

5-((4-(6-(bis(4-chlorophenyl)methyl)-2-cyclopropyl-1H-benzo[d]imidazol-1-yl)piperidin-1-yl)methyl)nicotinic acid

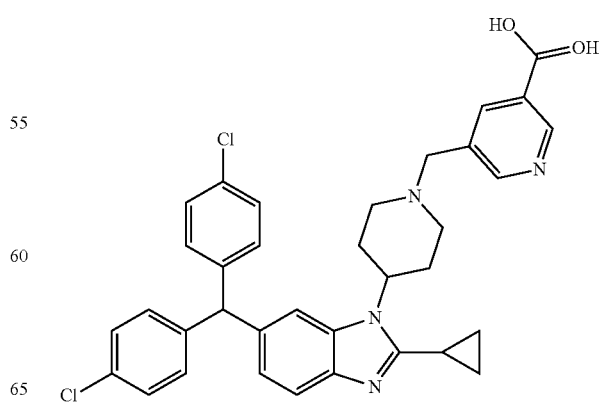

183

The title compound was prepared according to the procedure as described in Example PH-53 substituting methyl 5-formylpyridine-3-carboxylate methyl 3-formylbenzoate, in Step 1.

$^1$H NMR (300 MHz, DMSO) δ: 8.89 (s, 1H), 8.45 (s, 1H), 8.09 (s, 1H), 7.38-7.44 (m, 6H), 7.13 (d, J=8.4 Hz, 4H), 6.80 (d, J=8.8 Hz, 1H), 5.85 (s, 1H), 4.52-4.58 (m, 1H), 3.59 (s, 2H), 2.95-2.97 (m, 2H), 2.18-2.36 (m, 5H), 1.79-1.82 (m, 2H), 0.96-1.04 (m, 4H). LC/MS (ES, m/z): 611 [M+H]+.

Example PH-68

5-((4-(6-(bis(4-chlorophenyl)methyl)-2-cyclopropyl-1H-benzo[d]imidazol-1-yl)piperidin-1-yl)methyl)nicotinamide 2,2,2-trifluoroacetate

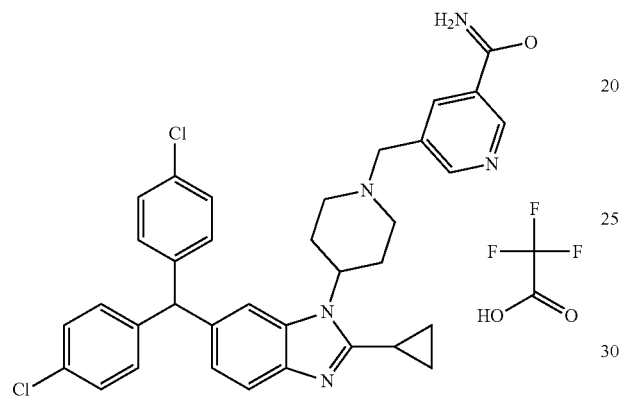

The title compound was prepared according to the procedure as described in Example PH-54 substituting 5-((4-(6-(bis(4-chlorophenyl)methyl)-2-cyclopropyl-1H-benzo[d]imidazol-1-yl)piperidin-1-yl)methyl)nicotinic acid for 3-((4-(6-(bis(4-chlorophenyl)methyl)-2-cyclopropyl-1H-benzo[d]imidazol-1-yl)piperidin-1-yl)methyl)benzoic acid.

$^1$H NMR (300 MHz, CD3OD) δ: 9.12 (s, 1H), 8.85 (s, 1H), 8.45 (s, 1H), 7.86 (s, 1H), 7.62 (d, J=8.4 Hz, 1H), 7.23-7.29 (m, 5H), 7.06 (d, J=8.4 Hz, 4H), 5.79 (s, 1H), 5.20-5.35 (m, 1H), 4.52 (s, 2H), 3.74-3.78 (m, 2H), 3.32-3.50 (m, 2H), 2.76-2.80 (m, 2H), 2.50-2.56 (m, 1H), 2.37-2.41 (m, 2H), 1.45-1.51 (m, 2H), 1.28-1.35 (m, 2H). LC/MS (ES, m/z): 610 [M+H]+.

Example PH-69

5-((4-(6-(bis(4-chlorophenyl)methyl)-2-cyclopropyl-1H-benzo[d]imidazol-1-yl)piperidin-1-yl)methyl)picolinamide 2,2,2-trifluoroacetate

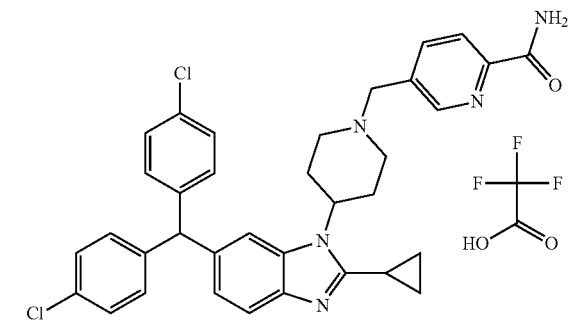 [SMILES: NC(=O)c1ccc(CN2CCC(n3c(C4CC4)nc4ccc(C(c5ccc(Cl)cc5)c5ccc(Cl)cc5)cc43)CC2)cn1 ; O=C(O)C(F)(F)F]

184

The title compound was prepared according to the procedure as described in Example PH-53 and PH-54, substituting methyl 5-formylpyridine-2-carboxylate for methyl 3-formylbenzoate in Step 1.

$^1$H NMR (300 MHz, DMSO) δ: 8.82 (s, 1H), 8.16-8.25 (m, 2H), 7.95 (s, 1H), 7.69 (d, J=8.4 Hz, 1H), 7.27-7.34 (m, 5H), 7.10 (d, J=8.4 Hz, 4H), 5.83 (s, 1H), 5.19-5.30 (m, 1H), 4.51 (s, 2H), 3.73-3.83 (m, 2H), 3.34-3.56 (m, 2H), 2.88-3.09 (m, 2H), 2.50-2.60 (m, 1H), 2.34-2.38 (m, 2H), 1.26-1.49 (m, 4H). LC/MS (ES, m/z): 610 [M+H]+.

Example PH-70

3-((4-(6-(bis(4-chlorophenyl)methyl)-2-cyclopropyl-1H-benzo[d]imidazol-1-yl)piperidin-1-yl)methyl)-2-fluorobenzoic acid

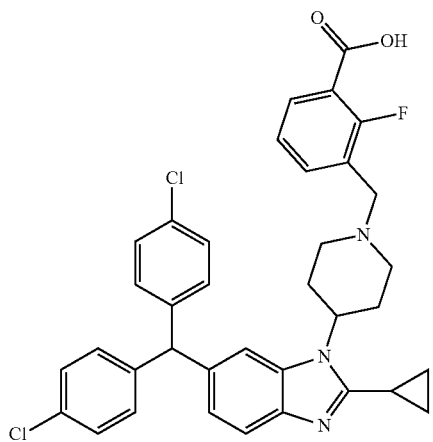

Step 1: Synthesis of methyl 3-[(4-[6-[bis(4-chlorophenyl)methyl]-2-cyclopropyl-1H-1,3-benzodiazol-1-yl]piperidin-1-yl)methyl]-2-fluorobenzoate Into a 100-mL round-bottom flask, was placed a solution of 6-[bis(4-chlorophenyl)methyl]-2-cyclopropyl-1-(piperidin-4-yl)-1H-1,3-benzodiazole (250 mg, 0.52 mmol, 1.00 equiv) in CH$_3$CN (15 mL), methyl 3-(bromomethyl)-2-fluorobenzoate (155 mg, 0.63 mmol, 1.20 equiv) and potassium carbonate (219 mg, 1.58 mmol, 3.00 equiv). The resulting solution was stirred overnight at room temperature. The resulting mixture was concentrated under vacuum. The resulting solution was diluted with water (20 mL). The resulting solution was extracted with ethyl acetate (3×30 mL) and the organic layers combined, then dried over anhydrous sodium sulfate. The resulting mixture was concentrated under vacuum. The residue was applied onto a silica gel column with ethyl acetate/petroleum ether (35%) to yield methyl 3-[(4-[6-[bis(4-chlorophenyl)methyl]-2-cyclopropyl-1H-1,3-benzodiazol-1-yl]piperidin-1-yl)methyl]-2-fluorobenzoate as colorless oil.

Step 2: Synthesis of 3-[(4-[6-[bis(4-chlorophenyl)methyl]-2-cyclopropyl-1H-1,3-benzodiazol-1-yl]piperidin-1-yl)methyl]-2-fluorobenzoic acid Into a 100-mL round-bottom flask, was placed a solution of methyl 3-[(4-[6-[bis(4-chlorophenyl)methyl]-2-cyclopropyl-1H-1,3-benzodiazol-1-yl]piperidin-1-yl)methyl]-2-fluorobenzoate (290 mg, 0.45 mmol, 1.00 equiv) in methanol/THF/H₂O (4 ml/12 ml/4 mL), and LiOH.H₂O (927 mg, 22.09 mmol, 50.00 equiv). The resulting solution was stirred overnight at room temperature. The resulting mixture was concentrated under vacuum. The pH value of the solution was adjusted to pH 4-5 with hydrogen chloride (1%). The solids were collected by filtration. The residue was applied onto a C18 silica gel column with CH₃CN/H₂O (TFA) (30%) to yield 3-[(4-[6-[bis(4-chlorophenyl)methyl]-2-cyclopropyl-1H-1,3-benzodiazol-1-yl]piperidin-1-yl)methyl]-2-fluorobenzoic acid as a white solid.

1H NMR (300 MHz, CD3OD) δ: 7.92 (t, J=6.0 Hz, 1H), 7.61-7.67 (m, 2H), 7.48 (d, J=8.4 Hz, 1H), 7.28-7.35 (m, 5H), 7.09 (d, J=8.7 Hz, 4H), 6.94 (d, J=1.2 Hz, 1H), 5.70 (s, 1H), 4.08 (s, 2H), 3.43 (d, J=12.3 Hz, 2H), 2.87 (t, J=11.4 Hz, 2H), 2.60-2.73 (m, 2H), 2.23-2.30 (m, 1H), 2.05 (d, J=10.2 Hz, 2H), 1.09-1.21 (m, 4H). LC/MS (ES, m/z): 628 [M+H]+.

Example PH-71

3-((4-(6-(bis(4-chlorophenyl)methyl)-2-cyclopropyl-1H-benzo[d]imidazol-1-yl)piperidin-1-yl)methyl)-4-fluorobenzoic acid

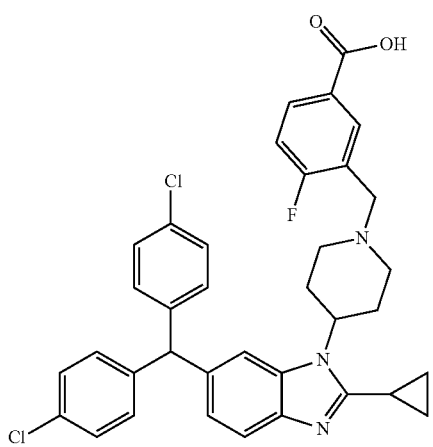 [SMILES: O=C(O)c1ccc(F)c(CN2CCC(n3c(C4CC4)nc4ccc(C(c5ccc(Cl)cc5)c5ccc(Cl)cc5)cc43)CC2)c1]

The title compound was prepared according to the procedure as described in Example PH-70 substituting methyl 3-(bromomethyl)-4-fluorobenzoate for methyl 3-(bromomethyl)-2-fluorobenzoate in Step 1.

¹H NMR (400 MHz, CD3OD) δ: 8.35 (d, J=7.2 Hz, 1H), 8.24-8.28 (m, 1H), 7.91 (s, 1H), 7.66 (s, 1H), 7.44 (t, J=9.2 Hz, 1H), 7.27-7.34 (m, 5H), 7.11 (d, J=8.4 Hz, 4H), 5.82 (s, 1H), 5.27 (s, 1H), 4.54 (s, 2H), 3.81 (d, J=12.4 Hz, 2H), 3.40-3.46 (m, 2H), 2.90 (t, J=11.6 Hz, 2H), 2.53-2.57 (m, 1H), 2.38 (d, J=12.8 Hz, 2H), 1.45-1.50 (m, 2H), 1.32-1.36 (m, 2H). LC/MS (ES, m/z): 628 [M+H]+.

Example PH-72

3-((4-(6-(bis(4-chlorophenyl)methyl)-2-cyclopropyl-1H-benzo[d]imidazol-1-yl)piperidin-1-yl)methyl)-5-fluorobenzoicacid

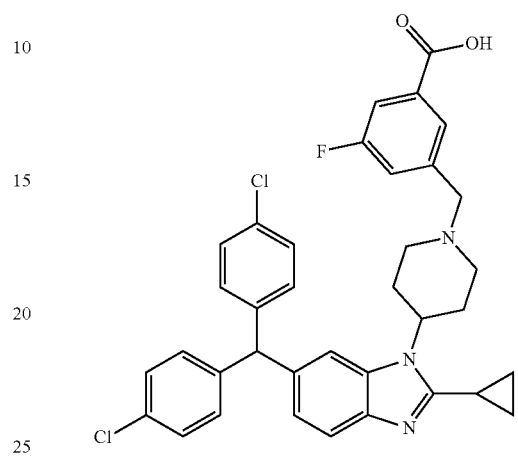

The title compound was prepared according to the procedure as described in Example PH-70 substituting methyl 3-(bromomethyl)-5-fluorobenzoate for methyl 3-(bromomethyl)-2-fluorobenzoate in Step 1.

¹H NMR (400 MHz, CD3OD) δ: 8.08 (s, 1H), 7.92 (s, 1H), 7.88 (d, J=7.6 Hz, 1H), 7.61-7.67 (m, 2H), 7.32-7.34 (m, 4H), 7.27 (d, J=8.8 Hz, 1H), 7.11 (d, J=8.4 Hz, 4H), 5.83 (s, 1H), 5.19-5.30 (m, 1H), 4.47 (s, 2H), 3.75 (d, J=12.0 Hz, 2H), 3.32-3.37 (m, 1H), 2.84-2.93 (m, 2H), 2.52-2.59 (m, 1H), 2.36 (d, J=13.2 Hz, 2H), 1.44-1.49 (m, 2H), 1.31-1.35 (m, 2H). LC/MS (ES, m/z): 628 [M+H]+.

Example PH-73

2,2,2-trifluoroacetic acid compound with 5-((4-(6-(bis(4-chlorophenyl)methyl)-2-cyclopropyl-1H-benzo[d]imidazol-1-yl)piperidin-1-yl)methyl)-2-fluorobenzoic acid (1:1)

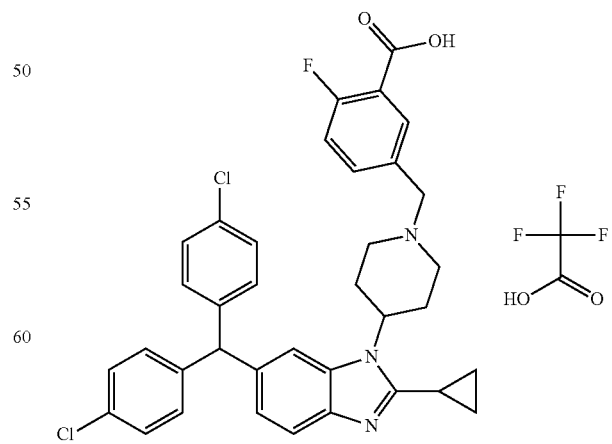

The title compound was prepared according to the procedure as described in Example PH-70 substituting methyl 5-(bromomethyl)-2-fluorobenzoate for methyl 3-(bromomethyl)-2-fluorobenzoate in Step 1.

¹H NMR (300 MHz, CD3OD) δ: 8.17 (d, J=1.8 Hz, 1H), 7.78-7.88 (m, 2H), 7.64 (d, J=8.4 Hz, 1H), 7.19-7.42 (m, 6H), 7.08 (d, J=8.4 Hz, 4H), 5.81 (s, 1H), 5.22 (brs, 1H), 4.43 (s, 2H), 3.72-3.75 (m, 2H), 3.31-3.32 (m, 2H), 2.82-2.96 (m, 2H), 2.41-2.55 (m, 1H), 2.03-2.37 (m, 2H), 1.31-1.45 (m, 4H). LC/MS (ES, m/z): 628 [M+H]+.

Example PH-74

3-((4-(6-(bis(4-chlorophenyl)methyl)-2-cyclopropyl-1H-benzo[d]imidazol-1-yl)piperidin-1-yl)methyl)-2-chlorobenzoic acid

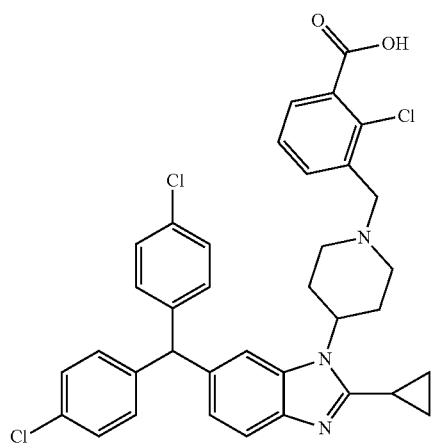 [SMILES: O=C(O)c1cccc(CN2CCC(n3c(C4CC4)nc4ccc(C(c5ccc(Cl)cc5)c5ccc(Cl)cc5)cc43)CC2)c1Cl]

Step 1: Synthesis of 3-[(4-[6-[bis(4-chlorophenyl)methyl]-2-cyclopropyl-1H-1,3-benzodiazol-1-yl]piperidin-1-yl)methyl]-2-chlorobenzonitrile Into a 50-mL round-bottom flask, was placed a solution of 6-[bis(4-chlorophenyl)methyl]-2-cyclopropyl-1-(piperidin-4-yl)-1H-1,3-benzodiazole (200 mg, 0.42 mmol, 1.00 equiv) in dichloromethane (8 mL), 2-chloro-3-formylbenzonitrile (77 mg, 0.47 mmol, 1.10 equiv) and TEA (0.5 mL). The resulting solution was stirred overnight at room temperature. To the mixture was then added NaBH(OAc)₃ (233 mg, 1.10 mmol, 2.50 equiv). The resulting solution was stirred for 3 h at room temperature. The resulting mixture was concentrated under vacuum. The residue was applied onto a silica gel column with ethyl acetate/petroleum ether (45%) to yield 3-[(4-[6-[bis(4-chlorophenyl)methyl]-2-cyclopropyl-1H-1,3-benzodiazol-1-yl]piperidin-1-yl)methyl]-2-chlorobenzonitrile as a pink solid. LC/MS (ES, m/z): 626 [M+H]+.

Step 2: Synthesis of 3-[(4-[6-[bis(4-chlorophenyl)methyl]-2-cyclopropyl-1H-1,3-benzodiazol-1-yl]piperidin-1-yl)methyl]-2-chlorobenzoic acid Into a 100-mL round-bottom flask, was placed a solution of 3-[(4-[6-[bis(4-chlorophenyl)methyl]-2-cyclopropyl-1H-1,3-benzodiazol-1-yl]piperidin-1-yl)methyl]-2-chlorobenzonitrile (200 mg, 0.32 mmol, 1.00 equiv) in ethanol (10 mL) and a solution of sodium hydroxide (128 mg, 3.20 mmol, 10.00 equiv) in water (10 mL). The resulting solution was stirred overnight at 80° C. in an oil bath. The resulting mixture was concentrated under vacuum. The pH value of the solution was adjusted to pH 4-5 with hydrogen chloride (1%). The solids were collected by filtration. The residue was applied onto a C18 reversed column with CH₃CN/H₂O (TFA) (55%) to yield 3-[(4-[6-[bis(4-chlorophenyl)methyl]-2-cyclopropyl-1H-1,3-benzodiazol-1-yl]piperidin-1-yl)methyl]-2-chlorobenzoic acid as a white solid.

¹H NMR (400 MHz, CD3OD) δ: 7.84-7.96 (m, 3H), 7.65 (d, J=8.4 Hz, 1H), 7.58 (t, J=7.6 Hz, 1H), 7.33 (d, J=8.4 Hz, 4H), 7.25 (d, J=8.4 Hz, 1H), 7.11 (d, J=8.4 Hz, 4H), 5.82 (s, 1H), 5.26-5.32 (m, 1H), 4.61 (s, 2H), 3.79 (d, J=10.8 Hz, 2H), 3.46-3.54 (m, 2H), 2.79-2.98 (m, 2H), 2.53-2.53 (m, 1H), 2.35 (d, J=13.2 Hz, 2H), 1.46 (d, J=8.4 Hz, 2H), 1.28-1.34 (m, 2H). LC/MS (ES, m/z): 644 [M+H]+.

Example PH-75

2,2,2-trifluoroacetic acid compound with 3-((4-(6-(bis(4-chlorophenyl)methyl)-2-cyclopropyl-1H-benzo[d]imidazol-1-yl)piperidin-1-yl)methyl)-4-chlorobenzoic acid (1:1)

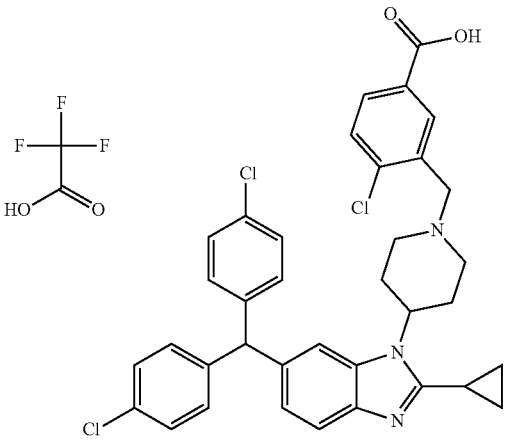 [SMILES: O=C(O)C(F)(F)F ; O=C(O)c1ccc(Cl)c(CN2CCC(n3c(C4CC4)nc4ccc(C(c5ccc(Cl)cc5)c5ccc(Cl)cc5)cc43)CC2)c1]

The title compound was prepared according to the procedure as described in Example PH-70 substituting methyl 3-(bromomethyl)-4-chlorobenzoate for methyl 3-(bromomethyl)-2-fluorobenzoate in Step 1.

¹H NMR (300 MHz, CD3OD) δ: 8.37 (s, 1H), 8.14 (d, J=6.3 Hz, 1H), 7.86 (brs, 1H), 7.73 (d, J=8.4 Hz, 1H), 7.65 (d, J=8.7 Hz, 1H), 7.25-7.33 (m, 5H), 7.09 (d, J=8.7 Hz, 4H), 5.81 (s, 1H), 5.26 (brs, 1H), 4.60-4.66 (m, 2H), 3.73-3.76 (m, 2H), 3.46-3.55 (m, 2H), 2.79-2.89 (m, 2H), 2.53-2.56 (m, 1H), 2.33-2.37 (m, 2H), 1.45-1.47 (m, 2H), 1.34 (brs, 2H). LC/MS (ES, m/z): 644 [M+H]+.

Example PH-76

3-(1-(4-(6-(bis(4-chlorophenyl)methyl)-2-cyclopropyl-1H-benzo[d]imidazol-1-yl)piperidin-1-yl)ethyl)benzoic acid

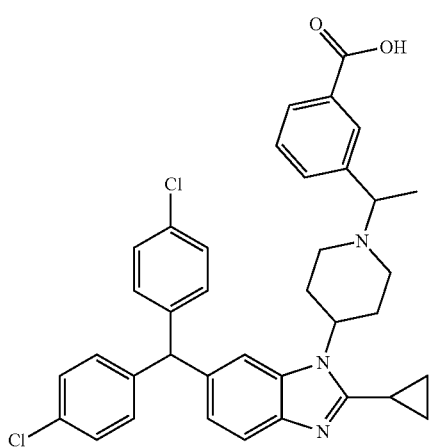 [SMILES: CC(c1cccc(C(=O)O)c1)N1CCC(n2c(C3CC3)nc3ccc(C(c4ccc(Cl)cc4)c4ccc(Cl)cc4)cc32)CC1]

The title compound was prepared according to the procedure as described in Example PH-70 substituting methyl 3-(1-bromoethyl)benzoate for methyl 3-(bromomethyl)-2-fluorobenzoate in Step 1.

$^1$H NMR (300 MHz, DMSO) δ: 12.88 (brs, 1H), 7.84-7.90 (m, 2H), 7.47-7.59 (m, 2H), 7.31-7.42 (m, 6H), 7.14 (d, J=8.1 Hz, 4H), 6.83 (d, J=9.0 Hz, 1H), 5.83 (s, 1H), 4.43-4.48 (m, 1H), 3.63-3.68 (m, 1H), 3.04-3.07 (m, 1H), 2.90-2.94 (m, 1H), 2.00-2.27 (m, 5H), 1.73-1.81 (m, 2H), 1.35-1.37 (m, 3H), 0.83-1.00 (m, 4H). LC/MS (ES, m/z): 624 [M+H]+.

Example PH-77

2,2,2-trifluoroacetic acid compound with 4-((4-(6-(bis(4-chlorophenyl)methyl)-2-cyclopropyl-1H-benzo[d]imidazol-1-yl)piperidin-1-yl)methyl)picolinic acid (1:1)

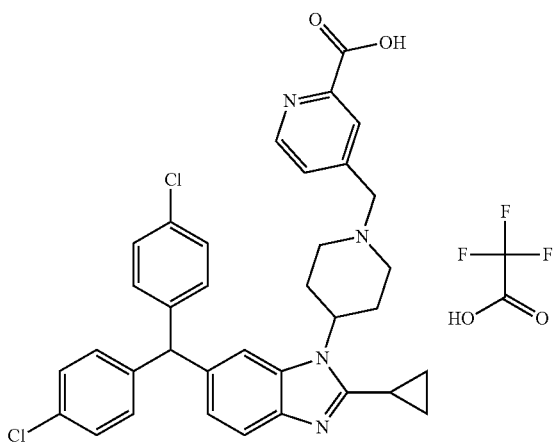 [SMILES: O=C(O)c1cc(CN2CCC(n3c(C4CC4)nc4ccc(C(c5ccc(Cl)cc5)c5ccc(Cl)cc5)cc43)CC2)ccn1 ; O=C(O)C(F)(F)F]

The title compound was prepared according to the procedure as described in Example PH-70 substituting methyl 4-(bromomethyl)pyridine-2-carboxylate for methyl 3-(bromomethyl)-2-fluorobenzoate in Step 1.

$^1$H NMR (400 MHz, CD3OD) δ: 8.80 (d, J=4.4 Hz, 1H), 8.37 (s, 1H), 7.92 (s, 1H), 7.82-7.86 (m, 1H), 7.67 (d, J=8.4 Hz, 1H), 7.20-7.44 (m, 5H), 7.13 (d, J=8.4 Hz, 4H), 5.86 (s, 1H), 5.19 (m, 1H), 4.44 (s, 2H), 3.50-3.62 (m, 2H), 3.11-3.34 (m, 2H), 2.82-2.88 (m, 2H), 2.55-2.64 (m, 1H), 2.28-2.31 (m, 2H), 1.42-1.49 (m, 2H), 1.28-1.35 (m, 2H). LC/MS (ES, m/z): 611 [M+H]+.

Example PH-78

2-((4-(6-(bis(4-chlorophenyl)methyl)-2-cyclopropyl-1H-benzo[d]imidazol-1-yl)piperidin-1-yl)methyl)isonicotinic acid

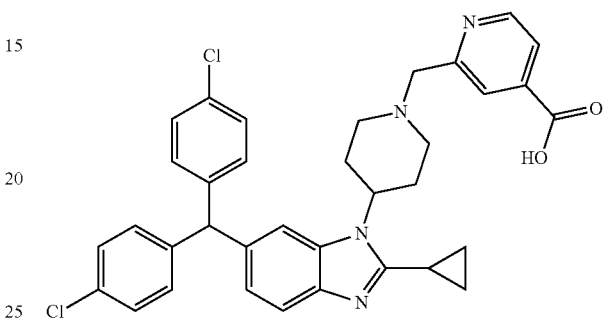

The title compound was prepared according to the procedure as described in Example PH-70 substituting methyl 2-(bromomethyl)pyridine-4-carboxylate in step 1 was used instead of methyl 3-(bromomethyl)-2-fluorobenzoate in Step 1.

$^1$H NMR (400 MHz, CD3OD) δ: 8.90 (d, J=5.2 Hz, 1H), 8.10 (s, 1H), 8.00 (s, 2H), 7.67 (d, J=8.4 Hz, 1H), 7.34 (t, J=8.0 Hz, 4H), 7.28 (d, J=8.4 Hz, 1H), 7.12 (d, J=8.8 Hz, 4H), 5.85 (s, 1H), 5.28-5.35 (m, 1H), 4.66 (s, 2H), 3.88 (d, J=12.4 Hz, 2H), 3.50 (t, J=11.2 Hz, 2H), 2.92-3.01 (m, 2H), 2.55-2.62 (m, 1H), 2.39 (d, J=13.2 Hz, 2H), 1.45-1.50 (m, 2H), 1.33-1.37 (m, 2H). LC/MS (ES, m/z): 611[M+H]+.

Example PH-79

2-[1-(4-[6-[bis(4-chlorophenyl)methyl]-2-cyclopropyl-1H-1,3-benzodiazol-1-yl]piperidin-1-yl)ethyl]pyridine-4-carboxylic acid

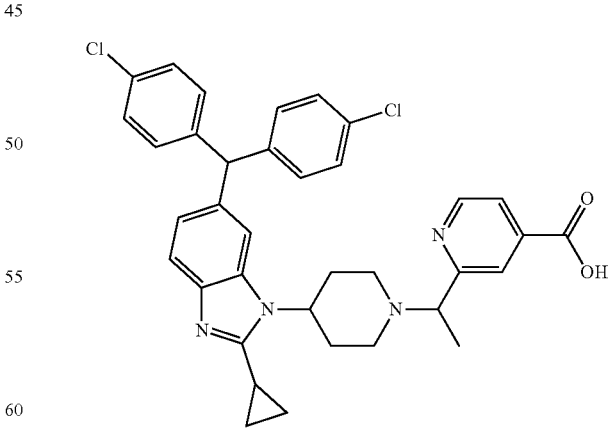

The title compound was prepared according to the procedure as described in Example PH-70 substituting methyl 2-(1-bromoethyl)pyridine-4-carboxylate for methyl 3-(bromomethyl)-2-fluorobenzoate in Step 1.

$^1$H NMR (300 MHz, DMSO) δ: 8.72 (d, J=5.1 Hz, 1H), 7.88 (s, 1H), 7.70 (d, J=5.1 Hz, 1H), 7.36-7.41 (m, 6H), 7.13

(d, J=7.5 Hz, 4H), 6.82 (d, J=7.2 Hz, 1H), 5.82 (s, 1H), 4.32-4.52 (m, 1H), 3.90-3.92 (m, 1H), 3.01-3.11 (m, 1H), 2.92-2.99 (m, 1H), 2.22-2.27 (m, 5H), 1.72-1.83 (m, 2H), 1.41 (d, J=6.9 Hz, 3H), 0.95-0.99 (m, 4H). LC/MS (ES, m/z): 625 [M+H]+.

Example PH-80

5-(1-(4-(6-(bis(4-chlorophenyl)methyl)-2-cyclopropyl-1H-benzo[d]imidazol-1-yl)piperidin-1-yl)ethyl)furan-2-carboxylic acid

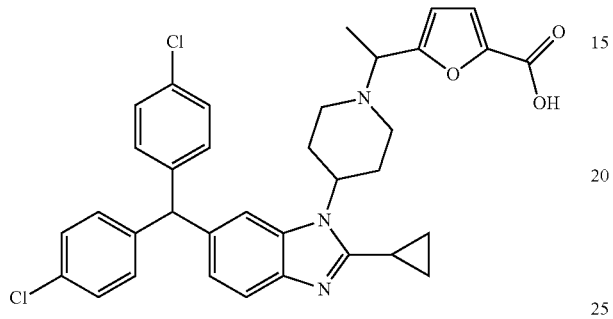

The title compound was prepared according to the procedure as described in Example PH-70 substituting methyl 5-(1-bromoethyl)furan-2-carboxylate for methyl 3-(bromomethyl)-2-fluorobenzoate in Step 1.

$^1$H NMR (300 MHz, CD3OD) δ: 7.64 (s, 1H), 7.47 (d, J=8.4 Hz, 1H), 7.30 (d, J=8.4 Hz, 4H), 7.05-7.11 (m, 5H), 6.93 (d, J=9.6 Hz, 1H), 6.59 (d, J=3.3 Hz, 1H), 5.71 (s, 1H), 4.77-5.00 (m, 1H), 4.34-4.41 (m, 1H), 3.41 (s, 2H), 2.93 (t, J=10.8 Hz, 1H), 2.58-2.75 (m, 3H), 2.18-2.27 (m, 1H), 2.05 (d, J=11.7 Hz, 2H), 1.66 (d, J=6.9 Hz, 3H), 1.06-1.17 (m, 4H). LC/MS (ES, m/z): 614 [M+H]+.

Example PH-81

3-[1-(4-[6-[bis(4-chlorophenyl)methyl]-2-cyclopropyl-1H-1,3-benzodiazol-1-yl]piperidin-1-yl)propyl]benzoic acid; trifluoroacetic acid

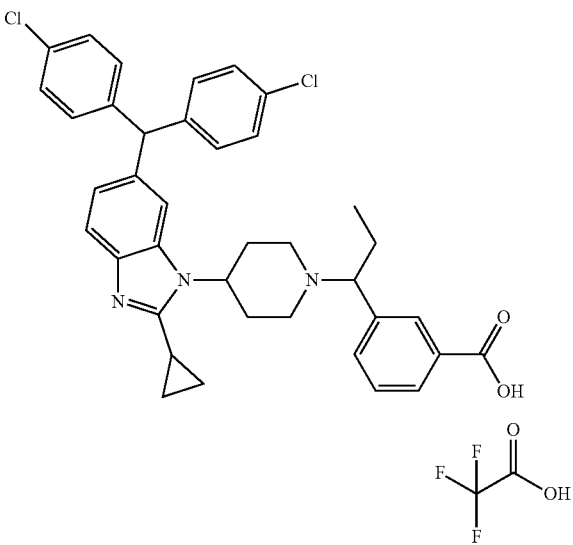

The title compound was prepared according to the procedure as described in Example PH-70 substituting methyl 3-(1-bromopropyl)benzoate for methyl 3-(bromomethyl)-2-fluorobenzoate, in Step 1.

$^1$H NMR (300 MHz, DMSO-d6) δ: 9.90 (brs, 1H), 8.15 (s, 1H), 8.08 (d, J=7.5 Hz, 1H), 7.72 (d, J=9.6 Hz, 1H), 7.66-7.69 (m, 2H), 7.54 (d, J=8.4 Hz, 1H), 7.38 (d, J=8.4 Hz, 4H), 7.10 (d, J=2.4 Hz, 4H), 6.93 (d, J=8.1 Hz, 1H), 5.72 (s, 1H), 4.90-5.08 (m, 1H), 4.58-4.61 (m, 1H), 3.79 (m, 1H), 3.65 (m, 1H), 2.94-2.97 (m, 2H), 2.68-2.72 (m, 2H), 2.34-2.36 (m, 2H), 2.14-2.17 (m, 3H), 1.14 (s, 4H), 0.71 (t, J=6.9 Hz, 3H). LC/MS (ES, m/z): 638 [M+H]+.

Example PH-82

2,2,2-trifluoroacetic acid compound with 3-((4-(6-(bis(4-chlorophenyl)methyl)-2-cyclopropyl-1H-benzo[d]imidazol-1-yl)piperidin-1-yl)methyl)-2-hydroxybenzoic acid (1:1)

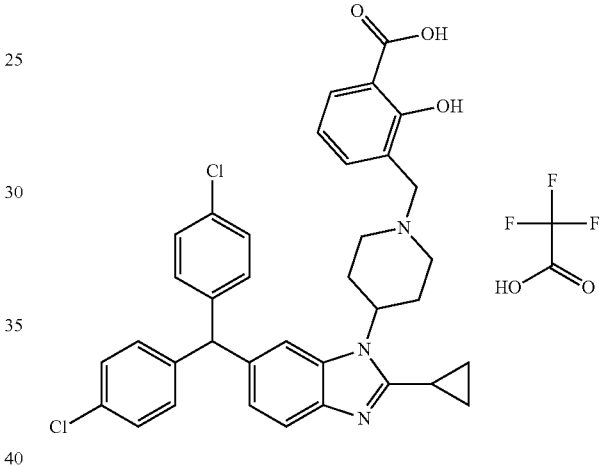

Step 1: Synthesis of 2-cyclopropyl-1H-1,3-benzodiazol-1-yl]piperidin-1-yl)methyl]-6-bromophenol Into a 100-mL round-bottom flask, was placed a solution of 6-[bis(4-chlorophenyl)methyl]-2-cyclopropyl-1-(piperidin-4-yl)-1H-1,3-benzodiazole (300 mg, 0.63 mmol, 1.00 equiv) in dichloromethane (30 mL), 3-bromo-2-hydroxybenzaldehyde (127 mg, 0.63 mmol, 1.00 equiv) and acetic acid (a catalytic amount). The resulting solution was stirred for 4 h at room temperature NaBH(OAc)$_3$ (335 mg, 2.50 equiv). The resulting solution was stirred for overnight at room temperature. The residue was applied onto a silica gel column with ethyl acetate/petroleum ether (1:1) to yield 2-[(4-[6-[bis(4-chlorophenyl)methyl]-2-cyclopropyl-1H-1,3-benzodiazol-1-yl]piperidin-1-yl)methyl]-6-bromophenol as a white solid. LC/MS (ES, m/z): 661 [M+H]+

Step 2: Synthesis of 6-[bis(4-chlorophenyl)methyl]-1-(1-[[3-bromo-2-(methoxymethoxy) phenyl]methyl]piperidin-4-yl)-2-cyclopropyl-1H-1,3-benzodiazole Into a 50-mL round-bottom flask, was placed a solution of 2-[(4-[6-[bis(4-chlorophenyl)methyl]-2-cyclopropyl-1H-1,3-benzodiazol-1-yl]piperidin-1-yl)methyl]-6-bromophenol (170 mg, 0.26 mmol, 1.00 equiv) in tetrahydrofuran (10 mL), sodium hydride (15.5 mg, 0.39 mmol, 1.50 equiv) and MOMBr (42 mg, 1.30 equiv). The resulting solution was stirred for 2 h at room temperature. The reaction was then quenched by the addition of water (2 mL). The resulting solution was extracted with ethyl acetate (3×5 mL) and the organic layers combined, then dried over anhydrous sodium sulfate and concentrated under vacuum to yield 6-[bis(4-chlorophenyl)methyl]-1-(1-[[3-bromo-2-(methoxymethoxy)phenyl]methyl]piperidin-4-yl)-2-cyclopropyl-1H-1,3-benzodiazole as a yellow solid. LC/MS (ES, m/z): 705.5 [M+H]+

Step 3: Synthesis of methyl 3-[(4-[6-[bis(4-chlorophenyl)methyl]-2-cyclopropyl-1H-1,3-benzodiazol-1-yl]piperidin-1-yl)methyl]-2-(methoxymethoxy)benzoate Into a 30-mL pressure tank reactor (3.5 atm), was placed a solution of 6-[bis(4-chlorophenyl)methyl]-1-(1-[[3-bromo-2-(methoxymethoxy)phenyl]methyl]piperidin-4-yl)-2-cyclopropyl-1H-1,3-benzodiazole (100 mg, 0.14 mmol, 1.00 equiv) in DMF/MeOH (1/1 mL), Pd(OAc)$_2$ (3.0 mg, 0.01 mmol, 0.10 equiv), dppf (7.4 mg, 0.01 mmol, 0.10 equiv) and triethylamine (1.3 mg, 0.01 mmol, 0.10 equiv). To the resulting mixture was then introduced CO(g). The resulting solution was stirred overnight at 130° C. The resulting mixture was concentrated under vacuum to yield methyl 3-[(4-[6-[bis(4-chlorophenyl)methyl]-2-cyclopropyl-1H-1,3-benzodiazol-1-yl]piperidin-1-yl)methyl]-2-(methoxymethoxy)benzoate as brown oil. LC/MS (ES, m/z): 685 [M+H]+

Step 4: Synthesis of methyl 3-[(4-[6-[bis(4-chlorophenyl)methyl]-2-cyclopropyl-1H-1,3-benzodiazol-1-yl]piperidin-1-yl)methyl]-2-hydroxybenzoate Into a 50-mL round-bottom flask, was placed a solution of methyl 3-[(4-[6-[bis(4-chlorophenyl)methyl]-2-cyclopropyl-1H-1,3-benzodiazol-1-yl]piperidin-1-yl)methyl]-2-(methoxymethoxy)benzoate (170 mg, 0.25 mmol, 1.00 equiv) in dichloromethane (20 mL) and CF$_3$COOH (10 mL). The resulting solution was stirred overnight at room temperature. The resulting mixture was concentrated under vacuum to yield methyl 3-[(4-[6-[bis(4-chlorophenyl)methyl]-2-cyclopropyl-1H-1,3-benzodiazol-1-yl]piperidin-1-yl)methyl]-2-hydroxybenzoate as brown oil. LC/MS (ES, m/z): 641 [M+H]+

Step 5: Synthesis of 3-[(4-[6-[bis(4-chlorophenyl)methyl]-2-cyclopropyl-1H-1,3-benzodiazol-1-yl]piperidin-1-yl)methyl]-2-hydroxybenzoic acid trifluoroacetic acid Into a 50-mL round-bottom flask, was placed a solution of methyl 3-[(4-[6-[bis(4-chlorophenyl)methyl]-2-cyclopropyl-1H-1,3-benzodiazol-1-yl]piperidin-1-yl)methyl]-2-hydroxybenzoate (100 mg, 0.16 mmol, 1.00 equiv) in tetrahydrofuran/MeOH (20/5 mL) and LiOH (20 mL). The resulting solution was stirred overnight at room temperature. The resulting mixture was concentrated under vacuum. The pH value of the solution was adjusted to pH 6 with hydrogen chloride (12 mol/L). The solids were collected by filtration. The product residue (50 mg) was purified by Prep-HPLC with the following conditions (Waters 2767-1)): Column, Sunfire Prep C18, 5 um, 19*100 mm; mobile phase, trifluoroacetic acid in water and CH$_3$CN (25% CH$_3$CN up to 50% in 10 min); Detector, UV 254 nm to yield 3-[(4-[6-[bis(4-chlorophenyl)methyl]-2-cyclopropyl-1H-1,3-benzodiazol-1-yl]piperidin-1-yl)methyl]-2-hydroxybenzoic acid trifluoroacetic acid as a pink solid.

$^1$H NMR (300 MHz, CD3OD) δ: 8.07 (d, J=7.5 Hz, 1H), 7.97 (s, 1H), 7.64-7.73 (m, 2H), 7.26-7.42 (m, 5H), 7.08-7.11 (m, 5H), 5.81 (s, 1H), 5.29 (s, 1H), 4.31-4.59 (m, 2H), 3.63-3.96 (m, 2H), 3.38-3.55 (m, 2H), 2.71-3.11 (m, 2H), 2.45-2.68 (m, 1H), 2.22-2.37 (m, 2H), 1.45-1.94 (m, 2H), 1.23-1.34 (m, 2H). LC/MS (ES, m/z): 626 [M+H]+.

Example PH-83

2,2,2-trifluoroacetic acid compound with 5-((4-(6-(bis(4-chlorophenyl)methyl)-2-cyclopropyl-1H-benzo[d]imidazol-1-yl)piperidin-1-yl)methyl)-2-hydroxybenzoic acid (1:1)

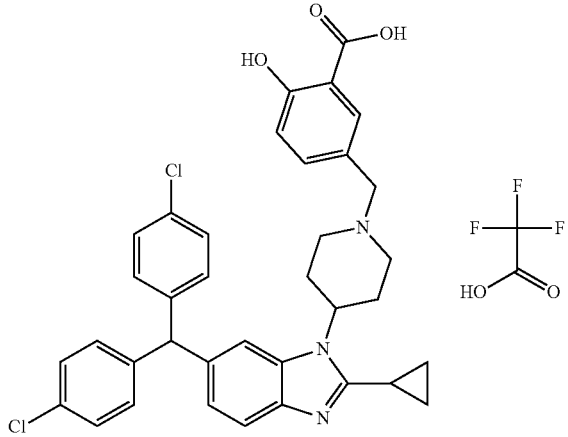 [SMILES: O=C(O)c1cc(CN2CCC(n3c(C4CC4)nc4ccc(C(c5ccc(Cl)cc5)c5ccc(Cl)cc5)cc43)CC2)ccc1O ; O=C(O)C(F)(F)F]

The title compound was prepared according to the procedure as described in Example PH-53 substituting methyl 5-formyl-2-hydroxybenzoate for methyl 3-formylbenzoate in Step 1.

$^1$H NMR (400 MHz, CDCl3) δ 8.13 (s, 1H), 7.99 (s, 1H), 7.66-7.77 (m, 2H), 7.31-7.77 (m, 4H), 7.25-7.27 (d, J=8.4 Hz, 1H), 7.01-7.17 (m, 5H), 5.81 (s, 1H), 5.27 (s, 1H), 4.31-4.39 (m, 2H), 3.76-3.79 (m, 2H), 3.51-3.53 (m, 2H), 2.77-2.92 (m, 2H), 2.48-2.55 (m, 1H), 2.35-2.39 (m, 2H), 1.25-1.47 (m, 4H). LC/MS (ES, m/z): 626 [M+H]+.

Example PH-84

4-[6-[bis(4-chlorophenyl)methyl]-2-cyclopropyl-1H-1,3-benzodiazol-1-yl]-N-phenylpiperidine-1-carboxamide; trifluoroacetic acid

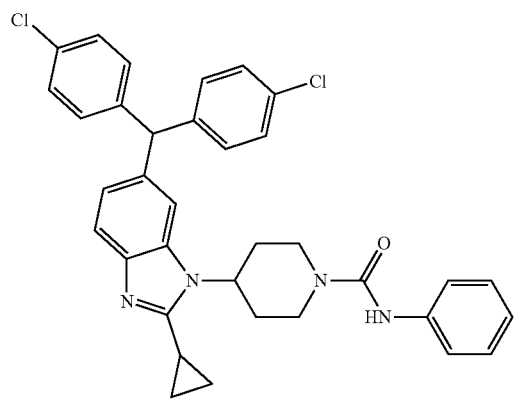 [SMILES: O=C(Nc1ccccc1)N1CCC(n2c(C3CC3)nc3ccc(C(c4ccc(Cl)cc4)c4ccc(Cl)cc4)cc32)CC1]

Into a 50-mL round-bottom flask, was placed a solution of 6-[bis(4-chlorophenyl)methyl]-2-cyclopropyl-1-(piperidin-4-yl)-1H-1,3-benzodiazole (150 mg, 0.31 mmol, 1.00 equiv) in dichloromethane (10 mL), isocyanatobenzene (45 mg, 0.38 mmol, 1.20 equiv) and triethylamine (96 mg, 0.95 mmol, 3.00 equiv). The resulting solution was stirred overnight at room temperature. The resulting mixture was concentrated under vacuum. The product residue was purified by Prep-HPLC with the following conditions (Waters 2767-1): Column, Sunfire Prep C18, 5 um, 19*100 mm; mobile phase, 0.03% ammonia in water and CH$_3$CN (55% CH$_3$CN up to 95% in 10 min); Detector, UV 254 nm to yield 4-[6-[bis(4-chlorophenyl)methyl]-2-cyclopropyl-1H-1,3-benzodiazol-1-yl]-N-phenylpiperidine-1-carboxamide as a white solid.

$^1$H NMR (400 MHz, DMSO-d6) δ: 8.62 (s, 1H), 7.49 (d, J=7.6 Hz, 2H), 7.44 (d, J=4.4 Hz, 2H), 7.32 (d, J=8.4 Hz, 4H), 7.24 (t, J=7.6 Hz, 2H), 7.09 (d, J=8.4 Hz, 4H), 6.95 (t, J=7.6 Hz, 1H), 6.84 (d, J=8.8 Hz, 1H), 5.77 (s, 1H), 4.84-4.90 (m, 1H), 4.33 (d, J=13.2 Hz, 2H), 3.02 (t, J=12.4 Hz, 2H), 2.21-2.34 (m, 3H), 1.91 (d, J=10.8 Hz, 2H), 1.00-1.08 (m, 4H). LC/MS (ES, m/z): 595 [M+H]+.

Example PH-85

N-benzyl-4-[6-[bis(4-chlorophenyl)methyl]-2-cyclopropyl-1H-1,3-benzodiazol-1-yl]piperidine-1-carboxamide

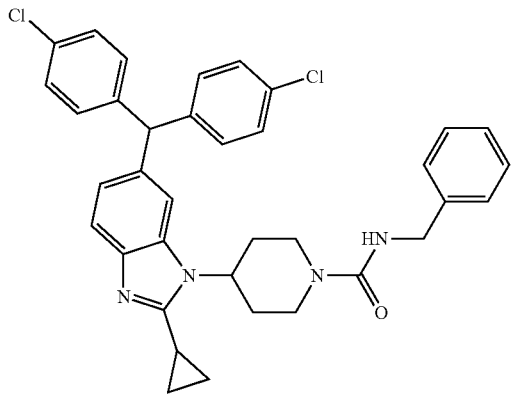 [SMILES: O=C(NCc1ccccc1)N1CCC(n2c(C3CC3)nc3ccc(C(c4ccc(Cl)cc4)c4ccc(Cl)cc4)cc32)CC1]

The title compound was prepared according to the procedure as described in Example PH-84 substituting (isocyanatomethyl)benzene for isocyanatobenzene in Step 1.

$^1$H NMR (300 MHz, DMSO-d6) δ: 7.29-7.44 (m, 6H), 7.26-7.27 (m, 4H), 7.16-7.22 (m, 2H), 7.09-7.12 (m, 4H), 6.82 (d, J=6.2 Hz, 1H), 5.75 (s, 1H), 4.80 (br s, 1H), 4.26 (d, J=5.7 Hz, 2H), 4.16-4.20 (m, 2H), 2.87-2.95 (m, 2H), 2.15-2.27 (m, 3H), 1.81-1.85 (m, 2H), 1.00-1.02 (m, 4H). LC/MS (ES, m/z): 609 [M+H]+.

Example PH-86

4-(6-(bis(4-chlorophenyl)methyl)-2-cyclopropyl-1H-benzo[d]imidazol-1-yl)-N-ethylpiperidine-1-carboxamide

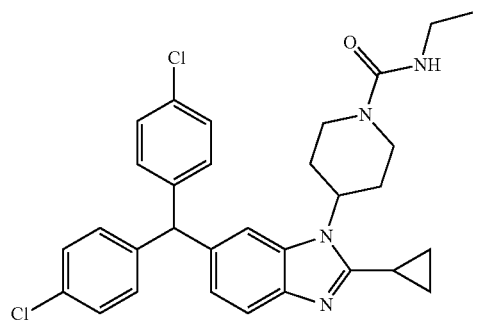 [SMILES: CCNC(=O)N1CCC(n2c(C3CC3)nc3ccc(C(c4ccc(Cl)cc4)c4ccc(Cl)cc4)cc32)CC1]

The title compound was prepared according to the procedure as described in Example PH-84 substituting (isocyanatomethyl)benzene for isocyanatoethane in Step 1.

$^1$H NMR (400 MHz, DMSO-d6) δ: 7.43 (d, J=8.4 Hz, 1H), 7.35-7.38 (m, 5H), 7.10-7.12 (m, 4H), 6.76-6.85 (m, 1H), 6.56 (s, 1H), 5.77 (s, 1H), 4.76-4.89 (m, 1H), 4.11-4.15 (m, 2H), 3.05-3.08 (m, 2H), 2.85-2.96 (m, 2H), 2.29-2.31 (m, 1H), 2.10-2.20 (m, 2H), 1.75-1.87 (m, 2H), 1.00-1.03 (m, 7H). LC/MS (ES, m/z) 547 [M+H]+.

Example PH-87 phenyl 4-(6-(bis(4-chlorophenyl)methyl)-2-cyclopropyl-1H-benzo[d]imidazol-1-yl)piperidine-1-carboxylate 2,2,2-trifluoroacetate

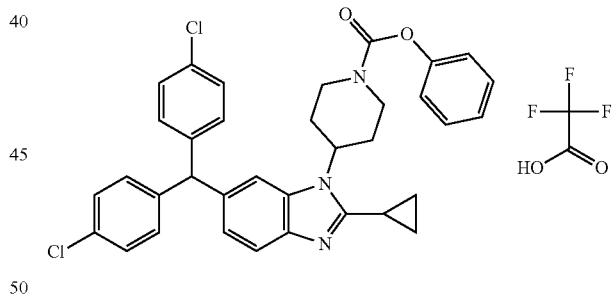

Into a 100-mL round-bottom flask, was placed a solution of 6-[bis(4-chlorophenyl)methyl]-2-cyclopropyl-1-(piperidin-4-yl)-1H-1,3-benzodiazole (100 mg, 0.21 mmol, 1.00 equiv) in dichloromethane (30 mL), phenyl chloroformate (40 mg, 0.26 mmol, 1.20 equiv) and triethylamine (64 mg, 0.63 mmol, 3.00 equiv). The resulting solution was stirred overnight at room temperature. The resulting mixture was concentrated under vacuum. The product residue was purified by Prep-HPLC with the following conditions (Waters 2767-1): Column, Sunfire Prep C18, 5 um, 19*100 mm; mobile phase, 0.05% trifluoroacetic acid in water and CH$^3$CN (CH$_3$CN 10% up to 60% in 9 min); Detector, 254 nm to yield phenyl 4-[6-[bis(4-chlorophenyl)methyl]-2-cyclopropyl-1H-1,3-benzodiazol-1-yl]piperidine-1-carboxylate; trifluoroacetic acid as a white solid.

$^1$H NMR (300 MHz, DMSO-d6) δ: 7.84 (s, 1H), 7.62 (d, J=8.4 Hz, 1H), 7.37-7.44 (m, 6H), 7.21-7.28 (m, 1H), 7.12-7.15 (m, 7H), 5.94 (m, 1H), 5.01-5.94 (m, 1H), 4.11-4.36 (m, 2H), 3.15-3.28 (m, 2H), 2.55-2.64 (m, 1H), 2.41-2.29 (m, 2H), 2.04-2.08 (m, 2H), 1.25-1.27 (m, 4H). LC/MS (ES, m/z) 596 [M+H]+.

Example PH-88 benzyl 4-(6-(bis(4-chlorophenyl)methyl)-2-cyclopropyl-1H-benzo[d]imidazol-1-yl)piperidine-1-carboxylate

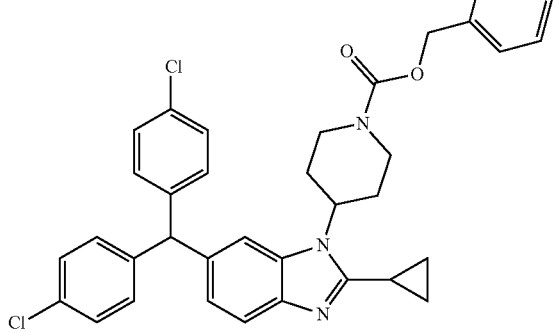

The title compound was prepared according to the procedure as described in Example PH-87 substituting benzyl carbonochloridate for phenyl chloroformate in Step 1.
$^1$H NMR (400 MHz, DMSO-d6) δ: 7.30-7.44 (m, 11H), 7.11 (m, 4H), 6.82 (d, J=8.4 Hz, 1H), 5.79 (s, 1H), 5.14 (brs, 2H), 4.80-4.86 (m, 2H), 3.02 (brs, 2H), 2.08-2.34 (m, 3H), 1.86-1.89 (m, 2H), 1.01-1.06 (m, 4H). LC/MS (ES, m/z): 610 [M+H]+.

Example PH-89 cyclopentyl 4-(6-(bis(4-chlorophenyl)methyl)-2-cyclopropyl-1H-benzo[d]imidazol-1-yl)piperidine-1-carboxylate

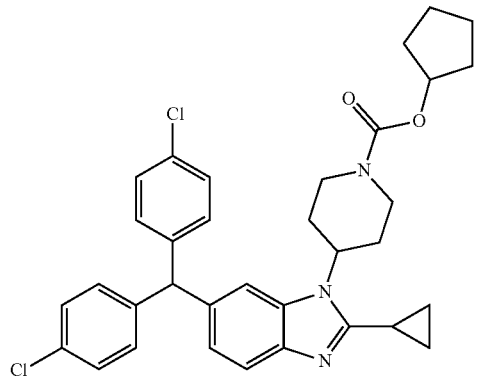 [SMILES: O=C(OC1CCCC1)N1CCC(n2c(C3CC3)nc3ccc(C(c4ccc(Cl)cc4)c4ccc(Cl)cc4)cc32)CC1]

The title compound was prepared according to the procedure as described in Example PH-87 substituting cyclopentyl carbonochloridate for phenyl chloroformate in Step 1.
$^1$H NMR (400 MHz, DMSO-d6) δ: 7.30-7.44 (m, 6H), 7.11 (d, J=8.4 Hz, 4H), 6.82 (d, J=8.7 Hz, 1H), 5.79 (s, 1H), 5.14 (brs, 2H), 4.80-4.86 (m, 2H), 2.90-3.06 (m, 2H), 2.08-2.34 (m, 3H), 1.70-1.89 (m, 4H), 1.51-1.69 (m, 6H), 1.01-1.06 (m, 4H). LC/MS (ES, m/z): 588 [M+H]+.

Example PH-90 ethyl 4-(6-(bis(4-chlorophenyl)methyl)-2-cyclopropyl-1H-benzo[d]imidazol-1-yl)piperidine-1-carboxylate

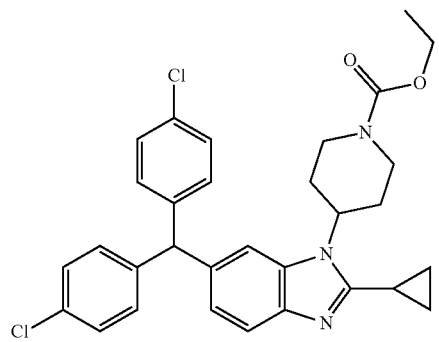 [SMILES: CCOC(=O)N1CCC(n2c(C3CC3)nc3ccc(C(c4ccc(Cl)cc4)c4ccc(Cl)cc4)cc32)CC1]

The title compound was prepared according to the procedure as described in Example PH-87 substituting ethyl carbonochloridate for phenyl chloroformate in Step 1.
$^1$H NMR (300 MHz, DMSO-d6) δ: 7.34-7.35 (m, 6H), 7.10-7.13 (m, 4H), 6.82 (d, J=8.4 Hz, 1H), 5.80 (s, 1H), 4.77-4.85 (m, 1H), 4.04-4.17 (m, 4H), 2.90-3.10 (brs, 2H), 2.12-2.33 (m, 3H), 1.83-1.86 (m, 2H), 1.18-1.23 (m, 3H), 1.01-1.04 (m, 4H). LC/MS (ES, m/z): 548 [M+H]+.

Example PH-91

2,2,2-trifluoroacetic acid compound with 3-((3-(6-(bis(4-chlorophenyl)methyl)-2-cyclopropyl-1H-benzo[d]imidazol-1-yl)azetidin-1-yl)methyl)benzoic acid (1:1)

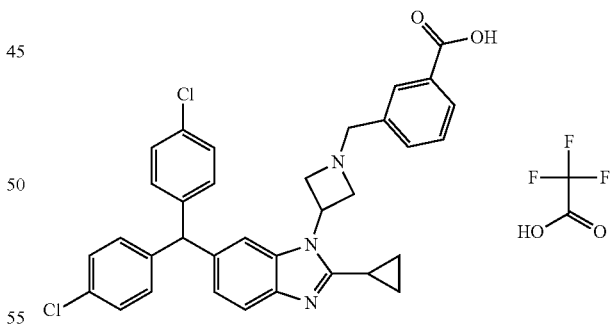

Step 1: Synthesis of methyl 2,2-bis(4-chlorophenyl)-2-(3-fluoro-4-nitrophenyl)acetate Into a 1000-mL 3-necked round-bottom flask purged and maintained with an inert atmosphere of nitrogen, was placed a solution of methyl 2,2-bis(4-chlorophenyl) acetate (54 g, 182.95 mmol, 1.00 equiv) in tetrahydrofuran (250 mL). To the mixture was then added t-BuOK (201 mL, 1.10 equiv) dropwise with stirring at 0° C. in 20 min. To the resulting mixture was added a solution of 2,4-difluoro-1-nitrobenzene (37.5 g, 235.72 mmol, 1.05 equiv) in tetrahydrofuran (250 mL) dropwise with stirring. The resulting solution was stirred overnight at room temperature. The residue was applied onto a silica gel column with ethyl acetate/petroleum ether (1:20) to yield methyl 2,2-bis(4-chlorophenyl)-2-(3-fluoro-4-nitrophenyl)acetate as yellow oil.

Step 2: Synthesis of yield tert-butyl3-([5-[1,1-bis(4-chlorophenyl)-2-methoxy-2-oxoethyl]-2-nitrophenyl] amino)azetidine-1-carboxylate Into a 250-mL round-bottom flask, was placed tert-butyl 3-aminoazetidine-1-carboxylate (2.38 g, 13.82 mmol, 1.20 equiv), DIEA (4.45 g, 34.43 mmol, 3.00 equiv), CH$_3$CN (100 mL) and methyl 2,2-bis(4-chlorophenyl)-2-(3-fluoro-4-nitrophenyl)acetate (5.0 g, 11.51 mmol, 1.00 equiv). The resulting solution was heated to reflux for 72 h in an oil bath. The resulting mixture was concentrated under vacuum. The residue was applied onto a silica gel column with ethyl acetate/petroleum ether (1:5) to yield tert-butyl3-([5-[1,1-bis(4-chlorophenyl)-2-methoxy-2-oxoethyl]-2-nitrophenyl] amino)azetidine-1-carboxylate as yellow oil. LC/MS (ES, m/z): 586 [M+H]+.

Step 3: Synthesis of tert-butyl 3-([2-amino-5-[1,1-bis(4-chlorophenyl)-2-methoxy-2-oxoethyl]phenyl] amino)azetidine-1-carboxylate Into a 250-mL round-bottom flask, was placed a solution of tert-butyl 3-([5-[1,1-bis(4-chlorophenyl)-2-methoxy-2-oxoethyl]-2-nitrophenyl]amino)azetidine-1-carboxylate (4.4 g, 7.50 mmol, 1.00 equiv) in tetrahydrofuran/MeOH (60/30 mL) and Raney Ni (8 g). Hydrogen was then introduced into the resulting mixture. The resulting solution was stirred overnight at room temperature. The solids were filtered out. The resulting mixture was concentrated under vacuum to yield tert-butyl 3-([2-amino-5-[1,1-bis(4-chlorophenyl)-2-methoxy-2-oxoethyl]phenyl]amino)azetidine-1-carboxylate as yellow oil. LC/MS (ES, m/z): 556 [M+H]+.

Step 4: Synthesis of tert-butyl 3-([5-[1,1-bis(4-chlorophenyl)-2-methoxy-2-oxoethyl]-2-cyclopropaneamidophenyl]amino)azetidine-1-carboxylate Into a 250-mL round-bottom flask, was placed a solution of tert-butyl 3-([2-amino-5-[1,1-bis(4-chlorophenyl)-2-methoxy-2-oxoethyl]phenyl]amino)azetidine-1-carboxylate (3.87 g, 6.12 mmol, 1.00 equiv, 88%) in dichloromethane (100 mL), triethylamine (2.112 g, 20.87 mmol, 3.00 equiv) and cyclopropanecarbonyl chloride (729 mg, 6.97 mmol, 1.00 equiv). The resulting solution was stirred overnight at room temperature. The resulting mixture was concentrated under vacuum. The resulting mixture was washed with water (1×100 mL). The resulting solution was extracted with DCM (2×100 mL) and the organic layers combined, then concentrated under vacuum to yield tert-butyl 3-([5-[1,1-bis(4-chlorophenyl)-2-methoxy-2-oxoethyl]-2-cyclopropaneamidophenyl]amino)azetidine-1-carboxylate as light yellow oil. LC/MS (ES, m/z): 625 [M+H]+.

Step 5: Synthesis of tert-butyl 3-[6-[1,1-bis(4-chlorophenyl)-2-methoxy-2-oxoethyl]-2-cyclopropyl-1H-1,3-benzodiazol-1-yl]azetidine-1-carboxylate Into a 250-mL round-bottom flask, was placed tert-butyl 3-([5-[1,1-bis(4-chlorophenyl)-2-methoxy-2-oxoethyl]-2-cyclopropaneamidophenyl]amino)azetidine-1-carboxylate (4.38 g, 7.01 mmol, 1.00 equiv) and acetic acid (150 mL). The resulting solution was stirred for 3 h at 120° C. The resulting mixture was concentrated under vacuum. The residue was applied onto a silica gel column with ethyl acetate/petroleum ether (1:5) to yield tert-butyl 3-[6-[1,1-bis(4-chlorophenyl)-2-methoxy-2-oxoethyl]-2-cyclopropyl-1H-1,3-benzodiazol-1-yl]azetidine-1-carboxylate as light yellow oil.

Step 6: Synthesis of 2-(1-[1-[(tert-butoxy)carbonyl] azetidin-3-yl]-2-cyclopropyl-1H-1,3-benzodiazol-6-yl)-2,2-bis(4-chlorophenyl)acetic acid Into a 250-mL round-bottom flask, was placed tert-butyl 3-[6-[1,1-bis(4-chlorophenyl)-2-methoxy-2-oxoethyl]-2-cyclopropyl-1H-1,3-benzodiazol-1-yl]azetidine-1-carboxylate (1.6 g, 2.64 mmol, 1.00 equiv), sodium hydroxide (6.0 g, 150.00 mmol, 57.00 equiv), methanol (50 mL), water (50 mL) and tetrahydrofuran (20 mL). The resulting solution was stirred overnight at room temperature. The resulting mixture was concentrated under vacuum. The pH value of the solution was adjusted to pH 7.0 with hydrogen chloride (3 mol/L). The solids were collected by filtration to yield 2-(1-[1-[(tert-butoxy)carbonyl]azetidin-3-yl]-2-cyclopropyl-1H-1,3-benzodiazol-6-yl)-2,2-bis(4-chlorophenyl)acetic acid as a white solid.

Step 7: Synthesis of tert-butyl 3-[6-[bis(4-chlorophenyl)methyl]-2-cyclopropyl-1H-1,3-benzodiazol-1-yl]azetidine-1-carboxylate Into a 100-mL round-bottom flask, was placed 2-(1-[1-[(tert-butoxy)carbonyl]azetidin-3-yl]-2-cyclopropyl-1H-1,3-benzodiazol-6-yl)-2,2-bis(4-chlorophenyl)acetic acid (1.0 g, 1.69 mmol, 1.00 equiv), toluene (30 mL) and DBU (1.27 g, 8.34 mmol, 6.00 equiv). The resulting solution was stirred for 3 h at 90° C. in an oil bath. The resulting mixture was washed with water (100 mL). The resulting solution was extracted with ethyl acetate (3×100 mL) and the organic layers combined, then dried over anhydrous sodium sulfate. The residue was applied onto a silica gel column with ethyl acetate/petroleum ether (1:1) to yield tert-butyl 3-[6-[bis(4-chlorophenyl)methyl]-2-cyclopropyl-1H-1,3-benzodiazol-1-yl]azetidine-1-carboxylate as light yellow oil.

Step 8: Synthesis of 1-(azetidin-3-yl)-6-[bis(4-chlorophenyl)methyl]-2-cyclopropyl-1H-1,3-benzodiazole Into a 50-mL round-bottom flask, was placed tert-butyl 3-[6-[bis(4-chlorophenyl)methyl]-2-cyclopropyl-1H-1,3-benzodiazol-1-yl]azetidine-1-carboxylate (800 mg, 1.46 mmol, 1.00 equiv), dichloromethane (15 mL) and trifluoroacetic acid (5 mL). The resulting solution was stirred for 3 h at room temperature. The resulting mixture was concentrated under vacuum. The residue was applied onto a silica gel column with ethyl acetate/petroleum ether (3:1) to yield 1-(azetidin-3-yl)-6-[bis(4-chlorophenyl)methyl]-2-cyclopropyl-1H-1,3-benzodiazole as a white solid.

Step 9: Synthesis of methyl 3-[(3-[6-[bis(4-chlorophenyl)methyl]-2-cyclopropyl-1H-1,3-benzodiazol-1-yl]azetidin-1-yl)methyl]benzoate Into a 50-mL round-bottom flask, was placed a solution of 1-(azetidin-3-yl)-6-[bis(4-chlorophenyl)methyl]-2-cyclopropyl-1H-1,3-benzodiazole (200 mg, 0.45 mmol, 1.00 equiv) in dichloromethane (30 mL), methyl 3-formylbenzoate (88 mg, 0.54 mmol, 1.20 equiv), acetic acid (0.1 mL), NaBH(OAc)$_3$ (285 mg, 1.34 mmol, 3.00 equiv). The resulting solution was stirred overnight at room temperature. The resulting mixture was concentrated under vacuum. The residue was applied onto a silica gel column with ethyl acetate/petroleum ether (1:1) to yield methyl 3-[(3-[6-[bis(4-chlorophenyl)methyl]-2-cyclopropyl-1H-1,3-benzodiazol-1-yl]azetidin-1-yl)methyl]benzoate as a white solid. LC/MS (ES, m/z): 597 [M+H]+.

Step 10: Synthesis of 3-[(3-[6-[bis(4-chlorophenyl)methyl]-2-cyclopropyl-1H-1,3-benzodiazol-1-yl]azetidin-1-yl)methyl]benzoic acid trifluoroacetic acid Into a 50-mL round-bottom flask, was placed a solution of methyl 3-[(3-[6-[bis(4-chlorophenyl)methyl]-2-cyclopropyl-1H-1,3-benzodiazol-1-yl]azetidin-1-yl)methyl]benzoate (160 mg, 0.27 mmol, 1.00 equiv) in tetrahydrofuran/MeOH (20/2 mL) and LiOH (20 mL). The resulting solution was stirred overnight at room temperature e. The resulting mixture was concentrated under vacuum. The pH value of the solution was adjusted to pH 7 with hydrogen chloride (12 mol/L). The solids were collected by filtration. The product residue (100 mg) was purified by Prep-HPLC with the following conditions (Waters 2767-1): Column, Sunfire Prep C18, 5 um, 19*100 mm; mobile phase, 0.05% trifluoroacetic acid in water and CH$_3$CN (25% CH$_3$CN up to 50% in 10 min); Detector, 254 nm to yield 3-[(3-[6-[bis(4-chlorophenyl)methyl]-2-cyclopropyl-1H-1,3-benzodiazol-1-yl] azetidin-1-yl)methyl]benzoic acid trifluoroacetic acid as a white solid.
$^1$H NMR (300 MHz, CD3OD) δ: 8.10-8.12 (m, 2H), 7.77 (s, 1H), 7.55-7.66 (m, 3H), 7.33 (d, J=1.8 Hz, 5H), 7.18 (d, J=8.4 Hz, 4H), 5.86 (s, 2H), 4.52-4.62 (brs, 1H), 4.41-4.48 (m, 2H), 4.31 (s, 1H), 2.29-2.38 (m, 1H), 1.29-1.44 (m, 4H). LC/MS (ES, m/z): 582 [M+H]+.

Example PH-92

2,2,2-trifluoroacetic acid compound with 3-(1-(4-(6-(bis(4-chlorophenyl)methyl)-2-cyclopropyl-1H-benzo[d]imidazol-1-yl)piperidin-1-yl)propyl)benzoic acid (1:1)

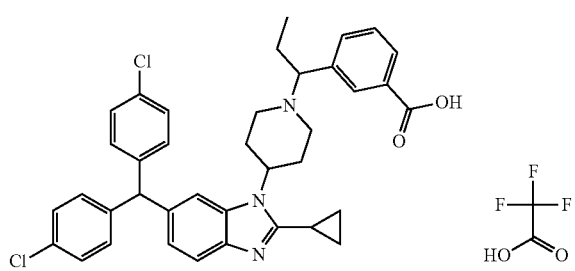 [SMILES: CCC(c1cccc(C(=O)O)c1)N1CCC(n2c(C3CC3)nc3ccc(C(c4ccc(Cl)cc4)c4ccc(Cl)cc4)cc32)CC1 ; O=C(O)C(F)(F)F]

The title compound was prepared according to the procedure as described in Example PH-70 substituting methyl 3-(1-bromopropyl)benzoate for methyl 3-(bromomethyl)-2-fluorobenzoate in Step 1.
$^1$H NMR (300 MHz, DMSO-d6) δ: 9.98 (brs, 1H), 8.15 (s, 1H), 8.08 (d, J=7.5 Hz, 1H), 7.84-7.86 (m, 1H), 7.66-7.74 (m, 2H), 7.53-7.55 (m, 1H), 7.37-7.40 (m, 4H), 7.07-7.10 (m, 4H), 6.92-6.95 (m, 1H), 5.72 (s, 1H), 4.99-5.02 (m, 1H), 4.58-4.61 (m, 1H), 3.60-3.85 (m, 2H), 2.90-3.10 (m, 2H), 2.68-2.72 (m, 2H), 2.34-2.36 (m, 2H), 2.14-2.17 (m, 3H), 1.14 (s, 4H), 0.69-0.74 (m, 3H). LC/MS (ES, m/z): 638 [M+H]+.

Example PH-93

3-((4-(6-((4-chlorophenyl)(phenyl)methyl)-2-cyclopropyl-1H-benzo[d]imidazol-1-yl)piperidin-1-yl)methyl)benzoic acid

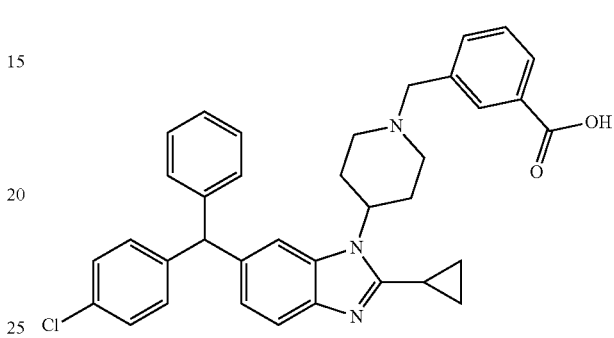

Step 1: Synthesis of methyl 3-fluoro-4-nitrobenzoate

Into a 500-mL round-bottom flask, was placed a solution of 3-fluoro-4-nitrobenzoic acid (20 g, 108.04 mmol, 1.00 equiv) in methanol (300 mL), sulfuric acid (20 mL). The resulting solution was stirred overnight at 70° C. The resulting mixture was concentrated under vacuum. The reaction was then quenched by the addition of water (100 mL). The pH value of the solution was adjusted to pH 7 with NaOH. The resulting solution was extracted with ethyl acetate (3×100 mL) and the organic layers combined, then and dried over anhydrous sodium sulfate and concentrated under vacuum to yield methyl 3-fluoro-4-nitrobenzoate as a light yellow solid. LC/MS (ES, m/z): 200 [M+H]+

Step 2: Synthesis of tert-butyl 4-[[5-(methoxycarbonyl)-2-nitrophenyl]amino]piperidine-1-carboxylate Into a 500-mL round-bottom flask, was placed a solution of methyl 3-fluoro-4-nitrobenzoate (21 g, 105.46 mmol, 1.00 equiv) in CH$_3$CN (300 mL), tert-butyl 4-aminopiperidine-1-carboxylate (25 g, 124.83 mmol, 1.20 equiv) and DIEA (34 g, 263.08 mmol, 2.50 equiv). The resulting solution was stirred overnight at 85° C. The resulting mixture was concentrated under vacuum. The residue was applied onto a silica gel column with ethyl acetate/petroleum ether (1:1) to yield tert-butyl 4-[[5-(methoxycarbonyl)-2-nitrophenyl]amino]piperidine-1-carboxylate as a yellow solid. LC/MS (ES, m/z): 380 [M+H]+.

Step 3: Synthesis of tert-butyl 4-[[2-amino-5-(methoxycarbonyl)phenyl]amino]piperidine-1-carboxylate Into a 500-mL round-bottom flask, was placed a solution of tert-butyl 4-[[5-(methoxycarbonyl)-2-nitrophenyl]amino] piperidine-1-carboxylate (18 g, 47.44 mmol, 1.00 equiv) in methanol (200 mL) and Pd/C (2 g). To the resulting mixture was then introduced H$_2$(g). The resulting solution was stirred overnight at room temperature. The solids were filtered out. The resulting mixture was concentrated under vacuum to yield tert-butyl 4-[[2-amino-5-(methoxycarbonyl)phenyl]amino]piperidine-1-carboxylate as a gray solid. LC/MS (ES, m/z): 350 [M+H]+

Step 4: Synthesis of tert-butyl 4-[[2-cyclopropaneamido-5-(methoxycarbonyl)phenyl]amino]piperidine-1-carboxylate Into a 500-mL round-bottom flask, was placed a solution of tert-butyl 4-[[2-amino-5-(methoxycarbonyl)phenyl]amino]piperidine-1-carboxylate (15 g, 42.93 mmol, 1.00 equiv) in dichloromethane (300 mL) and triethylamine (13 g, 128.47 mmol, 3.00 equiv). To the mixture was then added cyclopropanecarbonyl chloride (4.47 g, 42.76 mmol, 1.00 equiv) dropwise with stirring at 0° C. The resulting solution was stirred overnight at room temperature. The resulting mixture was concentrated under vacuum to yield tert-butyl 4-[[2-cyclopropaneamido-5-(methoxycarbonyl)phenyl]amino]piperidine-1-carboxylate as a gray solid. LC/MS (ES, m/z): 418 [M+H]+

Step 5: Synthesis of methyl 2-cyclopropyl-1-(piperidin-4-yl)-1H-1,3-benzodiazole-6-carboxylate Into a 500-mL round-bottom flask, was placed a solution of tert-butyl 4-[[2-cyclopropaneamido-5-(methoxycarbonyl)phenyl]amino]piperidine-1-carboxylate (20 g, 47.90 mmol, 1.00 equiv) in acetic acid (300 mL). The resulting solution was stirred overnight at room temperature. The resulting mixture was concentrated under vacuum to yield methyl 2-cyclopropyl-1-(piperidin-4-yl)-1H-1,3-benzodiazole-6-carboxylate as brown oil. LC/MS (ES, m/z): 300 [M+H]+

Step 6: Synthesis of methyl 1-[1-[(tert-butoxy)carbonyl]piperidin-4-yl]-2-cyclopropyl-1H-1,3-benzodiazole-6-carboxylate Into a 1000-mL round-bottom flask, was placed a solution of methyl 2-cyclopropyl-1-(piperidin-4-yl)-1H-1,3-benzodiazole-6-carboxylate (17 g, 56.79 mmol, 1.00 equiv) in dichloromethane (300 mL) and a solution of sodium bicarbonate in Water (300 mL). To the mixture was then added di-tert-butyl dicarbonate (15 g, 68.73 mmol, 1.20 equiv) at 0° C. The resulting solution was stirred overnight at room temperature. The resulting solution was extracted with DCM (3×300 mL) and the organic layers combined, then concentrated under vacuum. The residue was applied onto a silica gel column with ethyl acetate/petroleum ether (1:1) to yield methyl 1-[1-[(tert-butoxy)carbonyl]piperidin-4-yl]-2-cyclopropyl-1H-1,3-benzodiazole-6-carboxylate as an off-white solid. LC/MS (ES, m/z): 400 [M+H]+.

Step 7: Synthesis of 4 tert-butyl 4-[2-cyclopropyl-6-[methoxy(methyl)carbamoyl]-1H-1,3-benzodiazol-1-yl]piperidine-1-carboxylate Into a 250-mL round-bottom flask, was placed a solution of methyl 1-[1-[(tert-butoxy)carbonyl]piperidin-4-yl]-2-cyclopropyl-1H-1,3-benzodiazole-6-carboxylate (4.5 g, 11.26 mmol, 1.00 equiv) in tetrahydrofuran (50 mL) and methoxy(methyl)amine hydrochloride (1.31 g, 13.43 mmol, 1.20 equiv). To the mixture was then added LiHMDS (13.5 mL, 1.20 equiv) dropwise with stirring at 0° C. The resulting solution was stirred overnight at room temperature. The mixture was concentrated under vacuum. The residue was applied onto a silica gel column with ethyl acetate/petroleum ether (1:0) to yield 4 tert-butyl 4-[2-cyclopropyl-6-[methoxy(methyl)carbamoyl]-1H-1,3-benzodiazol-1-yl]piperidine-1-carboxylate as yellow oil. LC/MS (ES, m/z): 429 [M+H]+

Step 8: Synthesis of tert-butyl 4-[6-[(4-chlorophenyl)carbonyl]-2-cyclopropyl-1H-1,3-benzodiazol-1-yl]piperidine-1-carboxylate Into a 100-mL round-bottom flask, was placed a solution of tert-butyl 4-[2-cyclopropyl-6-[methoxy(methyl)carbamoyl]-1H-1,3-benzodiazol-1-yl]piperidine-1-carboxylate (4.2 g, 9.80 mmol, 1.00 equiv) in tetrahydrofuran (30 mL) and a solution of bromo(4-chlorophenyl)magnesium (14.7 mL, 1.50 equiv, 1M) in toluene. The resulting solution was stirred overnight at room temperature. The mixture was concentrated under vacuum. The residue was applied onto a silica gel column with ethyl acetate/petroleum ether (9:1) to yield tert-butyl 4-[6-[(4-chlorophenyl)carbonyl]-2-cyclopropyl-1H-1,3-benzodiazol-1-yl]piperidine-1-carboxylate as an off-white solid. LC/MS (ES, m/z): 480 [M+H]+

Step 9: Synthesis of tert-butyl 4-[6-[(4-chlorophenyl)(hydroxy)benzyl]-2-cyclopropyl-1H-1,3-benzodiazol-1-yl]piperidine-1-carboxylate Into a 50-mL 3-necked round-bottom flask purged and maintained with an inert atmosphere of nitrogen, was placed Mg (150 mg, 6.00 equiv), a solution of iodobenzene (1.024 g, 5.02 mmol, 5.00 equiv) in tetrahydrofuran (5 mL) and $I_2$ (a catalytic amount). The mixture was stirred for 3 hour at 60° C. To the mixture was then added a solution of tert-butyl 4-6-[(4-chlorophenyl)carbonyl]-2-cyclopropyl-1H-1,3-benzodiazol-1-ylpiperidine-1-carboxylate (500 mg, 1.04 mmol, 1.00 equiv) in tetrahydrofuran (25 mL) dropwise with stirring. The mixture was stirred for overnight at 25° C. The resulting mixture was concentrated under vacuum. The residue was applied onto a silica gel column with dichloromethane/methanol (1:10) to yield tert-butyl 4-[6-[(4-chlorophenyl)(hydroxy)benzyl]-2-cyclopropyl-1H-1,3-benzodiazol-1-yl]piperidine-1-carboxylate as an off-white solid. LC/MS (ES, m/z): 558 [M+H]+

Step 10: Synthesis of 6-[(4-chlorophenyl)(phenyl)methyl]-2-cyclopropyl-1-(piperidin-4-yl)-1H-1,3-benzodiazole Into a 50-mL round-bottom flask, was placed a solution of tert-butyl 4-[6-[(4-chlorophenyl)(hydroxy)benzyl]-2-cyclopropyl-1H-1,3-benzodiazol-1-yl]piperidine-1-carboxylate (350 mg, 0.63 mmol, 1.00 equiv) in dichloromethane (30 mL), $CF_3COOH$ (6 mL) and $Et_3SiH$ (3 mL). The resulting solution was stirred overnight at room temperature. The resulting mixture was concentrated under vacuum. The reaction was then quenched by the addition of water (50 mL). The resulting solution was extracted with DCM (3×50 mL) and the organic layers combined, then dried over anhydrous sodium sulfate and concentrated under vacuum. The residue was applied onto a silica gel column with dichloromethane/methanol (1:10) to yield 6-[(4-chlorophenyl)(phenyl)methyl]-2-cyclopropyl-1-(piperidin-4-yl)-1H-1,3-benzodiazole as a light yellow solid. LC/MS (ES, m/z): 442 [M+H]+

Step 11: Synthesis of methyl 3-[(4-[6-[(4-chlorophenyl)(phenyl)methyl]-2-cyclopropyl-1H-1,3-benzodiazol-1-yl]piperidin-1-yl)methyl]benzoate Into a 100-mL round-bottom flask, was placed a solution of 6-[(4-chlorophenyl)(phenyl)methyl]-2-cyclopropyl-1-

(piperidin-4-yl)-1H-1,3-benzodiazole (300 mg, 0.68 mmol, 1.00 equiv) in dichloromethane (20 mL), methyl 3-formylbenzoate (112 mg, 0.68 mmol, 1.00 equiv) and triethylamine (catalytic amount). The resulting solution was stirred overnight at room temperature. To the mixture was added NaBH(OAc)₃ (361 mg, 1.70 mmol, 2.50 equiv). The resulting solution was allowed to react, with stirring for an additional 4 h at room temperature. The resulting mixture was concentrated under vacuum. The residue was applied onto a silica gel column with ethyl acetate/petroleum ether (1:1) to yield methyl 3-[(4-[6-[(4-chlorophenyl)(phenyl)methyl]-2-cyclopropyl-1H-1,3-benzodiazol-1-yl]piperidin-1-yl) methyl]benzoate as colorless oil. LC/MS (ES, m/z): 590 [M+H]+

Step 12: Synthesis of yield 3-[(4-[6-[(4-chlorophenyl)(phenyl)methyl]-2-cyclopropyl-1H-1,3-benzodiazol-1-yl]piperidin-1-yl)methyl]benzoic acid Into a 100-mL round-bottom flask, was placed a solution of methyl 3-[(4-[6-[(4-chlorophenyl)(phenyl)methyl]-2-cyclopropyl-1H-1,3-benzodiazol-1-yl]piperidin-1-yl)methyl] benzoate (280 mg, 0.47 mmol, 1.00 equiv) in tetrahydrofuran/MeOH (30/5 mL) and LiOH (30 mL). The resulting solution was stirred overnight at room temperature. The resulting mixture was concentrated under vacuum. The pH value of the solution was adjusted to pH 7 with hydrogen chloride (12 mol/L). The solids were collected by filtration. The product residue (100 mg) was purified by Prep-HPLC with the following conditions (Waters 2767-1): Column, SunFire Prep C18, 5 um, 19*100 mm; mobile phase, 0.03% NH₃.H₂O in water and CH₃CN (50% CH₃CN up to 65% in 8 min); Detector, UV 254 nm to yield 3-[(4-[6-[(4-chlorophenyl)(phenyl)methyl]-2-cyclopropyl-1H-1,3-benzodiazol-1-yl]piperidin-1-yl)methyl]benzoic acid as a white solid.
¹H NMR (300 MHz, DMSO-d6) δ: 12.97 (brs, 1H), 7.85-7.91 (m, 2H), 7.49-7.59 (m, 2H), 7.31-7.42 (m, 6H), 7.21-7.26 (m, 1H), 7.14 (d, J=8.4 Hz, 4H), 6.85 (d, J=9.3 Hz, 1H), 5.80 (s, 1H), 4.56 (brs, 1H), 3.60 (m, 2H), 2.93 (brs, 2H), 2.17-2.43 (m, 5H), 1.775 (s, 2H), 0.95-1.24 (m, 4H). LC/MS (ES, m/z): 576 [M+H]+.

Example PH-94

2,2,2-trifluoroacetic acid compound with 3-((4-(6-((4-chlorophenyl)(4-fluorophenyl)methyl)-2-cyclopropyl-1H-benzo[d]imidazol-1-yl)piperidin-1-yl) methyl)benzoic acid (1:1)

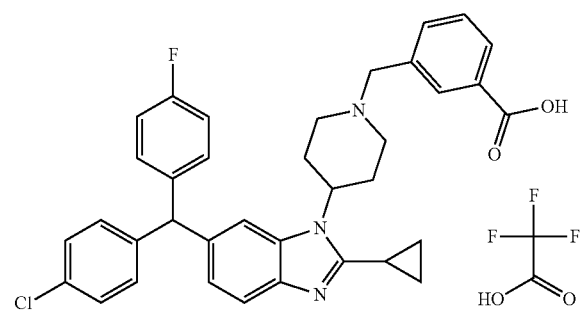

The title compound was prepared according to the procedure as described in Example PH-93 substituting (4-fluorophenyl)magnesium bromide for phenylmagnesium bromide in Step 9.
¹H NMR (300 MHz, CD3OD) δ: 8.24 (s, 1H), 8.19 (d, J=7.8 Hz, 1H), 7.88 (s, 1H), 7.79 (d, J=7.5 Hz, 1H), 7.63-7.68 (m, 2H), 7.24-7.33 (m, 3H), 7.01-7.15 (m, 6H), 5.81 (s, 1H), 5.20-5.29 (m, 1H), 4.49 (s, 2H), 3.74-3.78 (m, 2H), 3.37-3.41 (m, 2H), 2.79-2.91 (m, 2H), 2.49-2.56 (m, 1H), 2.34-2.38 (m, 2H), 1.40-1.49 (m, 2H), 1.30-1.35 (m, 2H). LC/MS: (m/z) 594 [M+H]+

Example PH-95

3-((4-(6-((4-chlorophenyl)(p-tolyl)methyl)-2-cyclopropyl-1H-benzo[d]imidazol-1-yl)piperidin-1-yl) methyl)benzoic acid

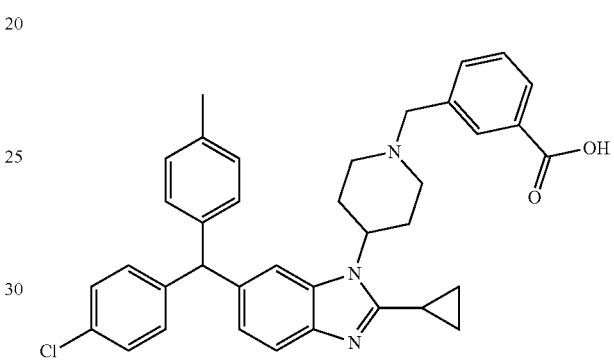

The title compound was prepared according to the procedure as described in Example PH-93 substituting p-tolylmagnesium bromide for phenylmagnesium bromide in Step 9.
¹H NMR (300 MHz, DMSO-d6) δ: 7.85-7.91 (m, 2H), 7.50-7.59 (m, 2H), 7.35-7.41 (m, 4H), 7.11-7.20 (m, 4H), 6.99-7.02 (m, 2H), 6.81 (d, J=8.4 Hz, 1H), 5.74 (s, 1H), 4.50-4.60 (m, 1H), 3.61 (s, 2H), 2.85-3.00 (m, 2H), 2.17-2.29 (m, 8H), 1.77-1.81 (m, 2H), 0.98-1.05 (m, 4H). LC/MS (ES, m/z): 590 [M+H]+.

Example PH-96

2,2,2-trifluoroacetic acid compound with 3-((4-(6-((4-chlorophenyl)(4-(trifluoromethyl)phenyl) methyl)-2-cyclopropyl-1H-benzo[d]imidazol-1-yl) piperidin-1-yl)methyl)benzoic acid (1:1)

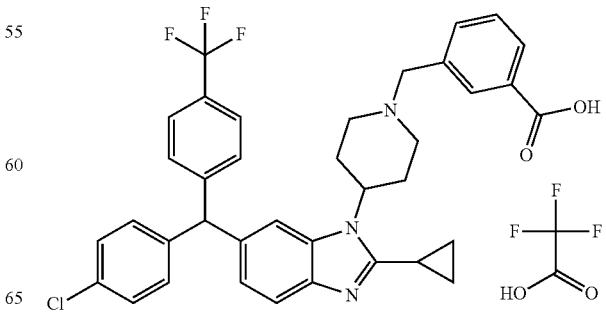

The title compound was prepared according to the procedure as described in Example PH-93 substituting (4-(trifluoromethyl)phenyl)magnesium bromide for phenylmagnesium bromide in Step 9.

1H NMR (300 MHz, CD3OD) δ 9.96 (s, 1H), 8.17-8.25 (m, 1H), 7.92-7.96 (m, 1H), 7.79-7.82 (d, J=7.5 Hz), 7.61-7.68 (m, 4H), 7.24-7.35 (m, 5H), 7.10-7.13 (m, 2H), 5.91 (s, 1H), 5.08-5.31 (m, 1H), 4.50 (s, 1H), 3.69-3.79 (m, 2H), 3.38-3.42 (m, 2H), 2.87-2.99 (m, 2H), 2.52-2.60 (m, 1H), 2.26-2.39 (m, 2H), 1.40-1.47 (m, 2H), 1.33 (m, 2H). LC/MS (ES, m/z): 644 [M+H]+.

Example PH-97

2,2,2-trifluoroacetic acid compound with 3-((4-(6-(bis(4-fluorophenyl)methyl)-2-cyclopropyl-1H-benzo[d]imidazol-1-yl)piperidin-1-yl)methyl)benzoic acid (1:1)

The title compound was prepared according to the procedure as described in Example PH-93 substituting (4-fluorophenyl)magnesium bromide for (4-chlorophenyl)magnesium bromide in Step 8, and substituting (4-fluorophenyl)magnesium bromide for phenylmagnesium bromide in Step 9.

$^1$H NMR (300 MHz, CD3OD) δ 8.25 (s, 1H), 8.19 (d, J=8.7 Hz, 1H), 7.89 (s, 1H), 7.79-7.81 (m, 1H), 7.63-7.68 (m, 2H), 7.24-7.73 (m, 1H), 7.01-7.14 (m, 8H), 5.82 (s, 1H), 5.21-5.25 (m, 1H), 4.49 (s, 2H), 3.74-3.78 (m, 2H), 3.32-3.42 (m, 2H), 2.80-2.91 (m, 2H), 2.49-2.54 (m, 1H), 2.34-2.38 (m, 2H), 1.38-1.46 (m, 2H), 1.29-1.34 (m, 2H). LC/MS (ES, m/z): 578 [M+H]+.

Example PH-98

2,2,2-trifluoroacetic acid compound with 3-((4-(2-cyclopropyl-6-(dip-tolylmethyl)-1H-benzo[d]imidazol-1-yl)piperidin-1-yl)methyl)benzoic acid (1:1)

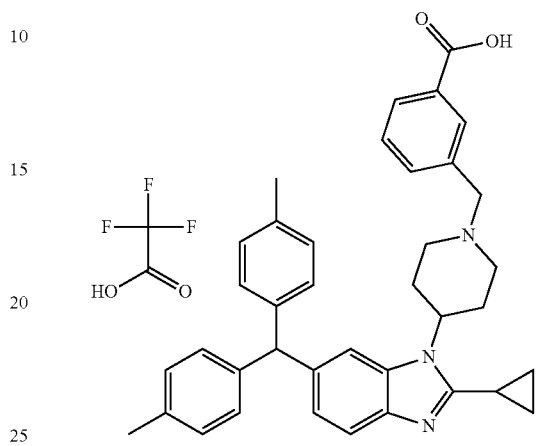

The title compound was prepared according to the procedure as described in Example PH-93 substituting p-tolylmagnesium bromide for (4-chlorophenyl)magnesium bromide in Step 8.

$^1$H NMR (300 MHz, CD3OD) δ: 8.18-8.23 (m, 2H), 7.87 (s, 1H), 7.78-7.80 (m, 1H), 7.60-7.68 (m, 2H), 7.28 (d, J=8.7 Hz, 1H), 7.08-7.11 (m, 4H), 6.95-6.98 (m, 4H), 5.72 (s, 1H), 5.23-5.27 (m, 1H), 4.48 (s, 2H), 3.740-3.78 (m, 2H), 3.32-3.43 (m, 2H), 2.79-2.87 (m, 2H), 2.50-2.58 (m, 1H), 2.35-2.39 (m, 2H), 2.29 (s, 6H), 1.42-1.48 (m, 2H), 1.35-1.39 (m, 2H). LC/MS (ES, m/z): 570 [M+H]+.

Example PH-99

2,2,2-trifluoroacetic acid compound with 3-((4-(2-(2-aminoethyl)-6-(bis(4-chlorophenyl)methyl)-1H-benzo[d]imidazol-1-yl)piperidin-1-yl)methyl)benzoic acid (1:1)

Step 1: Synthesis of ethyl 3-([4-[1,1-bis(4-chlorophenyl)-2-methoxy-2-oxoethyl]-2-[(piperidin-4-yl)amino]phenyl]carbamoyl)propanoate Into a 250-mL round-bottom flask, was placed a solution of tert-butyl 4-([2-amino-5-[1,1-bis(4-chlorophenyl)-2-methoxy-2-oxoethyl]phenyl]amino)piperidine-1-carboxylate (3.7 g, 6.33 mmol, 1.00 equiv) in dichloromethane (30 mL), ethyl 4-chloro-4-oxobutanoate (1.25 g, 7.59 mmol, 1.20 equiv) and triethylamine (1.9 g, 18.78 mmol, 3.00 equiv). The resulting solution was stirred overnight at room temperature. The resulting mixture was concentrated under vacuum to yield ethyl 3-([4-[1,1-bis(4-chlorophenyl)-2-methoxy-2-oxoethyl]-2-[(piperidin-4-yl)amino]phenyl]carbamoyl)propanoate as brown oil. LC/MS (ES, m/z): 613 [M+H]+.

Step 2: Synthesis of tert-butyl 4-[6-[1,1-bis(4-chlorophenyl)-2-methoxy-2-oxoethyl]-2-(3-ethoxy-3-oxopropyl)-1H-1,3-benzodiazol-1-yl]piperidine-1-carboxylate Into a 250-mL round-bottom flask, was placed a solution of ethyl 3-([4-[1,1-bis(4-chlorophenyl)-2-methoxy-2-oxoethyl]-2-[(piperidin-4-yl)amino]phenyl]carbamoyl)propanoate (5 g, 8.16 mmol, 1.00 equiv) in dichloromethane (50 mL), di-tert-butyl dicarbonate (2.14 g, 9.81 mmol, 1.20 equiv) and a saturated solution of sodium bicarbonate/$H_2O$ (50 mL). The resulting solution was stirred for 6 h at room temperature. The resulting mixture was concentrated under vacuum. The resulting solution was extracted with ethyl acetate (3×100 mL) and the organic layers combined, then dried over anhydrous sodium sulfate and concentrated under vacuum to yield tert-butyl 4-[6-[1,1-bis(4-chlorophenyl)-2-methoxy-2-oxoethyl]-2-(3-ethoxy-3-oxopropyl)-1H-1,3-benzodiazol-1-yl]piperidine-1-carboxylate as brown oil. LC/MS (ES, m/z): 695 [M+H]+.

Step 3: Synthesis of 3-[6-[bis(4-chlorophenyl)(carboxy)methyl]-1-[1-[(tert-butoxy)carbonyl]piperidin-4-yl]-1H-1,3-benzodiazol-2-yl]propanoic acid Into a 250-mL round-bottom flask, was placed a solution of tert-butyl 4-[6-[1,1-bis(4-chlorophenyl)-2-methoxy-2-oxoethyl]-2-(3-ethoxy-3-oxopropyl)-1H-1,3-benzodiazol-1-yl]piperidine-1-carboxylate (5 g, 7.20 mmol, 1.00 equiv) in tetrahydrofuran/MeOH (50/20 mL) and sodium hydroxide (20 mL). The resulting solution was stirred overnight at 50° C. The resulting mixture was concentrated under vacuum. The pH value of the solution was adjusted to pH 6 with hydrogen chloride (12 mol/L). The solids were collected by filtration to yield 3-[6-[bis(4-chlorophenyl)(carboxy)methyl]-1-[1-[(tert-butoxy)carbonyl]piperidin-4-yl]-1H-1,3-benzodiazol-2-yl]propanoic acid as a brown solid. LC/MS (ES, m/z): 653 [M+H]+.

Step 4: Synthesis of 3-[6-[bis(4-chlorophenyl)methyl]-1-[1-[(tert-butoxy)carbonyl]piperidin-4-yl]-1H-1,3-benzodiazol-2-yl]propanoic acid Into a 250-mL round-bottom flask, was placed a solution of 3-[6-[bis(4-chlorophenyl)(carboxy)methyl]-1-[1-[(tert-butoxy)carbonyl]piperidin-4-yl]-1H-1,3-benzodiazol-2-yl]propanoic acid (4 g, 6.13 mmol, 1.00 equiv) in toluene (50 ml) and DBU (5.6 g, 22.23 mmol, 6.00 equiv). The resulting solution was stirred for 3 h at 90° C. The resulting mixture was concentrated under vacuum. The residue was applied onto a silica gel column with DCM:MeOH (10:1) to yield 3-[6-[bis(4-chlorophenyl)methyl]-1-[1-[(tert-butoxy)carbonyl]piperidin-4-yl]-1H-1,3-benzodiazol-2-yl]propanoic acid as a solid. LC/MS (ES, m/z): 609 [M+H]+.

Step 5: Synthesis of 3-[6-[bis(4-chlorophenyl)methyl]-1-(piperidin-4-yl)-1H-1,3-benzodiazol-2-yl]propanoic acid Into a 250-mL round-bottom flask, was placed a solution of 3-[6-[bis(4-chlorophenyl)methyl]-1-[1-[(tert-butoxy)carbonyl]piperidin-4-yl]-1H-1,3-benzodiazol-2-yl]propanoic acid (1.2 g, 1.97 mmol, 1.00 equiv) in dichloromethane (30 ml) and trifluoroacetic acid (5 mL), (30 L). The resulting solution was stirred overnight at room temperature. The resulting mixture was concentrated under vacuum. The product residue (1.2 g) was purified by Flash-Prep-HPLC with the following conditions (CombiFlash-1): Column, C18 silica gel; mobile phase, water and $CH_3CN$ ($CH_3CN$ 10% up to 60% in 6 min; Detector, UV 254 nm. 700 mg product was obtained to yield 3-[6-[bis(4-chlorophenyl)methyl]-1-(piperidin-4-yl)-1H-1,3-benzodiazol-2-yl]propanoic acid as a yellow solid. LC/MS (ES, m/z): 508 [M+H]+.

Step 6: Synthesis of 3-[6-[bis(4-chlorophenyl)methyl]-1-(1-[[3-(methoxycarbonyl)phenyl]methyl]piperidin-4-yl)-1H-1,3-benzodiazol-2-yl]propanoic acid Into a 50-mL round-bottom flask, was placed a solution of 3-[6-[bis(4-chlorophenyl)methyl]-1-(piperidin-4-yl)-1H-1,3-benzodiazol-2-yl]propanoic acid (350 mg, 0.69 mmol, 1.00 equiv) in methanol (10 ml), methyl 3-formylbenzoate (136 mg, 0.83 mmol, 1.20 equiv), acetic acid (a catalytic amount) and $NaBH_3(CN)$ (130 mg, 3.00 equiv). The resulting solution was stirred overnight at room temperature. The resulting mixture was concentrated under vacuum. The residue was applied onto a silica gel column with DCM:MeOH (10:1) to yield 3-[6-[bis(4-chlorophenyl)methyl]-1-(1-[[3-(methoxycarbonyl)phenyl]methyl]piperidin-4-yl)-1H-1,3-benzodiazol-2-yl]propanoic acid as a white solid. LC/MS (ES, m/z): 656.6 [M+H]+.

Step 7: Synthesis of 254 nm 3-([4-[2-(2-aminoethyl)-6-[bis(4-chlorophenyl)methyl]-1H-1,3-benzodiazol-1-yl]piperidin-1-yl]methyl)benzoic acid; trifluoroacetic acid Into a 50-mL round-bottom flask, was placed a solution of 3-[6-[bis(4-chlorophenyl)methyl]-1-(1-[[3-(methoxycarbonyl)phenyl]methyl]piperidin-4-yl)-1H-1,3-benzodiazol-2-yl]propanoic acid (140 mg, 0.21 mmol, 1.00 equiv) in benzene (20 mL), DPPA (65 mg, 0.24 mmol, 1.10 equiv) and triethylamine (26 mg, 0.26 mmol, 1.20 equiv). The resulting solution was stirring for 2 h at reflux. The resulting solution was diluted with ethyl acetate (20 mL). The resulting mixture was washed with water (1×20 mL) and then brine (1×20 mL). The resulting mixture was concentrated under vacuum. To the resulting mixture was then added LiOH (10 mL, 1M) and tetrahydrofuran (20 mL). The resulting solution was stirred overnight at room temperature. The resulting solution was extracted with ethyl acetate (2×20 mL) and the organic layers combined. The resulting solution was extracted with DCM (2×20 mL) and the organic layers combined and concentrated under vacuum. The product residue was purified by Prep-HPLC with the following conditions (Waters 2767-1): Column, SunFire Prep C18, 5 um, 19*100 mm; mobile phase, 0.05% TFA in water and CH₃CN (45% CH₃CN up to 75% in 9 min); Detector, UV 254 nm 3-([4-[2-(2-aminoethyl)-6-[bis(4-chlorophenyl)methyl]-1H-1,3-benzodiazol-1-yl]piperidin-1-yl]methyl)benzoic acid; trifluoroacetic acid as a white solid.

$^1$H NMR (300 MHz, CD3OD) δ: 8.25 (s, 1H), 8.19-8.17 (d, J=7.5 Hz, 1H), 7.86-7.80 (m, 2H), 7.62-7.68 (m, 2H), 7.28-7.33 (m, 4H), 7.02-7.11 (m, 4H), 6.94 (d, J=3.6 Hz, 1H), 5.77 (s, 1H), 4.50 (s, 2H), 3.59-3.82 (m, 2H), 3.31-3.53 (m, 6H), 2.78-2.98 (m, 2H), 1.30-1.36 (m, 2H). LC/MS (ES, m/z): 613[M+H]+.

Example PH-100

4-((1s,4s)-4-(6-(bis(4-chlorophenyl)methyl)-2-cyclopropyl-1H-benzo[d]imidazol-1-yl)cyclohexylamino)benzoic acid

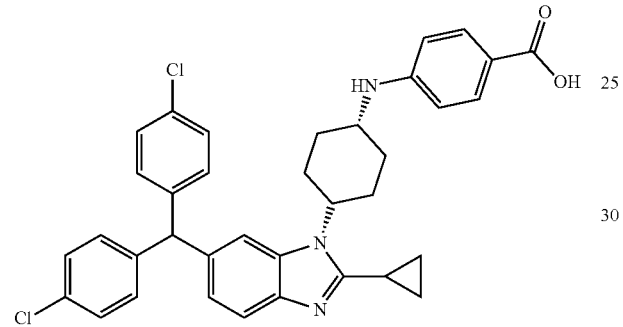

Step 1: Synthesis of methyl 2,2-bis(4-chlorophenyl)-2-(4-nitro-3-[[(1s,4s)-4-[[(tert-butoxy)carbonyl]amino]cyclohexyl]amino]phenyl)acetate Into a 500-mL round-bottom flask, was placed a solution of methyl 2,2-bis(4-chlorophenyl)-2-(3-fluoro-4-nitrophenyl)acetate (10 g, 23.03 mmol, 1.00 equiv) in CH₃CN (300 mL), tert-butyl N-[(1s,4s)-4-aminocyclohexyl]carbamate (5.44 g, 25.38 mmol, 1.10 equiv) and DIEA (14.8 g, 114.52 mmol, 4.97 equiv). The resulting solution was stirred overnight at 85° C. The resulting mixture was concentrated under vacuum. The residue was applied onto a silica gel column with ethyl acetate/petroleum ether (0:100-100:0) to yield methyl 2,2-bis(4-chlorophenyl)-2-(4-nitro-3-[[(1s,4s)-4-[[(tert-butoxy)carbonyl]amino]cyclohexyl]amino]phenyl)acetate as yellow oil. LC/MS (ES, m/z): 629 [M+H]+.

Step 2: Synthesis of yield methyl 2-(4-amino-3-[[(1s,4s)-4-[[(tert-butoxy)carbonyl]amino]cyclohexyl]amino]phenyl)-2,2-bis(4-chlorophenyl)acetate Into a 1000-mL round-bottom flask, was placed a solution of methyl 2,2-bis(4-chlorophenyl)-2-(4-nitro-3-[[(1s,4s)-4-[[(tert-butoxy)carbonyl]amino]cyclohexyl]amino]phenyl) acetate (9 g, 14.32 mmol, 1.00 equiv) in methanol/THF (400/50 mL) and Raney Ni (832 mg, 14.34 mmol, 1.00 equiv). To the reaction mixture was then introduced hydrogen. The resulting solution was stirred overnight at room temperature. The solids were filtered out. The resulting mixture was concentrated under vacuum to yield methyl 2-(4-amino-3-[[(1s,4s)-4-[[(tert-butoxy)carbonyl]amino]cy-clohexyl]amino]phenyl)-2,2-bis(4-chlorophenyl)acetate as light yellow oil. LC/MS (ES, m/z): 598.5 [M+H]+.

Step 3: Synthesis of methyl 2,2-bis(4-chlorophenyl)-2-(4-cyclopropaneamido-3-[[(1s,4s)-4-[[(tert-butoxy)carbonyl]amino]cyclohexyl]amino]phenyl)acetate Into a 500-mL round-bottom flask, was placed a solution of methyl 2-(4-amino-3-[[(1s,4s)-4-[[(tert-butoxy)carbonyl]amino]cyclohexyl]amino]phenyl)-2,2-bis(4-chlorophenyl)acetate (7.9 g, 13.20 mmol, 1.00 equiv) in dichloromethane (300 mL), triethylamine (4 g, 39.53 mmol, 3.00 equiv) and cyclopropanecarbonyl chloride (1.65 g, 15.78 mmol, 1.20 equiv). The resulting solution was stirred overnight at room temperature. The resulting mixture was concentrated under vacuum to yield methyl 2,2-bis(4-chlorophenyl)-2-(4-cyclopropaneamido-3-[[(1s,4s)-4-[[(tert-butoxy)carbonyl]amino]cyclohexyl]amino]phenyl)acetate as light yellow oil. LC/MS (ES, m/z): 667 [M+H]+.

Step 4: Synthesis of methyl 2,2-bis(4-chlorophenyl)-2-[2-cyclopropyl-1-[(1s,4s)-4-[[(tert-butoxy)carbonyl]amino]cyclohexyl]-1H-1,3-benzodiazol-6-yl]acetate Into a 500-mL round-bottom flask, was placed methyl 2,2-bis(4-chlorophenyl)-2-(4-cyclopropaneamido-3-[[(1s,4s)-4-[[(tert-butoxy)carbonyl]amino]cyclohexyl]amino]phenyl)acetate (8 g, 12.00 mmol, 1.00 equiv) and acetic acid (350 mL). The resulting solution was stirred for 3 h at 120° C. The resulting mixture was concentrated under vacuum. The residue was applied onto a silica gel column with ethyl acetate/petroleum ether (0:100-100:0) to yield methyl 2,2-bis(4-chlorophenyl)-2-[2-cyclopropyl-1-[(1s,4s)-4-[[(tert-butoxy)carbonyl]amino]cyclohexyl]-1H-1,3-benzodiazol-6-yl]acetate as colorless oil.

Step 5: Synthesis of yield 2,2-bis(4-chlorophenyl)-2-[2-cyclopropyl-1-[(1s,4s)-4-[[(tert-butoxy)carbonyl]amino]cyclohexyl]-1H-1,3-benzodiazol-6-yl] acetic acid Into a 1000-mL round-bottom flask, was placed a solution of methyl 2,2-bis(4-chlorophenyl)-2-[2-cyclopropyl-1-[(1s,4s)-4-[[(tert-butoxy)carbonyl]amino]cyclohexyl]-1H-1,3-benzodiazol-6-yl]acetate (7.2 g, 11.10 mmol, 1.00 equiv) in tetrahydrofuran/MeOH (300/50 mL) and sodium hydroxide (55.5 mL). The resulting solution was stirred overnight at 50° C. The resulting mixture was concentrated under vacuum. The residue was dissolved in ethyl acetate (300 mL). The resulting mixture was washed with water (3×300 mL). The organic phase was dried over anhydrous sodium sulfate and concentrated under vacuum to yield 2,2-bis(4-chlorophenyl)-2-[2-cyclopropyl-1-[(1s,4s)-4-[[(tert-butoxy)carbonyl]amino]cyclohexyl]-1H-1,3-benzodiazol-6-yl]acetic acid as a white solid. LC/MS (ES, m/z): 635 [M+H]+.

Step 6: Synthesis of tert-butyl N-[(1s,4s)-4-[6-[bis(4-chlorophenyl)methyl]-2-cyclopropyl-1H-1,3-benzodiazol-1-yl]cyclohexyl]carbamate Into a 500-mL round-bottom flask, was placed a solution of 2,2-bis(4-chlorophenyl)-2-[2-cyclopropyl-1-[(1s,4s)-4-

[[(tert-butoxy)carbonyl]amino]cyclohexyl]-1H-1,3-benzo-diazol-6-yl]acetic acid (6.5 g, 10.24 mmol, 1.00 equiv) in toluene (200 mL) and DBU (9.36 g, 61.48 mmol, 6.00 equiv). The resulting solution was stirred for 3 h at 90° C. The resulting mixture was concentrated under vacuum. The residue was dissolved in ethyl acetate (300 mL). The resulting mixture was washed with water (3×300 mL). The organic phase was dried over anhydrous sodium sulfate and concentrated under vacuum to yield tert-butyl N-[(1s,4s)-4-[6-[bis(4-chlorophenyl)methyl]-2-cyclopropyl-1H-1,3-benzodiazol-1-yl]cyclohexyl]carbamate as colorless oil. LC/MS (ES, m/z): 591 [M+H]+.

Step 7: Synthesis of (1s,4s)-4-[6-[bis(4-chlorophenyl)methyl]-2-cyclopropyl-1H-1,3-benzodiazol-1-yl]cyclohexan-1-amine Into a 100-mL round-bottom flask, was placed a solution of tert-butyl N-[(1s,4s)-4-[6-[bis(4-chlorophenyl)methyl]-2-cyclopropyl-1H-1,3-benzodiazol-1-yl]cyclohexyl]carbamate (5.7 g, 9.65 mmol, 1.00 equiv) in dichloromethane (50 mL) and trifluoroacetic acid (10 mL). The resulting solution was stirred overnight at room temperature. The resulting mixture was concentrated under vacuum. The residue was dissolved in DCM (100 mL). The resulting mixture was washed with sat. sodium bicarbonate (3×50 mL). The organic phase was dried over anhydrous sodium sulfate and concentrated under vacuum. The product residue was purified by re-crystallization from DCM to yield (1s,4s)-4-[6-[bis(4-chlorophenyl)methyl]-2-cyclopropyl-1H-1,3-benzodiazol-1-yl]cyclohexan-1-amine as a white solid. LC/MS (ES, m/z): 490 [M+H]+.

Step 8: Synthesis of methyl 4-[(4-[6-[bis(4-chlorophenyl)methyl]-2-cyclopropyl-1H-1,3-benzodiazol-1-yl]cyclohexyl)amino]benzoate Into a 100-mL round-bottom flask, was placed 4-[6-[bis(4-chlorophenyl)methyl]-2-cyclopropyl-1H-1,3-benzodiazol-1-yl]cyclohexan-1-amine (400 mg, 0.82 mmol, 1.00 equiv), methyl 4-bromobenzoate (352 mg, 1.64 mmol, 2.00 equiv), Pd$_2$(dba)$_3$.CHCl$_3$ (126 mg, 0.12 mmol, 0.15 equiv), X-phos (58 mg, 0.12 mmol, 0.15 equiv), Cs$_2$CO$_3$ (1.064 g, 3.27 mmol, 4.00 equiv) and toluene (20 mL). The resulting solution was stirred overnight at 90° C. in an oil bath. The reaction progress was monitored by LC-MS. The solids were filtered out. The resulting solution was extracted with ethyl acetate (3×30 mL) and the organic layers combined, then dried over anhydrous sodium sulfate and concentrated under vacuum. The residue was applied onto a silica gel column with ethyl acetate/petroleum ether (1/2) to yield methyl 4-[(4-[6-[bis(4-chlorophenyl)methyl]-2-cyclopropyl-1H-1,3-benzodiazol-1-yl]cyclohexyl)amino]benzoate as light yellow oil. LC/MS (ES, m/z): 625 [M+H]+.

Step 9: Synthesis of 4-[(4-[6-[bis(4-chlorophenyl)methyl]-2-cyclopropyl-1H-1,3-benzodiazol-1-yl]cyclohexyl)amino]benzoic acid Into a 100-mL round-bottom flask, was placed methyl 4-[(4-[6-[bis(4-chlorophenyl)methyl]-2-cyclopropyl-1H-1,3-benzodiazol-1-yl]cyclohexyl)amino]benzoate (270 mg, 0.43 mmol, 1.00 equiv), tetrahydrofuran (15 mL), water (15 mL), methanol (3 mL) and LiOH.H$_2$O (909 mg, 21.66 mmol, 50.00 equiv). The resulting solution was stirred overnight at room temperature. The reaction progress was monitored by LC-MS. The pH value of the solution was adjusted to pH 7.0 with hydrogen chloride solution (1 mol/L). The resulting solution was extracted with ethyl acetate (3×30 mL) and the organic layers combined and concentrated under vacuum. The residue was applied onto a silica gel column with dichloromethane/methanol (13/1). The product residue was purified by Prep-HPLC with the following conditions (Waters (2767-1)): Column, Sunfire Prep C18, 5 um, 19*100 mm; mobile phase, 0.05% NH$_4$HCO$_3$ in Water and CH$_3$CN (10% CH$_3$CN up to 55% in 13 min); Detector, UV 254 nm to yield 4-[(4-[6-[bis(4-chlorophenyl)methyl]-2-cyclopropyl-1H-1,3-benzodiazol-1-yl]cyclohexyl)amino]benzoic acid as a white solid.

$^1$H NMR (300 MHz, DMSO-d6) δ: 11.96 (s, 1H), 7.69 (d, J=8.7 Hz, 2H), 7.61 (s, 1H), 7.33-7.42 (m, 5H), 7.13-7.15 (d, J=8.4 Hz, 4H), 6.59-6.80 (m, 4H), 5.74 (s, 1H), 4.65-4.65 (m, 1H), 3.73 (s, 1H), 2.29-2.33 (m, 1H), 2.01-2.07 (m, 2H), 1.77-1.85 (m, 2H), 1.65-1.69 (m, 2H), 0.99-1.04 (m, 4H). LC/MS (ES, m/z): 610 [M+H]+.

Example PH-101

2,2,2-trifluoroacetic acid compound with 4-((1r,4r)-4-(6-(bis(4-chlorophenyl)methyl)-2-cyclopropyl-1H-benzo[d]imidazol-1-yl)cyclohexylamino)benzoic acid

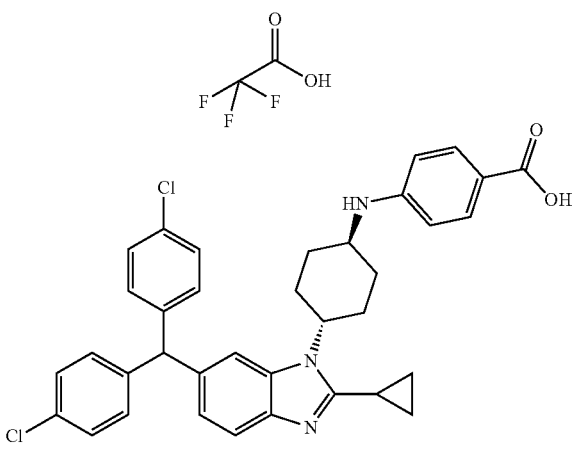 [SMILES: O=C(O)C(F)(F)F ; O=C(O)c1ccc(N[C@H]2CC[C@H](n3c(C4CC4)nc4ccc(C(c5ccc(Cl)cc5)c5ccc(Cl)cc5)cc43)CC2)cc1]

The title compound was prepared according to the procedure as described in Example PH-100 substituting tert-butyl N-[(1r, 4r)-4-aminocyclohexyl]carbamate for tert-butyl N-[(1s,4s)-4-aminocyclohexyl]carbamate in Step 1.

$^1$H NMR (400 MHz, DMSO) δ: 7.94 (s, 1H), 7.64-7.72 (m, 3H), 7.43 (d, J=8.4 Hz, 4H), 7.15-7.20 (m, 5H), 6.64 (d, J=8.8 Hz, 2H), 6.43 (brs, 1H), 5.95 (s, 1H), 4.82-4.84 (m, 1H), 3.48-3.51 (m, 1H), 2.66 (brs, 1H), 2.31-2.40 (m, 2H), 2.12-2.15 (m, 2H), 2.03-2.05 (m, 2H), 1.45-1.54 (m, 2H), 1.15-1.30 (m, 4H). LC/MS (ES, m/z): 610 [M+H]+.

Example PH-102

3-((1r, 4r)-4-(6-(bis(4-chlorophenyl)methyl)-2-cyclopropyl-1H-benzo[d]imidazol-1-yl)cyclohexylamino)phenol 2,2,2-trifluoroacetate

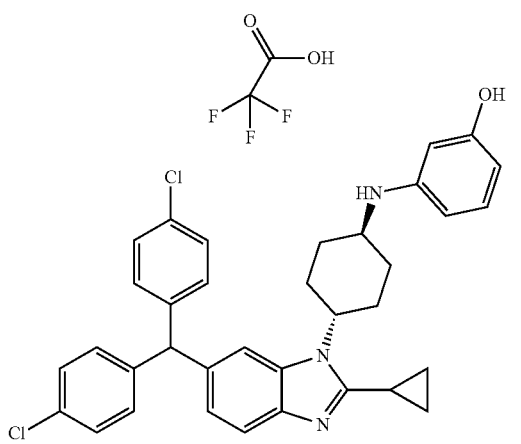 [SMILES: Oc1cccc(N[C@H]2CC[C@H](n3c(C4CC4)nc4ccc(C(c5ccc(Cl)cc5)c5ccc(Cl)cc5)cc43)CC2)c1 ; O=C(O)C(F)(F)F]

Step 1: Synthesis of 3-methoxy-N-[(1r, 4r)-4-[6-[bis(4-chlorophenyl)methyl]-2-cyclopropyl-1H-1,3-benzodiazol-1-yl]cyclohexyl]aniline Into a 100-mL round-bottom flask purged and maintained with an inert atmosphere of nitrogen, was placed a solution of (1r, 4r)-4-[6-[bis(4-chlorophenyl)methyl]-2-cyclopropyl-1H-1,3-benzodiazol-1-yl]cyclohexan-1-amine (400 mg, 0.82 mmol, 1.00 equiv) in Toluene (50 mL), 1-bromo-3-methoxybenzene (228.2 mg, 1.22 mmol, 1.50 equiv), $Pd_2(dba)_3 \cdot CHCl_3$ (127 mg, 0.12 mmol, 0.15 equiv), X-Phos (175 mg, 0.37 mmol, 0.45 equiv) and $Cs_2CO_3$ (2 g, 6.14 mmol, 7.53 equiv). The resulting solution was stirred overnight at 90° C. The resulting solution was diluted with ethyl acetate (50 mL). The resulting mixture was washed with water (3×50 mL). The organic phase was dried over anhydrous sodium sulfate and concentrated under vacuum. The residue was applied onto a silica gel column with ethyl acetate/petroleum ether (0:100-1:1) to yield 3-methoxy-N-[(1r, 4r)-4-[6-[bis(4-chlorophenyl)methyl]-2-cyclopropyl-1H-1,3-benzodiazol-1-yl]cyclohexyl]aniline as yellow oil. LC/MS (ES, m/z): 597 [M+H]+.

Step 2: Synthesis of 3-[[(1r, 4r)-4-[6-[bis(4-chlorophenyl)methyl]-2-cyclopropyl-1H-1,3-benzodiazol-1-yl]cyclohexyl]amino]phenol; trifluoroacetic acid Into a 100-mL round-bottom flask, was placed a solution of 3-methoxy-N-[(1r, 4r)-4-[6-[bis(4-chlorophenyl)methyl]-2-cyclopropyl-1H-1,3-benzodiazol-1-yl]cyclohexyl]aniline (250 mg, 0.42 mmol, 1.00 equiv) in dichloromethane (50 mL). To the mixture was then added $BBr_3$ (1.26 mL) dropwise with stirring at −78° C. The resulting solution was stirred overnight at room temperature. The resulting mixture was concentrated under vacuum. The residue was dissolved in DCM (100 mL). The resulting mixture was washed with sat. $NH_4Cl$ (3×50 mL). The organic phase was dried over anhydrous sodium sulfate and concentrated under vacuum. The product residue was purified by Prep-HPLC with the following conditions (Waters 2767-1): Column, SunFire Prep C18, 5 um, 19*100 mm; mobile phase, 0.05% trifluoroacetic acid in Water and $CH_3CN$ (18% $CH_3CN$ up to 50% in 8 min); Detector, UV 254 nm to yield 3-[[(1r, 4r)-4-[6-[bis(4-chlorophenyl)methyl]-2-cyclopropyl-1H-1,3-benzodiazol-1-yl]cyclohexyl]amino]phenol; trifluoroacetic acid as a white solid.

$^1$H NMR (300 MHz, DMSO-d6) δ: 9.10 (brs, 1H), 7.99 (s, 1H), 7.66 (d, J=8.7 Hz, 1H), 7.41-7.43 (m, 4H), 7.11-7.22 (m, 5H), 6.94-6.95 (m, 1H), 6.04-6.21 (m, 3H), 5.95 (s, 1H), 4.79-4.82 (m, 1H), 3.41-3.43 (m, 1H), 2.63-2.69 (m, 1H), 2.27-2.39 (m, 2H), 2.03-2.15 (m, 4H), 1.46-1.53 (m, 2H), 1.29-1.30 (m, 4H). LC/MS (ES, m/z): 582 [M+H]+.

Example PH-103

6-[bis(4-chlorophenyl)methyl]-2-cyclopropyl-1-[(3-methoxyphenyl)methyl]-1H-1,3-benzodiazole trifluoroacetic acid

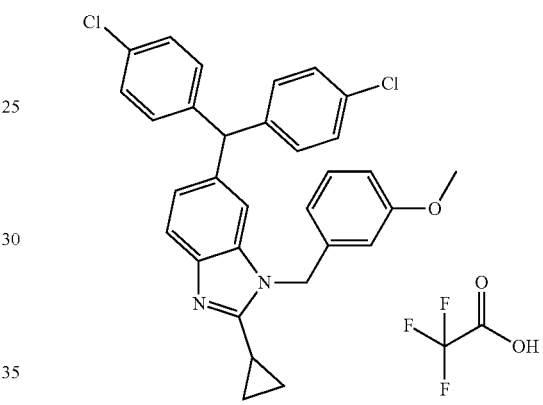

Step 1: Synthesis of methyl 2,2-bis(4-chlorophenyl)-2-(3-[[(3-hydroxyphenyl)methyl]amino]-4-nitrophenyl)acetate Into a 250-mL round-bottom flask, was placed methyl 2,2-bis(4-chlorophenyl)-2-(3-fluoro-4-nitrophenyl)acetate (4 g, 9.21 mmol, 1.00 equiv), (3-methylphenyl)methanamine (1.25 g, 10.32 mmol, 1.12 equiv) and a solution of DIEA (3 g, 23.21 mmol, 2.52 equiv) in $CH_3CN$ (100 mL). The resulting solution was stirred overnight at 75° C. The resulting mixture was concentrated under vacuum. The residue was applied onto a silica gel column with ethyl acetate/petroleum ether (1:5) to yield methyl 2,2-bis(4-chlorophenyl)-2-(3-[[(3-hydroxyphenyl)methyl]amino]-4-nitrophenyl)acetate as an orange solid. LC/MS (ES, m/z): 537 [M+H]+.

Step 2: Synthesis of methyl 2-(4-amino-3-[[(4-hydroxyphenyl)methyl]amino]phenyl)-2,2-bis(4-chlorophenyl)acetate Into a 250-mL round-bottom flask, was placed methyl 2,2-bis(4-chlorophenyl)-2-(3-[[(4-hydroxyphenyl)methyl]amino]-4-nitrophenyl)acetate (3 g, 5.58 mmol, 1.00 equiv) and a solution of Raney Ni (3 g, 1.00 equiv) in methanol (80 mL). To the resulting mixture was then introduced $H_2(g)$. The resulting solution was stirred overnight at room temperature. The solids were filtered out. The resulting mixture was concentrated under vacuum to yield methyl 2-(4-amino- 3-[[(4-hydroxyphenyl)methyl]amino]phenyl)-2,2-bis(4-chlorophenyl)acetate as a brown solid. LC/MS (ES, m/z): 507 [M+H]+.

Step 3: Synthesis of methyl 2,2-bis(4-chlorophenyl)-2-[2-cyclopropyl-1-[(3-hydroxyphenyl)methyl]-1H-1,3-benzodiazol-6-yl]acetate Into a 50-mL round-bottom flask, was placed methyl 2-(4-amino-3-[[(3-hydroxyphenyl)methyl]amino]phenyl)-2,2-bis(4-chlorophenyl)acetate (1 g, 1.97 mmol, 1.00 equiv) and a solution of cyclopropanecarbaldehyde (828 mg, 11.81 mmol, 5.99 equiv) in DMSO (10 mL). The resulting solution was stirred overnight at 50° C. The resulting solution was diluted with ethyl acetate (150 mL). The resulting mixture was washed with aq. sodium chloride (3×50 mL). The organic phase was dried over anhydrous sodium sulfate and concentrated under vacuum. The residue was applied onto a silica gel column with ethyl acetate/petroleum ether (1:1) to yield methyl 2,2-bis(4-chlorophenyl)-2-[2-cyclopropyl-1-[(3-hydroxyphenyl)methyl]-1H-1,3-benzodiazol-6-yl]acetate as a brown solid. LC/MS (ES, m/z): 557.5 [M+H]+.

Step 4: Synthesis of 2,2-bis(4-chlorophenyl)-2-[2-cyclopropyl-1-[(3-hydroxyphenyl)methyl]-1H-1,3-benzodiazol-6-yl]acetic acid Into a 100-mL round-bottom flask, was placed a solution of methyl 2,2-bis(4-chlorophenyl)-2-[2-cyclopropyl-1-[(3-hydroxyphenyl)methyl]-1H-1,3-benzodiazol-6-yl]acetate (700 mg, 1.26 mmol, 1.00 equiv) in tetrahydrofuran (20 mL) and a solution of LiOH.H$_2$O (527 mg, 12.56 mmol, 10.00 equiv) in water (20 mL). The resulting solution was stirred overnight at 50° C. The resulting mixture was concentrated under vacuum. The resulting solution was diluted with water (20 mL). The resulting solution was extracted with ethyl acetate (2×20 mL) and the organic layers combined, then dried in an oven under reduced pressure. and concentrated under vacuum to yield 2,2-bis(4-chlorophenyl)-2-[2-cyclopropyl-1-[(3-hydroxyphenyl)methyl]-1H-1,3-benzodiazol-6-yl]acetic acid as yellow oil. LC/MS (ES, m/z): 543 [M+H]+.

Step 5: Synthesis of 3-([6-[bis(4-chlorophenyl)methyl]-2-cyclopropyl-1H-1,3-benzodiazol-1-yl]methyl)phenol Into a 100-mL round-bottom flask, was placed 2,2-bis(4-chlorophenyl)-2-[2-cyclopropyl-1-[(3-hydroxyphenyl)methyl]-1H-1,3-benzodiazol-6-yl]acetic acid (600 mg, 1.10 mmol, 1.00 equiv) and a solution of DBU (1 g, 6.57 mmol, 6.00 equiv) in toluene (30 mL). The resulting solution was stirred for 2 h at 100° C. The resulting mixture was concentrated under vacuum. The residue was applied onto a silica gel column with ethyl acetate/petroleum ether (1:1) to yield 3-([6-[bis(4-chlorophenyl)methyl]-2-cyclopropyl-1H-1,3-benzodiazol-1-yl]methyl)phenol as a yellow solid.

Step 6: Synthesis of 6-[bis(4-chlorophenyl)methyl]-2-cyclopropyl-1-[(3-methoxyphenyl)methyl]-1H-1,3-benzodiazole trifluoroacetic acid Into a 50-mL round-bottom flask, was placed a solution of 3-([6-[bis(4-chlorophenyl)methyl]-2-cyclopropyl-1H-1,3-benzodiazol-1-yl]methyl)phenol (100 mg, 0.20 mmol, 1.00 equiv) in N,N-dimethylformamide (20 mL), potassium carbonate (83 mg, 0.60 mmol, 3.00 equiv) and iodomethane (32 mg, 0.23 mmol, 1.10 equiv). The resulting solution was stirred overnight at room temperature. The reaction was then quenched by the addition of water (20 mL). The resulting solution was extracted with ethyl acetate (3×20 mL) and the organic layers combined, then dried over anhydrous sodium sulfate and concentrated under vacuum. The product residue was purified by Prep-HPLC with the following conditions (Waters 2767-1): Column, SunFire Prep C18, um, 19*100 mm; mobile phase, water in 0.05% TFA and CH$_3$CN (20% CH$_3$CN up to 45% in 12 min); Detector, UV 254 nm to yield 6-[bis(4-chlorophenyl)methyl]-2-cyclopropyl-1-[(3-methoxyphenyl)methyl]-1H-1,3-benzodiazole trifluoroacetic acid as a white solid.

$^1$H NMR (300 MHz, CDCl3) δ: 7.90 (d, J=8.4 Hz, 1H), 7.21-7.30 (m, 6H), 6.89-6.94 (m, 6H), 6.60-6.62 (m, 2H), 5.60 (s, 1H), 5.42 (s, 2H), 3.78 (s, 3H), 2.07-2.11 (m, 1H), 1.67-1.69 (m, 2H), 1.38-1.43 (m, 2H). LC/MS (ES, m/z): 513 [M+H]+.

Example PH-104

Ethyl 2-[3-([6-[bis(4-chlorophenyl)methyl]-2-cyclopropyl-1H-1,3-benzodiazol-1-yl]methyl)phenoxy]acetate trifluoroacetic acid

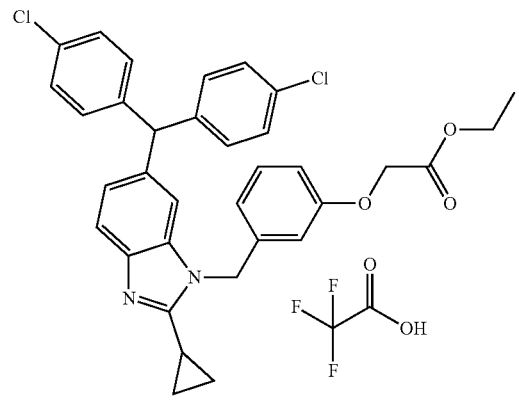

The title compound was prepared according to the procedure as described in Example PH-103 substituting ethyl 2-bromoacetate for (3-methylphenyl)methanamine in Step 6.

$^1$H NMR (300 MHz, CDCl3) δ: 7.90 (d, J=8.7 Hz, 1H), 7.28-7.31 (m, 1H), 7.20-7.25 (m, 5H), 6.84-6.96 (m, 6H), 6.65-6.67 (m, 2H), 5.60 (s, 1H), 5.42 (s, 2H), 4.60 (s, 2H), 4.25 (dd, J1=6.9 Hz, J2=14.1 Hz, 2H), 2.05-2.10 (m, 1H), 1.66-1.67 (m, 2H), 1.37-1.39 (m, 2H), 1.31 (t, J=6.9 Hz, 3H). LC/MS (ES, m/z): 585 [M+H]+.

Example PH-105

4-([6-[bis(4-chlorophenyl)methyl]-2-cyclopropyl-1H-1,3-benzodiazol-1-yl]methyl)phenol hydrochloride

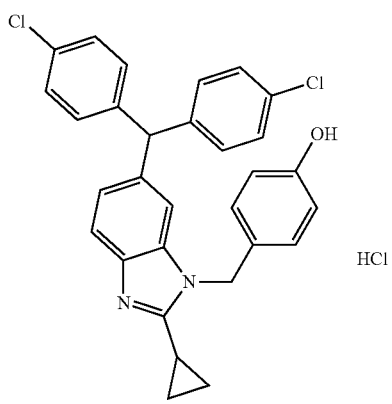 [SMILES: Oc1ccc(Cn2c(C3CC3)nc3ccc(C(c4ccc(Cl)cc4)c4ccc(Cl)cc4)cc32)cc1 ; Cl]

The title compound was prepared according to the procedure as described in Example PH-103 substituting 4-(aminomethyl)phenol for (3-methylphenyl)methanamine in Step 1.

$^1$H NMR (400 MHz, CD3OD) δ: 7.56 (d, J=8.4 Hz, 1H), 7.31 (d, J=8.4 Hz, 4H), 7.23 (d, J=8.4 Hz, 1H), 7.14 (s, 1H), 7.00-7.04 (m, 6H), 6.75 (d, J=8.4 Hz, 2H), 5.73 (s, 1H), 5.51 (s, 1H), 2.47-2.50 (m, 1H), 1.28-1.39 (m, 4H). LC/MS (ES, m/z): 499 [M+H]+.

Example PH-106

6-[bis(4-chlorophenyl)methyl]-2-cyclopropyl-1-(3-methoxyphenyl)-1H-1,3-benzodiazole hydrochloride

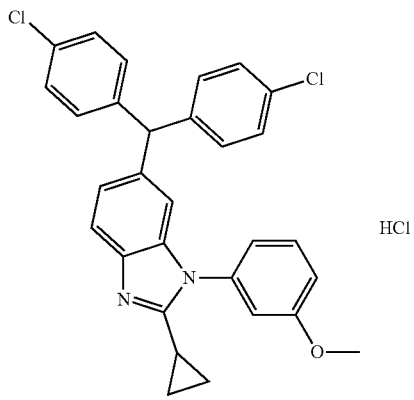 [SMILES: COc1cccc(-n2c(C3CC3)nc3ccc(C(c4ccc(Cl)cc4)c4ccc(Cl)cc4)cc32)c1 ; Cl]

The title compound was prepared according to the procedure as described in Example PH-103 substituting 3-methoxyaniline for (3-methylphenyl)methanamine in Step 1.

$^1$H NMR (400 MHz, CD3OD) δ: 7.56-7.65 (m, 2H), 7.20-7.36 (m, 6H), 7.06-7.15 (m, 6H), 7.00 (s, 1H), 5.76 (s, 1H), 3.85 (s, 1H), 2.11-2.12 (m, 1H), 1.25-1.31 (m, 4H). LC/MS (ES, m/z): 499 [M+H]+.

Example PH-107

3-[6-[bis(4-chlorophenyl)methyl]-2-cyclopropyl-1H-1,3-benzodiazol-1-yl]phenol hydrochloride

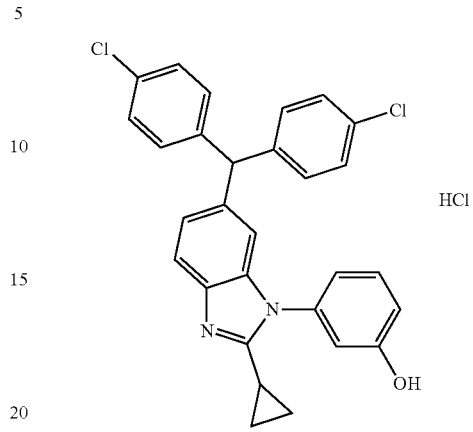

Into a 50-mL round-bottom flask, was placed a solution of 6-[bis(4-chlorophenyl)methyl]-2-cyclopropyl-1-(3-methoxyphenyl)-1H-1,3-benzodiazole (100 mg, 0.20 mmol, 1.00 equiv) in dichloromethane (10 mL). To the mixture was then added BBr$_3$ (500 mg, 1.99 mmol, 9.95 equiv) dropwise with stirring at 0° C. The resulting solution was stirred for 2 h at room temperature. The resulting mixture was concentrated under vacuum. The pH value of the solution was adjusted to pH 8 with sodium bicarbonate. The resulting solution was extracted with ethyl acetate (3×20 mL) and the organic layers combined, then concentrated under vacuum. The product residue was purified by Prep-HPLC with the following conditions (Waters-2767-1): Column, Sunfire prep C18, 5 um, 19*100 mm; mobile phase, 0.05% TFA in water and CH$_3$CN (20% CH$_3$CN up to 65% in 8 min); Detector, UV 254 nm to yield a residue. The CH$_3$CN was evaporated and conc. HCl (1 mL) was added. The mixture was lyophilized to yield 3-[6-[bis(4-chlorophenyl)methyl]-2-cyclopropyl-1H-1,3-benzodiazol-1-yl]phenol hydrochloride as an off-white solid.

$^1$H NMR (400 MHz, CD3OD) δ: 7.68 (d, J=8.4 Hz, 1H), 7.51 (t, J=11.6 Hz, 1H), 7.30-7.42 (m, 5H), 7.00-7.17 (m, 8H), 5.81 (s, 1H), 2.20-2.23 (m, 1H), 1.35-1.48 (m, 4H). LC/MS (ES, m/z): 485 [M+H]+.

Example PH-108

6-[bis(4-chlorophenyl)methyl]-2-cyclopropyl-1-(4-methoxyphenyl)-1H-1,3-benzodiazole hydrochloride

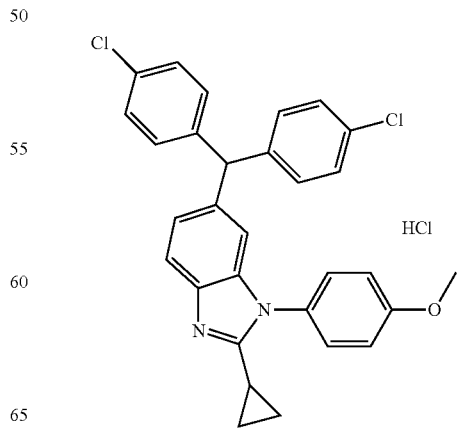

The title compound was prepared according to the procedure as described in Example PH-103 substituting 4-methoxyaniline for (3-methylphenyl)methanamine in Step 1.

1H NMR (400 MHz, CD3OD) δ: 7.56-7.68 (m, 3H), 7.35 (d, J=8.4 Hz, 4H), 7.06-7.21 (m, 8H), 5.84 (s, 1H), 3.84 (s, 3H), 1.94 (m, 1H), 1.15-1.28 (m, 4H). LC/MS (ES, m/z): 499 [M+H]+.

Example PH-109 ethyl 2-(4-[6-[bis(4-chlorophenyl)methyl]-2-cyclopropyl-1H-1,3-benzodiazol-1-yl]phenoxy)acetate hydrochloride

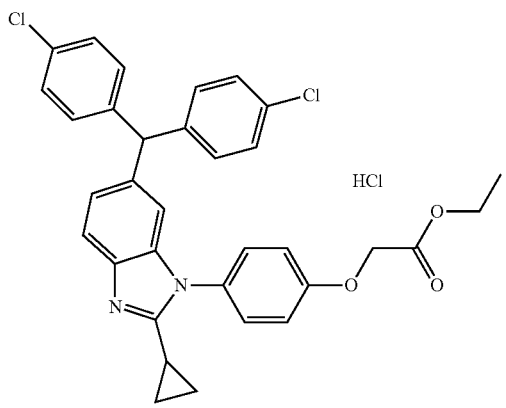 [SMILES: CCOC(=O)COc1ccc(-n2c(C3CC3)nc3ccc(C(c4ccc(Cl)cc4)c4ccc(Cl)cc4)cc32)cc1 ; Cl]

Step 1: Synthesis of 4-[6-[bis(4-chlorophenyl)methyl]-2-cyclopropyl-1H-1,3-benzodiazol-1-yl]phenol hydrochloride Into a 25-mL round-bottom flask, was placed a solution of 6-[bis(4-chlorophenyl)methyl]-2-cyclopropyl-1-(4-methoxyphenyl)-1H-1,3-benzodiazole (100 mg, 0.20 mmol, 1.00 equiv) in dichloromethane (10 mL). To the mixture was then added BBr₃ (500 mg, 1.99 mmol, 9.95 equiv) dropwise with stirring at 0° C. The resulting solution was stirred for 2 h at room temperature. The resulting mixture was concentrated under vacuum. The pH value of the solution was adjusted to pH 8 with sodium bicarbonate. The resulting solution was extracted with ethyl acetate (3×20 mL) and the organic layers combined, then concentrated under vacuum. The product residue was purified by Prep-HPLC with the following conditions (Waters-2767-1): Column, Sunfire prep C18, 5 um, 19*100 mm; mobile phase, 0.05% TFA in water and CH₃CN (22% CH₃CN up to 58% in 8 min); Detector, UV 254 nm to yield a residue. The CH₃CN was evaporated and conc. HCl (1 mL) was added. The mixture was lyophilized to yield 4-[6-[bis(4-chlorophenyl)methyl]-2-cyclopropyl-1H-1,3-benzodiazol-1-yl]phenol hydrochloride as an off-white solid. LC/MS (ES, m/z): 521.8 [M+H]+.

Step 2: Synthesis of ethyl 2-(4-[6-[bis(4-chlorophenyl)methyl]-2-cyclopropyl-1H-1,3-benzodiazol-1-yl]phenoxy)acetate hydrochloride Into a 25-mL round-bottom flask, was placed 4-[6-[bis(4-chlorophenyl)methyl]-2-cyclopropyl-1H-1,3-benzodiazol-1-yl]phenol (97 mg, 0.20 mmol, 1.00 equiv), potassium carbonate (83 mg, 0.60 mmol, 3.01 equiv) and a solution of BrCH₂CO₂CH₂CH₃ (50.1 mg, 0.30 mmol, 1.50 equiv) in N,N-dimethylformamide (5 mL). The resulting solution was stirred for 3 h at room temperature. The resulting solution was diluted with ethyl acetate (50 mL). The resulting mixture was washed with aq. sodium chloride (3×10 mL). The resulting mixture was concentrated under vacuum. The product residue was purified by Prep-HPLC with the following conditions (Waters-2767-1): Column, Sunfire prep C18, 5 um, 19*100 mm; mobile phase, 0.05% TFA in water and CH₃CN (25% CH₃CN up to 60% in 8 min); Detector, UV 254 nm to yield a residue. The CH₃CN was evaporated and conc. HCl (1 mL) was added. The mixture was lyophilized to yield ethyl 2-(4-[6-[bis(4-chlorophenyl)methyl]-2-cyclopropyl-1H-1,3-benzodiazol-1-yl]phenoxy)acetate hydrochloride as an off-white solid.

¹H NMR (400 MHz, CD3OD) δ: 7.70 (d, J=4.0 Hz, 1H), 7.58 (d, J=8.0 Hz, 2H), 7.39-7.51 (m, 1H), 7.31-7.37 (m, 4H), 7.28 (d, J=4.0 Hz, 2H), 7.06-7.09 (m, 5H), 5.79 (s, 1H), 4.95-5.00 (m, 1H), 4.86-4.91 (m, 1H), 4.22-4.32 (m, 2H), 2.14-2.21 (m, 1H), 1.40-1.42 (m, 4H), 1.26-1.34 (m, 3H). LC/MS (ES, m/z): 571 [M+H]+.

Example PH-110

2-(4-[6-[bis(4-chlorophenyl)methyl]-2-cyclopropyl-1H-1,3-benzodiazol-1-yl]phenoxy)acetamide hydrochloride

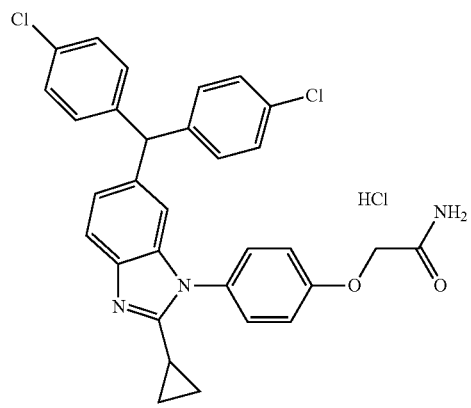 [SMILES: NC(=O)COc1ccc(-n2c(C3CC3)nc3ccc(C(c4ccc(Cl)cc4)c4ccc(Cl)cc4)cc32)cc1 ; Cl]

The title compound was prepared according to the procedure as described in Example PH-3 substituting ethyl 2-(4-(6-(bis(4-chlorophenyl)methyl)-2-cyclopropyl-1H-benzo[d]imidazol-1-yl)phenoxy)acetate for 4-(4-[6-[bis(4-chlorophenyl)methyl]-2-cyclopropyl-1H-1,3-benzodiazol-1-yl]piperidin-1-yl)-4-oxobutanoate.

¹H NMR (400 MHz, CD3OD) δ: 7.72 (d, J=8.4 Hz, 1H), 7.59 (d, J=9.6 Hz, 2H), 7.41 (d, J=8.4 Hz, 1H), 7.25-7.33 (m, 6H), 7.06-7.12 (m, 5H), 5.79 (s, 1H), 4.66 (s, 2H), 2.16-2.23 (m, 1H), 1.39-1.44 (m, 4H). LC/MS (ES, m/z): 542 [M+H]+.

Example PH-111

4-[6-[bis(4-chlorophenyl)methyl]-2-cyclopropyl-1H-1,3-benzodiazol-1-yl]cyclohexane-1-carboxamide; trifluoroacetic acid

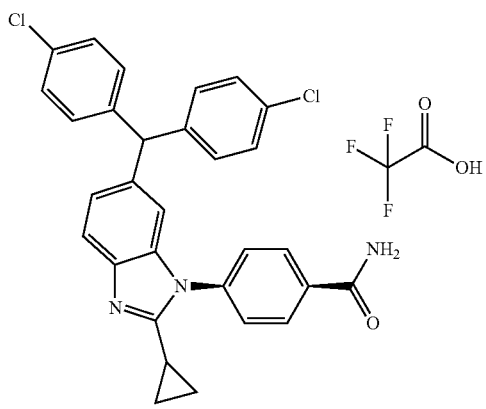

Step 1: Synthesis of methyl 4-([5-[1,1-bis(4-chlorophenyl)-2-methoxy-2-oxoethyl]-2-nitrophenyl]amino)cyclohexane-1-carboxylate Into a 250-mL round-bottom flask, was placed methyl 2,2-bis(4-chlorophenyl)-2-(3-fluoro-4-nitrophenyl)acetate (3 g, 6.91 mmol, 1.00 equiv), methyl 4-aminocyclohexane-1-carboxylate hydrochloride (1.6 g, 8.26 mmol, 1.20 equiv) and a solution of DIEA (4.47 g, 34.59 mmol, 5.01 equiv) in CH$_3$CN (100 mL). The resulting solution was heated to reflux overnight. The resulting mixture was concentrated under vacuum. The product residue was purified by Flash-Prep-HPLC with the following conditions (IntelFlash-1): Column, silica gel; mobile phase, EA:PE=5:100 increasing to EA:PE=20:100 within 50 min; Detector, UV 254 nm to yield methyl 4-([5-[1,1-bis(4-chlorophenyl)-2-methoxy-2-oxoethyl]-2-nitrophenyl]amino)cyclohexane-1-carboxylate as a yellow solid. LC/MS (ES, m/z): 571 [M+H]+.

Step 2: Synthesis of methyl 4-([2-amino-5-[1,1-bis(4-chlorophenyl)-2-methoxy-2-oxoethyl]phenyl]amino)cyclohexane-1-carboxylate Into a 250-mL round-bottom flask, was placed methyl 4-([5-[1,1-bis(4-chlorophenyl)-2-methoxy-2-oxoethyl]-2-nitrophenyl]amino)cyclohexane-1-carboxylate (2 g, 3.50 mmol, 1.00 equiv) and a solution of Raney Ni (3 g, 1.00 equiv) in methanol (80 mL). H$_2$(g) was then introduced into the resulting mixture. The resulting solution was stirred overnight at room temperature. The solids were filtered out. The resulting mixture was concentrated under vacuum to yield methyl 4-([2-amino-5-[1,1-bis(4-chlorophenyl)-2-methoxy-2-oxoethyl]phenyl]amino)cyclohexane-1-carboxylate as a white solid. LC/MS (ES, m/z): 541.5 [M+H]+.

Step 3: Synthesis of methyl 4-[6-[1,1-bis(4-chlorophenyl)-2-methoxy-2-oxoethyl]-2-cyclopropyl-1H-1,3-benzodiazol-1-yl]cyclohexane-1-carboxylate Into a 50-mL round-bottom flask, was placed methyl 4-([2-amino-5-[1,1-bis(4-chlorophenyl)-2-methoxy-2-oxoethyl]phenyl]amino)cyclohexane-1-carboxylate (1.08 g, 1.99 mmol, 1.00 equiv) and a solution of cyclopropanecarbaldehyde (840 mg, 11.98 mmol, 6.01 equiv) in DMSO (10 mL). The resulting solution was stirred overnight at 50° C. The resulting solution was diluted with ethyl acetate (100 mL). The resulting mixture was washed with aq. sodium chloride (3×20 mL). The organic phase was dried over anhydrous sodium sulfate, then concentrated under vacuum. The residue was applied onto a silica gel column with ethyl acetate/petroleum ether (1:2) to yield methyl 4-[6-[1,1-bis(4-chlorophenyl)-2-methoxy-2-oxoethyl]-2-cyclopropyl-1H-1,3-benzodiazol-1-yl]cyclohexane-1-carboxylate as yellow oil. LC/MS (ES, m/z): 592 [M+H]+.

Step 4: Synthesis of 4-[6-[bis(4-chlorophenyl)(carboxy)methyl]-2-cyclopropyl-1H-1,3-benzodiazol-1-yl]cyclohexane-1-carboxylic Into a 50-mL round-bottom flask, was placed a solution of methyl 4-[6-[1,1-bis(4-chlorophenyl)-2-methoxy-2-oxoethyl]-2-cyclopropyl-1H-1,3-benzodiazol-1-yl]cyclohexane-1-carboxylate (900 mg, 1.52 mmol, 1.00 equiv) in tetrahydrofuran (10 mL) and a solution of LiOH.H$_2$O (640 mg, 15.25 mmol, 10.02 equiv) in water (10 mL). The resulting solution was stirred overnight at 50° C. The resulting mixture was concentrated under vacuum. The pH value of the solution was adjusted to pH 3 with hydrogen chloride (1 mol/L). The resulting solution was extracted with ethyl acetate (3×50 mL) and the organic layers combined, then dried over anhydrous sodium sulfate and concentrated under vacuum to yield 4-[6-[bis(4-chlorophenyl)(carboxy)methyl]-2-cyclopropyl-1H-1,3-benzodiazol-1-yl]cyclohexane-1-carboxylic acid as a yellow solid.

Step 5: Synthesis of 4-[6-[bis(4-chlorophenyl)methyl]-2-cyclopropyl-1H-1,3-benzodiazol-1-yl]cyclohexane-1-carboxylic acid trifluoroacetic acid Into a 100-mL round-bottom flask, was placed a solution of 4-[6-[bis(4-chlorophenyl)(carboxy)methyl]-2-cyclopropyl-1H-1,3-benzodiazol-1-yl]cyclohexane-1-carboxylic acid (300 mg, 0.53 mmol, 1.00 equiv) in toluene (10 ml) and DBU (487 mg, 3.20 mmol, 6.00 equiv). The resulting solution was stirred for 3 h at 90° C. The resulting mixture was concentrated under vacuum. The reaction was then quenched by the addition of water (10 mL). The resulting solution was extracted with ethyl acetate (3×10 mL) and the organic layers combined, then dried over anhydrous sodium sulfate and concentrated under vacuum. The product residue was purified by Prep-HPLC with the following conditions (Waters 2767-1): Column, SunFire Prep C18, 5 um, 19*100 mm; mobile phase, 0.05% TFA in water and CH$_3$CN (25% CH$_3$CN up to 45% in 9 min); Detector, UV 254 nm to yield 4-[6-[bis(4-chlorophenyl)methyl]-2-cyclopropyl-1H-1,3-benzodiazol-1-yl]cyclohexane-1-carboxylic acid trifluoroacetic acid as a white solid.

Step 6: Synthesis of 4-[6-[bis(4-chlorophenyl)methyl]-2-cyclopropyl-1H-1,3-benzodiazol-1-yl]cyclohexane-1-carboxamide; trifluoroacetic acid Into a 25-mL round-bottom flask, was placed a solution of 4-[6-[bis(4-chlorophenyl)methyl]-2-cyclopropyl-1H-1,3-benzodiazol-1-yl]cyclohexane-1-carboxylic acid (110 mg, 0.21 mmol, 1.00 equiv) in N,N-dimethylformamide (10 mL), NH$_4$Cl (56 mg, 1.05 mmol, 5.00 equiv), HATU (97 mg, 0.26 mmol, 1.20 equiv) and DIEA (55 mg, 0.43 mmol, 2.00 equiv). The resulting solution was stirred overnight at room temperature. The reaction was then quenched by the addition of water (10 mL). The resulting solution was extracted with ethyl acetate (3×10 mL) and the organic layers combined, then dried over anhydrous sodium sulfate and concentrated under vacuum. The product residue was purified by Prep-HPLC with the following conditions (Waters 2767-1): Column, SunFire Prep C18, 5 um, 19*100 mm; mobile phase, 0.05% TFA in water and CH$_3$CN (25% CH$_3$CN up to 55% in 10 min); Detector, UV 254 nm to yield 4-[6-[bis(4-chlorophenyl)methyl]-2-cyclopropyl-1H-1,3-benzodiazol-1-yl]cyclohexane-1-carboxamide; trifluoroacetic acid as a white solid.

$_1$H NMR (300 MHz, CD3OD) δ: 7.75 (s, 1H), 7.63-7.66 (m, 1H), 7.33-7.38 (m, 5H), 7.12-7.18 (m, 4H), 5.90 (s, 1H), 2.55-2.65 (m, 1H), 2.42-2.55 (m, 1H), 2.13-2.42 (m, 6H), 1.73-1.83 (m, 2H), 1.43-1.52 (m, 2H), 1.31-1.40 (m, 2H). LC/MS (ES, m/z): 518 [M+H]+.

Example PH-112

2-((4-chlorophenyl)(3-(1-(trifluoromethylsulfonyl) piperidin-4-yl)-3H-benzo[d]imidazol-5-yl)methyl) thiazole

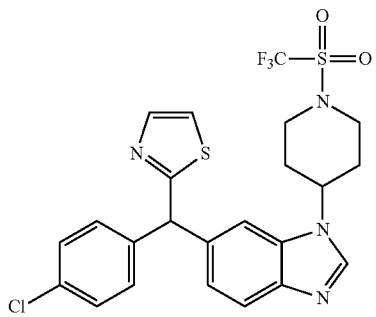 [SMILES: O=S(=O)(N1CCC(n2cnc3ccc(C(c4ccc(Cl)cc4)c4nccs4)cc32)CC1)C(F)(F)F]

Step 1: Synthesis of N-(5-fluoro-2-nitrophenyl)-1-(trifluoromethylsulfonyl)piperidin-4-amine Into a 250-mL round-bottom flask, was placed a solution of 2,4-difluoro-1-nitrobenzene (2.7 g, 16.98 mmol, 1.00 equiv) in CH$_3$CN (60 mL), triethylamine (5.2 g, 51.49 mmol, 3.03 equiv) and 1-(trifluoromethylsulfonyl) piperidin-4-amine hydrochloride (5.5 g, 20.52 mmol, 1.21 equiv). The resulting solution was stirred overnight at 90° C. in an oil bath. The reaction progress was monitored by LCMS. The reaction was then quenched by the addition of water (100 mL). The solids were collected by filtration. The solid was dried in an oven under reduced pressure to yield N-(5-fluoro-2-nitrophenyl)-1-(trifluoromethylsulfonyl)piperidin-4-amine as a yellow solid. LC/MS (ES, m/z): 371 [M+H]+.

Step 2: Synthesis of 2-(4-chlorophenyl)-2-(4-nitro-3-(1-(trifluoromethylsulfonyl)piperidin-4-ylamino) phenyl)acetonitrile Into a 500-mL round-bottom flask, was placed a solution of 2-(4-chlorophenyl) acetonitrile (5.4 g, 35.76 mmol, 1.11 equiv) in THF/i-PrOH (200/50 mL) and potassium 2-methylpropan-2-olate (9 g, 80.36 mmol, 2.48 equiv), and the resulting mixture stirred for 10 min at room temperature. To the reaction mixture was then added N-(5-fluoro-2-nitrophenyl)-1-(trifluoromethylsulfonyl)piperidin-4-amine (12 g, 32.35 mmol, 1.00 equiv). The resulting solution was stirred for 1 h at room temperature. The resulting mixture was washed with aq. sodium chloride (1×200 mL). The resulting solution was extracted with ethyl acetate (2×200 mL) and the organic layers combined, then dried over anhydrous sodium sulfate. The residue was applied onto a silica gel column with ethyl acetate/petroleum ether (1:15) to yield 2-(4-chlorophenyl)-2-(4-nitro-3-(1-(trifluoromethylsulfonyl)piperidin-4-ylamino)phenyl)acetonitrile as a reddish-brown solid. LC/MS (ES, m/z): 502 [M+H]+.

Step 3: Synthesis of 2-(4-chlorophenyl)-2-(4-nitro-3-(1-(trifluoromethylsulfonyl)piperidin-4-ylamino) phenyl)ethanethioamide Into a 150-mL sealed tube, was placed a solution of 2-(4-chlorophenyl)-2-(4-nitro-3-(1-(trifluoromethylsulfonyl)piperidin-4-ylamino)phenyl)acetonitrile (8.5 g, 16.93 mmol, 1.00 equiv) in ethanol (100 mL) and P$_2$S$_5$ (7.5 g, 33.78 mmol, 2.00 equiv). The resulting solution was stirred overnight at 70° C. in an oil bath. The reaction progress was monitored by LCMS. The reaction mixture was cooled to room temperature with a water/ice bath. The reaction was then quenched by the addition of water/ice (300 mL). The resulting solution was extracted with ethyl acetate (2×200 mL) and the organic layers combined, then dried over anhydrous sodium sulfate. The residue was applied onto a silica gel column with ethyl acetate/petroleum ether (1:5) to yield 2-(4-chlorophenyl)-2-(4-nitro-3-(1-(trifluoromethylsulfonyl)piperidin-4-ylamino)phenyl)ethanethioamide as an orange solid. LC/MS (ES, m/z): 536 [M+H]+.

Step 4: Synthesis of N-(5-((4-chlorophenyl)(thiazol-2-yl)methyl)-2-nitrophenyl)-1-(trifluoromethylsulfonyl)piperidin-4-amine Into a 250-mL round-bottom flask, was placed a solution of 2-(4-chlorophenyl)-2-(4-nitro-3-(1-(trifluoromethylsulfonyl) piperidin-4-ylamino) phenyl) ethanethioamide (10 g, 18.66 mmol, 1.00 equiv) in acetic acid (100 mL), 2-bromo-1,1-diethoxyethane (15 g, 76.53 mmol, 4.10 equiv) and water (4 mL). The resulting solution was stirred for 30 min at 100° C. in an oil bath. The reaction progress was monitored by LCMS. The resulting mixture was concentrated under vacuum. The resulting mixture was washed with aq. sodium bicarbonate (1×200 mL). The resulting solution was extracted with ethyl acetate (3×200 mL) and the organic layers combined. The resulting mixture was washed with aq. sodium bicarbonate (1×300 mL). The mixture was dried over anhydrous sodium sulfate. The residue was applied onto a silica gel column with ethyl acetate/petroleum ether (1:15) to N-(5-((4-chlorophenyl)(thiazol-2-yl)methyl)-2-nitrophenyl)-1-(trifluoromethylsulfonyl)piperidin-4-amine as an orange solid. LC/MS (ES, m/z): 560 [M+H]+.

Step 5: Synthesis of 5-((4-chlorophenyl)(thiazol-2-yl)methyl)-N1-(1-(trifluoromethylsulfonyl)piperidin-4-yl)benzene-1,2-diamine Into a 250-mL round-bottom flask purged and maintained with an inert atmosphere of nitrogen, was placed a solution of N-(5-((4-chlorophenyl)(thiazol-2-yl)methyl)-2-nitrophenyl)-1-(trifluoromethylsulfonyl)piperidin-4-amine (5 g, 8.93 mmol, 1.00 equiv) in tetrahydrofuran/MeOH (30/30 mL) and Raney Ni (2.5 g). To the resulting mixture was then introduced hydrogen. The resulting solution was stirred overnight at room temperature. The solids were collected by filtration. The resulting mixture was concentrated under vacuum to yield 5-((4-chlorophenyl)(thiazol-2-yl)methyl)-N1-(1-(trifluoromethylsulfonyl)piperidin-4-yl)benzene-1,2-diamine as a green solid. LC/MS (ES, m/z): 530 [M+H]+.

Step 6: Synthesis of 2-((4-chlorophenyl)(3-(1-(trifluoromethylsulfonyl)piperidin-4-yl)-3H-benzo[d]imidazol-5-yl) methyl)thiazole Into a 50-mL round-bottom flask, was placed 5-((4-chlorophenyl)(thiazol-2-yl)methyl)-N1-(1-(trifluoromethylsulfonyl)piperidin-4-yl)benzene-1,2-diamine (200 mg, 0.38 mmol, 1.00 equiv), triethoxymethane (3 mL) and hydrogen chloride (0.1 mL, con.). The resulting solution was stirred for 4 h at 125° C. in an oil bath. The reaction progress was monitored by LCMS. The resulting mixture was diluted with aq. sodium chloride (20 mL). The resulting solution was extracted with ethyl acetate (3×20 mL) and the organic layers combined, then dried over anhydrous sodium sulfate. The residue was applied onto a silica gel column with dichloromethane/methanol (60:1) to yield 2-((4-chlorophenyl)(3-(1-(trifluoromethylsulfonyl)piperidin-4-yl)-3H-benzo[d]imidazol-5-yl) methyl)thiazole as a light yellow solid.

$^1$H NMR (300 MHz, CDCl3) δ: 8.02 (s, 1H), 7.79-7.84 (m, 2H), 7.21-7.34 (m, 7H), 5.98 (s, 1H), 4.33-4.41 (m, 1H), 4.18-4.23 (m, 2H), 3.25-3.33 (m, 2H), 2.13-2.32 (m, 4H). LC/MS (ES, m/z): 541[M+H]+.

Example PH-113

2-((4-chlorophenyl)(2-methyl-3-(1-(trifluoromethylsulfonyl)piperidin-4-yl)-3H-benzo[d]imidazol-5-yl) methyl)thiazole

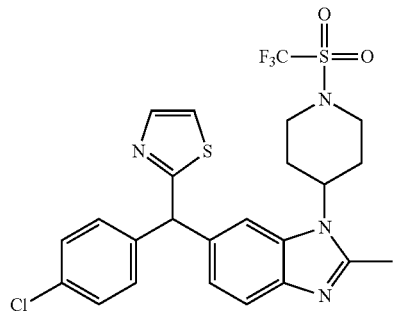 [SMILES: Cc1nc2ccc(C(c3ccc(Cl)cc3)c3nccs3)cc2n1C1CCN(S(=O)(=O)C(F)(F)F)CC1]

The title compound was prepared according to the procedure as described in Example PH-112 substituting acetaldehyde for triethoxymethane in Step 6.

$^1$H NMR (300 MHz, DMSO) δ: 7.81 (d, J=3.3 Hz, 1H), 7.67 (m, 1H), 7.56 (s, 1H), 7.49 (d, J=8.1 Hz, 1H), 7.37-7.40 (m, 2H), 7.31 (d, J=8.4 Hz, 2H), 7.08-7.12 (m, 1H), 6.16 (s, 1H), 4.61-4.69 (m, 1H), 3.97 (d, J=13.2 Hz, 2H), 3.44-3.52 (m, 2H), 2.58 (s, 3H), 2.25-2.28 (m, 2H), 1.99-2.03 (m, 2H). LC/MS (ES, m/z): 555 [M+H]+.

Example PH-114

2-((4-chlorophenyl)(2-ethyl-3-(1-(trifluoromethylsulfonyl)piperidin-4-yl)-3H-benzo[d]imidazol-5-yl) methyl)thiazole

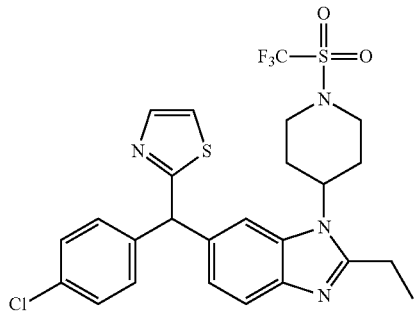 [SMILES: CCc1nc2ccc(C(c3ccc(Cl)cc3)c3nccs3)cc2n1C1CCN(S(=O)(=O)C(F)(F)F)CC1]

The title compound was prepared according to the procedure as described in Example PH-112 substituting propionaldehyde for triethoxymethane in Step 6.

$^1$H NMR (300 MHz, CDCl3) δ: 7.85 (s, 1H), 7.74 (d, J=8.1 Hz, 1H), 7.18-7.34 (m, 7H), 5.96 (s, 1H), 4.34-4.42 (m, 1H), 4.189-4.23 (m, 2H), 3.21-3.29 (m, 2H), 2.95-3.03 (m, 2H), 2.43-2.58 (m, 2H), 2.00-2.11 (m, 2H), 1.47 (t, J=7.2 Hz, 3H). LC/MS (ES, m/z): 569 [M+H]+.

Example PH-115

2-((4-chlorophenyl)(2-cyclopropyl-3-(1-(trifluoromethylsulfonyl)piperidin-4-yl)-3H-benzo[d]imidazol-5-yl)methyl)thiazole

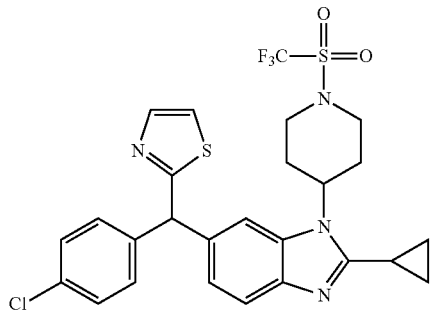 [SMILES: O=S(=O)(N1CCC(n2c(C3CC3)nc3ccc(C(c4ccc(Cl)cc4)c4nccs4)cc32)CC1)C(F)(F)F]

The title compound was prepared according to the procedure as described in Example PH-112 substituting cyclopropanecarbaldehyde for triethoxymethane in Step 6.

$^1$H NMR (300 MHz, DMSO-d6) δ: 7.80 (d, J=3.3 Hz, 1H), 7.66 (d, J=3.3 Hz, 1H), 7.57 (s, 1H), 7.45-7.51 (m, 1H), 7.39 (d, J=8.4 Hz, 2H), 7.30 (d, J=8.4 Hz, 2H), 7.08 (d, J=8.4 Hz, 1H), 6.14 (s, 1H), 4.95-5.03 (m, 1H), 3.99 (d, J=13.2 Hz, 2H), 1.05 (d, J=7.8 Hz, 4H). LC/MS (ES, m/z): 581 [M+H]+.

Example PH-116

2-((4-chlorophenyl)(2-(pyridin-3-yl)-3-(1-(trifluoromethylsulfonyl)piperidin-4-yl)-3H-benzo[d]imidazol-5-yl)methyl)thiazole

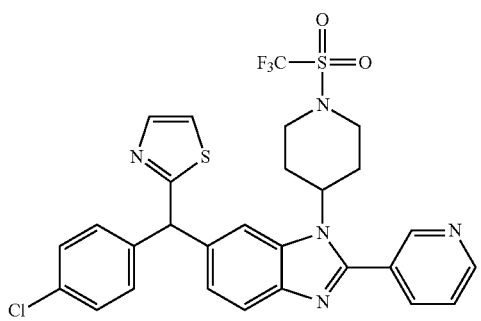 [SMILES: O=S(=O)(N1CCC(n2c(-c3cccnc3)nc3ccc(C(c4ccc(Cl)cc4)c4nccs4)cc32)CC1)C(F)(F)F]

The title compound was prepared according to the procedure as described in Example PH-112 substituting nicotinaldehyde for triethoxymethane in Step 6.

$^1$H NMR (300 MHz, CDCl3) δ: 8.83 (s, 2H), 8.02 (d, J=8.1 Hz, 1H), 7.80-7.88 (m, 2H), 7.52-7.56 (m, 1H), 7.47 (s, 1H), 7.26-7.36 (m, 4H), 6.01 (s, 1H), 4.43-4.51 (m, 1H), 4.14 (d, J=13.2 Hz, 2H), 3.07-3.16 (m, 2H), 2.52-2.64 (m, 2H), 2.02-2.09 (m, 2H). LC/MS (ES, m/z): 618 [M+H]+.

Example PH-117

2-((4-chlorophenyl)(3-(8-(trifluoromethylsulfonyl)-8-aza-bicyclo[3.2.1]octan-3-yl)-3H-benzo[d]imidazol-5-yl)methyl)thiazole

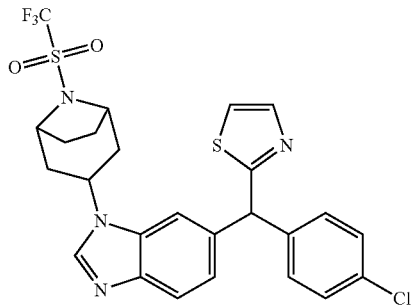 [SMILES: O=S(=O)(N1C2CCC1CC(n1cnc3ccc(C(c4ccc(Cl)cc4)c4nccs4)cc31)C2)C(F)(F)F]

The title compound was prepared according to the procedure as described in Example PH-112 substituting 8-(trifluoromethylsulfonyl)-8-aza-bicyclo [3.2.1] octan-3-amine for 1-(trifluoromethylsulfonyl) piperidin-4-amine hydrochloride in Step 1.

$^1$HNMR (300 MHz, DMSO-d6) δ: 8.47 (s, 1H), 7.83 (s, 1H), 7.62-7.82 (m, 2H), 7.34-7.42 (m, 5H), 7.19 (d, J=1.2 Hz, 1H), 6.22 (s, 1H), 4.46-4.58 (m, 3H), 2.60-2.70 (m, 2H), 2.07-2.14 (m, 4H), 1.90 (d, J=10.8 Hz, 2H). LC/MS (ES, m/z): 567 [M+H]+

Example YM-1

2-((4-chlorophenyl)(3-(1-(trifluoromethylsulfonyl)piperidin-4-yl)-3H-benzo[d]imidazol-5-yl)methyl)thiazole

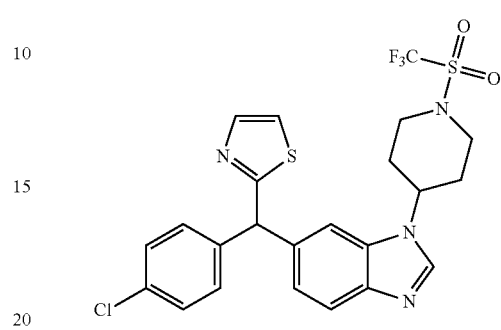

Step 1: N-(5-fluoro-2-nitrophenyl)-1-((trifluoromethyl)sulfonyl)piperidin-4-amine Into a 250-mL round-bottom flask, was placed a solution of 2,4-difluoro-1-nitrobenzene (2.7 g, 16.98 mmol, 1.00 equiv) in CH3CN (60 mL), triethylamine (5.2 g, 51.49 mmol, 3.03 equiv), 1-(trifluoromethylsulfonyl) piperidin-4-amine hydrochloride (5.5 g, 20.52 mmol, 1.21 equiv). The resulting solution was stirred overnight at 90° C. in an oil bath. The reaction progress was monitored by LCMS. The reaction was then quenched by the addition of water (100 mL). The solids were collected by filtration. The solid was dried in an oven under reduced pressure to yield N-(5-fluoro-2-nitrophenyl)-1-(trifluoromethylsulfonyl)piperidin-4-amine as a yellow solid.

LC/MS (ES, m/z): 413 [M+CH$_3$CN+H]$^+$

Step 2: 2-(4-chlorophenyl)-2-(4-nitro-3-((1-((trifluoromethyl)sulfonyl)piperidin-4-yl)amino)phenyl)acetonitrile Into a 500-mL round-bottom flask, was placed a solution of 2-(4-chlorophenyl) acetonitrile (5.4 g, 35.76 mmol, 1.11 equiv) in tetrahydrofuran/iPrOH (200/50 mL), potassium 2-methylpropan-2-olate (9 g, 80.36 mmol, 2.48 equiv). The resulting mixture was stirred for 10 min at room temperature, and then N-(5-fluoro-2-nitrophenyl)-1-(trifluoromethylsulfonyl)piperidin-4-amine (12 g, 32.35 mmol, 1.00 equiv) was added. The resulting solution was stirred for 1 h at room temperature. The resulting mixture was washed with aq. sodium chloride (1×200 mL). The resulting solution was extracted with ethyl acetate (2×200 mL) and the organic layers combined and dried over anhydrous sodium sulfate. The residue was applied onto a silica gel column with ethyl acetate/petroleum ether (1:15) to yield 2-(4-chlorophenyl)-2-(4-nitro-3-(1-(trifluoromethylsulfonyl)piperidin-4-ylamino)phenyl)acetonitrile as a reddish-brown solid.

LC/MS (ES, m/z): 503 [M+H]$^+$

Step 3 2-(4-chlorophenyl)-2-(4-nitro-3-((1-(((trifluoromethyl)sulfonyl)piperidin-4-yl)amino)phenyl)ethanethioamide Into a 150-mL sealed tube, was placed a solution of 2-(4-chlorophenyl)-2-(4-nitro-3-(1-(trifluoromethylsulfonyl)piperidin-4-ylamino)phenyl)acetonitrile (8.5 g, 16.93 mmol, 1.00 equiv) in ethanol (100 mL), $P_2S_5$ (7.5 g, 33.78 mmol, 2.00 equiv). The resulting solution was stirred overnight at 70° C. in an oil bath. The reaction progress was monitored by LCMS. The reaction mixture was cooled to room temperature with a water/ice bath. The reaction was then quenched by the addition of water/ice (300 mL). The resulting solution was extracted with ethyl acetate (2×200 mL) and the organic layers combined and dried over anhydrous sodium sulfate. The residue was applied onto a silica gel column with ethyl acetate/petroleum ether (1:5) to yield 2-(4-chlorophenyl)-2-(4-nitro-3-(1-(trifluoromethylsulfonyl)piperidin-4-ylamino)phenyl)ethanethioamide as an orange solid.

LC/MS (ES, m/z): 537 [M+H]⁺

Step 4 N-(5-((4-chlorophenyl)(thiazol-2-yl)methyl)-2-nitrophenyl)-1-((trifluoromethyl)sulfonyl)piperidin-4-amine Into a 250-mL round-bottom flask, was placed a solution of 2-(4-chlorophenyl)-2-(4-nitro-3-(1-(trifluoromethylsulfonyl) piperidin-4-ylamino) phenyl) ethanethioamide (10 g, 18.66 mmol, 1.00 equiv) in acetic acid (100 mL), 2-bromo-1,1-diethoxyethane (15 g, 76.53 mmol, 4.10 equiv), water (4 mL). The resulting solution was stirred for 30 min at 100° C. in an oil bath. The reaction progress was monitored by LCMS. The resulting mixture was concentrated under vacuum. The resulting mixture was washed with aq. sodium bicarbonate (1×200 mL). The resulting solution was extracted with ethyl acetate (3×200 mL) and the organic layers combined. The resulting mixture was washed with aq. sodium bicarbonate (1×300 mL). The mixture was dried over anhydrous sodium sulfate. The residue was applied onto a silica gel column with ethyl acetate/petroleum ether (1:15) to yield N-(5-((4-chlorophenyl)(thiazol-2-yl)methyl)-2-nitrophenyl)-1-(trifluoromethylsulfonyl)piperidin-4-amine as an orange solid.

LC/MS (ES, m/z): 561 [M+H]⁺

Step 5 5-((4-chlorophenyl)(thiazol-2-yl)methyl)-N1-(1-((trifluoromethyl)sulfonyl)piperidin-4-yl)benzene-1,2-diamine Into a 250-mL round-bottom flask purged and maintained with an inert atmosphere of nitrogen, was placed a solution of N-(5-((4-chlorophenyl)(thiazol-2-yl)methyl)-2-nitrophenyl)-1-(trifluoromethylsulfonyl)piperidin-4-amine (5 g, 8.93 mmol, 1.00 equiv) in tetrahydrofuran/MeOH (30/30 mL), Raney Ni (2.5 g). To the above was introduced hydrogen. The resulting solution was stirred overnight at room temperature. The solids were collected by filtration. The resulting mixture was concentrated under vacuum to yield 5-((4-chlorophenyl)(thiazol-2-yl)methyl)-N1-(1-(trifluoromethylsulfonyl)piperidin-4-yl)benzene-1,2-diamine as a green solid.

LC/MS (ES, m/z): 531 [M+H]⁺

Step 6 2-((4-chlorophenyl)(1-(1-((trifluoromethyl) sulfonyl)piperidin-4-yl)-1H-benzo[d]imidazol-6-yl) methyl)thiazole Into a 50-mL round-bottom flask, was placed 5-((4-chlorophenyl)(thiazol-2-yl)methyl)-N1-(1-(trifluoromethylsulfonyl)piperidin-4-yl)benzene-1,2-diamine (200 mg, 0.38 mmol, 1.00 equiv), triethoxymethane (3 mL), hydrogen chloride (0.1 mL, con.). The resulting solution was stirred for 4 h at 125° C. in an oil bath.

The reaction progress was monitored by LCMS. The resulting mixture was diluted with aq. sodium chloride (20 mL). The resulting solution was extracted with ethyl acetate (3×20 mL) and the organic layers combined and dried over anhydrous sodium sulfate. The residue was applied onto a silica gel column with dichloromethane/methanol (60:1) to yield 2-((4-chlorophenyl)(3-(1-(trifluoromethylsulfonyl)piperidin-4-yl)-3H-benzo[d]imidazol-5-yl) methyl)thiazole as a light yellow solid.

¹H NMR (300 MHz, CDCl₃) δ: 8.02 (s, 1H), 7.79-7.84 (m, 2H), 7.21-7.34 (m, 7H), 5.98 (s, 1H), 4.33-4.41 (m, 1H), 4.18-4.23 (d, J=13.5 Hz, 2H), 3.25-3.33 (m, 2H), 2.13-2.32 (m, 4H). LC/MS (ES, m/z): 541 [M+H]⁺

The following compounds were prepared in according to the procedure as described in Example YM-1 above, selecting and substituting suitable reactants and reagents, as would be readily recognized by those skilled in the art.

Example YM-2

2-((4-chlorophenyl)(2-methyl-3-(1-(trifluoromethylsulfonyl)piperidin-4-yl)-3H-benzo[d]imidazol-5-yl) methyl)thiazole

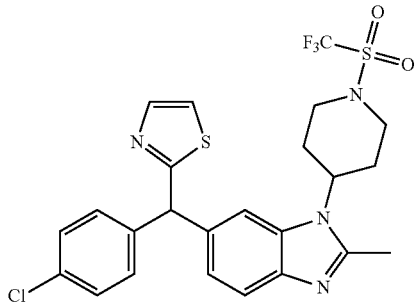 [SMILES: Cc1nc2ccc(C(c3ccc(Cl)cc3)c3nccs3)cc2n1C1CCN(S(=O)(=O)C(F)(F)F)CC1]

¹H NMR (300 MHz, DMSO) δ: 7.81 (d, J=3.3 Hz, 1H), 7.69 (s, 1H), 7.56 (s, 1H), 7.49 (d, J=8.1 Hz, 1H), 7.37-7.40 (m, 2H), 7.31 (d, J=8.4 Hz, 2H), 7.09-7.12 (m, 1H), 6.16 (s, 1H), 4.61-4.69 (m, 1H), 3.97 (d, J=13.2 Hz, 2H), 3.44-3.52 (m, 2H), 2.58 (s, 3H), 2.25-2.28 (m, 2H), 2.00-2.03 (m, 2H). LC/MS (ES, m/z): 555 [M+H]⁺.

Example YM-3

2-((4-chlorophenyl)(2-ethyl-3-(1-(trifluoromethylsulfonyl)piperidin-4-yl)-3H-benzo[d]imidazol-5-yl) methyl)thiazole

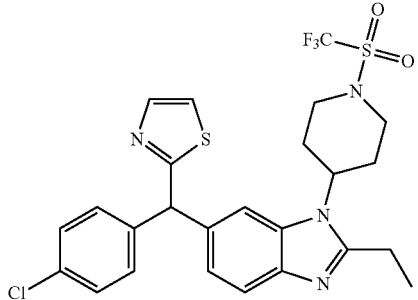 [SMILES: CCc1nc2ccc(C(c3ccc(Cl)cc3)c3nccs3)cc2n1C1CCN(S(=O)(=O)C(F)(F)F)CC1]

¹H NMR (300 MHz, CDCl₃) δ: 7.84 (s, 1H), 7.74 (d, J=8.4 Hz, 1H), 7.18-7.34 (m, 7H), 5.96 (s, 1H), 4.34-4.42 (m, 1H), 4.19-4.23 (m, 2H), 3.21-3.30 (m, 2H), 2.95-3.03 (m, 2H), 2.44-2.58 (m, 2H), 2.00-2.11 (m, 2H), 1.47 (t, J=7.2 Hz, 3H). LC/MS (ES, m/z): 569 [M+H]⁺.

Example YM-4

2-((4-chlorophenyl)(2-propyl-3-(1-(trifluoromethyl-sulfonyl)piperidin-4-yl)-3H-benzo[d]imidazol-5-yl)methyl)thiazole

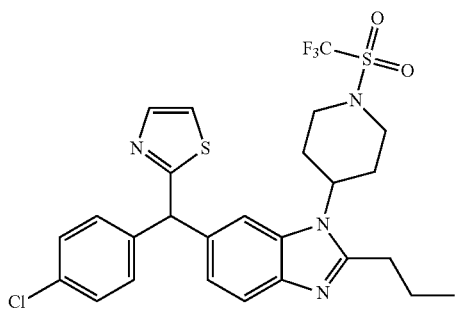 [SMILES: CCCc1nc2ccc(C(c3ccc(Cl)cc3)c3nccs3)cc2n1C1CCN(S(=O)(=O)C(F)(F)F)CC1]

¹H NMR (300 MHz, CDCl₃) δ: 7.85 (s, 1H), 7.72 (d, J=8.4 Hz, 1H), 7.17-7.34 (m, 7H), 5.96 (s, 1H), 4.25-4.45 (m, 1H), 4.19-4.22 (m, 2H), 3.21-3.30 (m, 2H), 2.92 (brm, 2H), 2.49-2.52 (m, 2H), 1.88-2.03 (m, 4H), 1.10 (t, J=7.2 Hz, 3H). LC/MS (ES, m/z): 583 [M+H]⁺.

Example YM-5

2-((4-chlorophenyl)(2-isobutyl-3-(1-(trifluoromethylsulfonyl)piperidin-4-yl)-3H-benzo[d]imidazol-5-yl)methyl)thiazole

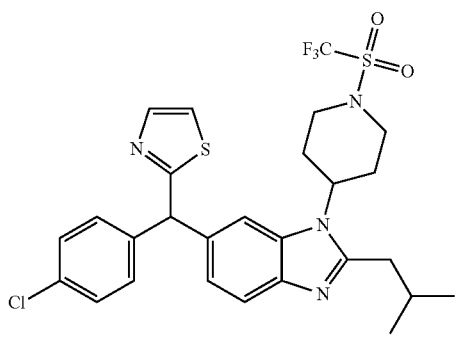 [SMILES: CC(C)Cc1nc2ccc(C(c3ccc(Cl)cc3)c3nccs3)cc2n1C1CCN(S(=O)(=O)C(F)(F)F)CC1]

¹H NMR (300 MHz, CDCl₃) δ: 7.85 (d, J=3.3 Hz, 1H), 7.72 (d, J=8.1 Hz, 1H), 7.17-7.34 (m, 7H), 5.96 (s, 1H), 4.35-4.41 (m, 1H), 4.20 (d, J=12.6 Hz, 2H), 3.20-3.29 (m, 2H), 2.81 (d, J=7.5 Hz, 2H), 2.46-2.58 (m, 2H), 2.18-2.23 (m, 1H), 1.97-2.01 (m, 2H), 1.07 (d, J=3.6 Hz, 6H). LC/MS (ES, m/z): 597 [M+H]⁺.

Example YM-6

2-((4-chlorophenyl)(2-cyclopropyl-3-(1-(trifluoromethylsulfonyl)piperidin-4-yl)-3H-benzo[d]imidazol-5-yl)methyl)thiazole

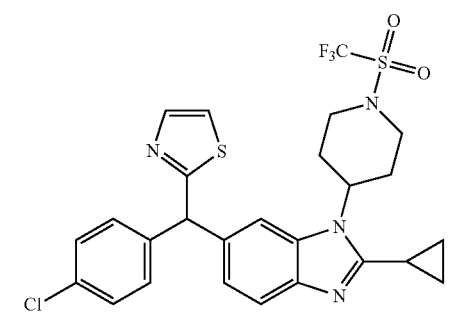 [SMILES: O=S(=O)(N1CCC(n2c(C3CC3)nc3ccc(C(c4ccc(Cl)cc4)c4nccs4)cc32)CC1)C(F)(F)F]

¹H NMR (300 MHz, DMSO) δ: 7.81 (d, J=3.3 Hz, 1H), 7.66 (d, J=3.3 Hz, 1H), 7.57 (brs, 1H), 7.49 (d, J=9.6 Hz, 1H), 7.38 (d, J=8.4 Hz, 2H), 7.31 (d, J=8.4 Hz, 2H), 7.09 (d, J=8.4 Hz, 1H), 6.14 (s, 1H), 4.95-5.03 (m, 1H), 4.00 (d, J=13.2 Hz, 2H), 3.47-0.355 (m, 2H), 2.28-2.35 (m, 3H), 2.01-2.05 (m, 2H), 1.03-1.06 (m, 4H). LC/MS (ES, m/z) 581 [M+H]⁺.

Example YM-7

2-((4-chlorophenyl)(2-cyclobutyl-3-(1-(trifluoromethylsulfonyl)piperidin-4-yl)-3H-benzo[d]imidazol-5-yl)methyl)thiazole

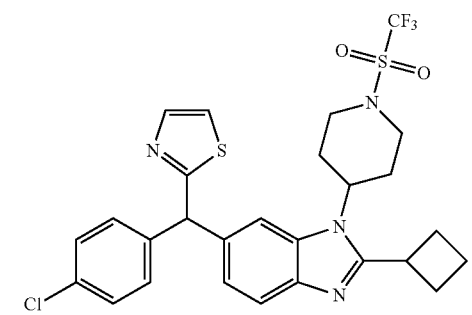 [SMILES: O=S(=O)(N1CCC(n2c(C3CCC3)nc3ccc(C(c4ccc(Cl)cc4)c4nccs4)cc32)CC1)C(F)(F)F]

¹H NMR (300 MHz, DMSO) δ: 7.81 (d, J=3.3 Hz, 1H), 7.66 (d, J=3.3 Hz, 1H), 7.55 (d, J=8.4 Hz, 2H), 7.30-7.40 (m, 4H), 7.11 (d, J=8.4 Hz, 1H), 6.17 (s, 1H), 4.52-4.55 (m, 1H), 3.88-3.97 (m, 3H), 3.49-3.54 (m, 2H), 2.37-2.50 (m, 4H), 2.28-2.27 (m, 2H), 2.05-2.08 (m, 1H), 1.90-1.94 (m, 3H). LC/MS (ES, m/z): 595 [M+H]⁺.

Example YM-8

2-((4-chlorophenyl)(2-cyclopentyl-3-(1-(trifluoromethylsulfonyl)piperidin-4-yl)-3H-benzo[d]imidazol-5-yl)methyl)thiazole

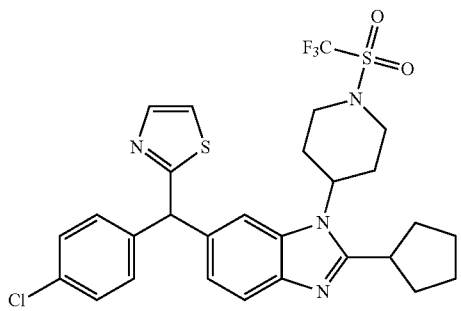 [SMILES: O=S(=O)(N1CCC(n2c(C3CCCC3)nc3ccc(C(c4ccc(Cl)cc4)c4nccs4)cc32)CC1)C(F)(F)F]

$^1$H NMR (300 MHz, CDCl$_3$) δ: 7.88 (m, 1H), 7.73 (d, J=8.4 Hz, 1H), 7.14-7.40 (m, 7H), 5.95 (s, 1H), 4.41-4.49 (m, 1H), 4.20 (d, J=13.2 Hz, 2H), 3.20-3.28 (m, 3H), 2.46-2.57 (m, 2H), 2.07-2.12 (m, 4H), 1.91-2.01 (m, 4H), 1.62-1.81 (m, 2H). LC/MS (ES, m/z): 609 [M+H]$^+$.

Example YM-9

2-((4-chlorophenyl)(2-(4-chlorophenyl)-3-(1-(trifluoromethylsulfonyl)piperidin-4-yl)-3H-benzo[d]imidazol-5-yl)methyl)thiazole

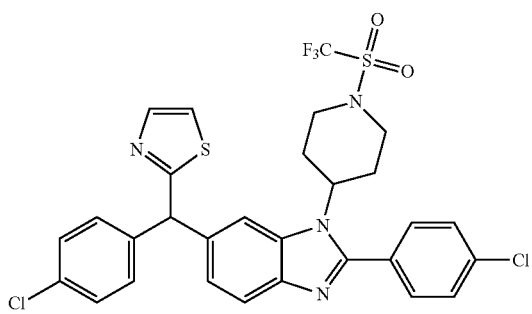 [SMILES: O=S(=O)(N1CCC(n2c(-c3ccc(Cl)cc3)nc3ccc(C(c4ccc(Cl)cc4)c4nccs4)cc32)CC1)C(F)(F)F]

LC/MS (ES, m/z): 651 [M+H]$^+$.

Example YM-10

2-((4-chlorophenyl)(2-(pyridin-2-yl)-3-(1-(trifluoromethylsulfonyl)piperidin-4-yl)-3H-benzo[d]imidazol-5-yl)methyl)thiazole

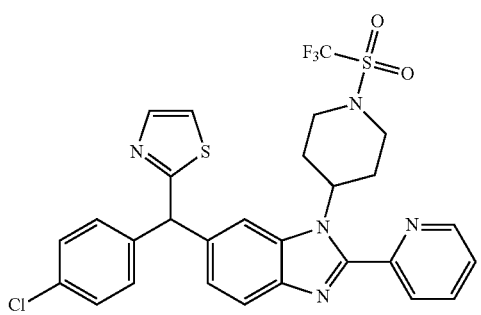 [SMILES: O=S(=O)(N1CCC(n2c(-c3ccccn3)nc3ccc(C(c4ccc(Cl)cc4)c4nccs4)cc32)CC1)C(F)(F)F]

$^1$H NMR (300 MHz, DMSO) δ: 8.75 (d, J=4.2 Hz, 1H), 8.15-8.17 (m, 1H), 8.03-8.05 (m, 1H), 7.84 (s, 1H), 7.68-7.75 (m, 3H), 7.54-7.58 (m, 1H), 7.34-7.43 (m, 4H), 7.24-7.26 (d, J=8.4 Hz, 1H), 6.26 (s, 1H), 5.58-5.66 (m, 1H), 3.97 (d, J=13.2 Hz, 2H), 3.40-3.44 (m, 2H), 2.40-2.50 (m, 2H), 2.10-2.13 (m, 2H). LC/MS (ES, m/z): 618 [M+H]$^+$.

Example YM-11

2-((4-chlorophenyl)(2-(pyridin-3-yl)-3-(1-(trifluoromethylsulfonyl)piperidin-4-yl)-3H-benzo[d]imidazol-5-yl)methyl)thiazole

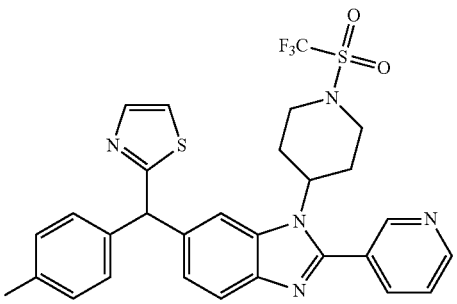

$^1$H NMR (300 MHz, CDCl$_3$) δ: 8.83 (s, 2H), 8.02 (d, J=8.1 Hz, 1H), 7.80-7.88 (m, 2H), 7.52-7.56 (m, 1H), 7.47 (s, 1H), 7.26-7.36 (m, 6H), 6.01 (s, 1H), 4.43-4.51 (m, 1H), 4.14 (d, J=13.2 Hz, 2H), 3.07-3.16 (m, 2H), 2.52-2.64 (m, 2H), 2.02-2.09 (m, 2H). LC/MS (ES, m/z): 618 [M+H]$^+$.

Example YM-12

2-((4-chlorophenyl)(2-(pyridin-4-yl)-3-(1-(trifluoromethylsulfonyl)piperidin-4-yl)-3H-benzo[d]imidazol-5-yl)methyl)thiazole

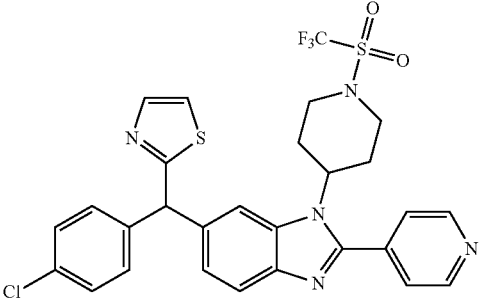 [SMILES: O=S(=O)(N1CCC(n2c(-c3ccncc3)nc3ccc(C(c4ccc(Cl)cc4)c4nccs4)cc32)CC1)C(F)(F)F]

LC/MS (ES, m/z): 618 [M+H]$^+$.

Example YM-13

Ethyl 6-((4-chlorophenyl)(thiazol-2-yl)methyl)-1-(1-(trifluoromethylsulfonyl)piperidin-4-yl)-1H-benzo[d]imidazole-2-carboxylate

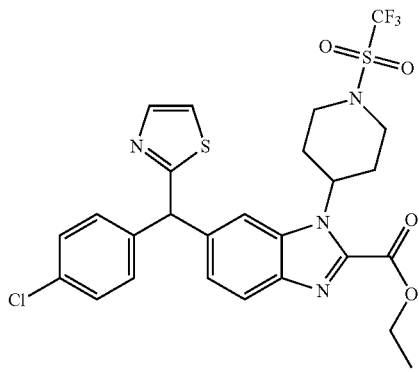 [SMILES: CCOC(=O)c1nc2ccc(C(c3ccc(Cl)cc3)c3nccs3)cc2n1C1CCN(S(=O)(=O)C(F)(F)F)CC1]

LC/MS (ES, m/z): 613 [M+H]$^+$.

Example YM-14

2-((4-chlorophenyl)(3-(8-(trifluoromethylsulfonyl)-8-aza-bicyclo[3.2.1]octan-3-yl)-3H-benzo[d]imidazol-5-yl)methyl)thiazole

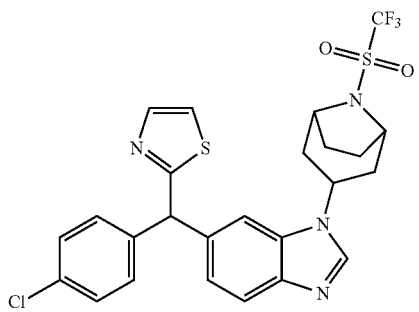 [SMILES: O=S(=O)(N1C2CCC1CC(n1cnc3ccc(C(c4ccc(Cl)cc4)c4nccs4)cc31)C2)C(F)(F)F]

Step 1 N-(5-fluoro-2-nitrophenyl)-8-((trifluoromethyl)sulfonyl)-8-azabicyclo[3.2.1]octan-3-amine Into a 500-mL round-bottom flask, was placed a solution of 2,4-difluoro-1-nitrobenzene (8.4 g, 52.83 mmol, 1.00 equiv) in CH$_3$CN (250 mL), 8-(trifluoromethylsulfonyl)-8-aza-bicyclo[3.2.1]octan-3-amine (15 g, 58.14 mmol, 1.10 equiv), triethylamine (16 g, 158.42 mmol, 3.00 equiv). The resulting solution was stirred overnight at 90° C. in an oil bath. The reaction progress was monitored by LCMS. The reaction was then quenched by the addition of brine (200 mL). The resulting solution was extracted with ethyl acetate (2×200 mL) and the organic layers combined and dried over anhydrous sodium sulfate. The residue was applied onto a silica gel column with dichloromethane/methanol to yield N-(5-fluoro-2-nitrophenyl)-8-(trifluoromethylsulfonyl)-8-aza-bicyclo[3.2.1]octan-3-amine as a yellow solid.

LC/MS (ES, m/z): 398 [M+H]$^+$

Step 2 2-(4-chlorophenyl)-2-(4-nitro-3-(8-(trifluoromethylsulfonyl)-8-aza-bicyclo[3.2.1]octan-3-ylamino)phenyl)acetonitrile Into a 500-mL round-bottom flask, was placed a solution of 2-(4-chlorophenyl)acetonitrile (3.6 g, 23.84 mmol, 1.11 equiv) in tetrahydrofuran/iPrOH (200/40 mL), potassium 2-methylpropan-2-olate (6 g, 53.57 mmol, 2.50 equiv), stirred for 10 min. To the mixture was then added N-(5-fluoro-2-nitrophenyl)-8-(trifluoromethylsulfonyl)-8-aza-bicyclo[3.2.1]octan-3-amine (8.5 g, 21.41 mmol, 1.00 equiv). The resulting solution was stirred for 30 min at room temperature. The resulting mixture was poured into water (200 mL), and the pH of the mixture adjusted to pH 7 with 2 M HCl. The resulting solution was extracted with ethyl acetate (2×200 mL) and the organic layers combined and dried over anhydrous sodium sulfate. The residue was applied onto a silica gel column with ethyl acetate/petroleum ether (1:15) to yield 2-(4-chlorophenyl)-2-(4-nitro-3-(8-(trifluoromethylsulfonyl)-8-aza-bicyclo[3.2.1]octan-3-ylamino)phenyl)acetonitrile as a yellow solid LC/MS (ES, m/z): 529 [M+H]$^+$

Step 3 2-(4-chlorophenyl)-2-(4-nitro-3-(8-(trifluoromethylsulfonyl)-8-aza-bicyclo[3.2.1]octan-3-ylamino)phenyl)ethanethioamide Into a 150-mL sealed tube, was placed a solution of 2-(4-chlorophenyl)-2-(4-nitro-3-(8-(trifluoromethylsulfonyl)-8-aza-bicyclo[3.2.1]octan-3-ylamino)phenyl)acetonitrile (9 g, 17.05 mmol, 1.00 equiv) in ethanol (100 mL), P$_2$S$_5$ (11.3 g, 50.90 mmol, 2.99 equiv). The resulting solution was stirred overnight at 70° C. in an oil bath. The reaction progress was monitored by LCMS. The reaction mixture was cooled to room temperature with a water/ice bath. The reaction was then quenched by the addition of water/ice (200 mL). The resulting solution was extracted with ethyl acetate (2×200 mL) and the organic layers combined and dried over anhydrous sodium sulfate. The residue was applied onto a silica gel column with DCM/MeOH (60:1) to yield 2-(4-chlorophenyl)-2-(4-nitro-3-(8-(trifluoromethylsulfonyl)-8-aza-bicyclo[3.2.1]octan-3-ylamino)phenyl)ethanethioamide as a yellow solid.

LC/MS (ES, m/z): 563 [M+H]$^+$

Step 4 N-(5-((4-chlorophenyl)(thiazol-2-yl)methyl)-2-nitrophenyl)-8-(trifluoromethylsulfonyl)-8-aza-bicyclo[3.2.1]octan-3-amine Into a 250-mL round-bottom flask, was placed a solution of 2-(4-chlorophenyl)-2-(4-nitro-3-(8-(trifluoromethylsulfonyl)-8-aza-bicyclo[3.2.1]octan-3-ylamino)phenyl)ethanethioamide (9 g, 16.01 mmol, 1.00 equiv) in acetic acid (100 mL), 2-bromo-1,1-diethoxyethane (12.5 g, 63.78 mmol, 3.98 equiv), water (4 mL). The resulting solution was stirred for 30 min at 100° C. in an oil bath. The reaction progress was monitored by LCMS. The resulting mixture was concentrated under vacuum. The reaction was then quenched by the addition of aq. sodium chloride (200 mL).

The resulting solution was extracted with ethyl acetate (3×200 mL) and the organic layers combined. The resulting mixture was washed with aq. sodium bicarbonate (1×300 mL). The mixture was dried over anhydrous sodium sulfate. The residue was applied onto a silica gel column with ethyl acetate/petroleum ether (1:15) to yield N-(5-((4-chlorophenyl)(thiazol-2-yl)methyl)-2-nitrophenyl)-8-(trifluoromethylsulfonyl)-8-aza-bicyclo[3.2.1]octan-3-amine as an orange solid.

LC/MS (ES, m/z): 587 [M+H]+

Step 5 5-((4-chlorophenyl)(thiazol-2-yl)methyl)-N1-(8-(trifluoromethylsulfonyl)-8-aza-bicyclo[3.2.1]octan-3-yl)benzene-1,2-diamine Into a 250-mL round-bottom flask purged and maintained with an inert atmosphere of nitrogen, was placed a solution of N-(5-((4-chlorophenyl)(thiazol-2-yl)methyl)-2-nitrophenyl)-8-(trifluoromethylsulfonyl)-8-aza-bicyclo[3.2.1]octan-3-amine (5.3 g, 9.04 mmol, 1.00 equiv) in tetrahydrofuran/MeOH (30/30 mL), Raney Ni (2.5 g). To the resulting mixture was introduced hydrogen. The resulting solution was stirred overnight at room temperature. The reaction progress was monitored by LCMS. The solids were filtered out. The resulting mixture was concentrated under vacuum to yield 5-((4-chlorophenyl)(thiazol-2-yl)methyl)-N1-(8-(trifluoromethylsulfonyl)-8-aza-bicyclo[3.2.1]octan-3-yl)benzene-1,2-diamine as a green solid.

LC/MS (ES, m/z): 557 [M+H]+

Step 6 2-((4-chlorophenyl)(3-(8-(trifluoromethylsulfonyl)-8-aza-bicyclo[3.2.1]octan-3-yl)-3H-benzo[d]imidazol-5-yl)methyl)thiazole Into a 50-mL round-bottom flask, was placed 5-((4-chlorophenyl)(thiazol-2-yl)methyl)-N1-(8-(trifluoromethylsulfonyl)-8-aza-bicyclo[3.2.1]octan-3-yl)benzene-1,2-diamine (200 mg, 0.36 mmol, 1.00 equiv), triethoxymethane (4 mL), hydrogen chloride (0.5 mL). The resulting solution was stirred for 4 h at 120° C. in an oil bath. The reaction progress was monitored by LCMS. The reaction was then quenched by the addition of brine (20 mL). The resulting solution was extracted with ethyl acetate and the organic layers combined and dried over anhydrous sodium sulfate. The residue was purified by TLC method with dichloromethane/methanol (100:1) to yield 2-((4-chlorophenyl)(3-(8-(trifluoromethylsulfonyl)-8-aza-bicyclo[3.2.1]octan-3-yl)-3H-benzo[d]imidazol-5-yl)methyl)thiazole as a yellow solid.

1H NMR (300 MHz, DMSO) δ: 8.47 (s, 1H), 7.83 (s, 1H), 7.62-7.82 (m, 2H), 7.33-7.42 (m, 5H), 7.17-7.20 (m, 1H), 6.22 (s, 1H), 4.47-4.58 (m, 3H), 2.60-2.70 (m, 2H), 2.07-2.14 (m, 4H), 1.88-1.92 (m, 2H). LC/MS (ES, m/z): 567 [M+H]+.

The following compounds were prepared according to the procedure as described in Example YM-14 above, selecting and substituting suitable reactants and reagents, as would be readily recognized by those skilled in the art.

Example YM-15

2-((4-chlorophenyl)(2-ethyl-3-(8-(trifluoromethylsulfonyl)-8-aza-bicyclo[3.2.1]octan-3-yl)-3H-benzo[d]imidazol-5-yl)methyl)thiazole

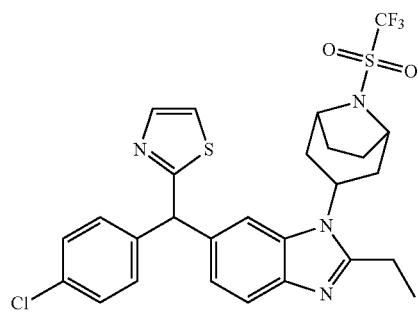 [SMILES: CCc1nc2ccc(C(c3ccc(Cl)cc3)c3nccs3)cc2n1C1CC2CCC(C1)N2S(=O)(=O)C(F)(F)F]

LC/MS (ES, m/z): 595 [M+H]+.

Example YM-16

2-((4-chlorophenyl)(2-(pyridin-3-yl)-3-(8-(trifluoromethylsulfonyl)-8-aza-bicyclo[3.2.1]octan-3-yl)-3H-benzo[d]imidazol-5-yl)methyl)thiazole

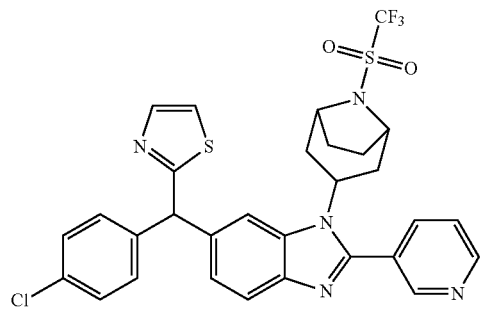 [SMILES: O=S(=O)(N1C2CCC1CC(n1c(-c3cccnc3)nc3ccc(C(c4ccc(Cl)cc4)c4nccs4)cc31)C2)C(F)(F)F]

LC/MS (ES, m/z): 644 [M+H]+.

Example YM-17

2-((4-chlorophenyl)(2-(pyridin-4-yl)-3-(8-(trifluoromethylsulfonyl)-8-aza-bicyclo[3.2.1]octan-3-yl)-3H-benzo[d]imidazol-5-yl)methyl)thiazole

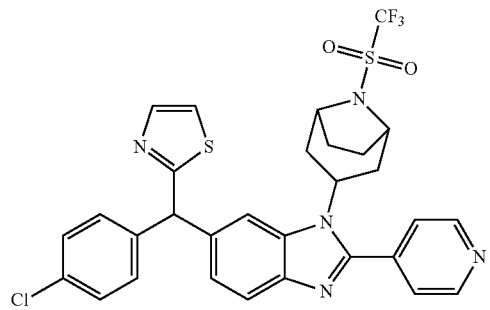 [SMILES: O=S(=O)(N1C2CCC1CC(n1c(-c3ccncc3)nc3ccc(C(c4ccc(Cl)cc4)c4nccs4)cc31)C2)C(F)(F)F]

Example YM-18 methyl 6-((4-chlorophenyl)(thiazol-2-yl)methyl)-1-(8-(trifluoromethylsulfonyl)-8-aza-bicyclo[3.2.1]octan-3-yl)-1H-benzo[d]imidazole-2-carboxylate

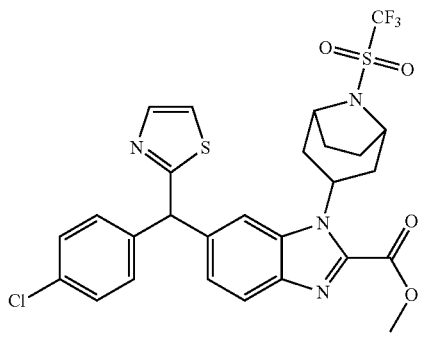 [SMILES: COC(=O)c1nc2ccc(C(c3ccc(Cl)cc3)c3nccs3)cc2n1C1CC2CCC(C1)N2S(=O)(=O)C(F)(F)F]

$^1$H NMR (300 MHz, DMSO) δ: 7.87 (d, J=3.3 Hz, 1H), 7.72-7.79 (m, 2H), 7.37-7.45 (m, 5H), 7.31 (d, J=9.0 Hz, 1H), 6.35 (s, 1H), 5.60 (brm, 1H), 4.48-4.52 (m, 2H), 3.92 (s, 3H), 2.65-2.73 (m, 2H), 2.19 (brm, 2H), 1.76-1.98 (m, 4H). LC/MS (ES, m/z): 625 [M+H]$^+$.

Example YM-19 ethyl 3-(6-((4-chlorophenyl)(thiazol-2-yl)methyl)-1H-benzo[d]imidazol-1-yl)-8-azabicyclo[3.2.1]octane-8-carboxylate

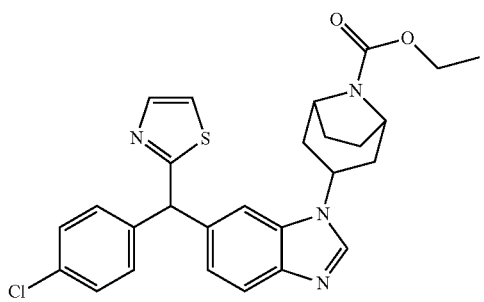 [SMILES: CCOC(=O)N1C2CCC1CC(n1cnc3ccc(C(c4ccc(Cl)cc4)c4nccs4)cc31)C2]

Step 1 ethyl 3-amino-8-azabicyclo[3.2.1]octane-8-carboxylate

Into a 1000-mL round-bottom flask, was placed a solution of Sm (19.7 mg, 100.00 mmol, 1.00 equiv) in ethanol/NH$_3$ (500 mL), Ti(OiPr)$_4$ (60 mL, 200 mmol, 2.00 equiv), stirred for overnight at room temperature. Then added NaBH$_4$ (6 g, 150.00 mmol, 1.50 equiv). The resulting solution was allowed to react, with stirring, for an additional 4 h at room temperature. The resulting solution was diluted with of 2 M NH$_3$/H$_2$O (500 mL). The solids were filtered out, washed with ethyl acetate (500 mL). The aqueous solution was extracted with ethyl acetate (3×500 mL) and the organic layers combined. The pH value of the solution was adjusted to 3-4 with hydrogen chloride (1 M). The aqueous phase was collected, and potassium hydroxide (2 M) was employed to adjust the pH to 10. The resulting solution was extracted with ethyl acetate (3×500 mL) of ethyl acetate and the organic layers combined and dried over anhydrous sodium sulfate and concentrated under vacuum to yield ethyl 3-amino-8-azabicyclo[3.2.1]octane-8-carboxylate as a white solid.

LC/MS (ES, m/z) 199 [M+H]$^+$.

Step 2 ethyl 3-((5-fluoro-2-nitrophenyl)amino)-8-azabicyclo[3.2.1]octane-8-carboxylate Into a 500-mL round-bottom flask, was placed a solution of 2,4-difluoro-1-nitrobenzene (13.29 g, 83.58 mmol, 1.00 equiv) in CH$_3$CN (350 mL), ethyl 3-amino-8-azabicyclo[3.2.1]octane-8-carboxylate (18.2 g, 91.92 mmol, 1.10 equiv), triethylamine (18.6 g, 184.16 mmol, 2.20 equiv). The resulting solution was stirred overnight at 90° C. The resulting mixture was concentrated under vacuum. The residue was dissolved in dichloromethane (500 mL). The resulting mixture was washed with sodium bicarbonate (1×100 mL) and brine (1×100 mL). The mixture was dried over anhydrous sodium sulfate and concentrated. The residue was applied onto a silica gel column with ethyl acetate/petroleum ether (1:50-1:10) to yield ethyl 3-((5-fluoro-2-nitrophenyl)amino)-8-azabicyclo[3.2.1]octane-8-carboxylate as a yellow solid.

LC/MS (ES, m/z) 338 [M+H]$^+$.

Step 3 2-(3-((8-butyryl-8-azabicyclo[3.2.1]octan-3-yl)amino)-4-nitrophenyl)-2-(4-chlorophenyl)acetonitrile Into a 1000-mL round-bottom flask, was placed a solution of ethyl 3-((5-fluoro-2-nitrophenyl)amino)-8-azabicyclo[3.2.1]octane-8-carboxylate (25.9 g, 76.85 mmol, 1.00 equiv) in tetrahydrofuran/i-PrOH (760/190 mL), 2-(4-chlorophenyl)acetonitrile (12.8 g, 84.53 mmol, 1.10 equiv), t-BuOK (21.52 g, 192.14 mmol, 2.50 equiv). The resulting solution was stirred for 30 min at room temperature. The resulting solution was diluted with water (400 mL). The resulting solution was extracted with dichloromethane (3×600 mL) and the organic layers combined. The resulting mixture was washed with water (2×100 mL) and brine (1×100 mL). The mixture was dried over anhydrous sodium sulfate and concentrated. The residue was applied onto a silica gel column with ethyl acetate/petroleum ether (1:20-1:5) to yield of 2-(3-((8-butyryl-8-azabicyclo[3.2.1]octan-3-yl)amino)-4-nitrophenyl)-2-(4-chlorophenyl)acetonitrile as a yellow solid.

LC/MS (ES, m/z) 467 [M+H]$^+$.

Step 4 ethyl 3-((5-(2-amino-1-(4-chlorophenyl)-2-thioxoethyl)-2-nitrophenyl)amino)-8-azabicyclo[3.2.1]octane-8-carboxylate Into a 250-mL sealed tube, was placed a solution of 2-(3-((8-butyryl-8-azabicyclo[3.2.1]octan-3-yl)amino)-4-nitrophenyl)-2-(4-chlorophenyl)acetonitrile (14.5 g, 30.98 mmol, 1.00 equiv) in ethanol (150 mL), P$_2$S$_5$ (9 g, 40.49 mmol, 2.00 equiv). The resulting solution was stirred overnight at 70° C. The resulting solution was diluted with water (100 mL). The resulting solution was extracted with ethyl acetate (3×250 mL) and the organic layers combined. The resulting mixture was washed with water (2×50 mL) and brine (50 mL). The mixture was dried over anhydrous sodium sulfate. The residue was applied onto a silica gel column with ethyl acetate/petroleum ether (1:20-1:5) to yield ethyl 3-((5-(2-amino-1-(4-chlorophenyl)-2-thioxoethyl)-2-nitrophenyl)amino)-8-azabicyclo[3.2.1]octane-8-carboxylate as a yellow solid.

LC/MS (ES, m/z) 503 [M+H]$^+$.

Step 5 ethyl 3-((5-((4-chlorophenyl)(thiazol-2-yl)methyl)-2-nitrophenyl)amino)-8-azabicyclo[3.2.1]octane-8-carboxylate Into a 500-mL round-bottom flask, was placed a solution of ethyl 3-((5-(2-amino-1-(4-chlorophenyl)-2-thioxoethyl)-2-nitrophenyl)amino)-8-azabicyclo[3.2.1]octane-8-carboxylate (13.5 g, 26.89 mmol, 1.00 equiv) in H$_2$O/HOAc (50/150 mL), 2-bromo-1,1-diethoxyethane (21 g, 106.60 mmol, 4.00 equiv). The resulting solution was stirred for 30 min at 100° C. The resulting solution was diluted with water (250 mL). The resulting solution was extracted with ethyl acetate (3×300 mL) and the organic layers combined. The resulting mixture was washed with sodium bicarbonate (3×100 mL) and brine (1×100 mL). The mixture was dried over anhydrous sodium sulfate. The residue was applied onto a silica gel column with ethyl acetate/petroleum ether (1:20-1:5) to yield ethyl 3-((5-((4-chlorophenyl)(thiazol-2-yl)methyl)-2-nitrophenyl)amino)-8-azabicyclo[3.2.1]octane-8-carboxylate as a yellow solid.
LC/MS (ES, m/z) 527 [M+H]$^+$.

Step 6 ethyl 3-((2-amino-5-((4-chlorophenyl)(thiazol-2-yl)methyl)phenyl)amino)-8-azabicyclo[3.2.1]octane-8-carboxylate Into a 250-mL round-bottom flask, was placed a solution of ethyl 3-((5-((4-chlorophenyl)(thiazol-2-yl)methyl)-2-nitrophenyl)amino)-8-azabicyclo[3.2.1]octane-8-carboxylate (9 g, 17.11 mmol, 1.00 equiv) in tetrahydrofuran/MeOH (80/80 mL), RaNi (3 g, 3.00 equiv). To the above hydrogen gas was bubbled in. The resulting solution was stirred overnight at room temperature. The solids were filtered out. The resulting mixture was concentrated under vacuum to yield ethyl 3-((2-amino-5-((4-chlorophenyl)(thiazol-2-yl)methyl)phenyl)amino)-8-azabicyclo[3.2.1]octane-8-carboxylate as a yellow solid.
LC/MS (ES, m/z) 497 [M+H]$^+$.

Step 7 ethyl 3-(6-((4-chlorophenyl)(thiazol-2-yl)methyl)-1H-benzo[d]imidazol-1-yl)-8-azabicyclo[3.2.1]octane-8-carboxylate Into a 10-mL round-bottom flask, was placed ethyl 3-((2-amino-5-((4-chlorophenyl)(thiazol-2-yl)methyl)phenyl)amino)-8-azabicyclo[3.2.1]octane-8-carboxylate (250 mg, 0.50 mmol, 1.00 equiv), trimethoxymethane (3 ml, 4.00 equiv), hydrogen chloride (0.02 ml). The resulting solution was heated to reflux for 6 hr. The resulting solution was diluted with water (20 mL). The resulting solution was extracted with ethyl acetate (3×50 mL) and the organic layers combined. The resulting mixture was washed with water (3×30 mL) and brine (30 mL). The mixture was dried over anhydrous sodium sulfate and concentrated. The residue was purified by TLC method with DCM:MeOH=50:1 to yield ethyl 3-(6-((4-chlorophenyl)(thiazol-2-yl)methyl)-1H-benzo[d]imidazol-1-yl)-8-azabicyclo[3.2.1]octane-8-carboxylate as a white solid.
$^1$H NMR (400 MHz, DMSO) δ: 8.42 (s, 1H), 7.82 (d, J=2.4 Hz, 1H), 7.67 (d, J=2.7 Hz, 1H), 7.62 (d, J=6.3 Hz, 1H), 7.34-7.41 (m, 5H), 7.16-7.18 (d, J=6.3 Hz, 1H), 6.19 (s, 1H), 4.35-4.39 (m, 1H), 4.30 (brm, 2H), 4.06-4.12 (m, 2H), 2.50-2.55 (m, 2H), 1.89-1.96 (m, 4H), 1.66-1.70 (m, 2H), 1.21 (t, J=7.2 Hz, 3H). LC/MS (ES, m/z): 507 [M+H]$^+$.

The following compounds were prepared according to the procedure as described in Example YM-19 above, selecting and substituting suitable reactants and reagents, as would be readily recognized by those skilled in the art.

Example YM-20 ethyl 3-(6-((4-chlorophenyl)(thiazol-2-yl)methyl)-2-ethyl-1H-benzo[d]imidazol-1-yl)-8-azabicyclo[3.2.1]octane-8-carboxylate

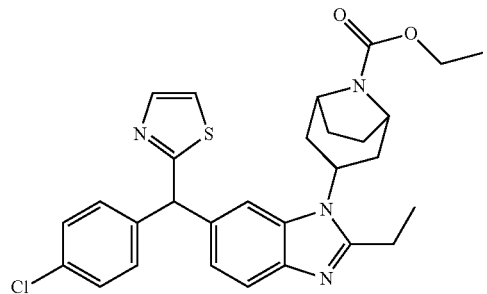 [SMILES: CCOC(=O)N1C2CCC1CC(n1c(CC)nc3ccc(C(c4ccc(Cl)cc4)c4nccs4)cc31)C2]

LC/MS (ES, m/z): 535 [M+H]$^+$.

Example YM-21 ethyl 3-(6-((4-chlorophenyl)(thiazol-2-yl)methyl)-2-propyl-1H-benzo[d]imidazol-1-yl)-8-azabicyclo[3.2.1]octane-8-carboxylate

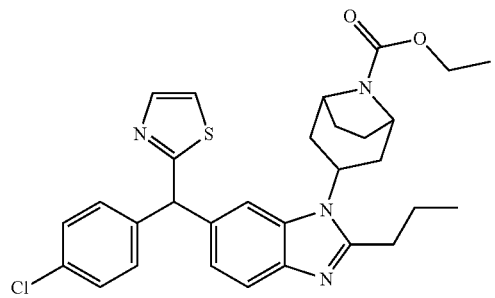 [SMILES: CCCc1nc2ccc(C(c3ccc(Cl)cc3)c3nccs3)cc2n1C1CC2CCC(C1)N2C(=O)OCC]

LC/MS (ES, m/z): 549 [M+H]$^+$.

Example YM-22 ethyl 3-(6-((4-chlorophenyl)(thiazol-2-yl)methyl)-2-isopropyl-1H-benzo[d]imidazol-1-yl)-8-azabicyclo[3.2.1]octane-8-carboxylate

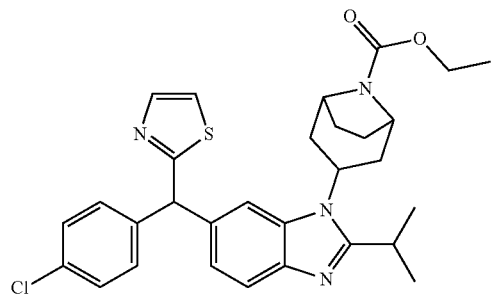 [SMILES: CCOC(=O)N1C2CCC1CC(n1c(C(C)C)nc3ccc(C(c4ccc(Cl)cc4)c4nccs4)cc31)C2]

LC/MS (ES, m/z): 549 [M+H]$^+$.

Example YM-23 ethyl 3-(6-((4-chlorophenyl)(thiazol-2-yl)methyl)-2-cyclopropyl-1H-benzo[d]imidazol-1-yl)-8-azabicyclo[3.2.1]octane-8-carboxylate

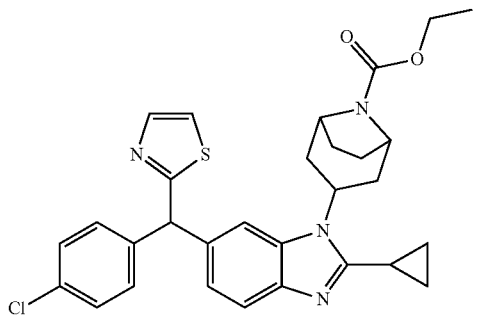 [SMILES: CCOC(=O)N1C2CCC1CC(n1c(C3CC3)nc3ccc(C(c4ccc(Cl)cc4)c4nccs4)cc31)C2]

LC/MS (ES, m/z): 547 [M+H]⁺.

Example YM-24 ethyl 3-(2-(4-chlorophenyl)-6-((4-chlorophenyl)(thiazol-2-yl)methyl-1H-benzo[d]imidazol-1-yl)-8-azabicyclo[3.2.1]octane-8-carboxylate

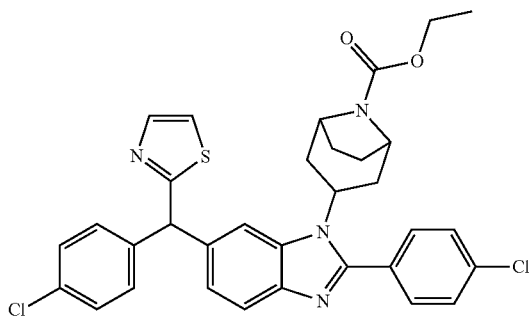 [SMILES: CCOC(=O)N1C2CCC1CC(n1c(-c3ccc(Cl)cc3)nc3ccc(C(c4ccc(Cl)cc4)c4nccs4)cc31)C2]

LC/MS (ES, m/z): 617 [M+H]⁺.

Example YM-25 ethyl 3-(6-((4-chlorophenyl)(thiazol-2-yl)methyl)-2-(pyridin-3-yl)-1H-benzo[d]imidazol-1-yl)-8-azabicyclo[3.2.1]octane-8-carboxylate

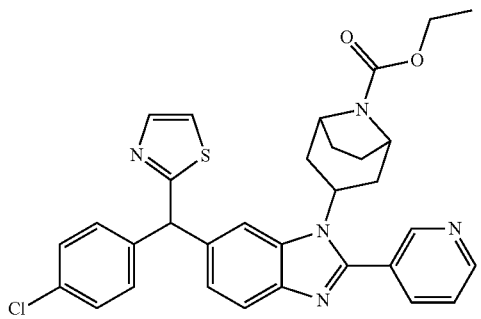 [SMILES: CCOC(=O)N1C2CCC1CC(n1c(-c3cccnc3)nc3ccc(C(c4ccc(Cl)cc4)c4nccs4)cc31)C2]

LC/MS (ES, m/z): 584 [M+H]⁺.

Example YM-26

6-(bis(4-chlorophenyl)methyl)-2-cyclopropyl-1-(1-(trifluoromethylsulfonyl)piperidin-4-yl)-1H-benzo[d]imidazole, Compound #

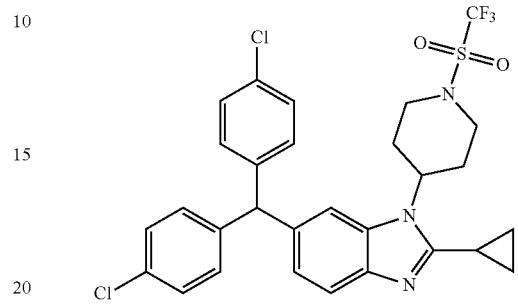

Step 1 1-(trifluoromethane)sulfonylpiperidin-4-amine hydrochloride

Into a 1-L round-bottom flask, was placed tert-butyl N-[1-(trifluoromethane)sulfonylpiperidin-4-yl]carbamate (70 g, 210.63 mmol, 1.00 equiv), 1,4-dioxane (200 mL), hydrogen chloride (100 mL, 3.00 equiv, 6M). The resulting solution was stirred overnight at 60° C. in an oil bath. The resulting mixture was concentrated under vacuum. The resulting residue was purified by re-crystallization from DCM to yield 1-(trifluoromethane)sulfonylpiperidin-4-amine hydrochloride as a light brown solid.

LC/MS (ES, m/z) 233 [M−HCl+H]⁺

Step 2 N-(5-bromo-2-nitrophenyl)-1-(trifluoromethane)sulfonylpiperidin-4-amine

Into a 500-mL round-bottom flask, was placed a solution of 1-(trifluoromethane)sulfonylpiperidin-4-amine hydrochloride (13.3 g, 49.50 mmol, 1.00 equiv) in CH₃CN (mL), 4-bromo-2-fluoro-1-nitrobenzene (10 g, 45.46 mmol, 1.00 equiv), triethylamine (14.5 g, 143.29 mmol, 3.20 equiv). The resulting solution was stirred for 1 overnight at 90° C. The solids were collected by filtration to yield N-(5-bromo-2-nitrophenyl)-1-(trifluoromethane)sulfonylpiperidin-4-amine as a yellow solid.

LC/MS (ES, m/z) 434 [M+H]⁺.

Step 3 5-bromo-1-N-[1-(trifluoromethane)sulfonylpiperidin-4-yl]benzene-1,2-diamine Into a 500-mL round-bottom flask, was placed N-(5-bromo-2-nitrophenyl)-1-(trifluoromethane)sulfonylpiperidin-4-amine (18 g, 41.65 mmol, 1.00 equiv), methanol (100 mL), tetrahydrofuran (200 mL), Ni (9 g). To the resulting mixture was introduced hydrogen. The resulting solution was stirred for 1 overnight at room temperature. The solids were filtered out. The resulting mixture was concentrated under vacuum to yield 5-bromo-1-N-[1-(trifluoromethane)sulfonylpiperidin-4-yl]benzene-1,2-diamine as brown oil.

LC/MS (ES, m/z) 402 [M+H]⁺.

Step 4 N-(4-bromo-2-[[1-(trifluoromethane)sulfonylpiperidin-4-yl]amino]phenyl)cyclopropanecarboxamide Into a 250-mL round-bottom flask, was placed 5-bromo-1-N-[1-(trifluoromethane)sulfonylpiperidin-4-yl]benzene-1,2-diamine (7 g, 17.40 mmol, 1.00 equiv), N,N-dimethylformamide (100 mL), HATU (8.581 g, 22.57 mmol, 1.30 equiv), DIEA (4.481 g, 34.67 mmol, 1.99 equiv), cyclopropanecarboxylic acid (1.643 g, 19.08 mmol, 1.10 equiv). The resulting solution was stirred overnight at room temperature. The reaction progress was monitored by LCMS. The reaction was then quenched by the addition of water (500 mL). The resulting solution was extracted with ethyl acetate (3×300 mL) and the organic layers combined and dried over anhydrous sodium sulfate. The solids were filtered out. The resulting mixture was concentrated under vacuum to yield of N-(4-bromo-2-[[1-(trifluoromethane)sulfonylpiperidin-4-yl]amino]phenyl)cyclopropanecarboxamide as a brown solid.

LC/MS (ES, m/z) 470 [M+H]$^+$.

Step 5 6-bromo-2-cyclopropyl-1-[1-(trifluoromethane)sulfonylpiperidin-4-yl]-1H-1,3-benzodiazole Into a 250-mL round-bottom flask, was placed N-(4-bromo-2-[[1-(trifluoromethane)sulfonylpiperidin-4-yl]amino]phenyl)cyclopropanecarboxamide (7.9 g, 16.80 mmol, 1.00 equiv), CF$_3$COOH (100 mL). The resulting solution was stirred overnight at 120° C. The resulting mixture was concentrated under vacuum. The resulting solution was diluted with ethyl acetate (200 mL). The resulting mixture was washed with 30% NaHCO$_3$ (3×100 mL). The resulting mixture was washed with sodium chloride (100 mL). The mixture was dried over anhydrous sodium sulfate. The solids were filtered out. The resulting mixture was concentrated under vacuum. The resulting residue was re-crystallized from ethyl acetate in the ratio of 1:10 to yield 6-bromo-2-cyclopropyl-1-[1-(trifluoromethane)sulfonylpiperidin-4-yl]-1H-1,3-benzodiazole as a pink solid.

LC/MS (ES, m/z) 452 [M+H]$^+$.

Step 6 bis(4-chlorophenyl)([2-cyclopropyl-1-[1-(trifluoromethane)sulfonylpiperidin-4-yl]-1H-1,3-benzodiazol-6-yl])methanol Into a 250-mL 3-necked-round-bottom flask purged and maintained with an inert atmosphere of nitrogen, was placed 6-bromo-2-cyclopropyl-1-[1-(trifluoromethane)sulfonylpiperidin-4-yl]-1H-1,3-benzodiazole (6 g, 13.27 mmol, 1.00 equiv), tetrahydrofuran (100 mL), n-BuLi (8 mL, 1.50 equiv, 2.5M) dropwise with stirring at −78° C. The resulting solution was stirred for 0.5 h at −78° C. Then bis(4-chlorophenyl)methanone (3.973 g, 15.82 mmol, 1.19 equiv) was added dropwise with stirring at −78° C. The resulting solution was stirred for 0.5 h at −78° C., then with stirring, overnight at room temperature. The reaction was then quenched by the addition of water (300 mL). The resulting solution was extracted with ethyl acetate (3×300 mL) and the organic layers combined and dried over anhydrous sodium sulfate. The solids were filtered out. The resulting mixture was concentrated under vacuum. The residue was applied onto a silica gel column with ethyl acetate/petroleum ether (1:3) to yield bis(4-chlorophenyl)([2-cyclopropyl-1-[1-(trifluoromethane)sulfonylpiperidin-4-yl]-1H-1,3-benzodiazol-6-yl])methanol as a white solid.

LC/MS (ES, m/z) 624 [M+H]$^+$.

Step 7 6-[bis(4-chlorophenyl)methyl]-2-cyclopropyl-1-[1-(trifluoromethane)sulfonylpiperidin-4-yl]-1H-1,3-benzodiazole Into a 250-mL round-bottom flask, was placed bis(4-chlorophenyl)([2-cyclopropyl-1-[1-(trifluoromethane)sulfonylpiperidin-4-yl]-1H-1,3-benzodiazol-6-yl])methanol (5 g, 8.01 mmol, 1.00 equiv), dichloromethane (100 mL), Et$_3$SiH (3.723 g, 32.02 mmol, 4.00 equiv). This was followed by the addition of CF$_3$COOH (22.87 g, 200.58 mmol, 25.06 equiv) dropwise with stirring. The resulting solution was stirred for 2 h at room temperature. The reaction progress was monitored by LCMS. The reaction was then quenched by the addition of water (500 mL). The resulting solution was extracted with ethyl acetate (3×300 mL) and the organic layers combined and dried over anhydrous sodium sulfate and concentrated under vacuum. The residue was applied onto a silica gel column with ethyl acetate/petroleum ether (1:5) to yield 6-[bis(4-chlorophenyl)methyl]-2-cyclopropyl-1-[1-(trifluoromethane)sulfonylpiperidin-4-yl]-1H-1,3-benzodiazole as a white solid.

$^1$H NMR (300 MHz, DMSO) δ: 7.46 (d, J=8.4 Hz, 1H), 7.38 (d, J=8.4 Hz, 4H), 7.31 (brs, 1H), 7.14 (d, J=8.4 Hz, 4H), 6.88 (d, J=8.4 Hz, 1H), 5.82 (s, 1H), 4.94-4.98 (m, 1H), 3.95-3.99 (m, 2H), 3.46-3.55 (m, 2H), 2.27-2.33 (m, 3H), 2.00-2.04 (m, 2H), 1.04-1.07 (m, 4H). LC/MS (ES, m/z): 608 [M+H]$^+$.

The following compound was prepared according to the procedure as described in Example YM-26 above, selecting and substituting suitable reactants and reagents, as would be readily recognized by those skilled in the art.

Example YM-27

6-(bis(4-chlorophenyl)methyl)-2-ethyl-1-(1-(trifluoromethylsulfonyl)piperidin-4-yl)-1H-benzo[d]imidazole hydrochloride

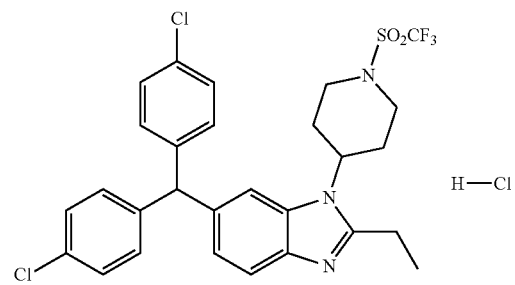

$^1$H NMR (300 MHz, DMSO) δ: 7.79 (d, J=8.4 Hz, 2H), 7.43 (d, J=8.4 Hz, 4H), 7.28 (d, J=8.4 Hz, 1H), 7.16 (d, J=8.4 Hz, 4H), 6.00 (s, 1H), 4.95 (brm, 1H), 3.99-4.06 (m, 2H), 3.49-3.52 (m, 2H), 3.21-3.28 (m, 2H), 2.29 (brm, 2H), 2.15-2.19 (m, 2H), 1.14 (t, J=7.5 Hz, 3H). LC/MS (ES, m/z): 596 [M−HCl+H]$^+$.

Example BZ-1

((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate; Compound #102

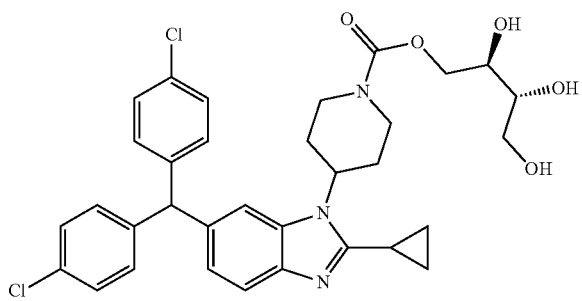 [SMILES: O=C(OC[C@@H](O)[C@H](O)CO)N1CCC(n2c(C3CC3)nc3ccc(C(c4ccc(Cl)cc4)c4ccc(Cl)cc4)cc32)CC1]

STEP A: (4-(6-(bis(4-chlorophenyl)methyl)-2-cyclopropyl-1H-benzo[d]imidazol-1-yl)piperidin-1-yl)(1H-imidazol-1-yl)methanone A solution of 6-(bis(4-chlorophenyl)methyl)-2-cyclopropyl-1-(piperidin-4-yl)-1H-benzo[d]imidazole (106 mg, 0.18 mmol), 1,1'-carbonyldiimidazole (44 mg, 0.27 mmol) and Et$_3$N (0.075 mL, 0.54 mmol) in THF (3 mL) was stirred at room temperature overnight. The resulting mixture was then diluted with EtOAc and washed with aq. NaHCO$_3$ and aqueous NaCl. The organic layer was dried over Na$_2$SO$_4$ and concentrated to yield (4-(6-(bis(4-chlorophenyl)methyl)-2-cyclopropyl-1H-benzo[d]imidazol-1-yl)piperidin-1-yl)(1H-imidazol-1-yl)methanone.

STEP B: ((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate A mixture of (4-(6-(bis(4-chlorophenyl)methyl)-2-cyclopropyl-1H-benzo[d]imidazol-1-yl)piperidin-1-yl)(1H-imidazol-1-yl)methanone (60 mg, 0.105 mmol), (−)-2,3-O-isopropylidene-D-threitol (34 mg, 0.21 mmol) and Cs$_2$CO$_3$ (34 mg, 0.105 mmol) in DMF (2 mL) was stirred at room temperature overnight. The reaction mixture was diluted with H$_2$O and filtered. The solid was collected and purified by chromatography (silica gel column, 2% MeOH/CH$_2$Cl$_2$) to yield ((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate.

STEP C: ((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate A solution of ((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate (30 mg, 0.045 mmol) in TFA (1 mL) and H$_2$O (1 mL) was stirred at room temperature for 3 hours. The mixture was concentrated. The resulting residue was diluted with EtOAc and washed with aq NaHCO$_3$ and aq NaCl. The organic solution was dried over Na$_2$SO$_4$ and concentrated. The resulting residue was purified by chromatography (silica gel column, 6% MeOH/CH$_2$Cl$_2$) to yield ((4R,5R)-5-(hydroxymethyl)-2,2-dimethyl-1,3-dioxolan-4-yl)methyl 4-(6-(bis(4-chlorophenyl)methyl)-2-cyclopropyl-1H-benzo[d]imidazol-1-yl)piperidine-1-carboxylate.

$^1$H NMR (CHLOROFORM-d) Shift: 7.58 (d, J=8.6 Hz, 1H), 7.19-7.36 (m, 4H), 6.95-7.18 (m, 5H), 6.88 (dd, J=8.3, 1.3 Hz, 1H), 5.61 (s, 1H), 4.50-4.70 (m, 1H), 4.31 (br d, J=10.6 Hz, 4H), 3.88-4.00 (m, 1H), 3.63-3.74 (m, 1H), 2.95 (br s, 2H), 2.32 (br s, 2H), 1.85-2.03 (m, 3H), 1.75 (br s, 2H), 1.06-1.24 (m, 4H). MS: 624.2 (M+H$^+$).

Example BZ-2

3-((4-(6-(bis(4-chlorophenyl)methyl)-2-cyclopropyl-1H-benzo[d]imidazol-1-yl)piperidin-1-yl)methyl)phenol; Compound #90

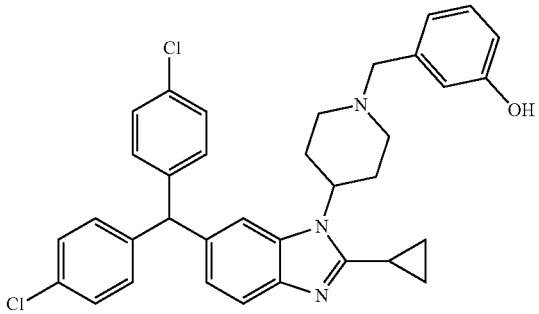 [SMILES: Oc1cccc(CN2CCC(n3c(C4CC4)nc4ccc(C(c5ccc(Cl)cc5)c5ccc(Cl)cc5)cc43)CC2)c1]

To a solution of 6-(bis(4-chlorophenyl)methyl)-2-cyclopropyl-1-(piperidin-4-yl)-1H-benzo[d]imidazole (100 mg, 0.17 mmol) and 3-hydroxy-benzaldehyde (31 mg, 0.25 mmol) in 1,2-dichloroethane (3 mL) at room temperature was added acetic acid (0.15 mL) followed by sodium triacetoxyborohydride (72 mg, 0.34 mmol). The reaction was stirred at room temperature for 6 hours. To the mixture was then added additional 3-hydroxy-benzaldehyde (31 mg, 0.25 mmol), acetic acid (0.15 mL), and sodium triacetoxyborohydride (72 mg, 0.34 mmol). The reaction was stirred at room temperature overnight before it was then quenched with aq NaHCO$_3$. The resulting mixture was extracted with EtOAc, and the organic layer was washed with aq NaCl, dried over Na$_2$SO$_4$ and concentrated. The resulting residue was purified by chromatography (silica gel column, 3% MeOH/CH$_2$Cl$_2$) to yield 3-((4-(6-(bis(4-chlorophenyl)methyl)-2-cyclopropyl-1H-benzo[d]imidazol-1-yl)piperidin-1-yl)methyl)phenol.

$^1$H NMR (CHLOROFORM-d) Shift: 7.54 (d, J=8.1 Hz, 1H), 7.17-7.31 (m, 6H), 7.00 (d, J=8.6 Hz, 4H), 6.82-6.91 (m, 2H), 6.76 (dd, J=8.1, 2.5 Hz, 2H), 5.54 (s, 1H), 4.65-4.65 (m, 1H), 4.40-4.49 (m, 1H), 3.53 (s, 2H), 3.10 (br d, J=11.6 Hz, 2H), 2.42-2.56 (m, 2H), 2.18 (br t, J=11.1 Hz, 2H), 1.90-2.08 (m, 1H), 1.84 (br d, J=10.1 Hz, 2H), 1.11-1.19 (m, 2H), 1.00-1.11 (m, 2H). MS: 581.8 (M+H$^+$).

Example BZ-3

6-(bis(4-chlorophenyl)methyl)-2-cyclopropyl-1-(1-(prop-2-yn-1-yl)piperidin-4-yl)-1H-benzo[d]imidazole; Compound #76

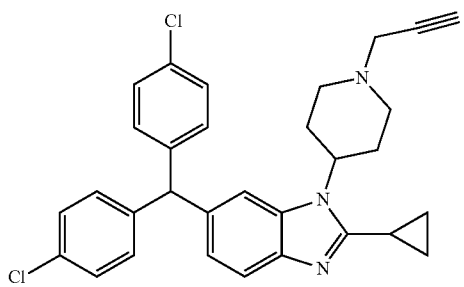 [SMILES: C#CCN1CCC(n2c(C3CC3)nc3ccc(C(c4ccc(Cl)cc4)c4ccc(Cl)cc4)cc32)CC1]

A mixture of 6-(bis(4-chlorophenyl)methyl)-2-cyclopropyl-1-(piperidin-4-yl)-1H-benzo[d]imidazole (200 mg, 0.34 mmol), propargyl bromide (80% in toluene, 0.057 mL, 0.51 mmol) and $K_2CO_3$ (94 mg, 0.68 mmol) in $CH_3CN$ (4 mL) was stirred at room temperature for 6 h. The mixture was diluted with EtOAc, washed with $H_2O$ and aqueous NaCl. The organic layer was dried over $Na_2SO_4$ and concentrated. The resulting residue was purified by chromatography (silica gel column, 3% MeOH/$CH_2Cl_2$) to yield 6-(bis(4-chlorophenyl)methyl)-2-cyclopropyl-1-(1-(prop-2-yn-1-yl)piperidin-4-yl)-1H-benzo[d]imidazole.

$^1$H NMR (CHLOROFORM-d) δ: 7.57 (d, J=8.6 Hz, 1H), 7.33 (s, 1H), 7.22-7.28 (m, 4H), 6.99-7.06 (m, 4H), 6.84 (dd, J=8.6, 1.5 Hz, 1H), 5.59 (s, 1H), 4.39-4.49 (m, 1H), 3.41 (d, J=2.5 Hz, 2H), 3.08 (br d, J=11.1 Hz, 2H), 2.41-2.60 (m, 4H), 2.31 (t, J=2.3 Hz, 1H), 1.86-2.05 (m, 3H), 1.05-1.28 (m, 4H). MS: 514.2 (M+H$^+$).

Example BZ-4

Methyl 2-(4-(6-(bis(4-chlorophenyl)methyl)-2-cyclopropyl-1H-benzo[d]imidazol-1-yl)piperidin-1-yl)acetate; Compound #64

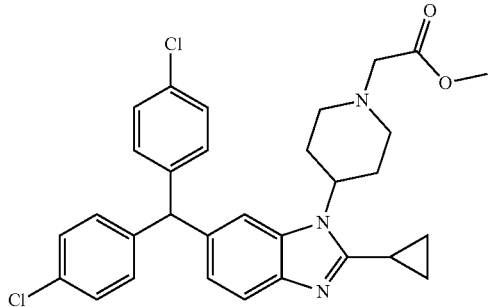 [SMILES: COC(=O)CN1CCC(n2c(C3CC3)nc3ccc(C(c4ccc(Cl)cc4)c4ccc(Cl)cc4)cc32)CC1]

Methyl 2-(4-(6-(bis(4-chlorophenyl)methyl)-2-cyclopropyl-1H-benzo[d]imidazol-1-yl)piperidin-1-yl)acetate was prepared according to the procedure as described in Example BZ-3 above, substituting methyl bromoacetate for propargyl bromide.

$^1$H NMR (CHLOROFORM-d) δ: 7.57 (d, J=8.6 Hz, 1H), 7.36 (s, 1H), 7.22-7.28 (m, 5H), 7.00-7.05 (m, 4H), 6.84 (dd, J=8.6, 1.5 Hz, 1H), 5.60 (s, 1H), 4.40-4.50 (m, 1H), 3.76 (s, 3H), 3.34 (s, 2H), 3.13 (br d, J=10.6 Hz, 2H), 2.45-2.63 (m, 4H), 1.97-2.05 (m, 1H), 1.84-1.93 (m, 2H), 1.06-1.28 (m, 4H). MS: 548.3 (M+H$^+$).

Example BZ-5

2-(4-(6-(bis(4-chlorophenyl)methyl)-2-cyclopropyl-1H-benzo[d]imidazol-1-yl)piperidin-1-yl)acetic acid; Compound #63

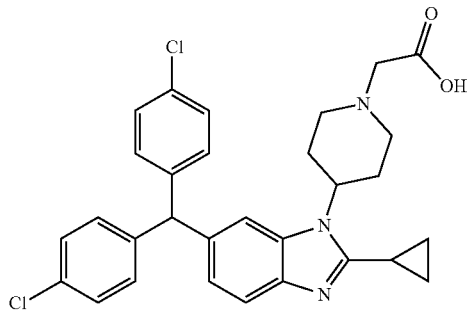 [SMILES: O=C(O)CN1CCC(n2c(C3CC3)nc3ccc(C(c4ccc(Cl)cc4)c4ccc(Cl)cc4)cc32)CC1]

A mixture of methyl 2-(4-(6-(bis(4-chlorophenyl)methyl)-2-cyclopropyl-1H-benzo[d]imidazol-1-yl)piperidin-1-yl)acetate (70 mg, 0.13 mmol) and LiOH.$H_2O$ (16 mg, 0.38 mmol) in THF (2 mL) and $H_2O$ (1 mL) was stirred at room temperature for 2 h. To the reaction mixture was added 1N HCl (0.38 mL) and $H_2O$. The organic solvent was removed and the mixture was filtered. The resulting solid was collected and dissolved in MeOH/$CH_2Cl_2$, and filtered. The solution was concentrated to yield 2-(4-(6-(bis(4-chlorophenyl)methyl)-2-cyclopropyl-1H-benzo[d]imidazol-1-yl)piperidin-1-yl)acetic acid. MS: 534.2 (M+H$^+$).

Example BZ-6

3-((4-(6-(bis(4-chlorophenyl)methyl)-2-cyclopropyl-1H-benzo[d]imidazol-1-yl)piperidin-1-yl)sulfonyl)aniline; Compound #52

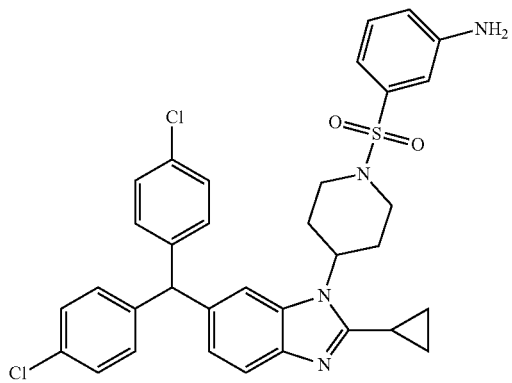 [SMILES: Nc1cccc(S(=O)(=O)N2CCC(n3c(C4CC4)nc4ccc(C(c5ccc(Cl)cc5)c5ccc(Cl)cc5)cc43)CC2)c1]

STEP A: 6-(bis(4-chlorophenyl)methyl)-2-cyclopropyl-1-(1-((3-nitrophenyl)sulfonyl)piperidin-4-yl)-1H-benzo[d]imidazole To a solution of 6-(bis(4-chlorophenyl)methyl)-2-cyclopropyl-1-(piperidin-4-yl)-1H-benzo[d]imidazole (400 mg, 0.68 mmol) and Et$_3$N (0.33 mL, 2.37 mmol) in CH$_2$Cl$_2$ (8 mL) at 0° C. was added 3-nitrobenzenesulfonyl chloride (195 mg, 0.88 mmol). The reaction was stirred at 0° C. for 30 min then warmed up to room temperature and stirred for 2 h. The reaction was quenched with aq NaHCO$_3$ and extracted with diethyl ether. The organic layer was washed with aq NaCl, dried over Na$_2$SO$_4$ and concentrated. The resulting residue was purified by chromatography (silica gel column, 70% EtOAc/heptane) to yield 6-(bis(4-chlorophenyl)methyl)-2-cyclopropyl-1-(1-((3-nitrophenyl)sulfonyl) piperidin-4-yl)-1H-benzo[d]imidazole.

STEP B: 3-((4-(6-(bis(4-chlorophenyl)methyl)-2-cyclopropyl-1H-benzo[d]imidazol-1-yl)piperidin-1-yl)sulfonyl)aniline To a solution of 6-(bis(4-chlorophenyl)methyl)-2-cyclopropyl-1-(1-((3-nitrophenyl)sulfonyl)piperidin-4-yl)-1H-benzo[d]imidazole (250 mg, 0.38 mmol) and NiCl$_2$ (71 mg, 0.76 mmol) in MeOH (15 mL) at 0° C. was added NaBH$_4$ (114 mg, 3.03 mmol). The reaction was stirred at 0° C. for 1 h before H$_2$O was added. The mixture was then concentrated to remove most of the organic solvent, and then filtered. The resulting solid was washed with 20% MeOH/CH$_2$Cl$_2$ for 3 times. The solution was combined and concentrated to yield compound 3-((4-(6-(bis(4-chlorophenyl)methyl)-2-cyclopropyl-1H-benzo[d]imidazol-1-yl)piperidin-1-yl)sulfonyl)aniline.

$^1$H NMR (DMSO-d$_6$) δ: 7.51 (s, 1H), 7.24-7.43 (m, 6H), 7.13 (d, J=8.1 Hz, 4H), 6.99 (t, J=1.8 Hz, 1H), 6.78-6.89 (m, 3H), 5.81 (s, 1H), 5.69 (s, 2H), 4.67 (br t, J=11.9 Hz, 1H), 3.80 (br d, J=11.6 Hz, 2H), 2.61 (br t, J=11.4 Hz, 2H), 2.27-2.47 (m, 2H), 2.10-2.19 (m, 1H), 1.89 (br d, J=10.1 Hz, 2H), 0.89-1.03 (m, 4H). MS: 631.2 (M+H$^+$).

Example BZ-7

N-(2-(2-(benzyloxy)ethoxy)ethyl)-3-((4-(6-(bis(4-chlorophenyl)methyl)-2-cyclopropyl-1H-benzo[d]imidazol-1-yl)piperidin-1-yl)sulfonyl)aniline; Compound of Formula (II)

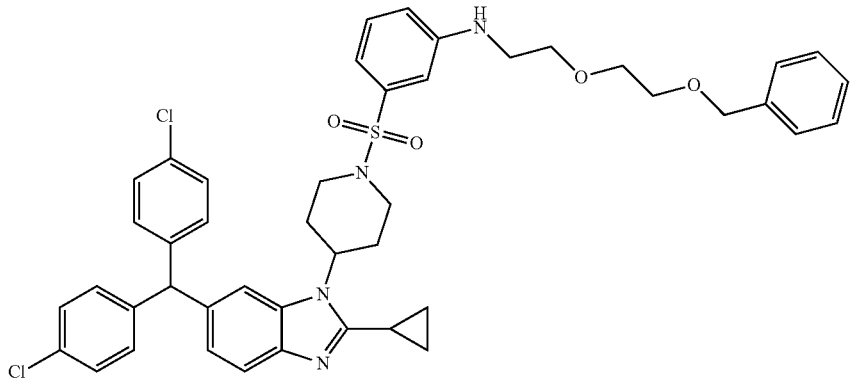 [SMILES: O=S(=O)(c1cccc(NCCOCCOCc2ccccc2)c1)N1CCC(n2c(C3CC3)nc3ccc(C(c4ccc(Cl)cc4)c4ccc(Cl)cc4)cc32)CC1]

To a solution of 3-((4-(6-(bis(4-chlorophenyl)methyl)-2-cyclopropyl-1H-benzo[d]imidazol-1-yl)piperidin-1-yl)sulfonyl)aniline (50 mg, 0.079 mmol) and 7a (50 mg, 0.26 mmol) in acetic acid (0.3 mL) and 1,2-dichloroethane (3 mL) at room temperature was added NaBH(OAc)$_3$ (50 mg, 0.24 mmol). The reaction mixture was stirred at room temperature over night before it was quenched with aq NaHCO$_3$. The resulting mixture was extracted with EtOAc, and the organic layer was washed with aq NaCl, dried over Na$_2$SO$_4$ and concentrated. The resulting residue was purified by chromatography (silica gel column, 60% EtOAc/heptane) to yield N-(2-(2-(benzyloxy)ethoxy)ethyl)-3-((4-(6-(bis(4-chlorophenyl)methyl)-2-cyclopropyl-1H-benzo[d]imidazol-1-yl)piperidin-1-yl)sulfonyl)aniline.

$^1$H NMR (CHLOROFORM-d) δ: 7.56 (d, J=8.4 Hz, 1H), 7.22-7.47 (m, 11H), 7.01-7.16 (m, 5H), 6.70-6.98 (m, 3H), 5.61 (s, 1H), 4.58 (s, 2H), 4.53 (m, 1H), 4.25-4.44 (m, 1H), 4.01 (br d, J=11.1 Hz, 2H), 3.59-3.86 (m, 6H), 3.33 (br d, J=4.0 Hz, 2H), 2.42-2.62 (m, 4H), 1.76-1.97 (m, 3H), 0.97-1.20 (m, 4H). MS: 809.2 (M+H$^+$).

Example BZ-8

2-((4-(6-(bis(4-chlorophenyl)methyl)-2-cyclopropyl-1H-benzo[d]imidazol-1-yl)piperidin-1-yl)sulfonyl)ethanamine; Compound #46

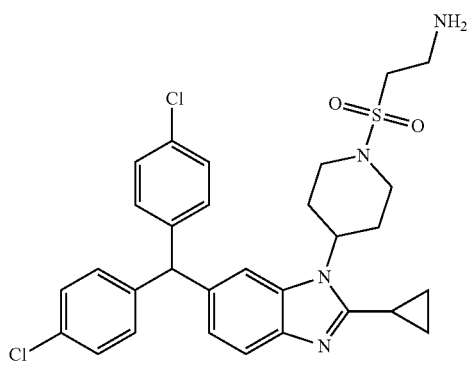 [SMILES: NCCS(=O)(=O)N1CCC(n2c(C3CC3)nc3ccc(C(c4ccc(Cl)cc4)c4ccc(Cl)cc4)cc32)CC1]

STEP A: 6-(bis(4-chlorophenyl)methyl)-2-cyclopropyl-1-(1-(vinylsulfonyl)piperidin-4-yl)-1H-benzo[d]imidazole To a solution of 6-(bis(4-chlorophenyl)methyl)-2-cyclopropyl-1-(piperidin-4-yl)-1H-benzo[d]imidazole (200 mg, 0.34 mmol) and Et$_3$N (0.19 mL, 1.36 mmol) in CH$_2$Cl$_2$ (4 mL) at 0° C. was added 2-chloroethanesulfonyl chloride (0.043 mL, 0.41 mmol). The reaction was stirred at 0° C. for 30 min before it was warmed up to room temperature and stirred for another 1 h. The reaction was quenched with aq NaHCO$_3$ and the resulting mixture was extracted with EtOAc. The organic layer was washed with aq NaCl, dried over Na₂SO₄ and concentrated. The resulting residue was purified by chromatography (silica gel column, 80% EtOAc/heptane) to yield 6-(bis(4-chlorophenyl)methyl)-2-cyclopropyl-1-(1-(vinylsulfonyl)piperidin-4-yl)-1H-benzo[d]imidazole.

STEP B: 2-((4-(6-(bis(4-chlorophenyl)methyl)-2-cyclopropyl-1H-benzo[d]imidazol-1-yl)piperidin-1-yl)sulfonyl)ethanamine A mixture of 6-(bis(4-chlorophenyl)methyl)-2-cyclopropyl-1-(1-(vinylsulfonyl)piperidin-4-yl)-1H-benzo[d]imidazole (34 mg, 0.06 mmol) and Cs₂CO₃ (20 mg, 0.06 mmol) in 28% NH₄OH aqueous solution (0.5 mL) and CH₃CN (2 mL) was stirred at room temperature for 2 days. The mixture was concentrated and the residue was diluted with CH₂Cl₂ and washed with aq NaCl. The organic layer was dried over Na₂SO₄ and concentrated. The resulting residue was purified by chromatography (silica gel column, 6% MeOH/CH₂Cl₂) to yield 2-((4-(6-(bis(4-chlorophenyl)methyl)-2-cyclopropyl-1H-benzo[d]imidazol-1-yl)piperidin-1-yl)sulfonyl)ethanamine.

MS: 583.2 (M+H⁺).

Example BZ-9

6-(bis(4-chlorophenyl)methyl)-2-cyclopropyl-1-(1-((2-(piperazin-1-yl)ethyl)sulfonyl)piperidin-4-yl)-1H-benzo[d]imidazole; Compound #45

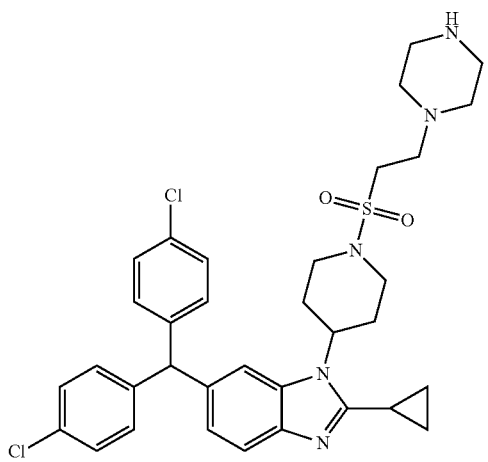 [SMILES: O=S(=O)(CCN1CCNCC1)N1CCC(n2c(C3CC3)nc3ccc(C(c4ccc(Cl)cc4)c4ccc(Cl)cc4)cc32)CC1]

6-(Bis(4-chlorophenyl)methyl)-2-cyclopropyl-1-(1-(vinylsulfonyl)piperidin-4-yl)-1H-benzo[d]imidazole was prepared according to the procedure as described in Example BZ-8 above, reacting N-Boc piperazine instead of 28% NH₄OH aqueous solution.

A solution of 6-(bis(4-chlorophenyl)methyl)-2-cyclopropyl-1-(1-(vinylsulfonyl)piperidin-4-yl)-1H-benzo[d]imidazole (34 mg, 0.045 mmol) in TFA (0.5 mL) and CH₂Cl₂ (2.5 mL) was stirred at room temperature for 2 h. The reaction mixture was concentrated and the residue was dissolved in CH₂Cl₂ and washed with aq NaHCO₃. The aqueous layer was extracted again with CH₂Cl₂. The organic layers were combined, dried over Na₂SO₄ and concentrated to yield 6-(bis(4-chlorophenyl)methyl)-2-cyclopropyl-1-(1-((2-(piperazin-1-yl)ethyl)sulfonyl)piperidin-4-yl)-1H-benzo[d]imidazole.

MS: 652.2 (M+H⁺).

Example BZ-10

3-(2-(4-(6-(bis(4-chlorophenyl)methyl)-2-cyclopropyl-1H-benzo[d]imidazol-1-ylpiperidin-1-yl)ethoxy)benzoic acid; Compound #44

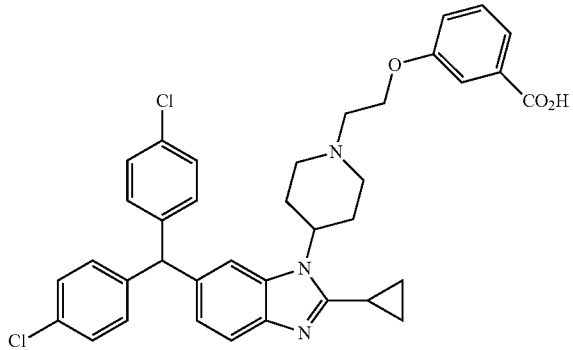 [SMILES: O=C(O)c1cccc(OCCN2CCC(n3c(C4CC4)nc4ccc(C(c5ccc(Cl)cc5)c5ccc(Cl)cc5)cc43)CC2)c1]

STEP A: 2-(4-(6-(bis(4-chlorophenyl)methyl)-2-cyclopropyl-1H-benzo[d]imidazol-1-yl)piperidin-1-yl)ethanol To a solution of methyl 2-(4-(6-(bis(4-chlorophenyl)methyl)-2-cyclopropyl-1H-benzo[d]imidazol-1-yl)piperidin-1-yl)acetate (81 mg, 0.15 mmol) in THF (4 mL) at room temperature was added LiBH₄ (2M solution in THF, 0.3 mL, 0.6 mmol). The reaction was stirred overnight, then quenched with H₂O and extracted with EtOAc. The organic layer was washed with aq NaCl, dried over Na₂SO₄ and concentrated. The resulting residue was dissolved in MeOH (2 mL)/1N NaOH (1 mL) and heated at 100° C. by microwave for 1 h. The reaction mixture was concentrated to remove MeOH and the remaining aqueous solution was extracted with CH₂Cl₂. The organic layer was dried over Na₂SO₄ and concentrated. The resulting residue was purified by chromatography (silica gel column, 3% MeOH/CH₂Cl₂) to yield 2-(4-(6-(bis(4-chlorophenyl)methyl)-2-cyclopropyl-1H-benzo[d]imidazol-1-yl)piperidin-1-yl)ethanol.

STEP B: methyl 3-(2-(4-(6-(bis(4-chlorophenyl)methyl)-2-cyclopropyl-1H-benzo[d]imidazol-1-yl)piperidin-1-yl)ethoxy)benzoate To a solution of 2-(4-(6-(bis(4-chlorophenyl)methyl)-2-cyclopropyl-1H-benzo[d]imidazol-1-yl)piperidin-1-yl)ethanol (35 mg, 0.067 mmol), methyl 3-hydroxybenzoate (30.7 mg, 0.20 mmol) and PPh₃ (53 mg, 0.20 mmol) in THF (2 mL) at room temperature was added DIAD (0.039 mL, 0.20 mmol). The reaction was stirred overnight. The resulting mixture was then concentrated and the resulting residue purified by chromatography (silica gel column, 80% EtOAc/heptane) to yield methyl 3-(2-(4-(6-(bis(4-chlorophenyl)methyl)-2-cyclopropyl-1H-benzo[d]imidazol-1-yl)piperidin-1-yl)ethoxy)benzoate.

STEP C: 3-(2-(4-(6-(bis(4-chlorophenyl)methyl)-2-cyclopropyl-1H-benzo[d]imidazol-1-yl)piperidin-1-yl)ethoxy)benzoic acid A solution of methyl 3-(2-(4-(6-(bis(4-chlorophenyl)methyl)-2-cyclopropyl-1H-benzo[d]imidazol-1-yl)piperidin-1-yl)ethoxy)benzoate (31 mg, 0.047 mmol) and LiOH (10 mg, 0.24 mmol) in H$_2$O (1 mL) and THF (2 mL) was stirred at room temperature for overnight. 1N HCl solution was added to the reaction mixture to adjust the pH to ~3. The mixture was extracted with CH$_2$Cl$_2$ for 3 times. The organic layers were combined, dried over Na$_2$SO$_4$ and concentrated. The resulting residue was purified by chromatography (silica gel column, 8% MeOH/CH$_2$Cl$_2$) to yield 3-(2-(4-(6-(bis(4-chlorophenyl)methyl)-2-cyclopropyl-1H-benzo[d]imidazol-1-yl)piperidin-1-yl)ethoxy)benzoic acid.

$^1$H NMR (CHLOROFORM-d) δ: 7.58-7.70 (m, 2H), 7.46-7.54 (m, 2H), 7.33-7.40 (m, 1H), 7.23 (d, J=8.1 Hz, 4H), 7.13 (dd, J=8.1, 2.0 Hz, 1H), 7.01 (d, J=8.6 Hz, 4H), 6.88 (dd, J=8.3, 1.3 Hz, 1H), 5.58 (s, 1H), 4.50-4.60 (m, 1H), 4.22 (t, J=5.3 Hz, 2H), 3.27-3.40 (m, 2H), 2.97 (br t, J=5.3 Hz, 2H), 2.55-2.73 (m, 2H), 2.41-2.53 (m, 2H), 2.00-2.09 (m, 1H), 1.92 (br d, J=10.6 Hz, 2H), 1.09-1.17 (m, 4H). MS: 640.2 (M+H$^+$).

Example BZ-11

2-(6-(bis(4-chlorophenyl)methyl)-2-cyclopropyl-1H-benzo[d]imidazol-1-yl)ethanol

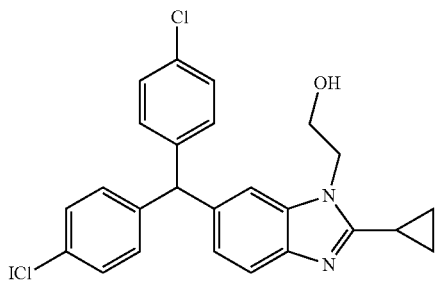

STEP A: methyl 2,2-bis(4-chlorophenyl)acetate methyl 2,2-bis(4-chlorophenyl)acetate A solution of 2,2-bis(4-chlorophenyl)acetic acid (5 g, 17.8 mmol) and H$_2$SO$_4$ (0.47 mL, 8.9 mmol) in MeOH (100 mL) was heated at 65° C. for 6 h, and was then stirred at room temperature overnight. The solution was concentrated and the residue was dissolved in diethyl ether and washed with aq NaHCO$_3$ and aq NaCl. The organic layer was dried over Na$_2$SO$_4$ and concentrated yield methyl 2,2-bis(4-chlorophenyl)acetate.

STEP B: methyl 2,2-bis(4-chlorophenyl)-2-(3-fluoro-4-nitrophenyl)acetate

To a solution of methyl 2,2-bis(4-chlorophenyl)acetate (1.0 g, 3.39 mmol) and 2,4-difluoro-1-nitrobenzene (0.39 mL, 3.56 mmol) in THF (15 mL) at −78° C. was slowly added LiHMDS (1M in THF, 3.7 mL, 3.7 mmol). The reaction was stirred at −78° C. for 20 min before it was warmed up to room temperature and stirred overnight. To the reaction was added aq NH$_4$Cl and the mixture was extracted with ethyl ether. The organic layer was washed with aq NaCl, dried over Na$_2$SO$_4$ and concentrated. The resulting residue was purified by chromatography (silica gel column, 30% CH$_2$Cl$_2$/heptane) to yield methyl 2,2-bis(4-chlorophenyl)-2-(3-fluoro-4-nitrophenyl)acetate.

STEP C: methyl 2,2-bis(4-chlorophenyl)-2-(3-((2-hydroxyethyl)amino)-4-nitrophenyl)acetate To a solution of methyl 2,2-bis(4-chlorophenyl)-2-(3-fluoro-4-nitrophenyl)acetate (275 mg) in CH$_3$CN (5 mL) at room temperature was added ethanolamine (0.076 mL, 1.27 mmol) followed by Hunig's base (0.22 mL, 1.27 mmol). The reaction was heated at 55° C. for 2 h, and was then cooled to room temperature and stirred overnight. The reaction mixture was concentrated and the resulting residue was dissolved in EtOAc and washed with aq NaHCO$_3$ and aq NaCl. The organic solution was dried over Na$_2$SO$_4$ and concentrated. The resulting residue was purified by chromatography (silica gel column, 40% EtOAc/heptane) to yield methyl 2,2-bis(4-chlorophenyl)-2-(3-((2-hydroxyethyl)amino)-4-nitrophenyl)acetate.

STEP D: methyl 2-(4-amino-3-((2-hydroxyethyl)amino)phenyl)-2,2-bis(4-chlorophenyl)acetate To a solution of methyl 2,2-bis(4-chlorophenyl)-2-(3-((2-hydroxyethyl)amino)-4-nitrophenyl)acetate (140 mg, 0.30 mmol) in EtOH (4 mL) and H$_2$O (1 mL) was added NH$_4$Cl (158 mg, 2.95 mmol) followed by Zn dust (96 mg, 1.47 mmol). The reaction was then heated at 70° C. for 1 h. The reaction mixture was cooled to room temperature and diluted with EtOAc. The solution was washed with aq NaHCO$_3$ and aq NaCl, dried Na$_2$SO$_4$ and concentrated to yield methyl 2-(4-amino-3-((2-hydroxyethyl)amino)phenyl)-2,2-bis(4-chlorophenyl)acetate.

STEP E: methyl 2,2-bis(4-chlorophenyl)-2-(2-cyclopropyl-1-(2-hydroxyethyl)-1H-benzo[d]imidazol-6-yl)acetate A solution of methyl 2-(4-amino-3-((2-hydroxyethyl)amino)phenyl)-2,2-bis(4-chlorophenyl)acetate (120 mg, 0.27 mmol) and cyclopropanecarboxaldehyde (0.04 mL, 0.54 mmol) in DMSO (1 mL) was stirred at room temperature under air for 2 days. The solution was diluted with CH$_2$Cl$_2$ and washed with H$_2$O and aq NaCl, dried over Na$_2$SO$_4$ and concentrated. The resulting residue was purified by chromatography (silica gel column, 40% EtOAc/heptane) to yield methyl 2,2-bis(4-chlorophenyl)-2-(2-cyclopropyl-1-(2-hydroxyethyl)-1H-benzo[d]imidazol-6-yl)acetate.

STEP F: 2-(6-(bis(4-chlorophenyl)methyl)-2-cyclopropyl-1H-benzo[d]imidazol-1-yl)ethanol A solution of methyl 2,2-bis(4-chlorophenyl)-2-(2-cyclopropyl-1-(2-hydroxyethyl)-1H-benzo[d]imidazol-6-yl)acetate (85 mg, 0.17 mmol) in 3N NaOH aqueous solution (1 mL, 3 mmol) and 1,4-dioxane (4 mL) was heated at 100° C. for 16 h. The reaction was cooled to room temperature and 1N HCl aqueous solution was added to adjust pH to ~7. The mixture was extracted with EtOAc and the organic solution was washed with aq NaCl, dried over Na$_2$SO$_4$, and concentrated. The resulting residue was purified by chromatography (silica gel column, 70% EtOAc/heptane) to yield 2-(6-(bis(4-chlorophenyl)methyl)-2-cyclopropyl-1H-benzo[d]imidazol-1-yl)ethanol.

MS: 437.1 (M+H$^+$).

Example BZ-12

4-(2-(6-(bis(4-chlorophenyl)methyl)-2-cyclopropyl-1H-benzo[d]imidazol-1-yl)ethyl)benzoic acid; Compound #38

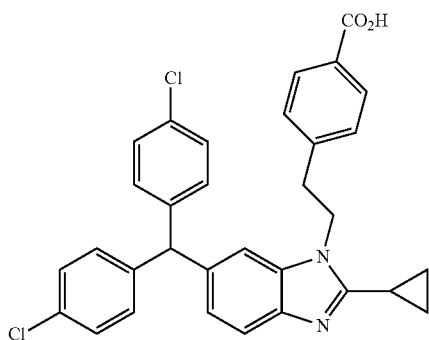 [SMILES: O=C(O)c1ccc(CCn2c(C3CC3)nc3ccc(C(c4ccc(Cl)cc4)c4ccc(Cl)cc4)cc32)cc1]

4-(2-(6-(Bis(4-chlorophenyl)methyl)-2-cyclopropyl-1H-benzo[d]imidazol-1-yl)ethyl)benzoic acid was prepared according to the procedure as described in Example BZ-11, substituting methyl 4-(2-aminoethyl)benzoate for ethanolamine.

MS: 541.0 (M+H$^+$).

Example BZ-13

4-(2-(6-(Bis(4-chlorophenyl)methyl)-2-cyclopropyl-1H-benzo[d]imidazol-1-yl)ethyl)phenol; Compound #37

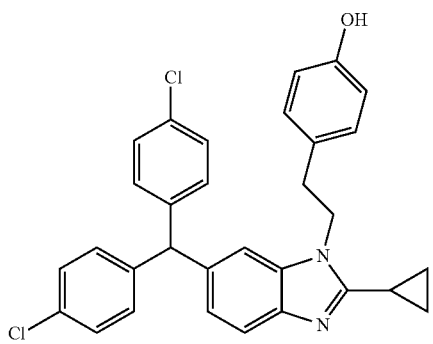 [SMILES: Oc1ccc(CCn2c(C3CC3)nc3ccc(C(c4ccc(Cl)cc4)c4ccc(Cl)cc4)cc32)cc1]

4-(2-(6-(Bis(4-chlorophenyl)methyl)-2-cyclopropyl-1H-benzo[d]imidazol-1-yl)ethyl)phenol was prepared according to the procedures described in Example BZ-11, substituting 4-(2-aminoethyl)phenol for ethanolamine.

MS: 513.2 (M+H$^+$).

Examples BZ-14 methyl 4-(2-(6-(bis(4-chlorophenyl)methyl)-2-cyclopropyl-1H-benzo[d]imidazol-1-yl)ethoxy)benzoate; Compound #36

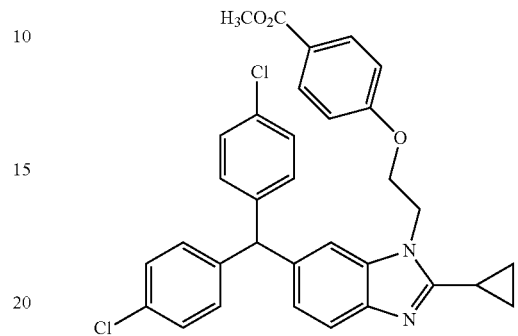

To a solution of 2-(6-(bis(4-chlorophenyl)methyl)-2-cyclopropyl-1H-benzo[d]imidazol-1-yl)ethanol (50 mg, 0.11 mmol), methyl 4-hydroxybenzoate (52 mg, 0.34 mmol) and PPh$_3$ (90 mg, 0.34 mmol) in THF (2 mL) was added DIAD (0.067 mL, 0.34 mmol). The reaction was stirred at room temperature overnight. The resulting mixture was then concentrated and purified by chromatography (silica gel column, 60% CH$_2$Cl$_2$/heptane) to yield methyl 4-(2-(6-(bis(4-chlorophenyl)methyl)-2-cyclopropyl-1H-benzo[d]imidazol-1-yl)ethoxy)benzoate.

MS: 571.2 (M+H$^+$).

Example BZ-15

4-(2-(6-(bis(4-chlorophenyl)methyl)-2-cyclopropyl-1H-benzo[d]imidazol-1-yl)ethoxy)benzoic acid; Compound #35

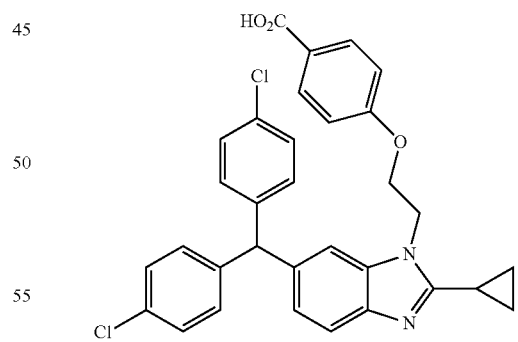

A solution of methyl 4-(2-(6-(bis(4-chlorophenyl)methyl)-2-cyclopropyl-1H-benzo[d]imidazol-1-yl)ethoxy)benzoate (38 mg, 0.067 mmol) and LiOH (10 mg, 0.42 mmol) in H$_2$O (1 mL) and THF (2 mL) was stirred at room temperature for 2 days. The reaction mixture was acidified with 1N HCl aq solution and extracted with EtOAc. The organic layer was washed with aq NaCl, dried over Na$_2$SO$_4$ and concentrated. The resulting residue was purified by chromatography (silica gel column, 3% MeOH/CH$_2$Cl$_2$) to yield 4-(2-(6-(bis(4-chlorophenyl)methyl)-2-cyclopropyl-1H-benzo[d]imidazol-1-yl)ethoxy)benzoic acid. MS: 557.1 (M+H+).

Example BZ-16 methyl 6-(2-(6-(bis(4-chlorophenyl)methyl)-2-cyclopropyl-1H-benzo[d]imidazol-1-yl)ethoxy)nicotinate; Compound #33

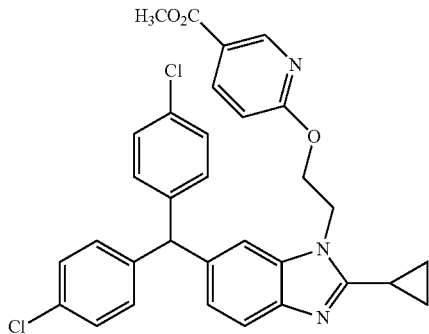 [SMILES: COC(=O)c1ccc(OCCn2c(C3CC3)nc3ccc(C(c4ccc(Cl)cc4)c4ccc(Cl)cc4)cc32)cc1]

Methyl 6-(2-(6-(bis(4-chlorophenyl)methyl)-2-cyclopropyl-1H-benzo[d]imidazol-1-yl)ethoxy)nicotinate was prepared according to the procedure as described in Example BZ-14, substituting methyl 6-hydroxynicotinate for methyl 4-hydroxybenzoate.

$^1$H NMR (CHLOROFORM-d) Shift: 8.72 (d, J=2.0 Hz, 1H), 8.08 (dd, J=8.6, 2.5 Hz, 1H), 7.56 (d, J=8.1 Hz, 1H), 7.23-7.28 (m, 4H), 6.99-7.05 (m, 4H), 6.92 (dd, J=8.3, 1.8 Hz, 1H), 6.42 (d, J=8.6 Hz, 1H), 5.61 (s, 1H), 4.68 (t, J=5.3 Hz, 2H), 4.58 (t, J=5.3 Hz, 2H), 3.92 (s, 3H), 2.00-2.08 (m, 1H), 1.16-1.34 (m, 2H), 1.06-1.14 (m, 2H). MS: 572.1 (M+H+).

Example BZ-17

6-(2-(6-(bis(4-chlorophenyl)methyl)-2-cyclopropyl-1H-benzo[d]imidazol-1-yl)ethoxy)nicotinic acid; Compound #35

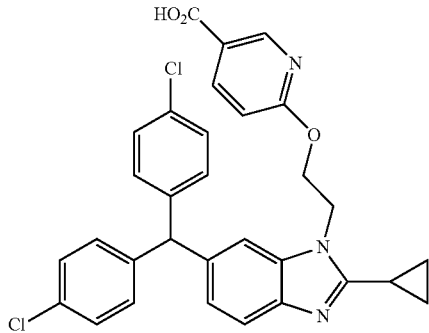 [SMILES: O=C(O)c1ccc(OCCn2c(C3CC3)nc3ccc(C(c4ccc(Cl)cc4)c4ccc(Cl)cc4)cc32)cc1]

6-(2-(6-(Bis(4-chlorophenyl)methyl)-2-cyclopropyl-1H-benzo[d]imidazol-1-yl)ethoxy)nicotinic acid was prepared according to the procedure as described in Example BZ-15.

MS: 558.2 (M+H+).

Example BZ-18 methyl 3-(2-(6-(bis(4-chlorophenyl)methyl)-2-cyclopropyl-1H-benzo[d]imidazol-1-yl)ethoxy)benzoate; Compound #26

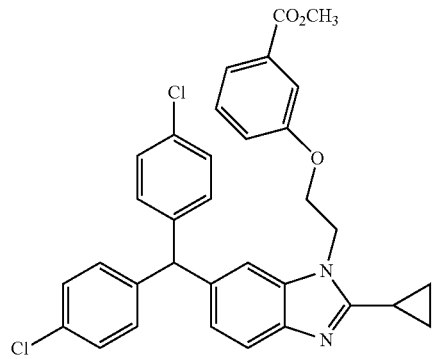 [SMILES: COC(=O)c1cccc(OCCn2c(C3CC3)nc3ccc(C(c4ccc(Cl)cc4)c4ccc(Cl)cc4)cc32)c1]

Methyl 3-(2-(6-(bis(4-chlorophenyl)methyl)-2-cyclopropyl-1H-benzo[d]imidazol-1-yl)ethoxy)benzoate was prepared according to the procedure as described in Example BZ-14, substituting methyl 3-hydroxybenzoate for methyl 4-hydroxybenzoate.

MS: 571.1 (M+H+).

Example BZ-19

3-(2-(6-(bis(4-chlorophenyl)methyl)-2-cyclopropyl-1H-benzo[d]imidazol-1-yl)ethoxy)benzoic acid; Compound #23

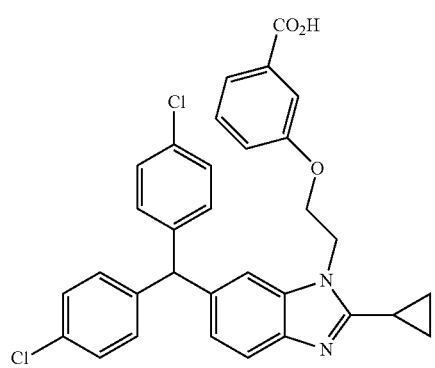 [SMILES: O=C(O)c1cccc(OCCn2c(C3CC3)nc3ccc(C(c4ccc(Cl)cc4)c4ccc(Cl)cc4)cc32)c1]

3-(2-(6-(Bis(4-chlorophenyl)methyl)-2-cyclopropyl-1H-benzo[d]imidazol-1-yl)ethoxy)benzoic acid was prepared according to the procedure as described in Example BZ-15 substituting NaOH for LiOH.

MS: 557.1 (M+H+).

Example BZ-20

6-(bis(4-chlorophenyl)methyl)-1-(4-bromophenethyl)-2-cyclopropyl-1H-benzo[d]imidazole; Compound #27

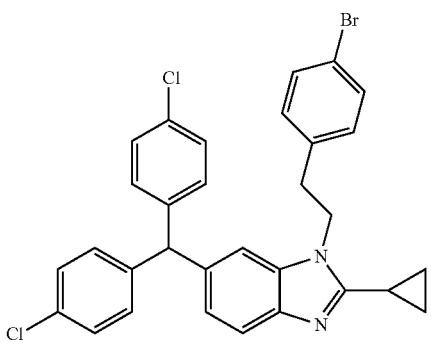

6-(Bis(4-chlorophenyl)methyl)-1-(4-bromophenethyl)-2-cyclopropyl-1H-benzo[d]imidazole was prepared according to the procedure as described in Example BZ-11, substituting 2-(4-bromophenyl)ethanamine for ethanolamine.

$^1$H NMR (CHLOROFORM-d) δ: 7.54 (d, J=8.1 Hz, 1H), 7.24-7.34 (m, 6H), 6.99 (d, J=8.1 Hz, 4H), 6.90 (dd, J=8.1, 1.5 Hz, 1H), 6.78 (d, J=8.1 Hz, 2H), 6.64 (s, 1H), 5.57 (s, 1H), 4.32 (t, J=6.8 Hz, 2H), 2.98 (t, J=6.8 Hz, 2H), 1.66-1.73 (m, 1H), 1.10-1.17 (m, 2H), 0.96-1.06 (m, 2H). MS: 577.0 (M+H$^+$).

Example BZ-21

4'-(2-(6-(bis(4-chlorophenyl)methyl)-2-cyclopropyl-1H-benzo[d]imidazol-1-yl)ethyl)-[1,1'-biphenyl]-4-carboxylic acid; Compound #25

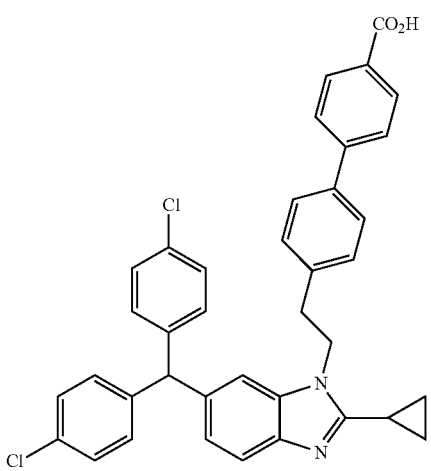 [SMILES: O=C(O)c1ccc(-c2ccc(CCn3c(C4CC4)nc4ccc(C(c5ccc(Cl)cc5)c5ccc(Cl)cc5)cc43)cc2)cc1]

A mixture of 6-(bis(4-chlorophenyl)methyl)-1-(4-bromophenethyl)-2-cyclopropyl-1H-benzo[d]imidazole (75 mg, 0.13 mmol), (4-methoxycarbonyl)phenyl) boronic acid (47 mg, 0.26 mmol), K$_2$CO$_3$ (36 mg, 0.26 mmol) and Pd(dppf)Cl$_2$ (5.3 mg, 0.0065 mmol) in EtOH (1 mL) and H$_2$O (0.2 mL) was heated at 130° C. by microwave for 30 min. The reaction mixture was cooled to room temperature and to it was added H$_2$O (1 mL), THF (2 mL) and LiOH.H$_2$O (42 mg, 1.0 mmol). The reaction was stirred at room temperature overnight before 1N HCl aq solution was added to adjust pH to ~3. The resulting mixture was extracted with EtOAc for 2 times. The organic layers were combined, washed with aq NaCl, dried over Na$_2$SO$_4$ and concentrated. The resulting residue was purified by chromatography (silica gel column, 3% MeOH/CH$_2$Cl$_2$) to yield 4'-(2-(6-(bis(4-chlorophenyl)methyl)-2-cyclopropyl-1H-benzo[d]imidazol-1-yl)ethyl)-[1,1'-biphenyl]-4-carboxylic acid.

MS: 617.3 (M+H$^+$).

Example BZ-22

4'-(2-(6-(bis(4-chlorophenyl)methyl)-2-cyclopropyl-1H-benzo[d]imidazol-1-yl)ethyl)-[1,1'-biphenyl]-3-carboxylic acid; Compound #24

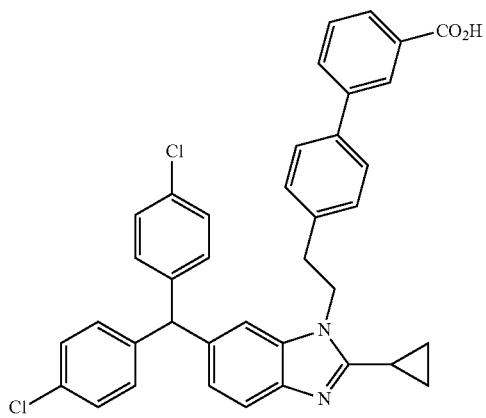 [SMILES: O=C(O)c1cccc(-c2ccc(CCn3c(C4CC4)nc4ccc(C(c5ccc(Cl)cc5)c5ccc(Cl)cc5)cc43)cc2)c1]

4'-(2-(6-(Bis(4-chlorophenyl)methyl)-2-cyclopropyl-1H-benzo[d]imidazol-1-yl)ethyl)-[1, 1'-biphenyl]-3-carboxylic acid was prepared according to the procedure described in Example BZ-21 substituting (3-methoxycarbonyl)phenyl) boronic acid for (4-methoxycarbonyl)phenyl) boronic acid.

MS: 617.1 (M+H$^+$).

Example BZ-23

6-(bis(4-chlorophenyl)methyl)-1-(3-bromophenethyl)-2-cyclopropyl-1H-benzo[d]imidazole; Compound #20

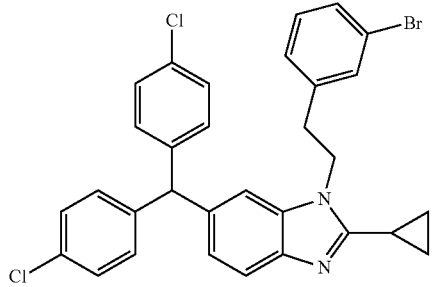 [SMILES: Clc1ccc(C(c2ccc(Cl)cc2)c2ccc3nc(C4CC4)n(CCc4cccc(Br)c4)c3c2)cc1]

6-(Bis(4-chlorophenyl)methyl)-1-(3-bromophenethyl)-2-cyclopropyl-1H-benzo[d]imidazole was prepared according to the procedure described in Example BZ-11 substituting 2-(3-bromophenyl)ethanamine for ethanolamine.

¹H NMR (CHLOROFORM-d) Shift: 7.55 (d, J=8.1 Hz, 1H), 7.25-7.32 (m, 5H), 7.18 (s, 1H), 6.96-7.08 (m, 5H), 6.90 (dd, J=8.1, 1.5 Hz, 1H), 6.79 (d, J=7.6 Hz, 1H), 6.69 (s, 1H), 5.57 (s, 1H), 4.34 (t, J=6.8 Hz, 2H), 3.00 (t, J=6.8 Hz, 2H), 1.71-1.79 (m, 1H), 1.11-1.18 (m, 2H), 0.88-1.09 (m, 2H). MS: 577.0 (M+H⁺).

Example BZ-24

2-(1-(3-bromophenethyl)-2-cyclopropyl-1H-benzo[d]imidazol-6-yl)-2,2-bis(4-chlorophenyl)acetic acid; Compound #19

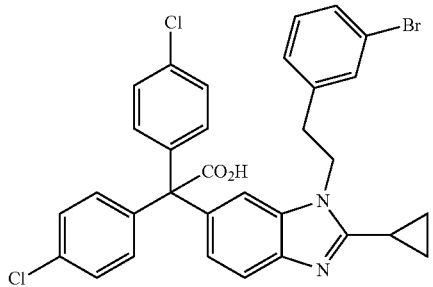 [SMILES: O=C(O)C(c1ccc(Cl)cc1)(c1ccc(Cl)cc1)c1ccc2nc(C3CC3)n(CCc3cccc(Br)c3)c2c1]

Methyl 2-(1-(3-bromophenethyl)-2-cyclopropyl-1H-benzo[d]imidazol-6-yl)-2,2-bis(4-chlorophenyl)acetate was prepared according to the procedure described in Example BZ-11 (Step E) substituting 2-(3-bromophenyl)ethanamine for ethanolamine.

A solution of methyl 2-(1-(3-bromophenethyl)-2-cyclopropyl-1H-benzo[d]imidazol-6-yl)-2,2-bis(4-chlorophenyl) acetate (66 mg, 0.01 mmol) and 3N NaOH aq solution (0.5 mL, 1.5 mmol) in THF (2 mL) and MeOH (1 mL) was stirred at room temperature for 4 days. 1N HCl aq solution was added to adjust the pH to ~3. The mixture was extracted with EtOAc. The organic layer was washed with aq NaCl, dried over Na₂SO₄ and concentrated to yield 2-(1-(3-bromophenethyl)-2-cyclopropyl-1H-benzo[d]imidazol-6-yl)-2,2-bis(4-chlorophenyl)acetic acid.

MS: 621.0 (M+H⁺).

Example BZ-25 methyl 3-(2-(6-(bis(4-chlorophenyl)methyl)-2-cyclopropyl-1H-benzo[d]imidazol-1-yl)ethoxy)-5-(trifluoromethyl)benzoate Compound #18

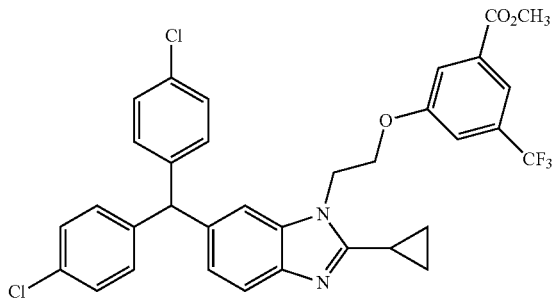 [SMILES: COC(=O)c1cc(OCCn2c(C3CC3)nc3ccc(C(c4ccc(Cl)cc4)c4ccc(Cl)cc4)cc32)cc(C(F)(F)F)c1]

Methyl 3-(2-(6-(bis(4-chlorophenyl)methyl)-2-cyclopropyl-1H-benzo[d]imidazol-1-yl)ethoxy)-5-(trifluoromethyl)benzoate was prepared according to the procedure described in Example BZ-14 substituting methyl 3-hydroxy-5-(trifluoromethyl)benzoate for methyl 4-hydroxybenzoate.

MS: 639.2 (M+H⁺).

Example BZ-26

3-(2-(6-(bis(4-chlorophenyl)methyl)-2-cyclopropyl-1H-benzo[d]imidazol-1-yl)ethoxy)-5-(trifluoromethyl)benzoic acid; Compound #16

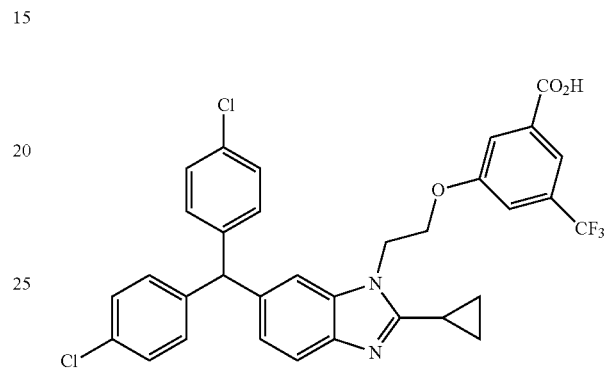

3-(2-(6-(Bis(4-chlorophenyl)methyl)-2-cyclopropyl-1H-benzo[d]imidazol-1-yl)ethoxy)-5-(trifluoromethyl)benzoic acid was prepared according to the procedure described in Example BZ-15.

MS: 625.2 (M+H⁺).

Example BZ-27

3'-(2-(6-(bis(4-chlorophenyl)methyl)-2-cyclopropyl-1H-benzo[d]imidazol-1-yl)ethyl)-[1,1'-biphenyl]-4-carboxylic acid; Compound #17

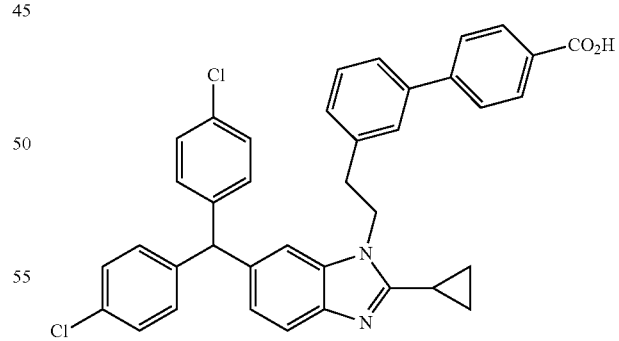

3'-(2-(6-(Bis(4-chlorophenyl)methyl)-2-cyclopropyl-1H-benzo[d]imidazol-1-yl)ethyl)-[1,1'-biphenyl]-4-carboxylic acid was prepared according to the procedure described in Example BZ-21 substituting 6-(Bis(4-chlorophenyl)methyl)-1-(3-bromophenethyl)-2-cyclopropyl-1H-benzo[d]imidazole for 6-(bis(4-chlorophenyl)methyl)-1-(4-bromophenethyl)-2-cyclopropyl-1H-benzo[d]imidazole.

MS: 617.1 (M+H⁺).

Example BZ-28

3'-(2-(6-(bis(4-chlorophenyl)methyl)-2-cyclopropyl-1H-benzo[d]imidazol-1-yl)ethyl)-[1,1'-biphenyl]-3-carboxylic acid; Compound #11

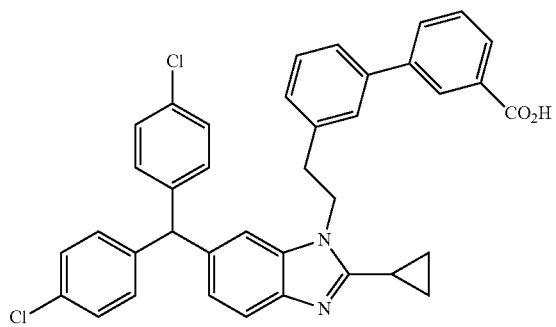 [SMILES: O=C(O)c1cccc(-c2cccc(CCn3c(C4CC4)nc4ccc(C(c5ccc(Cl)cc5)c5ccc(Cl)cc5)cc43)c2)c1]

3'-(2-(6-(bis(4-chlorophenyl)methyl)-2-cyclopropyl-1H-benzo[d]imidazol-1-yl)ethyl)-[1, 1'-biphenyl]-3-carboxylic acid was prepared according to the procedure described in Example BZ-22 substituting 6-(Bis(4-chlorophenyl)methyl)-1-(3-bromophenethyl)-2-cyclopropyl-1H-benzo[d]imidazole for 6-(bis(4-chlorophenyl)methyl)-1-(4-bromophenethyl)-2-cyclopropyl-1H-benzo[d]imidazole.

$^1$H NMR (CHLOROFORM-d) Shift: 8.01-8.14 (m, 2H), 7.67 (br d, J=8.1 Hz, 1H), 7.46-7.58 (m, 2H), 7.40 (br d, J=7.6 Hz, 1H), 7.22-7.35 (m, 1H), 7.17 (br d, J=8.6 Hz, 4H), 7.06 (br s, 1H), 6.99 (br d, J=7.1 Hz, 1H), 6.87-6.95 (m, 5H), 6.65 (br s, 1H), 5.50 (s, 1H), 4.43 (br s, 2H), 3.13 (br s, 2H), 1.80 (br s, 1H), 1.26 (br s, 2H), 1.04 (br d, J=5.6 Hz, 2H). MS: 617.3 (M+H$^+$).

Example BZ-29

5-(3-(2-(6-(bis(4-chlorophenyl)methyl)-2-cyclopropyl-1H-benzo[d]imidazol-1-yl)ethyl)phenyl)thiophene-2-carboxylic acid; Compound #6

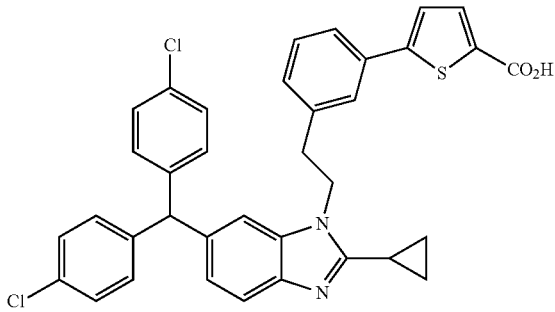 [SMILES: O=C(O)c1ccc(-c2cccc(CCn3c(C4CC4)nc4ccc(C(c5ccc(Cl)cc5)c5ccc(Cl)cc5)cc43)c2)s1]

5-(3-(2-(6-(bis(4-chlorophenyl)methyl)-2-cyclopropyl-1H-benzo[d]imidazol-1-yl)ethyl)phenyl)thiophene-2-carboxylic acid was prepared according to the procedure described in Example BZ-27 substituting (5-(methoxycarbonyl)thiophen-2-yl)boronic acid for (4-methoxycarbonyl)phenyl) boronic acid.

$^1$H NMR (CHLOROFORM-d) Shift: 7.58-7.87 (m, 2H), 7.42 (br d, J=8.1 Hz, 1H), 7.14-7.36 (m, 5H), 6.99-7.11 (m, 1H), 6.84-6.99 (m, 7H), 6.70 (s, 1H), 5.53 (s, 1H), 4.29-4.48 (m, 2H), 3.08 (br t, J=6.3 Hz, 2H), 1.71 (br s, 1H), 1.14-1.39 (m, 2H), 1.01 (br d, J=6.1 Hz, 2H). MS: 623.1 (M+H$^+$).

Example BZ-30

6-(bis(4-chlorophenyl)methyl)-1-(2-(3-bromophenoxy)ethyl)-2-cyclopropyl-1H-benzo[d]imidazole; Compound #7

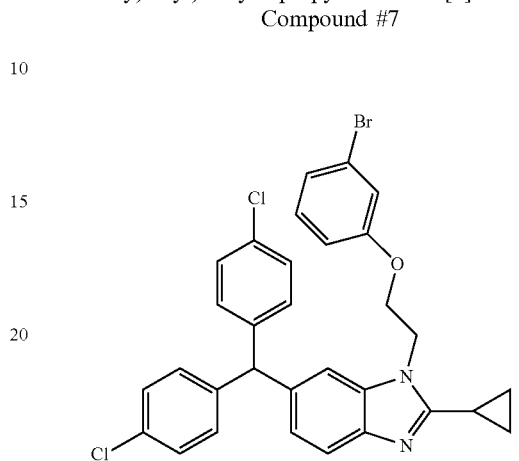

6-(Bis(4-chlorophenyl)methyl)-1-(2-(3-bromophenoxy)ethyl)-2-cyclopropyl-1H-benzo[d]imidazole was prepared according to the procedure described in Example BZ-14 substituting 3-bromophenol for methyl 4-hydroxybenzoate.

$^1$H NMR (CHLOROFORM-d) Shift: 7.57 (d, J=8.6 Hz, 1H), 7.23-7.36 (m, 5H), 6.89-7.10 (m, 8H), 6.54-6.59 (m, 1H), 5.64 (s, 1H), 4.56 (t, J=5.3 Hz, 2H), 4.23 (t, J=5.1 Hz, 2H), 2.02-2.12 (m, 1H), 1.07-1.31 (m, 4H). MS: 593.1 (M+H$^+$).

Example BZ-31 methyl 2,2-bis(4-chlorophenyl)-2-(2-cyclopropyl-1-((1-(((trifluoromethyl)sulfonyl)piperidin-4-yl)methyl)-1H-benzo[d]imidazol-6-yl)acetate; Compound #14

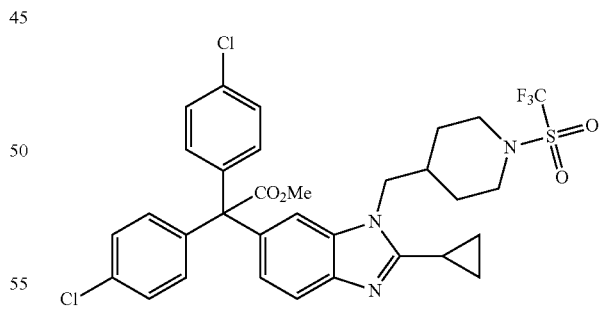

tert-Butyl 4-((6-(1,1-bis(4-chlorophenyl)-2-methoxy-2-oxoethyl)-2-cyclopropyl-1H-benzo[d]imidazol-1-yl)methyl)piperidine-1-carboxylate was prepared according to the procedure as described in Example BZ-11 (Step E) substituting tert-butyl 4-(aminomethyl)piperidine-1-carboxylate for ethanolamine.

A solution of tert-butyl 4-((6-(1,1-bis(4-chlorophenyl)-2-methoxy-2-oxoethyl)-2-cyclopropyl-1H-benzo[d]imidazol-1-yl)methyl)piperidine-1-carboxylate (75 mg, 0.12 mmol) in TFA (0.5 mL) and CH$_2$Cl$_2$ (2.5 mL) was stirred at room temperature for 1.5 h before It was concentrated. The resulting residue was dissolved in CH$_2$Cl$_2$ and washed with aq NaHCO$_3$ solution and aq NaCl solution. The organic layer was dried over Na$_2$SO$_4$ and concentrated to yield a residue. To a solution of the residue in CH$_2$Cl$_2$ (3 mL) at 0° C. was added Et$_3$N (0.08 mL, 0.58 mmol) followed by trifluoromethanesulfonic anhydride (Tf$_2$O, 0.039 mL, 0.23 mmol). The reaction was stirred at 0° C. for 1 h then warmed up to room temperature and stirred for another 1 h. To the reaction was added aq NaHCO$_3$ solution and the mixture was extracted with EtOAc. The organic layer was washed with aq NaCl solution, dried over Na$_2$SO$_4$ and concentrated. The resulting residue was purified by chromatography (silica gel column, 60% EtOAc/heptane) to yield methyl 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetate.

1H NMR (CHLOROFORM-d) Shift: 7.56 (d, J=8.6 Hz, 1H), 7.20-7.33 (m, 4H), 7.05-7.17 (m, 4H), 6.93-7.06 (m, 1H), 6.90 (d, J=1.5 Hz, 1H), 3.89-4.08 (m, 4H), 3.81 (s, 3H), 2.78-3.02 (m, 2H), 1.79-1.98 (m, 2H), 1.60-1.74 (m, 2H), 1.00-1.48 (m, 6H). MS: 680.1 (M+H$^+$).

Example BZ-32

2,2-bis(4-chlorophenyl)-2-(2-cyclopropyl-1-((1-((trifluoromethyl)sulfonyl)piperidin-4-yl)methyl)-1H-benzo[d]imidazol-6-yl)acetic acid; Compound #12

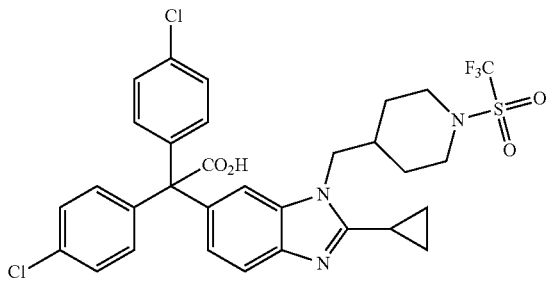 [SMILES: O=C(O)C(c1ccc(Cl)cc1)(c1ccc(Cl)cc1)c1ccc2nc(C3CC3)n(CC3CCN(S(=O)(=O)C(F)(F)F)CC3)c2c1]

2,2-Bis(4-chlorophenyl)-2-(2-cyclopropyl-1-((1-((trifluoromethyl)sulfonyl)piperidin-4-yl)methyl)-1H-benzo[d]imidazol-6-yl)acetic acid was prepared from methyl 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetate according to the procedure as described in Example BZ-24.

MS: 666.2 (M+H$^+$).

Example BZ-33

4-((4-((6-(bis(4-chlorophenyl)methyl)-2-cyclopropyl-1H-benzo[d]imidazol-1-yl)methyl)piperidin-1-yl)sulfonyl)benzoic acid; Compound #15

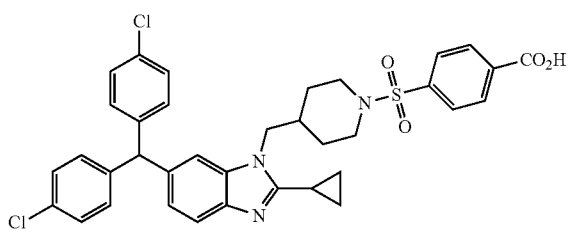 [SMILES: O=C(O)c1ccc(S(=O)(=O)N2CCC(Cn3c(C4CC4)nc4ccc(C(c5ccc(Cl)cc5)c5ccc(Cl)cc5)cc43)CC2)cc1]

STEP A: 6-(bis(4-chlorophenyl)methyl)-2-cyclopropyl-1-(piperidin-4-ylmethyl)-1H-benzo[d]imidazole tert-Butyl 4-((6-(bis(4-chlorophenyl)methyl)-2-cyclopropyl-1H-benzo[d]imidazol-1-yl)methyl)piperidine-1-carboxylate was prepared according to the procedure described in Example BZ-11 substituting tert-butyl 4-(aminomethyl)piperidine-1-carboxylate for ethanolamine.

A solution of tert-butyl 4-((6-(bis(4-chlorophenyl)methyl)-2-cyclopropyl-1H-benzo[d]imidazol-1-yl)methyl)piperidine-1-carboxylate (125 mg, 0.21 mmol) in TFA (1 mL) and CH$_2$Cl$_2$ (5 mL) was stirred at room temperature for 1.5 h. The resulting mixture was then concentrated and the residue dissolved in CH$_2$Cl$_2$. The resulting solution was washed with aq NaHCO$_3$ solution and aq NaCl solution, dried over Na$_2$SO$_4$ and concentrated to yield 6-(bis(4-chlorophenyl)methyl)-2-cyclopropyl-1-(piperidin-4-ylmethyl)-1H-benzo[d]imidazole.

STEP B: 4-((4-((6-(bis(4-chlorophenyl)methyl)-2-cyclopropyl-1H-benzo[d]imidazol-1-yl)methyl)piperidin-1-yl)sulfonyl)benzoic acid To a solution of 6-(bis(4-chlorophenyl)methyl)-2-cyclopropyl-1-(piperidin-4-ylmethyl)-1H-benzo[d]imidazole (38 mg, 0.078 mmol) in CH$_2$Cl$_2$ (2 mL) at room temperature was added Et$_3$N (0.043 mL, 0.31 mmol) followed by methyl 4-(chlorosulfonyl)benzoate (27 mg, 0.12 mmol). The reaction was stirred overnight. The reaction mixture was concentrated and to the resulting residue was added THF (2 mL) and 1N NaOH aq solution (1 mL). The reaction was stirred at room temperature for 2 h before 1N HCl aq solution was added to adjust pH to ~3. The mixture was extracted with EtOAc. The organic layer was washed with aq NaCl solution, dried over Na$_2$SO$_4$ and concentrated. The resulting residue was purified by chromatography (silica gel column, 4% MeOH/CH$_2$Cl$_2$) to yield 4-((4-((6-(bis(4-chlorophenyl)methyl)-2-cyclopropyl-1H-benzo[d]imidazol-1-yl)methyl)piperidin-1-yl)sulfonyl)benzoic acid.

MS: 674.2 (M+H$^+$)

Examples BZ-34 methyl 3-((4-((6-(bis(4-chlorophenyl)methyl)-2-cyclopropyl-1H-benzo[d]imidazol-1-yl)methyl)piperidin-1-yl)methyl)benzoate; Compound #13

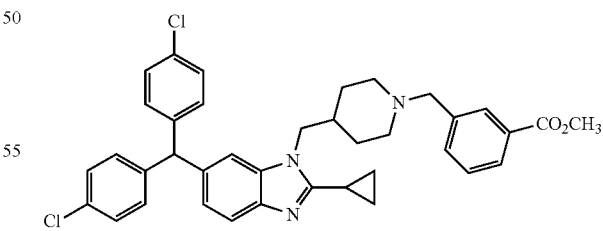

A mixture of 6-(bis(4-chlorophenyl)methyl)-2-cyclopropyl-1-(piperidin-4-ylmethyl)-1H-benzo[d]imidazole (28 mg, 0.057 mmol), methyl 3-(bromomethyl)benzoate (13 mg, 0.057 mmol) and K$_2$CO$_3$ (16 mg, 0.11 mmol) in CH$_3$CN (2 mL) was stirred at room temperature for 2 h. The reaction mixture was diluted with EtOAc and washed with H$_2$O and aq NaCl aq solution. The organic layer was dried over Na$_2$SO$_4$ and concentrated. The resulting residue was purified by chromatography (silica gel column, 90% EtOAc/heptane) to yield methyl 3-((4-((6-(bis(4-chlorophenyl)methyl)-2-cyclopropyl-1H-benzo[d]imidazol-1-yl)methyl)piperidin-1-yl)methyl)benzoate.

MS: 638.3 (M+H$^+$).

Example BZ-35

3-((4-((6-(bis(4-chlorophenyl)methyl)-2-cyclopropyl-1H-benzo[d]imidazol-1-yl)methyl)piperidin-1-yl)methyl)benzoic acid; Compound #10

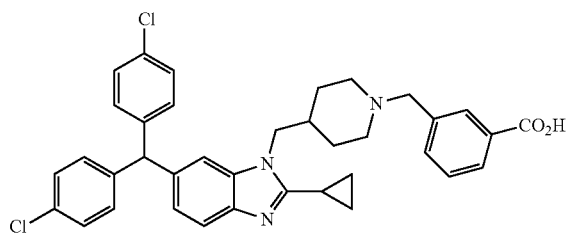 [SMILES: O=C(O)c1cccc(CN2CCC(Cn3c(C4CC4)nc4ccc(C(c5ccc(Cl)cc5)c5ccc(Cl)cc5)cc43)CC2)c1]

A solution of methyl 3-((4-((6-(bis(4-chlorophenyl)methyl)-2-cyclopropyl-1H-benzo[d]imidazol-1-yl)methyl)piperidin-1-yl)methyl)benzoate (25 mg, 0.039 mmol) and LiOH.H$_2$O (12 mg, 0.29 mmol) in H$_2$O (1 mL) and THF (2 mL) was stirred at room temperature overnight. To the reaction mixture was added 1N HCl aq solution to adjust pH to ~4. The resulting mixture was extracted with EtOAc. The organic layer was washed with aq NaCl solution, dried over Na$_2$SO$_4$ and concentrated to yield 3-((4-((6-(bis(4-chlorophenyl)methyl)-2-cyclopropyl-1H-benzo[d]imidazol-1-yl)methyl)piperidin-1-yl)methyl)benzoic acid.

MS: 624.3 (M+H$^+$).

Example BZ-36

N-(3-(6-(bis(4-chlorophenyl)methyl)-2-cyclopropyl-1H-benzo[d]imidazol-1-yl)propyl)-3-bromobenzenesulfonamide; Compound #9

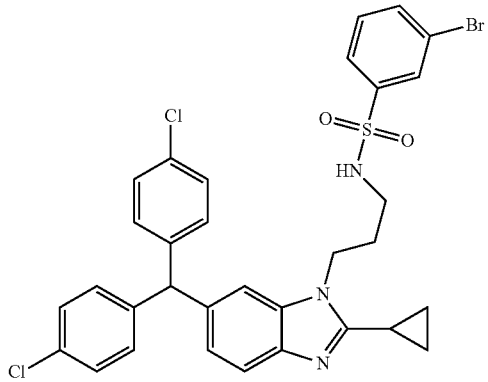 [SMILES: O=S(=O)(NCCCn1c(C2CC2)nc2ccc(C(c3ccc(Cl)cc3)c3ccc(Cl)cc3)cc21)c1cccc(Br)c1]

tert-Butyl (3-(6-(bis(4-chlorophenyl)methyl)-2-cyclopropyl-1H-benzo[d]imidazol-1-yl)propyl)carbamate was prepared according to the procedure as described in Example BZ-11 substituting tert-butyl (3-aminopropyl)carbamate for ethanolamine.

3-(6-(Bis(4-chlorophenyl)methyl)-2-cyclopropyl-1H-benzo[d]imidazol-1-yl)propan-1-amine was prepared according to the procedure as described in Example BZ-33 (Step A).

To a solution of 3-(6-(bis(4-chlorophenyl)methyl)-2-cyclopropyl-1H-benzo[d]imidazol-1-yl)propan-1-amine (0.19 mmol) in CH$_2$Cl$_2$ (3 mL) at 0° C. was added Et$_3$N (0.11 mL, 0.76 mmol) followed by 3-bromobenzene-1-sulfonyl chloride (0.041 mL, 0.29 mmol). The reaction was warmed up to room temperature and stirred overnight. To the reaction was added aq NaHCO$_3$ solution and the resulting mixture was extracted with EtOAc. The organic layer was washed with aq NaCl solution, dried over Na$_2$SO$_4$ and concentrated. The resulting residue was purified by chromatography (silica gel column, 60% EtOAc/heptane) to yield N-(3-(6-(bis(4-chlorophenyl)methyl)-2-cyclopropyl-1H-benzo[d]imidazol-1-yl)propyl)-3-bromobenzenesulfonamide.

$^1$H NMR (CHLOROFORM-d) Shift: 7.95 (t, J=1.8 Hz, 1H), 7.69 (ddd, J=8.1, 3.3, 1.8 Hz, 2H), 7.53 (d, J=8.6 Hz, 1H), 7.35 (t, J=7.9 Hz, 1H), 7.21-7.28 (m, 4H), 6.90-7.05 (m, 6H), 5.60 (s, 1H), 5.10 (t, J=6.3 Hz, 1H), 4.24 (t, J=6.8 Hz, 2H), 2.96 (q, J=6.2 Hz, 2H), 1.97-2.06 (m, 2H), 1.84-1.93 (m, 1H), 1.01-1.20 (m, 4H). MS: 670.0 (M+H$^+$).

Example BZ-37

3'-(N-(3-(6-(bis(4-chlorophenyl)methyl)-2-cyclopropyl-1H-benzo[d]imidazol-1-yl)propyl)sulfamoyl)-[1,1'-biphenyl]-4-carboxylic acid; Compound #8

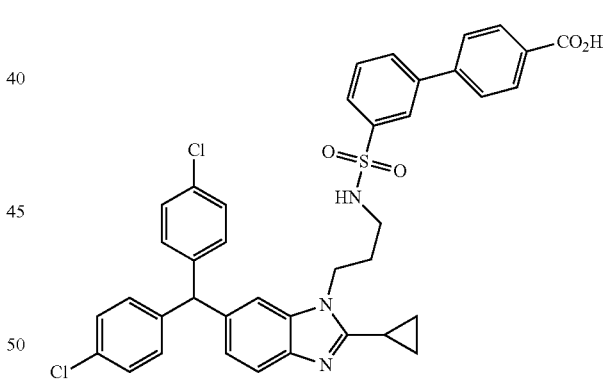

3'-(N-(3-(6-(bis(4-chlorophenyl)methyl)-2-cyclopropyl-1H-benzo[d]imidazol-1-yl)propyl)sulfamoyl)-[1,1'-biphenyl]-4-carboxylic acid was prepared according to the procedure as described in Example BZ-21, substituting N-(3-(6-(bis(4-chlorophenyl)methyl)-2-cyclopropyl-1H-benzo[d]imidazol-1-yl)propyl)-3-bromobenzenesulfonamide for 6-(bis(4-chlorophenyl)methyl)-1-(4-bromophenethyl)-2-cyclopropyl-1H-benzo[d]imidazole.

$^1$H NMR (CHLOROFORM-d) Shift: 8.01-8.17 (m, 3H), 7.73-7.88 (m, 2H), 7.52-7.68 (m, 4H), 7.20-7.29 (m, 4H), 6.97-7.09 (m, 5H), 6.92 (dd, J=8.3, 1.3 Hz, 1H), 5.60 (s, 1H), 4.27 (br t, J=7.1 Hz, 2H), 2.96 (t, J=6.3 Hz, 2H), 1.84-2.05 (m, 3H), 0.98-1.30 (m, 4H). MS: 710.3 (M+H$^+$).

Examples BZ-38

Methyl 2-(4-((6-(bis(4-chlorophenyl)methyl)-2-cyclopropyl-1H-benzo[d]imidazol-1-yl)methyl)piperidin-1-yl)pyrimidine-5-carboxylate; Compound #5

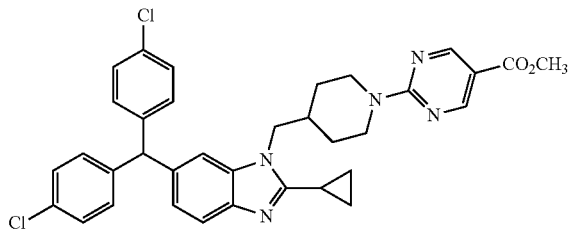 [SMILES: COC(=O)c1cnc(N2CCC(Cn3c(C4CC4)nc4ccc(C(c5ccc(Cl)cc5)c5ccc(Cl)cc5)cc43)CC2)nc1]

A solution of 6-(bis(4-chlorophenyl)methyl)-2-cyclopropyl-1-(piperidin-4-ylmethyl)-1H-benzo[d]imidazole (27 mg, 0.055 mmol), methyl 2-bromopyrimidine-5-carboxylate (16 mg, 0.072 mmol) and Hunig's base (0.03 mL, 0.17 mmol) in $CH_3CN$ (2 mL) was stirred at room temperature overnight. The reaction mixture was concentrated and the residue was dissolved in EtOAc. The resulting solution was washed with aq $NaHCO_3$ solution and aq NaCl solution, dried over $Na_2SO_4$ and concentrated. The resulting residue was purified by chromatography (silica gel column, 60% EtOAc/heptane) to yield methyl 2-(4-((6-(bis(4-chlorophenyl)methyl)-2-cyclopropyl-1H-benzo[d]imidazol-1-yl)methyl)piperidin-1-yl)pyrimidine-5-carboxylate.

$^1$H NMR (CHLOROFORM-d) Shift: 8.77-8.93 (m, 2H), 7.57 (d, J=8.6 Hz, 1H), 7.17-7.34 (m, 5H), 6.81-7.11 (m, 5H), 5.54-5.72 (m, 1H), 4.94 (br d, J=13.6 Hz, 2H), 3.98-4.14 (m, 2H), 3.88 (s, 3H), 2.84 (br t, J=11.9 Hz, 2H), 2.05-2.26 (m, 1H), 1.83-2.02 (m, 1H), 1.60-1.81 (m, 2H), 1.18-1.39 (m, 4H), 1.03-1.15 (m, 2H). MS: 626.2 (M+H$^+$).

Example BZ-39

2-(4-((6-(bis(4-chlorophenyl)methyl)-2-cyclopropyl-1H-benzo[d]imidazol-1-yl)methyl)piperidin-1-yl)pyrimidine-5-carboxylic acid; Compound #4

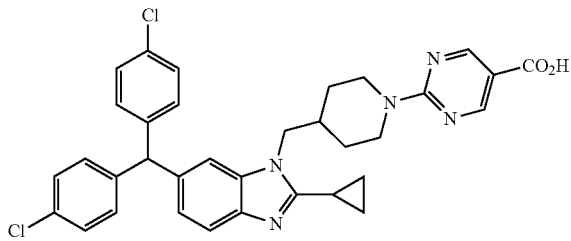 [SMILES: O=C(O)c1cnc(N2CCC(Cn3c(C4CC4)nc4ccc(C(c5ccc(Cl)cc5)c5ccc(Cl)cc5)cc43)CC2)nc1]

A solution of methyl 2-(4-((6-(bis(4-chlorophenyl)methyl)-2-cyclopropyl-1H-benzo[d]imidazol-1-yl)methyl)piperidin-1-yl)pyrimidine-5-carboxylate (25 mg, 0.04 mmol) and LiOH.$H_2O$ (6.7 mg, 0.16 mmol) in $H_2O$ (1 mL) and THF (2 mL) was stirred at room temperature overnight. To the reaction solution was added 1N HCl aq solution to adjust pH to ~3. The resulting mixture was extracted with EtOAc. The organic layer was washed with aq NaCl solution, dried over $Na_2SO_4$ and concentrated yield 2-(4-((6-(bis(4-chlorophenyl)methyl)-2-cyclopropyl-1H-benzo[d]imidazol-1-yl)methyl)piperidin-1-yl)pyrimidine-5-carboxylic acid.

$^1$H NMR (CHLOROFORM-d) δ: 8.90 (s, 2H), 7.78 (br d, J=6.1 Hz, 1H), 7.21-7.34 (m, 4H), 6.97-7.09 (m, 5H), 6.94 (br s, 1H), 5.64 (s, 1H), 4.98 (br d, J=12.6 Hz, 2H), 3.99-4.16 (m, 2H), 2.87 (br t, J=12.4 Hz, 2H), 2.09-2.20 (m, 1H), 1.87-2.07 (m, 3H), 1.72 (br d, J=11.6 Hz, 2H), 1.17-1.38 (m, 4H). MS: 612.2 (M+H$^+$).

Example BZ-40

2-(4-((6-(bis(4-chlorophenyl)methyl)-2-cyclopropyl-1H-benzo[d]imidazol-1-yl)methyl)piperidin-1-yl)pyrimidine-4-carboxylic acid; Compound #2

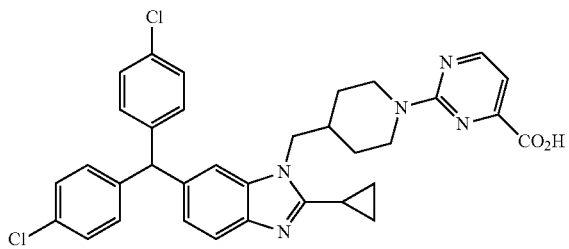 [SMILES: O=C(O)c1ccnc(N2CCC(Cn3c(C4CC4)nc4ccc(C(c5ccc(Cl)cc5)c5ccc(Cl)cc5)cc43)CC2)n1]

2-(4-((6-(Bis(4-chlorophenyl)methyl)-2-cyclopropyl-1H-benzo[d]imidazol-1-yl)methyl)piperidin-1-yl)pyrimidine-4-carboxylic acid was prepared according to the procedure as described in Example BZ-39, substituting methyl 2-bromopyrimidine-4-carboxylate for methyl 2-bromopyrimidine-5-carboxylate.

MS: 612.0 (M+H$^+$).

Example BZ-41

4-(4-((6-(bis(4-chlorophenyl)methyl)-2-cyclopropyl-1H-benzo[d]imidazol-1-yl)methyl)piperidin-1-yl)benzoic acid; Compound #1

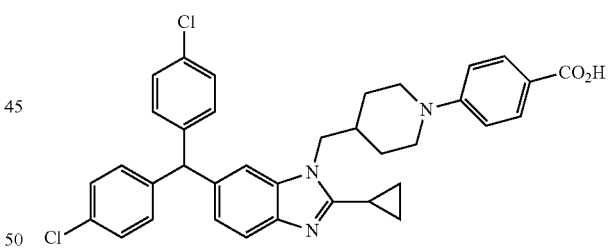

STEP A: methyl 4-(4-((6-(bis(4-chlorophenyl)methyl)-2-cyclopropyl-1H-benzo[d]imidazol-1-yl)methyl)piperidin-1-yl)benzoate A mixture of 6-(bis(4-chlorophenyl)methyl)-2-cyclopropyl-1-(piperidin-4-ylmethyl)-1H-benzo[d]imidazole (30 mg, 0.06 mmol), methyl 4-bromobenzoate (26 mg, 0.12 mmol), $Cs_2C_3$ (40 mg, 0.12 mmol), dicyclohexyl(2',4',6'-triisopropyl-[1, 1'-biphenyl]-2-yl)phosphine (8.7 mg, 0.018 mmol) and Pd(OAc)$_2$ (2.1 mg, 0.009 mmol) in 1,4-dioxane (1.5 mL) was heated at 140° C. by microwave for 3 h. The reaction mixture was cooled to room temperature, diluted with EtOAc, and filtered. The solution was concentrated and purified by chromatography (silica gel column, 60% EtOAc/ heptane) to yield methyl 4-(4-((6-(bis(4-chlorophenyl)methyl)-2-cyclopropyl-1H-benzo[d]imidazol-1-yl)methyl)piperidin-1-yl)benzoate.

STEP B: 4-(4-((6-(bis(4-chlorophenyl)methyl)-2-cyclopropyl-1H-benzo[d]imidazol-1-yl)methyl)piperidin-1-yl)benzoic acid To a solution of methyl 4-(4-((6-(bis(4-chlorophenyl)methyl)-2-cyclopropyl-1H-benzo[d]imidazol-1-yl)methyl)piperidin-1-yl)benzoate (30 mg, 0.05 mmol) in H₂O (1 mL) and THF (2 mL) at room temperature was added 1N NaOH aq solution (0.38 mL, 0.38 mmol). The reaction was stirred for 5 days before 1N HCl aq solution was added to adjust pH to ~3. The resulting mixture was extracted with EtOAc. The organic layer was washed with aq NaCl solution, dried over Na₂SO₄ and concentrated. The resulting residue was purified by chromatography (silica gel column, 5% MeOH/CH₂Cl₂) to yield 4-(4-((6-(bis(4-chlorophenyl)methyl)-2-cyclopropyl-1H-benzo[d]imidazol-1-yl)methyl)piperidin-1-yl)benzoic acid.
$^1$H NMR (CHLOROFORM-d) δ: 7.99 (br d, J=8.6 Hz, 2H), 7.61 (d, J=8.6 Hz, 1H), 7.21-7.31 (m, 4H), 7.03 (d, J=8.1 Hz, 4H), 6.83-6.97 (m, 4H), 5.62 (s, 1H), 3.97-4.15 (m, 2H), 3.71-3.96 (m, 2H), 2.78 (br t, J=11.9 Hz, 2H), 2.05 (m, 1H), 1.87-2.01 (m, 1H), 1.69 (br d, J=11.6 Hz, 2H), 1.33-1.46 (m, 2H), 1.23-1.33 (m, 2H), 1.04-1.16 (m, 2H). MS: 610.3 (M+H⁺).

Example MP-1 bis(4-chlorophenyl)(2-(tetrahydrofuran-2-yl)-1-(1-((trifluoromethyl)sulfonyl)piperidin-4-yl)-1H-benzo[d]imidazol-6-yl)methanol

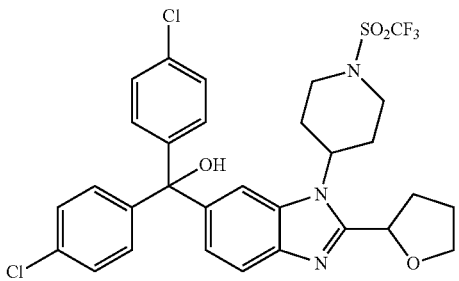

and 6-(bis(4-chlorophenyl)methyl)-2-(tetrahydrofuran-2-yl)-1-(1-((trifluoromethyl)sulfonyl)piperidin-4-yl)-1H-benzo[d]imidazole

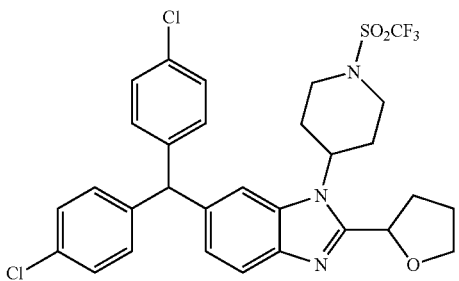

Step 1: 6-bromo-2-(tetrahydrofuran-2-yl)-1-(1-((trifluoromethyl)sulfonyl)piperidin-4-yl)-1H-benzo[d]imidazole A solution of 5-bromo-N1-(1-((trifluoromethyl)sulfonyl)piperidin-4-yl)benzene-1,2-diamine (484 mg, 1.20 mmol, prepared as described in Example YM-4) and 2-tetrahydrofuroic acid (279 mg, 2.41 mmol) in THF (2 mL) was heated at reflux temperature overnight. The solution was diluted with saturated aqueous NaHCO₃ and the mixture was extracted with ethyl acetate. The organic layer was concentrated and the residue purified by chromatography on silica gel eluting with a 0-40% ethyl acetate in dichloromethane gradient to yield 6-bromo-2-(tetrahydrofuran-2-yl)-1-(1-((trifluoromethyl)sulfonyl)piperidin-4-yl)-1H-benzo[d]imidazole as an off-white solid.

Step 2: bis(4-chlorophenyl)(2-(tetrahydrofuran-2-yl)-1-(1-((trifluoromethyl)sulfonyl)piperidin-4-yl)-1H-benzo[d]imidazol-6-yl)methanol A solution of 6-bromo-2-(tetrahydrofuran-2-yl)-1-(1-((trifluoromethyl)sulfonyl)piperidin-4-yl)-1H-benzo[d]imidazole (205 mg, 0.43 mmol) and 4,4'-dichlorobenzophenone (107 mg, 0.43 mmol) in THF (3 mL) was cooled to −78° C. tert-Butyllithium (1.7M in pentane, 0.625 mL, 1.06 mmol) was added slowly by syringe. The reaction was stirred at −78° C. for 15 minutes, and then the cooling bath was removed. The reaction mixture was stirred overnight at room temperature. The reaction was quenched by addition of saturated aqueous NaHCO₃ and extracted with ethyl acetate. The organic layer was concentrated and the residue purified by chromatography on silica gel eluting with a 0-40% ethyl acetate in dichloromethane gradient to yield bis(4-chlorophenyl)(2-(tetrahydrofuran-2-yl)-1-(1-((trifluoromethyl)sulfonyl)piperidin-4-yl)-1H-benzo[d]imidazol-6-yl)methanol as a white solid. MS: 654.2 (M+H⁺); $^1$H NMR (400 MHz, CDCl₃) δ: 7.67 (d, J=8.6 Hz, 1H), 7.53 (s, 1H), 7.33-7.29 (m, 3H), 7.27-7.21 (m, 5H), 7.05 (br d, J=8.6 Hz, 1H), 5.15 (t, J=6.6 Hz, 1H), 4.86-4.74 (m, 1H), 4.13 (br d, J=13.0 Hz, 1H), 3.95-3.87 (m, 1H), 3.87-3.78 (m, 1H), 3.23 (q, J=12.3 Hz, 2H), 2.94 (td, J=6.6, 13.4 Hz, 1H), 2.88 (br s, 1H), 2.54-2.40 (m, 1H), 2.40-2.29 (m, 2H), 2.18 (td, J=6.4, 13.1 Hz, 1H), 2.12-2.01 (m, 3H), 1.98 (br d, J=13.2 Hz, 1H).

Step 3: 6-(bis(4-chlorophenyl)methyl)-2-(tetrahydrofuran-2-yl)-1-(1-((trifluoromethyl)sulfonyl)piperidin-4-yl)-1H-benzo[d]imidazole A solution of bis(4-chlorophenyl)(2-(tetrahydrofuran-2-yl)-1-(1-((trifluoromethyl)sulfonyl)piperidin-4-yl)-1H-benzo[d]imidazol-6-yl)methanol (138 mg, 0.21 mmol), boron trifluoride diethyl etherate (0.029 mL, 0.23 mmol), and triethylsilane (123 mg, 1.05 mmol) in dichloromethane (2 mL) was stirred at room temperature for 3 days. The solution was diluted with saturated aqueous NaHCO₃ and the mixture was extracted with dichloromethane. The organic layer was concentrated and the residue purified by chromatography on silica gel eluting with a 0-40% ethyl acetate in dichloromethane gradient to yield 6-(bis(4-chlorophenyl)methyl)-2-(tetrahydrofuran-2-yl)-1-(1-((trifluoromethyl)sulfonyl)piperidin-4-yl)-1H-benzo[d]imidazole as a white solid. MS: 638.1 (M+H⁺); $^1$H NMR (400 MHz, CDCl₃) δ: 7.69 (d, J=8.6 Hz, 1H), 7.30-7.24 (m, 4H), 7.18 (s, 1H), 7.04 (d, J=8.6 Hz, 4H), 6.98 (dd, J=1.3, 8.3 Hz, 1H), 5.63 (s, 1H), 5.15 (dd, J=6.1, 7.1 Hz, 1H), 4.80 (ddd, J=4.0, 8.1, 12.1 Hz, 1H), 4.23-4.08 (m, 2H), 3.91 (dt, J=5.8, 7.7 Hz, 1H), 3.87-3.79 (m, 1H), 3.23 (q, J=12.5 Hz, 2H), 3.00-2.91 (m, 1H), 2.52-2.40 (m, 1H), 2.40-2.29 (m, 2H), 2.22-2.12 (m, 1H), 2.12-1.95 (m, 3H).

Example MP-2

6-(benzo[d][1,3]dioxol-5-yl(4-chlorophenyl)methyl)-2-cyclopropyl-1-(1-((trifluoromethyl)sulfonyl)piperidin-4-yl)-1H-benzo[d]imidazole

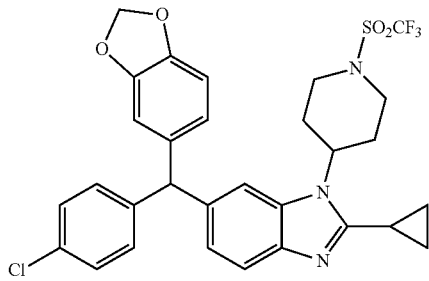

Step 1: benzo[d][1,3]dioxol-5-yl(4-chlorophenyl)(2-cyclopropyl-1-(1-((trifluoromethyl)sulfonyl)piperidin-4-yl)-1H-benzo[d]imidazol-6-yl)methanol A solution of 6-bromo-2-cyclopropyl-1-(1-((trifluoromethyl)sulfonyl)piperidin-4-yl)-1H-benzo[d]imidazole (106 mg, 0.23 mmol, prepared as described in Example YM-4) and 1,3-benzodioxol-5-yl(4-chlorophenyl)methanone (61.1 mg, 0.23 mmol) in THF (1 mL) was cooled to −78° C. tert-Butyllithium (1.7M in pentane, 0.345 mL, 0.59 mmol) was added and the reaction was stirred at −78° C. for 15 minutes. The cooling bath was removed and the reaction mixture was warm to room temperature over 1 hour. The reaction was quenched by addition of saturated aqueous NaHCO₃ and extracted with ethyl acetate. The organic layer was concentrated and the residue purified by chromatography on silica gel eluting with a 0-50% ethyl acetate in heptane gradient to yield benzo[d][1,3]dioxol-5-yl(4-chlorophenyl)(2-cyclopropyl-1-(1-((trifluoromethyl)sulfonyl)piperidin-4-yl)-1H-benzo[d]imidazol-6-yl)methanol as a white solid.

Step 2: 6-(benzo[d][1,3]dioxol-5-yl(4-chlorophenyl)methyl)-2-cyclopropyl-1-(1-((trifluoromethyl)sulfonyl)piperidin-4-yl)-1H-benzo[d]imidazole To a solution of benzo[d][1,3]dioxol-5-yl(4-chlorophenyl)(2-cyclopropyl-1-(1-((trifluoromethyl)sulfonyl)piperidin-4-yl)-1H-benzo[d]imidazol-6-yl)methanol (50 mg, 0.079 mmol) and triethylsilane (45.8 mg, 0.39 mmol) in dichloromethane (4 mL) was added trifluoroacetic acid (1 mL). The reaction mixture turned deep red upon addition of trifluoroacetic acid but faded within minutes leaving a clear, colorless solution. After 1 hour, the reaction mixture was diluted with saturated aqueous NaHCO₃ and the mixture was extracted with dichloromethane. The organic layer was concentrated to yield 6-(benzo[d][1,3]dioxol-5-yl(4-chlorophenyl)methyl)-2-cyclopropyl-1-(1-((trifluoromethyl)sulfonyl)piperidin-4-yl)-1H-benzo[d]imidazole. MS: 617.8 (M+H⁺); ¹H NMR (400 MHz, CDCl₃) δ: 7.58 (d, J=8.3 Hz, 1H), 7.28-7.22 (m, 2H), 7.11-7.00 (m, 3H), 6.96 (dd, J=1.3, 8.4 Hz, 1H), 6.74 (d, J=8.1 Hz, 1H), 6.58 (d, J=1.7 Hz, 1H), 6.57-6.51 (m, 1H), 5.94 (q, J=1.3 Hz, 2H), 5.56 (s, 1H), 4.70-4.57 (m, 1H), 4.22-4.14 (m, 2H), 3.24 (br t, J=12.5 Hz, 2H), 2.57-2.38 (m, 2H), 2.10-1.98 (m, 2H), 1.94 (tt, J=5.0, 8.2 Hz, 1H), 1.23-1.17 (m, 2H), 1.13-1.06 (m, 2H).

Example MP-3 bis(4-chlorophenyl)(2-cyclobutyl-1-(1-((trifluoromethyl)sulfonyl)piperidin-4-yl)-1H-benzo[d]imidazol-6-yl)methanol

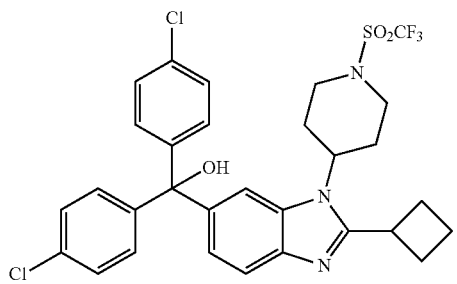

and 6-(bis(4-chlorophenyl)methyl)-2-cyclobutyl-1-(1-((trifluoromethyl)sulfonyl)piperidin-4-yl)-1H-benzo[d]imidazoles

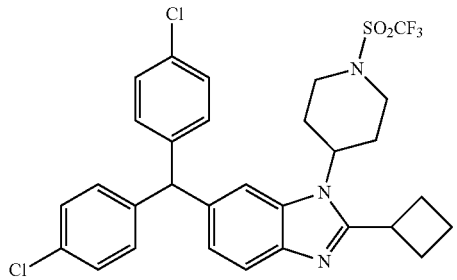

Step 1: 6-bromo-2-cyclobutyl-1-(1-((trifluoromethyl)sulfonyl)piperidin-4-yl)-1H-benzo[d]imidazole A solution of 5-bromo-N1-(1-((trifluoromethyl)sulfonyl)piperidin-4-yl)benzene-1,2-diamine (724 mg, 1.8 mmol, prepared as described in Example YM-4) and cyclobutanecarboxaldehyde (167 mg, 1.98 mmol) in DMSO (10 mL) was stirred at room temperature overnight open to air. The solution was diluted with brine and the mixture was extracted with ethyl acetate. The organic layer was concentrated and the residue purified by chromatography on silica gel eluting with a 0-40% ethyl acetate in dichloromethane gradient to yield 6-bromo-2-cyclobutyl-1-(1-((trifluoromethyl)sulfonyl)piperidin-4-yl)-1H-benzo[d]imidazole as a white solid.

Step 2: bis(4-chlorophenyl)(2-cyclobutyl-1-(1-((trifluoromethyl)sulfonyl)piperidin-4-yl)-1H-benzo[d]imidazol-6-yl)methanol A solution of 6-bromo-2-cyclobutyl-1-(1-((trifluoromethyl)sulfonyl)piperidin-4-yl)-1H-benzo[d]imidazole (95 mg, 0.20 mmol) and 4,4'-dichlorobenzophenone (51.2 mg, 0.20 mmol) in THF (2 mL) was cooled to −78° C. tert-Butyllithium (1.7M in pentane, 0.3 mL, 0.51 mmol) was added slowly by syringe. The reaction was stirred at −78° C. for 15 minutes and then allowed to warm to room temperature. The reaction mixture was stirred for 4 hours, quenched by addition of saturated aqueous NaHCO$_3$, and extracted with ethyl acetate. The organic layer was concentrated and the residue purified by chromatography on silica gel eluting with a 25-40% ethyl acetate in dichloromethane gradient to yield bis(4-chlorophenyl)(2-cyclobutyl-1-(1-((trifluoromethyl)sulfonyl)piperidin-4-yl)-1H-benzo[d]imidazol-6-yl)methanol as a white solid. MS: 638.1 (M+H$^+$).

Step 3: 6-(bis(4-chlorophenyl)methyl)-2-cyclobutyl-1-(1-((trifluoromethyl)sulfonyl)piperidin-4-yl)-1H-benzo[d]imidazole A solution of bis(4-chlorophenyl)(2-cyclobutyl-1-(1-((trifluoromethyl)sulfonyl)piperidin-4-yl)-1H-benzo[d]imidazol-6-yl)methanol (66 mg, 0.103 mmol) and triethylsilane (60.1 mg, 0.517 mmol) were combined in dry dichloromethane and the solution cooled to 0° C. Boron trifluoride diethyl etherate (0.014 mL, 0.114 mmol) was added and the reaction mixture was stirred at room temperature overnight. The reaction was quenched with saturated aqueous NaHCO$_3$ and the mixture was extracted with dichloromethane. The organic layer was concentrated and the residue purified by chromatography on silica gel eluting with a 25-40% ethyl acetate in dichloromethane gradient to yield 6-(bis(4-chlorophenyl)methyl)-2-cyclobutyl-1-(1-((trifluoromethyl)sulfonyl)piperidin-4-yl)-1H-benzo[d]imidazole as a colorless oil. MS: 622.1 (M+H$^+$); $^1$H NMR (400 MHz, CDCl$_3$) δ: 7.69 (d, J=8.1 Hz, 1H), 7.30-7.23 (m, 4H), 7.1-7.07 (m, 1H), 7.07-7.00 (m, 4H), 6.96 (dd, J=1.3, 8.3 Hz, 1H), 5.62 (s, 1H), 4.25-4.15 (m, 2H), 3.74-3.65 (m, 1H), 3.18 (br t, J=12.6 Hz, 2H), 2.66-2.53 (m, 2H), 2.48-2.33 (m, 4H), 2.23-2.10 (m, 1H), 2.08-2.00 (m, 2H), 1.92 (br d, J=11.1 Hz, 2H).

Example MP-4 ethyl 4-(6-(bis(4-chlorophenyl)methyl)-2-ethyl-1H-benzo[d]imidazol-1-yl)piperidine-1-carboxylate

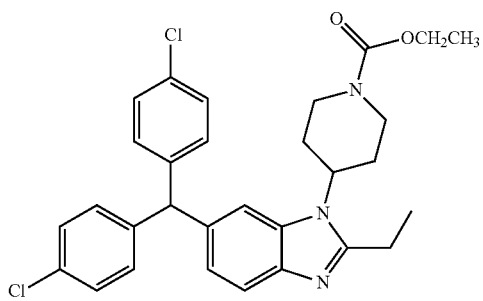 [SMILES: CCOC(=O)N1CCC(n2c(CC)nc3ccc(C(c4ccc(Cl)cc4)c4ccc(Cl)cc4)cc32)CC1]

Step 1:
3-fluoro-N-methoxy-N-methyl-4-nitrobenzamide

3-Fluoro-4-nitrobenzoic acid (15.2 g, was suspended in dichloromethane (300 mL) and the mixture was cooled to 0° C. and stirred vigorously. Oxalyl chloride (45.16 mL, 90.32 mmol, 2M in dichloromethane) was added slowly by addition funnel, maintaining the temperature below 10° C. After the addition of oxalyl chloride was complete, the ice bath was removed and the reaction, still a suspension, was allowed to warm to room temperature. Gas evolution was evident. After 2 hours, the solution was homogeneous and gas evolution had ceased. The flask was returned to an ice bath and cooled to 0° C. A mixture of N,O-dimethylhydroxylamine hydrochloride (9.61 g, 98.54 mmol) and triethylamine (57.07 mL, 410.56 mmol) in dichloromethane (100 mL) was added slowly by addition funnel, maintaining a temperature less than 25° C. Once this mixture was added, the ice bath was removed and the orange reaction mixture was stirred at room temperature for 1 hour. The reaction mixture was diluted with saturated aqueous NaHCO$_3$ and water and then extracted with dichloromethane. The organic layer was concentrated to yield 3-fluoro-N-methoxy-N-methyl-4-nitrobenzamide as a dark red-orange solid, which was used without further purification in the next step.

Step 2: ethyl 4-((5-(methoxy(methyl)carbamoyl)-2-nitrophenyl)amino)piperidine-1-carboxylate A solution of 3-fluoro-N-methoxy-N-methyl-4-nitrobenzamide (17.5 g, 76.69 mmol), ethyl 4-amino-1-piperidinecarboxylate (13.81 mL, 80.53 mmol), and diisopropylethylamine (19.83 mL, 115.04 mmol) in acetonitrile (300 mL) was heated at reflux temperature for 18 hours and then stirred at room temperature for an additional 48 hours. The reaction mixture was concentrated to ~50 mL and then diluted with EtOAc (500 mL). The organic mixture was washed with saturated aqueous NaHCO$_3$ and then brine. The organic layer was concentrated to a dark oil and then purified by silica gel chromatography using a gradient of 50:50 EtOAc:heptane to 100% EtOAc as the eluent to yield ethyl 4-((5-(methoxy(methyl)carbamoyl)-2-nitrophenyl)amino)piperidine-1-carboxylate as an orange oil.

Step 3: ethyl 4-((5-(4-chlorobenzoyl)-2-nitrophenyl)amino)piperidine-1-carboxylate To a solution of ethyl 4-((5-(methoxy(methyl)carbamoyl)-2-nitrophenyl)amino)piperidine-1-carboxylate (8.50 g, 22.33 mmol) in THF (250 mL) cooled to 0° C. was added 4-chlorophenylmagnesium bromide (24.57 mL, 24.57 mmol, 1M in diethyl ether) slowly by addition funnel. The cooling bath was removed and the reaction mixture was stirred at room temperature of 2 hours. The reaction was quenched with saturated aqueous NaHCO$_3$ and the mixture extracted with ethyl acetate. The organic layer was concentrated and the residue purified by chromatography on silica gel using heptane/ethyl acetate as the eluent to yield ethyl 4-((5-(4-chlorobenzoyl)-2-nitrophenyl)amino)piperidine-1-carboxylate as a yellow solid.

Step 4: ethyl 4-((5-(bis(4-chlorophenyl)(hydroxy)methyl)-2-nitrophenyl)amino)piperidine-1-carboxylate To a solution of ethyl 4-((5-(4-chlorobenzoyl)-2-nitrophenyl)amino)piperidine-1-carboxylate (7.45 g, 17.25 mmol) in THF (200 mL) cooled to 0° C. was added 4-chlorophenylmagnesium bromide (37.95 mL, 27.95 mmol, 1M in diethyl ether) slowly by syringe. After 1 hour at 0° C., the reaction was quenched with saturated aqueous NaHCO$_3$ and extracted with ethyl acetate. The organic layer was concentrated and the residue purified by chromatography on silica gel eluting with a 10-40% ethyl acetate in heptane gradient to yield ethyl 4-((5-(bis(4-chlorophenyl)(hydroxy)methyl)-2-nitrophenyl)amino)piperidine-1-carboxylate.

Step 5: ethyl 4-((5-(bis(4-chlorophenyl)methyl)-2-nitrophenyl)amino)piperidine-1-carboxylate To a solution of ethyl 4-((5-(bis(4-chlorophenyl)(hydroxy)methyl)-2-nitrophenyl)amino)piperidine-1-carboxylate (6.38 g, 1171 mmol) and triethylsilane (5.45 g, 46.84 mmol) in dichloromethane (589 mL) was added trifluoroacetic acid (39.3 mL). The reaction mixture was stirred overnight at room temperature and then neutralized with saturated aqueous NaHCO$_3$. The reaction mixture was extracted with dichloromethane. The organic layer was concentrated and the residue purified by chromatography on silica gel to yield ethyl 4-((5-(bis(4-chlorophenyl)methyl)-2-nitrophenyl)amino)piperidine-1-carboxylate.

Step 6: ethyl 4-((2-amino-5-(bis(4-chlorophenyl)methyl)phenyl)amino)piperidine-1-carboxylate Ethyl 4-((5-(bis(4-chlorophenyl)methyl)-2-nitrophenyl)amino)piperidine-1-carboxylate (3.32 g, 6.28 mmol) was dissolved in ethyl acetate (250 mL) and nitrogen was bubbled through the solution for a few minutes. Raney nickel (300 mg, 5.11 mmol) was added and the reaction mixture was placed on a Parr shaker under 45 psi H$_2$ for 5 hours. The catalyst was filtered through CELITE and the filtrate was evaporated in vacuo. The residue was purified by chromatography on silica gel to yield ethyl 4-((2-amino-5-(bis(4-chlorophenyl)methyl)phenyl)amino)piperidine-1-carboxylate as a brown solid.

Step 7: ethyl 4-(6-(bis(4-chlorophenyl)methyl)-2-ethyl-1H-benzo[d]imidazol-1-yl)piperidine-1-carboxylate A solution of ethyl 4-((2-amino-5-(bis(4-chlorophenyl)methyl)phenyl)amino)piperidine-1-carboxylate (209 mg, 0.42 mmol) and propionaldehyde (48.7 mg, 0.84 mmol) in DMSO (3 mL) was stirred at room temperature open to air for 72 hours. The solution was diluted with brine and the mixture was extracted with ethyl acetate. The organic layer was concentrated and the residue purified by chromatography on silica gel to yield ethyl 4-(6-(bis(4-chlorophenyl)methyl)-2-ethyl-1H-benzo[d]imidazol-1-yl)piperidine-1-carboxylate. $^1$H NMR (400 MHz, CDCl$_3$) δ: 7.63 (d, J=8.6 Hz, 1H), 7.30-7.20 (m, 4H), 7.17 (s, 1H), 7.03 (d, J=8.6 Hz, 4H), 6.90 (dd, J=1.5, 8.3 Hz, 1H), 5.61 (s, 1H), 4.53-4.34 (m, 2H), 4.29 (tdd, J=4.1, 8.3, 12.3 Hz, 1H), 4.19 (q, J=7.1 Hz, 2H), 2.98-2.82 (m, 4H), 2.40-2.15 (m, 2H), 1.85 (br d, J=11.7 Hz, 2H), 1.44 (t, J=7.5 Hz, 3H), 1.30 (t, J=7.1 Hz, 3H)

Example MP-5 ethyl 4-(6-(bis(4-chlorophenyl)methyl)-2-(pyridin-3-yl)-1H-benzo[d]imidazol-1-yl)piperidine-1-carboxylate

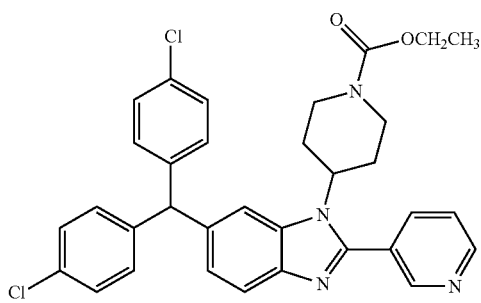 [SMILES: CCOC(=O)N1CCC(n2c(-c3cccnc3)nc3ccc(C(c4ccc(Cl)cc4)c4ccc(Cl)cc4)cc32)CC1]

Ethyl 4-(6-(bis(4-chlorophenyl)methyl)-2-(pyridin-3-yl)-1H-benzo[d]imidazol-1-yl)piperidine-1-carboxylate was prepared according to the procedure as described in Example MP-4 above, modifying the procedure used in Step 7 as follows:

A solution of ethyl 4-((2-amino-5-(bis(4-chlorophenyl)methyl)phenyl)amino)piperidine-1-carboxylate (147 mg, 0.30 mmol) and pyridine-3-carboxaldehyde (31.6 mg, 0.30 mmol) in DMSO (1 mL) was stirred at room temperature open to air overnight. The solution was diluted with brine and the mixture was extracted with ethyl acetate. The organic layer was concentrated and the resulting brown oil purified by chromatography on silica gel using a gradient of 10-50% ethyl acetate in heptane followed by 5% methanol in dichloromethane as eluent to yield ethyl 4-(6-(bis(4-chlorophenyl)methyl)-2-(pyridin-3-yl)-1H-benzo[d]imidazol-1-yl)piperidine-1-carboxylate as an orange oil. $^1$H NMR (400 MHz, CDCl$_3$) δ: 8.84 (d, J=1.5 Hz, 1H), 8.78 (dd, J=1.7, 4.9 Hz, 1H), 8.00 (td, J=1.9, 7.9 Hz, 1H), 7.75 (d, J=8.6 Hz, 1H), 7.50 (ddd, J=0.7, 4.9, 7.8 Hz, 1H), 7.32 (s, 1H), 7.30-7.24 (m, 4H), 7.10-7.04 (m, 4H), 7.02 (dd, J=1.5, 8.6 Hz, 1H), 5.66 (s, 1H), 4.46-4.27 (m, 3H), 4.18 (q, J=7.1 Hz, 2H), 2.76 (br t, J=12.5 Hz, 2H), 2.35 (br d, J=8.8 Hz, 2H), 1.90 (br d, J=11.2 Hz, 2H), 1.29 (t, J=7.1 Hz, 3H).

Example MP-6 bis(4-chlorophenyl)(2-ethyl-1-(1-((trifluoromethyl)sulfonyl)piperidin-4-yl)-1H-benzo[d]imidazol-6-yl)methanol

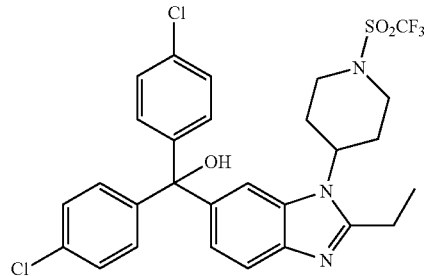

A solution of 6-bromo-2-ethyl-1-(1-((trifluoromethyl)sulfonyl)piperidin-4-yl)-1H-benzo[d]imidazole (700 mg, 1.59 mmol, prepared according to the procedures as described in YM-4, Steps 4 and 5) and 4,4'-dichlorobenzophenone (399.2 mg, 1.59 mmol) in THF (2 mL) was cooled to −78° C. tert-Butyllithium (1.7M in pentane, 2.34 mL, 3.98 mmol) was added slowly by syringe. The reaction was stirred at −78° C. for 15 minutes and then allowed to warm to room temperature. The reaction mixture was stirred for 3 hours, quenched by addition of saturated aqueous NaHCO$_3$, and extracted with ethyl acetate. The organic layer was concentrated and the residue purified by chromatography on silica gel eluting with a 0-40% ethyl acetate in dichloromethane gradient to yield bis(4-chlorophenyl)(2-ethyl-1-(1-((trifluoromethyl)sulfonyl)piperidin-4-yl)-1H-benzo[d]imidazol-6-yl)methanol as a white solid. MS: 611.8 (M+H$^+$).

Example MP-7

6-(bis(4-methoxyphenyl)methyl)-2-cyclobutyl-1-(1-((trifluoromethyl)sulfonyl)piperidin-4-yl)-1H-benzo[d]imidazole

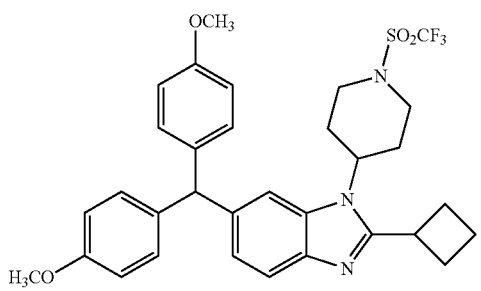

Step 1: (2-cyclobutyl-1-(1-((trifluoromethyl)sulfonyl)piperidin-4-yl)-1H-benzo[d]imidazol-6-yl)bis(4-methoxyphenyl)methanol A solution of 6-bromo-2-cyclobutyl-1-(1-((trifluoromethyl)sulfonyl)piperidin-4-yl)-1H-benzo[d]imidazole (131 mg, 0.28 mmol, prepared as described in Example MP-3) and 4,4'-dimethoxybenzophenone (68.1 mg, 0.28 mmol) in THF (2 mL) was cooled to −78° C. tert-Butyllithium (1.7M in pentane, 0.41 mL, 0.70 mmol) was added slowly by syringe. The reaction was stirred at −78° C. for 15 minutes and then allowed to warm to room temperature. The reaction mixture was stirred for 1 hour, quenched by addition of saturated aqueous NaHCO$_3$, and extracted with ethyl acetate. The organic layer was concentrated and the residue purified by chromatography on silica gel eluting with a 10-40% ethyl acetate in heptane gradient to yield (2-cyclobutyl-1-(1-((trifluoromethyl)sulfonyl)piperidin-4-yl)-1H-benzo[d]imidazol-6-yl)bis(4-methoxyphenyl)methanol as a white solid.

Step 2: 6-(bis(4-methoxyphenyl)methyl)-2-cyclobutyl-1-(1-((trifluoromethyl)sulfonyl)piperidin-4-yl)-1H-benzo[d]imidazole To a solution of (2-cyclobutyl-1-(1-((trifluoromethyl)sulfonyl)piperidin-4-yl)-1H-benzo[d]imidazol-6-yl)bis(4-methoxyphenyl)methanol (114 mg, 0.181 mmol) and triethylsilane (46.2 mg, 0.40 mmol) in dichloromethane (2 mL) was added trifluoroacetic acid (0.25 mL) and the reaction mixture was stirred at room temperature overnight. An additional amount of triethylsilane (100 μL) and trifluoroacetic acid (259 μL) were added and stirring was continued at room temperature overnight. The reaction mixture was neutralized with saturated aqueous NaHCO$_3$ extracted with dichloromethane, and the solvent removed in vacuo. The residue was purified by chromatography on silica gel eluting with a 10-50% ethyl acetate in heptane gradient to yield 6-(bis(4-methoxyphenyl)methyl)-2-cyclobutyl-1-(1-((trifluoromethyl)sulfonyl)piperidin-4-yl)-1H-benzo[d]imidazole as a white solid. MS: 614.0 (M+H$^+$).

Example MP-8 ethyl 4-(6-((4-chlorophenyl)(thiazol-2-yl)methyl)-2-cyclopropyl-1H-benzo[d]imidazol-1-yl)piperidine-1-carboxylate

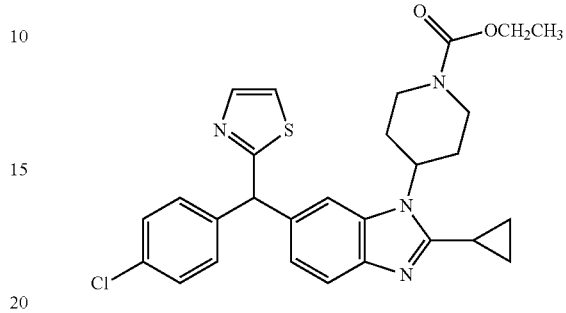

Step 1: ethyl 4-((5-chloro-2-nitrophenyl)amino)piperidine-1-carboxylate

A solution of 2,4-dichloronitrobenzene (19.2 g, 100 mmol), ethyl 4-amino-1-piperidine-carboxylate (18.95 g, 110 mmol), and triethylamine (16.619 mL, 120 mmol) in acetonitrile (75 mL) was heated at reflux temperature for 13 days. The solvent was evaporated, the residue was dissolved in dichloromethane (5400 mL), and the resulting solution was washed with a 1N HCl solution (250 mL). The organic layer was further washed with brine (100 mL), dried over MgSO$_4$, filtered, and evaporated. The residue was purified by chromatography on silica gel using a 0-10% methanol in dichloromethane gradient as eluent to yield ethyl 4-((5-chloro-2-nitrophenyl)amino)piperidine-1-carboxylate as an orange solid.

Step 2: ethyl 4-((5-((4-chlorophenyl)(cyano)methyl)-2-nitrophenyl)amino)piperidine-1-carboxylate To a solution of 4-chlorophenylacetonitrile (4.78 g, 31.5 mmol) in THF (50 mL) and isopropyl alcohol (10 mL) was added t-BuOK (8.42 g, 75 mmol) and the mixture was stirred at room temperature for 15 minutes. Compound 8a (9.83 g, 30 mmol) was added and the reaction was stirred at room temperature overnight. Water (200 mL) was added and the mixture extracted with ethyl acetate (500 mL). The organic layer was washed with brine (50 mL), dried over MgSO$_4$, and evaporated in vacuo. The residue was purified by silica gel chromatography using a 20-60% ethyl acetate in heptane gradient as eluent to yield ethyl 4-((5-((4-chlorophenyl)(cyano)methyl)-2-nitrophenyl)amino)piperidine-1-carboxylate as a bright yellow-orange solid.

Step 3: ethyl 4-((5-(2-amino-1-(4-chlorophenyl)-2-thioxoethyl)-2-nitrophenyl)amino)piperidine-1-carboxylate To a solution of ethyl 4-((5-((4-chlorophenyl)(cyano)methyl)-2-nitrophenyl)amino)piperidine-1-carboxylate (6.18 g, 13.95 mmol) in EtOH (50 mL) was added phosphorus pentasulfide (6.82 g, 15.35 mmol) and the reaction mixture was heated to 70° C. overnight. The reaction mixture was cooled in an ice-water bath, water (150 mL) was added dropwise and a bright orange oil separated. The mixture was filtered over a bed of CELITE (the orange oil stayed on top) and the oily residue on the filter was washed with water (200 mL). The residue on the filter was dissolved in dichloromethane (200 mL) and the resulting solution was dried over MgSO4, filtered, and evaporated to give 11.3 g of a bright orange oil. The material was purified by silica gel chromatography using a 40-80% ethyl acetate in heptane gradient as eluent, to yield ethyl 4-((5-(2-amino-1-(4-chlorophenyl)-2-thioxoethyl)-2-nitrophenyl)amino)piperidine-1-carboxylate as a bright orange solid.

Step 4: ethyl 4-((5-((4-chlorophenyl)(thiazol-2-yl)methyl)-2-nitrophenyl)amino)piperidine-1-carboxylate To a solution of ethyl 4-((5-(2-amino-1-(4-chlorophenyl)-2-thioxoethyl)-2-nitrophenyl)amino)piperidine-1-carboxylate (6.15 g, 12.89 mmol) and bromoacetaldehyde diethylacetal (7.76 mL, 51.57 mmol) in acetic acid (75 mL) was added water (3 mL). The reaction mixture was heated to 100° C. for 30 minutes, cooled to room temperature, and water (150 mL) was added. The mixture was extracted with ethyl acetate (2×250 mL) and the combined organic layers were washed with brine (50 mL). The organic layer was dried over MgSO$_4$, filtered, and evaporated. The residue was purified by silica gel chromatography using a 30-70% ethyl acetate in heptane gradient to yield ethyl 4-((5-((4-chlorophenyl)(thiazol-2-yl)methyl)-2-nitrophenyl)amino)piperidine-1-carboxylates an orange solid.

Step 5: ethyl 4-((2-amino-5-((4-chlorophenyl)(thiazol-2-yl)methyl)phenyl)amino)piperidine-1-carboxylate A solution of ethyl 4-((5-((4-chlorophenyl)(thiazol-2-yl)methyl)-2-nitrophenyl)amino)piperidine-1-carboxylate (5.9 g, 11.78 mmol) in THF (25 mL) and methanol (25 mL) in a 200 mL Parr flask was purged with nitrogen and Raney nickel (0.5 g, 8.52 mmol) was added. The mixture was hydrogenated at room temperature overnight on a Parr apparatus under 30 psi hydrogen pressure. The catalyst was removed by filtration over CELITE and the solvent was evaporated. The residue was stored under vacuum for 3 days, to yield ethyl 4-((2-amino-5-((4-chlorophenyl)(thiazol-2-yl)methyl)phenyl)amino)piperidine-1-carboxylate as a purple solid.

Step 6: ethyl 4-(6-((4-chlorophenyl)(thiazol-2-yl)methyl)-2-cyclopropyl-1H-benzo[d]imidazol-1-yl)piperidine-1-carboxylate A stirred solution of ethyl 4-((2-amino-5-((4-chlorophenyl)(thiazol-2-yl)methyl)phenyl)amino)piperidine-1-carboxylate (147 mg, 0.30 mmol) and cyclopropanecarboxaldehyde (31.59 mg, 0.30 mmol) in DMSO (1 mL) was kept at room temperature in the presence of air overnight. The reaction mixture was diluted with brine and extracted with ethyl acetate. The organic layer was concentrated to a brown oil and purified by chromatography on silica gel using a 10-50% ethyl acetate in heptane gradient followed by 5% methanol in dichloromethane as eluent to yield ethyl 4-(6-((4-chlorophenyl)(thiazol-2-yl)methyl)-2-cyclopropyl-1H-benzo[d]imidazol-1-yl)piperidine-1-carboxylates an orange oil. The ethyl 4-(6-((4-chlorophenyl)(thiazol-2-yl)methyl)-2-cyclopropyl-1H-benzo[d]imidazol-1-yl)piperidine-1-carboxylate solid was converted to the corresponding HCl salt with 1N HCl in diethyl ether. MS: 585.2 (M+H$^+$).

Example MP-9 ethyl 4-(6-((4-chlorophenyl)(thiazol-2-yl)methyl)-2-isobutyl-1H-benzo[d]imidazol-1-yl)piperidine-1-carboxylate

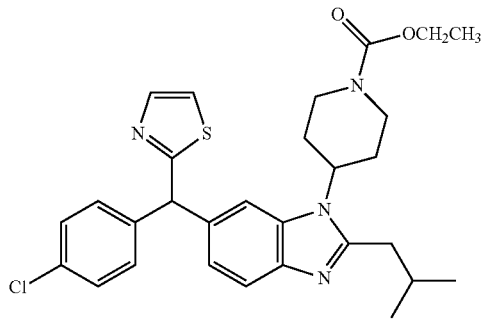 [SMILES: CCOC(=O)N1CCC(n2c(CC(C)C)nc3ccc(C(c4ccc(Cl)cc4)c4nccs4)cc32)CC1]

Ethyl 4-(6-((4-chlorophenyl)(thiazol-2-yl)methyl)-2-isobutyl-1H-benzo[d]imidazol-1-yl)piperidine-1-carboxylate was prepared according to the procedure as described in Example MP-8 above, substituting isovaleraldehyde for cyclopropanecarboxaldehyde in Step 6. MS: 537.0 (M+H$^+$).

Example MP-10 ethyl 6-((4-chlorophenyl)(thiazol-2-yl)methyl)-1-(1-(ethoxycarbonyl)piperidin-4-yl)-1H-benzo[d]imidazole-2-carboxylate

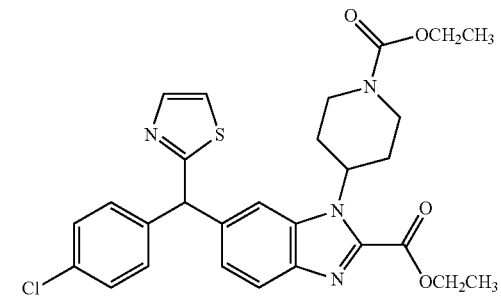 [SMILES: CCOC(=O)c1nc2ccc(C(c3ccc(Cl)cc3)c3nccs3)cc2n1C1CCN(C(=O)OCC)CC1]

Ethyl 6-((4-chlorophenyl)(thiazol-2-yl)methyl)-1-(1-(ethoxycarbonyl)piperidin-4-yl)-1H-benzo[d]imidazole-2-carboxylate was prepared according to the procedure as in Example MP-8 above, substituting ethyl glyoxalate for cyclopropanecarboxaldehyde in Step 6. MS: 553.2 (M+H$^+$).

Example MP-11 ethyl 4-(6-((4-chlorophenyl)(thiazol-2-yl)methyl)-2-(tetrahydrofuran-2-yl)-1H-benzo[d]imidazol-1-yl)piperidine-1-carboxylate

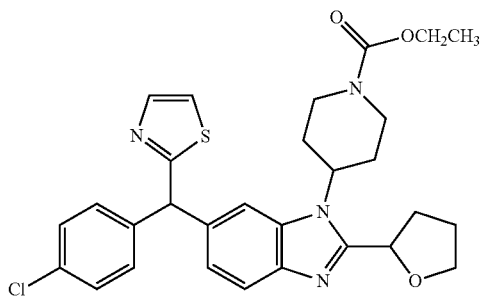 [SMILES: CCOC(=O)N1CCC(n2c(C3CCCO3)nc3ccc(C(c4ccc(Cl)cc4)c4nccs4)cc32)CC1]

Ethyl 4-(6-((4-chlorophenyl)(thiazol-2-yl)methyl)-2-(tetrahydrofuran-2-yl)-1H-benzo[d]imidazol-1-yl)piperidine-1-carboxylate was prepared according to the procedure as described in Example MP-8 above, substituting tetrahydrofuran-3-carboxaldehyde for cyclopropanecarboxaldehyde in Step 6. MS: 551.2 (M+H$^+$).

Example MP-12 ethyl 4-(6-((4-chlorophenyl)(thiazol-2-yl)methyl)-2-propyl-1H-benzo[d]imidazol-1-yl)piperidine-1-carboxylate

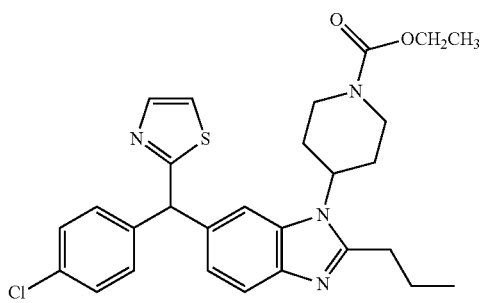 [SMILES: CCCc1nc2ccc(C(c3ccc(Cl)cc3)c3nccs3)cc2n1C1CCN(C(=O)OCC)CC1]

Ethyl 4-(6-((4-chlorophenyl)(thiazol-2-yl)methyl)-2-propyl-1H-benzo[d]imidazol-1-yl)piperidine-1-carboxylate was prepared according to the procedure as described Example MP-8 above, substituting butyraldehyde for cyclopropanecarboxaldehyde in Step 6. MS: 523.2 (M+H$^+$).

Example MP-13 ethyl 4-(6-((4-chlorophenyl)(thiazol-2-yl)methyl)-2-(tetrahydro-2H-pyran-4-yl)-1H-benzo[d]imidazol-1-yl)piperidine-1-carboxylate

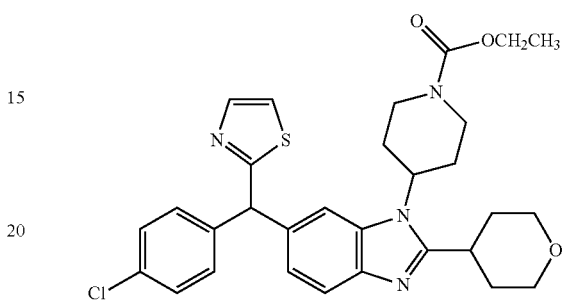

Ethyl 4-(6-((4-chlorophenyl)(thiazol-2-yl)methyl)-2-(tetrahydro-2H-pyran-4-yl)-1H-benzo[d]imidazol-1-yl)piperidine-1-carboxylate was prepared according to the procedure as described in Example MP-8 above, substituting tetrahydropyran-4-carboxaldehyde for cyclopropanecarboxaldehyde in Step 6. MS: 565.2 (M+H$^+$).

Example MP-14 ethyl 4-(2-(4-chlorophenyl)-6-((4-chlorophenyl)(thiazol-2-yl)methyl)-1H-benzo[d]imidazol-1-yl)piperidine-1-carboxylate

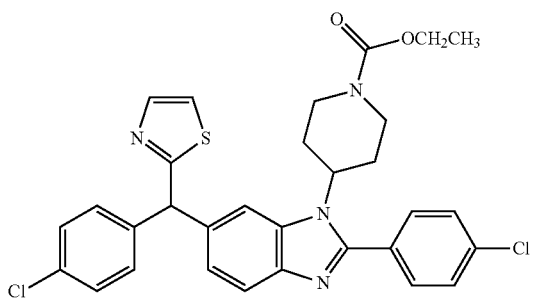 [SMILES: CCOC(=O)N1CCC(n2c(-c3ccc(Cl)cc3)nc3ccc(C(c4ccc(Cl)cc4)c4nccs4)cc32)CC1]

Ethyl 4-(2-(4-chlorophenyl)-6-((4-chlorophenyl)(thiazol-2-yl)methyl)-1H-benzo[d]imidazol-1-yl)piperidine-1-carboxylate was prepared according to the procedure as described in Example MP-8 above, substituting 4-chlorobenzaldehyde for cyclopropanecarboxaldehyde in Step 6. MS: 591.1 (M+H$^+$).

Example MP-15 ethyl 4-(6-((4-chlorophenyl)(thiazol-2-yl)methyl)-2-(thiazol-2-yl)-1H-benzo[d]imidazol-1-yl)piperidine-1-carboxylate

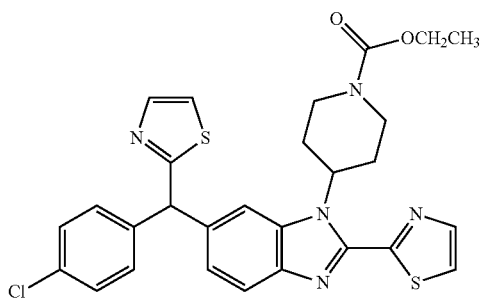 [SMILES: CCOC(=O)N1CCC(n2c(-c3nccs3)nc3ccc(C(c4ccc(Cl)cc4)c4nccs4)cc32)CC1]

Ethyl 4-(6-((4-chlorophenyl)(thiazol-2-yl)methyl)-2-(thiazol-2-yl)-1H-benzo[d]imidazol-1-yl)piperidine-1-carboxylate was prepared according to the procedure as described in Example MP-8 above, substituting 2-thiazolecarboxaldehyde for cyclopropanecarboxaldehyde in Step 6. MS: 564.0 (M+H$^+$).

Example MP-16 ethyl 4-(2-(1-(tert-butoxycarbonyl)azetidin-3-yl)-6-((4-chlorophenyl)(thiazol-2-yl)methyl)-1H-benzo[d]imidazol-1-yl)piperidine-1-carboxylate

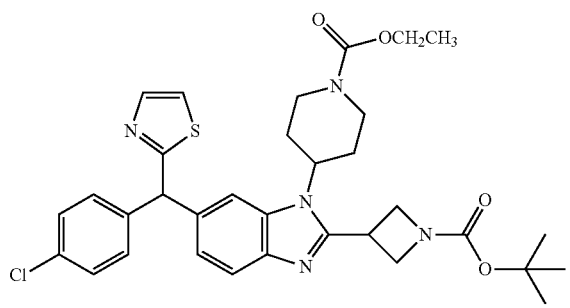 [SMILES: CCOC(=O)N1CCC(n2c(C3CN(C(=O)OC(C)(C)C)C3)nc3ccc(C(c4ccc(Cl)cc4)c4nccs4)cc32)CC1]

and ethyl 4-(2-(azetidin-3-yl)-6-((4-chlorophenyl)(thiazol-2-yl)methyl-1H-benzo[d]imidazol-1-yl)piperidine-1-carboxylate

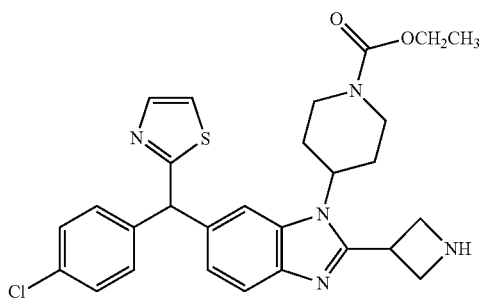 [SMILES: CCOC(=O)N1CCC(n2c(C3CNC3)nc3ccc(C(c4ccc(Cl)cc4)c4nccs4)cc32)CC1]

Step 1: ethyl 4-(2-(1-(tert-butoxycarbonyl)azetidin-3-yl)-6-((4-chlorophenyl)(thiazol-2-yl)methyl)-1H-benzo[d]imidazol-1-yl)piperidine-1-carboxylate Ethyl 4-(2-(1-(tert-butoxycarbonyl)azetidin-3-yl)-6-((4-chlorophenyl)(thiazol-2-yl)methyl)-1H-benzo[d]imidazol-1-yl)piperidine-1-carboxylate was prepared according to the procedure as described in Example MP-8 above, substituting 1-t-butoxycarbonyl-3-azetidinecarboxaldehyde for cyclopropanecarboxaldehyde in Step 6. MS: 636.0 (M+H$^+$).

Step 2: ethyl 4-(2-(azetidin-3-yl)-6-((4-chlorophenyl)(thiazol-2-yl)methyl)-1H-benzo[d]imidazol-1-yl)piperidine-1-carboxylate Ethyl 4-(2-(1-(tert-butoxycarbonyl)azetidin-3-yl)-6-((4-chlorophenyl)(thiazol-2-yl)methyl)-1H-benzo[d]imidazol-1-yl)piperidine-1-carboxylate (20 mg, 0.030 mmol) was dissolved in 1,4-dioxane (1 mL) and 4N HCl/1,4-dioxane (1 mL, 4 mmol) was added. The resulting solution was stirred for 4 hours at room temperature. The solvent was evaporated to yield ethyl 4-(2-(azetidin-3-yl)-6-((4-chlorophenyl)(thiazol-2-yl)methyl)-1H-benzo[d]imidazol-1-yl)piperidine-1-carboxylate as its corresponding HCl salt. MS: 536.2 (M+H$^+$).

Example MP-17

(2-(tert-butyl)-1-(1-(((trifluoromethyl)sulfonyl)piperidin-4-yl)-1H-benzo[d]imidazol-6-yl)bis(4-chlorophenyl)methanol

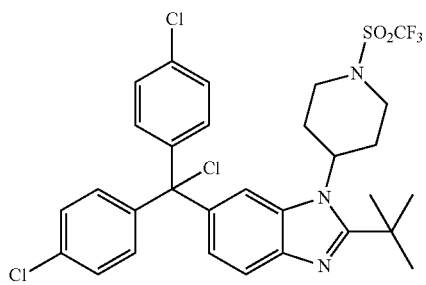

and 6-(bis(4-chlorophenyl)methyl)-2-(tert-butyl)-1-(1-(((trifluoromethyl)sulfonyl)piperidin-4-yl)-1H-benzo[d]imidazole

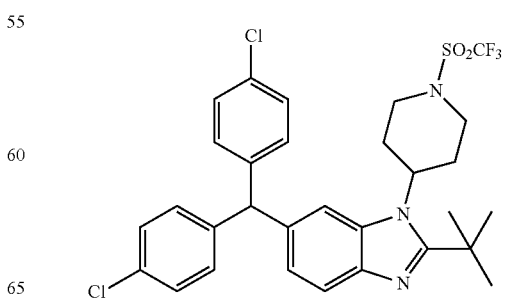

Step 1: N-(4-bromo-2-((1-((trifluoromethyl)sulfonyl)piperidin-4-yl)amino)phenyl)pivalamide A solution of 5-bromo-N1-(1-((trifluoromethyl)sulfonyl)piperidin-4-yl)benzene-1,2-diamine (362 mg, 0.9 mmol, prepared as described in Example YM-26), pivaloyl chloride (119 mg, 0.99 mmol), and 4-dimethylaminopyridine (121 mg, 0.99 mmol) in dichloromethane (5 mL) was stirred at room temperature overnight. The solution was diluted with saturated aqueous NaHCO$_3$ and the mixture was extracted with dichloromethane. The organic layer was concentrated to yield N-(4-bromo-2-((1-((trifluoromethyl)sulfonyl)piperidin-4-yl)amino)phenyl)pivalamide as an off-white solid, which was sufficiently pure to use in the next step.

Step 2: 6-bromo-2-(tert-butyl)-1-(1-((trifluoromethyl)sulfonyl)piperidin-4-yl)-1H-benzo[d]imidazole A solution of N-(4-bromo-2-((1-((trifluoromethyl)sulfonyl)piperidin-4-yl)amino)phenyl)pivalamide (426 mg, 0.876 mmol) in acetic acid (2 mL) was heated to reflux temperature for 20 hours and then stirred at room temperature for 40 hours. Water (1 mL) was added and the mixture heated to reflux temperature overnight. The solvent was evaporated and the resulting dark oil was quenched with saturated aqueous NaHCO$_3$. The aqueous mixture was extracted with dichloromethane and the organic layer was evaporated. The residue was purified by chromatography on silica gel eluting with a 0-40% ethyl acetate in dichloromethane gradient to yield 6-bromo-2-(tert-butyl)-1-(1-((trifluoromethyl)sulfonyl)piperidin-4-yl)-1H-benzo[d]imidazole.

Step 3: (2-(tert-butyl)-1-(1-((trifluoromethyl)sulfonyl)piperidin-4-yl)-1H-benzo[d]imidazol-6-yl)bis(4-chlorophenyl)methanol A solution of 6-bromo-2-(tert-butyl)-1-(1-((trifluoromethyl)sulfonyl)piperidin-4-yl)-1H-benzo[d]imidazole (128 mg, 0.27 mmol) and 4,4'-dichlorobenzophenone (68.6 mg, 0.27 mmol) in THF (5 mL) was cooled to −78° C. tert-Butyllithium (1.7M in pentane, 0.40 mL, 0.68 mmol) was added slowly by syringe. The reaction was stirred at −78° C. for 15 minutes and then allowed to warm to room temperature. The reaction mixture was stirred for 2 hours, quenched by addition of saturated aqueous NaHCO$_3$, and extracted with ethyl acetate. The organic layer was concentrated and the residue purified by chromatography on silica gel eluting with a 0-40% ethyl acetate in dichloromethane gradient to yield (2-(tert-butyl)-1-(1-((trifluoromethyl)sulfonyl)piperidin-4-yl)-1H-benzo[d]imidazol-6-yl)bis(4-chlorophenyl)methanol as a white solid. MS: 640.1 (M+H$^+$).

Step 4: 6-(bis(4-chlorophenyl)methyl)-2-(tert-butyl)-1-(1-((trifluoromethyl)sulfonyl)piperidin-4-yl)-1H-benzo[d]imidazole A solution of (2-(tert-butyl)-1-(1-((trifluoromethyl)sulfonyl)piperidin-4-yl)-1H-benzo[d]imidazol-6-yl)bis(4-chlorophenyl)methanol (26 mg, 0.041 mmol), boron trifluoride diethyl etherate (0.006 mL, 0.048 mmol), and triethylsilane (23.6 mg, 0.203 mmol) in dichloromethane (1 mL) was stirred at room temperature for 2 hours. The solution was diluted with saturated aqueous NaHCO$_3$ and the mixture was extracted with dichloromethane. The organic layer was concentrated and the residue purified by chromatography on silica gel eluting with a 0-40% ethyl acetate in dichloromethane gradient to yield 6-(bis(4-chlorophenyl)methyl)-2-(tert-butyl)-1-(1-((trifluoromethyl)sulfonyl)piperidin-4-yl)-1H-benzo[d]imidazole as a colorless oil. MS: 624.2 (M+H$^+$). The oil was converted to the corresponding HCl salt by reacting with 1N HCl in diethyl ether to yield the HCl salt as a white powder.

Example MP-18 ethyl 4-(2-(tert-butyl)-6-((4-chlorophenyl)(thiazol-2-yl)methyl)-1H-benzo[d]imidazol-1-yl)piperidine-1-carboxylate

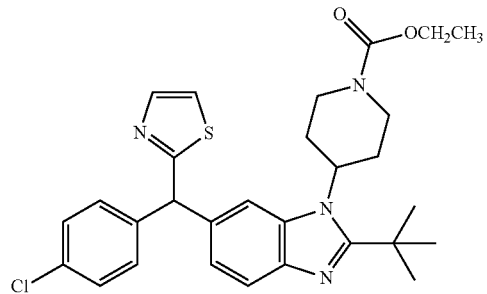 [SMILES: CCOC(=O)N1CCC(n2c(C(C)(C)C)nc3ccc(C(c4ccc(Cl)cc4)c4nccs4)cc32)CC1]

Ethyl 4-(2-(tert-butyl)-6-((4-chlorophenyl)(thiazol-2-yl)methyl)-1H-benzo[d]imidazol-1-yl)piperidine-1-carboxylate was prepared according to the procedure as described in Example MP-8 above, substituting pivaldehyde for cyclopropanecarboxaldehyde in Step 6. MS: 537.2 (M+H$^+$).

Example MP-19 bis(4-chlorophenyl)(2-(hydroxymethyl)-1-(1-((trifluoromethyl)sulfonyl)piperidin-4-yl)-1H-benzo[d]imidazol-6-yl)methanol

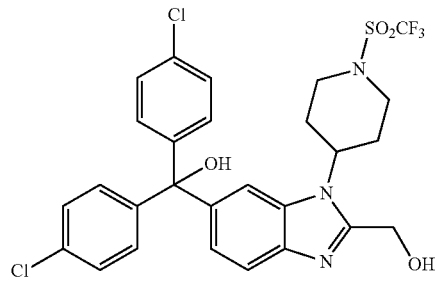

Step 1: 6-bromo-2-(((tert-butyldimethylsilyl)oxy)methyl)-1-(1-((trifluoromethyl)sulfonyl)piperidin-4-yl)-1H-benzo[d]imidazole A solution of 5-bromo-N1-(1-((trifluoromethyl)sulfonyl)piperidin-4-yl)benzene-1,2-diamine (484 mg, 1.20 mmol, prepared as described in Example YM-26) and tert-butyldimethylsilyloxyacetaldehyde (0.255 mL, 1.20 mmol) in DMSO (3 mL) was stirred at room temperature overnight open to air. The solution was diluted with brine and the mixture was extracted with ethyl acetate. The organic layer was concentrated and the residue purified by chromatography on silica gel eluting with a 0-25% ethyl acetate in dichloromethane gradient to yield 6-bromo-2-(((tert-butyldimethylsilyl)oxy)methyl)-1-(1-((trifluoromethyl)sulfonyl)piperidin-4-yl)-1H-benzo[d]imidazole as an off-white solid.

Step 2: (2-(((tert-butyldimethylsilyl)oxy)methyl)-1-(1-((trifluoromethyl)sulfonyl)piperidin-4-yl)-1H-benzo[d]imidazol-6-yl)bis(4-chlorophenyl)methanol A solution of 6-bromo-2-(((tert-butyldimethylsilyl)oxy)methyl)-1-(1-((trifluoromethyl)sulfonyl)piperidin-4-yl)-1H-benzo[d]imidazole (195 mg, 0.35 mmol) and 4,4'-dichlorobenzophenone (88.0 mg, 0.35 mmol) in THF (3 mL) was cooled to −78° C. tert-Butyllithium (1.7M in pentane, 0.53 mL, 0.88 mmol) was added slowly by syringe. The reaction was stirred at −78° C. for 15 minutes and then allowed to warm to room temperature. The reaction mixture was stirred for 2 hours, quenched by addition of saturated aqueous NaHCO$_3$, and extracted with ethyl acetate. The organic layer was concentrated and the residue purified by chromatography on silica gel eluting with a 0-40% ethyl acetate in dichloromethane gradient to yield (2-(((tert-butyldimethylsilyl)oxy)methyl)-1-(1-((trifluoromethyl)sulfonyl)piperidin-4-yl)-1H-benzo[d]imidazol-6-yl)bis(4-chlorophenyl)methanol as a yellow oil.

Step 3: bis(4-chlorophenyl)(2-(hydroxymethyl)-1-(1-((trifluoromethyl)sulfonyl)piperidin-4-yl)-1H-benzo[d]imidazol-6-yl)methanol A solution of (2-(((tert-butyldimethylsilyl)oxy)methyl)-1-(1-((trifluoromethyl)sulfonyl)piperidin-4-yl)-1H-benzo[d]imidazol-6-yl)bis(4-chlorophenyl)methanol (50 mg, 0.069 mmol), triethylsilane (39.9 mg, 0.343 mmol), and boron trifluoride diethyl etherate (0.017 mL, 0.137 mmol) in dichloromethane (2 mL) was stirred at room temperature overnight. The reaction was quenched with saturated aqueous NaHCO$_3$ and the mixture was extracted with dichloromethane. The organic layer was concentrated and the residue purified by chromatography on silica gel eluting with a 0-40% ethyl acetate in dichloromethane gradient to yield bis(4-chlorophenyl)(2-(hydroxymethyl)-1-(1-((trifluoromethyl)sulfonyl)piperidin-4-yl)-1H-benzo[d]imidazol-6-yl)methanol as a white solid. MS: 614.1 (M+H$^+$).

Example DL-1

6-(bis(4-chlorophenyl)methyl)-2-cyclobutyl-1-((1-((trifluoromethyl)sulfonyl)piperidin-4-yl)methyl)-1H-benzo[d]imidazole

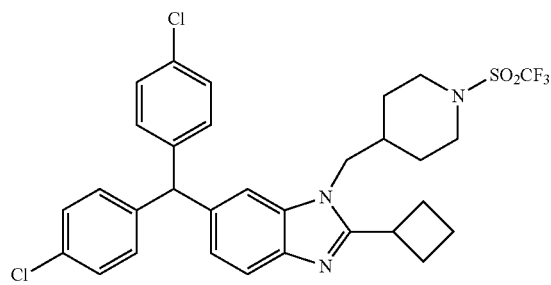

Step 1: methyl 2,2-bis(4-chlorophenyl)acetate

A solution of 2,2-bis(4-chlorophenyl)acetic acid (4 g, 13.9 mmol) and H$_2$SO$_4$ (0.37 mL, 7.0 mmol) in MeOH (20 mL) was heated at reflux temperature overnight. The solution was concentrated, water added to the residue, and the mixture extracted with ethyl ether. The organic layer was dried over Na$_2$SO$_4$ and concentrated in vacuo to yield methyl 2,2-bis(4-chlorophenyl)acetate as a clear oil. The residue was purified by chromatography on silica gel eluting with a 0-70% dichloromethane:heptane gradient to yield methyl 2,2-bis(4-chlorophenyl)acetate as a clear oil, which overtime became a white solid.

Step 2: methyl 2,2-bis(4-chlorophenyl)-2-(3-fluoro-4-nitrophenyl)acetate

To a solution of methyl 2,2-bis(4-chlorophenyl)acetate (1.92 g, 6.51 mmol) and 2,4-difluoro-1-nitrobenzene (0.76 mL, 6.83 mmol) in THF (40 mL) at −37° C. to −32° C. was added t-BuOK (1M in THF, 7.2 mL, 7.2 mmol) over 10 minutes. The reaction was allowed to warm slowly to room temperature and then stirred overnight. To the reaction was added ethyl acetate and the resulting organic mixture was washed with aq NH$_4$Cl and brine. The organic layer was dried over MgSO$_4$ and concentrated in vacuo to yield a red oil. The residue was purified by silica gel chromatography with a 0-70% dichloromethane:heptane gradient as eluent to yield methyl 2,2-bis(4-chlorophenyl)-2-(3-fluoro-4-nitrophenyl)acetate as a pale yellow oil.

Step 3: methyl 2,2-bis(4-chlorophenyl)-2-(4-nitro-3-(((1-((trifluoromethyl)sulfonyl)piperidin-4-yl)methyl)amino)phenyl)acetate To a solution of methyl 2,2-bis(4-chlorophenyl)-2-(3-fluoro-4-nitrophenyl)acetate (0.45 g, 1.036 mmol) and diisopropylethylamine (0.446 mL, 2.591 mmol) in CH$_3$CN (2.25 mL) at room temperature was added 4-aminomethyl-1-trifluoromethylsulfonylpiperidine hydrochloride (396.9 mg, 1.24 mmol). The resulting reaction mixture was heated to reflux temperature for 4 hours and the solvent was removed in vacuo. The residue was purified by silica gel chromatography using a 50-100% dichloromethane:heptane gradient as eluent to yield methyl 2,2-bis(4-chlorophenyl)-2-(4-nitro-3-(((1-((trifluoromethyl)sulfonyl)piperidin-4-yl)methyl)amino)phenyl)acetate as a yellow solid.

Step 4: methyl 2-(4-amino-3-(((1-((trifluoromethyl)sulfonyl)piperidin-4-yl)methyl)amino)phenyl)-2,2-bis(4-chlorophenyl)acetate To a solution of methyl 2,2-bis(4-chlorophenyl)-2-(4-nitro-3-(((1-((trifluoromethyl)sulfonyl)piperidin-4-yl)methyl)amino)phenyl)acetate (0.62 g, 0.94 mmol) in MeOH (200 mL) was added Raney nickel catalyst (200 mg, 3.41 mmol) and the mixture was placed under 40 psi hydrogen and left overnight. The reaction mixture was filtered through CELITE and the solvent evaporated in vacuo to yield methyl 2-(4-amino-3-(((1-((trifluoromethyl)sulfonyl)piperidin-4-yl)methyl)amino)phenyl)-2,2-bis(4-chlorophenyl)acetate as an off-white solid.

Step 5: methyl 2,2-bis(4-chlorophenyl)-2-(2-cyclobutyl-1-((1-((trifluoromethyl)sulfonyl)piperidin-4-yl)methyl)-1H-benzo[d]imidazol-6-yl)acetate A rapidly stirred solution of methyl 2-(4-amino-3-(((1-((trifluoromethyl)sulfonyl)piperidin-4-yl)methyl)amino)

phenyl)-2,2-bis(4-chlorophenyl)acetate (0.19 g, 0.30 mmol) and cyclobutanecarboxaldehyde (0.052 g, 0.60 mmol) in DMSO (1 mL) was kept at room temperature in the presence of air for 4 days. The reaction mixture was purified by silica gel chromatography using a 0-2% methanol:dichloromethane gradient as eluent to yield methyl 2,2-bis(4-chlorophenyl)-2-(2-cyclobutyl-1-((1-((trifluoromethyl)sulfonyl)piperidin-4-yl)methyl)-1H-benzo[d]imidazol-6-yl)acetate.

Step 6: 2,2-bis(4-chlorophenyl)-2-(2-cyclobutyl-1-((1-((trifluoromethyl)sulfonyl)piperidin-4-yl)methyl)-1H-benzo[d]imidazol-6-yl)acetic acid A solution of methyl 2,2-bis(4-chlorophenyl)-2-(2-cyclobutyl-1-((1-((trifluoromethyl)sulfonyl)piperidin-4-yl)methyl)-1H-benzo[d]imidazol-6-yl)acetate (180 mg, 0.26 mmol) in 3N NaOH aqueous solution (2 mL, 6 mmol) and methanol (8 mL) was heated at 50° C. The reaction was cooled to room temperature and 1N HCl aqueous solution was added (8 mL). The mixture was extracted with EtOAc and the organic solution was washed with brine and evaporated in vacuo to yield 2,2-bis(4-chlorophenyl)-2-(2-cyclobutyl-1-((1-((trifluoromethyl)sulfonyl)piperidin-4-yl)methyl)-1H-benzo[d]imidazol-6-yl)acetic acid as a pale green oil.

Step 7: 6-(bis(4-chlorophenyl)methyl)-2-cyclobutyl-1-((1-((trifluoromethyl)sulfonyl)piperidin-4-yl)methyl)-1H-benzo[d]imidazole A solution of 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetic acid (360 mg, 0.53 mmol) and DBU (0.2 mL, 1.34 mmol) in toluene (10 mL) was heated at 90° C. overnight. After evaporation of the solvent, the residue was purified by reverse phase HPLC and the fractions containing the product were lyophilized to yield 6-(bis(4-chlorophenyl)methyl)-2-cyclobutyl-1-((1-((trifluoromethyl)sulfonyl)piperidin-4-yl)methyl)-1H-benzo[d]imidazole trifluoroacetate salt as a white solid. MS: 636.2 (M+H$^+$); $^1$H NMR (400 MHz, CDCl$_3$) δ: 7.89 (d, J=8.6 Hz, 1H), 7.33-7.28 (m, 5H), 6.98 (br d, J=8.3 Hz, 4H), 6.96 (br s, 1H), 5.68 (s, 1H), 4.19-3.95 (m, 4H), 3.81 (td, J=8.7, 17.7 Hz, 1H), 2.92 (br t, J=12.7, 2H), 2.86-2.74 (m, 2H), 2.52 (d, J=8.6 Hz, 2H), 2.29-2.19 (m, 1H), 2.19-2.10 (m, 1H), 1.95-1.83 (m, 1H), 1.66 (br d, J=12.5 Hz, 2H), 1.44-1.28 (m, 2H).

Example DL-2

6-(bis(4-chlorophenyl)methyl)-2-cyclopropyl-1-(4-(trifluoromethyl)phenethyl)-1H-benzo[d]imidazole

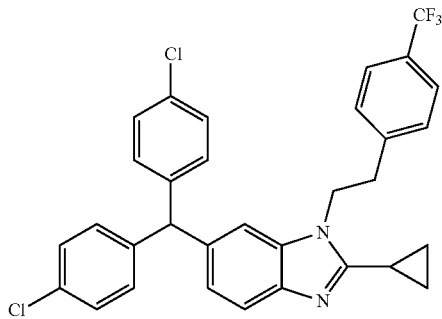 [SMILES: FC(F)(F)c1ccc(CCn2c(C3CC3)nc3ccc(C(c4ccc(Cl)cc4)c4ccc(Cl)cc4)cc32)cc1]

Step 1: methyl 2-(3-chloro-4-nitrophenyl)-2,2-bis(4-chlorophenyl)acetate

To a solution of compound methyl 2,2-bis(4-chlorophenyl)acetate (5.06 g, 17.14 mmol), prepared as described in Example DL-1, and 2-chloro-4-fluoro-1-nitrobenzene (3.16 g, 18.00 mmol) in THF (100 mL) at −45° C. to −40° C. was added t-BuOK (1M in THF, 18.86 mL, 18.86 mmol) over 5 minutes. The reaction was allowed to warm slowly to room temperature and then stirred overnight. To the reaction was added ethyl acetate and the resulting organic mixture was washed with aq NH$_4$Cl and brine. The organic layer was dried over MgSO$_4$ and concentrated in vacuo to yield a red oil. The residue was purified by silica gel chromatography using a 25-60% dichloromethane:heptane gradient as eluent to yield methyl 2-(3-chloro-4-nitrophenyl)-2,2-bis(4-chlorophenyl)acetate as a clear viscous oil.

Step 2: 5-(bis(4-chlorophenyl)methyl)-2-nitro-N-(4-(trifluoromethyl)phenethyl)aniline To a solution of methyl 2-(3-chloro-4-nitrophenyl)-2,2-bis(4-chlorophenyl)acetate (600 mg, 1.33 mmol) and 4-trifluoromethylphenethylamine (626 mg, 2.66 mmol) in 1,4-dioxane (3 mL) was added diisopropylethylamine (0.574 mL, 3.33 mmol) and DBU (0.497 mL, 3.33 mmol). The resulting reaction mixture was heated under argon at 95° C. for 4 days. After evaporation of the solvent, ethyl acetate was added to the residue and the organic mixture was washed with water, aqueous NaHCO$_3$, and brine. The organic layer was evaporated in vacuo to yield a yellow oil. The residue was purified by silica gel chromatography to yield 5-(bis(4-chlorophenyl)methyl)-2-nitro-N-(4-(trifluoromethyl)phenethyl)aniline as a yellow oil.

Step 3: 5-(bis(4-chlorophenyl)methyl)-N1-(4-(trifluoromethyl)phenethyl)benzene-1,2-diamine To a solution of 5-(bis(4-chlorophenyl)methyl)-2-nitro-N-(4-(trifluoromethyl)phenethyl)aniline (530 mg, 0.97 mmol) in MeOH (200 mL) was added 5% Pd/C sulfide (100 mg) and the mixture was placed under 60 psi hydrogen at room temperature for 24 hours. The reaction mixture was filtered through CELITE and the solvent evaporated in vacuo to yield 5-(bis(4-chlorophenyl)methyl)-N1-(4-(trifluoromethyl)phenethyl)benzene-1,2-diamine as a dark solid.

Step 4: 6-(bis(4-chlorophenyl)methyl)-2-cyclopropyl-1-(4-(trifluoromethyl)phenethyl)-1H-benzo[d]imidazole A rapidly stirred solution of 5-(bis(4-chlorophenyl)methyl)-N1-(4-(trifluoromethyl)phenethyl)benzene-1,2-diamine (440 mg, 0.85 mmol) and cyclopropanecarboxaldehyde (0.13 mL, 1.71 mmol) in DMSO (2 mL) was kept at room temperature in the presence of air for 3 days. The reaction mixture was purified by reverse phase HPLC and the fractions containing the product were lyophilized to yield 0.24 g of compound 2 trifluoroacetate salt as an off-white solid. The free base of 6-(bis(4-chlorophenyl)methyl)-2-cyclopropyl-1-(4-(trifluoromethyl)phenethyl)-1H-benzo[d]imidazole was prepared by partitioning the solid between ethyl acetate and aqueous NaHCO$_3$, separating the organic layer, and removing the solvent in vacuo. The free base was purified by silica gel chromatography to yield 6-(bis(4-chlorophenyl)methyl)-2-cyclopropyl-1-(4-(trifluoromethyl)phenethyl)-1H-benzo[d]imidazole as a clear oil. Addition of 0.30 mL 1N HCl in Et$_2$O and evaporation under vacuum yielded 6-(bis(4-chlorophenyl)methyl)-2-cyclopropyl-1-(4-(trifluoromethyl)phenethyl)-1H-benzo[d]imidazole as its corresponding HCl salt. MS: 565.2 (M+H$^+$); $^1$H NMR (400 MHz, DMSO-d$_6$) δ: 7.66-7.56 (m, 3H), 7.51 (s, 1H), 7.42 (d, J=8.6 Hz, 4H), 7.36 (br d, J=7.6 Hz, 2H), 7.23 (br d, J=8.6 Hz, 1H), 7.11 (d, J=8.6 Hz, 4H), 5.83 (s, 1H), 4.77 (br t, J=6.6 Hz, 2H), 3.20 (br t, J=6.6 Hz, 2H), 2.48-2.41 (m, 1H), 1.36-1.22 (m, 4H).

Example DL-3

6-(bis(4-chlorophenyl)methyl)-2-ethyl-1-((1-((trifluoromethyl)sulfonyl)piperidin-4-yl)methyl)-1H-benzo[d]imidazole

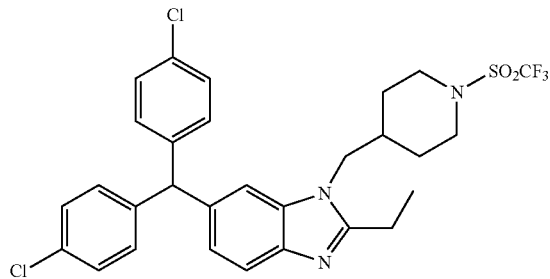

6-(Bis(4-chlorophenyl)methyl)-2-ethyl-1-((1-((trifluoromethyl)sulfonyl)piperidin-4-yl)methyl)-1H-benzo[d]imidazole was prepared according to the procedure as described in Example DL-1 above substituting propionaldehyde for cyclobutanecarboxaldehyde in Step 5. MS: 609.9 (M+H$^+$); $^1$H NMR (400 MHz, DMSO-d$_6$) δ: 7.79 (s, 1H), 7.74 (d, J=8.6 Hz, 1H), 7.43-7.38 (m, 4H), 7.31 (d, J=8.1 Hz, 1H), 7.17 (d, J=8.6 Hz, 4H), 5.88 (s, 1H), 4.34 (br d, J=7.3 Hz, 2H), 3.79 (br d, J=13.2 Hz, 2H), 3.18 (q, J=7.5 Hz, 2H), 3.06 (br t, J=12.6, 2H), 2.12-1.99 (m, 1H), 1.64 (br d, J=11.5 Hz, 2H), 1.42 (t, J=7.5 Hz, 3H), 1.35 (br d, J=11.2 Hz, 2H).

Example DL-4

2-((1-(3-chlorophenethyl)-2-cyclopropyl-1H-benzo[d]imidazol-6-yl)(4-chlorophenyl)methyl)thiazole

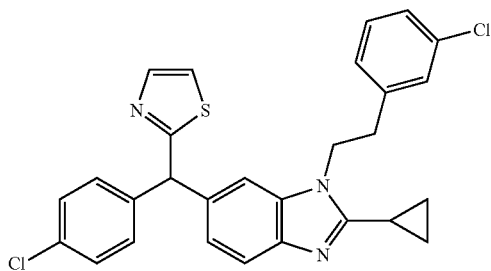 [SMILES: Clc1ccc(C(c2ccc3nc(C4CC4)n(CCc4cccc(Cl)c4)c3c2)c2nccs2)cc1]

Step 1:
5-chloro-N-(3-chlorophenethyl)-2-nitroaniline

To a solution of 2,4-dichloronitrobenzene (6.43 g, 32.49 mmol) and m-chlorophenethylamine (5.73 g, 35.73 mmol) in acetonitrile (15 mL) was added a solution of triethylamine (5.418 mL, 38.98 mmol) in acetonitrile (15 mL). The reaction mixture was stirred at room temperature overnight, heated to 50° C. for 24 hours, and then heated at reflux temperature for 48 hours. The solvent was evaporated, triethylamine (5 mL) in acetonitrile (10 mL) was added to the residue, and the reaction mixture heated at reflux temperature for another 2 hours. Water was added (20 mL), the resulting mixture stirred for 30 minutes, and 5-chloro-N-(3-chlorophenethyl)-2-nitroaniline was isolated by filtrations an orange solid.

Step 2: 2-(3-((3-chlorophenethyl)amino)-4-nitrophenyl)-2-(4-chlorophenyl)acetonitrile To a stirred solution of 4-chlorophenylacetonitrile (4.34 g, 27.50 mmol) in THF (40 mL) cooled to 0° C. was added t-BuOK (1M in t-BuOH, 37.50 mL, 37.50 mmol). After 10 minutes 5-chloro-N-(3-chlorophenethyl)-2-nitroaniline (7.78 g, 25.00 mmol) was added to the reaction mixture. The reaction mixture was allowed to warm to room temperature and then stirred overnight. To the thick dark solution was added THF (20 mL), 4-chlorophenylacetonitrile (0.90 g), and isopropyl alcohol (5 mL). 2N HCl (25 mL) was added and the mixture extracted with ethyl acetate. The organic layer was washed with brine, dried over MgSO$_4$, and evaporated in vacuo to yield a reddish oil. The residue was purified by silica gel chromatography using a 0-80% dichloromethane:heptane gradient as eluent to yield 2-(3-((3-chlorophenethyl)amino)-4-nitrophenyl)-2-(4-chlorophenyl)acetonitrile.

Step 3: 2-(3-((3-chlorophenethyl)amino)-4-nitrophenyl)-2-(4-chlorophenyl)ethanethioamide To a solution of 2-(3-((3-chlorophenethyl)amino)-4-nitrophenyl)-2-(4-chlorophenyl)acetonitrile (3.54 g, 8.30 mmol) in EtOH (90 mL) was added phosphorus pentasulfide (7.38 g, 16.61 mmol) and the reaction mixture was heated to reflux temperature for 24 hours. An additional 2.9 g of phosphorus pentasulfide was added and the resulting mixture was heated to reflux temperature overnight. The reaction mixture was poured into ice water and extracted with ethyl acetate. The organic layer was washed with water, brine, and dried over MgSO$_4$. The solvent was removed in vacuo and the residue was purified by silica gel chromatography using a 50-100% dichloromethane:heptane gradient as eluent to yield 2-(3-((3-chlorophenethyl)amino)-4-nitrophenyl)-2-(4-chlorophenyl)ethanethioamide as a red amorphous solid.

Step 4: N-(3-chlorophenethyl)-5-((4-chlorophenyl)(thiazol-2-yl)methyl)-2-nitroaniline To a solution of 2-(3-((3-chlorophenethyl)amino)-4-nitrophenyl)-2-(4-chlorophenyl)ethanethioamide (3.45 g, 7.49 mmol) in acetic acid (40 mL) was added water (1.5 mL) and bromoacetaldehyde diethylacetal (4.65 mL, 29.98 mmol). The reaction mixture was heated to 100° C. for 30 minutes and then poured into water (200 mL) and the resulting mixture was extracted with ethyl ether. The organic layer was washed with water (4×), saturated NaHCO$_3$, and brine and then dried over MgSO$_4$. Removal of the solvent in vacuo to a residue, which was purified by silica gel chromatography using a 50-100% dichloromethane:heptane gradient to yield N-(3-chlorophenethyl)-5-((4-chlorophenyl)(thiazol-2-yl)methyl)-2-nitroanilines a red oil.

Step 5: N1-(3-chlorophenethyl)-5-((4-chlorophenyl)(thiazol-2-yl)methyl)benzene-1,2-diamine To a 10 mL graduated cylinder was added 8 mL of Raney nickel (50% slurry in water). The catalyst was washed twice with EtOH and the solvent decanted. The catalyst was washed into a hydrogenation flask with ethyl alcohol (60 mL) under an argon atmosphere and additional ethyl alcohol (48 mL) was added. N-(3-chlorophenethyl)-5-((4-chlorophenyl)(thiazol-2-yl)methyl)-2-nitroaniline (2.61 g, 5.39 mmol) dissolved in THF (24 mL) was added to flask and the reaction mixture was placed under a hydrogen atmosphere for 72 hours. The catalyst was filtered off and the filtrate was evaporated in vacuo to yield a residue. Purification by silica gel chromatography using a 0-2% 1:1 MeOH:DCM/DCM gradient yielded N1-(3-chlorophenethyl)-5-((4-chlorophenyl)(thiazol-2-yl)methyl)benzene-1,2-diamine as a light red oil.

Step 6: 2-((1-(3-chlorophenethyl)-2-cyclopropyl-1H-benzo[d]imidazol-6-yl)(4-chlorophenyl)methyl)thiazole A rapidly stirred solution of N1-(3-chlorophenethyl)-5-((4-chlorophenyl)(thiazol-2-yl)methyl)benzene-1,2-diamine (100 mg, 0.22 mmol) and cyclopropanecarboxaldehyde (0.034 mL, 0.44 mmol) in DMSO (1 mL) was kept at room temperature in the presence of air for 24 hours. The reaction mixture was purified by reverse phase HPLC and the fractions containing the product were lyophilized to yield 2-((1-(3-chlorophenethyl)-2-cyclopropyl-1H-benzo[d]imidazol-6-yl)(4-chlorophenyl)methyl)thiazoletrifluoroacetate salt as a white solid. MS: 504.0 (M+H$^+$); $^1$H NMR (400 MHz, DMSO-d$_6$) δ: 7.95-7.81 (m, 1H), 7.79-7.71 (m, 2H), 7.65 (br d, J=8.6 Hz, 1H), 7.49-7.38 (m, 3H), 7.36-7.29 (m, 3H), 7.25 (br d, J=3.9 Hz, 2H), 7.13-7.06 (m, 1H), 6.18 (s, 1H), 4.74 (br t, J=6.7 Hz, 2H), 3.13 (br t, J=6.8 Hz, 2H), 2.48-2.41 (m, 1H), 1.35-1.18 (m, 4H).

Example DL-5

6-(bis(4-chlorophenyl)methyl)-1-(3-chlorophenethyl)-2-ethyl-1H-benzo[d]imidazole

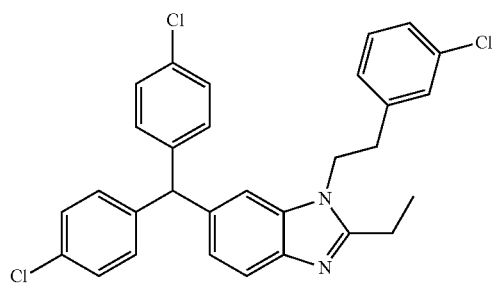 [SMILES: CCc1nc2ccc(C(c3ccc(Cl)cc3)c3ccc(Cl)cc3)cc2n1CCc1cccc(Cl)c1]

Step 1: methyl 2-(3-((3-chlorophenethyl)amino)-4-nitrophenyl)-2,2-bis(4-chlorophenyl)acetate To a solution of methyl 2-(3-chloro-4-nitrophenyl)-2,2-bis(4-chlorophenyl)acetate (400 mg, 0.89 mmol), prepared as described in Example DL-2 above, and potassium fluoride (258 mg, 4.44 mmol) in acetonitrile (4 mL) was added m-chlorophenethylamine (0.19 mL, 1.33 mmol) and diisopropylethylamine (0.31 mL, 1.78 mmol) and the resulting mixture placed under an argon atmosphere. The reaction mixture was heated to reflux temperature for 72 hours. An additional 0.191 mL of m-chlorophenethylamine was added and the reaction mixture was heated to reflux temperature for an additional 48 hours. The solvent was evaporated in vacuo, water was added to the residue, and the mixture was extracted with ethyl acetate. The organic layer was washed with water and brine and then dried over Na$_2$SO$_4$. Evaporation of the solvent in vacuo yielded a residue as a reddish oil, which was purified by silica gel chromatography using a 30-70% dichloromethane:heptane gradient to yield methyl 2-(3-((3-chlorophenethyl)amino)-4-nitrophenyl)-2,2-bis(4-chlorophenyl)acetate as a yellow solid.

Step 2: methyl 2-(4-amino-3-((3-chlorophenethyl)amino)phenyl)-2,2-bis(4-chlorophenyl)acetate To a solution of methyl 2-(3-((3-chlorophenethyl)amino)-4-nitrophenyl)-2,2-bis(4-chlorophenyl)acetate (200 mg, 0.35 mmol) in MeOH (100 mL) was added Raney nickel catalyst (100 mg, 1.70 mmol) and the mixture was placed under 35 psi hydrogen and left overnight. The reaction mixture was filtered through CELITE and the solvent evaporated in vacuo to yield methyl 2-(4-amino-3-((3-chlorophenethyl)amino)phenyl)-2,2-bis(4-chlorophenyl)acetate.

Step 3: methyl 2-(1-(3-chlorophenethyl)-2-ethyl-1H-benzo[d]imidazol-6-yl)-2,2-bis(4-chlorophenyl)acetate A solution of methyl 2-(4-amino-3-((3-chlorophenethyl)amino)phenyl)-2,2-bis(4-chlorophenyl)acetate (200 mg, 0.37 mmol) and propionaldehyde (0.055 mL, 0.74 mmol) in DMSO (2 mL) was stirred at room temperature in the presence of air for 3 days. The reaction mixture was purified by reverse phase HPLC and lyophilized to yield methyl 2-(1-(3-chlorophenethyl)-2-ethyl-1H-benzo[d]imidazol-6-yl)-2,2-bis(4-chlorophenyl)acetate as a white solid.

Step 4: 2-(1-(3-chlorophenethyl)-2-ethyl-1H-benzo[d]imidazol-6-yl)-2,2-bis(4-chlorophenyl)acetic acid A solution of methyl 2-(1-(3-chlorophenethyl)-2-ethyl-1H-benzo[d]imidazol-6-yl)-2,2-bis(4-chlorophenyl)acetate (120 mg, 0.21 mmol) in 3N NaOH aqueous solution (2.04 mL, 6.13 mmol) and methanol (8 mL) was heated at 45° C. overnight. The solvent was removed in vacuo and then water and 6 mL 1N HCl was added. The mixture was extracted with ethyl acetate and the organic layer was dried over MgSO$_4$ and evaporated in vacuo to yield 2-(1-(3-chlorophenethyl)-2-ethyl-1H-benzo[d]imidazol-6-yl)-2,2-bis(4-chlorophenyl)acetic acid as a yellow oil.

Step 5: 6-(bis(4-chlorophenyl)methyl)-1-(3-chlorophenethyl)-2-ethyl-1H-benzo[d]imidazole A solution of 2-(1-(3-chlorophenethyl)-2-ethyl-1H-benzo[d]imidazol-6-yl)-2,2-bis(4-chlorophenyl)acetic acid (100 mg, 0.18 mmol) and DBU (0.11 mL, 0.71 mmol) in toluene (10 mL) was heated at 90° C. overnight under argon. An additional 0.104 mL of DBU was added and the reaction mixture was heated at 90° C. for another 3 hours. After evaporation of the solvent, the residue was purified by reverse phase HPLC and the fractions containing the product were lyophilized to yield 6-(bis(4-chlorophenyl)methyl)-1-(3-chlorophenethyl)-2-ethyl-1H-benzo[d]imidazoletrifluoroacetate salt as a white solid. MS: 520.8 (M+H⁺); ¹H NMR (400 MHz, CDCl₃) δ: 7.81 (d, J=8.6 Hz, 1H), 7.37-7.29 (m, 5H), 7.25-7.20 (m, 1H), 7.20-7.15 (m, 1H), 7.01 (t, J=1.8 Hz, 1H), 6.99-6.93 (m, 4H), 6.89 (s, 1H), 6.67 (d, J=7.6 Hz, 1H), 5.63 (s, 1H), 4.39 (t, J=6.8 Hz, 2H), 3.04 (t, J=6.6 Hz, 2H), 2.93 (q, J=7.6, 2H), 1.41 (t, J=7.3 Hz, 3H).

Example DL-6 bis(4-chlorophenyl)(2-cyclopropyl-1-(1-(((trifluoromethyl)sulfonyl)piperidin-4-yl)-1H-benzo[d]imidazol-6-yl)methanol

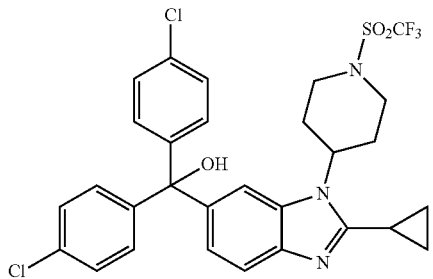

To a solution of 6-(bis(4-chlorophenyl)methyl)-2-cyclopropyl-1-(1-(((trifluoromethyl)sulfonyl)piperidin-4-yl)-1H-benzo[d]imidazole hydrochloride salt (130 mg, 0.202 mmol) in DMSO (6 mL) was added 3N NaOH (0.4 mL) and the reaction mixture was stirred in air for 72 hours. Water was added and the mixture was extracted with ethyl acetate. The organic layer was evaporated in vacuo, the residue purified by reverse phase HPLC, and fractions containing the product were lyophilized to yield bis(4-chlorophenyl)(2-cyclopropyl-1-(1-(((trifluoromethyl)sulfonyl)piperidin-4-yl)-1H-benzo[d]imidazol-6-yl)methanol as a white solid. MS: 624.1 (M+H⁺); ¹H NMR (400 MHz, CDCl₃) δ: 7.84 (s, 1H), 7.74 (d, J=8.6 Hz, 1H), 7.32-7.28 (m, 4H), 7.26-7.22 (m, 1H), 7.19-7.14 (m, 4H), 4.88 (ddd, J=4.0, 8.6, 12.6 Hz, 1H), 4.24 (br d, J=13.6 Hz, 2H), 3.31 (br t, J=12.1 Hz, 2H), 2.55 (dq, J=4.8, 12.7 Hz, 2H), 2.21-2.10 (m, 3H), 1.57-1.49 (m, 2H), 1.49-1.37 (m, 2H).

Example DL-7

6-(bis(4-chlorophenyl)methyl)-2-ethyl-1-(4-(trifluoromethyl)phenethyl)-1H-benzo[d]imidazole

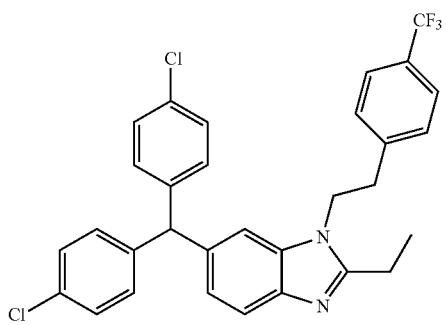 [SMILES: CCc1nc2ccc(C(c3ccc(Cl)cc3)c3ccc(Cl)cc3)cc2n1CCc1ccc(C(F)(F)F)cc1]

Step 1: methyl 2,2-bis(4-chlorophenyl)-2-(4-nitro-3-((4-(trifluoromethyl)phenethyl)amino)phenyl)acetate A solution of compound methyl 2,2-bis(4-chlorophenyl)-2-(3-fluoro-4-nitrophenyl)acetate (100 mg, 0.23 mmol), prepared as described in Example DL-2 above, p-trifluoromethylphenethylamine hydrochloride (90.5 mg, 0.35 mmol), and potassium carbonate (95.5 mg, 0.69 mmol) in DMSO (1 mL) was degassed with nitrogen and heated at 80° C. overnight. Ethyl ether was added and the mixture was washed with water and brine. The solvent was removed in vacuo to yield a yellow semi-solid, which was purified by reverse phase HPLC and fractions containing the product were lyophilized to yield methyl 2,2-bis(4-chlorophenyl)-2-(4-nitro-3-((4-(trifluoromethyl)phenethyl)amino)phenyl)acetate as a yellow oil.

Step 2: methyl 2-(4-amino-3-((4-(trifluoromethyl) phenethyl)amino)phenyl)-2,2-bis(4-chlorophenyl) acetate To a solution of methyl 2,2-bis(4-chlorophenyl)-2-(4-nitro-3-((4-(trifluoromethyl)phenethyl)amino)phenyl)acetate (100 mg, 0.17 mmol) in MeOH (100 mL) was added Raney nickel catalyst (200 mg, 3.41 mmol) and the mixture was placed under 30 psi hydrogen at room temperature for 4 hours. The reaction mixture was filtered through CELITE and the solvent evaporated in vacuo to yield methyl 2-(4-amino-3-((4-(trifluoromethyl)phenethyl)amino)phenyl)-2,2-bis(4-chlorophenyl)acetate as a white solid.

Step 3: methyl 2,2-bis(4-chlorophenyl)-2-(2-ethyl-1-(4-(trifluoromethyl)phenethyl)-1H-benzo[d]imidazol-6-yl)acetate A solution of methyl 2-(4-amino-3-((4-(trifluoromethyl) phenethyl)amino)phenyl)-2,2-bis(4-chlorophenyl)acetate (40 mg, 0.07 mmol) and propionaldehyde (0.01 mL, 0.14 mmol) in DMSO (0.5 mL) was rapidly stirred at room temperature in the presence of air overnight. An additional 0.015 mL of propionaldehyde was added and the reaction mixture rapidly stirred overnight. The reaction mixture was purified by reverse phase HPLC and the fractions containing product were lyophilized to yield methyl 2,2-bis(4-chlorophenyl)-2-(2-ethyl-1-(4-(trifluoromethyl)phenethyl)-1H-benzo[d]imidazol-6-yl)acetate.

Step 4: 2,2-bis(4-chlorophenyl)-2-(2-ethyl-1-(4-(trifluoromethyl)phenethyl)-1H-benzo[d]imidazol-6-yl)acetic acid A solution of methyl 2,2-bis(4-chlorophenyl)-2-(2-ethyl-1-(4-(trifluoromethyl)phenethyl)-1H-benzo[d]imidazol-6-yl)acetate (50 mg, 0.08 mmol) in 3N NaOH aqueous solution (1 mL, 3 mmol) and methanol (4 mL) was heated at 45° C. overnight. 2N HCl (1.5 mL) was added and the mixture was extracted with ethyl acetate. The organic layer was evaporated in vacuo to yield a first batch of 2,2-bis(4-chlorophenyl)-2-(2-ethyl-1-(4-(trifluoromethyl)phenethyl)-1H-benzo[d]imidazol-6-yl)acetic acid. The aqueous layer was also evaporated in vacuo. The residue was washed with acetonitrile, the solvent was decanted, and then evaporated to yield additional 2,2-bis(4-chlorophenyl)-2-(2-ethyl-1-(4-(trifluoromethyl)phenethyl)-1H-benzo[d]imidazol-6-yl)acetic acid.

Step 5: 6-(bis(4-chlorophenyl)methyl)-2-ethyl-1-(4-(trifluoromethyl)phenethyl)-1H-benzo[d]imidazole A solution of 2,2-bis(4-chlorophenyl)-2-(2-ethyl-1-(4-(trifluoromethyl)phenethyl)-1H-benzo[d]imidazol-6-yl)acetic acid (30 mg, 0.05 mmol) and DBU (0.017 mL, 0.12 mmol) in toluene (2 mL) was heated at 90° C. for 3 hours under argon. An additional 34.6 μL of DBU was added and the reaction mixture was heated at reflux temperature overnight. After evaporation of the solvent, the residue was purified by reverse phase HPLC and the fractions containing the product were lyophilized to yield 6-(bis(4-chlorophenyl)methyl)-2-ethyl-1-(4-(trifluoromethyl)phenethyl)-1H-benzo[d]imidazole trifluoroacetate salt as a clear oil. MS: 552.9 (M+H$^+$); $^1$H NMR (400 MHz, CDCl$_3$) δ: 7.89 (d, J=8.6 Hz, 1H), 7.56 (d, J=8.1 Hz, 2H), 7.33-7.28 (m, 5H), 7.03 (d, J=7.8 Hz, 2H), 6.97 (d, J=8.6 Hz, 4H), 6.88 (s, 1H), 5.64 (s, 1H), 4.38 (t, J=7.2 Hz, 2H), 3.10 (br t, J=7.1 Hz, 2H), 2.94 (q, J=7.7 Hz, 2H), 1.41 (t, J=7.6 Hz, 3H).

Example DL-8

2-((4-chlorophenyl)(1-(3-chlorophenyl)-2-ethyl-1H-benzo[d]imidazol-6-yl)methyl)thiazole

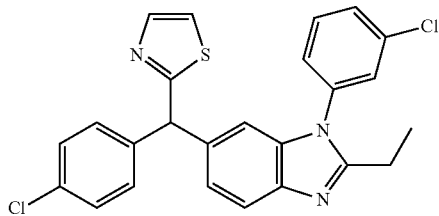 [SMILES: CCc1nc2ccc(C(c3ccc(Cl)cc3)c3nccs3)cc2n1-c1cccc(Cl)c1]

Step 1: 5-chloro-N-(3-chlorophenyl)-2-nitroaniline

To a solution of 2,4-dichloronitrobenzene (7 g, 35.36 mmol) and m-chloroaniline (4.13 mL, 38.90 mmol) in DMSO (2 mL) was added diisopropylethylamine (7.31 mL, 42.44 mmol). The reaction mixture was heated at 120° C. for 10 days. Water was added and the resulting mixture was extracted with ethyl ether. The organic layer was washed with brine and dried over Na$_2$SO$_4$. The solvent was removed in vacuo to yield a red oil. The oil was heated with heptane and the solvent decanted (3×). Dichloromethane was added to make it homogenous and the resulting orange solution was purified by silica gel chromatography using a 0-40% dichloromethane:heptane gradient to yield 5-chloro-N-(3-chlorophenyl)-2-nitroaniline as an orange solid.

Step 2: 2-(4-chlorophenyl)-2-(3-((3-chlorophenyl)amino)-4-nitrophenyl)acetonitrile To a stirred solution of 4-chlorophenylacetonitrile (2.20 g, 13.90 mmol) in THF (75 mL) and isopropyl alcohol (25 mL) cooled to 0° C. was added t-BuOK (1M in t-BuOH, 23.17 mL, 23.17 mmol). After 10 minutes 5-chloro-N-(3-chlorophenyl)-2-nitroaniline (3.28 g, 11.59 mmol) was added to the reaction mixture. The reaction mixture was allowed to warm to room temperature, stirred for 1.5 hours at room temperature, and then heated at 50° C. overnight. 1M HCl in ethyl ether (30 mL) was added and the solvent evaporated in vacuo. The residue was dissolved in ethyl acetate and the organic mixture washed with NaHCO$_3$ and brine, and then dried over Na$_2$SO$_4$. The solvent was evaporated in vacuo and the residue purified by silica gel chromatography using a 25-75% dichloromethane:heptane gradient to yield 2-(4-chlorophenyl)-2-(3-((3-chlorophenyl)amino)-4-nitrophenyl)acetonitrile as a red oil.

Step 3: 2-(4-chlorophenyl)-2-(3-((3-chlorophenyl)amino)-4-nitrophenyl)ethanethioamide To a solution of 2-(4-chlorophenyl)-2-(3-((3-chlorophenyl)amino)-4-nitrophenyl)acetonitrile (3.4 g, 8.53 mmol) in EtOH (85 mL) under argon was added phosphorus pentasulfide (7.59 g, 17.08 mmol) and the reaction mixture was heated to reflux temperature for 24 hours. The reaction mixture was poured into ice water and extracted with ethyl acetate (2×). The organic layer was dried over Na$_2$SO$_4$. The solvent was removed in vacuo and the residue was purified by silica gel chromatography using a 50-100% dichloromethane:heptane gradient as eluent to yield 2-(4-chlorophenyl)-2-(3-((3-chlorophenyl)amino)-4-nitrophenyl)ethanethioamide as a red amorphous solid.

Step 4: N-(3-chlorophenyl)-5-((4-chlorophenyl)(thiazol-2-yl)methyl)-2-nitroaniline To a solution of 2-(4-chlorophenyl)-2-(3-((3-chlorophenyl)amino)-4-nitrophenyl)ethanethioamide (4.55 g, 10.52 mmol) in acetic acid (50 mL) was added water (2 mL) and bromoacetaldehyde diethylacetal (6.53 mL, 42.10 mmol). The reaction mixture was heated at 100° C. for 30 minutes and then poured into water (200 mL) and the resulting mixture was extracted with ethyl acetate. The organic layer was washed with water, saturated NaHCO$_3$, and brine and then dried over MgSO$_4$. Removal of the solvent in vacuo yielded N-(3-chlorophenyl)-5-((4-chlorophenyl)(thiazol-2-yl)methyl)-2-nitroaniline as a red oil.

Step 5: N1-(3-chlorophenyl)-5-((4-chlorophenyl)(thiazol-2-yl)methyl)benzene-1,2-diamine To a 10 mL graduated cylinder was added 6 mL of Raney nickel (50% slurry in water). The catalyst was washed with EtOH and the solvent decanted. The catalyst was washed into a hydrogenation flask with ethyl alcohol (30 mL). N-(3-chlorophenyl)-5-((4-chlorophenyl)(thiazol-2-yl)methyl)-2-nitroaniline (4.37 g, 9.58 mmol) dissolved in EtOH (120 mL) and THF (24 mL) was added to flask and the reaction mixture was placed under a hydrogen atmosphere for 2 hours. The catalyst was filtered off and the filtrate was evaporated in vacuo to yield N1-(3-chlorophenyl)-5-((4-chlorophenyl)(thiazol-2-yl)methyl)benzene-1,2-diamine as a tan foam.

Step 6: 2-((4-chlorophenyl)(1-(3-chlorophenyl)-2-ethyl-1H-benzo[d]imidazol-6-yl)methyl)thiazole A solution of N1-(3-chlorophenyl)-5-((4-chlorophenyl)(thiazol-2-yl)methyl)benzene-1,2-diamine (100 mg, 0.24 mmol) and propionaldehyde (0.035 mL, 0.47 mmol) in DMSO (1 mL) was rapidly stirred at room temperature in the presence of air for 72 hours. Acetonitrile (0.5 mL) was added and the reaction mixture was purified by reverse phase HPLC. The fractions containing the product were lyophilized to yield 2-((4-chlorophenyl)(1-(3-chlorophenyl)-2-ethyl-1H-benzo[d]imidazol-6-yl)methyl)thiazole trifluoroacetate salt as a gummy gray solid. MS: 464.1

(M+H⁺); ¹H NMR (400 MHz, DMSO-d₆) δ: 7.85-7.83 (m, 1H), 7.83-7.78 (m, 2H), 7.78-7.71 (m, 2H), 7.67 (d, J=3.4 Hz, 1H), 7.66-7.63 (m, 1H), 7.46 (d, J=8.3 Hz, 1H), 7.42-7.34 (m, 3H), 7.34-7.27 (m, 2H), 6.23 (s, 1H), 2.87 (q, J=7.3 Hz, 2H), 1.27 (t, J=7.6 Hz, 3H).

Example DL-9

(R)-2-(6-(bis(4-chlorophenyl)methyl)-2-cyclopropyl-1H-benzo[d]imidazol-1-yl)-1-phenylethanol

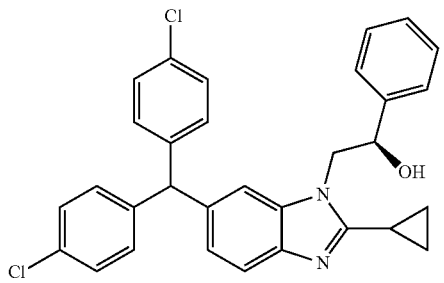 [SMILES: O[C@@H](Cn1c(C2CC2)nc2ccc(C(c3ccc(Cl)cc3)c3ccc(Cl)cc3)cc21)c1ccccc1]

Step 1: methyl 2,2-bis(4-chlorophenyl)-2-(3-fluoro-4-nitrophenyl)acetate

To a solution of methyl 2,2-bis(4-chlorophenyl)acetate (1.92 g, 6.51 mmol), prepared as described in Example DL-1 above, and 2,4-difluoro-1-nitrobenzene (0.76 mL, 6.83 mmol) in THF (40 mL) at −60° C. to −50° C. was added LHMDS (1M in THF, 7.2 mL, 7.2 mmol) over 10 minutes. The reaction was allowed to warm slowly to room temperature and then stirred overnight. To the reaction was added ethyl ether and the resulting organic mixture was washed with water, aq NH₄Cl, and brine. The organic layer was dried over MgSO₄ and concentrated in vacuo to yield a yellow oil. The residue was purified by silica gel chromatography with a 0-70% dichloromethane:heptane gradient as eluent to yield methyl 2,2-bis(4-chlorophenyl)-2-(3-fluoro-4-nitrophenyl)acetate as a pale yellow oil.

Step 2: (R)-methyl 2,2-bis(4-chlorophenyl)-2-(3-((2-hydroxy-2-phenylethyl)amino)-4-nitrophenyl)acetate A solution of methyl 2,2-bis(4-chlorophenyl)-2-(3-fluoro-4-nitrophenyl)acetate (300 mg, 0.69 mmol), (R)-2-amino-1-phenylethanol (126.4 mg, 0.83 mmol), and DIPEA (0.238 mL, 1.38 mmol) in acetonitrile (3 mL) was heated at reflux temperature for 48 hours. The solvent was removed in vacuo and the residue was purified by silica gel chromatography with 0-2% methanol:dichloromethane gradient as eluent to yield (R)-methyl 2,2-bis(4-chlorophenyl)-2-(3-((2-hydroxy-2-phenylethyl)amino)-4-nitrophenyl)acetate as a yellow oil.

Step 3: (R)-methyl 2-(4-amino-3-((2-hydroxy-2-phenylethyl)amino)phenyl)-2,2-bis(4-chlorophenyl)acetate To a solution of (R)-methyl 2,2-bis(4-chlorophenyl)-2-(3-((2-hydroxy-2-phenylethyl)amino)-4-nitrophenyl)acetate (260 mg, 0.47 mmol) in MeOH (100 mL) was added 5% Pd/C sulfide (100 mg) and the mixture was placed under 45 psi hydrogen at room temperature for 3 hours. The reaction mixture was filtered through CELITE and the solvent evaporated in vacuo to yield (R)-methyl 2-(4-amino-3-((2-hydroxy-2-phenylethyl)amino)phenyl)-2,2-bis(4-chlorophenyl)acetate as a yellowish oil.

Step 4: (R)-methyl 2,2-bis(4-chlorophenyl)-2-(2-cyclopropyl-1-(2-hydroxy-2-phenylethyl)-1H-benzo[d]imidazol-6-yl)acetate A solution of (R)-methyl 2-(4-amino-3-((2-hydroxy-2-phenylethyl)amino)phenyl)-2,2-bis(4-chlorophenyl)acetate (220 mg, 0.42 mmol) and cyclopropanecarboxaldehyde (59.14 mg, 0.84 mmol) in DMSO (2 mL) was rapidly stirred at room temperature in the presence of air overnight. An additional 0.015 mL of propionaldehyde was added and the reaction mixture rapidly stirred overnight. Ethyl acetate was added and the organic mixture was washed with water and brine. The organic layer was dried over MgSO₄ and evaporated in vacuo to yield a residue as a dirty yellow oil. The reaction mixture was purified by silica gel chromatography to yield (R)-methyl 2,2-bis(4-chlorophenyl)-2-(2-cyclopropyl-1-(2-hydroxy-2-phenylethyl)-1H-benzo[d]imidazol-6-yl)acetate.

Step 5: (R)-2,2-bis(4-chlorophenyl)-2-(2-cyclopropyl-1-(2-hydroxy-2-phenylethyl)-1H-benzo[d]imidazol-6-yl)acetic acid A solution of (R)-methyl 2,2-bis(4-chlorophenyl)-2-(2-cyclopropyl-1-(2-hydroxy-2-phenylethyl)-1H-benzo[d]imidazol-6-yl)acetate (160 mg, 0.28 mmol) in 3N NaOH aqueous solution (1 mL, 3 mmol) and methanol (4 mL) was stirred under argon for 5 days at 65° C. The methanol was evaporated and then water, 1N HCl, and 0.5 mL DBU were added. The mixture was extracted with dichloromethane, the organic layer separated, and the solvent evaporated to yield (R)-2,2-bis(4-chlorophenyl)-2-(2-cyclopropyl-1-(2-hydroxy-2-phenylethyl)-1H-benzo[d]imidazol-6-yl)acetic acid.

Step 6: (R)-2-(6-(bis(4-chlorophenyl)methyl)-2-cyclopropyl-1H-benzo[d]imidazol-1-yl)-1-phenylethanol A solution of (R)-2,2-bis(4-chlorophenyl)-2-(2-cyclopropyl-1-(2-hydroxy-2-phenylethyl)-1H-benzo[d]imidazol-6-yl)acetic acid (155 mg, 0.28 mmol) and DBU (0.5 mL, 3.35 mmol) in toluene (10 mL) was heated at 90° C. overnight under argon. After evaporation of the solvent, the residue was purified by silica gel chromatography with a 0-2% methanol:dichloromethane gradient as eluent to yield 0.07 g of a white solid. The solid was heated in acetonitrile, cooled, and filtered to yield (R)-2-(6-(bis(4-chlorophenyl)methyl)-2-cyclopropyl-1H-benzo[d]imidazol-1-yl)-1-phenylethanol as a white solid. MS: 513.2 (M+H⁺); ¹H NMR (400 MHz, DMSO-d₆) δ: 7.43-7.34 (m, 5H), 7.34-7.22 (m, 5H), 7.16-7.07 (m, 4H), 7.01 (s, 1H), 6.84 (br d, J=8.3 Hz, 1H), 5.76-5.69 (m, 2H), 4.88-4.81 (m, 1H), 4.34 (br dd, J=7.7, 14.5 Hz, 1H), 4.24 (br dd, J=4.0, 14.5 Hz, 1H), 2.26-2.18 (m, 1H), 1.10-1.03 (m, 1H), 0.99 (q, J=8.2 Hz, 2H), 0.91-0.81 (m, 1H).

Example DL-10

(R)-6-(bis(4-chlorophenyl)methyl)-2-ethyl-1-(2-phenylpropyl)-1H-benzo[d]imidazole

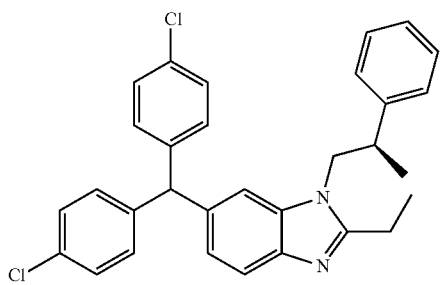 [SMILES: CCc1nc2ccc(C(c3ccc(Cl)cc3)c3ccc(Cl)cc3)cc2n1C[C@H](C)c1ccccc1]

(R)-6-(bis(4-chlorophenyl)methyl)-2-ethyl-1-(2-phenylpropyl)-1H-benzo[d]imidazole was prepared according to the procedure as described in Example DL-7 above substituting (R)-2-phenyl-1-propylamine for p-trifluoromethylphenethylamine hydrochloride in step 1. MS: 499.0 (M+H$^+$); $^1$H NMR (400 MHz, DMSO-d$_6$) δ: 7.67 (d, J=8.6 Hz, 1H), 7.45 (br s, 1H), 7.43 (dd, J=1.2, 8.6 Hz, 4H), 7.24-7.14 (m, 4H), 7.14-7.08 (m, 6H), 5.83 (s, 1H), 4.56 (dd, J=6.6, 14.7 Hz, 1H), 4.45 (dd, J=8.6, 14.4 Hz, 1H), 3.25-3.15 (m, 1H), 3.12-3.01 (m, 1H), 2.96-2.85 (m, 1H), 1.35-1.25 (m, 6H).

Example DL-11

6-(bis(4-chlorophenyl)methyl)-2-ethyl-1-(1-phenylpropan-2-yl)-1H-benzo[d]imidazole

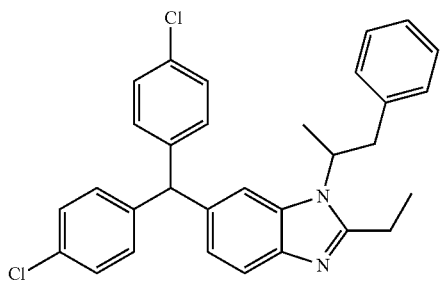 [SMILES: CCc1nc2ccc(C(c3ccc(Cl)cc3)c3ccc(Cl)cc3)cc2n1C(C)Cc1ccccc1]

6-(Bis(4-chlorophenyl)methyl)-2-ethyl-1-(1-phenylpropan-2-yl)-1H-benzo[d]imidazole was prepared according to the procedure as described in Example DL-9 above substituting 1-phenylpropan-2-amine for (R)-2-amino-1-phenylethanol in step 2 and propionaldehyde for cyclopropanecarboxaldehyde in step 4. MS: 533.1 (M+H$^+$).

Example DL-13

(S)-2-(6-(bis(4-chlorophenyl)methyl)-2-cyclopropyl-1H-benzo[d]imidazol-1-yl)-1-phenylethanol

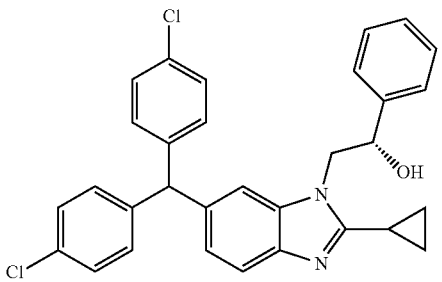 [SMILES: O[C@H](Cn1c(C2CC2)nc2ccc(C(c3ccc(Cl)cc3)c3ccc(Cl)cc3)cc21)c1ccccc1]

Step 1: (S)-methyl 2,2-bis(4-chlorophenyl)-2-(3-((2-hydroxy-2-phenylethyl)amino)-4-nitrophenyl)acetate A solution of methyl 2-(3-chloro-4-nitrophenyl)-2,2-bis(4-chlorophenyl)acetate (200 mg, 0.44 mmol), prepared as described in Example DL-2 above, (S)-2-amino-1-phenylethanol (126 mg, 0.89 mmol), and DIPEA (0.229 mL, 1.33 mmol) in 1,4-dioxane (2 mL) was heated under argon at 95° C. for 4 days. Ethyl acetate was added and the organic mixture was washed with water and brine and then dried over Na$_2$SO$_4$. The solvent was evaporated in vacuo and the yellow oily residue was purified by silica gel chromatography to yield (S)-methyl 2,2-bis(4-chlorophenyl)-2-(3-((2-hydroxy-2-phenylethyl)amino)-4-nitrophenyl)acetates a yellow oil.

Step 2: (S)-methyl 2-(4-amino-3-((2-hydroxy-2-phenylethyl)amino)phenyl)-2,2-bis(4-chlorophenyl)acetate To a solution of (S)-methyl 2,2-bis(4-chlorophenyl)-2-(3-((2-hydroxy-2-phenylethyl)amino)-4-nitrophenyl)acetate (100 mg, 0.18 mmol) in MeOH (200 mL) was added 5% Pd/C sulfide (65 mg) and the mixture was placed under 50 psi hydrogen at room temperature for 4.5 hours. The reaction mixture was filtered through CELITE and the solvent evaporated in vacuo to yield (S)-methyl 2-(4-amino-3-((2-hydroxy-2-phenylethyl)amino)phenyl)-2,2-bis(4-chlorophenyl)acetate as a white oil.

Step 3: (S)-methyl 2,2-bis(4-chlorophenyl)-2-(2-cyclopropyl-1-(2-hydroxy-2-phenylethyl)-1H-benzo[d]imidazol-6-yl)acetate A solution of (S)-methyl 2-(4-amino-3-((2-hydroxy-2-phenylethyl)amino)phenyl)-2,2-bis(4-chlorophenyl)acetate (100 mg, 0.19 mmol) and cyclopropanecarboxaldehyde (0.029 mL, 0.38 mmol) in DMSO (1 mL) was rapidly stirred at room temperature in the presence of air for 2 days. The reaction mixture was purified by reverse phase HPLC. Fractions containing the desired product were combined and lyophilized to yield (S)-methyl 2,2-bis(4-chlorophenyl)-2-

(2-cyclopropyl-1-(2-hydroxy-2-phenylethyl)-1H-benzo[d]imidazol-6-yl)acetate as a white solid.

Step 4: (S)-2,2-bis(4-chlorophenyl)-2-(2-cyclopropyl-1-(2-hydroxy-2-phenylethyl)-1H-benzo[d]imidazol-6-yl)acetic acid A solution of (S)-methyl 2,2-bis(4-chlorophenyl)-2-(2-cyclopropyl-1-(2-hydroxy-2-phenylethyl)-1H-benzo[d]imidazol-6-yl)acetate (75 mg, 0.11 mmol) in 3N NaOH aqueous solution (2 mL, 6 mmol) and methanol (8 mL) was stirred under argon overnight at 40° C. The temperature of the reaction mixture was increased to 50° C. and the reaction was stirred for another day. 1N HCl was added and the methanol was evaporated in vacuo. Water and 0.5 mL DBU were added and the mixture was extracted with dichloromethane. The organic layer was separated and the solvent evaporated to yield (S)-2,2-bis(4-chlorophenyl)-2-(2-cyclopropyl-1-(2-hydroxy-2-phenylethyl)-1H-benzo[d]imidazol-6-yl)acetic acid as a clear oil.

Step 5: (S)-2-(6-(bis(4-chlorophenyl)methyl)-2-cyclopropyl-1H-benzo[d]imidazol-1-yl)-1-phenylethanol A solution of (S)-2,2-bis(4-chlorophenyl)-2-(2-cyclopropyl-1-(2-hydroxy-2-phenylethyl)-1H-benzo[d]imidazol-6-yl)acetic acid (60.77 mg, 0.11 mmol) and DBU (0.08 mL, 0.55 mmol) in toluene (10 mL) was heated at 90° C. overnight under argon. After evaporation of the solvent, the residue was purified by reverse phase HPLC to yield (S)-2-(6-(bis(4-chlorophenyl)methyl)-2-cyclopropyl-1H-benzo[d]imidazol-1-yl)-1-phenylethanol as a white solid. MS: 513.2 (M+H$^+$); $^1$H NMR (400 MHz, DMSO-d$_6$) δ: 7.63 (d, J=8.6 Hz, 1H), 7.48 (s, 1H), 7.43 (dd, J=6.3, 8.3 Hz, 4H), 7.35 (d, J=4.0 Hz, 4H), 7.32-7.26 (m, 1H), 7.24 (br d, J=8.6 Hz, 1H), 7.14 (dd, J=3.8, 8.3 Hz, 4H), 5.87 (s, 1H), 4.95 (dd, J=3.8, 7.8 Hz, 1H), 4.67-4.51 (m, 2H), 2.64-2.55 (m, 1H), 1.34 (br d, J=6.1 Hz, 3H), 1.25 (br s, 1H).

Example DL-14

2-((1-(3-chlorophenethyl)-2-ethyl-1H-benzo[d]imidazol-6-yl)(4-chlorophenyl)methyl)thiazole

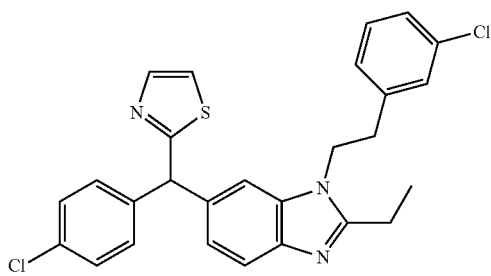 [SMILES: CCc1nc2ccc(C(c3ccc(Cl)cc3)c3nccs3)cc2n1CCc1cccc(Cl)c1]

2-((1-(3-Chlorophenethyl)-2-ethyl-1H-benzo[d]imidazol-6-yl)(4-chlorophenyl)methyl)thiazole was prepared according to the procedure as described in Example DL-4 above substituting propionaldehyde for cyclopropanecarboxaldehyde in Step 6. MS: 492.0 (M+H$^+$); $^1$H NMR (400 MHz, DMSO-d$_6$) δ: 7.86 (d, J=3.4 Hz, 1H), 7.81-7.72 (m, 3H), 7.48 (d, J=8.6 Hz, 1H), 7.44 (d, J=8.6 Hz, 2H), 7.36-7.29 (m, 3H), 7.29-7.23 (m, 2H), 7.16-7.09 (m, 1H), 6.19 (s, 1H), 4.70-4.58 (m, 2H), 3.15-3.03 (m, 4H), 1.32 (t, J=7.5 Hz, 3H).

Example DL-15

(S)-6-(bis(4-chlorophenyl)methyl)-2-ethyl-1-(2-phenylpropyl)-1H-benzo[d]imidazole

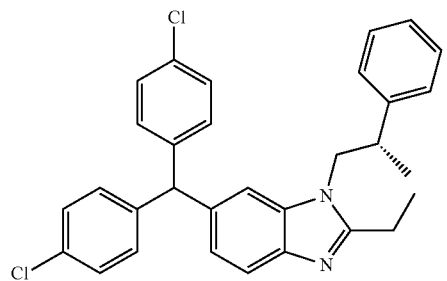 [SMILES: CCc1nc2ccc(C(c3ccc(Cl)cc3)c3ccc(Cl)cc3)cc2n1C[C@@H](C)c1ccccc1]

(S)-6-(Bis(4-chlorophenyl)methyl)-2-ethyl-1-(2-phenylpropyl)-1H-benzo[d]imidazole was prepared according to the procedure as described in Example DL-7 above substituting (S)-2-phenyl-1-propylamine for p-trifluoromethylphenethylamine hydrochloride in Step 1. MS: 498.9 (M+H$^+$); $^1$H NMR (400 MHz, CDCl$_3$) δ: 7.80 (d, J=8.6 Hz, 1H), 7.34-7.28 (m, 4H), 7.28-7.21 (m, 4H), 6.96 (d, J=8.1 Hz, 4H), 6.92-6.81 (m, 3H), 5.63 (s, 1H), 4.30 (dd, J=5.6, 14.7 Hz, 1H), 4.15 (dd, J=8.8, 14.4 Hz, 1H), 3.20-3.10 (m, 1H), 2.79 (td, J=7.6, 15.5 Hz, 1H), 2.74-2.63 (m, 1H), 1.42 (d, J=7.1 Hz, 3H), 1.33 (t, J=7.6 Hz, 3H).

Example DL-16

2-((1-(4-chlorophenethyl)-2-cyclopropyl-1H-benzo[d]imidazol-6-yl)(4-chlorophenyl)methyl)thiazole

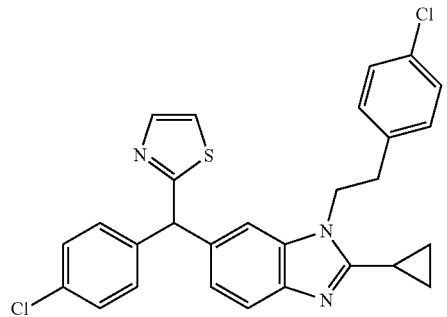 [SMILES: Clc1ccc(CCn2c(C3CC3)nc3ccc(C(c4ccc(Cl)cc4)c4nccs4)cc32)cc1]

Step 1: 2-(3-amino-4-nitrophenyl)-2-(4-chlorophenyl)acetonitrile

To a stirred solution of 4-chlorophenylacetonitrile (6.46 g, 40.89 mmol) in THF (100 mL) cooled to 0° C. was added t-BuOK (1M in THF, 74.97 mL, 23.17 mmol). After 10 minutes 5-fluoro-2-nitroaniline (3.28 g, 11.59 mmol) was added to the reaction mixture. The reaction mixture was allowed to warm to room temperature and stirred overnight at room temperature. THF (25 mL) was added and saturated NH$_4$Cl was added until the deep purple color disappeared.

The mixture was extracted with ethyl ether and the organic layer was washed with brine and dried over MgSO$_4$. The solvent was removed in vacuo to yield 2-(3-amino-4-nitrophenyl)-2-(4-chlorophenyl)acetonitrile as a red oil. The oil was dissolved in 40 mL of 3:2 dichloromethane:heptane and the resulting yellow precipitate was collected by filtration (7.63 g). The filtrate was evaporated and the residue was purified by silica gel chromatography eluting with a 75% dichloromethane:heptane to 100% dichloromethane gradient to yield additional 2-(3-amino-4-nitrophenyl)-2-(4-chlorophenyl)acetonitrile.

Step 2:
(3-chloro-4-nitrophenyl)(4-chlorophenyl)methanone

To a solution of CuCl$_2$ (5.18 g, 38.54 mmol) and t-butylnitrite (6.55 mL, 49.56 mmol) in CH$_3$CN (160 mL) heated to 65° C. was added 2-(3-amino-4-nitrophenyl)-2-(4-chlorophenyl)acetonitrile (7.92 g, 27.53 mmol). The reaction mixture was heated at 65° C. for 2 hours with the argon atmosphere maintained over the reaction by bubbling the gas through a mixture of 3N NaOH/bleach. An additional amount of t-butylnitrite was added (1.45 mL) and the reaction mixture was heated overnight. The reaction was cooled in ice and 300 mL of 2N HCl was added. The mixture was extracted with ethyl ether and the organic layer was washed with water, brine, and then dried over MgSO$_4$. The solvent was evaporated to yield a residue as a yellow solid. The solid was recrystallized with isopropanol to yield (3-chloro-4-nitrophenyl)(4-chlorophenyl)methanone as an orange solid. The filtrate was concentrated and the residue was purified by silica gel chromatography using a 25-50% dichloromethane:heptane gradient as eluent to yield additional (3-chloro-4-nitrophenyl)(4-chlorophenyl)methanone as a white solid.

Step 3: (3-chloro-4-nitrophenyl)(4-chlorophenyl)(thiazol-2-yl)methanol

A solution of thiazole (2.28 mL, 31.75 mmol) in THF (100 mL) was cooled to −78° C. and treated dropwise with n-BuLi (10M in hexanes, 3.49 mL, 34.92 mmol). After 30 minutes a solution of (3-chloro-4-nitrophenyl)(4-chlorophenyl)methanone (4.7 g, 15.87 mmol) in THF (100 mL) was added dropwise and the reaction mixture was allowed to warm to room temperature and stirred overnight. Water was added and the mixture was extracted with ethyl ether. The organic layer was washed with brine and dried over MgSO$_4$. The solvent was evaporated to yield a dark oil. The oil was purified by silica gel chromatography eluting with a gradient of 1:1 dichloromethane:hexane to dichloromethane to yield (3-chloro-4-nitrophenyl)(4-chlorophenyl)(thiazol-2-yl)methanol as a yellow-orange gum.

Step 4: (3-((4-chlorophenethyl)amino)-4-nitrophenyl)(4-chlorophenyl)(thiazol-2-yl)methanol A solution of (3-chloro-4-nitrophenyl)(4-chlorophenyl)(thiazol-2-yl)methanol (250 mg, 0.66 mmol), p-chlorophenethylamine (0.28 mL, 1.97 mmol), and potassium fluoride (190 mg, 3.28 mmol) in DMSO (1 mL) was heated under argon at 100° C. for 72 hours. Water was added and the mixture was extracted with ethyl ether. The organic layer was washed with water (2×) and brine (1×) and then dried over MgSO$_4$. Evaporation of the solvent in vacuo to yield residue, which was purified by silica gel chromatography using a 50% dichloromethane:heptane to 100% dichloromethane gradient to yield (3-((4-chlorophenethyl)amino)-4-nitrophenyl)(4-chlorophenyl)(thiazol-2-yl)methanol as an orange solid.

Step 5: Mixture of N1-(4-chlorophenethyl)-5-((4-chlorophenyl)(thiazol-2-yl)methyl)benzene-1,2-diamine and N-(2-((4-chlorophenethyl)amino)-4-((4-chlorophenyl)(thiazol-2-yl)methyl)phenyl)acetamide To a solution of (3-((4-chlorophenethyl)amino)-4-nitrophenyl)(4-chlorophenyl)(thiazol-2-yl)methanol (130 mg, 0.26 mmol) in acetic acid (3.75 mL) was added tin chloride dihydrate (293 mg, 1.30 mmol) and water (0.25 mL). The reaction mixture was heated at 50° C. and the solvent was evaporated in vacuo. Water and 3N NaOH were added to the residue and the mixture was extracted with dichloromethane (3×). The organic layer was dried over Na$_2$SO$_4$, filtered, and the solvent evaporated in vacuo to yield a mixture of N1-(4-chlorophenethyl)-5-((4-chlorophenyl)(thiazol-2-yl)methyl)benzene-1,2-diamine and N-(2-((4-chlorophenethyl)amino)-4-((4-chlorophenyl)(thiazol-2-yl)methyl)phenyl)acetamide as a brown oil.

Step 6: 2-((1-(4-chlorophenethyl)-2-cyclopropyl-1H-benzo[d]imidazol-6-yl)(4-chlorophenyl)methyl)thiazole A solution of N1-(4-chlorophenethyl)-5-((4-chlorophenyl)(thiazol-2-yl)methyl)benzene-1,2-diamine and N-(2-((4-chlorophenethyl)amino)-4-((4-chlorophenyl)(thiazol-2-yl)methyl)phenyl)acetamide (140 mg, 0.31 mmol) and cyclopropanecarboxaldehyde (0.047 mL, 0.62 mmol) in DMSO (1 mL) was rapidly stirred at room temperature in the presence of air. The reaction mixture was purified by reverse phase HPLC. The fractions containing the product were lyophilized to yield 2-((1-(4-chlorophenethyl)-2-cyclopropyl-1H-benzo[d]imidazol-6-yl)(4-chlorophenyl)methyl)thiazole trifluoroacetate salt. MS: 504.0 (M+H$^+$).

Example DL-17

2-((4-chlorophenyl)(1-(3-chlorophenyl)-2-cyclopropyl-1H-benzo[d]imidazol-6-yl)methyl)thiazole

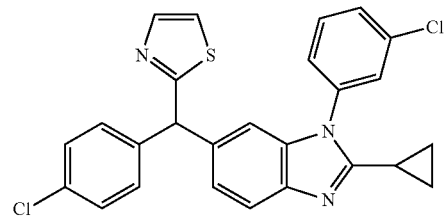 [SMILES: Clc1ccc(C(c2ccc3nc(C4CC4)n(-c4cccc(Cl)c4)c3c2)c2nccs2)cc1]

2-((4-Chlorophenyl)(1-(3-chlorophenyl)-2-cyclopropyl-1H-benzo[d]imidazol-6-yl)methyl)thiazole was prepared according to the procedure as described in Example DL-8 above substituting cyclopropanecarboxaldehyde for propionaldehyde in Step 6. MS: 476.0 (M+H$^+$).

Example DL-18

2-((4-chlorophenyl)(1-(3-chlorophenyl)-2-propyl-1H-benzo[d]imidazol-6-yl)methyl)thiazole

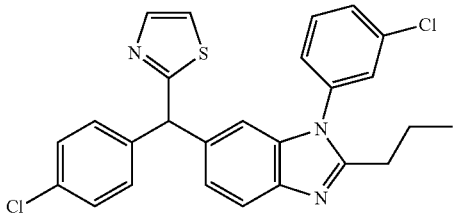 [SMILES: CCCc1nc2ccc(C(c3ccc(Cl)cc3)c3nccs3)cc2n1-c1cccc(Cl)c1]

2-((4-Chlorophenyl)(1-(3-chlorophenyl)-2-propyl-1H-benzo[d]imidazol-6-yl)methyl)thiazole was prepared according to the procedure as described in Example DL-8 above substituting 1-butyraldehyde for propionaldehyde in Step 6. MS: 478.0 (M+H$^+$).

Example DL-19

2-((4-chlorophenyl)(1-(1-(4-chlorophenyl)propan-2-yl)-2-ethyl-1H-benzo[d]imidazol-6-yl)methyl)thiazole

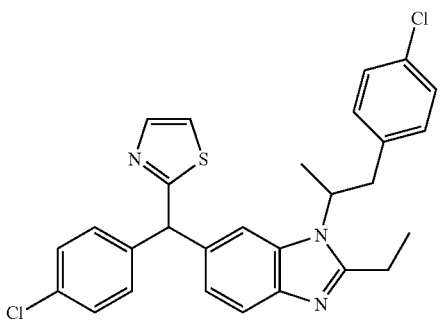 [SMILES: CCc1nc2ccc(C(c3ccc(Cl)cc3)c3nccs3)cc2n1C(C)Cc1ccc(Cl)cc1]

Step 1: (4-chlorophenyl)(3-((1-(4-chlorophenyl)propan-2-yl)amino)-4-nitrophenyl)(thiazol-2-yl)methanol A solution of (3-chloro-4-nitrophenyl)(4-chlorophenyl)(thiazol-2-yl)methanol (500 mg, 1.31 mmol), prepared as described in Example DL-16 above, 2-(4-chlorophenyl)-1-methylethylamine hydrochloride (828 mg, 3.94 mmol), potassium fluoride (381 mg, 6.56 mmol), and K$_2$CO$_3$ (544 mg, 3.94 mmol) in DMSO (2 mL) was heated under argon at 100° C. for 72 hours. Water was added and the mixture was extracted with ethyl ether. The organic layer was washed with water (2×) and brine (1×) and then dried over MgSO$_4$. Evaporation of the solvent in vacuo yielded an orange solid, which was purified by silica gel chromatography using a 50% dichloromethane:heptane to 100% dichloromethane gradient to yield (4-chlorophenyl)(3-((1-(4-chlorophenyl)propan-2-yl)amino)-4-nitrophenyl)(thiazol-2-yl)methanols an orange solid.

Step 2: 5-((4-chlorophenyl)(thiazol-2-yl)methyl)-N1-(1-(4-chlorophenyl)propan-2-yl)benzene-1,2-diamine To a solution of (4-chlorophenyl)(3-((1-(4-chlorophenyl)propan-2-yl)amino)-4-nitrophenyl)(thiazol-2-yl)methanol (420 mg, 0.82 mmol) in acetic acid (15 mL) under an argon atmosphere was added tin chloride dihydrate (921 mg, 4.08 mmol) and conc. HCl (1 mL). The reaction mixture was heated at 50° C. for 5 days and then another 0.95 g of tin chloride dihydrate was added and the reaction mixture stirred at 50° C. for 16 hours. Ice and 3N NaOH (90 mL) were added to the residue and the mixture was extracted with ethyl acetate. The organic layer was washed with water and brine and then dried over Na$_2$SO$_4$. Evaporation of the solvent in vacuo yielded a green oil. The oil was purified by silica gel chromatography using a 0-2% methanol:dichloromethane gradient to yield 5-((4-chlorophenyl)(thiazol-2-yl)methyl)-N1-(1-(4-chlorophenyl)propan-2-yl)benzene-1,2-diamine as a green oil.

Step 3: 2-((4-chlorophenyl)(1-(1-(4-chlorophenyl)propan-2-yl)-2-ethyl-1H-benzo[d]imidazol-6-yl)methyl)thiazole A solution of 5-((4-chlorophenyl)(thiazol-2-yl)methyl)-N1-(1-(4-chlorophenyl)propan-2-yl)benzene-1,2-diamine (550 mg, 1.17 mmol) and propionaldehyde (0.175 mL, 2.35 mmol) in DMSO (1 mL) was rapidly stirred at room temperature in the presence of air for 72 hours. The reaction mixture was purified by reverse phase HPLC. The fractions containing the product were lyophilized to yield 2-((4-chlorophenyl)(1-(1-(4-chlorophenyl)propan-2-yl)-2-ethyl-1H-benzo[d]imidazol-6-yl)methyl)thiazole trifluoroacetate salt. MS: 506.2 (M+H$^+$).

Example DL-20

6-(bis(4-chlorophenyl)methyl)-2-cyclopropyl-1-(2,3-dihydro-1H-inden-2-yl)-1H-benzo[d]imidazole

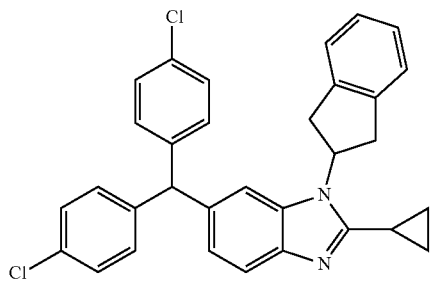 [SMILES: Clc1ccc(C(c2ccc(Cl)cc2)c2ccc3nc(C4CC4)n(C4Cc5ccccc5C4)c3c2)cc1]

Step 1: methyl 2,2-bis(4-chlorophenyl)-2-(3-((2,3-dihydro-1H-inden-2-yl)amino)-4-nitrophenyl)acetate and N-(5-(bis(4-chlorophenyl)methyl)-2-nitrophenyl)-2,3-dihydro-1H-inden-2-amine A solution of methyl 2-(3-chloro-4-nitrophenyl)-2,2-bis(4-chlorophenyl)acetate (670 mg, 1.49 mmol), prepared as described in Example DL-2 above, (S)-2-indanamine (0.38 mL, 2.97 mmol), and DIPEA (0.538 mL, 3.12 mmol) in 1,4-dioxane (2 mL) was heated under argon at 95° C. for 18 hours. The solvent was evaporated to the point that the mixture became thick, another 0.38 g of 2-indanamine was added, and the reaction was heated at 110° C. for 72 hours. The remaining solvent was evaporated in vacuo and the residue was purified by reverse phase HPLC. The fractions containing the product were lyophilized to yield methyl 2,2-bis(4-chlorophenyl)-2-(3-((2,3-dihydro-1H-inden-2-yl)amino)-4-nitrophenyl)acetate and N-(5-(bis(4-chlorophenyl)methyl)-2-nitrophenyl)-2,3-dihydro-1H-inden-2-amine trifluoroacetate salts as green solids. MS: 489 (M+H$^+$).

Step 2: 5-(bis(4-chlorophenyl)methyl)-N1-(2,3-dihydro-1H-inden-2-yl)benzene-1,2-diamine To a solution of N-(5-(bis(4-chlorophenyl)methyl)-2-nitrophenyl)-2,3-dihydro-1H-inden-2-amine (140 mg, 0.29 mmol) in MeOH (100 mL) was added 5% Pd/C sulfide (130 mg) and the mixture was placed under 40 psi hydrogen at room temperature for 5.5 hours. The reaction mixture was filtered through CELITE and the solvent evaporated in vacuo. The residue was purified by silica gel chromatography using a 50% dichloromethane:heptane to 100% dichloromethane gradient to yield 5-(bis(4-chlorophenyl)methyl)-N1-(2,3-dihydro-1H-inden-2-yl)benzene-1,2-diamine as a white solid.

Step 3: 6-(bis(4-chlorophenyl)methyl)-2-cyclopropyl-1-(2,3-dihydro-1H-inden-2-yl)-1H-benzo[d]imidazole A solution of 5-(bis(4-chlorophenyl)methyl)-N1-(2,3-dihydro-1H-inden-2-yl)benzene-1,2-diamine (70 mg, 0.12 mmol) and cyclopropanecarboxaldehyde (0.019 mL, 0.24 mmol) in DMSO (0.7 mL) was rapidly stirred at room temperature in the presence of air for 18 hours. The reaction mixture was purified by reverse phase HPLC. Fractions containing the desired product were combined and lyophilized to yield 6-(bis(4-chlorophenyl)methyl)-2-cyclopropyl-1-(2,3-dihydro-1H-inden-2-yl)-1H-benzo[d]imidazole as a white solid.

Example DL-21

2-((4-chlorophenyl)(2-cyclopropyl-1-(1,2,3,4-tetrahydronaphthalen-2-yl)-1H-benzo[d]imidazol-6-yl)methyl)thiazole

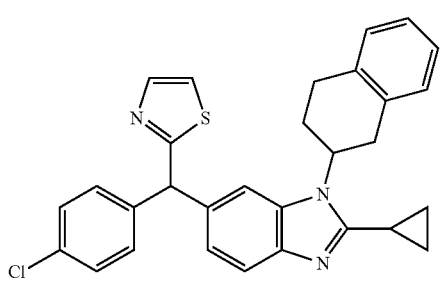 [SMILES: Clc1ccc(C(c2ccc3nc(C4CC4)n(C4CCc5ccccc5C4)c3c2)c2nccs2)cc1]

and (4-chlorophenyl)(2-cyclopropyl-1-(1,2,3,4-tetrahydronaphthalen-2-yl)-1H-benzo[d]imidazol-6-yl)(thiazol-2-yl)methanol

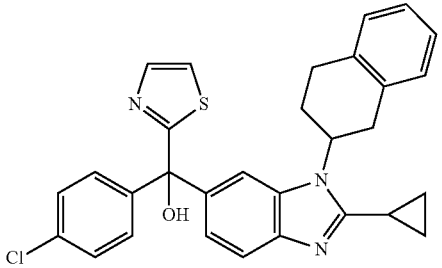 [SMILES: OC(c1ccc(Cl)cc1)(c1ccc2nc(C3CC3)n(C3CCc4ccccc4C3)c2c1)c1nccs1]

Step 1: (4-chlorophenyl)(4-nitro-3-((1,2,3,4-tetrahydronaphthalen-2-yl)amino)phenyl)(thiazol-2-yl)methanol A solution of (3-chloro-4-nitrophenyl)(4-chlorophenyl)(thiazol-2-yl)methanol (200 mg, 0.53 mmol), prepared as described in Example DL-16 above, 2-aminotetralin (89.4 mg, 0.58 mmol), potassium fluoride (152 mg, 2.62 mmol), and diisopropylethylamine (0.181 mL, 1.05 mmol) in DMSO (1 mL) was heated under argon at 100° C. for 18 hours. An additional 2 equivalents of diisopropylethylamine were added and the reaction was heated at 100° C. for 3 hours. An additional 90 mg of 2-aminotetralin were added and the reaction heated at 100° C. for 72 hours. Saturated NaHCO$_3$ was added and the reaction mixture was extracted with a mixture of ethyl ether and ethyl acetate. The organic layer was washed with water and brine and then dried over MgSO$_4$. Evaporation of the solvent in vacuo yielded a brown oil, which was purified by silica gel chromatography using a 50% dichloromethane:heptane to 100% dichloromethane gradient to yield (4-chlorophenyl)(4-nitro-3-((1,2,3,4-tetrahydronaphthalen-2-yl)amino)phenyl)(thiazol-2-yl)methanol.

Step 2: (4-chlorophenyl)(4-nitro-3-((1,2,3,4-tetrahydronaphthalen-2-yl)amino)phenyl)(thiazol-2-yl)methanol and N-(4-((4-chlorophenyl)(thiazol-2-yl)methyl)-2-((1,2,3,4-tetrahydronaphthalen-2-yl)amino)phenyl)acetamide To a solution of (4-chlorophenyl)(4-nitro-3-((1,2,3,4-tetrahydronaphthalen-2-yl)amino)phenyl)(thiazol-2-yl)methanol (160 mg, 0.33 mmol) in acetic acid (3.75 mL) under an argon atmosphere was added tin chloride dihydrate (367 mg, 1.63 mmol) and conc. HCl (0.25 mL). The reaction mixture was heated at 50° C. for 1.5 hours. Water and 3N NaOH were added and the mixture was extracted with dichloromethane (3×). The organic layer was dried over Na$_2$SO$_4$ and the solvent was evaporated in vacuo to yield 0.15 g of a mixture of (4-chlorophenyl)(4-nitro-3-((1,2,3,4-tetrahydronaphthalen-2-yl)amino)phenyl)(thiazol-2-yl)methanol and N-(4-((4-chlorophenyl)(thiazol-2-yl)methyl)-2-((1,2,3,4-tetrahydronaphthalen-2-yl)amino)phenyl)acetamide as a brown foam.

Step 3: 2-((4-chlorophenyl)(2-cyclopropyl-1-(1,2,3,4-tetrahydronaphthalen-2-yl)-1H-benzo[d]imidazol-6-yl)methyl)thiazole and (4-chlorophenyl)(2-cyclopropyl-1-(1,2,3,4-tetrahydronaphthalen-2-yl)-1H-benzo[d]imidazol-6-yl)(thiazol-2-yl)methanol trifluoroacetate salt A solution of (4-chlorophenyl)(4-nitro-3-((1,2,3,4-tetrahydronaphthalen-2-yl)amino)phenyl)(thiazol-2-yl)methanol (75 mg, 0.17 mmol) and cyclopropanecarboxaldehyde (0.026 mL, 0.34 mmol) in DMSO (1 mL) was rapidly stirred at room temperature in the presence of air. The reaction mixture was purified by reverse phase HPLC. The fractions containing the products were lyophilized to yield 2-((4-chlorophenyl)(2-cyclopropyl-1-(1,2,3,4-tetrahydronaphthalen-2-yl)-1H-benzo[d]imidazol-6-yl)methyl)thiazole trifluoroacetate salt [MS: 496.0 (M+H$^+$)] and (4-chlorophenyl)(2-cyclopropyl-1-(1,2,3,4-tetrahydronaphthalen-2-yl)-1H-benzo[d]imidazol-6-yl)(thiazol-2-yl)methanol trifluoroacetate salt [MS: 512.1 (M+H$^+$)].

Example DL-22

2-((4-chlorophenyl)(1-(3-chlorophenyl)-2-isopropyl-1H-benzo[d]imidazol-6-yl)methyl)thiazole

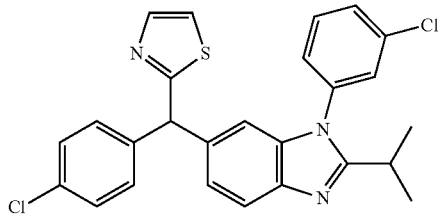 [SMILES: CC(C)c1nc2ccc(C(c3ccc(Cl)cc3)c3nccs3)cc2n1-c1cccc(Cl)c1]

2-((4-Chlorophenyl)(1-(3-chlorophenyl)-2-isopropyl-1H-benzo[d]imidazol-6-yl)methyl)thiazole was prepared according to the procedure as described in Example DL-8 above substituting isobutyraldehyde for propionaldehyde in Step 6. MS: 478.0 (M+H$^+$).

Example DL-23

2-((1-(3-chlorophenethyl)-2-methyl-1H-benzo[d]imidazol-6-yl)(4-chlorophenyl)methyl)thiazole

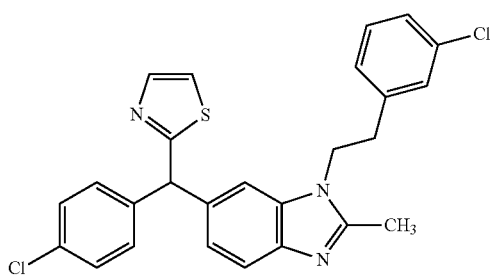 [SMILES: Cc1nc2ccc(C(c3ccc(Cl)cc3)c3nccs3)cc2n1CCc1cccc(Cl)c1]

Step 1: 2-(3-((3-chlorophenethyl)amino)-4-nitrophenyl)-2-(4-chlorophenyl)ethanethioamide To a solution of 2-(3-((3-chlorophenethyl)amino)-4-nitrophenyl)-2-(4-chlorophenyl)acetonitrile (1.04 g, 2.44 mmol), prepared as described in Example DL-4 above, and triethylamine (0.679 mL, 4.88 mmol) in pyridine (12 mL) was bubbled hydrogen sulfide gas (0.831 g, 24.40 mmol) for 2 hours. The reaction mixture was stirred at room temperature overnight. Acetonitrile was added to the reaction mixture and the solvent was evaporated to yield an orange solid which was dissolved in ethyl ether. The organic solution was washed with saturated NaHCO$_3$ and brine, and then dried over K$_2$CO$_3$. The solvent was evaporated in vacuo to yield 2-(3-((3-chlorophenethyl)amino)-4-nitrophenyl)-2-(4-chlorophenyl)ethanethioamide as an orange solid (1.51 g).

Steps 2 and 3: N-(3-chlorophenethyl)-5-((4-chlorophenyl)(thiazol-2-yl)methyl)-2-nitroaniline and N1-(3-chlorophenethyl)-5-((4-chlorophenyl)(thiazol-2-yl)methyl)benzene-1,2-diamine N-(3-chlorophenethyl)-5-((4-chlorophenyl)(thiazol-2-yl)methyl)-2-nitroaniline and N1-(3-chlorophenethyl)-5-((4-chlorophenyl)(thiazol-2-yl)methyl)benzene-1,2-diamine were prepared as described in Example DL-4 above.

Step 4: 2-((1-(3-chlorophenethyl)-2-methyl-1H-benzo[d]imidazol-6-yl)(4-chlorophenyl)methyl)thiazole To a solution of N1-(3-chlorophenethyl)-5-((4-chlorophenyl)(thiazol-2-yl)methyl)benzene-1,2-diamine (100 mg, 0.22 mmol) in trimethylorthoacetate (3 mL, 23.34 mmol) was added concentrated HCl (0.02 mL) and the solution was heated at reflux temperature for 18 hours. The reaction mixture was purified by reverse phase HPLC and the fractions containing the product were lyophilized to yield 2-((1-(3-chlorophenethyl)-2-methyl-1H-benzo[d]imidazol-6-yl)(4-chlorophenyl)methyl)thiazole trifluoroacetate salt as a light brown oil. MS: 478.0 (M+H$^+$).

Example DL-24

2-((4-chlorophenyl)(1-(2,3-dihydro-1H-inden-2-yl)-2-methyl-1H-benzo[d]imidazol-6-yl)methyl)thiazole

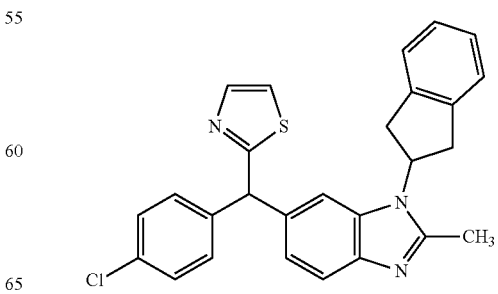

and 2-((4-chlorophenyl)(2-cyclopropyl-1-(2,3-di-
hydro-1H-inden-2-yl)-1H-benzo[d]imidazol-6-yl)
methyl)thiazole

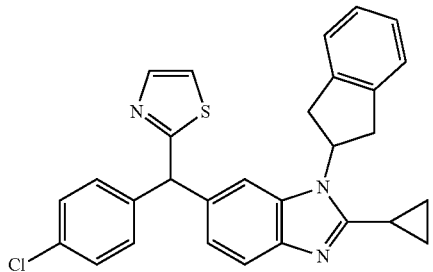 [SMILES: Clc1ccc(C(c2ccc3nc(C4CC4)n(C4Cc5ccccc5C4)c3c2)c2nccs2)cc1]

Step 1: (4-chlorophenyl)(3-((2,3-dihydro-1H-inden-
2-yl)amino)-4-nitrophenyl)(thiazol-2-yl)methanol A solution of (3-chloro-4-nitrophenyl)(4-chlorophenyl)
(thiazol-2-yl)methanol (220 mg, 0.58 mmol), prepared as
described in Example DL-16 above and 2-indanamine (0.39
g, 2.89 mmol) in n-butanol (1 mL) was heated in a microwave at 160° C. for 1 hour. Ethyl acetate was added and the resulting mixture was washed with water (4×) and brine (1×). The organic layer was evaporated and the residue purified by silica gel chromatography using a 50% dichloromethane:heptane to 100% dichloromethane gradient to yield (4-chlorophenyl)(3-((2,3-dihydro-1H-inden-2-yl)amino)-4-nitrophenyl)(thiazol-2-yl)methanol as a yellow oil.

Step 2: A mixture of 5-((4-chlorophenyl)(thiazol-2-
yl)methyl)-N1-(2,3-dihydro-1H-inden-2-yl)benzene-
1,2-diamine, N-(4-((4-chlorophenyl)(thiazol-2-yl)
methyl)-2-((2,3-dihydro-1H-inden-2-yl)amino)
phenyl)acetamide and 2-((4-chlorophenyl)(1-(2,3-
dihydro-1H-inden-2-yl)-2-methyl-1H-benzo[d]
imidazol-6-yl)methyl)thiazole To a solution of (4-chlorophenyl)(3-((2,3-dihydro-1H-inden-2-yl)amino)-4-nitrophenyl)(thiazol-2-yl)methanol (0.08 g, 0.33 mmol) in acetic acid (3 mL) under an argon atmosphere was added tin chloride dihydrate (0.19 g, 0.84 mmol) and conc. HCl (0.2 mL). The reaction mixture was heated at 50° C. for 18 hours. The solvent was evaporated, ethyl ether and dichloromethane were added, and the mixture was washed with 1N NaOH. The organic layer was separated and the solvent was evaporated in vacuo to yield a mixture of 5-((4-chlorophenyl)(thiazol-2-yl)methyl)-N1-(2,3-dihydro-1H-inden-2-yl)benzene-1,2-diamine, N-(4-((4-chlorophenyl)(thiazol-2-yl)methyl)-2-((2,3-dihydro-1H-inden-2-yl)amino)phenyl)acetamide and 2-((4-chlorophenyl)(1-(2,3-dihydro-1H-inden-2-yl)-2-methyl-1H-benzo[d]imidazol-6-yl)methyl)thiazole.

Step 3: 2-((4-chlorophenyl)(2-cyclopropyl-1-(2,3-
dihydro-1H-inden-2-yl)-1H-benzo[d]imidazol-6-yl)
methyl)thiazole and 2-((4-chlorophenyl)(1-(2,3-
dihydro-1H-inden-2-yl)-2-methyl-1H-benzo[d]
imidazol-6-yl)methyl)thiazole A solution of the mixture of 5-((4-chlorophenyl)(thiazol-2-yl)methyl)-N1-(2,3-dihydro-1H-inden-2-yl)benzene-1,2-diamine, N-(4-((4-chlorophenyl)(thiazol-2-yl)methyl)-2-((2,3-dihydro-1H-inden-2-yl)amino)phenyl)acetamide and 2-((4-chlorophenyl)(1-(2,3-dihydro-1H-inden-2-yl)-2-methyl-1H-benzo[d]imidazol-6-yl)methyl)thiazole from Step 2 above (70 mg, 0.152 mmol) and cyclopropanecarboxaldehyde (0.025 mL, 0.32 mmol) in DMSO (1 mL) was rapidly stirred at room temperature in the presence of air. The reaction mixture was purified by reverse phase HPLC. The fractions containing the desired products were lyophilized to yield 2-((4-chlorophenyl)(2-cyclopropyl-1-(2,3-dihydro-1H-inden-2-yl)-1H-benzo[d]imidazol-6-yl)methyl)thiazole trifluoroacetate salt [MS: 482.1 (M+H$_+$)] and 2-((4-chlorophenyl)(1-(2,3-dihydro-1H-inden-2-yl)-2-methyl-1H-benzo[d]imidazol-6-yl)methyl)thiazole trifluoroacetate salt [MS: 456 (M+H$^+$)].

Example DL-25

2-((4-chlorophenyl)(1-(1-(4-chlorophenyl)propan-2-
yl)-2-cyclopropyl-1H-benzo[d]imidazol-6-yl)
methyl)thiazole

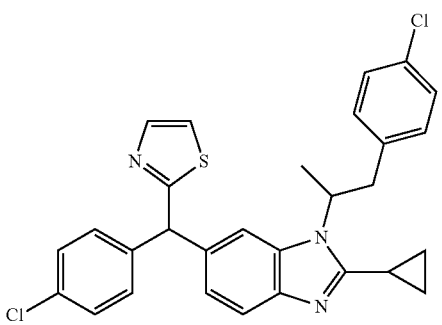 [SMILES: CC(Cc1ccc(Cl)cc1)n1c(C2CC2)nc2ccc(C(c3ccc(Cl)cc3)c3nccs3)cc21]

2-((4-Chlorophenyl)(1-(1-(4-chlorophenyl)propan-2-yl)-2-cyclopropyl-1H-benzo[d]imidazol-6-yl)methyl)thiazole was prepared according to the procedure as described in Example DL-19 above substituting cyclopropanecarboxaldehyde for propionaldehyde in Step 3. MS: 518.2 (M+H$^+$).

Example DL-26

2-((4-chlorophenyl)(1-(2-(4-chlorophenyl)propyl)-2-
cyclopropyl-1H-benzo[d]imidazol-6-yl)methyl)thi-
azole

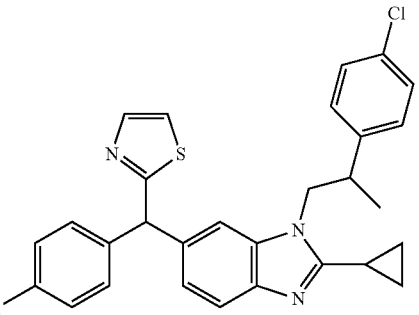

2-((4-Chlorophenyl)(1-(2-(4-chlorophenyl)propyl)-2-cyclopropyl-1H-benzo[d]imidazol-6-yl)methyl)thiazole was prepared according to the procedure as described in Example DL-25 above substituting 2-methyl-2-(4-chlorophenyl)ethylamine hydrochloride for 1-methyl-2-(4-chlorophenyl)ethylamine hydrochloride in Step 1. MS: 518.0 (M+H⁺).

Example DL-27

2-((1-(3-chlorophenethyl)-2-propyl-1H-benzo[d]imidazol-6-yl)(4-chlorophenyl)methyl)thiazole

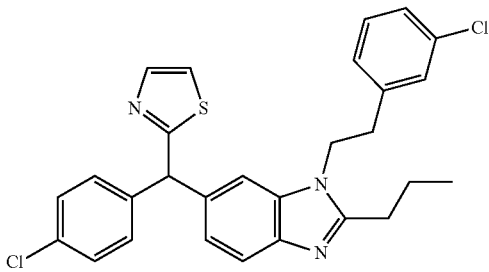 [SMILES: CCCc1nc2ccc(C(c3ccc(Cl)cc3)c3nccs3)cc2n1CCc1cccc(Cl)c1]

2-((1-(3-Chlorophenethyl)-2-propyl-1H-benzo[d]imidazol-6-yl)(4-chlorophenyl)methyl)thiazole was prepared according to the procedure as described in Example DL-4 above substituting butyraldehyde for cyclopropanecarboxaldehyde in Step 6. MS: 506.1 (M+H⁺).

Example DL-28

2-((1-(3-chlorophenethyl)-1H-benzo[d]imidazol-6-yl)(4-chlorophenyl)methyl)thiazole

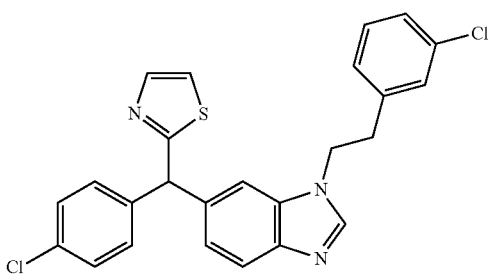 [SMILES: Clc1ccc(C(c2ccc3ncn(CCc4cccc(Cl)c4)c3c2)c2nccs2)cc1]

2-((1-(3-Chlorophenethyl)-1H-benzo[d]imidazol-6-yl)(4-chlorophenyl)methyl)thiazole was prepared according to the procedure as described in Example DL-23 above substituting trimethylorthoformate for trimethylorthoacetate in Step 4. MS: 464.0 (M+H⁺).

Example DL-29

1-(4-chlorophenyl)-2-(6-((4-chlorophenyl)(thiazol-2-yl)methyl)-2-ethyl-1H-benzo[d]imidazol-1-yl)ethanol

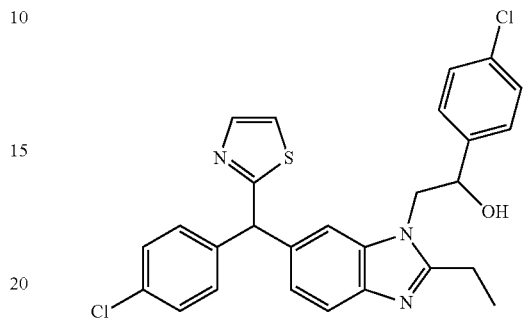

1-(4-Chlorophenyl)-2-(6-((4-chlorophenyl)(thiazol-2-yl)methyl)-2-ethyl-1H-benzo[d]imidazol-1-yl)ethanol was prepared according to the procedure as described in Example DL-19 above substituting 2-(4-chlorophenyl)-2-hydroxyethylamine hydrochloride for 2-(4-chlorophenyl)-1-methylethylamine hydrochloride in Step 1. MS: 508.0 (M+H⁺).

Example DL-30

2-((4-chlorophenyl)(1-(1-(4-chlorophenyl)propan-2-yl)-2-(difluoromethyl)-1H-benzo[d]imidazol-6-yl)methyl)thiazole

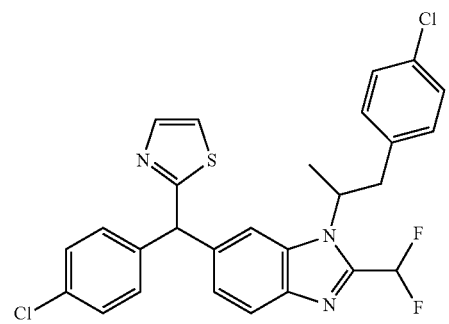 [SMILES: CC(Cc1ccc(Cl)cc1)n1c(C(F)F)nc2ccc(C(c3ccc(Cl)cc3)c3nccs3)cc21]

A solution of 5-((4-chlorophenyl)(thiazol-2-yl)methyl)-N1-(1-(4-chlorophenyl)propan-2-yl)benzene-1,2-diamine (550 mg, 1.17 mmol), prepared as described in Example DL-19 above, and difluoroacetic acid (1 mL) was heated at 50° C. under an argon atmosphere for 72 hours. The solvent was evaporated in vacuo and the residue was purified by reverse phase HPLC. The fractions containing the product were lyophilized to yield 2-((4-chlorophenyl)(1-(1-(4-chlorophenyl)propan-2-yl)-2-(difluoromethyl)-1H-benzo[d]imidazol-6-yl)methyl)thiazole trifluoroacetate salt [MS: 528.1 (M+H⁺)].

Example DL-31

6-((4-chlorophenyl)(phenyl)methyl)-2-cyclopropyl-1-((S)-2-phenylpropyl)-1H-benzo[d]imidazole

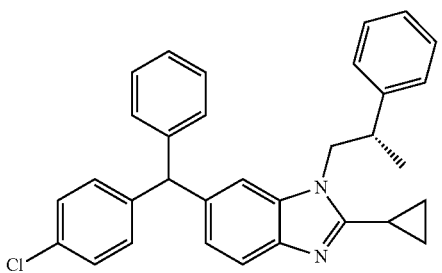 [SMILES: C[C@H](Cn1c(C2CC2)nc2ccc(C(c3ccccc3)c3ccc(Cl)cc3)cc21)c1ccccc1]

and (S)-6-benzhydryl-2-cyclopropyl-1-(2-phenylpropyl)-1H-benzo[d]imidazole

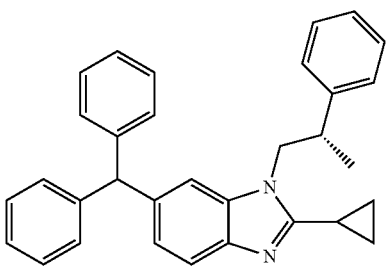 [SMILES: C[C@H](Cn1c(C2CC2)nc2ccc(C(c3ccccc3)c3ccccc3)cc21)c1ccccc1]

Step 1: Mixture of (S)-bis(4-chlorophenyl)(4-nitro-3-((2-phenylpropyl)amino)phenyl)methanol, (S)-methyl 2,2-bis(4-chlorophenyl)-2-(4-nitro-3-((2-phenylpropyl)amino)phenyl)acetate and (S)-5-(bis(4-chlorophenyl)methyl)-2-nitro-N-(2-phenylpropyl)aniline A solution of methyl 2-(3-chloro-4-nitrophenyl)-2,2-bis(4-chlorophenyl)acetate (400 mg, 0.89 mmol), prepared as described in Example DL-2 above, (S)-2-phenylpropylamine (180 mg, 1.33 mmol), potassium carbonate (368 mg, 2.66 mmol), and potassium fluoride (258 mg, 4.44 mmol) in DMSO (2 mL) was heated under argon at 100° C. for 18 hours. Ethyl acetate was added and the organic mixture was washed with water and brine and then evaporated in vacuo to yield a yellow semi-solid. The residue was purified by reverse phase HPLC and fractions containing the products were lyophilized to yield (S)-bis(4-chlorophenyl)(4-nitro-3-((2-phenylpropyl)amino)phenyl)methanol as an orange solid as well as a mixture of (S)-methyl 2,2-bis(4-chlorophenyl)-2-(4-nitro-3-((2-phenylpropyl)amino)phenyl)acetate and (S)-5-(bis(4-chlorophenyl)methyl)-2-nitro-N-(2-phenylpropyl)aniline as an orange oil.

Step 2: A mixture of (S)-5-(bis(4-chlorophenyl)methyl)-N1-(2-phenylpropyl)benzene-1,2-diamine, 5-((4-chlorophenyl)(phenyl)methyl)-N1-((S)-2-phenylpropyl)benzene-1,2-diamine and (S)-5-benzhydryl-N1-(2-phenylpropyl)benzene-1,2-diamine To a solution of (S)-bis(4-chlorophenyl)(4-nitro-3-((2-phenylpropyl)amino)phenyl)methanol (80 mg, 0.158 mmol) in MeOH (80 mL) and ethyl acetate (80 mL) was added 5% Pd/C sulfide (420 mg) and the mixture was placed under 50 psi hydrogen at room temperature for 2.5 hours. The reaction mixture was filtered through CELITE elite and the solvent evaporated in vacuo to yield a mixture of (S)-5-(bis(4-chlorophenyl)methyl)-N1-(2-phenylpropyl)benzene-1,2-diamine, 5-((4-chlorophenyl)(phenyl)methyl)-N1-((S)-2-phenylpropyl)benzene-1,2-diamine and (S)-5-benzhydryl-N1-(2-phenylpropyl)benzene-1,2-diamine.

Step 3: 6-((4-chlorophenyl)(phenyl)methyl)-2-cyclopropyl-1-((S)-2-phenylpropyl)-1H-benzo[d]imidazole and (S)-6-benzhydryl-2-cyclopropyl-1-(2-phenylpropyl)-1H-benzo[d]imidazole A solution of the mixture of (S)-5-(bis(4-chlorophenyl)methyl)-N1-(2-phenylpropyl)benzene-1,2-diamine, 5-((4-chlorophenyl)(phenyl)methyl)-N1-((S)-2-phenylpropyl)benzene-1,2-diamine and (S)-5-benzhydryl-N1-(2-phenylpropyl)benzene-1,2-diamine (120 mg, 0.26 mmol) and cyclopropanecarboxaldehyde (0.040 mL, 0.52 mmol) in DMSO (2 mL) was rapidly stirred at room temperature in the presence of air for 4 days. The reaction mixture was purified by reverse phase HPLC. Fractions containing the desired products were combined and lyophilized to yield 6-((4-chlorophenyl)(phenyl)methyl)-2-cyclopropyl-1-((S)-2-phenylpropyl)-1H-benzo[d]imidazole (12.7 mg) as a white foam and (S)-6-benzhydryl-2-cyclopropyl-1-(2-phenylpropyl)-1H-benzo[d]imidazole as a white foam.

Example DL-32

(S)-6-(bis(4-chlorophenyl)methyl)-2-methyl-1-(2-phenylpropyl)-1H-benzo[d]imidazole

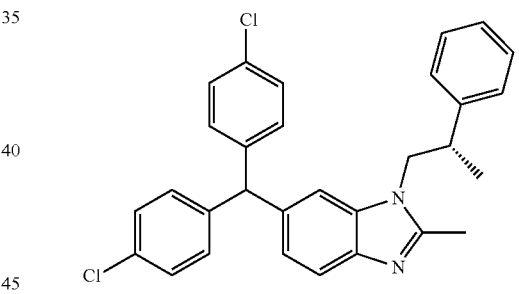

Step 1: (S)-methyl 2,2-bis(4-chlorophenyl)-2-(2-methyl-1-(2-phenylpropyl)-1H-benzo[d]imidazol-6-yl)acetate To a solution of (S)-methyl 2-(4-amino-3-((2-phenylpropyl)amino)phenyl)-2,2-bis(4-chlorophenyl)acetate (114 mg, 0.22 mmol), prepared as described in Example DL-15 above, in trimethylorthoacetate (3 mL, 23.34 mmol) is added concentrated HCl (0.02 mL) and the solution is heated at reflux temperature for 18 hours. The reaction mixture is purified by reverse phase HPLC and the fractions containing the product are lyophilized to yield (S)-methyl 2,2-bis(4-chlorophenyl)-2-(2-methyl-1-(2-phenylpropyl)-1H-benzo[d]imidazol-6-yl)acetate trifluoroacetate salt.

Step 2: (S)-2,2-bis(4-chlorophenyl)-2-(2-methyl-1-(2-phenylpropyl)-1H-benzo[d]imidazol-6-yl)acetic acid To a solution of (S)-methyl 2,2-bis(4-chlorophenyl)-2-(2-methyl-1-(2-phenylpropyl)-1H-benzo[d]imidazol-6-yl)acetate (117 mg, 0.215 mmol) in MeOH (4 mL) is added 3N NaOH (1 mL, 3 mmol) and the solution is heated at 45° C. overnight. The solvent is removed in vacuo and then water and 3 mL 1N HCl is added. The mixture is extracted with ethyl acetate and the organic layer is dried over MgSO$_4$ and evaporated in vacuo to yield (S)-2,2-bis(4-chlorophenyl)-2-(2-methyl-1-(2-phenylpropyl)-1H-benzo[d]imidazol-6-yl) acetic acid.

Step 3: (S)-6-(bis(4-chlorophenyl)methyl)-2-methyl-1-(2-phenylpropyl)-1H-benzo[d]imidazole A solution of (S)-2,2-bis(4-chlorophenyl)-2-(2-methyl-1-(2-phenylpropyl)-1H-benzo[d]imidazol-6-yl)acetic acid (117 mg, 0.221 mmol) and DBU (0.099 mL, 0.66 mmol) in toluene (10 mL) is heated at 90° C. overnight under argon. After evaporation of the solvent, the residue is purified by reverse phase HPLC and the fractions containing the product are lyophilized to yield (S)-6-(bis(4-chlorophenyl)methyl)-2-methyl-1-(2-phenylpropyl)-1H-benzo[d]imidazole trifluoroacetate salt. MS: 485.0 (M+H$^+$).

Example DL-33

1-(4-chlorophenyl)-2-(6-((4-chlorophenyl)(thiazol-2-yl)methyl)-2-cyclopropyl-1H-benzo[d]imidazol-1-yl)ethanol

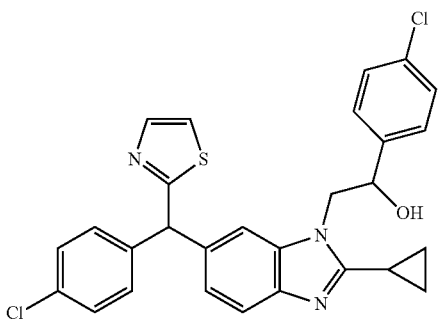 [SMILES: OC(Cn1c(C2CC2)nc2ccc(C(c3ccc(Cl)cc3)c3nccs3)cc21)c1ccc(Cl)cc1]

1-(4-Chlorophenyl)-2-(6-((4-chlorophenyl)(thiazol-2-yl)methyl)-2-cyclopropyl-1H-benzo[d]imidazol-1-yl)ethanol was prepared according to the procedure as described in Example DL-29 above substituting cyclopropanecarboxaldehyde for propionaldehyde in the final step. MS: 520.0 (M+H$^+$).

Example DL-34 ethyl 1-(3-chlorophenyl)-6-((4-chlorophenyl)(thiazol-2-yl)methyl)-1H-benzo[d]imidazole-2-carboxylate

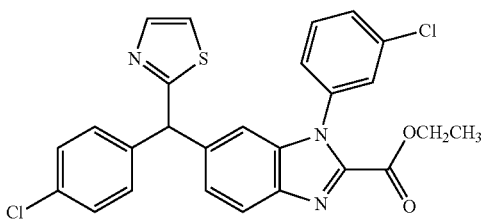 [SMILES: CCOC(=O)c1nc2ccc(C(c3ccc(Cl)cc3)c3nccs3)cc2n1-c1cccc(Cl)c1]

Ethyl 1-(3-chlorophenyl)-6-((4-chlorophenyl)(thiazol-2-yl)methyl)-1H-benzo[d]imidazole-2-carboxylate was prepared according to the procedure as described in Example DL-8 above substituting ethyl glyoxalate (50% in toluene) for propionaldehyde in Step 6. MS: 508.0 (M+H$^+$).

Example DL-35

2-((4-chlorophenyl)(1-(3-chlorophenyl)-2-(furan-3-yl)-1H-benzo[d]imidazol-6-yl)methyl)thiazole

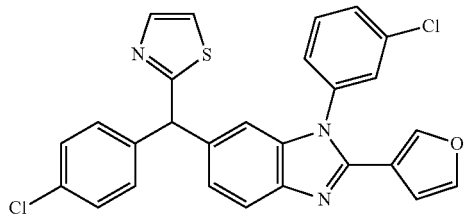 [SMILES: Clc1ccc(C(c2ccc3nc(-c4ccoc4)n(-c4cccc(Cl)c4)c3c2)c2nccs2)cc1]

2-((4-Chlorophenyl)(1-(3-chlorophenyl)-2-(furan-3-yl)-1H-benzo[d]imidazol-6-yl)methyl)thiazole was prepared according to the procedure as described in Example DL-8 above substituting 3-furancarboxaldehyde for propionaldehyde in Step 6. MS: 502.0 (M+H$^+$).

Example DL-36

2-((4-chlorophenyl)(1-(3-chlorophenyl)-2-methyl-1H-benzo[d]imidazol-6-yl)methyl)thiazole

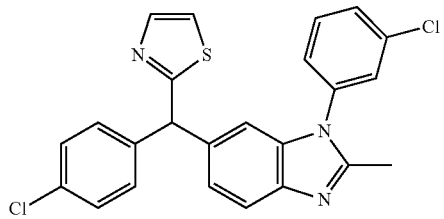 [SMILES: Cc1nc2ccc(C(c3ccc(Cl)cc3)c3nccs3)cc2n1-c1cccc(Cl)c1]

To a solution of N1-(3-chlorophenyl)-5-((4-chlorophenyl)(thiazol-2-yl)methyl)benzene-1,2-diamine (200 mg, 0.47 mmol), prepared as described in Example DL-8 above, in trimethylorthoacetate (3 mL, 23.34 mmol) was added concentrated HCl (0.02 mL) and the solution was heated at reflux temperature for 18 hours. The reaction mixture was purified by reverse phase HPLC and the fractions containing the product were lyophilized to yield 2-((4-chlorophenyl)(1-(3-chlorophenyl)-2-methyl-1H-benzo[d]imidazol-6-yl)methyl)thiazole trifluoroacetate salt as a white solid. MS: 450.1 (M+H$^+$).

Example DL-37

2-((4-chlorophenyl)(2-cyclopropyl-1-(pyridin-2-ylmethyl)-1H-benzo[d]imidazol-6-yl)methyl)thiazole

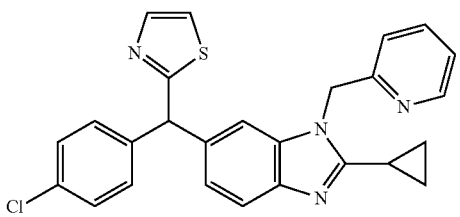 [SMILES: Clc1ccc(C(c2ccc3nc(C4CC4)n(Cc4ccccn4)c3c2)c2nccs2)cc1]

Step 1:
5-fluoro-2-nitro-N-(pyridin-2-ylmethyl)aniline

To a solution of 2,4-difluoronitrobenzene (10 mL, 90.29 mmol) and 2-aminomethylpyridine (10.14 mL, 99.32 mmol) in acetonitrile (60 mL) was added triethylamine (15.061 mL, 108.35 mmol). The reaction mixture was stirred at room temperature overnight. Water (50 mL) was added, the mixture stirred for 30 minutes, and the resulting yellow precipitate was filtered off to yield 5-fluoro-2-nitro-N-(pyridin-2-ylmethyl)aniline. Excess water was added to the filtrate to yield additional 5-fluoro-2-nitro-N-(pyridin-2-ylmethyl)aniline as a yellow solid.

Step 2: 2-(4-chlorophenyl)-2-(4-nitro-3-((pyridin-2-ylmethyl)amino)phenyl)acetonitrile To a stirred solution of 4-chlorophenylacetonitrile (7.32 mL, 55.1 mmol) in THF (80 mL) and isopropyl alcohol (8 mL) was added t-BuOK (14.73 g, 131 mmol) and the mixture was stirred at room temperature for 5 minutes. The temperature of the reaction was lowered to 0° C. and 5-fluoro-2-nitro-N-(pyridin-2-ylmethyl)aniline (12.98 g, 52.50 mmol) in THF (40 mL) was added and the reaction mixture was stirred overnight at room temperature. Water was added and the mixture was extracted with ethyl acetate. The yellow precipitate that formed was filtered off and discarded. The organic layer was washed with aqueous NaHCO$_3$, dried over Na$_2$SO$_4$, and the solvent was evaporated in vacuo to yield a black oil. The residue was subjected to silica gel chromatography using a methanol/dichloromethane solvent gradient to yield 2-(4-chlorophenyl)-2-(4-nitro-3-((pyridin-2-ylmethyl)amino)phenyl)acetonitrile as a residue. Final purification by silica gel chromatography using dichloromethane as eluent yielded 2-(4-chlorophenyl)-2-(4-nitro-3-((pyridin-2-ylmethyl)amino)phenyl)acetonitrile.

Step 3: 2-(4-chlorophenyl)-2-(4-nitro-3-((pyridin-2-ylmethyl)amino)phenyl)ethanethioamide To a solution of 2-(4-chlorophenyl)-2-(4-nitro-3-((pyridin-2-ylmethyl)amino)phenyl)acetonitrile (2.9 g, 4.29 mmol) in EtOH (75 mL) under an argon atmosphere was added phosphorus pentasulfide (3.81 g, 8.57 mmol) and the reaction mixture was heated to reflux temperature for 24 hours. The solvent was evaporated and the residue was subjected to silica gel chromatography reaction mixture was poured into ice water and extracted with ethyl acetate. The organic layer was washed with water, brine, and dried over MgSO$_4$. The solvent was removed in vacuo and the residue was purified by silica gel chromatography using a dichloromethane to 5% methanol:dichloromethane gradient as eluent to yield 2-(4-chlorophenyl)-2-(4-nitro-3-((pyridin-2-ylmethyl)amino)phenyl)ethanethioamide.

Step 4: 5-((4-chlorophenyl)(thiazol-2-yl)methyl)-2-nitro-N-(pyridin-2-ylmethyl)aniline To a solution of 2-(4-chlorophenyl)-2-(4-nitro-3-((pyridin-2-ylmethyl)amino)phenyl)ethanethioamide (0.94 g, 1.37 mmol) in acetic acid (15 mL) was added water (0.5 mL) and bromoacetaldehyde diethylacetal (0.847 mL, 5.46 mmol). The reaction mixture was heated to 100° C. for 30 minutes and then aqueous NaHCO$_3$. The resulting mixture was extracted with ethyl ether and the organic layer was washed with brine and evaporated in vacuo to yield 0.75 g a dark oil. The residue was purified by silica gel chromatography using a dichloromethane to 4% methanol:dichloromethane gradient to yield 5-((4-chlorophenyl)(thiazol-2-yl)methyl)-2-nitro-N-(pyridin-2-ylmethyl)aniline as a yellow oil.

Step 5: 5-((4-chlorophenyl)(thiazol-2-yl)methyl)-N1-(pyridin-2-ylmethyl)benzene-1,2-diamine A solution of 5-((4-chlorophenyl)(thiazol-2-yl)methyl)-2-nitro-N-(pyridin-2-ylmethyl)aniline (0.63 g, 1.44 mmol) in ethyl alcohol (150 mL) was placed under a hydrogen atmosphere in the presence of 3 mL of Raney nickel (50% slurry in water) overnight. The catalyst was filtered off and the filtrate was evaporated in vacuo to yield 5-((4-chlorophenyl)(thiazol-2-yl)methyl)-N1-(pyridin-2-ylmethyl)benzene-1,2-diamine as a dark gum.

Step 6: 2-((4-chlorophenyl)(2-cyclopropyl-1-(pyridin-2-ylmethyl)-1H-benzo[d]imidazol-6-yl)methyl)thiazole A rapidly stirred solution of 5-((4-chlorophenyl)(thiazol-2-yl)methyl)-N1-(pyridin-2-ylmethyl)benzene-1,2-diamine (140 mg, 0.34 mmol) and cyclopropanecarboxaldehyde (0.053 mL, 0.69 mmol) in DMSO (1.4 mL) was kept at room temperature in the presence of air for 4 days. The reaction mixture was purified by reverse phase HPLC and the fractions containing the product were lyophilized to yield 35.8 mg of 2-((4-chlorophenyl)(2-cyclopropyl-1-(pyridin-2-ylmethyl)-1H-benzo[d]imidazol-6-yl)methyl)thiazole bistrifluoroacetate salt as a white solid. MS: 457.0 (M+H$^+$).

Example DL-38

(1 S,2R)-2-(6-(bis(4-chlorophenyl)methyl)-2-cyclopropyl-1H-benzo[d]imidazol-1-yl)-1-phenylpropan-1-ol

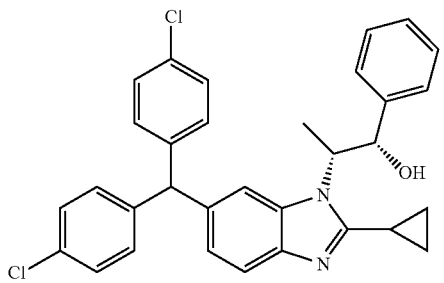

(1S,2R)-2-(6-(bis(4-chlorophenyl)methyl)-2-cyclopropyl-1H-benzo[d]imidazol-1-yl)-1-phenylpropan-1-ol was prepared according to the procedure as described in Example DL-13 above substituting (+)-(1S,2R)-norephedrine for (S)-2-amino-1-phenylethanol in Step 1. MS: 527.2 (M+H⁺).

Example DL-39

6-(bis(4-chlorophenyl)methyl)-1-(2,3-dihydro-1H-inden-2-yl)-2-ethyl-1H-benzo[d]imidazole

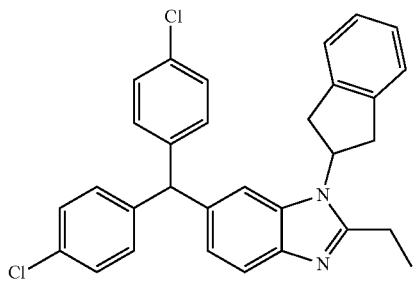 [SMILES: CCc1nc2ccc(C(c3ccc(Cl)cc3)c3ccc(Cl)cc3)cc2n1C1Cc2ccccc2C1]

Step 1: methyl 2,2-bis(4-chlorophenyl)-2-(3-((2,3-dihydro-1H-inden-2-yl)amino)-4-nitrophenyl)acetate and N-(5-(bis(4-chlorophenyl)methyl)-2-nitrophenyl)-2,3-dihydro-1H-inden-2-amine A solution of methyl 2-(3-chloro-4-nitrophenyl)-2,2-bis(4-chlorophenyl)acetate (670 mg, 1.49 mmol), prepared as described in Example DL-2 above, 2-indanamine (0.381 mL, 2.97 mmol), and DIPEA (0.538 mL, 3.12 mmol) in 1,4-dioxane (2 mL) was heated under argon at 95° C. overnight. Sufficient 1,4-dioxane was evaporated to produce a thick reaction mixture, another 0.38 g of 2-indanamine was added, and then the reaction mixture was heated at 110° C. for 72 hours. The solvent was evaporated and the residue was purified by reverse phase HPLC. Fractions containing the products of the reaction were combined and lyophilized to yield methyl 2,2-bis(4-chlorophenyl)-2-(3-((2,3-dihydro-1H-inden-2-yl)amino)-4-nitrophenyl)acetate trifluoroacetate salt and N-(5-(bis(4-chlorophenyl)methyl)-2-nitrophenyl)-2,3-dihydro-1H-inden-2-amine trifluoroacetate salt (140 mg) as green solids.

Step 2: 5-(bis(4-chlorophenyl)methyl)-N1-(2,3-dihydro-1H-inden-2-yl)benzene-1,2-diamine To a solution of N-(5-(bis(4-chlorophenyl)methyl)-2-nitrophenyl)-2,3-dihydro-1H-inden-2-amine trifluoroacetate salt (60 mg, 0.099 mmol) in MeOH (100 mL) was added 5% Pt/C sulfide (110 mg) and the mixture was placed under 45 psi hydrogen at room temperature for 4 hours. The reaction mixture was filtered through CELITE and the solvent evaporated in vacuo to yield 5-(bis(4-chlorophenyl)methyl)-N1-(2,3-dihydro-1H-inden-2-yl)benzene-1,2-diamine.

Step 3: 6-(bis(4-chlorophenyl)methyl)-1-(2,3-dihydro-1H-inden-2-yl)-2-ethyl-1H-benzo[d]imidazole A solution of 5-(bis(4-chlorophenyl)methyl)-N1-(2,3-dihydro-1H-inden-2-yl)benzene-1,2-diamine (56.5 mg, 0.12 mmol) and propionaldehyde (0.018 mL, 0.25 mmol) in DMSO (1 mL) was rapidly stirred at room temperature in the presence of air for 18 hours. The reaction mixture was purified by reverse phase HPLC. Fractions containing the desired product were combined and lyophilized to yield 6-(bis(4-chlorophenyl)methyl)-1-(2,3-dihydro-1H-inden-2-yl)-2-ethyl-1H-benzo[d]imidazole trifluoroacetate salt as a clear oil. MS: 497.2 (M+H⁺).

Example DL-40

6-(bis(4-chlorophenyl)methyl)-1-(2,3-dihydro-1H-inden-2-yl)-1H-benzo[d]imidazole

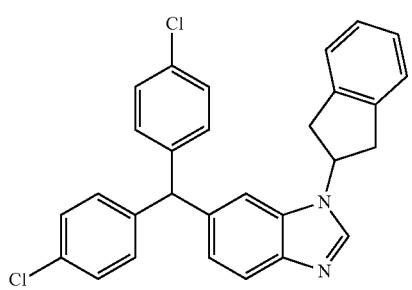 [SMILES: Clc1ccc(C(c2ccc(Cl)cc2)c2ccc3ncn(C4Cc5ccccc5C4)c3c2)cc1]

To a solution of 5-(bis(4-chlorophenyl)methyl)-N1-(2,3-dihydro-1H-inden-2-yl)benzene-1,2-diamine (100 mg, 0.22 mmol), prepared as described in Example DL-39 above, in trimethylorthoacetate (3 mL, 23.34 mmol) is added concentrated HCl (0.02 mL) and the solution is heated at reflux temperature for 18 hours. The reaction mixture is purified by reverse phase HPLC and the fractions containing the product are lyophilized to yield 6-(bis(4-chlorophenyl)methyl)-1-(2,3-dihydro-1H-inden-2-yl)-1H-benzo[d]imidazole trifluoroacetate salt. MS: 469.1 (M+H⁺).

Example DL-41

2-((4-chlorophenyl)(1-(3-chlorophenyl)-2-(thiophen-3-yl)-1H-benzo[d]imidazol-6-yl)methyl)thiazole

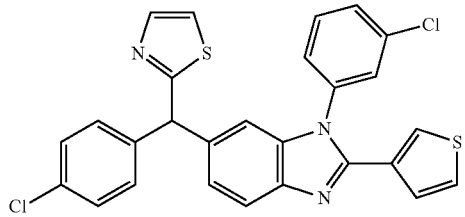 [SMILES: Clc1ccc(C(c2ccc3nc(-c4ccsc4)n(-c4cccc(Cl)c4)c3c2)c2nccs2)cc1]

2-((4-Chlorophenyl)(1-(3-chlorophenyl)-2-(thiophen-3-yl)-1H-benzo[d]imidazol-6-yl)methyl)thiazole was prepared according to the procedure as described in Example DL-8 above substituting 3-thiophenecarboxaldehyde for propionaldehyde in Step 6. MS: 518.0 (M+H⁺).

Example DL-42 tert-butyl 3-(1-(3-chlorophenyl)-6-((4-chlorophenyl)(thiazol-2-yl)methyl)-1H-benzo[d]imidazol-2-yl)azetidine-1-carboxylate

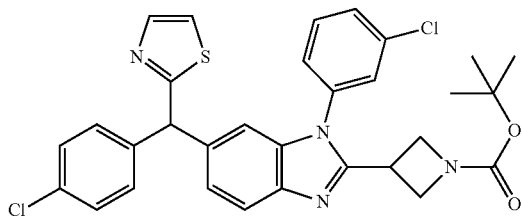 [SMILES: CC(C)(C)OC(=O)N1CC(c2nc3ccc(C(c4ccc(Cl)cc4)c4nccs4)cc3n2-c2cccc(Cl)c2)C1]

A solution of N1-(3-chlorophenyl)-5-((4-chlorophenyl)(thiazol-2-yl)methyl)benzene-1,2-diamine (100 mg, 0.24 mmol), prepared as described in Example DL-8 above, and 1-t-butyloxycarbonylazetidine-3-carboxaldehyde (88.7 mg, 0.47 mmol) in DMSO (1 mL) was rapidly stirred at room temperature in the presence of air for 4 days. The reaction mixture was heated at 50° C. for another 4 days. The reaction mixture was purified by reverse phase HPLC. Fractions containing the desired product were combined and lyophilized to yield tert-butyl 3-(1-(3-chlorophenyl)-6-((4-chlorophenyl)(thiazol-2-yl)methyl)-1H-benzo[d]imidazol-2-yl)azetidine-1-carboxylate trifluoroacetate salt (64.4 mg). MS: 591.0 (M+H$^+$).

Example DL-43

(R)-2-(6-(bis(4-chlorophenyl)(hydroxy)methyl)-2-cyclopropyl-1H-benzo[d]imidazol-1-yl)-1-phenylethanol

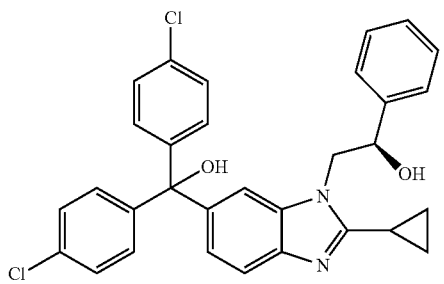 [SMILES: O[C@@H](Cn1c(C2CC2)nc2ccc(C(O)(c3ccc(Cl)cc3)c3ccc(Cl)cc3)cc21)c1ccccc1]

(R)-2-(6-(bis(4-chlorophenyl)(hydroxy)methyl)-2-cyclopropyl-1H-benzo[d]imidazol-1-yl)-1-phenylethanol was prepared according to the procedure as described in Example DL-6 above substituting (R)-2-(6-(bis(4-chlorophenyl)methyl)-2-cyclopropyl-1H-benzo[d]imidazol-1-yl)-1-phenylethanol in the reaction. MS: 529.1 (M+H$^+$).

Example DL-44

(1-(3-chlorophenyl)-6-((4-chlorophenyl)(thiazol-2-yl)methyl)-1H-benzo[d]imidazol-2-yl)methanol

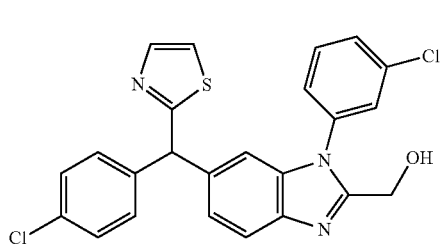 [SMILES: OCc1nc2ccc(C(c3ccc(Cl)cc3)c3nccs3)cc2n1-c1cccc(Cl)c1]

(1-(3-Chlorophenyl)-6-((4-chlorophenyl)(thiazol-2-yl)methyl)-1H-benzo[d]imidazol-2-yl)methanol was prepared according to the procedure as described in Example DL-8 above substituting glycolaldehyde for propionaldehyde in Step 6. MS: 466.0 (M+H$^+$).

Example DL-45

2-((4-chlorophenyl)(1-(2-(4-chlorophenyl)propyl)-2-(2,2,2-trifluoroethyl)-1H-benzo[d]imidazol-6-yl)methyl)thiazole

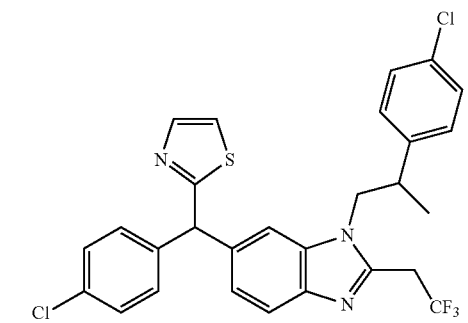 [SMILES: CC(Cn1c(CC(F)(F)F)nc2ccc(C(c3ccc(Cl)cc3)c3nccs3)cc21)c1ccc(Cl)cc1]

2-((4-Chlorophenyl)(1-(2-(4-chlorophenyl)propyl)-2-(2,2,2-trifluoroethyl)-1H-benzo[d]imidazol-6-yl)methyl)thiazole was prepared according to the procedure as described in Example DL-19 above substituting 2-methyl-2-(4-chlorophenyl)ethylamine hydrochloride for 1-methyl-2-(4-chlorophenyl)ethylamine hydrochloride in Step 1 and 3,3,3-trifluoropropionaldehyde for propionaldehyde in Step 3. MS: 560.0 (M+H$^+$).

Example DL-46

2-((1-(3-chlorophenethyl)-2-(2,2,2-trifluoroethyl)-1H-benzo[d]imidazol-6-yl)(4-chlorophenyl)methyl)thiazole

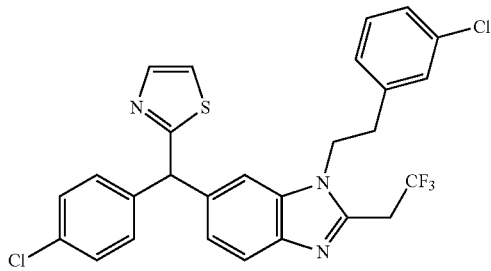

and (1-(3-chlorophenethyl)-2-(2,2,2-trifluoroethyl)-1H-benzo[d]imidazol-6-yl)(4-chlorophenyl)(thiazol-2-yl)methanol

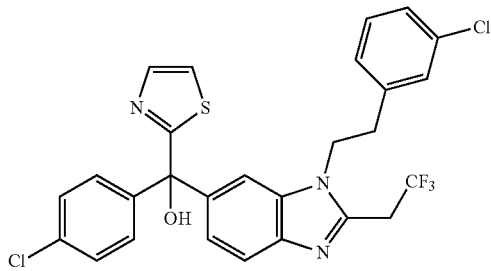 [SMILES: OC(c1ccc(Cl)cc1)(c1ccc2nc(CC(F)(F)F)n(CCc3cccc(Cl)c3)c2c1)c1nccs1]

A rapidly stirred solution of N1-(3-chlorophenethyl)-5-((4-chlorophenyl)(thiazol-2-yl)methyl)benzene-1,2-diamine (210 mg, 0.46 mmol), prepared as described in Example DL-4 above, and 3,3,3-trifluoropropionaldehyde (103.6 mg, 0.92 mmol) in DMSO (1 mL) was kept at room temperature in the presence of air for 48 hours. The reaction mixture was purified by reverse phase HPLC and the fractions containing the products were lyophilized to yield 2-((1-(3-chlorophenethyl)-2-(2,2,2-trifluoroethyl)-1H-benzo[d]imidazol-6-yl)(4-chlorophenyl)methyl)thiazole trifluoroacetate salt [MS: 546.0 (M+H$^+$)] and (1-(3-chlorophenethyl)-2-(2,2,2-trifluoroethyl)-1H-benzo[d]imidazol-6-yl)(4-chlorophenyl)(thiazol-2-yl)methanol trifluoroacetate salt [MS: 546.0 (M+H$^+$)] as white solids.

Example DL-47 tert-butyl 3-(1-(3-chlorophenethyl)-6-((4-chlorophenyl)(thiazol-2-yl)methyl)-1H-benzo[d]imidazol-2-yl)azetidine-1-carboxylate

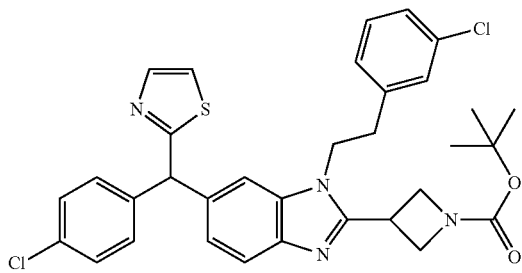 [SMILES: CC(C)(C)OC(=O)N1CC(c2nc3ccc(C(c4ccc(Cl)cc4)c4nccs4)cc3n2CCc2cccc(Cl)c2)C1]

tert-Butyl 3-(1-(3-chlorophenethyl)-6-((4-chlorophenyl)(thiazol-2-yl)methyl)-1H-benzo[d]imidazol-2-yl)azetidine-1-carboxylate was prepared according to the procedure as described in Example DL-4 above substituting 1-t-butyloxycarbonylazetidine-3-carboxaldehyde for cyclopropanecarboxaldehyde in Step 6. MS: 619.0 (M+H$^+$).

Example DL-48

2-((1-(3-chlorophenethyl)-2-(trifluoromethyl)-1H-benzo[d]imidazol-6-yl)(4-chlorophenyl)methyl)thiazole

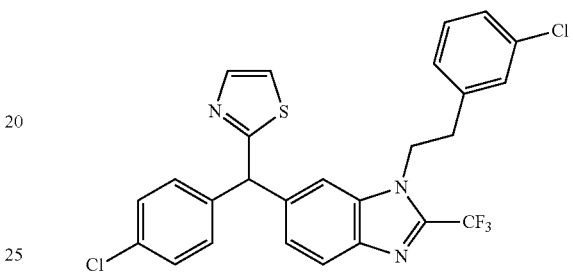

A solution of N1-(3-chlorophenethyl)-5-((4-chlorophenyl)(thiazol-2-yl)methyl)benzene-1,2-diamine (100 mg, 0.22 mmol), prepared as described in Example DL-4 above, and trifluoroacetic acid (2 mL) was stirred at room temperature under an argon atmosphere for 18 hours. The solvent was evaporated in vacuo and the residue was purified by reverse phase HPLC. The fractions containing the product were lyophilized to yield 2-((1-(3-chlorophenethyl)-2-(trifluoromethyl)-1H-benzo[d]imidazol-6-yl)(4-chlorophenyl)methyl)thiazole trifluoroacetate salt. MS: 532.0 (M+H$^+$).

Example DL-49

(1-(3-chlorophenethyl)-1H-benzo[d]imidazol-6-yl)(4-chlorophenyl)(thiazol-2-yl)methanol

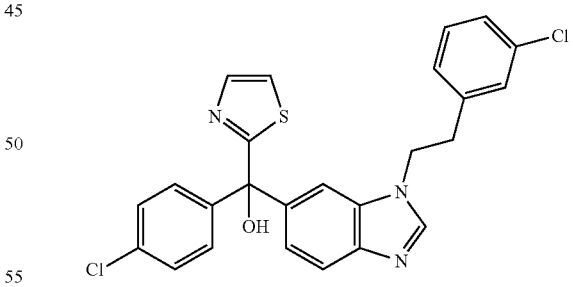

Step 1: 2-((1-(3-chlorophenethyl)-1H-benzo[d]imidazol-6-yl)(4-chlorophenyl)methyl)thiazole A rapidly stirred solution of N1-(3-chlorophenethyl)-5-((4-chlorophenyl)(thiazol-2-yl)methyl)benzene-1,2-diamine (350 mg, 0.77 mmol), prepared as described in Example DL-4 above, and ethyl glyoxalate (0.305 mL, 1.54 mmol) in DMSO (3.5 mL) was kept at room temperature in the presence of air for 7 days. The reaction mixture was purified by reverse phase HPLC and the fractions containing the product were lyophilized to yield 2-((1-(3-chlorophenethyl)-1H-benzo[d]imidazol-6-yl)(4-chlorophenyl)methyl)thiazole trifluoroacetate salt. MS: 464 (M+H⁺).

Step 2: (1-(3-chlorophenethyl)-1H-benzo[d]imidazol-6-yl)(4-chlorophenyl)(thiazol-2-yl)methanol To a solution of 2-((1-(3-chlorophenethyl)-1H-benzo[d]imidazol-6-yl)(4-chlorophenyl)methyl)thiazole trifluoroacetate salt (63.5 mg, 0.11 mmol) in DMSO (1.5 mL) was added saturated KOH (20 µL) and the reaction mixture was stirred rapidly at room temperature under a stream of air. t-Butyl alcohol (0.5 mL) and DMSO (5 mL) were added and the solution was stirred for 4 hours. The solution was then heated to 50° C. for 96 hours. The reaction mixture was purified by reverse phase HPLC, and fractions containing the product were lyophilized to yield (1-(3-chlorophenethyl)-1H-benzo[d]imidazol-6-yl)(4-chlorophenyl)(thiazol-2-yl)methanol as the trifluoroacetate salt. The purified compound was dissolved in dichloromethane and the organic solution was washed with saturated NaHCO₃. The organic layer was dried over Na₂SO₄ and the solvent evaporated in vacuo to yield (1-(3-chlorophenethyl)-1H-benzo[d]imidazol-6-yl)(4-chlorophenyl)(thiazol-2-yl)methanol. MS: 480 (M+H⁺).

Example DL-50

2-((4-chlorophenyl)(1-(1-(4-chlorophenyl)ethyl)-2-cyclopropyl-1H-benzo[d]imidazol-6-yl)methyl)thiazole

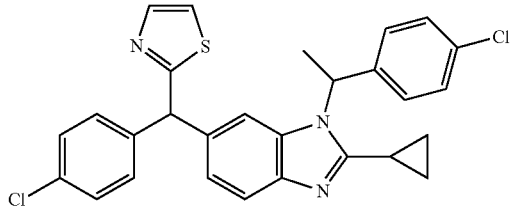 [SMILES: CC(c1ccc(Cl)cc1)n1c(C2CC2)nc2ccc(C(c3ccc(Cl)cc3)c3nccs3)cc21]

Step 1: 3-fluoro-4-nitrobenzoyl chloride

A solution of 3-fluoro-4-nitrobenzoic acid (2 g, 10.80 mmol) in thionyl chloride (10 mL) and DMF (0.05 mL) was heated to reflux temperature for 4 hours and then stirred at room temperature overnight. The thionyl chloride was evaporated in vacuo and heptane was added and evaporated (2×) to yield 3-fluoro-4-nitrobenzoyl chloride as a yellow oil, which was used as such in the next step.

Step 2: (4-chlorophenyl)(3-fluoro-4-nitrophenyl)methanone

To 3-fluoro-4-nitrobenzoyl chloride (2.2 g, 10.81 mmol) in chloroform (12 mL) under an argon atmosphere was added aluminum chloride (1.67 g, 12.54 mmol) and chlorobenzene (2.20 mL, 21.62 mmol). The reaction mixture was stirred overnight at room temperature and then heated to reflux temperature for 1 hour. The reaction mixture was poured on ice, concentrated HCl (3.2 mL) was added, and the resulting mixture stirred for 1 hour. The reaction mixture was extracted with dichloromethane and the organic layer was washed with brine and dried over Na₂SO₄. The solvent was evaporated in vacuo to yield a red solid. The residue was subjected to silica gel chromatography using a gradient of 40-75% dichloromethane:heptane as the eluent to yield a clear oil. The oil was slurried in acetonitrile (100 mL) at 40° C. for 30 minutes, the mixture was cooled in ice, and the orange precipitate filtered off. Evaporation of the filtrate yielded (4-chlorophenyl)(3-fluoro-4-nitrophenyl)methanone as an amber oil.

Step 3: (4-chlorophenyl)(3-((1-(4-chlorophenyl)ethyl)amino)-4-nitrophenyl)methanone To (4-chlorophenyl)(3-fluoro-4-nitrophenyl)methanone (0.82 g, 2.93 mmol) and p-chloro-α-methylbenzylamine (0.51 g, 2.93 mmol) in acetonitrile (10 mL) was added triethylamine (0.448 mL, 3.23 mmol). The reaction mixture was heated at 50° C. for 16 hours, heated at 80° C. for the next 6 hours, and then heated at 82° C. for 18 hours. The solvent was evaporated to yield 1.37 g of an orange semi-solid. The residue was purified by silica gel chromatography using a 25-75% dichloromethane:heptane gradient as the eluent to yield (4-chlorophenyl)(3-((1-(4-chlorophenyl)ethyl)amino)-4-nitrophenyl)methanone as a yellow solid.

Step 4: (4-chlorophenyl)(3-((1-(4-chlorophenyl)ethyl)amino)-4-nitrophenyl)(thiazol-2-yl)methanol A solution of thiazole (0.156 mL, 2.17 mmol) in THF (10 mL) was cooled to −78° C. and treated dropwise with n-BuLi (10M in hexane, 0.221 mL, 2.21 mmol). After 30 minutes a solution of (4-chlorophenyl)(3-((1-(4-chlorophenyl)ethyl)amino)-4-nitrophenyl)methanone (0.45 g, 1.08 mmol) in THF (10 mL) was added dropwise and the reaction mixture was allowed to warm to room temperature and stirred overnight. Water was added and the mixture was extracted with ethyl acetate. The organic layer was washed with brine and dried over Na₂SO₄. The solvent was evaporated and the residue was purified by silica gel chromatography eluting with dichloromethane to yield (4-chlorophenyl)(3-((1-(4-chlorophenyl)ethyl)amino)-4-nitrophenyl)(thiazol-2-yl)methanol as a yellow oil.

Step 5: 5-((4-chlorophenyl)(thiazol-2-yl)methyl)-N1-(1-(4-chlorophenyl)ethyl)benzene-1,2-diamine To a solution of (4-chlorophenyl)(3-((1-(4-chlorophenyl)ethyl)amino)-4-nitrophenyl)(thiazol-2-yl)methanol (0.32 g, 0.64 mmol) in acetic acid (7.5 mL) was added tin chloride dihydrate (721 mg, 3.20 mmol) and concentrated HCl (0.5 mL). The reaction mixture was heated at 50° C. overnight and the solvent was evaporated in vacuo. Ethyl acetate was added to the residue, the organic layer was washed with water and brine and then dried over Na₂SO₄. Evaporation of the solvent yielded the residue, which was purified by silica gel chromatography using dichloromethane as the eluent to yield 5-((4-chlorophenyl)(thiazol-2-yl)methyl)-N1-(1-(4-chlorophenyl)ethyl)benzene-1,2-diamine as a brown foam.

Step 6: 2-((4-chlorophenyl)(1-(1-(4-chlorophenyl)ethyl)-2-cyclopropyl-1H-benzo[d]imidazol-6-yl)methyl)thiazole A solution of 5-((4-chlorophenyl)(thiazol-2-yl)methyl)-N1-(1-(4-chlorophenyl)ethyl)benzene-1,2-diamine (80 mg, 0.31 mmol) and cyclopropanecarboxaldehyde (0.027 mL, 0.35 mmol) in DMSO (1 mL) was rapidly stirred at room temperature in the presence of air. The reaction mixture was purified by reverse phase HPLC. The fractions containing the product were lyophilized to yield 2-((4-chlorophenyl)(1-(1-(4-chlorophenyl)ethyl)-2-cyclopropyl-1H-benzo[d]imidazol-6-yl)methyl)thiazole trifluoroacetate salt as a white solid. MS: 504.0 (M+H$^+$).

Example DL-51

2-((2-(azetidin-3-yl)-1-(3-chlorophenethyl)-1H-benzo[d]imidazol-6-yl)(4-chlorophenyl)methyl)thiazole

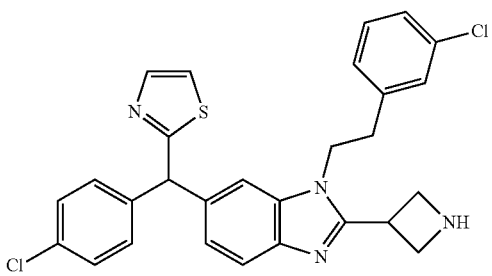 [SMILES: Clc1ccc(C(c2ccc3nc(C4CNC4)n(CCc4cccc(Cl)c4)c3c2)c2nccs2)cc1]

A solution of tert-butyl 3-(1-(3-chlorophenethyl)-6-((4-chlorophenyl)(thiazol-2-yl)methyl)-1H-benzo[d]imidazol-2-yl)azetidine-1-carboxylate (100 mg, 0.16 mmol), prepared as described in Example DL-47 above, in dichloromethane (10 mL) was cooled in ice and trifluoroacetic acid (1 mL) was added. The reaction mixture was stirred overnight at room temperature and then washed with 13.8 mL of 1N NaOH. The organic layer was dried over Na$_2$SO$_4$ and evaporated to yield a white foam. The residue was purified by reverse phase HPLC and the fractions containing the product were lyophilized to yield 2-((2-(azetidin-3-yl)-1-(3-chlorophenethyl)-1H-benzo[d]imidazol-6-yl)(4-chlorophenyl)methyl)thiazole trifluoroacetate salt. MS: 519.0 (M+H$^+$).

Example DP-1

1-((trifluoromethyl)sulfonyl)piperidin-4-one

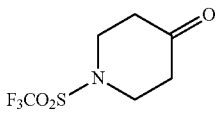

4-Piperidone HCl salt monohydrate (2 g, 12.89 mmol) was placed in a 40 mL vial equipped with a stir bar then dichloromethane (25 mL) was added. 3M NaOH (4.30 mL, 12.89 mmol) was added and the mixture was stirred until the solid dissolved (~30 min). The organic phase was separated then the aqueous layer was extracted with dichloromethane (3×20 mL). The combined organic extracts were dried over MgSO$_4$ and filtered into a 200 mL round bottom flask equipped with a stir bar. Diisopropylethylamine (3.33 mL, 19.34 mmol) was added then triflic anhydride (1M solution in dichloromethane, 1.289 mL, 12.89 mmol) was placed in a dropping funnel and the solution was added dropwise over 30 min. After completion of addition, the reaction was stirred at room temperature for 2 hours then the solvent was removed under reduced pressure. The residue was purified by chromatography on silica gel eluting with 0-80% ethyl acetate/heptane gradient to yield 1-((trifluoromethyl)sulfonyl)piperidin-4-one.

Example DP-2

6-(bis(4-chlorophenyl)methyl)-2-cyclopropyl-4-methoxy-1-(1-((trifluoromethyl)sulfonyl)piperidin-4-yl-1H-benzo[d]imidazole

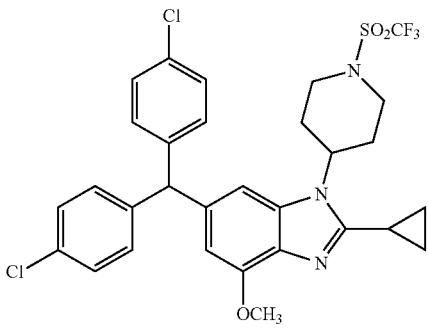

Step 1: 2-amino-5-bromo-3-nitrophenol

2-Amino-3-nitrophenol (3 g, 19.465 mmol) was placed in a 200 mL round bottom flask equipped with a stir bar then AcOH (45 mL) was added. Bromine (3.111 g, 19.465 mmol) in acetic acid (25 mL) was placed in a dropping funnel and the solution was added dropwise over 1 hour. The mixture was stirred at room temperature for 18 hours then ethanol (100 mL) and ethyl acetate (300 mL) were added. The solution was neutralized with 2 N NaOH to pH 5 then the organic phase was separated, washed with brine (100 mL), and dried over Na$_2$SO$_4$ and filtered. The solvent was removed under reduced pressure yielding 2-amino-5-bromo-3-nitrophenol as a red solid, which was used in the next step without further purification.

Step 2: 4-bromo-2-methoxy-6-nitroaniline

2-Amino-5-bromo-3-nitrophenol (0.74 g, 3.176 mmol) was placed in a 20 mL vial equipped with a stir bar then K$_2$CO$_3$ (570.6 mg, 4.128 mmol) and DMF (10 mL) were added. CH$_3$I (0.217 mL, 3.493 mmol) was added dropwise then the reaction was stirred at room temperature for 3 hours. The reaction was poured into H$_2$O (50 mL) and the precipitate was isolated by filtration. The solid was washed with H$_2$O (3×30 mL) then dissolved in ethyl acetate (100 mL). The solution was dried over MgSO$_4$ and filtered. The solvent was removed under reduced pressure to yield 4-bromo-2-methoxy-6-nitroaniline, which was in the next step without further purification.

Step 3: N-(4-bromo-2-methoxy-6-nitrophenyl)cyclopropanecarboxamide

4-Bromo-2-methoxy-6-nitroaniline (743.1 mg, 3.008 mmol) was placed in a 100 mL round bottom flask equipped with a stir bar then the vial was evacuated and filled with argon. Dry tetrahydrofuran (30 mL) was added via syringe then the solution was cooled to 0° C. Sodium hydride (360.9 mg, 9.024 mmol, 60% dispersion in mineral oil) was added as a solid and the reaction turned blood-red immediately. The mixture was stirred at 0° C. for 5 minutes then cyclopropanecarbonyl chloride (0.303 mL, 3.309 mmol) was added. The reaction was stirred at 0° C. for 1.5 hours then additional cyclopropanecarbonyl chloride (0.15 mL) was added. The reaction was warmed to room temperature and stirred for 1 hour then additional sodium hydride (100 mg) was added. The reaction was stirred at room temperature for 18 hours. An additional amount of cyclopropanecarbonyl chloride (0.15 mL) was added and the reaction was stirred for 3 days.

The reaction mixture was diluted with $H_2O$ (20 mL) and stirred at room temperature for 1 hour. The reaction was warmed to 60° C. and stirred for 2 hours. 3M NaOH (2 mL) was added and the reaction mixture was stirred at 60° C. for 6 hours. The reaction was cooled to room temperature then diluted with ethyl acetate (50 mL) and the organic phase was separated. The aqueous phase was extracted with ethyl acetate (3×30 mL) then the organic extracts were combined, washed with brine (30 mL), dried over $MgSO_4$ and filtered. The solvent was removed under reduced pressure. The residue was purified by chromatography on silica gel eluting with 0-60% ethyl acetate/heptane gradient to yield N-(4-bromo-2-methoxy-6-nitrophenyl)cyclopropanecarboxamide.

Step 4: N-(2-amino-4-bromo-6-methoxyphenyl) cyclopropanecarboxamide

N-(4-bromo-2-methoxy-6-nitrophenyl)cyclopropanecarboxamide (851.3 mg, 2.701 mmol) was placed in a 40 mL vial equipped with a stir bar then iron powder (754.3 mg, 13.507 mmol) and ammonium chloride (1.445 g, 27.015 mmol) were added. Anhydrous ethanol (25 mL) and water (10 mL) were added and the reaction was stirred at 50° C. for 2 hours. The reaction mixture was cooled to room temperature, diluted with ethyl acetate (10 mL), then filtered through a CELITE cartridge. The filter cake was washed with ethyl acetate (3×20 mL) and water (2×10 mL) then the organic layer was separated and washed with brine (20 mL). The combined aqueous extracts were extracted with ethyl acetate (2×20 mL). The organic extracts were combined, dried over $Na_2SO_4$, and filtered. The solvent was removed under reduced pressure to yield N-(2-amino-4-bromo-6-methoxyphenyl)cyclopropanecarboxamide, which was used in the next step without further purification.

Step 5: N-(4-bromo-2-methoxy-6-((1-((trifluoromethyl)sulfonyl)piperidin-4-yl)amino)phenyl)cyclopropanecarboxamide N-(2-amino-4-bromo-6-methoxyphenyl)cyclopropanecarboxamide (785.8 mg, 2.756 mmol) and 1-((trifluoromethyl)sulfonyl)piperidin-4-one (637.1 mg, 2.756 mmol) were placed in an 8 mL vial equipped with a stir bar then dichloroethane (50 mL) and acetic acid (0.316 mL, 5.512 mmol) were added. The mixture was stirred at room temperature for 30 minutes then sodium triacetoxyborohydride (564 mg, 2.756 mmol) was added as a solid. The reaction mixture was stirred at room temperature for 4 hours then additional sodium triacetoxyborohydride (564 mg, 2.756 mmol) was added. The reaction mixture was stirred at room temperature for 4 hours then additional sodium triacetoxyborohydride (564 mg, 2.756 mmol) was added. The reaction was stirred at room temperature for 18 h then additional sodium triacetoxyborohydride (1564 mg, 2.756 mmol) was added. The reaction was stirred at room temperature for 3 days then additional 1-((trifluoromethyl)sulfonyl)piperidin-4-one (637.1 mg, 2.756 mmol) was added and stirred for 18 hours. The reaction mixture was diluted with water (20 mL) and stirred for 30 minutes then the mixture was poured into saturated sodium bicarbonate solution (20 mL) and extracted with dichloromethane (3×20 mL). The organic extracts were combined, dried over $Na_2SO_4$, and filtered. The solvent was removed under reduced pressure. The residue was purified by chromatography on silica gel eluting with a 0-100% ethyl acetate/heptane gradient to yield a mixture of N-(4-bromo-2-methoxy-6-((1-((trifluoromethyl)sulfonyl)piperidin-4-yl)amino)phenyl)cyclopropanecarboxamide and the corresponding compound in which the trifluorosulfonylpiperidin-4-yl moiety is replaced with an ethyl group (882.5 mg).

Step 6: 6-bromo-2-cyclopropyl-4-methoxy-1-(1-((trifluoromethyl)sulfonyl)piperidin-4-yl)-1H-benzo[d]imidazole The mixture of compounds prepared in (882.5 mg, 1.764 mmol) was placed in a 40 mL vial equipped with a stir bar then glacial acetic acid (10 mL) was added. The reaction was stirred at 80° C. for 3 days then cooled to room temperature, poured into water (100 mL) and extracted with ethyl acetate (3×30 mL). The organic extracts were combined, washed with 3 M NaOH (30 mL), dried over $MgSO_4$, and filtered. The solvent was removed under reduced pressure. The residue was purified by chromatography on silica gel eluting with a 0-100% ethyl acetate/heptane gradient to yield 6-bromo-2-cyclopropyl-4-methoxy-1-(1-((trifluoromethyl)sulfonyl)piperidin-4-yl)-1H-benzo[d]imidazole and the corresponding compound in which the trifluorosulfonylpiperidin-4-yl moiety is replaced with an ethyl group.

Step 7: bis(4-chlorophenyl)(2-cyclopropyl-4-methoxy-1-(1-((trifluoromethyl)sulfonyl)piperidin-4-yl)-1H-benzo[d]imidazol-6-yl)methanol 6-Bromo-2-cyclopropyl-4-methoxy-1-(1-((trifluoromethyl)sulfonyl)piperidin-4-yl)-1H-benzo[d]imidazole (496 mg, 1.028 mmol) and 4,4'-dichlorobenzophenone (284.1 mg, 1.131 mmol) were placed in a 40 mL vial equipped with a stir bar then the vial was evacuated and filled with argon. Dry tetrahydrofuran (4.66 mL) was added then the solution was cooled to −78° C. t-BuLi (1.209 mL, 2.057 mmol, 1.7 M in pentane) was added dropwise and the reaction mixture was stirred at −78° C. for 2 hours then the dry ice bath was allowed to reach room temperature overnight (18 hours). The reaction mixture was quenched with saturated ammonium chloride solution (20 mL) and extracted with ethyl acetate (3×15 mL). The combined organic extracts were dried over $MgSO_4$, filtered, and the solvent removed under reduced pressure. The resulting reaction mixture was purified by chromatography on silica gel eluting with a 0-80% ethyl acetate/heptane gradient yield bis(4-chlorophenyl)(2-cyclopropyl-4-methoxy-1-(1-((trifluoromethyl)sulfonyl)piperidin-4-yl)-1H-benzo[d]imidazol-6-yl)methanol, which was isolated as a 1:1 mixture with 2-cyclopropyl-4-methoxy-1-(1-((trifluoromethyl)sulfonyl)piperidin-4-yl)-1H-benzo[d]imidazole (515.5 mg).

Step 8: 6-(bis(4-chlorophenyl)methyl)-2-cyclopropyl-4-methoxy-1-(1-((trifluoromethyl)sulfonyl)piperidin-4-yl)-1H-benzo[d]imidazole Bis(4-chlorophenyl)(2-cyclopropyl-4-methoxy-1-(1-((trifluoromethyl)sulfonyl)piperidin-4-yl)-1H-benzo[d]imidazol-6-yl)methanol (515.5 mg, 0.788 mmol, used as a 1:1 mixture as described above) was placed in a 40 mL vial equipped with a stir bar then dry dichloromethane (10 mL) and triethylsilane (0.629 mL, 3.938 mmol) were added. Trifluoroacetic acid (0.303 mL, 3.938 mmol) was added and the reaction was stirred at room temperature for 18 hours then the reaction mixture was washed with saturated sodium bicarbonate solution (50 mL), dried over $MgSO_4$, and filtered. The solvent was removed under reduced pressure. The resulting residue was purified by preparative thin layer chromatography on 4×2000 micron silica gel plates developed with 15% acetonitrile containing 0.1% trifluoroacetic acid/dichloromethane yield 6-(bis(4-chlorophenyl)methyl)-2-cyclopropyl-4-methoxy-1-(1-((trifluoromethyl)sulfonyl)piperidin-4-yl)-1H-benzo[d]imidazole.

MS: 638.0 (M+H+); $^1$H NMR (400 MHz, $CDCl_3$) δ: 7.27 (d, J=8.1 Hz, 4H), 7.04 (d, J=8.6 Hz, 4H), 6.66 (s, 1H), 6.38 (s, 1H), 5.58 (s, 1H), 4.61 (tt, J=12.4, 4.0 Hz, 1H), 4.16 (d, J=13.6 Hz, 2H), 3.85 (s, 3H), 3.23 (t, J=12.9 Hz, 2H), 2.43 (qd, J=12.6, 4.0 Hz, 2H), 2.00 (d, J=10.6 Hz, 2H), 1.86-1.95 (m, 1H), 1.21-1.28 (m, 2H), 1.03-1.10 (m, 2H).

Example DP-3 bis(4-chlorophenyl)(2-(oxetan-3-yl)-1-(1-((trifluoromethyl)sulfonyl)piperidin-4-yl)-1H-benzo[d]imidazol-6-yl)methanol

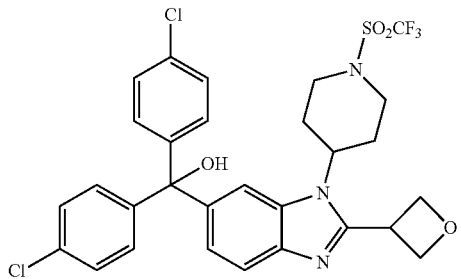

Step 1: N-(4-bromo-2-((1-((trifluoromethyl)sulfonyl)piperidin-4-yl)amino)phenyl)oxetane-3-carboxamide Oxetane-3-carboxylic acid (52.5 mg, 0.514 mmol) was placed in an 8 mL vial equipped with a stir bar then dry dichloromethane (5 mL) was added followed by diisopropylethylamine (0.114 mL, 0.637 mmol). 5-Bromo-N1-(1-((trifluoromethyl)sulfonyl)piperidin-4-yl)benzene-1,2-diamine (197 mg, 0.49 mmol, prepared as described in Example YM-26) was added followed by HATU (242.09 mg, 0.637 mmol). The reaction mixture was stirred at room temperature for 18 hours. The reaction mixture was diluted with water (30 mL) then extracted with dichloromethane (3×10 mL). The organic extracts were combined, dried over $Na_2SO_4$, and filtered. The solvent was removed under reduced pressure to yield N-(4-bromo-2-((1-((trifluoromethyl)sulfonyl)piperidin-4-yl)amino)phenyl)oxetane-3-carboxamide, which was used in the next step without further purification.

Step 2: 6-bromo-2-(oxetan-3-yl)-1-(1-((trifluoromethyl)sulfonyl)piperidin-4-yl)-1H-benzo[d]imidazole N-(4-bromo-2-((1-((trifluoromethyl)sulfonyl)piperidin-4-yl)amino)phenyl)oxetane-3-carboxamide (81.6 mg, 0.168 mmol) was placed in an 8 mL vial equipped with a stir bar then acetic acid (1 mL) was added. The mixture was stirred at 80° C. for 36 hours then cooled to room temperature. The reaction mixture was diluted with water (6 mL) then poured into saturated sodium bicarbonate solution (30 mL) and extracted with dichloromethane (3×20 mL). The organic extracts were combined, washed with brine (20 mL), dried over $Na_2SO_4$, and filtered. The solvent was removed under reduced pressure. The resulting residue was purified by preparative TLC using 2×2000 micron silica gel plates developed with 30% ethyl acetate/dichloromethane to yield 6-bromo-2-(oxetan-3-yl)-1-(1-((trifluoromethyl)sulfonyl)piperidin-4-yl)-1H-benzo[d]imidazole.

Step 3: bis(4-chlorophenyl)(2-(oxetan-3-yl)-1-(1-((trifluoromethyl)sulfonyl)piperidin-4-yl)-1H-benzo[d]imidazol-6-yl)methanol 6-Bromo-2-(oxetan-3-yl)-1-(1-((trifluoromethyl)sulfonyl)piperidin-4-yl)-1H-benzo[d]imidazole (56.1 mg, 0.12 mmol) and 4,4'-dichlorobenzophenone (33.09 mg, 0.132 mmol) were placed in a 8 mL vial equipped with a stir bar then the vial was evacuated and filled with argon. Dry tetrahydrofuran (1 mL) was added and the solution was cooled to −78° C. t-BuLi (176.17 μL, 0.299 mmol, 1.7M in pentane) was added dropwise then the reaction was stirred at −78° C. for 30 minutes. The reaction mixture was quenched with saturated ammonium chloride solution at −78° C. then warmed to room temperature, poured into saturated ammonium chloride solution (20 mL), and extracted with ethyl acetate (3×15 mL). The combined organic extracts were dried over $Na_2SO_4$, filtered, and the solvent removed under reduced pressure. The resulting residue was purified by preparative TLC on a 2000 micron silica gel plate developed with 30% ethyl acetate/dichloromethane. The isolated product was further purified by preparative reverse-phase HPLC yielding bis(4-chlorophenyl)(2-(oxetan-3-yl)-1-(1-((trifluoromethyl)sulfonyl)piperidin-4-yl)-1H-benzo[d]imidazol-6-yl)methanol as its TFA salt containing 1 eq of TFA as determined by NMR.

MS: 617.8 (M+H+); $^1$H NMR (400 MHz, $CDCl_3$+$CD_3OD$) δ: 7.67 (d, J=8.6 Hz, 1H), 7.65 (s, 1H), 7.29 (d, J=9.1 Hz, 4H), 7.22 (d, J=8.6 Hz, 4H), 7.15 (d, J=8.6 Hz, 1H), 5.12 (d, J=8.1 Hz, 4H), 4.74 (quin, J=7.7 Hz, 1H), 4.25 (tt, J=12.2, 4.0 Hz, 1H), 4.12-4.18 (m, 2H), 3.27 (t, J=12.9 Hz, 2H), 2.43 (qd, J=12.7, 4.3 Hz, 2H), 1.97 (d, J=10.6 Hz, 2H).

Example DP-4

6-(bis(4-chlorophenyl)methyl)-2-cyclopropyl-1-((tetrahydro-2H-pyran-4-yl)methyl)-1H-benzo[d]imidazole

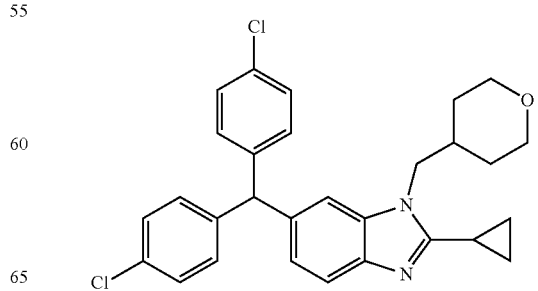

Step 1: methyl 2,2-bis(4-chlorophenyl)-2-(4-nitro-3-(((tetrahydro-2H-pyran-4-yl)methyl)amino)phenyl)acetate Methyl 2,2-bis(4-chlorophenyl)-2-(3-fluoro-4-nitrophenyl)acetate (1.033 g, 2.379 mmol, prepared as described in Example DL-1), 4-aminomethyltetrahydropyran (301.4 mg, 2.617 mmol), and potassium carbonate (493.1 mg, 3.568 mmol) were placed in a 20 mL vial equipped with a stir bar then dry DMSO (10 mL) was added. The mixture was stirred at 80° C. for 18 hours then the reaction was cooled to room temperature and poured into water (30 mL) and saturated ammonium chloride solution (30 mL). The solid was isolated by filtration and washed with water (2×10 mL). The precipitate was dissolved in ethyl acetate (50 mL), dried over MgSO$_4$, and filtered. The solvent was removed under reduced pressure to yield methyl 2,2-bis(4-chlorophenyl)-2-(4-nitro-3-(((tetrahydro-2H-pyran-4-yl)methyl)amino)phenyl)acetate, which was used in the next step without further purification.

Step 2: methyl 2-(4-amino-3-(((tetrahydro-2H-pyran-4-yl)methyl)amino)phenyl)-2,2-bis(4-chlorophenyl)acetate Methyl 2,2-bis(4-chlorophenyl)-2-(4-nitro-3-(((tetrahydro-2H-pyran-4-yl)methyl)amino)phenyl)acetate (529 mg, 0.999 mmol) was placed in a 40 mL vial equipped with a stir bar then iron powder (279 mg, 4.996 mmol) and ammonium chloride (534 mg, 9.992 mmol) were added. Anhydrous ethanol (16 mL) and water (4 mL) were added then the reaction was stirred at 80° C. for 4 hours. The reaction was cooled to room temperature and diluted with dichloromethane (20 mL) then the suspension was filtered through CELITE. The filter was washed with dichloromethane (3×10 mL) then the solvent was removed under reduced pressure. The residue was dissolved in dichloromethane (30 mL), dried over MgSO$_4$, and filtered. The solvent was removed under reduced pressure to yield methyl 2-(4-amino-3-(((tetrahydro-2H-pyran-4-yl)methyl)amino)phenyl)-2,2-bis(4-chlorophenyl)acetate, which was used directly in the next step without further purification.

Step 3: methyl 2,2-bis(4-chlorophenyl)-2-(2-cyclopropyl-1-((tetrahydro-2H-pyran-4-yl)methyl)-1H-benzo[d]imidazol-6-yl)acetate Methyl 2-(4-amino-3-(((tetrahydro-2H-pyran-4-yl)methyl)amino)phenyl)-2,2-bis(4-chlorophenyl)acetate (498.9 mg, 0.999 mmol) was placed in a 20 mL vial equipped with a stir bar then DMSO (1.91 mL) was added. Cyclopropanecarboxaldehyde (149.3 µL, 1.998 mmol) was added via syringe then the reaction was stirred at room temperature for 5 days. The reaction was diluted with water (10 mL) then the mixture was extracted with ethyl acetate (3×15 mL). The organic extracts were combined, washed with brine (20 mL), dried over MgSO$_4$, and filtered. The solvent was removed under reduced pressure. The residue was purified by chromatography on silica gel eluting with a 0-60% ethyl acetate/heptane gradient to yield methyl 2,2-bis(4-chlorophenyl)-2-(2-cyclopropyl-1-((tetrahydro-2H-pyran-4-yl)methyl)-1H-benzo[d]imidazol-6-yl)acetate.

Step 4: 2,2-bis(4-chlorophenyl)-2-(2-cyclopropyl-1-((tetrahydro-2H-pyran-4-yl)methyl)-1H-benzo[d]imidazol-6-yl)acetic acid Methyl 2,2-bis(4-chlorophenyl)-2-(2-cyclopropyl-1-((tetrahydro-2H-pyran-4-yl)methyl)-1H-benzo[d]imidazol-6-yl)acetate (399.4 mg, 0.727 mmol) was placed in a 20 mL vial equipped with a stir bar then MeOH (4 mL), 1,4-dioxane (4 mL), and 3 M NaOH (2.737 mL, 8.21 mmol) were added. The reaction mixture was stirred at 60° C. for 18 hours then the solvent was removed under reduced pressure. The residue was treated with dichloromethane (30 mL) and 10% citric acid (30 mL) then the organic layer was separated. The aqueous phase was extracted with dichloromethane (2×30 mL) then the organic extracts were combined, dried over Na$_2$SO$_4$, and filtered. The solvent was removed under reduced pressure to yield 2,2-bis(4-chlorophenyl)-2-(2-cyclopropyl-1-((tetrahydro-2H-pyran-4-yl)methyl)-1H-benzo[d]imidazol-6-yl)acetic acid, which was used in the next step without further purification.

Step 5: 6-(bis(4-chlorophenyl)methyl)-2-cyclopropyl-1-((tetrahydro-2H-pyran-4-yl)methyl)-1H-benzo[d]imidazole 2,2-Bis(4-chlorophenyl)-2-(2-cyclopropyl-1-((tetrahydro-2H-pyran-4-yl)methyl)-1H-benzo[d]imidazol-6-yl)acetic acid (371.1 mg, 0.693 mmol) was placed in a 40 mL vial equipped with a stir bar then dry toluene (20 mL) was added. DBU (10.354 µL, 0.0693 mmol) was added via micro-syringe and the solution was heated to 90° C. and stirred for 2 hours. The reaction was cooled to room temperature then the solvent was removed under reduced pressure. The resulting residue was purified by chromatography on silica gel eluting with a 0-80% ethyl acetate/heptane gradient to yield 6-(bis(4-chlorophenyl)methyl)-2-cyclopropyl-1-((tetrahydro-2H-pyran-4-yl)methyl)-1H-benzo[d]imidazole.

MS: 491.2 (M+H$^+$); $^1$H NMR (400 MHz, CDCl$_3$) δ: 7.56 (d, J=8.1 Hz, 1H), 7.25 (d, J=8.1 Hz, 4H), 7.03 (d, J=8.6 Hz, 4H), 6.92 (dd, J=8.1, 1.5 Hz, 1H), 6.89 (s, 1H), 5.62 (s, 1H), 4.01 (d, J=7.6 Hz, 2H), 3.95 (dd, J=11.4, 3.3 Hz, 2H), 3.23-3.36 (m, 2H), 1.98-2.11 (m, 1H), 1.89-1.98 (m, 1H), 1.45-1.54 (m, 2H), 1.33-1.45 (m, 2H), 1.23-1.28 (m, 2H), 1.07-1.14 (m, 2H).

Example DP-5

6-(bis(4-chlorophenyl)methyl)-2-cyclopropyl-1-(1-((trifluoromethyl)sulfonyl)piperidin-4-yl)-1H-benzo[d]imidazol-4-ol

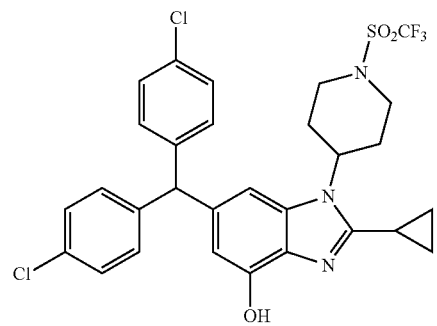

Step 1: 4-bromo-2-nitro-6-((2-(trimethylsilyl)ethoxy)methoxy)aniline

2-Amino-5-bromo-3-nitrophenol (1 g, 4.291 mmol, prepared as described in Example DP-2 above) was placed in a 20 mL vial equipped with a stir bar then potassium carbonate (771 mg, 5.579 mmol) and DMF (16 mL) were added. SEM chloride (0.835 mL, 4.721 mmol) was added dropwise then the reaction was stirred at room temperature for 24 hours. The reaction mixture was quenched with water (50 mL) and extracted with ethyl acetate (3×50 mL). The organic extracts were combined, washed with brine (30 mL), dried over $Na_2SO_4$, and filtered. The solvent was removed under reduced pressure. The residue was purified by chromatography on silica gel eluting with a 0-100% ethyl acetate/heptane gradient to yield 4-bromo-2-nitro-6-((2-(trimethylsilyl)ethoxy)methoxy)aniline.

Step 2: 5-bromo-3-((2-(trimethylsilyl)ethoxy)methoxy)benzene-1,2-diamine

4-Bromo-2-nitro-6-((2-(trimethylsilyl)ethoxy)methoxy) aniline (363 mg, 1 mmol) was placed in a 20 mL vial equipped with a stir bar then iron powder (279 mg, 5 mmol) and ammonium chloride (534 mg, 10 mmol) were added. Anhydrous ethanol (9 mL) and water (3 mL) were added then the reaction was stirred at 80° C. for 1 hour. The reaction was cooled to room temperature and diluted with dichloromethane (10 mL) then the suspension was filtered through a CELITE cartridge. The filter cake was washed with dichloromethane (3×10 mL) and water (2×10 mL) then the organic layer was separated and washed with brine (20 mL). The combined aqueous extracts were extracted with dichloromethane (2×20 mL). The organic extracts were combined, dried over $Na_2SO_4$, and filtered. The solvent was removed under reduced pressure to yield 5-bromo-3-((2-(trimethylsilyl)ethoxy)methoxy)benzene-1,2-diamine, which was used in the next step without further purification.

Step 3: 5-bromo-N1-(1-((trifluoromethyl)sulfonyl)piperidin-4-yl)-3-((2-(trimethylsilyl)ethoxy)methoxy)benzene-1,2-diamine 5-Bromo-3-((2-(trimethylsilyl)ethoxy)methoxy)benzene-1,2-diamine (332.5 mg, 0.998 mmol) and 1-((trifluoromethyl)sulfonyl)piperidin-4-one (231 mg, 0.998 mmol) were placed in a 20 mL vial equipped with a stir bar then dichloroethane (5 mL) and acetic acid (114 µL, 1.995 mmol) were added. The mixture was stirred at room temperature for 30 minutes then sodium triacetoxyborohydride (634 mg, 2.993 mmol) was added as a solid. The reaction was stirred at room temperature for 36 hours. The reaction was diluted with water (3 mL) and stirred for 30 minutes then the mixture was poured into saturated sodium bicarbonate solution (20 mL) and extracted with dichloromethane (3×20 mL). The organic extracts were combined, dried over $Na_2SO_4$, and filtered. The solvent was removed under reduced pressure. The residue was purified by chromatography on silica gel eluting with a 0-100% ethyl acetate/heptane gradient to yield 5-bromo-N1-(1-((trifluoromethyl) sulfonyl)piperidin-4-yl)-3-((2-(trimethylsilyl)ethoxy)methoxy)benzene-1,2-diamine, in a mixture with other aromatic amine impurities.

Step 4: 6-bromo-2-cyclopropyl-1-(1-((trifluoromethyl)sulfonyl)piperidin-4-yl)-4-((2-(trimethylsilyl)ethoxy)methoxy)-1H-benzo[d]imidazole 5-Bromo-N1-(1-((trifluoromethyl)sulfonyl)piperidin-4-yl)-3-((2-(trimethylsilyl)ethoxy)methoxy)benzene-1,2-diamine (372 mg, 0.677 mmol, used as the mixture described above) was placed in a 20 mL vial equipped with a stir bar then DMSO (1.295 mL) was added. Cyclopropanecarboxaldehyde (101.25 µL, 1.355 mmol) was added via syringe then the reaction mixture was stirred at room temperature for 3 days. The reaction mixture was diluted with ethyl acetate (10 mL) then poured into a mixture of water (40 mL) and saturated sodium chloride solution (20 mL). The organic phase was separated then the aqueous layer was extracted with ethyl acetate (3×30 mL). The combined organic extracts were washed with brine (30 mL) then dried over $MgSO_4$ and filtered. The solvent was removed under reduced pressure. The resulting residue was purified by chromatography on silica gel eluting with a 0-80% ethyl acetate/heptane gradient. The isolated product was further purified by chromatography on silica gel eluting with a 40% ethyl acetate/heptane isocratic to yield 6-bromo-2-cyclopropyl-1-(1-((trifluoromethyl)sulfonyl)piperidin-4-yl)-4-((2-(trimethylsilyl)ethoxy)methoxy)-1H-benzo[d]imidazole.

Step 5: bis(4-chlorophenyl)(2-cyclopropyl-1-(1-((trifluoromethyl)sulfonyl)piperidin-4-yl)-4-((2-(trimethylsilyl)ethoxy)methoxy)-1H-benzo[d]imidazol-6-yl)methanol 6-Bromo-2-cyclopropyl-1-(1-((trifluoromethyl)sulfonyl) piperidin-4-yl)-4-((2-(trimethylsilyl)ethoxy)methoxy)-1H-benzo[d]imidazole (112.8 mg, 0.188 mmol) and 4,4'-dichlorobenzophenone (52 mg, 0.207 mmol) were placed in an 8 mL vial equipped with a stir bar then the vial was evacuated and filled with argon. Dry tetrahydrofuran (0.854 mL) was added then the solution was cooled to −78° C. t-BuLi (221.7 µL, 0.377 mmol, 1.7 M in pentane) was added dropwise and the reaction was stirred at −78° C. for 2 hour then the dry ice bath was allowed to reach room temperature overnight (18 hours). The reaction mixture was quenched with water (0.6 mL) then the mixture was poured into saturated ammonium chloride solution (20 mL) and extracted with ethyl acetate (3×15 mL). The combined organic extracts were dried over $Na_2SO_4$, filtered, and the solvent removed under reduced pressure. The resulting reaction mixture was purified by chromatography on silica gel eluting with a 0-80% ethyl acetate/heptane gradient to yield bis(4-chlorophenyl)(2-cyclopropyl-1-(1-((trifluoromethyl)sulfonyl)piperidin-4-yl)-4-((2-(trimethylsilyl)ethoxy)methoxy)-1H-benzo[d]imidazol-6-yl)methanol.

Step 6: 6-(bis(4-chlorophenyl)methyl)-2-cyclopropyl-1-(1-((trifluoromethyl)sulfonyl)piperidin-4-yl)-1H-benzo[d]imidazol-4-ol Bis(4-chlorophenyl)(2-cyclopropyl-1-(1-((trifluoromethyl)sulfonyl)piperidin-4-yl)-4-((2-(trimethylsilyl)ethoxy) methoxy)-1H-benzo[d]imidazol-6-yl)methanol (112.8 mg, 0.188 mmol) was placed in an 8 mL vial equipped with a stir bar then dry dichloromethane (1 mL) was added. Trifluoroacetic acid (0.2 mL) was added then the reaction mixture was stirred at room temperature for 1 hour. The solvent was removed under reduced pressure then the residue was dissolved in dichloromethane (1 mL) and triethylsilane (36.3 µL, 0.227 mmol) was added. TFA (17.4 µL, 0.227 mmol) was added then the reaction was stirred at room temperature for 24 hours. The reaction mixture was diluted with dichloromethane (20 mL) and washed with saturated sodium bicarbonate solution (20 mL) then the organic layer was separated. The aqueous phase was extracted with dichloromethane (3×10 mL) then the organic extracts were combined, dried over $MgSO_4$, and filtered. The solvent was removed under reduced pressure and the resulting residue was purified by chromatography on silica gel eluting with a 0-100% ethyl acetate/heptane gradient to yield 6-(bis(4-chlorophenyl)methyl)-2-cyclopropyl-1-(1-((trifluoromethyl)sulfonyl)piperidin-4-yl)-1H-benzo[d]imidazol-4-ol.

MS: 491.2 (M+H$^+$); $^1$H NMR (400 MHz, CDCl3) δ: 8.71 (br. s., 1H), 7.25 (d, J=8.1 Hz, 4H), 7.04 (d, J=8.6 Hz, 4H), 6.65 (s, 1H), 6.48 (s, 1H), 5.54 (s, 1H), 4.61 (tt, J=12.4, 4.0 Hz, 1H), 4.14-4.24 (m, 2H), 3.23 (t, J=12.6 Hz, 2H), 2.47 (qd, J=12.6, 4.0 Hz, 2H), 2.00 (d, J=11.1 Hz, 2H), 1.85-1.94 (m, 1H), 1.00-1.14 (m, 4H).

Example DP-6

4-((4-chlorophenyl)(2-cyclopropyl-1-(1-((trifluoromethyl)sulfonyl)piperidin-4-yl)-1H-benzo[d]imidazol-6-yl)(hydroxy)methyl)benzoic acid

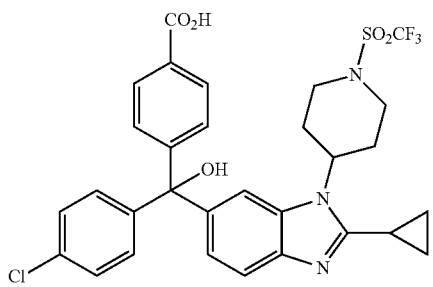

and 4-((4-chlorophenyl)(2-cyclopropyl-1-(1-((trifluoromethyl)sulfonyl)piperidin-4-yl)-1H-benzo[d]imidazol-6-yl)methyl)benzoic acid

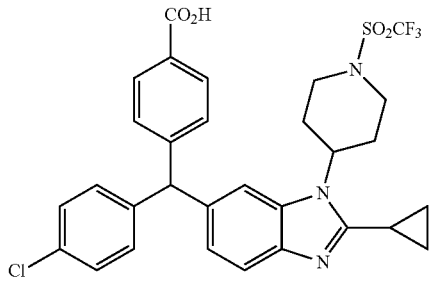

Step 1: (4-chlorophenyl)(2-cyclopropyl-1-(1-((trifluoromethyl)sulfonyl)piperidin-4-yl)-1H-benzo[d]imidazol-6-yl)methanol and (4-chlorophenyl)(2-cyclopropyl-1-(1-((trifluoromethyl)sulfonyl)piperidin-4-yl)-1H-benzo[d]imidazol-6-yl)methanone 6-Bromo-2-cyclopropyl-1-(1-((trifluoromethyl)sulfonyl)piperidin-4-yl)-1H-benzo[d]imidazole (209.3 mg, 0.463 mmol, prepared as described in Example YM-26) was placed in an 8 mL vial equipped with a stir bar then the vial was evacuated and filled with argon. Dry tetrahydrofuran (1 mL) was added then the solution was cooled to −78° C. n-BuLi (318.1 μL, 0.509 mmol, 1.6 M in hexane) was added dropwise then the reaction was stirred at −78° C. for 5 minutes.

4-Chlorobenzaldehyde (130 mg, 0.926 mmol) was placed in an 8 mL vial equipped with a stir bar then the vial was evacuated and filled with argon. Dry tetrahydrofuran (1 mL) was added then the solution was added dropwise to the stirred aryllithium solution at −78° C. The reaction mixture was allowed to warm to room temperature, stirred for 18 hours, then poured into saturated ammonium chloride solution (20 mL) and extracted with ethyl acetate (3×5 mL). The combined organic extracts were dried over Na$_2$SO$_4$, filtered, and the solvent was removed under reduced pressure. The resulting reaction mixture was purified by chromatography on silica gel eluting with a 0-100% ethyl acetate/heptane gradient to yield (4-chlorophenyl)(2-cyclopropyl-1-(1-((trifluoromethyl)sulfonyl)piperidin-4-yl)-1H-benzo[d]imidazol-6-yl)methanol and a smaller amount (4-chlorophenyl)(2-cyclopropyl-1-(1-((trifluoromethyl)sulfonyl)piperidin-4-yl)-1H-benzo[d]imidazol-6-yl)methanone.

Step 2: (4-chlorophenyl)(2-cyclopropyl-1-(1-((trifluoromethyl)sulfonyl)piperidin-4-yl)-1H-benzo[d]imidazol-6-yl)methanone (4-Chlorophenyl)(2-cyclopropyl-1-(1-((trifluoromethyl)sulfonyl)piperidin-4-yl)-1H-benzo[d]imidazol-6-yl)methanol (141.7 mg, 0.276 mmol) was placed in an 8 mL vial equipped with a stir bar then dichloromethane (2 mL) was added. Dess-Martin periodinane (128.6 mg, 0.303 mmol) was added as a solid then the reaction mixture was stirred at room temperature for 18 hours. The reaction mixture was diluted with dichloromethane (100 mL) and washed with 10% Na$_2$S$_2$O$_3$ (50 mL) and 2 M Na$_2$CO$_3$ solution (50 mL), then dried over MgSO$_4$ and filtered. The solvent was removed under reduced pressure. The residue was combined with the small amount of product prepared in the previous step and purified by chromatography on silica gel eluting with a 0-100% ethyl acetate/heptane gradient to yield (4-chlorophenyl)(2-cyclopropyl-1-(1-((trifluoromethyl)sulfonyl)piperidin-4-yl)-1H-benzo[d]imidazol-6-yl)methanone.

Step 3: (4-(1,3-dioxolan-2-yl)phenyl)(4-chlorophenyl)(2-cyclopropyl-1-(1-((trifluoromethyl)sulfonyl)piperidin-4-yl)-1H-benzo[d]imidazol-6-yl)methanol (4-Chlorophenyl)(2-cyclopropyl-1-(1-((trifluoromethyl)sulfonyl)piperidin-4-yl)-1H-benzo[d]imidazol-6-yl)methanone (50 mg, 0.098 mmol) was placed in an 8 mL vial equipped with a stir bar then the vial was evacuated and filled with argon. Dry tetrahydrofuran (1 mL) was added then (4-(1,3-dioxolan-2-yl)phenyl)magnesium bromide (0.391 mL, 0.195 mmol, 0.5 M in tetrahydrofuran) was added at room temperature. The mixture was stirred at room temperature for 18 hours then quenched with saturated ammonium chloride solution (2 mL). The mixture was extracted with ethyl acetate (3×5 mL) then the organic extracts were combined, dried over MgSO$_4$, and filtered. The solvent was removed under reduced pressure. The resulting residue was purified by preparative TLC on a 2000 micron silica gel plate developed with 30% ethyl acetate/dichloromethane. The isolated product fraction was further purified by preparative TLC on a 2000 micron silica gel plate developed with 30% ethyl acetate/dichloromethane to yield (4-(1,3-dioxolan-2-yl)phenyl)(4-chlorophenyl)(2-cyclopropyl-1-(1-((trifluoromethyl)sulfonyl)piperidin-4-yl)-1H-benzo[d]imidazol-6-yl)methanol.

Step 4: 4-((4-chlorophenyl)(2-cyclopropyl-1-(1-((trifluoromethyl)sulfonyl)piperidin-4-yl)-1H-benzo[d]imidazol-6-yl)(hydroxy)methyl)benzaldehyde (4-(1,3-Dioxolan-2-yl)phenyl)(4-chlorophenyl)(2-cyclopropyl-1-(1-((trifluoromethyl)sulfonyl)piperidin-4-yl)-1H-benzo[d]imidazol-6-yl)methanol (72.3 mg, 0.109 mmol) was placed in an 8 mL vial equipped with a stir bar then acetone (3 mL) and water (1 mL) were added. AMBERLYST™ 15 resin (70 mg) was added then the mixture was stirred at 60° C. for 2 h. The reaction mixture was cooled to room temperature then the resin was filtered off and rinsed with acetone. The solvent was removed under reduced pressure. The residue was dissolved in dichloromethane (20 mL) then dried over $MgSO_4$ and filtered. The solvent was removed under reduced pressure. The resulting residue was purified by preparative TLC on a 2000 micron silica gel plate developed with 30% ethyl acetate/dichloromethane to yield 4-((4-chlorophenyl)(2-cyclopropyl-1-(1-((trifluoromethyl)sulfonyl)piperidin-4-yl)-1H-benzo[d]imidazol-6-yl)(hydroxy)methyl)benzaldehyde.

Step 5: 4-((4-chlorophenyl)(2-cyclopropyl-1-(1-((trifluoromethyl)sulfonyl)piperidin-4-yl)-1H-benzo[d]imidazol-6-yl)(hydroxy)methyl)benzoic acid 4-((4-chlorophenyl)(2-cyclopropyl-1-(1-((trifluoromethyl)sulfonyl)piperidin-4-yl)-1H-benzo[d]imidazol-6-yl)(hydroxy)methyl)benzaldehyde (43.5 mg, 0.07 mmol) was dissolved in 1,4-dioxane (4 mL) then sulfamic acid (15.03 mg, 0.155 mmol) was added as a solid. A solution of sodium chlorite (17.50 mg, 0.155 mmol) in water (2 mL) was added dropwise with stirring and then the reaction mixture was stirred at room temperature for 15 hours. The reaction mixture was diluted with ethyl acetate (20 mL) and washed with brine (10 mL) then the organic layer was dried over $MgSO_4$ and filtered. The solvent was removed under reduced pressure. The residue was purified by preparative TLC on a 2000 micron silica gel plate developed with 10% methanol/dichloromethane to yield 4-((4-chlorophenyl)(2-cyclopropyl-1-(1-((trifluoromethyl)sulfonyl)piperidin-4-yl)-1H-benzo[d]imidazol-6-yl)(hydroxy)methyl)benzoic acid.

MS: 634.2 (M+H$^+$); $^1$H NMR (400 MHz, CDCl$_3$+CD$_3$OD) δ: 7.94 (d, J=8.1 Hz, 2H), 7.57 (s, 1H), 7.48 (d, J=8.6 Hz, 1H), 7.32 (d, J=8.1 Hz, 2H), 7.28 (d, J=8.6 Hz, 2H), 7.23 (d, J=8.6 Hz, 2H), 7.01 (d, J=8.1 Hz, 1H), 4.75 (tt, J=12.3, 3.9 Hz, 1H), 4.16 (d, J=12.6 Hz, 2H), 3.31 (t, J=13.1 Hz, 2H), 2.52 (q, J=12.3 Hz, 2H), 2.00-2.11 (m, 3H), 1.16 (d, J=7.1 Hz, 4H).

Step 6: 4-((4-chlorophenyl)(2-cyclopropyl-1-(1-((trifluoromethyl)sulfonyl)piperidin-4-yl)-1H-benzo[d]imidazol-6-yl)methyl)benzoic acid 4-((4-Chlorophenyl)(2-cyclopropyl-1-(1-((trifluoromethyl)sulfonyl)piperidin-4-yl)-1H-benzo[d]imidazol-6-yl)(hydroxy)methyl)benzoic acid (24.9 mg, 0.039 mmol) was placed in an 8 mL vial equipped with a stir bar then dry dichloromethane (1 mL) and triethylsilane (31.36 μL, 0.196 mmol) were added. Trifluoroacetic acid (15.13 μL, 0.196 mmol) was added then the reaction mixture was stirred at room temperature for 4 days at which time additional trifluoroacetic acid (15.13 μL, 0.196 mmol) and triethylsilane (31.36 μL, 0.196 mmol) were added. The reaction mixture was stirred at room temperature for 24 hours. An additional amount of trifluoroacetic acid (15.13 μL, 0.196 mmol) and triethylsilane (31.36 μL, 0.196 mmol) were added. The reaction mixture was stirred for an additional 5 days then the solvent was removed under reduced pressure. The residue was triturated with diethyl ether (3 mL) then the supernatant was decanted. This was repeated once more then the residual solvent was removed under reduced pressure to yield 4-((4-chlorophenyl)(2-cyclopropyl-1-(1-((trifluoromethyl)sulfonyl)piperidin-4-yl)-1H-benzo[d]imidazol-6-yl)methyl)benzoic acid trifluoroacetate salt as a white powder.

MS: 618.1 (M+H$^+$); $^1$H NMR (400 MHz, DMSO-d6) δ: 7.90 (d, J=8.6 Hz, 2H), 7.55 (d, J=8.6 Hz, 1H), 7.50 (br. s., 1H), 7.36-7.43 (m, J=8.6 Hz, 2H), 7.20-7.28 (m, J=8.1 Hz, 2H), 7.15 (d, J=8.6 Hz, 2H), 7.04 (d, J=8.1 Hz, 1H), 5.94 (s, 1H), 5.05 (t, J=11.9 Hz, 1H), 3.98 (d, J=12.1 Hz, 2H), 3.52 (br. s., 2H), 2.38-2.45 (m, 1H), 2.17-2.36 (m, 2H), 2.08 (d, J=11.1 Hz, 2H), 1.09-1.24 (m, 4H).

Example DP-8

6-(bis(4-chlorophenyl)methyl)-2-cyclopropyl-1-(tetrahydro-2H-pyran-4-yl)-1H-benzo[d]imidazole

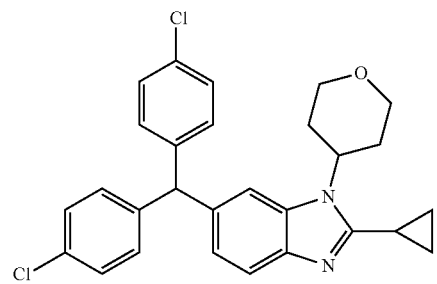 [SMILES: Clc1ccc(C(c2ccc(Cl)cc2)c2ccc3nc(C4CC4)n(C4CCOCC4)c3c2)cc1]

6-(Bis(4-chlorophenyl)methyl)-2-cyclopropyl-1-(tetrahydro-2H-pyran-4-yl)-1H-benzo[d]imidazole was prepared by according to the procedure as described in Example DP-4 above, substituting 4-aminotetrahydropyran for 4-aminomethyltetrahydropyran in Step 1.

MS: 515.2 (M+H$^+$); $^1$H NMR (400 MHz, CDCl$_3$) δ: 8.09 (d, J=9.1 Hz, 1H), 8.00 (d, J=6.6 Hz, 1H), 7.30 (d, J=8.6 Hz, 4H), 7.10 (d, J=8.6 Hz, 4H), 6.52 (dd, J=9.1, 2.0 Hz, 1H), 6.42 (d, J=2.0 Hz, 1H), 3.91-3.99 (m, 2H), 3.83 (s, 3H), 3.32-3.41 (m, 2H), 3.22-3.32 (m, 1H), 1.80 (d, J=12.6 Hz, 2H), 1.49-1.62 (m, 2H).

Example DP-9

2-(6-(bis(4-chlorophenyl)methyl)-1-(1-((trifluoromethyl)sulfonyl)piperidin-4-yl)-1H-benzo[d]imidazol-2-yl)prop-2-en-1-ol

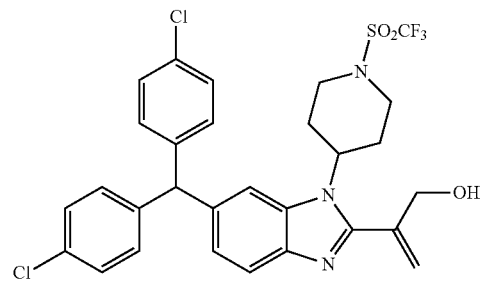

Step 1: methyl 2,2-bis(4-chlorophenyl)-2-(4-nitro-3-((1-(((trifluoromethyl)sulfonyl)piperidin-4-yl)amino)phenyl)acetate Methyl 2,2-bis(4-chlorophenyl)-2-(3-fluoro-4-nitrophenyl)acetate (589.2 mg, 1.357 mmol, prepared as described in Example DL-1), 4-aminopiperidine-1-trifluoromethylsulfonyl hydrochloride (401 mg, 1.49 mmol) and $K_2CO_3$ (563 mg, 4.07 mmol) were placed in an 8 mL vial equipped with a stir bar then dry DMSO (5 mL) was added. The reaction mixture was stirred at 80° C. for 3 days, cooled to room temperature, and poured into water (30 mL). The solid was isolated by filtration and washed with water (2×10 mL). The precipitate was dissolved in ethyl acetate (50 mL), dried over $MgSO_4$, and filtered. The solvent was removed under reduced pressure. The resulting residue was purified by chromatography on silica gel eluting with a 0-40% ethyl acetate/heptane gradient to yield methyl 2,2-bis(4-chlorophenyl)-2-(4-nitro-3-((1-(((trifluoromethyl)sulfonyl)piperidin-4-yl)amino)phenyl)acetate.

Step 2: methyl 2-(4-amino-3-((1-(((trifluoromethyl)sulfonyl)piperidin-4-yl)amino)phenyl)-2,2-bis(4-chlorophenyl)acetate Methyl 2,2-bis(4-chlorophenyl)-2-(4-nitro-3-((1-(((trifluoromethyl)sulfonyl)piperidin-4-yl)amino)phenyl)acetate (612.2 mg, 0.947 mmol) was placed in a 40 mL vial equipped with a stir bar then iron powder (264.4 mg, 4.735 mmol) and ammonium chloride (506.6 mg, 9.47 mmol) were added. Anhydrous ethanol (16 mL) and water (4 mL) were added then the reaction was stirred at 80° C. for 4 hours. The reaction mixture was cooled to room temperature and diluted with dichloromethane (20 mL) then the suspension was filtered through CELITE. The filter was washed with dichloromethane (3×10 mL) then the solvent was removed under reduced pressure. The residue was dissolved in dichloromethane (30 mL), dried over $MgSO_4$, and filtered. The solvent was removed under reduced pressure to yield methyl 2-(4-amino-3-((1-(((trifluoromethyl)sulfonyl)piperidin-4-yl)amino)phenyl)-2,2-bis(4-chlorophenyl)acetate, which was used directly in the next step without further purification.

Step 3: methyl 2,2-bis(4-chlorophenyl)-2-(4-(oxetane-3-carboxamido)-3-((1-(((trifluoromethyl)sulfonyl)piperidin-4-yl)amino)phenyl)acetate Oxetane-3-carboxylic acid (43.5 mg, 0.426 mmol) was placed in an 8 mL vial equipped with a stir bar then dry dichloromethane (5 mL) was added followed by diisopropylethylamine (0.094 mL, 0.527 mmol). Methyl 2-(4-amino-3-((1-(((trifluoromethyl)sulfonyl)piperidin-4-yl)amino)phenyl)-2,2-bis(4-chlorophenyl)acetate (250 mg, 0.406 mmol) was added followed by HBTU (199.9 mg, 0.527 mmol). The reaction was stirred at room temperature for 18 hours. The reaction mixture was diluted with water (30 mL) then extracted with dichloromethane (3×10 mL). The organic extracts were combined, dried over $MgSO_4$, and filtered. The solvent was removed under reduced pressure. The resulting residue was purified by chromatography on silica gel eluting with a 0-100% ethyl acetate/heptane gradient to yield methyl 2,2-bis(4-chlorophenyl)-2-(4-(oxetane-3-carboxamido)-3-((1-(((trifluoromethyl)sulfonyl)piperidin-4-yl)amino)phenyl)acetate.

Step 4: methyl 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetate Methyl 2,2-bis(4-chlorophenyl)-2-(4-(oxetane-3-carboxamido)-3-((1-(((trifluoromethyl)sulfonyl)piperidin-4-yl)amino)phenyl)acetate (126.4 mg, 0.18 mmol) was placed in an 8 mL vial equipped with a stir bar then acetic acid (1 mL) was added. The reaction mixture was stirred at 80° C. for 36 hours then cooled to room temperature. The reaction was diluted with water (6 mL) then poured into saturated sodium bicarbonate solution (30 mL) and extracted with dichloromethane (3×20 mL). The organic extracts were combined, washed with brine (20 mL), dried over $Na_2SO_4$, and filtered. The solvent was removed under reduced pressure. The resulting residue was purified by preparative TLC using 2×2000 micron silica gel plates developed with 30% ethyl acetate/dichloromethane to yield methyl 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetate.

Step 5: 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetic acid Methyl 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetate (16.1 mg, 0.024 mmol) was placed in an 8 mL vial equipped with a stir bar then methanol (1 mL) and 3 M sodium hydroxide (88.8 μL, 0.266 mmol) were added. The reaction mixture was stirred at 60° C. for 36 hours, then 10% citric acid solution (3 mL) and dichloromethane (3 mL) were added. The organic layer was separated then the aqueous phase was extracted with dichloromethane (3×3 mL). The organic extracts were combined, dried over $MgSO_4$, and filtered. The solvent was removed under reduced pressure to yield 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetic acid, which was used directly in the next step without further purification.

Step 6: 2-(6-(bis(4-chlorophenyl)methyl)-1-(1-(((trifluoromethyl)sulfonyl)piperidin-4-yl)-1H-benzo[d]imidazol-2-yl)prop-2-en-1-ol 2,2-bis(4-chlorophenyl)-2-(2-(3-hydroxyprop-1-en-2-yl)-1-(1-(((trifluoromethyl)sulfonyl)piperidin-4-yl)-1H-benzo[d]imidazol-6-yl)acetic acid (9.2 mg, 0.0138 mmol) was placed in an 8 mL vial equipped with a stir bar then dry toluene (1 mL) was added. DBU (0.206 μL, 0.0014 mmol) was added via microsyringe and the solution was heated to 90° C. and stirred for 2 hours. The reaction mixture was cooled to room temperature, diluted with dichloromethane (1 mL) then applied to a 2000 micron silica gel preparative TLC plate. The plate was developed with 50% ethyl acetate/heptane to yield 2-(6-(bis(4-chlorophenyl)methyl)-1-(1-((trifluoromethyl)sulfonyl)piperidin-4-yl)-1H-benzo[d]imidazol-2-yl)prop-2-en-1-ol.

MS: 624.1 (M+H$^+$); $^1$H NMR (400 MHz, CDCl$_3$) δ: 7.68 (d, J=8.6 Hz, 1H), 7.29 (d, J=8.6 Hz, 4H), 7.22 (s, 1H), 7.00-7.07 (m, 5H), 5.88 (s, 1H), 5.65 (s, 1H), 5.36 (s, 1H), 4.71 (tt, J=12.5, 3.9 Hz, 1H), 4.55 (s, 2H), 4.13 (d, J=13.6 Hz, 2H), 3.17 (t, J=12.9 Hz, 2H), 2.47 (qd, J=12.9, 4.3 Hz, 2H), 1.93-2.03 (m, 2H).

Example BD-1 bis(4-chlorophenyl)(2-cyclopropyl-1-((1-((trifluoromethyl)sulfonyl)piperidin-4-yl)methyl)-1H-benzo[d]imidazol-6-yl)methanol

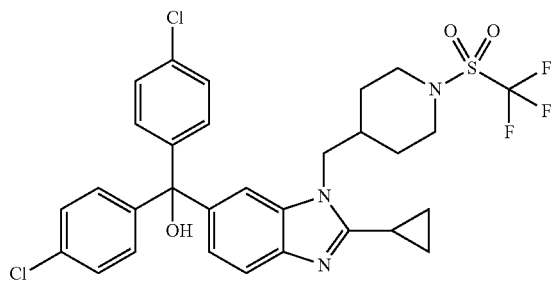 [SMILES: O=S(=O)(N1CCC(Cn2c(C3CC3)nc3ccc(C(O)(c4ccc(Cl)cc4)c4ccc(Cl)cc4)cc32)CC1)C(F)(F)F]

Step 1: methyl 2,2-bis(4-chlorophenyl)-2-(3-fluoro-4-nitrophenyl)acetate

To a solution of methyl 2,2-bis(4-chlorophenyl)acetate (4.427 g; 15 mmol) in tetrahydrofuran (80 mL) under Argon was added potassium a 1M solution of tert-butoxide in THF (15 mL; 1M in THF; 15 mmol). The mixture was stirred for 15 min at 0° C. and a solution of 2,4-difluoronitrobenzene (2.531 g; 15.75 mmol) in tetrahydrofuran (20 mL) was added dropwise. The mixture was allowed to stir at room temperature overnight. The reaction mixture was quenched with a sat NH$_4$Cl solution (20 mL). The organic phase was separated and dried over MgSO$_4$, filtered, and evaporated. The residue was purified via flash column chromatography (eluent gradient: 0 to 70% CH$_2$Cl$_2$ in heptane). The desired fractions were combined and evaporated to yield methyl 2,2-bis(4-chlorophenyl)-2-(3-fluoro-4-nitrophenyl)acetate as a yellow oil.

Rf (CH$_2$Cl$_2$:heptane; 1:1)=0.31; No clear molecular ion observed; Purity: 78% pure @ 214 nm and 92% @ 254 nm

Step 2: tert-butyl 4-(((5-(1,1-bis(4-chlorophenyl)-2-methoxy-2-oxoethyl)-2-nitrophenyl)amino)methyl)piperidine-1-carboxylate Methyl 2,2-bis(4-chlorophenyl)-2-(3-fluoro-4-nitrophenyl)acetate (2.171 g; 5 mmol), tert-butyl 4-(aminomethyl)-4-hydroxypiperidine-1-carboxylate (1.286 g; 6 mmol), and diisopropylethylamine (2.154 mL; 12.5 mmol) were dissolved in acetonitrile (10.856 mL) in a sealable tube and the mixture was heated at 75° C. for 1 hour. HPLC/MS analysis of an aliquot revealed mostly desired material. The reaction mixture was purified via flash column chromatography to tert-butyl 4-(((5-(1,1-bis(4-chlorophenyl)-2-methoxy-2-oxoethyl)-2-nitrophenyl)amino)methyl)piperidine-1-carboxylate. The material was used in the next reaction without further purification.

(M−Boc)+=528.2/530.1

Step 3: tert-butyl 4-(((2-amino-5-(1,1-bis(4-chlorophenyl)-2-methoxy-2-oxoethyl)phenyl)amino)methyl)piperidine-1-carboxylate A solution of tert-butyl 4-(((5-(1,1-bis(4-chlorophenyl)-2-methoxy-2-oxoethyl)-2-nitrophenyl)amino)methyl)piperidine-1-carboxylate (1.6 g; 2.546 mmol) in THF (90 mL) and methanol (10 mL) in a 200 mL Parr flask was purged with nitrogen, and Raney-Ni (0.5 g) was added. The mixture was hydrogenated at room temperature overnight on a Parr apparatus under 15 psi hydrogen pressure. The catalyst was removed via filtration over CELITE and the filtrate was evaporated, yielding tert-butyl 4-(((2-amino-5-(1,1-bis(4-chlorophenyl)-2-methoxy-2-oxoethyl)phenyl)amino)methyl)piperidine-1-carboxylate, which was used in the next reaction without further purification.

Purity: 77% pure @ 214 nm and 90% @ 254 nm; M+Na=620.2/622.2

Step 4: tert-butyl 4-((6-(1,1-bis(4-chlorophenyl)-2-methoxy-2-oxoethyl)-2-cyclopropyl-1H-benzo[d]imidazol-1-yl)methyl)piperidine-1-carboxylate To a solution of tert-butyl 4-(((2-amino-5-(1,1-bis(4-chlorophenyl)-2-methoxy-2-oxoethyl)phenyl)amino)methyl)piperidine-1-carboxylate (1.53 g; 2.55 mmol) in DMSO (5 mL) was added cyclopropanecarboxaldehyde (0.953 mL; 12.75 mmol) and the mixture was stirred for 2½ days at room temperature while open to the air. HPLC/MS analysis of an aliquot revealed complete disappearance of starting material with formation of desired product. The reaction mixture was diluted with water (50 mL) and extracted with a 1:1 mixture of diethyl ether and EtOAc (100 mL each). The organic layer was separated, dried over MgSO$_4$, filtered, and evaporated. The residue was purified via flash column chromatography (eluent gradient: 30:70 EtOAc:heptane to 100% EtOAc). The desired fractions were combined and evaporated to yield tert-butyl 4-((6-(1,1-bis(4-chlorophenyl)-2-methoxy-2-oxoethyl)-2-cyclopropyl-1H-benzo[d]imidazol-1-yl)methyl)piperidine-1-carboxylate as an off-white solid.

Rf (100% EtOAc)=0.65; Purity: 91% pure @ 214 nm and 254 nm; MH+=648.3/650.3

Step 5: methyl 2,2-bis(4-chlorophenyl)-2-(2-cyclopropyl-1-(piperidin-4-ylmethyl)-1H-benzo[d]imidazol-6-yl)acetate To a solution of tert-butyl 4-((6-(1,1-bis(4-chlorophenyl)-2-methoxy-2-oxoethyl)-2-cyclopropyl-1H-benzo[d]imidazol-1-yl)methyl)piperidine-1-carboxylate (500 mg; 0.771 mmol) in diethyl ether (9.23 mL) and 1,4-dioxane (4.61 mL) was added a 4N HCl in 1,4-dioxane solution (10 mL) and the mixture was stirred overnight at room temperature under Argon. Diethyl ether (50 mL) was added, and the mixture was stirred vigorously for 10 min. The solid was allowed to settle and the solvent was decanted. The residue was treated with additional diethyl ether (50 mL) and again decanted. Residual solvent was removed via evaporation and drying under vacuum to methyl 2,2-bis(4-chlorophenyl)-2-(2-cyclopropyl-1-(piperidin-4-ylmethyl)-1H-benzo[d]imidazol-6-yl)acetate as a tan solid.

Purity: 88% pure @ 214 nm and 92% pure @ 254 nm; MH+=548.3/550.2

Step 6: evaporated methyl 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetate To a solution of methyl 2,2-bis(4-chlorophenyl)-2-(2-cyclopropyl-1-(piperidin-4-ylmethyl)-1H-benzo[d]imidazol-6-yl)acetate (0.5 g; 0.805 mmol) and trimethylamine (0.336 mL; 2.414 mmol) in methylene chloride (20 mL) at 0° C. under Argon was added dropwise a 1M solution of triflic anhydride (1M in CH$_2$Cl$_2$; 0.966 mL). The reaction mixture was allowed to stir for 1 hour at 0° C. HPLC/MS analysis of an aliquot revealed 2/3 conversion to desired material. Additional of triflic anhydride (1.932 mL; 1.932 mmol, 1M in CH$_2$Cl$_2$) was added, and the mixture was stirred for another hour at 0° C. HPLC/MS analysis of an aliquot revealed complete disappearance starting material and formation of desired product. Sat. NaHCO$_3$ (10 mL) was added, and the mixture was stirred for 5 min. The organic layer was separated, dried over MgSO$_4$, filtered, and evaporated. The residue was purified via flash column chromatography (eluent gradient: 20% EtOAc in heptane to 100% EtOAc). The desired fractions were combined and evaporated methyl 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetate as a tan solid.

Step 7: 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetic acid To a solution of methyl 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetate (260 mg; 0.382 mmol) in methanol (5 mL) in a sealable tube was added 3N NaOH in water (2 mL). The tube was sealed and the mixture was heated at 45° C. overnight. HPLC/MS analysis of an aliquot revealed complete disappearance of starting material and formation of desired material. EtOAc (50 mL) was added, followed by 2N HCl (6 mL). The organic phase was separated, and the aqueous layer was extracted with an additional EtOAc (50 mL). The combined organic layers were dried over MgSO$_4$, filtered, and evaporated to yield 2,2-bis(4-chlorophenyl)-2-(2-cyclopropyl-1-((1-((trifluoromethyl)sulfonyl)piperidin-4-yl)methyl)-1H-benzo[d]imidazol-6-yl)acetic acid.

Purity: >95% pure @ 214 nm; 79% pure @ 254 nm; MH+=666.2/668.1

Step 8: 6-(Bis(4-chlorophenyl)methyl)-2-cyclopropyl-1-((1-((trifluoromethyl)sulfonyl)piperidin-4-yl)methyl)-1H-benzo[d]imidazole 2,2-Bis(4-chlorophenyl)-2-(2-cyclopropyl-1-((1-((trifluoromethyl)sulfonyl)piperidin-4-yl)methyl)-1H-benzo[d]imidazol-6-yl)acetic acid (260 mg; 0.39 mmol) and DBU (0.35 mL; 2.34 mmol) were combined in toluene (10 mL) under Argon and heated to 90° C. for 3 hours. HPLC/MS analysis of an aliquot revealed complete disappearance of starting material. The mixture was evaporated, dissolved in CH$_3$CN (4 mL) and purified via reverse phase HPLC. The desired fractions were combined and lyophilized to 6-(Bis(4-chlorophenyl)methyl)-2-cyclopropyl-1-((1-((trifluoromethyl)sulfonyl)piperidin-4-yl)methyl)-1H-benzo[d]imidazole as a white solid.

Purity: 94% pure @ 214 nm and 95% pure @ 254 nm; MH+=622.2/624.2; $^1$H NMR (400 MHz, DMSO-d$_6$) δ ppm 1.25-1.45 (m, 7H) 1.69 (br d, J=12.72 Hz, 2H) 2.12 (brs, 1H) 3.09 (br t, J=12.72 Hz, 2H) 3.74-3.84 (m, 2H) 4.41 (br d, J=5.62 Hz, 2H) 5.85 (s, 1H) 7.12-7.22 (m, 5H) 7.40 (d, J=8.07 Hz, 4H) 7.61 (br d, J=8.31 Hz, 1H) 7.71 (br s, 1H)

Step 9: bis(4-chlorophenyl)(2-cyclopropyl-1-((1-((trifluoromethyl)sulfonyl)piperidin-4-yl)methyl)-1H-benzo[d]imidazol-6-yl)methanol 6-(Bis(4-chlorophenyl)methyl)-2-cyclopropyl-1-((1-((trifluoromethyl)sulfonyl)piperidin-4-yl)methyl)-1H-benzo[d]imidazole (80 mg; 0.109 mmol) and K$_2$CO$_3$ (150.1 mg; 1.085 mmol) were combined in DMSO (10 mL) in a 2 mL vial and the mixture was stirred overnight at room temperature while open to the air. HPLC/MS analysis of an aliquot revealed only presence of 1 A. Two pellets (~400 mg) of NaOH were added, and the mixture was continued to stir for 2½ days at room temperature while air was being bubbled through the reaction mixture. HPLC/MS analysis of an aliquot revealed complete conversion to desired material. Water (50 mL) and diethyl ether (250 mL) were added to the reaction mixture, and the organic phase was separated. The aqueous layer was extracted with diethyl ether (150 mL), and the combined organic layers were washed with brine (25 mL), dried over K$_2$CO$_3$, filtered, and evaporated. The residue was purified over a short silica column (eluent: 100% EtOAc). The desired fractions were combined and evaporated to yield bis(4-chlorophenyl)(2-cyclopropyl-1-((1-((trifluoromethyl)sulfonyl)piperidin-4-yl)methyl)-1H-benzo[d]imidazol-6-yl)methanol as a white powder.

Purity: >95% pure @ 214 and 254 nm; MH+=638.1/640.2; $^1$H NMR (400 MHz, DMSO-d$_6$) δ ppm 1.11-1.39 (m, 6H) 1.60 (br d, J=13.20 Hz, 2H) 2.01 (br d, J=15.16 Hz, 1H) 2.19-2.38 (m, 1H) 3.09 (br t, J=12.10 Hz, 2H) 3.78 (br d, J=11.25 Hz, 2H) 4.18 (br d, J=6.85 Hz, 2H) 6.63 (s, 1H) 6.81-6.96 (m, 1H) 7.15-7.46 (m, 0H)

Example BD-2

4-((6-(bis(4-chlorophenyl)methyl)-2-cyclopropyl-1H-benzo[d]imidazol-1-yl)methyl)-1-((trifluoromethyl)sulfonyl)piperidin-4-ol

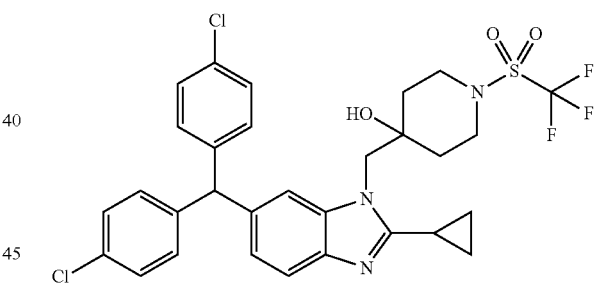

Step 1: tert-butyl 4-(((5-(1,1-bis(4-chlorophenyl)-2-methoxy-2-oxoethyl)-2-nitrophenyl)amino)methyl)-4-hydroxypiperidine-1-carboxylate Methyl 2,2-bis(4-chlorophenyl)-2-(3-fluoro-4-nitrophenyl)acetate (2.171 g; 5 mmol), tert-butyl 4-(aminomethyl)-4-hydroxy-tetrahydro-1(2H)-pyridinecarboxylate (1.382 g; 6 mmol), and diisopropylethylamine (2.154 mL; 12.5 mmol) were dissolved in acetonitrile (10.9 mL) in a sealable tube and the mixture was heated at 75° C. for 1 hour. HPLC/MS analysis of an aliquot revealed mostly desired material. The reaction mixture was purified via flash column chromatography to yield tert-butyl 4-(((5-(1,1-bis(4-chlorophenyl)-2-methoxy-2-oxoethyl)-2-nitrophenyl)amino)methyl)-4-hydroxypiperidine-1-carboxylate. The material was used in the next reaction without further purification.

Purity: >95% pure @ 214 and 254 nm; M−Boc=544.2/546.2

Step 2: tert-butyl 4-(((2-amino-5-(1,1-bis(4-chlorophenyl)-2-methoxy-2-oxoethyl)phenyl)amino)methyl)-4-hydroxypiperidine-1-carboxylate A solution of tert-butyl 4-(((5-(1,1-bis(4-chlorophenyl)-2-methoxy-2-oxoethyl)-2-nitrophenyl)amino)methyl)-4-hydroxypiperidine-1-carboxylate (2.05 g; 3.181 mmol) in tetrahydrofuran (100 mL) and methanol (10 mL) in a 200 mL Parr flask was purged with nitrogen, and $H_2$ was added. The mixture was hydrogenated at room temperature for 6 hours in a Parr apparatus under 12 psi hydrogen pressure. HPLC/MS analysis of an aliquot revealed complete conversion to desired material. The catalyst was removed via filtration over CELITE. The filtrate was evaporated to dryness and stored under vacuum overnight to yield tert-butyl 4-(((2-amino-5-(1,1-bis(4-chlorophenyl)-2-methoxy-2-oxoethyl)phenyl)amino)methyl)-4-hydroxypiperidine-1-carboxylate.

Purity: 93% pure @ 214 nm; >95% pure @ 254 nm; M+Na=636.2/638.3

Step 3: tert-butyl 4-((6-(1,1-bis(4-chlorophenyl)-2-methoxy-2-oxoethyl)-2-cyclopropyl-1H-benzo[d]imidazol-1-yl)methyl)-4-hydroxypiperidine-1-carboxylate To a solution of tert-butyl 4-(((2-amino-5-(1,1-bis(4-chlorophenyl)-2-methoxy-2-oxoethyl)phenyl)amino)methyl)-4-hydroxypiperidine-1-carboxylate (1.954 g; 3.18 mmol) in dimethyl sulfoxide (5 mL) was added cyclopropylcarboxaldehyde (1.188 mL; 15.9 mmol) and the mixture was stirred overnight at room temperature while open to the air. HPLC/MS analysis of an aliquot revealed complete disappearance of starting material with formation of desired product. The reaction mixture diluted with water (50 mL) and extracted with a 1:1 mixture of diethyl ether and EtOAc (100 mL each). The organic layer was separated, dried over $MgSO_4$, filtered, and evaporated. The residue was purified via flash column chromatography (eluent gradient: 1:1 EtOAc:heptane to 100% EtOAc). The desired fractions were combined and evaporated to yield tert-butyl 4-((6-(1,1-bis(4-chlorophenyl)-2-methoxy-2-oxoethyl)-2-cyclopropyl-1H-benzo[d]imidazol-1-yl)methyl)-4-hydroxypiperidine-1-carboxylate as an off-white solid.

Rf (100% EtOAc)=0.52; Purity: >95% pure @ 214 and 254 nm; MH+=664.2/666.3

Step 4: 2,2-bis(4-chlorophenyl)-2-(2-cyclopropyl-1-((4-hydroxypiperidin-4-yl)methyl)-1H-benzo[d]imidazol-6-yl)acetate To a solution of tert-butyl 4-((6-(1,1-bis(4-chlorophenyl)-2-methoxy-2-oxoethyl)-2-cyclopropyl-1H-benzo[d]imidazol-1-yl)methyl)-4-hydroxypiperidine-1-carboxylate (615 mg; 0.925 mmol) in diethyl ether (2.9 mL) and 1,4-dioxane (1.45 mL) was added a 4N HCl in 1,4-dioxane solution (8 mL) and the mixture was stirred overnight at room temperature under Argon. Diethyl ether (50 mL) was added, and the mixture was stirred vigorously for 10 min. The solid was allowed to settle and the solvent was decanted. The residue was treated with additional diethyl ether (50 mL) and again decanted. Residual solvent was removed via evaporation and drying under vacuum to yield methyl 2,2-bis(4-chlorophenyl)-2-(2-cyclopropyl-1-((4-hydroxypiperidin-4-yl)methyl)-1H-benzo[d]imidazol-6-yl)acetate as a white solid.

Purity: >95% pure @ 214 and 254 nm; MH+=564.2/566.2

Step 5: A mixture of methyl 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetate and methyl 2,2-bis(4-chlorophenyl)-2-(3-(((4-hydroxy-1-(((trifluoromethyl)sulfonyl)piperidin-4-yl)methyl)amino)-4-(trifluoromethylsulfonamido)phenyl)acetate To a solution of methyl 2,2-bis(4-chlorophenyl)-2-(2-cyclopropyl-1-((4-hydroxypiperidin-4-yl)methyl)-1H-benzo[d]imidazol-6-yl)acetate (0.637 g, 1 mmol) and 2,6-di-tert-butyl-4-methylpyridine (718.7 mg, 3.5 mmol) in methylene chloride (20 mL) at 0° C. under Argon was added dropwise 1M triflic anhydride in methylene chloride (1.2 mL, 1.2 mmol). The reaction mixture was allowed to stir for 1 hour at 0° C. HPLC/MS analysis of an aliquot revealed 1/3 conversion to desired material and formation of about equal amounts of P2. An additional 2.4 equiv of 1M triflic anhydride in methylene chloride (2.4 mL, 2.4 mmol) was added, and the mixture was stirred for another hour at 0° C. HPLC/MS analysis of an aliquot revealed complete disappearance of 1 A and formation of roughly equal amounts of product. Sat. $NaHCO_3$ (4 mL) was added, and the mixture was stirred for 10 min. The organic layer was separated, dried over $MgSO_4$, filtered, and evaporated. The residue was purified via flash column chromatography (eluent gradient: 20% EtOAc in heptane to 100% EtOAc). The desired fractions were combined and evaporated to yield a ~1:1 mixture of methyl 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetate and methyl 2,2-bis(4-chlorophenyl)-2-(3-(((4-hydroxy-1-((trifluoromethyl)sulfonyl)piperidin-4-yl)methyl)amino)-4-(trifluoromethylsulfonamido)phenyl)acetate, contaminated with ~15% of an third unknown compound. The material was used as in the next reaction without further purification.

Step 6: A mixture of 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetic acid and 2,2-bis(4-chlorophenyl)-2-(3-(((4-hydroxy-1-((trifluoromethyl)sulfonyl)piperidin-4-yl)methyl)amino)-4-(trifluoromethylsulfonamido)phenyl)acetic acid To a solution of methyl 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetate (230 mg; 33.0%) and methyl 2,2-bis(4-chlorophenyl)-2-(3-(((4-hydroxy-1-((trifluoromethyl)sulfonyl)piperidin-4-yl)methyl)amino)-4-(trifluoromethylsulfonamido)phenyl)acetate (220 mg; 28.1%) in methanol (10 mL) in a sealable tube was added 3N NaOH in water (3 mL). The tube was sealed and the mixture was heated at 45° C. overnight. HPLC/MS analysis of an aliquot revealed complete disappearance of starting material and formation of desired material, contaminated with several impurities. EtOAc (50 mL) was added, followed by 2N HCl (6 mL). The organic phase was separated, and the aqueous layer was extracted with additional EtOAc (50 mL). The combined organic layers were dried over $MgSO_4$, filtered, and evaporated. The residue, a mixture of 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetic acid and 2,2-bis(4-chlorophenyl)-2-(3-(((4-hydroxy-1-((trifluoromethyl)sulfonyl)piperidin-4-yl)methyl)amino)-4-

(trifluoromethylsulfonamido)phenyl)acetic acid, which was used in the next reaction without further purification.
MH+=682.0/684.2 and MH+=764.1/766.0

Step 7: Mixture of 4-((6-(bis(4-chlorophenyl)methyl)-2-cyclopropyl-1H-benzo[d]imidazol-1-yl)methyl)-1-((trifluoromethyl)sulfonyl)piperidin-4-ol and N-(4-(bis(4-chlorophenyl)methyl)-2-(((4-hydroxy-1-((trifluoromethyl)sulfonyl)piperidin-4-yl)methyl)amino)phenyl)-1,1,1-trifluoromethanesulfonamide A mixture of 2,2-bis(4-chlorophenyl)-2-(2-cyclopropyl-1-((4-hydroxy-1-((trifluoromethyl)sulfonyl)piperidin-4-yl)methyl)-1H-benzo[d]imidazol-6-yl)acetic acid and 2,2-bis(4-chlorophenyl)-2-(3-(((4-hydroxy-1-((trifluoromethyl)sulfonyl)piperidin-4-yl)methyl)amino)-4-(trifluoromethylsulfonamido)phenyl)acetic acid (430 mg) and DBU (3.78 mmol; 0.565 mL) were combined in toluene (10 mL) under Argon and heated to 90° C. for 3 hours. HPLC/MS analysis of an aliquot revealed complete disappearance of starting material. The mixture was evaporated, dissolved in CH$_3$CN (4 mL) and purified via reverse phase HPLC. The desired fractions were combined and lyophilized to yield a mixture of 4-((6-(bis(4-chlorophenyl)methyl)-2-cyclopropyl-1H-benzo[d]imidazol-1-yl)methyl)-1-((trifluoromethyl)sulfonyl)piperidin-4-ol as a white solid and N-(4-(bis(4-chlorophenyl)methyl)-2-(((4-hydroxy-1-((trifluoromethyl)sulfonyl)piperidin-4-yl)methyl)amino)phenyl)-1,1,1-trifluoromethanesulfonamide as a pink solid.
Purity: >95% pure @ 214 and 254 nm; MH+=638.1/640.2; $^1$H NMR (400 MHz, DMSO-d$_6$) δ ppm 1.32 (br s, 4H) 1.56 (br d, J=12.96 Hz, 2H) 1.77 (br d, J=12.47 Hz, 2H) 2.33 (br s, 1H) 3.24-3.33 (m, 2H) 3.66 (br d, J=12.23 Hz, 2H) 4.49 (brs, 2H) 5.84 (s, 1H) 7.16 (br d, J=8.31 Hz, 4H) 7.26 (br d, J=7.09 Hz, 1H) 7.40 (d, J=8.31 Hz, 4H) 7.61 (br d, J=8.07 Hz, 1H) 7.73 (br s, 1H)

Example BD-3

2-((4-chlorophenyl)(2-ethyl-1-((1-((trifluoromethyl)sulfonyl)piperidin-4-yl)methyl)-1H-benzo[d]imidazol-6-yl)methyl)thiazole

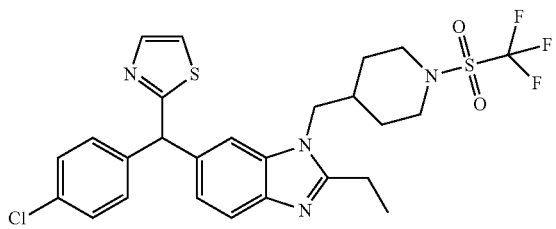 [SMILES: CCc1nc2ccc(C(c3ccc(Cl)cc3)c3nccs3)cc2n1CC1CCN(S(=O)(=O)C(F)(F)F)CC1]

Step 1: tert-butyl ((1-((trifluoromethyl)sulfonyl)piperidin-4-yl)methyl)carbamate To a solution of tert-butyl (piperidin-4-ylmethyl)carbamate (35.93 mmol; 7.7 g) and triethylamine (107.8 mmol; 15 mL) in dichloromethane (150 mL) at 0° C. under Argon was added triflic anhydride (46.71 mmol; 7.86 mL) dissolved in dichloromethane (50 mL), and the reaction mixture was stirred overnight at room temperature. A sat NaHCO$_3$ solution (75 mL) was added, and the mixture was stirred for 10 min. The organic phase was separated, dried over MgSO$_4$, filtered, and evaporated. A brown oil was obtained that was treated with diethyl ether (200 mL) and stirred vigorously for 15 min. No solid formed. The diethyl ether was evaporated to yield tert-butyl ((1-((trifluoromethyl)sulfonyl)piperidin-4-yl)methyl)carbamate as an orange oil. The material was used in the next reaction, without further purification.
(M−Boc)+=246.9

Step 2: (1-((trifluoromethyl)sulfonyl)piperidin-4-yl)methanamine

To a solution of tert-butyl ((1-((trifluoromethyl)sulfonyl)piperidin-4-yl)methyl)carbamate in diethyl ether (50 mL) and methanol (5 mL), a 4N HCl in 1,4-dioxane (50 mL) was added dropwise. The mixture was allowed to stir vigorously overnight at room temperature. An oil separated. Diethyl ether (100 mL) was added slowly, and the mixture was stirred vigorously for 10 min. The mixture was decanted and the residue was evaporated. The residue was stored overnight under vacuum, yielding (1-((trifluoromethyl)sulfonyl)piperidin-4-yl)methanamine as a brown solid. The material was used in the next reaction without further purification.
MH+=246.9

Step 3: 5-fluoro-2-nitro-N-((1-((trifluoromethyl)sulfonyl)piperidin-4-yl)methyl)aniline To a solution of 2,4-difluoronitrobenzene (6 mmol; 0.955 g) and triethylamine (18 mmol; 2.502 mL) in acetonitrile (20 mL) was added (1-((trifluoromethyl)sulfonyl)piperidin-4-yl)methanamine (7.8 mmol; 2.205 mg), and the mixture was stirred overnight at room temperature under Argon. Methylene chloride (50 mL) was added, and the solution was washed with brine. The organic phase was dried over MgSO$_4$, filtered, and evaporated. The residue was purified via flash column chromatography (eluent gradient: 10% to 50% EtOAc in heptane), yielding 5-fluoro-2-nitro-N-((1-((trifluoromethyl)sulfonyl)piperidin-4-yl)methyl)aniline as a yellow solid.
Rf (heptane:EtOAc; 3:1)=0.36

Step 4: 2-(4-chlorophenyl)-2-(4-nitro-3-(((1-((trifluoromethyl)sulfonyl)piperidin-4-yl)methyl)amino)phenyl)acetonitrile To a solution of 4-chlorobenzyl cyanide (3.893 mmol; 0.615 g) in tetrahydrofuran (25 mL) and isopropanol (5 mL) at room temperature under Argon was added potassium tert-butoxide (8.11 mmol; 0.91 mg) and the mixture was stirred for 10 min. A solution of 5-fluoro-2-nitro-N-((1-((trifluoromethyl)sulfonyl)piperidin-4-yl)methyl)aniline (3.244 mmol; 1.25 g) in tetrahydrofuran (10 mL) was added in one portion over a 5 min period and the reaction mixture turned a deep blue. The mixture was allowed to stir for 2 hours at room temperature. Sat NH$_4$Cl (10 mL) and EtOAc (50 mL) were added, and the mixture was stirred vigorously for 10 min. The organic layer was separated, washed with brine (10 mL), dried over MgSO$_4$, filtered, and evaporated. The residue was purified via flash column chromatography (eluent gradient: 10 to 50% EtOAc in heptane). The desired fractions were combined and evaporated to yield 2-(4-chlorophenyl)-2-(4-nitro-3-(((1-((trifluoromethyl)sulfonyl)piperidin-4-yl)methyl)amino)phenyl)acetonitrile as a bright yellow solid.

Rf (heptane:EtOAc; 3:1)=0.20; M+Na=538.8; Purity: >95% @ 214 and 254 nm

Step 5: 2-(4-amino-3-(((1-((trifluoromethyl)sulfonyl)piperidin-4-yl)methyl)amino)phenyl)-2-(4-chlorophenyl)acetonitrile A solution of 2-(4-chlorophenyl)-2-(4-nitro-3-(((1-((trifluoromethyl)sulfonyl)piperidin-4-yl)methyl)amino)phenyl)acetonitrile (2.9 mmol; 1.5 g) in tetrahydrofuran (50 mL) and water (5 mL) in a 200 mL Parr flask was purged with nitrogen, and Raney-Nickel (4.26 mmol; 0.25 g) was added. The mixture was hydrogenated at room temperature overnight on a Parr apparatus under 25 psi hydrogen pressure. HPLC/MS analysis of an aliquot revealed complete conversion to desired material. The catalyst was removed via filtration over CELITE. The filtrate was evaporated and the residue was used in the next reaction without further purification.

Step 6: 2-(4-chlorophenyl)-2-(2-ethyl-1-((1-((trifluoromethyl)sulfonyl)-piperidin-4-yl)methyl)-1H-benzo[d]imidazol-6-yl)acetonitrile To a solution of 2-(4-amino-3-(((1-((trifluoromethyl)sulfonyl)piperidin-4-yl)methyl)amino)phenyl)-2-(4-chlorophenyl)acetonitrile (1.45 mmol; 705.66 mg) in DMSO (4 mL) in a 20 mL vial was added propanal (7.25 mmol; 1.02 mL) and the mixture was stirred overnight at room temperature while open to the air. HPLC/MS analysis of an aliquot revealed partial disappearance of starting material with formation of desired product. Additional propanal (7.25 mmol, 1.02 mL) was added, and the mixture was stirred overnight while the vial was capped. HPLC/MS analysis of an aliquot revealed complete disappearance of starting material with formation of desired product. The reaction mixture was purified via reverse phase HPLC (eluent gradient: 25 to 70% CH$_3$CN in H$_2$O containing 0.1% TFA). The desired fractions were combined and lyophilized to yield 2-(4-chlorophenyl)-2-(2-ethyl-1-((1-((trifluoromethyl)sulfonyl)-piperidin-4-yl)methyl)-1H-benzo[d]imidazol-6-yl)acetonitrile as a white solid.

MH+=524.8; Purity: ~95% @ 214 and 254 nm

Step 7: 2-(4-chlorophenyl)-2-(2-ethyl-1-((1-((trifluoromethyl)sulfonyl)piperidin-4-yl)methyl)-1H-benzo[d]imidazol-6-yl)ethanethioamide 2-(4-chlorophenyl)-2-(2-ethyl-1-((1-((trifluoromethyl)sulfonyl)piperidin-4-yl)methyl)-1H-benzo[d]imidazol-6-yl)acetonitrile (0.372 mmol; 195.5 mg) and phosphorous pentasulfide (0.447 mmol; 0.2 g) were combined in ethanol (10 mL) in a sealable flask. The mixture was heated to 70° C. and the flask was sealed. The mixture was heated overnight at 70° C. and HPLC/MS analysis of an aliquot revealed clean conversion to desired material. The mixture was allowed to cool to room temperature, and brine (20 mL) and ethyl acetate (100 mL) were added. The organic layer was separated and washed with brine (50 mL). The organic layer was dried over MgSO$_4$, filtered, and evaporated. The residue was purified via flash column chromatography (eluent gradient: 100% EtOAc) to yield 2-(4-chlorophenyl)-2-(2-ethyl-1-((1-((trifluoromethyl)sulfonyl)piperidin-4-yl)methyl)-1H-benzo[d]imidazol-6-yl)ethanethioamide as a white solid.

Rf (100% EtOAc)=0.33; MH+=558.8; Purity: 90% pure @ 214 nm and >95% pure @ 254 nm Step 8: 2-((4-chlorophenyl)(2-ethyl-1-((1-((trifluoromethyl)sulfonyl)piperidin-4-yl)methyl)-1H-benzo[d]imidazol-6-yl)methyl)thiazole 2-(4-chlorophenyl)-2-(2-ethyl-1-((1-((trifluoromethyl)sulfonyl)piperidin-4-yl)methyl)-1H-benzo[d]imidazol-6-yl)ethanethioamide (0.116 mmol; 65 mg) and bromoacetaldehyde diethylacetal (0.465 mmol; 0.07 mL) were combined in acetic acid (5 mL) and water (0.2 mL) was added. The mixture was heated for 1 hour at 80° C. HPLC/MS analysis of an aliquot revealed complete conversion to desired material. The reaction mixture was lyophilized and the residue was purified via reverse phase HPLC (eluent gradient: 20% to 70% CH$_3$CN in H$_2$O, both containing 0.1% TFA). The desired fractions were combined and lyophilized to yield 2-((4-chlorophenyl)(2-ethyl-1-((1-((trifluoromethyl)sulfonyl)piperidin-4-yl)methyl)-1H-benzo[d]imidazol-6-yl)methyl)thiazole as an off-white solid.

Rf (EtOAc:heptane; 1:1)=0.27; 1H-NMR (DMSO-d6): $^1$H NMR (400 MHz, DMSO-d$_6$) δ ppm 1.41 (t, J=7.46 Hz, 3H) 1.68 (br d, J=12.72 Hz, 2H) 2.11 (br 1H) 2.23-2.44 (m, 1H) 3.03-3.22 (m, 4H) 3.67 (br s, 1H) 3.80 (br d, J=13.20 Hz, 2H) 4.31-4.57 (m, 2H) 6.24 (s, 1H) 7.36-7.53 (m, 5H) 7.72 (d, J=3.15 Hz, 1H) 7.76 (d, J=8.63 Hz, 1H) 7.83 (d, J=3.18 Hz, 1H) 8.02 (s, 1H); MH+=582.7; Purity: 93% pure @ 214 nm and >95% pure @ 254 nm Example BD-4

2-((4-chlorophenyl)(2-cyclopropyl-1-((1-((trifluoromethyl)sulfonyl)piperidin-4-yl)methyl)-1H-benzo[d]imidazol-6-yl)methyl)thiazole

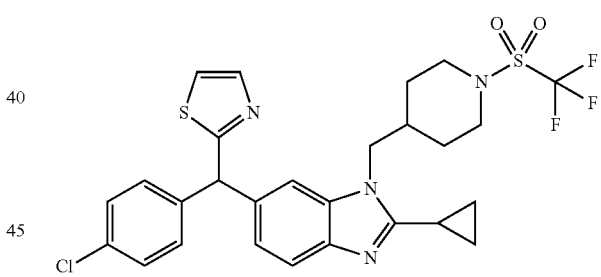

Step 1: 2-(4-chlorophenyl)-2-(2-cyclopropyl-1-((1-((trifluoromethyl)sulfonyl)piperidin-4-yl)methyl)-1H-benzo[d]imidazol-6-yl)acetonitrile To a solution of 2-(4-amino-3-(((1-((trifluoromethyl)sulfonyl)piperidin-4-yl)methyl)amino)phenyl)-2-(4-chlorophenyl)acetonitrile (0.75 mmol; 365.21 mg) in DMSO (4 mL) in a 20 mL vial was added propanal (2.25 mmol; 157.71 mL) and the mixture was stirred overnight at room temperature while open to the air. HPLC/MS analysis of an aliquot revealed partial disappearance of starting material. The reaction mixture was purified via reverse phase HPLC (eluent gradient: 35 to 55% CH$_3$CN in H$_2$O containing 0.1% TFA). The desired fractions were combined and lyophilized to yield 2-(4-chlorophenyl)-2-(2-cyclopropyl-1-((1-((trifluoromethyl)sulfonyl)piperidin-4-yl)methyl)-1H-benzo[d]imidazol-6-yl)acetonitrile as a white solid.

MH+=536.8; Purity: 95% @ 214 and 254 nm

Step 2: 2-(4-chlorophenyl)-2-(2-cyclopropyl-1-((1-((trifluoromethyl)sulfonyl)piperidin-4-yl)methyl)-1H-benzo[d]imidazol-6-yl)ethanethioamide 2-(4-chlorophenyl)-2-(2-cyclopropyl-1-((1-((trifluoromethyl)sulfonyl)piperidin-4-yl)methyl)-1H-benzo[d]imidazol-6-yl)acetonitrile (0.372 mmol; 200 mg) and phosphorous pentasulfide (0.45 mmol; 0.2 g) were combined in ethanol (10 mL) in a sealable flask. The mixture was heated to 70° C. and the flask was sealed. The mixture was heated overnight at 70° C. and HPLC/MS analysis of an aliquot revealed clean conversion to desired material. The mixture was allowed to cool to room temperature, and brine (20 mL) and ethyl acetate (100 mL) were added. The organic layer was separated and washed with brine (50 mL). The organic layer was dried over $MgSO_4$, filtered, and evaporated. The residue was purified via flash column chromatography (eluent gradient: 100% EtOAc) to yield 2-(4-chlorophenyl)-2-(2-cyclopropyl-1-((1-((trifluoromethyl)sulfonyl)piperidin-4-yl)methyl)-1H-benzo[d]imidazol-6-yl)ethanethioamide as a white solid.

Rf (100% EtOAc)=0.59; MH+=570.8; Purity: 90% pure @ 214 nm and >95% pure @ 254 nm

Step 3: 2-((4-chlorophenyl)(2-cyclopropyl-1-((1-((trifluoromethyl)sulfonyl)piperidin-4-yl)methyl)-1H-benzo[d]imidazol-6-yl)methyl)thiazole 2-(4-chlorophenyl)-2-(2-cyclopropyl-1-((1-((trifluoromethyl)sulfonyl)piperidin-4-yl)methyl)-1H-benzo[d]imidazol-6-yl)ethanethioamide (0.263 mmol; 150 mg) and bromoacetaldehyde diethylacetal (1.051 mmol; 0.158 mL) were combined in acetic acid (5 mL) and water (0.2 mL) was added. The mixture was heated for 1 hour at 80° C. HPLC/MS analysis of an aliquot revealed complete conversion to desired material. The reaction mixture was lyophilized and the residue was purified via reverse phase HPLC (eluent gradient: 20% to 70% $CH_3CN$ in $H_2O$, both containing 0.1% TFA). The desired fractions were combined and lyophilized to yield 2-((4-chlorophenyl)(2-cyclopropyl-1-((1-((trifluoromethyl)sulfonyl)piperidin-4-yl)methyl)-1H-benzo[d]imidazol-6-yl)methyl)thiazole as an off-white solid.

Rf (EtOAc:heptane; 1:1)=0.27; 1H-NMR (DMSO-d6): 1H NMR (400 MHz, DMSO-$d_6$) δ ppm 1.32-1.48 (m, 6H) 1.73 (br d, J=12.47 Hz, 2H) 2.17 (br s, 1H) 2.54-2.63 (m, 1H) 3.11 (br t, J=12.23 Hz, 2H) 3.81 (br d, J=12.47 Hz, 2H) 4.44 (br d, J=4.89 Hz, 2H) 6.20 (s, 1H) 7.35-7.46 (m, 5H) 7.65 (d, J=8.31 Hz, 1H) 7.71 (d, J=3.42 Hz, 1H) 7.83 (d, J=3.18 Hz, 1H) 7.94 (s, 1H); MH+=594.8; Purity: 95% pure @ 214 nm and >95% pure @ 254 nm

Biological Examples $CB_1$ and $CB_2$ receptors are $G_i$-coupled GPCR. Activation of $CB_1$ and $CB_2$ receptors results in a decrease in cAMP production. An inverse agonist of the $CB_1$ or $CB_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+TBP-NHS Cryptate (supplied as part of the assay kit). The specific signal (i.e. energy transfer) is inversely proportional to the concentration of cAMP in the standard or sample.

Biological Example 1: CB-1 and CB-2 In Vitro Assay

Preparation of Cells

Human $CB_1R$ (Cannabinoid receptor 1) was stably transfected in HEK-293 cells (DiscoveRx, cat: 93-0200C1). Human $CB_2R$ (Cannabinoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/ml Hygromycin B (Invitrogen Cat#10687-010), 600 μg/mL G418 (Invitrogen Cat#10131-035), and 1×Penn/Strep (Invitrogen 15140-122). After cell expansion, aliquots were cryo-stored in media containing 5% DMSO (Pierce Cat#20684).

Plating Cells from Cryostore

One day prior to experiments media was warmed to 37° C. and the cryo-stored cells were thawed in a 37° C. water bath. The cells were then added to media (10× volume) and the mixture was centrifuged at 1000 RPM for 5 min. The supernate was removed and the cells were re-suspended in media. A sample of the cell suspension was evaluated on a Cedex XS automated cell counter (Innovatis Systems) to determine viable cells/ml. Additional media was added to the cells to achieve a final cell density of 4E5 cells/mL. The cells were then plated into 384 well PDL white solid bottom plates (Greiner, Cat#781945) at 20 μL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% $CO_2$, 95% humidity) overnight.

Preparation of Compound Plates

DMSO was added to all wells of 384 well V bottom polystyrene plate (Greiner, Cat#781280) except to columns 1 and 13, rows O and P and wells M13-M23 and N13-N23. Test compounds (60 μL, 10 mM) were added to Column 1 and 13 (A1 through N1 and A13 through L13). Test compounds were serially diluted 1/3 by transferring and mixing 20 μl sample with 40 μL DMSO. This process resulted in a plate of 26 compounds, 11 doses per compound, 10 mM to 0.5 μM.

Preparation of Control Plate

DMSO (40 μL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 μL, 10 mM) was added to 01; and 1-(2,4-dichlorophenyl)-7-[(4-fluorophenyl)methylene]-4,5,6,7-tetrahydro-N-1-piperidinyl-1H-benzimidazole-3-carboxamide (60 μL, 10 mM) was added to N13. The control was serially diluted 1/3 by transferring and mixing 20 μl sample with 40 μL DMSO. This process resulted 11 doses per control, 10 mM to 0.5 μM.

cAMP Assay Protocol

Cells plated the day prior to the assay in clear bottom plates were viewed on an inverse microscope to ensure confluency in the range of 60-75%.

The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma 15879) in Buffer 1; (c) 1 μM cAMP Standard (50 μM stock, Perkin Elmer Cat# AD0262) diluted in Buffer 2 and serially diluted in Buffer 2, 12 doses @ 1/2 dilutions resulting in a dose range of 1 μM to 0.5 nM; (d) d2 labelled cAMP (CisBio HTRF Detection Kit Cat #62AM4PEB reconstituted with 6 ml dH$_2$O) diluted 1/20 with lysis buffer (CisBio HTRF Detection Kit Cat #62AM4PEB); (e) anti-cAMP (CisBio HTRF Detection Kit Cat #62AM4PEB reconstituted with 5 ml dH$_2$O) diluted 1/20 with lysis buffer (CisBio HTRF Detection Kit Cat #62AM4PEB); and (f) Forskolin (Sigma Cat# F6886, 10 mM in DMSO) diluted first in DMSO to 1 mM and then to 1.5 μM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 μl per well). Media as "dumped" from the cell plate and 30 μL Buffer 1 was added to each well using a Multidrop. The content of the cell plate was again "dumped" and 10 μL Buffer 2 was added to each well using a Flexdrop. 12.5 nL test compound dilutions or control compound dilutions (10 mM to 0.5 μM) were added to the cell plate using an ECHO 555 (Labcyte). The cell plate was mixed (Speed 6, Lab-Line Instruments Titer Plate Shaker) and centrifuged (1000 RPMs, 1 min). Using the Flexdrop, 2 μl additions were made into the cell plate: Buffer 2 was added to Column 24; and, 1.5 μM Forskolin was added to columns 1 through 23. Final volume of the cell plate was 12 μl with 250 nM Forskolin in all wells except column 12, and serial dilutions of test compound or control ranging from μM to 0.5 nM. The cell plate was again mixed (speed 6) and centrifuged (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 μL d2 labelled cAMP and 6 μL of Anti-cAMP were added to all wells of the cell plate using a BioMek FX (Beckman Coulter). The cell plate was again mixed (speed 6) and centrifuged (1000 RPMs, 1 min) and was incubated for 60 minutes in the dark at room Temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence×10,000 (Normalized signal (NS)). Amount of cAMP in nM was calculated for each well (based on NS) from a cAMP standard curve located on each plate (at P1-12 and P13-24). EC$_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of formula (I) of the present invention were tested for activity against the CB-1 and CB-2 receptors, according to assay protocol as outlined in Biological Example 1, with EC$_{50}$ results (in micromolar) as listed in Table BIO-1, below. Where a compound was tested more than once, the result presented below represents a mean of the individual measurements.

TABLE BIO-1

Biological Activity Against CB-1 and CB-2 Receptors

| ID No. | CB1 HEK_cAMP EC$_{50}$ μM | CB2 HEK_cAMP EC$_{50}$ μM |
|---|---|---|
| 1 | 0.0114 | 2.8458 |
| 2 | 0.4790 | 5.0304 |
| 3 | NT | NT |
| 4 | 0.0098 | 2.1597 |
| 5 | 0.0330 | 0.6324 |
| 6 | 0.0283 | 3.8761 |
| 7 | 0.0267 | 7.5998 |
| 8 | 0.0339 | 0.0782 |
| 9 | 0.0170 | 0.7978 |
| 10 | 0.3219 | 1.7494 |
| 11 | 0.0494 | 4.9694 |
| 12 | >10 | >10 |
| 13 | >10 | >10 |
| 14 | 0.0170 | >10 |
| 15 | 0.0730 | 0.6997 |
| 16 | 0.1732 | 0.6981 |
| 17 | 0.0829 | 9.3994 |
| 18 | 0.0533 | >10 |
| 19 | 0.0938 | >10 |
| 20 | 0.0156 | >10 |
| 21 | 0.2526 | 4.5436 |
| 22 | 0.0890 | 1.5237 |
| 23 | 0.1817 | 1.8763 |
| 24 | 1.9364 | 7.2996 |
| 25 | 1.6523 | >10 |
| 26 | 0.1028 | 3.3136 |
| 27 | 0.0110 | >10 |
| 28 | 0.0215 | >10 |
| 29 | NT | NT |
| 30 | 0.0402 | 1.6222 |
| 31 | 0.1500 | 2.9999 |
| 32 | 0.0395 | 2.1563 |
| 33 | 3.8001 | 2.8774 |
| 34 | 0.0375 | 6.7999 |
| 35 | 3.3435 | 4.3631 |
| 36 | 0.0854 | 0.8692 |
| 37 | 0.0876 | 7.2594 |
| 38 | 4.3003 | 1.6971 |
| 40 | 0.1044 | 5.1156 |
| 41 | 0.0306 | >41.9952 |
| 42 | 0.0908 | 8.6956 |
| 43 | 0.1135 | 12.1199 |
| 44 | 0.0146 | 2.4378 |
| 45 | 0.5933 | >41.9952 |
| 46 | 0.4503 | >41.9952 |
| 47 | 0.0024 | 17.1317 |
| 48 | 0.0030 | 3.8415 |
| 49 | 0.0085 | 4.3954 |
| 50 | 0.0481 | >10 |
| 52 | 0.0092 | >10 |
| 53 | 0.0267 | 3.0033 |
| 54 | 0.5962 | 3.9600 |
| 55 | 0.0123 | 2.7353 |
| 56 | 0.0193 | >10 |
| 57 | 0.0649 | 8.8389 |
| 59 | 0.0038 | >20.9991 |
| 61 | 0.0190 | >20.9991 |
| 63 | >10 | >20.9991 |
| 64 | 0.0026 | 2.3534 |
| 65 | 0.1543 | >10 |
| 67 | 0.3633 | 6.8945 |
| 68 | 0.1304 | 10.2991 |
| 69 | 0.0086 | 1.2067 |
| 70 | 0.0083 | 5.8237 |
| 71 | 0.0274 | 4.8764 |
| 72 | NT | NT |
| 73 | 0.0185 | 5.2481 |
| 74 | 0.0706 | 5.3889 |
| 75 | 0.0357 | 1.1476 |
| 76 | 0.0067 | 2.0578 |
| 77 | 0.0356 | >10 |
| 78 | 0.1506 | >20.9991 |
| 79 | 0.0326 | 5.0910 |
| 80 | 0.0866 | 11.3606 |
| 81 | 0.0141 | 3.2033 |

TABLE BIO-1-continued

Biological Activity Against CB-1 and CB-2 Receptors

| ID No. | CB1 HEK_cAMP EC$_{50}$ μM | CB2 HEK_cAMP EC$_{50}$ μM |
|---|---|---|
| 82 | 0.9949 | >41.9952 |
| 83 | 0.0426 | 11.3006 |
| 84 | 0.0677 | >10 |
| 85 | 0.0174 | 8.1003 |
| 86 | 0.0150 | 10.2000 |
| 87 | 0.0090 | 8.9991 |
| 88 | 0.0330 | >10 |
| 89 | 0.0072 | 7.8995 |
| 90 | 0.0224 | >10 |
| 91 | 0.0324 | 9.3994 |
| 92 | 0.0159 | 5.1916 |
| 93 | 0.0639 | 1.7494 |
| 94 | 0.0261 | 4.7621 |
| 95 | 0.0112 | >10 |
| 96 | 0.0273 | 7.9232 |
| 97 | 0.0187 | >10 |
| 98 | 0.0162 | >10 |
| 99 | 0.0188 | 4.7370 |
| 100 | 0.0194 | 6.2994 |
| 101 | 0.0285 | >10 |
| 102 | 0.0333 | 8.1414 |
| 104 | 0.0121 | 5.9993 |
| 105 | 0.0051 | 8.0002 |
| 106 | 0.0601 | >10 |
| 118 | 0.0980 | >10 |
| 119 | 0.0949 | 6.7406 |
| 120 | 0.0249 | 5.4338 |
| 121 | 0.0051 | 7.9689 |
| 122 | 0.0049 | 9.0991 |
| 123 | 0.0134 | 7.5007 |
| 124 | 0.0349 | >10 |
| 125 | 0.0177 | 9.8992 |
| 126 | 0.0042 | 7.7965 |
| 127 | 0.0050 | >10 |
| 128 | 0.0069 | 4.8933 |
| 129 | 0.0198 | >10 |
| 130 | 0.0155 | 8.1003 |
| 131 | 0.0080 | 6.4998 |
| 132 | >10 | >10 |
| 133 | 0.8125 | 3.5003 |
| 134 | 4.3441 | >10 |
| 135 | 0.0532 | >10 |
| 136 | 0.0320 | 9.0991 |
| 137 | 8.9970 | >10 |
| 138 | 0.0139 | 3.9048 |
| 140 | 0.0799 | >10 |
| 141 | 0.0033 | >10 |
| 142 | 0.0215 | 5.2481 |
| 143 | 3.9228 | >10 |
| 144 | 0.0152 | 4.7000 |
| 145 | 0.4316 | >10 |
| 146 | 0.0337 | >10 |
| 147 | 0.0102 | 7.5631 |
| 148 | 0.0096 | 4.9272 |
| 150 | 0.9721 | >10 |
| 151 | 0.0665 | >10 |
| 152 | 1.5907 | 6.4003 |
| 153 | 0.0087 | 3.6058 |
| 154 | 0.3111 | 8.0002 |
| 155 | 0.0067 | >10 |
| 157 | 0.1897 | 3.3822 |
| 158 | 0.0679 | 5.7996 |
| 159 | 0.2897 | 3.6208 |
| 160 | 0.0364 | 5.7996 |
| 161 | 0.0080 | 2.1086 |
| 162 | 0.0062 | 4.4864 |
| 163 | 0.0916 | 7.7768 |
| 164 | 0.0275 | >10 |
| 165 | >10 | >10 |
| 166 | 0.0037 | 5.0153 |
| 167 | 0.0854 | 4.3995 |
| 168 | 0.0912 | >10 |
| 169 | 0.0450 | 7.8995 |
| 170 | 0.0044 | 0.3143 |
| 171 | 0.1673 | >10 |
| 172 | 0.0812 | >10 |
| 173 | 0.0559 | 9.2003 |
| 174 | 6.5524 | >10 |
| 175 | 5.4225 | 4.7479 |
| 176 | >10 | >10 |
| 177 | 0.0967 | 7.8995 |
| 178 | 0.0675 | >10 |
| 179 | 0.0017 | >10 |
| 180 | 0.0171 | >10 |
| 181 | 0.0250 | >10 |
| 182 | 0.2552 | 2.9322 |
| 183 | 0.0314 | 6.2994 |
| 184 | 0.0314 | >10 |
| 185 | 0.1407 | 7.5998 |
| 186 | 0.0253 | >10 |
| 187 | 0.0518 | >10 |
| 188 | 0.1600 | >10 |
| 189 | 0.0295 | >10 |
| 190 | 0.0113 | 0.6987 |
| 191 | 0.0210 | >10 |
| 192 | 5.0478 | >10 |
| 193 | >10 | >10 |
| 198 | 4.7995 | >10 |
| 199 | 0.1732 | 6.4998 |
| 200 | 4.7239 | 6.3067 |
| 201 | 0.0638 | 0.9899 |
| 202 | 0.0312 | >10 |
| 203 | 0.0324 | >10 |
| 204 | 0.0944 | >10 |
| 205 | 0.0367 | 5.7319 |
| 206 | 0.1007 | >10 |
| 207 | 0.0064 | 4.6612 |
| 211 | 0.5888 | 10.2000 |
| 212 | 3.7420 | >10 |
| 213 | 8.3081 | >10 |
| 214 | 0.0225 | 5.0478 |
| 215 | 0.0020 | >10 |
| 216 | 0.0062 | >10 |
| 217 | 0.0092 | >10 |
| 218 | 0.0072 | 1.4421 |
| 220 | 1.3674 | 5.8398 |
| 221 | 0.0085 | 3.2984 |
| 222 | 0.0110 | 4.9636 |
| 223 | 0.0248 | 3.3435 |
| 224 | 0.0060 | >10 |
| 225 | 0.0415 | >10 |
| 226 | 0.0167 | 7.8235 |
| 227 | 2.0446 | >10 |
| 228 | 8.3004 | >10 |
| 229 | 0.0137 | 1.7750 |
| 230 | 0.0919 | 5.8993 |
| 231 | 0.7089 | >10 |
| 232 | 0.0176 | 8.8573 |
| 234 | 0.0161 | 9.5280 |
| 235 | 0.9404 | >10 |
| 238 | 0.0019 | >10 |
| 239 | 0.0100 | 2.6455 |
| 240 | 0.0149 | 2.1023 |
| 241 | 0.4589 | 7.8995 |
| 242 | 0.0180 | 5.6872 |
| 243 | 0.0359 | 0.3470 |
| 244 | 0.5337 | >10 |
| 245 | 0.2834 | >10 |
| 246 | 1.4325 | >10 |
| 247 | 0.1285 | >10 |
| 248 | 4.2355 | >10 |
| 249 | 0.0050 | 1.7147 |
| 250 | 0.0029 | 9.3994 |
| 251 | 0.0058 | 0.7301 |
| 252 | 0.0131 | 6.2445 |
| 253 | 0.0047 | 2.4221 |
| 254 | 0.0366 | 1.2491 |
| 255 | 0.0073 | >10 |
| 256 | 0.1287 | >10 |
| 257 | 0.0054 | >10 |

TABLE BIO-1-continued

Biological Activity Against CB-1 and CB-2 Receptors

| ID No. | CB1 HEK_cAMP EC$_{50}$ μM | CB2 HEK_cAMP EC$_{50}$ μM |
| --- | --- | --- |
| 258 | 0.0201 | >10 |
| 259 | 0.0037 | >10 |
| 260 | 0.0015 | >10 |
| 261 | 0.0219 | >10 |
| 262 | 0.0155 | >10 |
| 266 | 0.0184 | >10 |
| 267 | 0.0070 | >10 |
| 268 | 0.8764 | >10 |
| 269 | 1.0316 | >10 |
| 270 | 0.0066 | 9.8992 |
| 271 | 0.0021 | >10 |
| 272 | 0.0108 | >10 |
| 273 | 0.0336 | 9.6006 |
| 274 | 0.1327 | >10 |
| 275 | 0.0016 | >10 |
| 276 | 0.0093 | 2.6080 |
| 277 | 0.0047 | >10 |
| 278 | 0.0505 | >10 |
| 279 | 0.0322 | >10 |
| 280 | 0.0105 | >10 |
| 281 | 0.0125 | >10 |
| 282 | 0.0073 | >10 |
| 283 | 0.0036 | 0.9601 |
| 284 | 0.0057 | >10 |
| 285 | 0.0034 | >10 |
| 286 | 0.0382 | >10 |
| 287 | 0.0024 | 4.5888 |
| 288 | 0.0023 | >10 |
| 289 | 0.0292 | >10 |
| 291 | 2.2646 | >10 |
| 292 | 2.8913 | >10 |
| 293 | 7.4302 | >10 |
| 294 | 0.0046 | >10 |
| 295 | 0.0050 | 8.9991 |
| 297 | 0.6148 | >10 |
| 298 | 0.9057 | 8.9991 |
| 299 | 0.5778 | 1.0280 |
| 300 | 0.1631 | >10 |
| 301 | 0.0433 | >10 |
| 303 | 0.0174 | >10 |
| 305 | 2.8145 | >10 |
| 306 | 0.4100 | >10 |
| 308 | 0.0636 | >10 |
| 309 | 0.0034 | 5.2000 |
| 311 | 0.0172 | 8.6000 |
| 312 | 0.0492 | 1.5000 |
| 313 | 0.4163 | >10 |
| 314 | 0.0201 | 2.7855 |
| 315 | 0.0053 | 5.4001 |
| 316 | 0.0028 | 3.8646 |
| 317 | 0.0332 | 3.6543 |
| 318 | 0.0069 | >10 |
| 319 | 0.0225 | >10 |
| 320 | 0.0693 | >10 |
| 321 | 0.0062 | 4.0253 |
| 322 | 0.6206 | >10 |
| 323 | 0.0165 | >10 |
| 324 | 0.0102 | 3.8833 |
| 328 | 0.0084 | >13.9991 |
| 329 | 0.3788 | >10 |
| 330 | 0.1624 | >10 |
| 331 | 0.2395 | >10 |
| 332 | 0.0147 | 4.7000 |
| 333 | 0.4365 | >10 |
| 334 | 0.3158 | >10 |
| 335 | 0.0056 | >10 |
| 336 | 0.2597 | 7.2260 |
| 337 | 1.1779 | >10 |
| 338 | 0.0597 | 4.0004 |
| 339 | 2.4082 | >10 |
| 340 | 1.4421 | >10 |
| 341 | 1.3289 | >10 |
| 342 | 0.1842 | >10 |
| 343 | 0.1959 | >10 |
| 344 | >10 | >10 |
| 345 | >10 | >10 |
| 346 | 0.0324 | >10 |
| 347 | 2.7829 | >10 |
| 348 | 0.8670 | >10 |
| 349 | 7.2410 | >10 |
| 350 | 0.0347 | >10 |
| 351 | >10 | >10 |
| 352 | >10 | >10 |
| 353 | >10 | >10 |
| 354 | 5.4375 | >10 |
| 355 | 0.0129 | 1.9670 |
| 356 | >10 | |
| 357 | >10 | |
| 358 | >10 | |
| 359 | >10 | |
| 360 | >10 | |
| 361 | 2.0179 | >10 |
| 362 | 0.2125 | >10 |
| 363 | 2.2930 | >10 |
| 366 | >10 | >10 |
| 367 | 1.0770 | 2.7657 |
| 368 | >10 | >10 |
| 369 | >10 | >10 |
| 374 | 1.1179 | >10 |
| 375 | 0.7549 | >10 |
| 376 | 0.4410 | 0.2720 |
| 377 | >10 | >10 |
| 378 | >10 | >10 |
| 379 | >10 | >10 |
| 380 | 0.2430 | >10 |
| 381 | 0.7190 | >10 |
| 382 | 4.3241 | >10 |
| 383 | 2.7240 | >10 |
| 384 | 0.0120 | >10 |
| 385 | 0.5240 | >10 |
| 386 | 0.0220 | >10 |
| 387 | 0.5509 | >10 |
| 388 | 1.7591 | 1.6308 |
| 389 | >10 | >10 |
| 390 | 0.2420 | >10 |
| 391 | 0.0600 | >10 |
| 393 | 0.0280 | 0.0630 |
| 394 | 4.8362 | >10 |
| 395 | 0.1370 | >10 |
| 396 | 0.2210 | 0.0910 |
| 397 | >10 | >10 |
| 398 | 0.0210 | >10 |
| 399 | 0.1630 | >10 |
| 400 | 0.0060 | >10 |
| 401 | 6.0200 | >10 |
| 402 | 0.1920 | >10 |
| 403 | 0.5690 | >10 |
| 404 | 6.1518 | >10 |
| 405 | 4.4926 | 3.3504 |
| 406 | 1.6912 | >10 |
| 408 | 3.1463 | >10 |
| 409 | 0.0478 | >10 |
| 410 | 0.3078 | >10 |
| 411 | 0.3762 | >10 |
| 412 | 0.6232 | >10 |
| 413 | 0.3146 | >10 |
| 414 | 1.4894 | >10 |
| 415 | >10 | >10 |
| 416 | 0.3923 | >10 |
| 417 | 2.5369 | >10 |
| 418 | 1.0777 | >10 |
| 419 | 1.1836 | >10 |
| 420 | 0.2312 | >10 |
| 421 | 0.1117 | >10 |
| 422 | 0.5977 | >10 |
| 423 | 0.0170 | >10 |
| 424 | 2.3163 | >10 |
| 429 | 0.4374 | >10 |
| 431 | 0.1114 | >10 |
| 432 | 0.0643 | >10 |

TABLE BIO-1-continued

Biological Activity Against CB-1 and CB-2 Receptors

| ID No. | CB1 HEK_cAMP $EC_{50}$ μM | CB2 HEK_cAMP $EC_{50}$ μM |
|---|---|---|
| 433 | >10 | >10 |
| 434 | 0.0227 | >10 |
| 435 | >10 | >10 |
| 436 | 0.4730 | >10 |
| 437 | 0.1920 | >10 |
| 438 | 0.3150 | >10 |
| 439 | >10 | >10 |
| 440 | 0.9991 | >10 |
| 441 | 2.0907 | >10 |
| 442 | 3.4041 | >10 |
| 443 | 1.4332 | 4.9454 |
| 444 | 0.5353 | >10 |
| 445 | 0.9473 | >10 |
| 446 | 0.0899 | >10 |
| 448 | 0.1000 | >10 |
| 449 | >10 | >10 |
| 451 | | |
| 452 | 0.8128 | >6.70039 |
| 455 | 2.4149 | >7.39946 |
| 456 | >10 | >9.20026 |
| 460 | >10 | >10 |
| 462 | >10 | >6.59933 |
| 463 | 0.1642 | >7.59976 |
| 464 | 0.2116 | >7.19946 |
| 465 | 0.2428 | >10 |
| 466 | >8.69961 | 1.4315 |
| 474 | NT | NT |

NT = Not Tested

Additionally, the compound of formula (II) was tested according to the procedures as described above and measured to exhibit the following activity against the CB-1 and CB-2 ($IC_{50}$ in micromolar):
  CB-1 receptor: $IC_{50}$=0.0135 μM
  CB-1 receptor: $IC_{50}$=>10 μM Biological Example 2—Prophetic Example CB-1 & CB-2 Receptor Binding Assay Experimental Procedure CB-1 Membrane Binding:

Into Greiner V bottom polypropylene plates, hCB1-CHO-K1 membranes (2 μg/well final concentration) in assay buffer (50 mM Tris-HCl pH 7.4, 5 mM $MgCl_2$ and 0.5 mg/ml (0.05%) Ultra fatty acid free BSA) are dispensed. Membranes were purchased from Perkin Elmer. Test compounds are then added to each well and then [$^3$H] CP 55,940 (0.4 nM final well concentration) in assay buffer (50 mM Tris-HCl pH 7.4, 5 mM $MgCl_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed seven times with ice cold rinse buffer. Filter plates are then dried overnight at room temperature. The next day, plate bottoms are sealed with plate tape and 15 μl MicroScint 20 is added to each well. Plates are incubated for 2 h and radioactivity is measured by Topcount.

Experimental Procedure CB-2 Membrane Binding—Prophetic Example

Into Greiner V bottom polypropylene plates, hCB2-HEK293 membranes (2 μg/well final concentration) in assay buffer (50 mM Tris-HCl pH 7.4, 5 mM $MgCl_2$ and 0.5 mg/ml (0.05%) Ultra fatty acid free BSA) are dispensed. Membranes are prepared as described in FELDER, C. C., et al., Molecular Pharmacology, 1992, pp 838-845, Vol. 42. Test compounds are then added to each well and then [$^3$H] CP 55,940 (0.5 nM final well concentration) in assay buffer (50 mM Tris-HCl pH 7.4, 5 mM $MgCl_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed nine times with ice cold rinse buffer. Filter plates are then dried overnight at room temperature. The next day, plate bottoms are sealed with plate tape and 15 uL MicroScint 20 is added to each well. Plates are incubated for 2 h and radioactivity is measured by Topcount.

Total Binding:
  Total Binding levels are achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):
  Non-Specific Binding (NSB) levels are achieved by combining membrane, 10 μM final concentration WIN-55,212 (also known as (R)-(+)-[2,3-dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H] CP-55,940 (also known as 5-(1,1-dimethylheptyl)-2-[(1R,2R,5R)-5-hydroxy-2-(3-hydroxypropyl)cyclohexyl]-phenol).

Data Analysis:
  Top Count raw data files are used for data analysis as follows:
  Non-specific binding (NSB=10 μM WIN-55,212+Membrane+[$^3$H] CP-55,940) is used as the negative control, while the Total Binding (TB=DMSO+Membrane+[$^3$H] CP-55,940) is used as the positive control.
  Excel data file reports are generated by the PE TopCount and imported into Excel for calculations or are imported into a macro driven Excel template maintained by Lead Generation—Biology.
  $IC_{50}$ data is calculated using raw CPM values. Curves are fitted individually from singlet 11 point dosing curves+1% DMSO Control. $IC_{50}$ values are fit appropriately and calculated using the following equation:

$$v = V_{min} + \frac{V_0 + V_{min}}{1 + ([I]/IC_{50})^h}$$

$V_{min}$, CPM at maximum inhibition; $V_o$, CPM at zero inhibition; $IC_{50}$, inhibitor concentration at 50% inhibition; h, Hill coefficient.
  Maximal compound % inhibition of control treated wells is also noted since some compounds may exhibit values suitable for calculating $IC_{50}$'s.

% Inhibition of Total Binding=(1−(CPM Compound Treated Well/CPM Control Treated Well))*100

In Vivo Biological Assays

Animals, Diets and Test Compound:
  Male 14-20-week old diet-induced obese mice are ordered from Taconic. Mice were started on a 60% fat diet (D12492, Research Diets, New Brunswick, N.J.) at 6 weeks of age. Mice are single-housed.

Male Sprague Dawley rats are ordered from Charles River (225-250 gm upon arrival). They are fed standard chow diet (Purina 5001) and housed 2 per cage. Male C57bl/6j mice are ordered from Charles River at 22-25 g and housed 3 per cage. They are fed standard chow (Purina 5001). All animals are housed in a temperature-controlled room with 12-hour light/dark cycle. Animals are given food and water ad libitum, except as noted.

Test compounds are formulated in 10% PEG400 and 10% solutol or 10% PEG400 and 20% solutol. Test compounds are administered by oral gavage (5 ml kg$^{-1}$ or 10 ml kg$^{-1}$).

Biological Example 3: Mouse Fast PK/BBB

Male C57bl/6j mice were dosed with test compounds at 20 or 30 mg/kg. Plasma was collected via retro-orbital bleeding at 1 hr and 4 hrs after dosing. Whole brain without cerebellum was collected at 4 hrs after dosing. Wet brain weight was recorded before freezing. Brains were homogenized in saline and sent for analysis for determination of concentration of test compound.

Representative compounds of formula (I) of the present invention were tested according to the procedure described above, with results as listed in Table BIO-2 below.

TABLE BIO-2

Mouse Fast PK/BBB Results

| ID No. | Dose | Time | Plasma Mean Conc. (ng/mL) ± Std. Dev (ng/mL) | Brain Mean Conc. (ng/mL) ± Std. Dev (ng/mL) |
|---|---|---|---|---|
| 400 | 20 | 1 hr | 1553 ± 65.7 | 362 ± 36.9 |
|  |  | 4 hr | 947 ± 191 | 292 ± 61.0 |
| 335 | 20 | 1 hr | 3943 ± 480 | 53.3 ± 14.0 |
|  |  | 4 hr | 2265 ± 822 | 104 ± 19 |
| 328 | 20 | 1 hr | 2644 ± 337 | 39.1 ± 1.95 |
|  |  | 4 hr | 1601 ± 109 | 99.3 ± 13.3 |
| 320 | 20 | 1 hr | 2895.0 ± 244.9 | 121.5 ± 18.1 |
|  |  | 4 hr | 1609.4 ± 207.2 | 167.4 ± 9.4 |
| 318 | 20 | 1 hr | 5876 ± 1294 | 57.8 ± 14.8 |
|  |  | 4 hr | 2131 ± 245 | 69.4 ± 4.4 |
| 316 | 20 | 1 hr | 3979 ± 448 | 22.9 ± 2.7 |
|  |  | 4 hr | 247 ± 36 | 30.2 ± 5.2 |
| 315 | 20 | 1 hr | 2870.2 ± 441.2 | 33.8 ± 5.0 |
|  |  | 4 hr | 785.4 ± 190.6 | 48.4 ± 0.4 |
| 276 | 20 | 1 hr | 227 ± 67.2 | BLOQ ± NA |
|  |  | 4 hr | 27.7 ± 13.1 | BLOQ ± NA |
| 259 | 20 | 1 hr | 1422 ± 489 | BLOQ ± NA |
|  |  | 4 hr | 436 ± 83 | BLOQ ± NA |
| 242 | 20 | 1 hr | 789 ± NA | BLOQ ± NA |
|  |  | 4 hr | 62.1 ± 20.0 | BLOQ ± NA |
| 232 | 30 | 1 hr | 81.9 ± 22.7 | BLOQ ± NA |
|  |  | 4 hr | 7.11 ± 6.55 | BLOQ ± NA |
| 221 | 20 | 1 hr | 160 ± 69.7 | BLOQ ± NA |
|  |  | 4 hr | 33.8 ± 11.2 | BLOQ ± NA |
| 148 | 30 | 1 hr | 13541.7 ± 272.8 | 334.0 ± 108.4 |
|  |  | 4 hr | 7745.9 ± 3102.4 | 417.4 ± 50.0 |
| 129 | 30 | 1 hr | 1368 ± 749 | BLOQ ± NA |
|  |  | 4 hr | 84.6 ± 62.9 | BLOQ ± NA |
| 125 | 30 | 1 hr | 4493 ± 1011 | BLOQ ± NA |
|  |  | 4 hr | 390 ± 157 | BLOQ ± NA |
| 124 | 30 | 1 hr | 2023 ± 555 | BLOQ ± NA |
|  |  | 4 hr | 297 ± 107 | BLOQ ± NA |
| 92 | 30 | 1 hr | 11383 ± 2021 | 72.4 ± 11.1 |
|  |  | 4 hr | 5193 ± 277 | 89.2 ± 27.7 |
| 89 | 30 | 1 hr | 7190 ± 488 | 92.6 ± 20.4 |
|  |  | 4 hr | 4427 ± 227 | 129 ± 33.2 |

BLOQ = below level of quantitation;
NA = Not applicable

Biological Example 4: Five-Day Study in DIO Mice

The test compound was formulated in 10% PEG400 and 10% solutol. DIO mice (n=9) received vehicle or test compound daily for four days at 4 PM. Body weight and food weight were monitored daily at this time. On day 5, fed blood glucose, body weight, and food weight were measured at 9 AM and the mice were dosed at this time. Two hours later, mice were bled via the retro-orbital sinus under 70% $CO_2$/30% $O_2$ anesthesia. Plasma was used to determine insulin levels and compound concentration.

Three mice from each treatment group were anesthetized IP with 0.1 ml of a 4/1 mixture of Ketaset:AnaSed. (Prepared 10 ml Ketaset (100 mg/ml Ketamine)+2.5 ml AnaSed (20 mg/ml Xylazine) and then perfused with 60 ml heparinized saline through the left ventricle of the heart. The brains were removed and homogenized in PBS (4 ml/gm tissue). The samples were submitted for determination of plasma and brain compound levels.

Compound #335 was tested according to the procedure as described above, with results as listed in BIO-3A through BIO-3E, below.

TABLE BIO-3A

Mean Daily Food Intake (in Grams (Std Err))

|  | Vehicle | 30 mg/kg |
|---|---|---|
| Day 1 | 2.7 (0.2) | 0.4 (0.1) |
| Day 2 | 2.6 (0.2) | 0.5 (0.1) |
| Day 3 | 2.5 (0.1) | 0.5 (0.1) |
| Day 4 | 2.4 (0.1) | 1.1 (0.1) |

TABLE BIO-3B

Mean Body Weight (in Grams (Std Err))

|  | Vehicle | 30 mg/kg |
|---|---|---|
| Day 0 | 45.4 (0.7) | 45.4 (0.7) |
| Day 1 | 45.5 (0.7) | 42.8 (0.8) |
| Day 2 | 45.3 (0.7) | 41.4 (0.7) |
| Day 3 | 45.3 (0.8) | 40.3 (0.6) |
| Day 4 | 45.1 (0.7) | 39.4 (0.6) |

TABLE BIO-3C

Plasma Insulin (in ng/mL (Std Err))

|  | Plasma Insulin |
|---|---|
| Vehicle | 6.10 (0.98) |
| 30 mg/kg | 2.72 (0.61) |

TABLE BIO-3D

Fed Blood Glucose (in mg/dL (Std Err))

|  | Day 0 | Day 4 |
|---|---|---|
| Vehicle | 187 (9) | 202 (9) |
| 30 mg/kg | 187 (9) | 160 (6) |

TABLE BIO-3E

Plasma and Brain Concentrations, 2 Hours Post Dose, Day 5

|  | Plasma ng/mL (Std Dev) | Brain ng/g (Std Dev) |
|---|---|---|
| 30 mg/kg | 7662 (1587) | 208 (46) |

Compound #328 was tested according to the procedure as described above, with results as listed in BIO-4A through BIO-4E, below.

TABLE BIO-4A

Mean Daily Food Intake (in Grams (Std Err))

|       | Vehicle   | 30 mg/kg  |
|-------|-----------|-----------|
| Day 1 | 2.1 (0.2) | 0.5 (0.1) |
| Day 2 | 2.5 (0.2) | 0.5 (0.1) |
| Day 3 | 2.4 (0.2) | 0.7 (0.1) |
| Day 4 | 2.3 (0.1) | 1.2 (0.1) |

TABLE BIO-4B

Mean Body Weight (in Grams (Std Err))

|       | Vehicle    | 30 mg/kg   |
|-------|------------|------------|
| Day 0 | 43.4 (0.7) | 43.6 (0.7) |
| Day 1 | 43.4 (0.7) | 41.2 (0.7) |
| Day 2 | 43.0 (0.7) | 39.6 (0.6) |
| Day 3 | 42.9 (0.7) | 38.6 (0.6) |
| Day 4 | 42.7 (0.7) | 38.2 (0.7) |

TABLE BIO-4C

Plasma Insulin (in ng/mL (Std Err))

|          | Plasma Insulin |
|----------|----------------|
| Vehicle  | 3.32 (0.58)    |
| 30 mg/kg | 1.31 (0.13)    |

TABLE BIO-4D

Fed Blood Glucose (in mg/dL (Std Err))

|          | Day 0   | Day 4   |
|----------|---------|---------|
| Vehicle  | 183 (9) | 182 (6) |
| 30 mg/kg | 183 (9) | 154 (7) |

TABLE BIO-4E

Plasma and Brain Concentrations, 2 Hours Post Dose, Day 5

|          | Plasma ng/mL (Std Dev) | Brain ng/g (Std Dev) |
|----------|------------------------|----------------------|
| 30 mg/kg | 8364 (959)             | 291 (84.3)           |

Biological Example 5: Chronic DIO Mouse

The test compound was formulated in 10% PEG400 and 10% solutol. DIO mice received vehicle, test compound (@ 1, 3, 10, and 30 mg/kg) daily for 26 days. At the end of the experiment, the mice were euthanized and blood and tissues were collected.

Body weight and food weight (food intake) were monitored daily for days 1-5 and twice weekly thereafter.

An insulin tolerance test (0.7 U/kg Humulin, ip) was performed on day 21 after a 4 hour food removal. Blood glucose was measured at 0, 15, 30, 60 and 120 minutes after insulin. After an overnight fast, an oral glucose tolerance test (2 g/kg glucose) was performed on day 23. Blood glucose was measured at 0, 30, 60 and 120 minutes after glucose challenge.

Blood glucose was measured from the tail vein with a Lifescan glucometer. Plasma insulin was measured with an ELISA or HTRF kit (Cisbio). Plasma parameters were measured with an Olympus clinical chemistry analyzer.

Compound #148 was tested according to the procedure as described above, with results as listed in Table BIO-5A through Table BIO-5F, below.

TABLE BIO-5A

Mean Daily Food Intake (in Grams (Std Err))

|        | Vehicle   | 1 mg/kg   | 3 mg/kg   | 10 mg/kg  | 30 mg/kg  |
|--------|-----------|-----------|-----------|-----------|-----------|
| Day 2  | 2.1 (0.2) | 2.3 (0.1) | 2.0 (0.2) | 0.5 (0.1) | 0.1 (0.1) |
| Day 3  | 1.9 (0.2) | 2.3 (0.1) | 2.0 (0.1) | 0.9 (0.1) | 0.5 (0.1) |
| Day 4  | 1.9 (0.3) | 2.2 (0.1) | 1.9 (0.2) | 1.7 (0.2) | 0.7 (0.1) |
| Day 5  | 2.0 (0.3) | 2.4 (0.1) | 1.8 (0.2) | 1.8 (0.2) | 1.0 (0.2) |
| Day 8  | 1.9 (0.2) | 2.1 (0.1) | 1.7 (0.1) | 1.7 (0.1) | 1.3 (0.2) |
| Day 11 | 2.1 (0.1) | 2.3 (0.1) | 1.8 (0.1) | 2.0 (0.1) | 1.7 (0.2) |
| Day 15 | 2.5 (0.1) | 2.4 (0.1) | 2.5 (0.1) | 2.3 (0.1) | 2.3 (0.1) |
| Day 18 | 2.0 (0.2) | 1.6 (0.3) | 2.2 (0.1) | 2.3 (0.1) | 1.8 (0.2) |
| Day 24 | 2.3 (0.1) | 2.1 (0.2) | 2.2 (0.1) | 2.2 (0.2) | 2.4 (0.1) |

TABLE BIO-5B

Mean Body Weight (in Grams (Std Err))

|        | Vehicle      | 1 mg/kg      | 3 mg/kg      | 10 mg/kg     | 30 mg/kg     |
|--------|--------------|--------------|--------------|--------------|--------------|
| Day 0  | 41.42 (0.63) | 42.03 (0.80) | 42.28 (0.49) | 42.09 (0.85) | 42.46 (0.58) |
| Day 1  | 41.59 (0.77) | 42.63 (0.79) | 42.94 (0.45) | 42.69 (0.74) | 43.13 (0.69) |
| Day 2  | 41.18 (0.77) | 42.56 (0.86) | 42.12 (0.43) | 40.46 (0.66) | 39.64 (0.68) |
| Day 3  | 40.87 (0.83) | 42.46 (0.91) | 41.85 (0.47) | 39.85 (0.68) | 38.53 (0.66) |
| Day 4  | 40.63 (0.92) | 42.26 (0.87) | 41.42 (0.44) | 39.44 (0.70) | 37.46 (0.75) |
| Day 5  | 40.29 (0.97) | 42.31 (0.81) | 41.3 (0.36)  | 38.78 (0.70) | 36.67 (0.75) |
| Day 8  | 39.48 (1.08) | 41.62 (0.79) | 39.78 (0.29) | 37.4 (0.67)  | 34.95 (0.78) |
| Day 11 | 39.74 (0.98) | 41.91 (0.77) | 39.1 (0.41)  | 36.99 (0.78) | 33.79 (0.87) |
| Day 15 | 40.72 (0.98) | 42.67 (1.02) | 40.43 (0.40) | 37.33 (0.84) | 34.19 (0.64) |
| Day 18 | 39.4 (1.17)  | 40.54 (1.23) | 39.84 (0.53) | 37.02 (0.88) | 32.47 (0.92) |
| Day 24 | 40.94 (1.21) | 41.11 (1.30) | 40.48 (0.48) | 36.42 (1.25) | 32.86 (0.91) |

TABLE BIO-5C

Insulin Tolerance Test
Mean Blood Glucose (in mg/dL (Std Err))

|  | Vehicle | 1 mg/kg | 3 mg/kg | 10 mg/kg | 30 mg/kg |
|---|---|---|---|---|---|
| 0 min | 184.2 (12.70) | 194.8 (14.64) | 185.9 (6.57) | 168.8 (7.13) | 143 (12.69) |
| 15 min | 179.4 (14.38) | 193.3 (13.87) | 160.9 (7.24) | 172.6 (9.66) | 147.6 (14.57) |
| 30 min | 145 (14.33) | 155 (15.40) | 138.9 (9.10) | 139.1 (7.03) | 119.8 (12.67) |
| 60 min | 154.2 (14.08) | 161.3 (18.83) | 150.9 (11.66) | 146.7 (5.80) | 121.3 (13.19) |
| 120 min | 161.8 (13.33) | 150 (13.98) | 136.3 (9.51) | 144.8 (5.86) | 104.5 (10.01) |
| AUC (mg/dL*min) | 19128 (1598.23) | 19606.5 (1737.27) | 17812.5 (1054.85) | 17930.25 (556.44) | 14575.5 (1441.54) |

TABLE BIO-5D

Oral Glucose Tolerance Test
Mean Blood Glucose (in mg/dL (Std Err))

|  | Vehicle | 1 mg/kg | 3 mg/kg | 10 mg/kg | 30 mg/kg |
|---|---|---|---|---|---|
| 0 min | 151.80 (9.25) | 139.90 (7.77) | 154.89 (4.54) | 141.60 (6.97) | 125.30 (9.30) |
| 30 min | 172.1 (9.53) | 179.2 (13.61) | 153.11 (11.51) | 190.1 (6.14) | 184.5 (9.25) |
| 60 min | 164.3 (7.75) | 168.5 (10.65) | 183.89 (7.37) | 176.2 (5.23) | 179 (4.31) |
| 120 min | 158.6 (11.17) | 143.5 (9.60) | 150.44 (3.48) | 132.8 (5.33) | 126.9 (10.95) |
| AUC (mg/dL*min) | 19591.5 (698.06) | 19362 (816.66) | 19705 (543.73) | 19740 (577.36) | 19276.5 (638.04) |

TABLE BIO-5E

Plasma Insulin (in ng/mL (Std Err))

|  | Plasma Insulin |
|---|---|
| Vehicle | 5.90 (0.64) |
| 1 mg/kg | 5.92 (0.92) |
| 3 mg/kg | 4.74 (0.83) |
| 10 mg/kg | 2.20 (0.13) |
| 30 mg/kg | 2.85 (0.27) |

TABLE BIO 5F

Plasma and Brain Concentrations, 2 Hours Post Dose, Day 25

|  | Plasma ng/mL (Std Dev) | Brain ng/g (Std Dev) |
|---|---|---|
| 1 mg/kg | 288 (56.2) | 18.2 (7.56) |
| 3 mg/kg | 1346 (321) | 29.9 (13.8) |
| 10 mg/kg | 3431 (152) | 42 (28.3) |
| 30 mg/kg | 15237 (11647) | 73.5 (93.3) |

Biological Example 6: Open Field Locomotor Activity in Rats (CNS Activity)

Prophetic Example

Male SD rats are weighed and transferred to the Activity Chambers with access to water. After a 2-hr acclimation period, the rats are dosed with vehicle or test compound (@ 3 and 10 mg/kg). The Activity Chamber monitoring software program is initiated and automatically records rat activity in each chamber for a period of 4 hours. At the end of the 4 hour monitoring period, the software is stopped and the rats are removed from the activity chambers. The rats are anesthetized and blood samples are obtained via retro-orbital puncture to determine plasma concentration of compounds. The rats are immediately euthanized with $CO_2$ and the brains are removed, washed with PBS, frozen on dry ice and stored at $-80°$ C. for receptor occupancy (RO) analysis.

Satellite groups of 3 rats are dosed with test compound at 3 mg/kg and 10 mg/kg respectively. Four hours later, the rats are anesthetized. Blood is collected from these rats and then perfused with 400 ml heparinized saline through the left ventricle of the heart. The brains are removed and homogenized in PBS (4 ml/gm tissue). The samples are submitted for determination of plasma and brain compound levels.

Formulation Example 1

Solid, Oral Dosage Form—Prophetic Example

As a specific embodiment of an oral composition, 100 mg of the Compound #335 or Compound #328 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

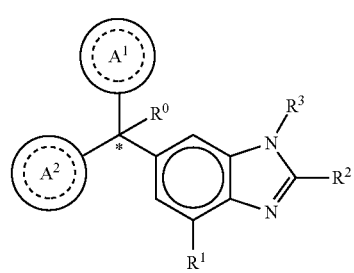

(I)

wherein
R⁰ is selected from the group consisting of hydrogen, —OH, —C(O)OH, —C(O)O—(C$_{1-4}$alkyl), —CH$_2$—OH, —CH$_2$—O—(C$_{1-2}$alkyl) and —CH$_2$—O—(C$_{1-2}$alkyl)-CO$_2$H;

is selected from the group consisting of cylopropyl, cyclobutyl, cyclopentyl, cyclohexyl, phenyl, furyl, thienyl, thiazolyl, benzothiazolyl and benzo[d][1,3]dioxolyl;

wherein the phenyl, furyl, thienyl, thiazolyl or benzothiazolyl is optionally substituted with one or more substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, cyano, —C(O)OH, —C(O)O—(C$_{1-4}$alkyl), —C(O)NR$^A$R$^B$ and NR$^A$R$^B$; wherein R$^A$ and R$^B$ are each independently selected from the group consisting of hydrogen, alkyl and hydroxy substituted C$_{1-2}$alkyl; provided that each substituent is bound to a carbon atom;

is selected from the group consisting of cylopropyl, cyclobutyl, cyclopentyl, cyclohexyl, phenyl, furyl, thienyl, thiazolyl, benzothiazolyl and benzo[d][1,3]dioxolyl;

wherein the phenyl, furyl, thienyl, thiazolyl or benzothiazolyl is optionally substituted with one or more substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, cyano, —C(O)OH, —C(O)O—(C$_{1-4}$alkyl), —C(O)NR$^C$R$^D$ and NR$^C$R$^D$; wherein R$^C$ and R$^D$ are each independently selected from the group consisting of hydrogen, alkyl and hydroxy substituted C$_{1-2}$alkyl; provided that each substituent is bound to a carbon atom;

R$^1$ is selected from the group consisting of hydrogen, hydroxy and C$_{1-4}$alkoxy;

R$^2$ is selected from the group consisting of hydrogen, halogen, C$_{1-4}$alkyl, fluorinated C$_{1-2}$alkyl, —(C$_{1-2}$alkyl)-OH, —(C$_{1-2}$alkyl)-C(O)OH, —(C$_{1-2}$alkyl)-NR$^E$R$^F$, —(C$_{2-4}$alkenyl)-OH, —C(O)OH, —C(O)O—(C$_{1-2}$alkyl), —NR$^E$R$^F$, C$_{3-6}$cycloalkyl, phenyl, furyl, thienyl, pyridyl, azetidin-3-yl, oxetan-3-yl, tetrahydrofuran-2-yl and tetrahydropyran-4-yl;

wherein the phenyl is optionally substituted with one to two halogen; wherein the azetidin-3-yl is optionally substituted with —C(O)O—(C$_{1-4}$alkyl); and wherein R$^E$ and R$^F$ are each independently selected from the group consisting of hydrogen and C$_{1-4}$alkyl;

provided that when R$^2$ is selected from the group consisting of pyridyl, furyl and thienyl, then the R$^2$ is bound to the benzimidazole core through a carbon atom;

R$^3$ is selected from the group consisting of (a) through (k); wherein (a) is

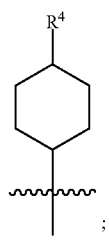

wherein R$^4$ is selected from the group consisting of hydrogen, —C(O)OH, —C(O)O—(C$_{1-2}$alkyl), —C(O)NR$^G$R$^H$, —NH-(phenyl), and —NH—SO$_2$-(phenyl); wherein the phenyl is optionally substituted with one or more substituents independently selected from the group consisting of halogen, hydroxy and carboxy; and wherein R$^G$ and R$^H$ are each independently selected from the group consisting of hydrogen and C$_{1-4}$alkyl;

(b) is

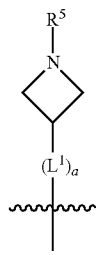

(c) is

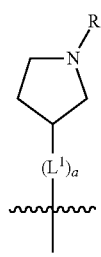

(d) is

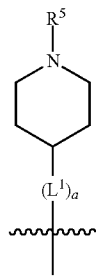

(e) is

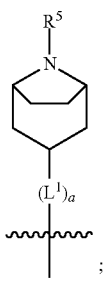

(f) is

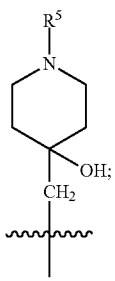

wherein a is an integer from 0 to 1;
wherein L¹ is selected from the group consisting of —CH₂—, —CH₂—CH₂, —CH₂CH₂CH₂—, —CH(CH₃)CH₂— and —CH₂—CH(CH₃)—;
wherein R⁵ is selected from the group consisting of hydrogen, $C_{1-2}$alkyl, fluorinated $C_{1-2}$alkyl, $C_{2-4}$alkenyl, —($C_{1-2}$alkyl)-C(O)OH, —($C_{1-2}$alkyl)-C(O)O—($C_{1-2}$alkyl), —($C_{2-3}$alkyl)-O-(phenyl), —C(O)—($C_{1-2}$alkyl)-OH, —C(O)—($C_{1-2}$alkyl)-C(O)OH, —C(O)—($C_{1-2}$alkyl)-C(O)O—($C_{1-2}$alkyl), —C(O)—($C_{1-2}$alkyl)-C(O)—NH₂, —C(O)OH, —C(O)O—($C_{1-4}$alkyl), —C(O)O—($C_{3-5}$cycloalkyl), —C(O)—NR$^J$R$^K$, —C(O)NH—($C_{3-5}$cycloalkyl), —C(O)NH-(phenyl), —C(O)NH—($C_{1-2}$alkyl)-(phenyl), —SO₂—($C_{1-2}$alkyl), —SO₂-(fluorinated $C_{1-2}$alkyl), —SO₂—($C_{1-2}$alkyl)-C(O)OH, —SO₂—($C_{1-2}$alkyl)-C(O)O—($C_{1-2}$alkyl), —SO₂—NR$^J$R$^K$, —SO₂—($C_{1-2}$alkyl)-C(O)NR$^J$R$^K$, phenyl, —($C_{1-3}$alkyl)-phenyl, —C(O)-(phenyl), —C(O)O-(phenyl), —C(O)O—($C_{1-2}$alkyl)-(phenyl), —SO₂-(phenyl), pyrimidin-2-yl, pyridyl, —($C_{1-2}$alkyl)-pyridyl, —C(O)-(pyridyl), —SO₂-(pyridyl), furyl, —($C_{1-2}$alkyl)-furyl, —C(O)-furyl, —SO₂-(furyl), thienyl, —($C_{1-2}$alkyl)-thienyl, —C(O)-thienyl, —SO₂-(thienyl), —C(O)-(1,2,3-triazol-4-yl), —C(O)-(1,2,4,-triazol-3-yl) and —SO₂—($C_{1-2}$alkyl)-(piperazin-1-yl);
wherein the phenyl, pyrimidin-2-yl, pyridyl, furyl, thienyl or pyridyl, is optionally substituted with one or more substituents independently selected from the group consisting of halogen, hydroxy, $C_{1-4}$alkyl, fluorinated $C_{1-2}$alkyl, —($C_{1-2}$alkyl)-OH, —($C_{1-2}$alkyl)-C(O)OH, —($C_{1-2}$alkyl)-C(O)O—($C_{1-2}$alkyl), —C($_{1-2}$alkyl)-C(O)OH, —($C_{1-2}$alkyl)-C(O)O—($C_{1-2}$alkyl), —($C_{1-2}$alkyl)-C(O)—NR$^L$R$^M$, —O—($C_{1-4}$alkyl), —O-(fluorinated $C_{1-2}$alkyl), —O—($C_{2-6}$alkenyl), —O—($C_{1-2}$alkyl)-C(O)OH, —O—($C_{1-2}$alkyl)-C(O)O—($C_{1-2}$alkyl), —O—($C_{1-2}$alkyl)-C(O)NR$^L$R$^M$, —O—($C_{1-2}$alkyl)-C(O)—NR$^L$R$^M$, —C(O)OH, —C(O)O—($C_{1-4}$alkyl), —C(O)—NR$^L$R$^M$, —C(O)—NH—($C_{1-3}$alkyl)-OH, —C(O)—NH—($C_{1-2}$alkyl)-C(O)OH, —C(O)—NH—($C_{1-2}$alkyl)-C(O)O—($C_{1-2}$alkyl), —NR$^L$R$^M$ and —SO₂—NR$^L$R$^M$;
wherein R$^J$ and R$^K$ are each independently selected from the group consisting of hydrogen and $C_{1-4}$alkyl; and wherein R$^L$ and R$^M$ are each independently selected from the group consisting of hydrogen and $C_{1-4}$alkyl;
(g) is

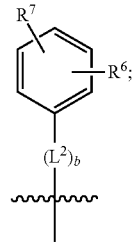

wherein b is an integer from 0 to 1;
wherein L² is selected from the group consisting of —CH₂—, —CH₂CH₂—, —CH(CH₃)—, —CH(CH₃)—CH₂—, —CH₂—CH(CH₃)—, —CH₂CH₂—O—, —CH₂—CH(OH)—, —CH(CH₃)—CH(OH) and —CH₂CH₂CH₂—NH—SO₂—;
wherein R⁶ is selected from the group consisting of hydrogen, halogen, hydroxy, $C_{1-2}$alkyl, fluorinated $C_{1-2}$alkyl, $C_{1-2}$alkoxy, fluorinated $C_{1-2}$alkoxy, —C(O)OH, —C(O)O—($C_{1-2}$alkyl), —O—($C_{1-2}$alkyl)-O—($C_{1-2}$alkyl), —O—($C_{1-2}$alkyl)-C(O)OH, —O—($C_{1-2}$alkyl)-C(O)O—($C_{1-2}$alkyl), —C(O)—NR$^N$R$^P$, —O—($C_{1-2}$alkyl)-C(O)—NR$^N$R$^P$, phenyl, furyl and thienyl; wherein the phenyl, furyl or thienyl is optionally substituted with a substituent selected from the group consisting of halogen, $C_{1-4}$alkyl and carboxy; and wherein R$^N$ and R$^P$ are each independently selected from the group consisting of hydrogen and $C_{1-4}$alkyl;
wherein R⁷ is selected from the group consisting of hydrogen, halogen, hydroxy, $C_{1-4}$alkyl, fluorinated $C_{1-2}$alkyl, $C_{1-4}$alkoxy, fluorinated $C_{1-2}$alkoxy, —C(O)OH and —C(O)O—($C_{1-4}$alkyl);
(h) is

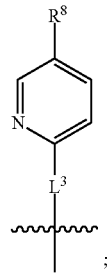

wherein L³ is selected from the group consisting of —CH₂—, —CH₂CH₂—, —CH₂CH₂CH₂—, —CH(CH₃)CH₂—, —CH₂CH(CH₃)— and —CH₂CH₂—O—;
wherein R⁸ is selected from the group consisting of hydrogen, halogen, $C_{1-4}$alkyl, $C_{1-4}$alkoxy, —C(O)OH and —C(O)O—($C_{1-4}$alkyl);

(i) is

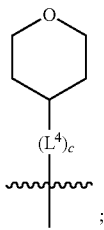

wherein c is an integer from 0 to 1;
and wherein $L^4$ is selected from the group consisting of —CH$_2$— and —CH$_2$—CH$_2$—;

(j) is

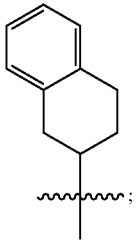

and (k) is

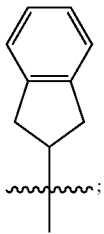 [SMILES: *C1Cc2ccccc2C1]

or a stereoisomer, tautomer or pharmaceutically acceptable salt thereof.

2. A compound as in claim 1, wherein $R^0$ is selected from the group consisting of hydrogen, —OH, —C(O)OH, —C(O)O—(C$_{1-2}$alkyl), —CH$_2$—OH, —CH$_2$—O—(C$_{1-2}$alkyl) and —CH$_2$—O—(C$_{1-2}$alkyl)-CO$_2$H;

is selected from the group consisting of phenyl, thiazolyl, and benzo[d][1,3]dioxolyl;
wherein the phenyl or thiazolyl is optionally substituted with one to two substituents independently selected from the group consisting of halogen C$_{1-4}$alkyl, fluorinated C$_{1-2}$alkyl, C$_{1-2}$alkoxy, fluorinated C$_{1-2}$alkoxy, —C(O)OH and —C(O)O—(C$_{1-4}$alkyl);

is selected from the group consisting of phenyl, thiazolyl and benzo[d][1,3]dioxolyl;
wherein the phenyl or thiazolyl is optionally substituted with one to two substituents independently selected from the group consisting of halogen C$_{1-4}$alkyl, fluorinated C$_{1-2}$alkyl, C$_{1-2}$alkoxy, fluorinated C$_{1-2}$alkoxy, —C(O)OH and —C(O)O—(C$_{1-4}$alkyl);

$R^1$ is selected from the group consisting of hydrogen, hydroxy and C$_{1-2}$alkoxy;

$R^2$ is selected from the group consisting of hydrogen, halogen, C$_{1-4}$alkyl, fluorinated C$_{1-2}$alkyl, —(C$_{1-2}$alkyl)-OH, —(C$_{1-2}$alkyl)-C(O)OH, —(C$_{1-2}$alkyl)-NH$_2$, —(C$_{2-4}$alkenyl)-OH, —C(O)O—(C$_{1-2}$alkyl), —NR$^E$R$^F$, C$_{3-6}$cycloalkyl, phenyl, furyl, thienyl, pyridyl, oxetan-3-yl, azetidin-3-yl, tetrahydrofuran-2-yl and tetrahydropyran-4-yl;
wherein the phenyl is optionally substituted with one to two halogen; wherein the azetidin-3-yl is optionally substituted with —C(O)O—(C$_{1-4}$alkyl); and wherein $R^E$ and $R^F$ are each independently selected from the group consisting of hydrogen and C$_{1-4}$alkyl;

provided that when $R^2$ is selected from the group consisting of pyridyl, furyl and thienyl, then the $R^2$ is bound to the benzimidazole core through a carbon atom;

$R^3$ is selected from the group consisting of (a) through (k); wherein (a) is

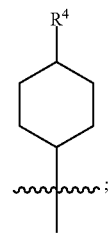

wherein $R^4$ is selected from the group consisting of hydrogen, —C(O)OH, —C(O)O—(C$_{1-2}$alkyl), —C(O)NR$^G$R$^H$, —NH-(phenyl), and —NH—SO$_2$-(phenyl);
wherein the phenyl is optionally substituted with hydroxy or carboxy; and wherein $R^G$ and $R^H$ are each independently selected from the group consisting of hydrogen and methyl;

(b) is

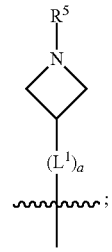

(c) is

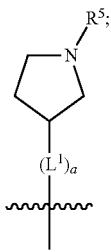

(d) is

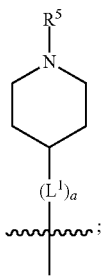

(e) is

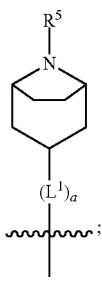

(f) is

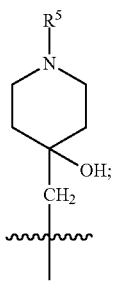

wherein a is an integer from 0 to 1;
wherein $L^1$ is selected from the group consisting of —CH$_2$—, —CH$_2$—CH$_2$, —CH(CH$_3$)CH$_2$— and —CH$_2$—CH(CH$_3$)—;
wherein $R^5$ is selected from the group consisting of hydrogen, C$_{1-2}$alkyl, fluorinated C$_{1-2}$alkyl, C$_{2-4}$alkenyl, —(C$_{1-2}$alkyl)-C(O)OH, —(C$_{1-2}$alkyl)-C(O)O—(C$_{1-2}$alkyl), —(C$_2$alkyl)-O-(phenyl), —C(O)—(C$_{1-2}$alkyl)-OH, —C(O)—(C$_{1-2}$alkyl)-C(O)OH, —C(O)—(C$_{1-2}$alkyl)-C(O)O—(C$_{1-2}$alkyl), —C(O)—(C$_{1-2}$alkyl)-C(O)—NH$_2$, —C(O)O—(C$_{1-4}$alkyl), —C(O)O—(C$_{3-5}$cycloalkyl), —C(O)O-(phenyl), —C(O)O—CH$_2$-(phenyl), —C(O)—NH$_2$, —C(O)NH—(C$_{1-2}$alkyl), —C(O)NH—(C$_{3-5}$cycloalkyl), —C(O)NH-(phenyl), —C(O)NH—(C$_{1-2}$alkyl)-(phenyl), —SO$_2$—(C$_{1-2}$alkyl), —SO$_2$-(fluorinated C$_{1-2}$alkyl), —SO$_2$—(C$_{1-2}$alkyl)-C(O)OH, —SO$_2$—(C$_{1-2}$alkyl)-C(O)O—(C$_{1-2}$alkyl), —SO$_2$—NH$_2$, —SO$_2$—NH—(C$_{1-2}$alkyl), —SO$_2$—(C$_{1-2}$alkyl)-C(O)NH$_2$, phenyl, —(C$_{1-3}$alkyl)-phenyl, —C(O)-(phenyl), —C(O)O-(phenyl), —C(O)O—(C$_{1-2}$alkyl)-(phenyl), —SO$_2$-(phenyl), pyrimidin-2-yl, pyrid-2-yl, pyrid-3-yl, —(C$_{1-2}$alkyl)-pyrid-2-yl, —(C$_{1-2}$alkyl)-pyrid-3-yl, —(C$_{1-2}$alkyl)-fur-2-yl, —(C$_{1-2}$alkyl)-thien-2-yl, —C(O)-fur-2-yl, —C(O)-thien-2-yl, —C(O)-(pyrid-3-yl), —C(O)-(1,2,3-triazol-4-yl), —C(O)-(1,2,4,-triazol-3-yl), —SO$_2$—(C$_{1-2}$alkyl)-(piperazin-1-yl), —SO$_2$-(fury-2-yl), —SO$_2$-(thien-2-yl) and —SO$_2$-(pyrid-3-yl);
wherein the phenyl, pyrimidin-2-yl, pyridyl, furyl, thienyl or pyridyl, is optionally substituted with one to three substituents independently selected from the group consisting of halogen, hydroxy, C$_{1-2}$alkyl, fluorinated C$_{1-2}$alkyl, —(C$_{1-2}$alkyl)-OH, —C$_{(1-2}$alkyl)-C(O)OH, —(C$_{1-2}$alkyl)-C(O)O—(C$_{1-2}$alkyl), —O—(C$_{1-2}$alkyl), —O-(fluorinated C$_{1-2}$alkyl), —O—(C$_{2-6}$alkenyl), —O—(C$_{1-2}$alkyl)-C(O)OH, —O—(C$_{1-2}$alkyl)-C(O)NH$_2$, —C(O)OH, —C(O)O—(C$_{1-4}$alkyl), —C(O)—NH$_2$, —C(O)—NH—(C$_{1-2}$alkyl), —C(O)—NH—(C$_{1-3}$alkyl)-OH, —C(O)—NH—(C$_{1-2}$alkyl)-C(O)OH, —C(O)—NH—(C$_{1-2}$alkyl)-C(O)O—(C$_{1-2}$alkyl), —(C$_{1-2}$alkyl)-C(O)—NH$_2$, —O—(C$_{1-2}$alkyl)-C(O)—NH$_2$, —O—(C$_{1-2}$alkyl)-C(O)OH, —NH$_2$, —NH(C$_{1-2}$alkyl), —SO$_2$—NH$_2$ and —SO$_2$—NH(C$_{1-2}$alkyl);
(g) is

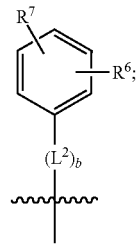

wherein b is an integer from 0 to 1;
wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and —CH$_2$CH$_2$CH$_2$—NH—SO$_2$—;
wherein $R^6$ is selected from the group consisting of hydrogen, halogen, hydroxy, C$_{1-2}$alkyl, fluorinated C$_{1-2}$alkyl, C$_{1-2}$alkoxy, fluorinated C$_{1-2}$alkoxy, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl, furyl and thienyl; wherein the phenyl, furyl or thienyl is optionally substituted with carboxy;
and wherein $R^7$ is selected from the group consisting of hydrogen, hydroxy, C$_{1-2}$alkyl, fluorinated C$_{1-2}$alkyl, C$_{1-2}$alkoxy, fluorinated C$_{1-2}$alkoxy, —C(O)OH and —C(O)O—(C$_{1-4}$alkyl);

(h) is

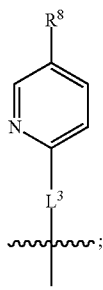

wherein L³ is selected from the group consisting of —CH₂—, —CH₂CH₂— and —CH₂CH₂—O—;
and wherein R⁸ is selected from the group consisting of hydrogen, -halogen, $C_{1-2}$alkyl, $C_{1-2}$alkoxy, —C(O)OH and —C(O)O—($C_{1-4}$alkyl);

(i) is

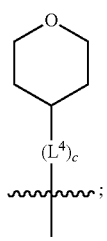

wherein c is an integer from 0 to 1;
and wherein L⁴ is selected from the group consisting of —CH₂— and —CH₂—CH₂—;

(j) is

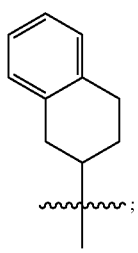

and (k) is

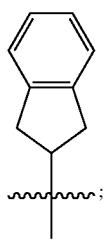

or a stereoisomer, tautomer or pharmaceutically acceptable salt thereof.

3. A compound as in claim 2, wherein

R⁰ is selected from the group consisting of hydrogen, —OH, —C(O)OH, —C(O)O—($C_{1-2}$alkyl), —CH₂—OH, —CH₂—O—($C_{1-2}$alkyl) and —CH₂—O—($C_{1-2}$alkyl)-CO₂H;

is phenyl; wherein the phenyl is optionally substituted a substituent selected from the group consisting of halogen and $C_{1-2}$alkoxy;

is selected from the group consisting of phenyl, thiazol-2-yl and benzo[d][1,3]dioxol-5-yl; wherein the phenyl or thiazol-2-yl is optionally substituted with a substituent selected from the group consisting of halogen, $C_{1-4}$alkyl, fluorinated $C_{1-2}$alkyl, $C_{1-2}$alkoxy and —C(O)OH;

R¹ is selected from the group consisting of hydrogen, hydroxy and $C_{1-2}$alkoxy;

R² is selected from the group consisting of hydrogen, halogen, $C_{1-4}$alkyl, fluorinated $C_{1-2}$alkyl, —($C_{1-2}$alkyl)-OH, —($C_{1-2}$alkyl)-C(O)OH, —($C_{1-2}$alkyl)-NH₂, —($C_{2-4}$alkenyl)-OH, —C(O)O—($C_{1-2}$alkyl), —NR$^E$R$^F$, $C_{3-6}$cycloalkyl, phenyl, fur-2-yl, fur-3-yl, thien-3-yl, pyrid-2-yl, pyrid-3-yl, pyrid-4-yl, oxetan-3-yl, azetidin-3-yl, tetrahydrofuran-2-yl and tetrahydropyran-4-yl;

wherein the phenyl is optionally substituted with one to two halogen; wherein the azetidin-3-yl is optionally substituted with —C(O)O—($C_{1-4}$alkyl); and wherein R$^E$ and R$^F$ are each independently selected from the group consisting of hydrogen, methyl and ethyl;

R³ is selected from the group consisting of (a) through (k); wherein (a) is

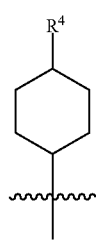

wherein R⁴ is selected from the group consisting of hydrogen, —C(O)OH, —C(O)NR$^G$R$^H$, —NH-(phenyl) and —NH—SO₂-(phenyl); wherein the phenyl is optionally substituted with hydroxy or carboxy; wherein R$^G$ and R$^H$ are each independently selected from the group consisting of hydrogen and methyl;

(b) is

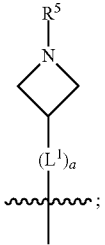

(c) is

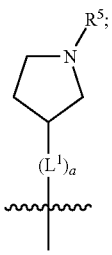

(d) is

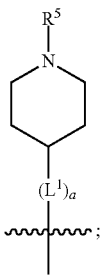

(e) is

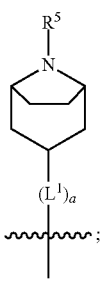

(f) is

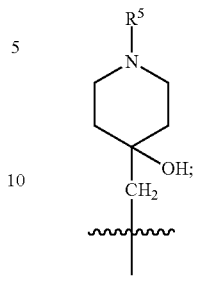

wherein a is an integer from 0 to 1; and wherein $L^1$ is selected from the group consisting of —$CH_2$— and —$CH_2$—$CH(CH_3)$—;

wherein $R^5$ is selected from the group consisting of hydrogen, $C_{2-4}$alkenyl, —($C_{1-2}$alkyl)-C(O)OH, —($C_{1-2}$ alkyl)-C(O)O—($C_{1-2}$alkyl), —($C_2$alkyl)-O-(phenyl), —C(O)—($C_{1-2}$alkyl)-OH, —C(O)—($C_{1-2}$ alkyl)-C(O)OH, —C(O)—($C_{1-2}$alkyl)-C(O)—$NH_2$, —C(O)O—($C_{1-4}$alkyl), —C(O)O-(hydroxy substituted $C_{1-4}$alkyl), —C(O)O—($C_{3-5}$cycloalkyl), —C(O)NH—($C_{1-2}$alkyl), —C(O)NH—($C_{3-5}$cycloalkyl), —C(O)NH-(phenyl), —C(O)NH—($C_{1-2}$alkyl)-(phenyl), —$SO_2$—($C_{1-2}$ alkyl), —$SO_2$-(fluorinated $C_{1-2}$alkyl), —$SO_2$—($C_{1-2}$ alkyl)-C(O)OH, —$SO_2$—$NH_2$, —$SO_2$—NH—($C_{1-2}$ alkyl), —$SO_2$—($C_{1-2}$alkyl)-C(O)$NH_2$, phenyl, —($C_{1-3}$ alkyl)-phenyl, —C(O)-(phenyl), —C(O)O-(phenyl), —C(O)O—($C_{1-2}$alkyl)-(phenyl), —$SO_2$-(phenyl), pyrimidin-2-yl, —($C_{1-2}$alkyl)-pyrid-2-yl, —($C_{1-2}$alkyl)-pyrid-3-yl, —($C_{1-2}$alkyl)-fur-2-yl, —($C_{1-2}$alkyl)-thien-2-yl, —C(O)-(pyrid-3-yl), —C(O)-(1,2,3-triazol-4-yl), —C(O)-(1,2,4,-triazol-3-yl), —$SO_2$—($C_{1-2}$alkyl)-(piperazin-1-yl), —$SO_2$-(fury-2-yl), —$SO_2$-(thien-2-yl) and —$SO_2$-(pyrid-3-yl);

wherein the phenyl is optionally substituted with one to three substituents independently selected from the group consisting of halogen, hydroxy, $C_{1-2}$alkyl, fluorinated $C_{1-2}$alkyl, —O—($C_{1-2}$alkyl), —O-(fluorinated $C_{1-2}$alkyl), —O—($C_{2-6}$alkenyl), —O—($C_{1-2}$alkyl)-C(O)OH, —O—($C_{1-2}$alkyl)-C(O)$NH_2$, —C(O)OH, —C(O)O—($C_{1-2}$alkyl), —C($_{1-2}$alkyl)-C(O)OH, —C(O)—$NH_2$, —C(O)—NH—($C_{1-2}$alkyl), —C(O)—NH—($C_{1-3}$alkyl)-OH, —C(O)—NH—($C_{1-2}$alkyl)-C(O)OH, —C(O)—NH—($C_{1-2}$alkyl)-C(O)O—($C_{1-2}$alkyl), —($C_{1-2}$alkyl)-C(O)—$NH_2$, —O—($C_{1-2}$alkyl)-C(O)—$NH_2$, —O—($C_{1-2}$alkyl)-C(O)OH, —$NH_2$ and —$SO_2$—$NH_2$;

and wherein the pyrimidin-2-yl, pyrid-2-yl, pyrid-3-yl, fur-2-yl or thien-2-yl is optionally substituted with one to two substituents independently selected from the group consisting of $C_{1-2}$alkyl, —($C_{1-2}$alkyl)-OH, —C(O)OH, —C(O)O—($C_{1-2}$alkyl), —C(O)—$NH_2$, —C(O)NH—($C_{1-2}$alkyl)-OH, —C(O)NH—($C_{1-2}$ alkyl)-C(O)OH and —C(O)NH—($C_{1-2}$alkyl)-C(O)O—($C_{1-2}$alkyl);

(g) is

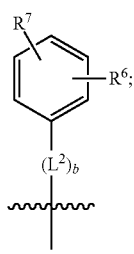

wherein b is an integer from 0 to 1; and wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$CH$_2$—O—, —CH$_2$—CH(OH)—, —CH(CH$_3$)—CH(OH) and —CH$_2$CH$_2$CH$_2$—NH—SO$_2$—;

wherein $R^6$ is selected from the group consisting of hydrogen, halogen, hydroxy, C$_{1-2}$alkoxy, fluorinated C$_{1-2}$alkyl, —C(O)OH, —C(O)O—(C$_{1-2}$alkyl), —O—(C$_{1-2}$alkyl)-C(O)OH, —O—(C$_{1-2}$alkyl)-C(O)O—(C$_{1-2}$alkyl), —C(O)—NH$_2$, —O—(C$_{1-2}$alkyl)-C(O)—NH$_2$, phenyl and thienyl; wherein the phenyl or thienyl is optionally substituted with carboxy; and wherein $R^7$ is selected from the group consisting of hydrogen and fluorinated C$_{1-2}$alkyl;

(h) is

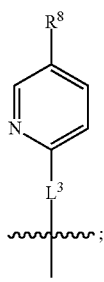

wherein $L^3$ is selected from the group consisting of —CH$_2$— and —CH$_2$CH$_2$—O—; and wherein $R^8$ is selected from the group consisting of hydrogen, —C(O)OH and —C(O)O—(C$_{1-2}$alkyl);

(i) is

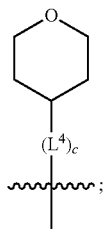

wherein c is an integer from 0 to 1; wherein $L^4$ is —CH$_2$—;

(j) is

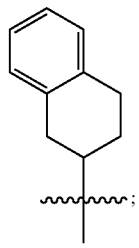

and (k) is

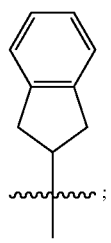

or a stereoisomer, tautomer or pharmaceutically acceptable salt thereof.

4. A compound as in claim 3, wherein
$R^0$ is selected from the group consisting of hydrogen, —OH, —C(O)OH, —C(O)OCH$_3$, —CH$_2$—OH, —CH$_2$—OCH$_3$ and —CH$_2$—OCH$_2$—CO$_2$H;

is selected from the group consisting of phenyl, 2-chlorophenyl, 4-chlorophenyl and 4-methoxyphenyl;

is selected from the group consisting of phenyl, 4-chlorophenyl, 4-fluorophenyl, 4-methylphenyl, 4-trifluoromethyl-phenyl, 4-carboxyphenyl, 4-methoxyphenyl, thiazol-2-yl, 4-ethyl-thiazol-2-yl, 5-ethyl-thiazol-2-yl, 4-t-butyl-thiazol-2-yl, 4-trifluoromethyl-thiazol-2-yl and benzo[d][1,3]dioxol-5-yl, $R^1$ is selected from the group consisting of hydrogen, hydroxy and methoxy;

$R^2$ is selected from the group consisting of hydrogen, chloro, methyl, ethyl, n-propyl, isopropyl, isobutyl, t-butyl, —CHF$_2$, —CF$_3$, —CH$_2$—CF$_3$, —CH$_2$OH, —CH$_2$CH$_2$—C(O)OH, —CH$_2$CH$_2$—NH$_2$, —C(=CH$_2$)—CH$_2$OH, —C(O)OCH$_3$, —C(O)OCH$_2$CH$_3$, —NH$_2$, —N(CH$_3$)$_2$, cyclopropyl, cyclobutyl, cyclopentyl, oxetan-3-yl, azetidin-3-yl, 1-(t-butoxycarbonyl)-azetidin-3-yl, tetrahydrofuran-2-yl, tetrahydro-pyran-4-yl, 4-chlorophenyl, 2,4-dichlorophenyl, pyrid-2-yl, pyrid-3-yl, pyrid-4-yl, fur-2-yl, fur-3-yl and thien-3-yl;

$R^3$ is selected from the group consisting of (a) through (k); wherein (a) is

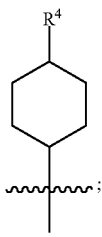

wherein $R^4$ is selected from the group consisting of hydrogen, —C(O)OH, —C(O)NH$_2$, —NH—SO$_2$-(3-carboxyphenyl), —NH-(3-hydroxyphenyl), —NH-(3-carboxyphenyl), —NH-(4-carboxyphenyl) and —NH—SO$_2$-(4-carboxyphenyl); and wherein the cyclohexyl is bound to the benzimidazole core in a cis-, trans- or racemic stereo-orientation;

(b) is

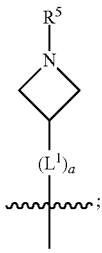

wherein a 0; and wherein $R^5$ is selected from the group consisting of 3-carboxybenzyl-, 4-carboxyphenyl-sulfonyl- and 5-carboxyfur-2-yl-sulfonyl-;

(c) is

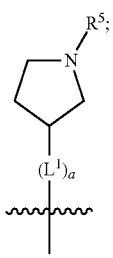

wherein a is 0; and wherein $R^5$ is selected from the group consisting of 3-carboxybenzyl-, 4-carboxyphenyl-sulfonyl- and 5-carboxy-fur-2-yl-sulfonyl-;

(d) is

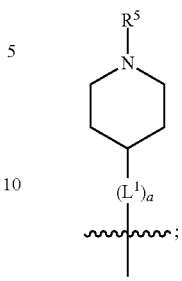

wherein a is an integer from 0 to 1;
wherein $L^1$ is selected from the group consisting of —CH$_2$— and —CH$_2$—CH(R*—CH$_3$)—;
wherein $R^5$ is selected from the group consisting of hydrogen, propyn-3-yl, carboxy-methyl-, methoxy-carbonyl-methyl-, 3-carboxyphenyl-oxy-ethyl-, 2-hydroxyethyl-carbonyl-, hydroxymethyl-carbonyl-, 2-carboxy-ethyl-carbonyl-, aminocarbonyl-methyl-carbonyl-, 2-(aminocarbonyl)-ethyl-carbonyl-, ethoxycarbonyl-, t-butoxycarbonyl-, cyclopentyloxy-carbonyl-, 2,3,4-trihydroxy-n-butyloxy-carbonyl-, 3-carboxyphenyl, 4-carboxyphenyl, 3-(carboxy-methyl)-phenyl, 4-(carboxy-methyl)-phenyl, 3-(methoxycarbonyl)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-(carboxy-methoxy)-phenyl, 4-(carboxy-methoxy)-phenyl, 3-hydroxy-benzyl, 3-(hex-2-en-1-yloxy)-benzyl, 2-trifluoromethyl-benzyl, 3-carboxy-benzyl, 4-carboxy-benzyl, 3-(methoxycarbonyl)-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-hydroxy-5-carboxy-benzyl, 2-fluoro-3-carboxy-benzyl, 2-fluoro-5-carboxy-benzyl, 2-chloro-3-carboxy-benzyl, 2-chloro-5-carboxy-benzyl, 2-trifluoromethyl-5-carboxy-benzyl, 3-fluoro-5-carboxy-benzyl, 3-carboxy-4-fluoro-benzyl, 3-carboxy-4-hydroxy-benzyl, 3-trifluoromethyl-5-carboxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 4-carboxy-pyrimidin-2-yl, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-amino-carbonyl-, 4-carboxy-phenyl-carbonyl-, 4-aminoarbonyl-phenyl-carbonyl-, 3-aminosulfonyl-phenyl-carbonyl-, 4-aminosulfonyl-phenyl-carbonyl-, 6-carboxy-pyrid-3-yl-carbonyl-, 6-aminocarbonylpyrid-3-yl-carbonyl-, 1,2,3-triazol-4-yl-carbonyl-, 1,2,4-triazol-3-yl-carbonyl-, methyl-sulfonyl-, trifluoromethyl-sulfonyl-, carboxymethyl-sulfonyl-, carboxyethyl-sulfonyl-, amino-sulfonyl-, amino-ethyl-sulfonyl-, aminocarbonyl-methyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 2-carboxyphenyl-sulfonyl-, 3-carboxyphenyl-sulfonyl-, 4-carboxy-phenyl-sulfonyl-, 4-carboxy-methoxy-phenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(carboxy-ethyl-amino-carbonyl)-phenyl-sulfonyl-, 3-(3-hydroxy-n-propyl-amino-carbonyl)-phenyl-sulfonyl-, 3-(2-(methoxycarbonyl)-ethyl-amino-carbonyl)-phenyl-sulfonyl-, 3-(2-hydroxyethyl-amino-carbonyl)-phenyl-sulfonyl-, 3-fluoro-4-hydroxy-phenyl-sulfonyl-, 3-fluoro-4-methoxy-phenyl-sulfonyl-, 3-fluoro-4-aminocabonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl-, 3-methyl-4-aminocarbonyl-phenyl-sulfonyl-, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl, 3-methoxy-4-carboxy-phenyl-sulfonyl, 3-methoxy-4-aminocarbonyl-phenyl-sulfonyl-, 3-carboxy-4-chloro-phenyl-sulfonyl-, 3-carboxy-4-fluoro-phenyl-sulfonyl-, 3-carboxy-4-methyl-phenyl-sulfonyl-, 3-carboxy-4-methoxy-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, piperazin-1-yl-ethyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-am inocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-;

(e) is

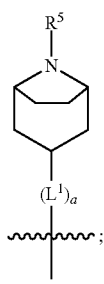

wherein a is 0; and wherein $R^5$ is selected from the group consisting of ethoxycarbonyl- and trifluoromethyl-sulfonyl-;

(f) is

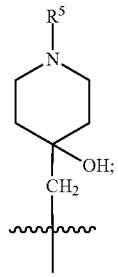

wherein $R^5$ is trifluoromethyl-sulfonyl-;

(g) is

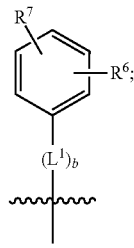

wherein b is an integer from 0 to 1;
wherein $L^2$ is selected from the group consisting of —CH$_2$—, —CH$_2$CH$_2$—, —CH(CH$_3$)—, —CH(CH$_3$)—CH$_2$—, —CH$_2$—CH(CH$_3$)—, —CH$_2$—CH(R*—CH$_3$)—, —CH$_2$—CH(S*—CH$_3$)—, —CH$_2$CH$_2$—O—, —CH$_2$—CH(OH)—, —CH$_2$—CH(R*—OH), —CH(CH$_3$)—CH(OH) and —CH$_2$CH$_2$CH$_2$—NH—SO$_2$—;
wherein $R^6$ is selected from the group consisting of hydrogen, 3-bromo, 3-chloro, 4-chloro, 3-hydroxy, 4-hydroxy, 3-methoxy, 4-methoxy, 4-trifluoromethyl, 3-carboxy, 4-carboxy, 3-carboxy-methoxy-, 4-carboxy-methoxy-, 3-methoxycarbonyl-, 4-methoxycarbonyl-, 3-ethoxy-carbonyl-methoxy-, 4-ethoxy-carbonyl-methoxy-, 4-aminocarbonyl-, 3-amino-carbonyl-methoxy-, 4-amino-carbonyl-methoxy-, 3-(3-carboxy-phenyl), 3-(4-carboxy-phenyl), 4-(3-carboxyphenyl), 4-(4-carboxyphenyl) and 3-(5-carboxy-thien-2-yl);
and wherein $R^7$ is selected from the group consisting of hydrogen and 5-trifluoromethyl;

(h) is

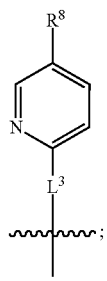

wherein L³ is selected from the group consisting of —CH₂— and —CH₂CH₂—O—; and wherein R⁸ is selected from the group consisting of hydrogen, carboxy and methoxycarbonyl-;

(i) is

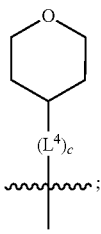

wherein c is an integer from 0 to 1; and wherein L⁴ is —CH₂—;

(j) is

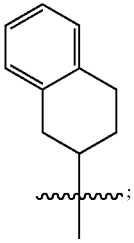 [SMILES: *C1CCc2ccccc2C1]

and (k) is

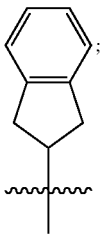 [SMILES: *C1Cc2ccccc2C1]

or a stereoisomer, tautomer or pharmaceutically acceptable salt thereof.

5. A compound as in claim 4, wherein
R⁰ is selected from the group consisting of hydrogen, —OH, —CO₂H, —C(O)OCH₃ and —CH₂OCH₃;

is selected from the group consisting of 4-chlorophenyl, 4-fluorophenyl, 4-methylphenyl and 4-methoxyphenyl;

is selected from the group consisting of phenyl, 4-chlorophenyl, 4-fluorphenyl, 4-methylphenyl, 4-trifluoromethyl-phenyl, 4-methoxyphenyl, 4-carboxyphenyl, thiazol-2-yl and benzo[d][1.3]dioxol-5-yl;

R¹ is selected from the group consisting of hydrogen, —OH and —OCH₃;

R² is selected from the group consisting of hydrogen, methyl, ethyl, cyclopropyl, cyclobutyl, amino-ethyl-, —C=(CH₂)—CH₂OH, oxetan-3-yl, tetrahydrofur-2-yl and pyrid-3-yl;

R³ is selected from the group consisting of (a), (b), (d), (f), (g), (h) and (i); wherein (a) is

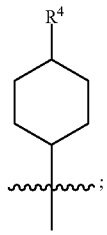

wherein the cyclohexyl group is bound in a cis-, trans- or racemic orientation; and wherein R⁴ is selected from the group consisting of hydrogen, aminocarbonyl-, 3-hydroxyphenyl-amino-, 3-carboxyphenyl-amino-, 4-carboxyphenyl-amino-, 3-carboxyphenyl-sulfonyl-amino- and 4-carboxyphenyl-sulfonyl-amino-;

(b) is

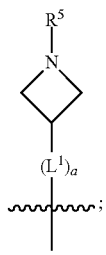

wherein a 0; and wherein R⁵ is selected from the group consisting of 3-carboxybenzyl- and 4-carboxyphenyl-sulfonyl-;

(d) is

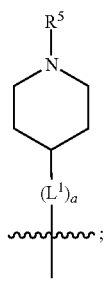

wherein a is an integer from 0 to 1; wherein L¹ is —CH₂—; and wherein R⁵ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, aminocarbonyl-methyl-carbonyl-, aminocarbonyl-ethyl-carbonyl-, ethoxycarbonyl-, t-butoxycarbonyl-, cyclopentyloxycarbonyl-, 2,3,4-trihydroxy-n-butyloxy-carbonyl-, 3-carboxyphenyl, 4-carboxyphenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl, 3-hydroxy-benzyl, 2-trifluoromethyl-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-hydroxy-3-carboxy-benzyl, 2-fluoro-5-carboxy-benzyl, 3-fluoro-5-carboxy-benzyl, 2-chloro-3-carboxy-benzyl, 2-chloro-5-carboxy-benzyl, 2-trifluoromethyl-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-methoxycarbonyl-pyrimidin-2-yl, 2-carboxy-pyrid-4-yl-methyl-, 4-carboxy-pyrid-2-yl-methyl-, 5-carboxy-pyrid-2-yl-methyl-, 6-carboxy-pyrid-2-yl-methyl-, 5-carboxy-pyrid-3-yl-methyl-, 6-carboxy-pyrid-3-yl-methyl-, 5-aminocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 1-(5-carboxy-fur-2-yl)-ethyl-, 5-aminocarbonyl-fur-2-yl-methyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, cyclopentyl-amino-carbonyl-, phenyl-aminocarbonyl-, benzyl-amino-carbonyl-, 4-aminocarbonyl-phenyl-carbonyl-, 3-aminosulfonyl-phenyl-carbonyl-, 4-aminosulfonyl-phenyl-carbonyl-, 6-aminocarbonyl-pyrid-3-yl-carbonyl-, 1,2,4-triazol-3-yl-carbonyl-, methylsulfonyl-, trifluoromethyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 4-trifluoromethoxy-phenyl-sulfonyl-, 3-carboxyphenyl-sulfonyl-, 4-carboxyphenyl-sulfonyl-, 3-aminophenyl-sulfonyl-, 4-aminophenyl-sulfonyl-, 2-aminocarbonyl-phenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-(2-(methoxycarbonyl)-ethyl-amino-carbonyl)-phenyl-sulfonyl-, 3-(2-hydroxyethyl-amino-carbonyl)-phenyl-sulfonyl-, 3-fluoro-4-methoxy-phenyl-sulfonyl-, 3-fluoro-4-aminocabonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-trifluoromethyl-4-aminocarbonyl-phenyl-sulfonyl, 3-methoxy-4-aminocarbonyl-phenyl-sulfonyl-, 3-methoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3-aminocarbonyl-4-methyl-phenyl-sulfonyl-, 3-aminocarbonyl-4-methoxy-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(am inocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl-, 6-(2-hydroxyethyl-amino-carbonyl)-pyrid-3-yl-sulfonyl-, 6-(carboxyethyl-amino-carbonyl)-pyrid-3-yl-sulfonyl- and 6-(methoxycarbonyl-ethyl-amino-carbonyl)-pyrid-3-yl-sulfonyl-;

(f) is

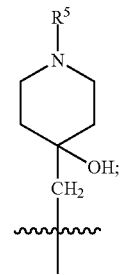

wherein $R^5$ is trifluoromethyl-sulfonyl-;

(g) is

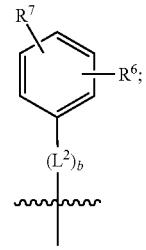

wherein b is an integer from 0 to 1; $L^2$ is selected from the group consisting of —$CH_2$—, —$CH_2CH_2$—, —$CH(CH_3)$—$CH_2$—, —$CH_2$—$CH(R*$—$CH_3)$—, —$CH_2$—$CH(S*$—$CH_3)$—, —$CH_2CH_2$—O—, —$CH_2$—CH(OH)— and —$CH_2CH_2CH_2$—NH—$SO_2$—; and wherein $R^6$ is selected from the group consisting of hydrogen, 3-chloro-, 4-chloro-, 3-bromo-, 4-bromo-, 3-hydroxy, 4-hydroxy-, 4-trifluoromethyl, 3-methoxy-, 4-methoxy-, 4-methoxycarbonyl-, 3-(ethoxy-carbonyl-methoxy)-, 4-(ethoxy-carbonyl-methoxy)-, 3-(aminocarbonyl-methoxy)-, 4-(aminocarbonyl-methoxy)-, 3-(3-carboxyphenyl), 3-(4-carboxyphenyl) and 3-(5-carboxy-thein-2-yl); and $R^7$ is selected from the group consisting of hydrogen and 5-trifluoromethyl;

(h) is

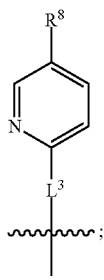

wherein $L^3$ is —CH$_2$CH$_2$— and wherein $R^8$ is 5-methoxycarbonyl-;

and (i) is

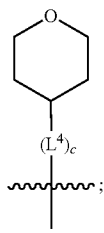

wherein c is an integer from 0 to 1; and wherein $L^4$ is —CH$_2$—;

or a stereoisomer, tautomer or pharmaceutically acceptable salt thereof.

6. A compound as in claim 4, wherein $R^0$ is selected from the group consisting of hydrogen, —OH, —CO$_2$H and —C(O)OCH$_3$;

is selected from the group consisting of 4-chlorophenyl, 4-fluorophenyl and 4-methylphenyl;

is selected from the group consisting of phenyl, 4-chlorophenyl, 4-fluorphenyl, 4-methylphenyl, 4-trifluoromethyl-phenyl, thiazol-2-yl and benzo[d][1.3]dioxol-5-yl;

$R^1$ is selected from the group consisting of hydrogen, —OH and —OCH$_3$;

$R^2$ is selected from the group consisting of hydrogen, methyl, ethyl, cyclopropyl, cyclobutyl, oxetan-3-yl and tetrahydrofur-2-yl;

$R^3$ is selected from the group consisting of (a), (b), (d), (f), (g) and (i); wherein (a) is

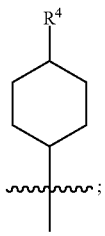

wherein the cyclohexyl group is bound in trans-orientation; and wherein $R^4$ is 3-hydroxyphenyl-amino-;

(b) is

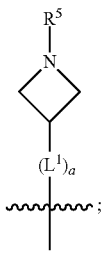

wherein a 0; and wherein $R^5$ is 3-carboxybenzyl-;

(d) is

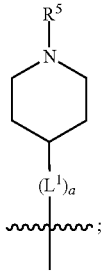

wherein a is an integer from 0 to 1; wherein $L^1$ is —CH$_2$—; and wherein $R^5$ is selected from the group consisting of propyn-3-yl, methoxy-carbonyl-methyl-, 3-carboxyphenyl-oxy-ethyl-, 2-hydroxyethyl-carbonyl-, hydroxymethyl-carbonyl-, ethoxycarbonyl-cyclopentyloxy-carbonyl-, 4-carboxyphenyl, 3-(aminocarbonyl)-phenyl, 4-(am inocarbonyl)-phenyl, 3-(aminocarbonyl-methyl)-phenyl, 4-(am inocarbonyl-methyl)-phenyl, 3-(aminocarbonyl-methoxy)-phenyl, 4-(aminocarbonyl-methoxy)-phenyl, 3-hydroxy-benzyl, 3-carboxy-benzyl, 4-carboxy-benzyl, 3-(aminocarbonyl)-benzyl, 4-(aminocarbonyl)-benzyl, 3-(2-hydroxyethyl-aminocarbonyl)-benzyl, 2-fluoro-5-carboxy-benzyl, 3-fluoro-5-carboxy-benzyl, 2-chloro-5-carboxy-benzyl, 3-carboxy-4-fluoro-benzyl, 3-carboxy-4-hydroxy-benzyl, 1-(3-hydroxyphenyl)-ethyl-, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-carboxy-pyrid-3-yl-methyl-, 6-carboxy-pyrid-3-yl-methyl-, 5-am inocarbonyl-pyrid-2-yl-methyl-, 6-aminocarbonyl-pyrid-2-yl-methyl-, 5-aminocarbonyl-pyrid-3-yl-methyl-, 6-aminocarbonyl-pyrid-3-yl-methyl-, 1-(4-carboxy-pyrid-2-yl)-ethyl-, 5-carboxy-fur-2-yl-methyl-, 5-aminocarbonyl-fur-2-yl-methyl-, 1-(5-carboxy-fur-2-yl)-ethyl-, 4-carboxy-thien-2-yl-methyl-, 5-carboxy-thien-2-yl-methyl-, 5-aminocarbonyl-thien-2-yl-methyl-, 4-aminocarbonyl-thien-2-yl-methyl-, phenoxy-carbonyl-, benzyloxy-carbonyl-, ethylamino-carbonyl-, 3-aminosulfonyl-phenyl-carbonyl-, 6-aminocarbonyl-pyrid-3-yl-carbonyl-, methylsulfonyl-, trifluoromethyl-sulfonyl-, phenyl-sulfonyl-, 4-fluorophenyl-sulfonyl-, 4-chlorophenyl-sulfonyl, 2-hydroxyphenyl-sulfonyl-, 3-hydroxyphenyl-sulfonyl-, 4-hydroxyphenyl-sulfonyl-, 2-methoxy-phenyl-sulfonyl-, 3-methoxy-phenyl-sulfonyl-, 4-methoxy-phenyl-sulfonyl-, 2-trifluoromethyl-phenyl-sulfonyl-, 3-trifluoromethyl-phenyl-sulfonyl-, 4-trifluoromethyl-phenyl-sulfonyl-, 3-carboxyphenyl-sulfonyl-, 4-carboxyphenyl-sulfonyl-, 3-aminophenyl-sulfonyl-, 3-aminocarbonyl-phenyl-sulfonyl-, 4-aminocarbonyl-phenyl-sulfonyl-, 4-aminocarbonyl-methoxy-phenyl-sulfonyl-, 3-(methylamino-carbonyl)-phenyl-sulfonyl-, 3-(3-hydroxy-n-propyl-amino-carbonyl)-phenyl-sulfonyl-, 3-fluoro-4-aminocabonyl-phenyl-sulfonyl-, 3-fluoro-4-carboxy-phenyl-sulfonyl-, 3-chloro-4-aminocarbonyl-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-am inocarbonyl-phenyl-sulfonyl-, 3-m ethoxy-4-carboxy-phenyl-sulfonyl-, 3-carboxy-4-chloro-phenyl-sulfonyl-, 3-carboxy-4-fluoro-phenyl-sulfonyl-, 3-aminocarbonyl-4-fluoro-phenyl-sulfonyl-, 3,5-dichloro-4-hydroxy-phenyl-sulfonyl-, 5-(hydroxymethyl)-fur-2-yl-sulfonyl-, 5-carboxy-fur-2-yl-sulfonyl-, 5-(aminocarbonyl)-fur-2-yl-sulfonyl-, 4-carboxy-thien-2-yl-sulfonyl-, 4-(aminocarbonyl)-thien-2-yl-sulfonyl-, 3-methyl-5-carboxy-thien-2-yl-sulfonyl-, 3-methyl-5-(aminocarbonyl)-thien-2-yl-sulfonyl-, 6-carboxy-pyrid-3-yl-sulfonyl-, 6-aminocarbonyl-pyrid-3-yl-sulfonyl- and 6-(methoxycarbonyl-ethyl-amino-carbonyl)-pyrid-3-yl-sulfonyl-;

(f) is

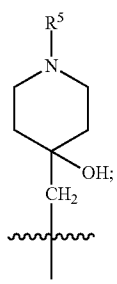

wherein $R^5$ is trifluoromethyl-sulfonyl-;

(g) is

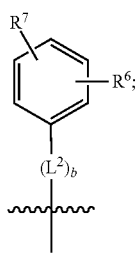

wherein b is an integer from 0 to 1; $L^2$ is selected from the group consisting of —CH$_2$—, —CH$_2$CH$_2$—, —CH$_2$—CH(R*—CH$_3$)—, —CH$_2$CH$_2$—O—, —CH$_2$—CH(OH)— and —CH$_2$CH$_2$CH$_2$—NH—SO$_2$—; and wherein $R^6$ is selected from the group consisting of hydrogen, 3-chloro-, 3-bromo-, 4-bromo-, 3-hydroxy, 4-trifluoromethyl, 3-methoxy-, 4-methoxy-, 3-(ethoxy-carbonyl-methoxy)-, 4-(ethoxy-carbonyl-methoxy)-, and 3-(5-carboxy-thein-2-yl); and $R^7$ is hydrogen;

and (i) is

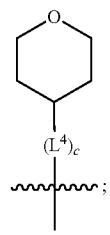

wherein c is 1; and wherein $L^4$ is —CH$_2$—;

or a stereoisomer, tautomer or pharmaceutically acceptable salt thereof.

7. A compound as in claim 4, wherein $R^0$ is selected from the group consisting of hydrogen, —OH and —CO$_2$H;

is 4-chlorophenyl;

is selected from the group consisting of 4-chlorophenyl, thiazol-2-yl and benzo[d][1.3]dioxol-5-yl;

$R^1$ is selected from the group consisting of hydrogen and —OCH$_3$;

$R^2$ is selected from the group consisting of ethyl, cyclopropyl, cyclobutyl, oxetan-3-yl and tetrahydrofur-2-yl;

$R^3$ is selected from the group consisting of (d), (f) and (g); wherein (d) is

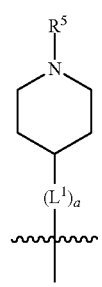

wherein a is an integer from 0 to 1; wherein $L^1$ is —CH$_2$—; and wherein $R^5$ is selected from the group consisting of propyn-3-yl, methoxy-carbonyl-methyl-, 3-(aminocarbonyl)-phenyl, 4-(aminocarbonyl)-phenyl, 3-(aminocarbonyl-methyl)-phenyl, 3-(aminocarbonyl-methoxy)-phenyl, 3-carboxy-benzyl, 3-(aminocarbonyl)-benzyl, 3-(2-hydroxyethyl-aminocarbonyl)-benzyl, 3-fluoro-5-carboxy-benzyl, 1-(3-carboxyphenyl)-ethyl-, 1R*-(3-carboxyphenyl)-ethyl-, 1-(3-carboxyphenyl)-n-propyl-, 5-carboxy-pyrimidin-2-yl, 5-aminocarbonyl-pyrid-2-yl-methyl-, 5-am inocarbonyl-pyrid-3-yl-methyl-, 6-aminocarbonyl-pyrid-3-yl-methyl-, 1-(4-carboxy-pyrid-2-yl)-ethyl-, 5-aminocarbonyl-fur-2-yl-methyl-, 5-carboxy-thien-2-yl-methyl-, 5-aminocarbonyl-thien-2-yl-methyl-, 4-aminocarbonyl-thien-2-yl-methyl-, benzyloxy-carbonyl-, methyl-sulfonyl-, trifluoromethyl-sulfonyl-, phenyl-sulfonyl-, 4-fluorophenyl-sulfonyl-, 4-chlorophenyl-sulfonyl, 3-hydroxyphenyl-sulfonyl-, 4-hydroxyphenyl-sulfonyl-, 2-methoxy-phenyl-sulfonyl-, 3-trifluoromethyl-phenyl-sulfonyl-, 4-carboxyphenyl-sulfonyl-, 3-amino-phenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-methyl-4-carboxy-phenyl-sulfonyl-, 3-trifluoromethyl-4-carboxy-phenyl-sulfonyl-, 3-methoxy-4-aminocarbonyl-phenyl-sulfonyl-, 3-methoxy-4-carboxy-phenyl-sulfonyl-, 5-(am inocarbonyl)-fur-2-yl-sulfonyl-, 4-carboxy-thien-2-yl-sulfonyl-, 4-(am inocarbonyl)-thien-2-yl-sulfonyl-, 3-methyl-5-carboxy-thien-2-yl-sulfonyl-, 3-methyl-5-(am inocarbonyl)-thien-2-yl-sulfonyl- and 6-aminocarbonyl-pyrid-3-yl-sulfonyl-;

(f) is

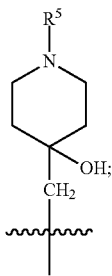

wherein $R^5$ is trifluoromethyl-sulfonyl-; and (g) is

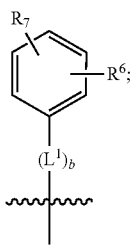

wherein b is an integer from 0 to 1; $L^2$ is —CH$_2$CH$_2$—; and wherein $R^6$ is selected from the group consisting of 3-chloro-, 4-trifluoromethyl, 4-methoxy- and 4-(ethoxy-carbonyl-methoxy)-; and $R^7$ is hydrogen;

or a stereoisomer, tautomer or pharmaceutically acceptable salt thereof.

8. A compound as in claim 4, wherein $R^0$ is selected from the group consisting of hydrogen and —OH;

is 4-chlorophenyl;

is 4-chlorophenyl;

$R^1$ is selected from the group consisting of hydrogen and —OCH$_3$;

$R^2$ is selected from the group consisting of cyclopropyl, cyclobutyl and tetrahydrofur-2-yl;

$R^3$ is selected from the group consisting of (d), (f) and (g); wherein (d) is

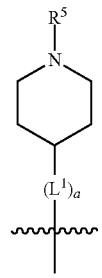

wherein a is an integer from 0 to 1; wherein $L^1$ is —CH$_2$—; and wherein $R^5$ is selected from the group consisting of methoxy-carbonyl-methyl-, 3-(aminocarbonyl)-benzyl, 1R*-(3-carboxyphenyl)-ethyl-, 5-aminocarbonyl-pyrid-2-yl-methyl-, 1-(4-carboxy-pyrid-2-yl)-ethyl 5-aminocarbonyl-thien-2-yl-methyl-, 4-aminocarbonyl-thien-2-yl-methyl-, trifluoromethyl-sulfonyl-, phenyl-sulfonyl-, 4-chlorophenyl-sulfonyl, 3-hydroxyphenyl-sulfonyl-, 2-methoxy-phenyl-sulfonyl-, 3-aminocarbonyl-phenyl-sulfonyl-, 4-aminocarbonyl-methoxy-phenyl-sulfonyl-, 3-chloro-4-carboxy-phenyl-sulfonyl, 3-trifluoromethyl-4-carboxy-phenyl-sulfonyl3-methyl-5-(am inocarbonyl)-thien-2-yl-sulfonyl- and 6-aminocarbonyl-pyrid-3-yl-sulfonyl-;

(f) is

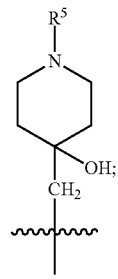

wherein $R^5$ is trifluoromethyl-sulfonyl-;

and (g) is

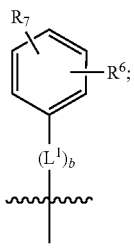

wherein b is an integer from 0 to 1; $L^2$ is —$CH_2CH_2$—; and wherein $R^6$ is selected from the group consisting of 4-trifluoromethyl, 4-methoxy- and 4-(ethoxy-carbonyl-methoxy)-; and $R^7$ is hydrogen;

or a stereoisomer, tautomer or pharmaceutically acceptable salt thereof.

9. A compound as in claim 4, wherein $R^0$ is hydrogen;

is selected from the group consisting of 4-chlorophenyl and 4-methoxyphenyl;

is selected from the group consisting of 4-chlorophenyl, 4-methoxyphenyl and thiazol-2-yl;

$R^1$ is hydrogen;

$R^2$ is selected from the group consisting of ethyl, cyclopropyl and cyclobutyl;

$R^3$ is selected from the group consisting of 1-(3-fluoro-5-carboxy-benzyl)-piperidin-4-yl, 1-(2-fluoro-5-carboxy-benzyl)-piperidin-4-yl, 1-(5-carboxy-pyrid-2-yl-methyl)-piperidin-4-yl, 1-(6-carboxy-pyrid-2-yl-methyl)-piperidin-4-yl, 1-(5-carboxy-thien-2-yl-methyl)-piperidin-4-yl, 1-(4-carboxy-thien-2-yl-sulfonyl)-piperidin-4-yl, 1-(5-carboxy-fur-2-yl-sulfonyl)-piperidin-4-yl, 1-(3-carboxy-benzyl)-piperidin-4-yl, 1-(3-carboxy-phenyl-sulfonyl)-piperidin-4-yl, 1-(3-hydroxy-phenyl-sulfonyl)-piperidin-4-yl, 1-(4-carboxy-phenyl-sulfonyl)-piperidin-4-yl, 1-trifluoromethyl-sulfonyl-piperidin-4-yl-methyl- and 1-trifluoromethyl-sulfonyl-piperidin-4-yl;

or a stereoisomer, tautomer or pharmaceutically acceptable salt thereof.

10. A compound as in claim 4, wherein $R^0$ is hydrogen,

is selected from the group consisting of 4-chlorophenyl and 4-methoxyphenyl;

is selected from the group consisting of 4-chlorophenyl and 4-methoxyphenyl;

$R^1$ is hydrogen;

$R^2$ is selected from the group consisting of ethyl, cyclopropyl and cyclobutyl;

$R^3$ is selected from the group consisting of 1-(3-fluoro-5-carboxy-benzyl)-piperidin-4-yl, 1-(2-fluoro-5-carboxy-benzyl)-piperidin-4-yl, 1-(5-carboxy-pyrid-2-yl-methyl)-piperidin-4-yl, 1-(6-carboxy-pyrid-2-yl-methyl)-piperidin-4-yl, 1-(5-carboxy-thien-2-yl-methyl)-piperidin-4-yl, 1-(3-carboxy-benzyl)-piperidin-4-yl, 1-(3-carboxy-phenyl-sulfonyl)-piperidin-4-yl, 1-(3-hydroxy-phenyl-sulfonyl)-piperidin-4-yl, 1-trifluoromethyl-sulfonyl-piperidin-4-yl-methyl-, 1-trifluoromethyl-sulfonyl-piperidin-4-yl, or a stereoisomer, tautomer or pharmaceutically acceptable salt thereof.

11. A compound of formula (II)

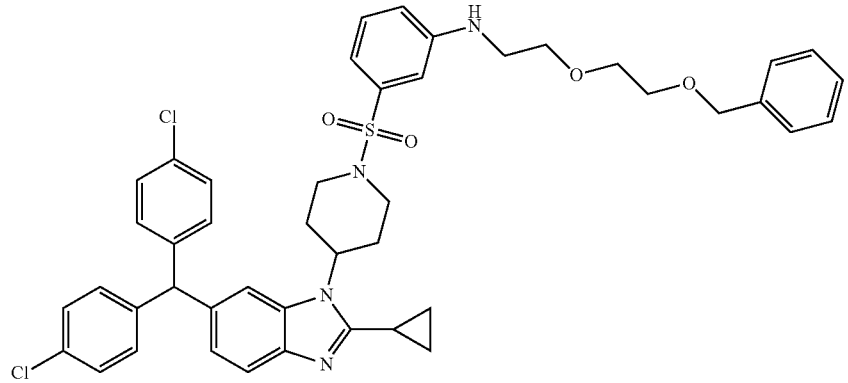

(II)

or a stereoisomer, tautomer or pharmaceutically acceptable salt thereof.

12. A pharmaceutical composition comprising a pharmaceutically acceptable carrier and a compound of claim 1 or claim 11.

13. A pharmaceutical composition made by mixing a compound of claim 1 or claim 11 and a pharmaceutically acceptable carrier.

14. A process for making a pharmaceutical composition comprising mixing a compound of claim 1 or claim 11 and a pharmaceutically acceptable carrier.

* * * * *